US009605000B2

(12) United States Patent
Kasai et al.

(10) Patent No.: US 9,605,000 B2
(45) Date of Patent: Mar. 28, 2017

(54) SPIRO AZETIDINE ISOXAZOLE DERIVATIVES AND THEIR USE AS SSTR ANTAGONISTS

(71) Applicant: Takeda Pharmaceutical Company Limited, Osaka (JP)

(72) Inventors: Shizuo Kasai, Fujisawa (JP); Masaki Ogino, Fujisawa (JP); Ryo Mizojiri, Fujisawa (JP); Takeshi Yamasaki, Fujisawa (JP); Hideki Hirose, Fujisawa (JP); Nobuyuki Takakura, Fujisawa (JP); Tohru Yamashita, Fujisawa (JP); Sachie Morimoto, Fujisawa (JP); Takashi Nakahata, Fujisawa (JP); Asato Kina, Fujisawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/775,265

(22) PCT Filed: Mar. 13, 2014

(86) PCT No.: PCT/JP2014/058144

§ 371 (c)(1),
(2) Date: Sep. 11, 2015

(87) PCT Pub. No.: WO2014/142363

PCT Pub. Date: Sep. 18, 2014

(65) Prior Publication Data

US 2016/0060273 A1 Mar. 3, 2016

(30) Foreign Application Priority Data

Mar. 14, 2013 (JP) ................................ 2013-052482

(51) Int. Cl.

| | |
|---|---|
| ***C07D 498/10*** | (2006.01) |
| ***A61P 3/00*** | (2006.01) |
| ***A61K 31/424*** | (2006.01) |

(52) U.S. Cl.
CPC ................................ *C07D 498/10* (2013.01)

(58) Field of Classification Search
CPC ........ A61P 3/00; A61K 31/424; C07D 498/10
USPC .......................................................... 546/184
See application file for complete search history.

(56) References Cited

U.S. PATENT DOCUMENTS

| | | | | |
|---|---|---|---|---|
| 9,120,777 B2 * | 9/2015 | Kasai | .................. | C07D 401/14 |
| 2012/0041012 A1 * | 2/2012 | Aster | .................. | C07D 471/10 514/275 |
| 2015/0099777 A1 * | 4/2015 | Kasai | .................. | C07D 471/04 514/300 |

FOREIGN PATENT DOCUMENTS

| | | |
|---|---|---|
| WO | WO 2010/027567 A2 | 3/2010 |
| WO | WO 2011/146324 A1 | 11/2011 |
| WO | WO 2012/024183 A1 | 2/2012 |
| WO | WO 2015/052910 A1 | 4/2015 |
| WO | WO 2015/064083 A1 | 5/2015 |

OTHER PUBLICATIONS

Dorwald; "Side Reactions in Organic Synthesis: A Guide to Successful Synthesis Design" 2005 Wiley-VCH Verlag GmbH & Co. KGaA, Wienheim, chapter 1.*
Schwetz; Am J Physiol Endocrinol Metab 2013 304, E211-E221.*
Sprecher; Regulatory Peptides 2010 159, 19-27.*
Chisholm et al., "Somastatin-28 regulates GLP-1 secretion via somatostatin receptor subtype 5 in rat intestinal cultures," American Journal of Physiology—Endocrinology and Metabolism, 2002, 283:E311-E317.
Patel, Y.C., "Molecular pharmacology of somatostatin receptor subtypes," Journal of Endocrinological Investigation, 1997, 20:348-367.

* cited by examiner

*Primary Examiner* — Noble Jarrell
*Assistant Examiner* — Daniel Carcanague
(74) *Attorney, Agent, or Firm* — Foley & Lardner LLP

(57) ABSTRACT

Provided is a compound represented by the following formula (1) or a salt thereof, which has an SSTR5 antagonistic action: wherein each symbol has the same definition as in the specification.

(1)

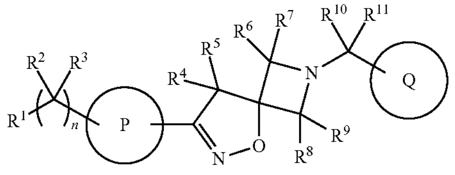

12 Claims, No Drawings

SPIRO AZETIDINE ISOXAZOLE DERIVATIVES AND THEIR USE AS SSTR ANTAGONISTS

CROSS-REFERENCE TO RELATED APPLICATIONS

This application is a National Stage application of PCT/JP2014/058144, filed Mar. 13, 2014, which claims priority from Japanese application no. JP 2013-052482, filed Mar. 14, 2013.

TECHNICAL FIELD

The present invention relates to a heterocyclic compound, which has a somatostatin receptor subtype 5 (which may be sometimes simply referred as "SSTR5" in the present specification) antagonistic action, and is useful for treating, improving, or preventing diseases or conditions such as diabetes mellitus, insulin resistance, dyslipidemia, obesity, arteriosclerosis, cardiovascular diseases, metabolic syndrome, and neuropathy.

BACKGROUND OF THE INVENTION

Diabetes mellitus (DM) is a disease in which a blood sugar level (glucose concentration in the blood) is pathologically elevated by insulin secretion failure or insulin resistance, and is known to be a risk factor for various severe complications. It is said that diabetes mellitus is developed by various environmental factors (such as lack of exercise, overeating, and obesity) involved, based on genetic factors, and it is expected that in the future, the number of diabetic patients will increase as the number of obese people increases. Diabetes mellitus is classified into an insulin-dependent type 1 diabetes mellitus (IDDM: Insulin Dependent Diabetes Mellitus) and non-insulin-dependent type 2 diabetes mellitus, and a majority (about 90%) of patients with diabetes mellitus are classified into the type 2 diabetes mellitus.

The type 1 diabetes mellitus is a disease in which β cells that secrete insulin in the islets of Langerhans in the pancreas die by various genetic factors or acquired factors, and the type 2 diabetes mellitus is a disease which is caused by reduction of the amount of insulin secreted in response to glucose in β cells and a decrease in insulin sensitivity in the peripheral tissues (such as the liver, the muscle, and fat).

With regard to treatment and prevention related to diabetes mellitus, drug therapy has also been performed, in addition to diets and exercise therapy.

Examples of the typical drug therapy at present include drug therapies in which insulin, insulin analogues, GLP-1 (glucagon-like peptide-1) analogues, or the like is subcutaneously administered, and drug therapies in which a hypoglycemic agent that can be orally administered is used Examples of the hypoglycemic agent that can be orally administered include sulfonylurea agents (SU drugs) such as glimepiride; biguanide agents (BG drugs) such as metformin; α-glucosidase inhibitors (αGI drugs) such as voglibose and miglitol; thiazolidine-based derivatives (TZD drugs) such as pioglitazone; and DPP-IV (dipeptidyl peptidase IV) inhibitors such as sitagliptin and alogliptin.

Somatostatin is widely distributed in the central nervous system, such as hypothalamus, islets of Langerhans in pancreas, intestinal mucosa, or the like, and plays an important role in the gastrointestinal motility, secretion of digestive juice, and regulation of glucose or lipid metabolism. In particular, in vivo, it has been known that somatostatin performs an inhibitory action on production or secretion of various hormones, proliferation factors, and physiologically active substances. Examples of the hormone on which somatostatin performs an inhibitory action include growth hormone (GH), thyroid stimulating hormone (TSH), prolactin, insulin, glucagon, gastrin, secretin, PYY (peptide YY), GIP (gastric inhibition polypeptide), GLP-1, CCK (cholecystokinin), VIP (vasoactive intestinal peptide), and Oxyntomodulin. Further, somatostatin also acts as paracrine in the islets of Langerhans in the pancreas or the mucosa of the digestive tract, in which δ cells are in contact with α cells and β cells. For this reason, somatostatin has various physiological functions in the endocrine system, the exocrine system, the nervous system, or the like.

The somatostatin receptor is one of the seven-transmembrane G protein-coupled receptors subtypes, and 5 kinds of subtypes thereof have now been found, which are named SSTR1, SSTR2, SSTR3, SSTR4, and SSTR5, respectively (Non-Patent Literature 1). Among these, SSTR5 has been shown to be involved in the regulation of secretion of insulin and incretins (Non-Patent Literature 2).

On the other hand, in Patent Literature 1, it has been reported that the following compound has an SSTR5 antagonistic action.

[Chem. 1]

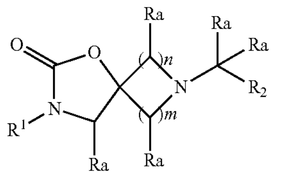

I

[in which Ra is independently selected from the group consisting of a hydrogen atom, a halogen atom, a $C_{1-10}$ alkyl group, and a $C_{1-10}$ alkyl group substituted with a halogen atom, $R^1$ is selected from the group consisting of a hydrogen atom, a substituted phenyl, and a substituted heterocycle, $R^2$ is selected from the group consisting of a substituted aryl and a substituted heterocycle, and n and m are independently selected from the group consisting of 1, 2, and 3.]

Furthermore, in Patent Literature 2, it has been reported that the following compound has an SSTR5 antagonistic action.

[Chem. 2]

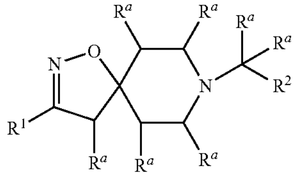

I

[in which Ra is independently selected from the group consisting of a hydrogen atom, a halogen atom, a $C_{1-10}$ alkyl group, and a $C_{1-10}$ alkyl group substituted with a halogen atom, $R^1$ is selected from the group consisting of a substituted phenyl and a substituted heterocycle, and $R^2$ is selected from the group consisting of a substituted phenyl group and a substituted heterocycle.]

PRIOR ART LITERATURE

Patent Literature

[Patent Literature 1] International Publication No. 2012/024183

[Patent Literature 2] International Publication No. 2011/146324

Non Patent Literature

[Non-Patent Literature 1] Patel Y C: "Molecular pharmacology of somatostatin receptor subtypes." J Endocrinol Invest 20:348-367, 1997

[Non-Patent Literature 2] Chisholm C et al.: "Somatostatin-28 regulates GLP-1 secretion via somatostatin receptor subtype 5 in rat intestinal cultures." Am J Physiol Endocrinol Metab 283: E311-317, 2002

SUMMARY OF THE INVENTION

Problems to be Solved by the Invention

There is a demand for the development of a compound which has an SSTR5 antagonistic action and is useful for treating, improving, or preventing diseases or conditions such as diabetes mellitus, insulin resistance, dyslipidemia, obesity, arteriosclerosis, cardiovascular diseases, metabolic syndrome, and neuropathy.

Means of Solving the Problems

The present inventors have found that a compound represented by the following formula:

[Chem. 3]

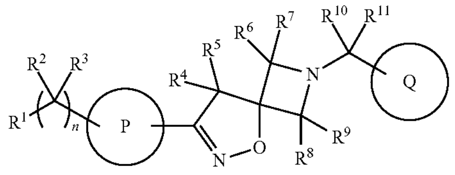

wherein ring P is an optionally substituted non-aromatic ring, ring Q is an optionally substituted $C_{6-14}$ aromatic hydrocarbon ring or an optionally substituted 5- to 14-membered heterocycle, $R^1$ is $CO_2Ra$ wherein Ra is a hydrogen atom or a $C_{1-6}$ alkyl group, $R^2$ and $R^3$ are each independently a hydrogen atom, a halogen atom or a $C_{1-6}$ alkyl group, $R^4$ and $R^5$ are each independently a hydrogen atom, a halogen atom, a $C_{1-6}$ alkyl group or a $C_{3-10}$ cycloalkyl group, $R^6$, $R^7$, $R^8$ and $R^9$ are each independently a hydrogen atom, a halogen atom or a $C_{1-6}$ alkyl group, $R^{10}$ and $R^{11}$ are each independently a hydrogen atom, a halogen atom or a $C_{1-6}$ alkyl group, and n is an integer of 0 to 2, or a salt thereof (which may be sometimes referred to as a compound (I)) has an excellent SSTR5 antagonistic action, is useful for treating, improving, or preventing diseases or conditions such as diabetes mellitus, insulin resistance, metabolic syndrome, dyslipidemia, obesity, arteriosclerosis, cardiovascular diseases, and neuropathy, and has an excellent drug efficacy. Based on these findings, the present inventors have conducted extensive studies and as a result, they have completed the present invention.

That is, the present invention relates to:

[1] a compound represented by the following formula:

[Chem. 4]

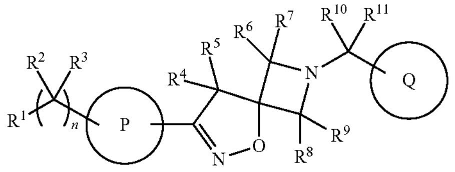

wherein ring P is an optionally substituted non-aromatic ring, ring Q is an optionally substituted $C_{6-14}$ aromatic hydrocarbon ring or an optionally substituted 5- to 14-membered heterocycle, $R^1$ is $CO_2Ra$ wherein Ra is a hydrogen atom or a $C_{1-6}$ alkyl group, $R^2$ and $R^3$ are each independently a hydrogen atom, a halogen atom or a $C_{1-6}$ alkyl group, $R^4$ and $R^5$ are each independently a hydrogen atom, a halogen atom, a $C_{1-6}$ alkyl group or a $C_{3-10}$ cycloalkyl group, $R^6$, $R^7$, $R^8$ and $R^9$ are each independently a hydrogen atom, a halogen atom or a $C_{1-6}$ alkyl group, $R^{10}$ and $R^{11}$ are each independently a hydrogen atom, a halogen atom or a $C_{1-6}$ alkyl group, and n is an integer of 0 to 2, or a salt thereof,

[2] the compound or a salt thereof as described in [1], wherein ring P is piperidine or cyclohexane, each optionally substituted with a $C_{1-6}$ alkyl group;

[3] the compound or a salt thereof as described in [1] or [2], wherein ring Q is benzene optionally substituted with 1 to 4 substituents selected from (a) a halogen atom, (b) a $C_{3-10}$ cycloalkyl group optionally substituted with 1 to 3 halogen atoms, (c) a $C_{1-6}$ alkoxy group optionally substituted with an optionally halogenated $C_{3-10}$ cycloalkyl group, (d) a 3- to 8-membered monocyclic non-aromatic heterocyclic group optionally substituted with 1 to 3 halogen atoms, and (e) a $C_{6-14}$ aryl group optionally substituted with 1 to 3 halogen atoms;

[4] the compound or a salt thereof as described in any one of [1] to [3], wherein $R^1$ is $CO_2H$;

[5] the compound or a salt thereof as described in any one of [1] to [4], wherein $R^4$, $R^5$, $R^6$, $R^7$, $R^8$, $R^9$, $R^{10}$ and $R^{11}$ are hydrogen atoms;

[6] the compound or a salt thereof as described in any one of [1] to [5], wherein n is 0;

[7] the compound or a salt thereof as described in any one of [1] to [6], wherein ring P is piperidine or cyclohexane, each optionally substituted with a $C_{1-6}$ alkyl group, ring Q is benzene optionally substituted with 1 to 4 substituents selected from (a) a halogen atom, (b) a $C_{3-10}$ cycloalkyl group optionally substituted with 1 to 3 halogen atoms, (c)

a $C_{1-6}$ alkoxy group optionally substituted with an optionally halogenated $C_{3-10}$ cycloalkyl group, (d) a 3- to 8-membered monocyclic non-aromatic heterocyclic group optionally substituted with 1 to 3 halogen atoms, and (e) a $C_{6-14}$ aryl group optionally substituted with 1 to 3 halogen atoms, $R^1$ is $CO_2H$, $R^4$, $R^5$, $R^6$, $R^7$, $R^8$, $R^9$, $R^{10}$ and $R^{11}$ are hydrogen atoms, and n is 0;

[8] the compound or a salt thereof as described in any one of [1] to [7], wherein ring P is piperidine optionally substituted with a $C_{1-6}$ alkyl group, ring Q is benzene optionally substituted with 3 to 4 substituents selected from (a) a halogen atom, (b) a $C_{3-10}$ cycloalkyl group, (c) a $C_{1-6}$ alkoxy group, and (d) a $C_{6-14}$ aryl group optionally substituted with 1 to 3 halogen atoms, $R^1$ is $CO_2H$, $R^4$, $R^5$, $R^6$, $R^7$, $R^8$, $R^9$, $R^{10}$ and $R^{11}$ are hydrogen atoms, and n is 0;

[9] 1-(2-((2-chloro-6-cyclopropyl-4'-fluoro-3-methoxybiphenyl-4-yl)methyl)-5-oxa-2,6-diazaspiro[3.4]octa-6-en-7-yl)-4-methylpiperidine-4-carboxylic acid or a salt thereof;

[10] 1-(2-((6-cyclopropyl-2,4'-difluoro-3-methoxybiphenyl-4-yl)methyl)-5-oxa-2,6-diazaspiro[3.4]octa-6-en-7-yl)-4-methylpiperidine-4-carboxylic acid or a salt thereof;

[11] 1-(2-((2,6-diethoxy-4'-fluorobiphenyl-4-yl)methyl)-5-oxa-2,6-diazaspiro[3.4]octa-6-en-7-yl)-4-methylpiperidine-4-carboxylic acid or a salt thereof;

[12] a pharmaceutical agent comprising the compound or the salt thereof as described in [1];

[13] the pharmaceutical agent as described in [12], which is a somatostatin receptor 5 antagonist;

[14] the pharmaceutical agent as described in [12], which is a prophylactic or therapeutic agent for diabetes mellitus;

[15] a method for preventing or treating diabetes mellitus in a mammal, comprising administering to the mammal an effective amount of the compound or a salt thereof as described in [1];

[16] a method for antagonizing a somatostatin receptor 5 in a mammal, comprising administering to the mammal an effective amount of the compound or a salt thereof as described in [1];

[17] use of the compound or a salt thereof as described in [1] for the preparation of a prophylactic or therapeutic agent for diabetes mellitus;

[18] the compound or a salt thereof as described in [1], for use in preventing or treating diabetes mellitus;

and the like.

Effects of the Invention

The compound (I) has an excellent SSTR5 antagonistic action, is useful for treating, improving, or preventing disease and/or conditions such as diabetes mellitus, insulin resistance, metabolic syndrome, dyslipidemia, obesity, arteriosclerosis, cardiovascular diseases, and neuropathy, and also has an excellent drug efficacy.

DETAILED DESCRIPTION OF THE INVENTION

Hereinbelow, the definitions of the terms in the present specification will be described in detail.

In the present specification, examples of the "halogen atom" include fluorine, chlorine, bromine, and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

In the present specification, examples of the "optionally halogenated $C_{1-6}$ alkyl group" include $C_{1-6}$ alkyl groups optionally having 1 to 7 halogen atoms, and preferably 1 to 5 halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, and adamantyl.

In the present specification, examples of the "optionally halogenated $C_{3-10}$ cycloalkyl group" include a $C_{3-10}$ cycloalkyl group optionally having 1 to 7 halogen atoms, and preferably 1 to 5 halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl, and cyclooctyl.

In the present specification, examples of the "$C_{3-10}$ cycloalkenyl group" include cyclopropenyl, cyclobutenyl, cyclopentenyl, cyclohexenyl, cycloheptenyl, and cyclooctenyl.

In the present specification, examples of the "$C_{6-14}$ aryl group" include phenyl, 1-naphthyl, 2-naphthyl, 1-anthryl, 2-anthryl, and 9-anthryl.

In the present specification, examples of the "$C_{7-16}$ aralkyl group" include benzyl, phenethyl, naphthylmethyl, and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy, and hexyloxy.

In the present specification, examples of the "optionally halogenated $C_{1-6}$ alkoxy group" include a $C_{1-6}$alkoxy group optionally having 1 to 7 halogen atoms, and preferably 1 to 5 halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy, and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio, and hexylthio.

In the present specification, examples of the "optionally halogenated $C_{1-6}$ alkylthio group" include a $C_{1-6}$ alkylthio group optionally having 1 to 7 halogen atoms, and preferably 1 to 5 halogen atoms. Specific examples thereof include methylthio, difluoromethylthio, trifluoromethylthio, ethylthio, propylthio, isopropylthio, butylthio, 4,4,4-trifluorobutylthio, pentylthio, and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl, and heptanoyl.

In the present specification, examples of the "optionally halogenated $C_{1-6}$ alkyl-carbonyl group" include a $C_{1-6}$ alkyl-carbonyl group optionally having 1 to 7 halogen atoms, and preferably 1 to 5 halogen atoms. Specific examples thereof include acetyl, chloroacetyl, trifluoroacetyl, trichloroacetyl, propanoyl, butanoyl, pentanoyl, and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, and hexyloxycarbonyl.

In the present specification, examples of the "$C_{6-14}$ aryl-carbonyl group" include benzoyl, 1-naphthoyl, and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclic carbonyl group" include nicotinoyl, isonicotinoyl, thenoyl, furoyl.

In the present specification, examples of the "3- to 14-membered non-aromatic heterocyclic carbonyl group" include morpholinylcarbonyl, piperidinylcarbonyl, and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl, and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl, and tert-butylsulfonyl.

In the present specification, examples of the "optionally halogenated $C_{1-6}$ alkylsulfonyl group" include a $C_{1-6}$ alkylsulfonyl group optionally having 1 to 7 halogen atoms, and preferably 1 to 5 halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-triftuorobutylsulfonyl, pentylsulfonyl, and hexylsulfonyl.

In the present specification, examples of the "$C_{6-14}$ arylsulfonyl group" include phenylsulfonyl, 1-naphthylsulfonyl, and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxyl group, an optionally substituted sulfanyl (SH) group, and an optionally substituted silyl group.

In the present specification, examples of the "hydrocarbon group" (including a "hydrocarbon group" in the "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group, and a $C_{7-16}$ aralkyl group.

In the present specification, examples of the "optionally substituted hydrocarbon group" include a hydrocarbon group optionally having a substituent selected from the following substituent group A.

[Substituent Group A]

(1) a halogen atom, (2) a nitro group, (3) a cyano group, (4) an oxo group, (5) a hydroxyl group, (6) an optionally halogenated $C_{1-6}$ alkoxy group, (7) a $C_{6-14}$ aryloxy group (e.g., phenoxy and naphthoxy), (8) a $C_{7-16}$ aralkyloxy group (e.g., benzyloxy), (9) a 5- to 14-membered aromatic heterocyclic oxy group (e.g., pyridyloxy),

(10) a 3- to 14-membered non-aromatic heterocyclic oxy group (e.g., morpholinyloxy and piperidinyloxy),

(11) a $C_{1-6}$ alkyl-carbonyloxy group (e.g., acetoxy and propanoyloxy),

(12) a $C_{6-14}$ aryl-carbonyloxy group (e.g., benzoyloxy, 1-naphthoyloxy, and 2-naphthoyloxy),

(13) a $C_{1-6}$ alkoxy-carbonyloxy group (e.g., methoxycarbonyloxy, ethoxycarbonyloxy, propoxycarbonyloxy, and butoxycarbonyloxy),

(14) a mono- or di-$C_{1-6}$ alkyl-carbamoyloxy group (e.g., methylcarbamoyloxy, ethylcarbamoyloxy, dimethylcarbamoyloxy, and diethylcarbamoyloxy),

(15) a $C_{6-14}$ aryl-carbamoyloxy group (e.g., phenylcarbamoyloxy and naphthylcarbamoyloxy),

(16) a 5- to 14-membered aromatic heterocyclic carbonyloxy group (e.g., nicotinoyloxy),

(17) a 3- to 14-membered non-aromatic heterocyclic carbonyloxy group (e.g., morpholinylcarbonyloxy and piperidinylcarbonyloxy),

(18) an optionally halogenated $C_{1-6}$ alkylsulfonyloxy group (e.g., methylsulfonyloxy and trifluoromethylsulfonyloxy),

(19) a $C_{6-14}$ arylsulfonyloxy group optionally substituted with a $C_{1-6}$ alkyl group (e.g., phenylsulfonyloxy and toluenesulfonyloxy),

(20) an optionally halogenated $C_{1-6}$ alkylthio group,

(21) a 5- to 14-membered aromatic heterocyclic group,

(22) a 3- to 14-membered non-aromatic heterocyclic group,

(23) a formyl group,

(24) a carboxyl group,

(25) an optionally halogenated $C_{1-6}$ alkyl-carbonyl group,

(26) a $C_{6-14}$ aryl-carbonyl group,

(27) a 5- to 14-membered aromatic heterocyclic carbonyl group,

(28) a 3- to 14-membered non-aromatic heterocyclic carbonyl group,

(29) a $C_{1-6}$ alkoxy-carbonyl group,

(30) a $C_{6-14}$ aryloxy-carbonyl group (e.g., phenyloxycarbonyl, 1-naphthyloxycarbonyl, and 2-naphthyloxycarbonyl),

(31) a $C_{7-16}$ aralkyloxy-carbonyl group (e.g., benzyloxycarbonyl and phenethyloxycarbonyl),

(32) a carbamoyl group,

(33) a thiocarbamoyl group,

(34) a mono- or di-$C_{1-6}$ alkyl-carbamoyl group,

(35) a $C_{6-14}$ aryl-carbamoyl group (e.g., phenylcarbamoyl),

(36) a 5- to 14-membered aromatic heterocyclic carbamoyl group (e.g., pyridylcarbamoyl and thienylcarbamoyl),

(37) a 3- to 14-membered non-aromatic heterocyclic carbamoyl group (e.g., morpholinylcarbamoyl and piperidinylcarbamoyl),

(38) an optionally halogenated $C_{1-6}$ alkylsulfonyl group,

(39) a $C_{6-14}$ arylsulfonyl group,

(40) a 5- to 14-membered aromatic heterocyclic sulfonyl group (e.g., pyridylsulfonyl and thienylsulfonyl),

(41) an optionally halogenated $C_{1-6}$ alkylsulfinyl group,

(42) a $C_{6-14}$ arylsulfinyl group (e.g., phenylsulfinyl, 1-naphthylsulfinyl, and 2-naphthylsulfinyl),

(43) a 5- to 14-membered aromatic heterocyclic sulfinyl group (e.g., pyridylsulfinyl and thienylsulfinyl),

(44) an amino group,

(45) a mono- or di-$C_{1-6}$ (alkylamino group (e.g., methylamino, ethylamino, propylamino, isopropylamino, butylamino, dimethylamino, diethylamino, dipropylamino, dibutylamino, and N-ethyl-N-methylamino),

(46) a mono- or di-$C_{6-14}$ arylamino group (e.g., phenylamino),

(47) a 5- to 14-membered aromatic heterocyclic amino group (e.g., pyridylamino),

(48) a $C_{7-16}$ aralkylamino group (e.g., benzylamino),

(49) a formylamino group,

(50) a $C_{1-6}$ alkyl-carbonylamino group (e.g., acetylamino, propanoylamino, and butanoylamino),

(51) a ($C_{1-6}$ alkyl)($C_{1-6}$ alkyl-carbonyl) amino group (e.g., N-acetyl-N-methylamino),

(52) a $C_{6-14}$ aryl-carbonylamino group (e.g., phenylcarbonylamino and naphthylcarbonylamino),

(53) a $C_{1-6}$ alkoxy-carbonylamino group (e.g., methoxycarbonylamino, ethoxycarbonylamino, propoxycarbonylamino, butoxycarbonylamino, and tert-butoxycarbonylamino),

(54) a $C_{7-16}$ aralkyloxy-carbonylamino group (e.g., benzyloxycarbonylamino),

(55) a $C_{1-6}$ alkylsulfonylamino group (e.g., methylsulfonylamino and ethylsulfonylamino),

(56) a $C_{6-14}$ arylsulfonylamino group optionally substituted with a $C_{1-6}$ alkyl group (e.g., phenylsulfonylamino and toluenesulfonylamino),

(57) an optionally halogenated $C_{1-6}$ alkyl group,

(58) a $C_{2-6}$ alkenyl group,

(59) a $C_{2-6}$ alkynyl group,

(60) a $C_{3-10}$ cycloalkyl group,

(61) a $C_{3-10}$ cycloalkenyl group, and

(62) a $C_{6-14}$ aryl group.

The number of the substituents in the "optionally substituted hydrocarbon group" is, for example, 1 to 5, and preferably 1 to 3. If the number of the substituents is 2 or more, the respective substituents may be the same as or different from each other.

In the present specification, examples of the "heterocyclic group" (including a "heterocyclic group" in the "optionally substituted heterocyclic group") include (i) an aromatic heterocyclic group, (ii) a non-aromatic heterocyclic group, and (iii) a 7- to 10-membered bridged heterocyclic group, each of which contains 1 to 4 heteroatoms selected from a nitrogen atom, a sulfur atom, and an oxygen atom other than a carbon atom as a ring-constituting atom.

In the present specification, examples of the "aromatic heterocyclic group" (including a "5- to 14-membered aromatic heterocyclic group") include a 5- to 14-membered (preferably 5- to 10-membered) aromatic heterocyclic group containing 1 to 4 heteroatoms selected from a nitrogen atom, a sulfur atom, and an oxygen atom other than a carbon atom as a ring-constituting atom.

Preferred examples of the "aromatic heterocyclic group" include 5- to 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, and triazinyl; and 8- to 14-membered fused polycyclic (preferably bi- or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, and phenoxazinyl.

In the present specification, examples of the "non-aromatic heterocyclic group" (including a "3- to 14-membered non-aromatic heterocyclic group") include a 3- to 14-membered (preferably 4- to 10-membered) non-aromatic heterocyclic group containing 1 to 4 heteroatoms selected from a nitrogen atom, a sulfur atom, and an oxygen atom other than a carbon atom as a ring-constituting atom.

Preferred examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, and diazepanyl; and 9- to 14-membered fused polycyclic (preferably bi- or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolidinyl, indolinyl, isoindolinyl, tetrahydrothieno[2,3-c]pyridinyl, tetrahydrobenzoazepinyl, tetrahydroquinoxalinyl, tetrahydrophenantridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, and octahydroisoquinolyl.

In the present specification, preferred examples of the "7- to 10-membered bridged heterocyclic group" include quinuclidinyl and 7-azabicyclo[2.2.1]heptanyl.

In the present specification, examples of the "nitrogen-containing heterocyclic group" include the "heterocyclic groups", which contains at least one nitrogen atoms as a ring-constituting atom.

In the present specification, examples of the "optionally substituted heterocyclic group" include a heterocyclic group optionally having a substituent selected from the substituent group A.

The number of the substituents in the "optionally substituted heterocyclic group" is, for example, 1 to 3. If the number of the substituents is 2 or more, the respective substituents may be the same as or different from each other.

In the present specification, examples of the "acyl group" include a formyl group, a carboxyl group, a carbamoyl group, a thiocarbamoyl group, a sulfino group, a sulfo group, a sulfamoyl group, and a phosphono group, each of which may have "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group, and a 3- to 14-membered non-aromatic heterocyclic group, each of which may have 1 to 3 substituents selected from a halogen atom, an optionally halogenated $C_{1-6}$ alkoxy group, a hydroxyl group, a nitro group, a cyano group, an amino group, and a carbamoyl group".

Furthermore, examples of the "acyl group" include a hydrocarbon-sulfonyl group, a heterocycle-sulfonyl group, a hydrocarbon-sulfinyl group, and a heterocycle-sulfinyl group.

Here, the hydrocarbon-sulfonyl group means a sulfonyl group bonded to a hydrocarbon group, the heterocycle-sulfonyl group means a sulfonyl group bonded to a heterocyclic group, the hydrocarbon-sulfinyl group means a sulfinyl group bonded to a hydrocarbon group, and the heterocycle-sulfinyl group means a sulfinyl group bonded to a heterocyclic group.

Preferred examples of "acyl group" include a formyl group, a carboxyl group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, and cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclic carbonyl group, a 3- to 14-membered non-aromatic heterocyclic carbonyl group, a $C_{1-6}$ alkoxy-carbonyl group, a $C_{6-14}$ aryloxy-carbonyl group (e.g., phenyloxycarbonyl and naphthyloxycarbonyl), a $C_{7-16}$ aralkyloxy-carbonyl group (e.g., benzyloxycarbonyl and phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclic carbamoyl group (e.g., pyridylcarbamoyl), a thiocarbamoyl group, a mono- or di-$C_{1-6}$ alkyl-thiocarbamoyl group (e.g., methylthiocarbamoyl and N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl and cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl and phenethylthiocarbamoyl), a 5- to 14-membered aromatic heterocyclicthiocarbamoyl group (e.g., pyridylthiocarbamoyl), a sulfino group, a $C_{1-6}$ alkylsulfinyl group (e.g., methylsulfinyl and ethylsulfinyl), a sulfo group, a $C_{1-6}$ alkylsulfonyl group, a $C_{6-14}$ arylsulfonyl group, a phosphono group, and a mono- or di-$C_{1-6}$ alkylphosphono group (e.g., dimethylphosphono, diethylphosphono, diisopropylphosphono, and dibutylphosphono).

In the present specification, examples of the "optionally substituted amino group" include amino groups, each optionally have 1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclic carbonyl group, a 3- to 14-membered non-aromatic heterocyclic carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group, and a $C_{6-14}$ arylsulfonyl group, each optionally have 1 to 3 substituents selected from the substituent group A.

Preferred examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ acylamino group (e.g., phenylamino), a mono- or di-$C_{7-16}$ aralkylamino group (e.g., benzylamino, dibenzylamino), a mono- or di-(optionally halogenated $C_{1-6}$ alkyl-carbonyl)amino group (e.g., acetylamino, propionylamino), a mono- or di-($C_{6-14}$ aryl-carbonyl)amino group (e.g., benzoylamino), a mono- or di-($C_{7-16}$ aralkyl-carbonyl)amino group (e.g., benzylcarbonylamino), a mono- or di-(5- to 14-membered aromatic heterocyclic carbonyl)amino group (e.g., nicotinoylamino, isonicotinoylamino), a mono- or di-(3- to 14-membered non-aromatic heterocyclic carbonyl)amino group (e.g., piperidinylcarbonylamino), a mono- or di-($C_{1-6}$ alkoxy-carbonyl)amino group (e.g., tert-butoxycarbonylamino), a 5- to 14-membered aromatic heterocyclic amino group (e.g., pyridylamino), carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, and ethylsulfonylamino), a $C_{6-14}$ arylsulfonylamino group (e.g., phenylsulfonylamino), a ($C_{1-6}$ alkyl)($C_{1-6}$ alkyl-carbonyl) amino group (e.g., N-acetyl-N-methylamino), and a ($C_{1-6}$ alkyl)($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclic carbonyl group, a 3- to 14-membered non-aromatic heterocyclic carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, and a mono- or di-$C_{7-16}$ aralkyl-carbamoyl group, each of which may have 1 to 3 substituents selected from the substituent group A".

Preferred examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl and cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonylcarbamoyl group (e.g., acetylcarbamoyl and propionylcarbamoyl), a mono- or di-$C_{6-14}$ aryl-carbonylcarbamoyl group (e.g., benzoylcarbamoyl), and a 5- to 14-membered aromatic heterocyclic carbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclic carbonyl group, a 3- to 14-membered non-aromatic heterocyclic carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, and a mono- or di-$C_{7-16}$ aralkyl-carbamoyl group, each optionally have 1 to 3 substituents selected from the substituent group A".

Preferred examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, and N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl and cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl and phenethylthiocarbamoyl), a mono- or di-$C_{1-6}$ alkyl-carbonyl-thiocarbamoyl group (e.g., acetylthiocarbamoyl and propionylthiocarbamoyl), a mono- or di-$C_{6-14}$ aryl-carbonyl-thiocarbamoyl group (e.g., benzoylthiocarbamoyl), and a 5- to 14-membered aromatic heterocyclic-thiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclic carbonyl group, a 3- to 14-membered non-aromatic heterocyclic carbonyl group, a $C_{1-6}$ alkoxy-carbonyl group, a 5- to 14-membered aromatic heterocylic group, a carbamoyl group, a mono- or di-$C_{1-6}$ alkyl-carbamoyl group, and a mono- or di-$C_{7-16}$ aralkyl-carbamoyl group, each optionally have 1 to 3 substituents selected from the substituent group A".

Preferred examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, and N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl and cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl and phenethylsulfamoyl), a mono- or di-$C_{1-6}$ alkyl-carbonyl-sulfamoyl group (e.g., acetylsulfamoyl and propionylsulfamoyl), a mono- or di-$C_{6-14}$ aryl-carbonyl-sulfamoyl group (e.g., benzoylsulfamoyl), and a 5- to 14-membered aromatic heterocyclic sulfamoyl group (e.g., pyridylsulfamoyl).

In the present specification, examples of the "optionally substituted hydroxyl group" include a hydroxyl group optionally having "a substituent selected from $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocylic carbonyl group, a 3- to 14-membered non-aromatic heterocyclic carbonyl group, a $C_{1-6}$ alkoxy-carbonyl group, a 5- to 14-membered aromatic heterocylic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group, and a $C_{6-14}$ arylsulfonyl group, each optionally have 1 to 3 substituents selected from the substituent group A".

Preferred examples of the optionally substituted hydroxyl group include a hydroxyl group, a $C_{1-6}$ alkoxy group, a $C_{2-6}$ alkenyloxy group (e.g., allyloxy, 2-butenyloxy, 2-pentenyloxy, and 3-hexenyloxy), a $C_{3-10}$ cycloalkyloxy group (e.g., cyclohexyloxy), a $C_{6-14}$ aryloxy group (e.g., phenoxy and naphthyloxy), a $C_{7-16}$ aralkyloxy group (e.g., benzyloxy and phenethyloxy), a $C_{1-6}$ alkyl-carbonyloxy group (e.g., acetyloxy, propionyloxy, butyryloxy, isobutyryloxy, and pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclic carbonyloxy group (e.g., nicotinoyloxy), a 3- to 14-membered non-aromatic heterocyclic carbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclic oxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy), and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, and a 5- to 14-membered aromatic heterocyclic group, each of which may have 1 to 3 substituents selected from the substituent group A" and a halogenated sulfanyl group.

Preferred examples of the optionally substituted sulfanyl group include a sulfanyl group, a $C_{1-6}$ alkylthio group, a $C_{2-6}$ alkenylthio group (e.g., allylthio, 2-butenylthio, 2-pentenylthio, and 3-hexenylthio), a $C_{3-10}$ cycloalkylthio group (e.g., cyclohexylthio), a $C_{6-14}$ arylthio group (e.g., phenylthio and naphthylthio), a $C_{7-16}$ aralkylthio group (e.g., benzylthio and phenethylthio), a $C_{1-6}$ alkyl-carbonylthio group (e.g., acetylthio, propionylthio, butyrylthio, isobutyrylthio, and pivaloylthio), a $C_{6-14}$ aryl-carbonylthio group (e.g., benzoylthio), a 5- to 14-membered aromatic heterocyclicthio group (e.g., pyridylthio), and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group, and a $C_{7-16}$ aralkyl group, each optionally have 1 to 3 substituents selected from the substituent group A".

Preferred examples of the optionally substituted silyl group include a tri-$C_{1-6}$ alkylsilyl group (e.g., trimethylsilyl and tert-butyl(dimethyl)silyl).

In the present specification, examples of the "hydrocarbon ring" include a $C_{6-14}$ aromatic hydrocarbon ring, a $C_{3-10}$ cycloalkane, and $C_{3-10}$ cycloalkene. In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane, and cyclooctane.

In the present specification, examples of the "$C_{3-10}$ cycloalkene" include cyclopropene, cyclobutene, cyclopentene, cyclohexene, cycloheptene, and cyclooctene.

In the present specification, examples of the "heterocycle" include an aromatic heterocycle and a non-aromatic heterocycle, each of which contains 1 to 4 heteroatoms selected from a nitrogen atom, a sulfur atom, and an oxygen atom other than a carbon atom as a ring-constituting atom.

In the present specification, examples of the "aromatic heterocycle" include a 5- to 14-membered (preferably 5- to 10-membered) aromatic heterocycle containing 1 to 4 heteroatoms selected from a nitrogen atom, a sulfur atom, and an oxygen atom other than a carbon atom as a ring-constituting atom. Preferred examples of the "aromatic heterocycle" include 5- to 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, and triazine; and 8- to 14-membered fused polycyclic (preferably bi- or tricyclic) aromatic heterocycles such as benzothiophene, benzofuran, benzimidazole, benzoxazole, benzisoxazole, benzothiazole, benzisothiazole, benzothiazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indoline, isoindoline, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, and phenoxazine.

In the present specification, examples of the "non-aromatic heterocycle" include a 3- to 14-membered (preferably 4- to 10-membered) non-aromatic heterocycle containing 1 to 4 heteroatoms selected from a nitrogen atom, a sulfur atom, and an oxygen atom other than a carbon atom as a ring-constituting atom. Preferred examples of the "non-aromatic heterocycle" include 3- to 8-membered monocyclic non-aromatic heterocycles such as aziridine, oxirane, thiirane, azetidine, oxetane, thiethane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, and oxepane; and 9- to 14-membered fused polycyclic (preferably bi- or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolidine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, and octahydroisoquinoline.

In the present specification, examples of the "nitrogen-containing heterocycle" include the "heterocycles" which contain at least one nitrogen atom as a ring-constituting atom.

In the present specification, examples of the "non-aromatic ring" include the "$C_{3-10}$ cycloalkane", the "$C_{3-10}$ cycloalkene", and the "non-aromatic heterocycle", which are 4- to 10-membered non-aromatic heterocycles.

Preferred examples of the "$C_{3-10}$ cycloalkane" include cyclopropane, cyclobutane, cyclopentane, cyclohexane, cycloheptane, cyclooctane, bicyclo[2.2.1]heptane, bicyclo[2.2.2]octane, bicyclo[3.2.1]octane, and adamantane.

Preferred examples of the "$C_{3-10}$ cycloalkene" include cyclopropene, cyclobutene, cyclopentene, cyclohexene, cycloheptene, and cyclooctene.

Preferred examples of the "4- to 10-membered non-aromatic heterocycle" include 4- to 8-membered monocyclic non-aromatic heterocycles such as tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azetidine, azepane, azepine, azocane, diazocane, and oxepane; and 9- to 10-membered fused bicyclic non-aromatic heterocycles such as dihydrobenzofuran, dihydrobenzimidazole, dihydrobenzoxazole, dihydrobenzothiazole, dihydrobenzisothiazole, tetrahydroisoquinoline, tetrahydroquinoline, 4H-quinolidine, indoline, isoindoline, tetrahydrothieno[2,3-c]pyridine, tetrahydroquinoxaline, tetrahydrophthalazine, tetrahydronaphthyridine, tetrahydroquinazoline, tetrahydrocinnoline, and octahydroisoquinoline.

In the present specification, examples of the "5- to 14-membered heterocycle" include the "aromatic heterocycles", which are "5- to 14-membered aromatic heterocycles", and the "non-aromatic heterocycles", which are 5- to 14-membered non-aromatic heterocycle.

Preferred examples of the "5- to 14-membered aromatic heterocycle" include 5- to 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, and triazine; and 8- to 14-membered fused polycyclic (preferably bi- or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, pyrazolothiazole, naphtho[2,3-b]thiophene, phenoxathiin, indoline, isoindoline, indole, indoline, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, and phenoxazine.

Preferred examples of the "5- to 14-membered non-aromatic heterocycle" include 5- to 8-membered monocyclic non-aromatic heterocycles such as tetrahydrothiophene, tetrahydropyran, pyrroline, pyrrolidine, imidazoline, imidazolidine, oxazoline, oxazolidine, pyrazoline, pyrazolidine, thiazoline, thiazolidine, tetahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, and oxepane; and 9- to 14-membered fused polycyclic (preferably bi- or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolidine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahyclroacridine, tetrahydrophenazine, tetrahydrothioxanthene, and octahydroisoquinoline.

Hereinbelow, the definitions of the respective symbols in the compound (I) will be described in detail.

Ring P is an optionally substituted non-aromatic ring.

The "non-aromatic ring" in the "optionally substituted non-aromatic ring" represented by ring P is preferably a $C_{3-10}$ cycloalkane or a 4- to 8-membered nitrogen-containing non-aromatic heterocycle.

Here, as the $C_{3-10}$ cycloalkane, cyclohexane, bicyclo[2.2.1]heptane, and bicyclo[2.2.2]octane are preferable. Further, in the case where ring P is an optionally substituted bicyclic $C_{4-10}$ cycloalkane, two carbon atoms on the bridgehead position of the bicycle are preferably bonded to a $R^1—(CR^2R^3)_n—$ group and an isoxazoline ring.

Here, as the 4- to 8-membered nitrogen-containing non-aromatic heterocycle, azetidine, pyrrolidine, piperidine, and azepane are preferable, and azetidine, pyrrolidine, and piperidine are more preferred. Preferred specific examples of the 4- to 8-membered nitrogen-containing non-aromatic heterocycle is piperidine.

In the case where ring P is an optionally substituted 4- to 8-membered nitrogen-containing non-aromatic heterocycle, the nitrogen atom constituting the 4- to 8-membered nitrogen-containing non-aromatic heterocycle is preferably bonded to an isoxazoline ring.

The "non-aromatic ring" in the "optionally substituted non-aromatic ring" represented by ring P is more preferably piperidine, cyclohexane, bicyclo[2.2.1]heptane, bicyclo[2.2.2]octane, azetidine, or pyrrolidine, and particularly preferably piperidine or cyclohexane. Preferred specific examples of the "non-aromatic ring" in the "optionally substituted non-aromatic ring" represented by ring P is piperidine.

The "non-aromatic ring" in the "optionally substituted non-aromatic ring" represented by ring P may have 1 to 5, and preferably 1 to 3 substituents at substitutable positions. If there are 2 or more substituents, the respective substituents may be the same as or different from each other. In the case where the non-aromatic ring has a substituent, the carbon atom bonded to a $R^1—(CR^2R^3)_n—$ group is preferably substituted.

Such a substituent is preferably a $C_{1-6}$ alkyl group (preferably methyl, or ethyl), a halogen atom (preferably fluorine), a hydroxyl group, a $C_{1-6}$ alkoxy group (preferably methoxy), a $C_{7-16}$ aralkyl group (preferably benzyl), and more preferably a $C_{1-6}$ alkyl group (preferably methyl or ethyl).

Ring P is preferably a $C_{3-10}$ cycloalkane or a 4- to 8-membered nitrogen-containing non-aromatic heterocycle, each of which optionally substituted.

Ring P is more preferably piperidine, cyclohexane, bicyclo[2.2.1]heptane, bicyclo[2.2.2]octane, azetidine, or pyrrolidine, each of which optionally substituted.

Preferred specific examples of ring P include piperidine, cyclohexane, bicyclo[2.2.1]heptane, bicyclo[2.2.2]octane, azetidine, or pyrrolidine, each of which optionally substituted with 1 to 3 substituents selected from a $C_{1-6}$ alkyl group (preferably methyl or ethyl), a halogen atom (preferably fluorine), a hydroxyl group, a $C_{1-6}$alkoxy group (preferably methoxy), and a $C_{7-16}$ aralkyl group (preferably benzyl).

Preferred specific examples of ring P include piperidine or cyclohexane, each of which optionally substituted with a $C_{1-6}$ alkyl group (preferably methyl or ethyl).

More preferred specific examples of ring P include piperidine optionally substituted with a $C_{1-6}$ alkyl group (preferably methyl or ethyl).

Further, in the case where ring P is piperidine, the nitrogen atom on the piperidine is preferably bonded to an isoxazoline ring and the carbon atom at position 4 is preferably bonded to a $R^1—(CR^2R^3)_n—$ group.

In another embodiment, preferred specific examples of ring P include piperidine substituted with 1 to 3 substituents selected from a $C_{1-6}$ alkyl group (preferably methyl or ethyl), a halogen atom (preferably fluorine), a hydroxyl group, a $C_{1-6}$ alkoxy group (preferably methoxy), and a $C_{7-16}$ aralkyl group (preferably benzyl).

Ring Q is an optionally substituted $C_{6-14}$ aromatic hydrocarbon ring or an optionally substituted 5- to 14-membered heterocycle.

The "$C_{6-14}$ aromatic hydrocarbon ring" in the "optionally substituted $C_{6-14}$ aromatic hydrocarbon ring" represented by ring Q is preferably benzene.

The "$C_{6-14}$ aromatic hydrocarbon ring" in the "optionally substituted $C_{6-14}$ aromatic hydrocarbon ring" represented by ring Q may have 1 to 5 substituents, preferably 1 to 3 substituents, and more preferably 3 substituents at substitutable positions. If there are 2 or more substituents, the respective substituents may be the same as or different from each other.

In another embodiment, the "$C_{6-14}$ aromatic hydrocarbon ring" in the "optionally substituted $C_{6-14}$ aromatic hydrocarbon ring" represented by ring Q may have 1 to 5 substituents, preferably 3 to 4 substituents, and more preferably 4 substituents at substitutable positions. If there are 2 or more substituents, the respective substituents may be the same as or different from each other.

Such a substituent is preferably cyano, a halogen atom (preferably fluorine, chlorine, bromine, or iodine), an optionally substituted hydroxyl group, an optionally substituted $C_{1-6}$ alkyl group (preferably methyl, ethyl or propyl), an optionally substituted $C_{3-10}$ cycloalkyl group (preferably cyclopropyl or cyclobutyl), an optionally substituted $C_{1-6}$ alkoxy group (preferably methoxy, ethoxy, propoxy, or isopropoxy), an optionally substituted non-aromatic heterocyclic group (preferably morpholinyl, tetrahydropyranyl, thiomorpholinyl, pyrrolidinyl, piperidinyl, or azetidinyl), an optionally substituted $C_{6-14}$ aryloxy group (preferably phenoxy), an optionally substituted aromatic heterocyclic group (preferably pyrazolyl, thiazolyl, isoxazolyl, pyrimidinyl, pyridinyl, or thienyl), a $C_{3-10}$ cycloalkyloxy group (preferably cyclopentyloxy), an optionally substituted $C_{6-14}$ aryl group (preferably phenyl), or a $C_{3-10}$ cycloalkenyl group (preferably cyclohexenyl).

Such a substituent is more preferably cyano, a halogen atom (preferably fluorine, chlorine, bromine, or iodine), an optionally substituted hydroxyl group, a $C_{1-6}$ alkyl group (preferably methyl, ethyl, or propyl) optionally substituted with one or more halogen atoms (preferably fluorine), a $C_{3-10}$ cycloalkyl group (preferably cyclopropyl or cyclobutyl) optionally substituted with one or more halogen atoms (preferably fluorine), a $C_{1-6}$ alkoxy group (preferably methoxy, ethoxy, propoxy, or isopropoxy) optionally substituted with one or more halogen atoms (preferably fluorine), an optionally substituted non-aromatic heterocyclic group (preferably morpholinyl, tetrahydropyranyl, thiomorpholinyl, pyrrolidinyl, piperidinyl, or azetidinyl), an optionally substituted $C_{6-14}$ aryloxy group (preferably phenoxy), an optionally substituted aromatic heterocyclic group (preferably pyrazolyl, thiazolyl, isoxazolyl, pyrimidinyl, pyridinyl, or thienyl), a $C_{3-10}$ cycloalkyloxy group (preferably cyclopentyloxy), an optionally substituted $C_{6-14}$ aryl group (preferably phenyl), or a $C_{3-10}$ cycloalkenyl group (preferably cyclohexenyl).

Here, the substituent in the optionally substituted hydroxyl group is preferably a non-aromatic heterocyclic group, and more preferably an oxetanyl.

Here, the "$C_{1-6}$ alkyl group" of the optionally substituted $C_{1-6}$ alkyl group may have 1 to 5 substituents, and preferably 1 to 3 substituents at substitutable positions. If there are 2 or more substituents, the respective substituents may be the same as or different from each other.

Such a substituent is preferably a halogen atom (preferably fluorine), a hydroxyl group, or a $C_{1-6}$ alkoxy group (preferably methoxy).

Here, the "$C_{3-10}$ cycloalkyl group" of the optionally substituted $C_{3-10}$ cycloalkyl group may have 1 to 5 substituents, and preferably 1 to 3 substituents at substitutable positions. If there are 2 or more substituents, the respective substituents may be the same as or different from each other. Such a substituent is preferably a halogen atom (preferably fluorine), a hydroxyl group, a $C_1$ alkyl group (preferably methyl), or a $C_{1-6}$alkoxy group (preferably methoxy).

Here, the "$C_{1-6}$ alkoxy group" of the optionally substituted $C_{1-6}$ alkoxy group may have 1 to 5 substituents, and preferably 1 to 3 substituents. If there are 2 or more substituents, the respective substituents may be the same as or different from each other. Such a substituent is preferably a halogen atom (preferably fluorine), a $C_{1-6}$ alkoxy group (preferably methoxy or ethoxy), a $C_{1-6}$ alkylsulfonyl group (preferably methylsulfonyl), a $C_{6-14}$ aryl group (preferably phenyl), an optionally halogenated $C_{3-10}$ cycloalkyl group (preferably cyclopropyl, 1-fluorocyclopropyl, or 2,2-difluorocyclopropyl), or an optionally substituted aromatic heterocyclic group (preferably 5-methyl-2-phenyl-1,3-oxazol-4-yl).

Here, the "non-aromatic heterocyclic group" of the optionally substituted non-aromatic heterocyclic group may have 1 to 5 substituents, and preferably 1 to 3 substituents at substitutable positions. If there are 2 or more substituents, the respective substituents may be the same as or different from each other. Such a substituent is preferably a halogen atom (preferably fluorine), an optionally halogenated $C_{1-6}$ alkyl group (preferably 2,2,3,3,3-pentafluoropropyl).

Here, "$C_{6-14}$ aryloxy group" of the optionally substituted $C_{6-14}$ aryloxy group may have 1 to 5 substituents, and preferably 1 to 3 substituents at substitutable positions. If there are 2 or more substituents, the respective substituents may be the same as or different from each other. Such a substituent is preferably a halogen atom (preferably fluorine).

Here, the "aromatic heterocyclic group" of the optionally substituted aromatic heterocyclic group may have 1 to 5 substituents, and preferably 1 to 3 substituents at substitutable positions. If there are 2 or more substituents, the respective substituents may be the same as or different from each other. Such a substituent is preferably a halogen atom (preferably fluorine or chlorine), an optionally halogenated $C_{1-6}$ alkyl group (preferably methyl or trifluoromethyl), or a $C_{1-6}$ alkoxy group (preferably methoxy).

Here, the "$C_{6-14}$ aryl group" of the optionally substituted $C_{6-14}$ aryl group may have 1 to 5 substituents, and preferably 1 to 3 substituents at substitutable positions. If there are 2 or more substituents, the respective substituents may be the same as or different from each other. Such a substituent is preferably a halogen atom (preferably fluorine or chlorine), cyano, an optionally substituted $C_{1-6}$ alkyl group (preferably methyl, trifluoromethyl, or methoxymethyl), a $C_{3-10}$ cycloalkyl group (preferably cyclopropyl), an optionally substituted $C_{1-6}$ alkoxy group (preferably methoxy, ethoxy, methoxyethoxy, benzyloxy, cyclopropylmethoxy, or 3,3,3-trifluoropropoxy), a $C_{1-6}$ alkylsulfonyl group (preferably methylsulfonyl), or an optionally substituted amino group (preferably dimethylamino).

The substituent which is had by the "$C_{6-14}$ aromatic hydrocarbon ring" in the "optionally substituted $C_{6-14}$ aromatic hydrocarbon ring" represented by ring Q has is more preferably (a) a halogen atom (preferably fluorine, chlorine, bromine, or iodine), (b) a $C_{3-10}$ cycloalkyl group (preferably cyclopropyl or cyclobutyl) optionally substituted with 1 to 3 halogen atoms, (c) a $C_{1-6}$ alkoxy group (preferably methoxy, ethoxy, propoxy, or isopropoxy) optionally substituted with an optionally halogenated $C_{3-10}$ cycloalkyl group, (d) a 3- to 8-membered monocyclic non-aromatic heterocyclic group (preferably morpholinyl, tetrahydropyranyl, thiomorpholinyl, pyrrolidinyl, piperidinyl, or azetidinyl) optionally substituted with 1 to 3 halogen atoms, or (e) a $C_{6-14}$ aryl group (preferably phenyl) optionally substituted with 1 to 3 halogen atoms.

In another embodiment, the substituent which the "$C_{6-14}$ aromatic hydrocarbon ring" in the "optionally substituted $C_{6-14}$ aromatic hydrocarbon ring" represented by ring Q has is more preferably (a) a halogen atom (preferably fluorine, chlorine, bromine, or iodine);

(b) a $C_{3-10}$ cycloalkyl group (preferably cyclopropyl, cyclobutyl, or cyclopentyl) optionally substituted with 1 to 3 substituents selected from a halogen atom (fluorine, chlorine, bromine, or iodine), an $C_{1-6}$ alkoxy group (preferably methoxy), a hydroxyl group, and an $C_{1-6}$ alkyl group (preferably methyl);

(c) a $C_{1-6}$ alkoxy group (preferably methoxy, ethoxy, propoxy, or isopropoxy) optionally substituted with 1 to 3 substituents selected from a halogen atom (preferably fluorine), an optionally halogenated $C_{3-10}$ cycloalkyl group (preferably cyclopropyl or difluorocyclopropyl), an $C_{1-6}$ alkoxy group (preferably methoxy or ethoxy), a $C_{6-14}$ aryl group (preferably phenyl), a $C_{6-14}$ heterocyclic group (preferably 5-methyl-2-phenyl-1,3-oxazol-4-yl), and an $C_{1-6}$ alkylsulfonyl group (preferably methanesulfonyl);

(d) a 3- to 8-membered monocyclic non-aromatic heterocyclic group (preferably morpholinyl, tetrahydropyranyl, thiomorpholinyl, pyrrolidinyl, piperidinyl, azetidinyl, or tetrahydropyranyl) optionally substituted with 1 to 3 substituents selected from a halogen atom (preferably fluorine), and a halogenated $C_{1-6}$ alkyl group (preferably pentafluoropropyl);

(e) a $C_{6-14}$ aryl group (preferably phenyl) optionally substituted with 1 to 3 substituents selected from a halogen atom (preferably fluorine, chlorine), an $C_{1-6}$ alkyl group (preferably methyl), a halogenated $C_{1-6}$ alkyl group (preferably trifluoromethyl), an optionally substituted amino group (preferably dimethylamino), a cyano group, an $C_{1-6}$ alkylsulfonyl group (preferably methanesulfonyl); an $C_{1-6}$ alkoxy group (preferably methoxy) optionally substituted with a $C_{6-14}$ aryl group (preferably phenyl) or a halogen atom (preferably fluorine), and a $C_{3-6}$ cycloalkyl group (preferably cyclopropyl);

(f) a $C_{1-6}$ alkyl group (preferably methyl, ethyl, propyl, or isopropyl) optionally substituted with 1 to 3 substituents selected from a halogen atom (preferably fluorine), an optionally halogenated $C_{3-10}$ cycloalkyl group, and an $C_{1-6}$ alkoxy group (preferably methoxy);

(g) a $C_{6-14}$ aryloxy group (preferably phenoxy) optionally substituted with 1 to 3 substituents selected from a halogen atom (preferably fluorine);

(h) a heterocyclic group (preferably pyridyl, pyrazolyl, oxazolyl, isoxazolyl, thiazolyl, thiophenyl, or pyrimidinyl) optionally substituted with 1 to 3 substituents selected from an optionally halogenated $C_{1-6}$ alkyl group (preferably methyl, or trifluoromethyl), a halogen atom (preferably fluorine or chlorine); and (i) a $C_{3-10}$ cycloalkyloxy group (preferably cyclopentyl), (j) a $C_{3-10}$ cycloalkenyl group (preferably cyclohex-1-en-1-yl).

The “5- to 14-membered heterocycle” in the “optionally substituted 5- to 14-membered heterocycle” represented by ring Q is preferably thiophene, thiazole, pyrazole, pyridine, indole, pyrazolothiazole, benzofuran, or dihydrobenzofuran.

The “5- to 14-membered heterocycle” in the “optionally substituted 5- to 14-membered heterocycle” represented by ring Q may have 1 to 5 substituents, preferably 1 to 3 substituents, and more preferably 3 substituents at substitutable positions. If there are 2 or more substituents, the respective substituents may be the same as or different from each other.

In another embodiment, the “5- to 14-membered heterocycle” in the “optionally substituted 5- to 14-membered heterocycle” represented by ring Q may have 1 to 5 substituents, preferably 3 to 4 substituents, and more preferably 4 substituents at substitutable positions. If there are 2 or more substituents, the respective substituents may be the same as or different from each other.

Such a substituent is preferably a halogen atom (preferably chlorine or bromine), a $C_{1-6}$ alkyl group (preferably methyl, ethyl, or isopropyl), a $C_{3-10}$ cycloalkyl group (preferably cyclopropyl), an optionally substituted $C_{1-6}$ alkoxy group (preferably methoxy or ethoxy), an aromatic heterocyclic group (preferably pyridinyl), an optionally substituted $C_{6-14}$ aryl group (preferably phenyl), a $C_{7-16}$ aralkyl group (preferably benzyl), or an optionally substituted amino group.

Here, the “$C_{1-6}$ alkoxy group” of the optionally substituted $C_{1-6}$ alkoxy group may have 1 to 5 substituents, and preferably 1 to 3 substituents at substitutable positions. If there are 2 or more substituents, the respective substituents may be the same as or different from each other. Such a substituent is preferably a halogen atom (preferably fluorine).

Here, the “$C_{6-14}$ aryl group” of the optionally substituted $C_{6-14}$ aryl group may have 1 to 5 substituents, and preferably 1 to 3 substituents at substitutable positions. If there are 2 or more substituents, the respective substituents may be the same as or different from each other. Such a substituent is preferably a halogen atom (preferably fluorine).

Here, the “amino group” of the optionally substituted amino group may have 1 or 2 substituents at substitutable positions. In the case where there are 2 substituents, the respective substituents may be the same as or different from each other. Such a substituent is preferably a $C_{6-14}$ aryl group (preferably phenyl).

In another embodiment, the substituent which the “5- to 14-membered heterocycle” in the “optionally substituted 5- to 14-membered heterocycle” represented by ring Q has is more preferably (a) a halogen atom (preferably chlorine or bromine), (b) a $C_{1-6}$ alkyl group (preferably methyl, ethyl, or isopropyl), (c) a $C_{3-10}$ cycloalkyl group (preferably cyclopropyl), (d) a $C_{1-6}$ alkoxy group (preferably methoxy or ethoxy) optionally substituted with 1 to 3 substituents selected from a halogen atom (preferably fluorine), a $C_{6-14}$ aryl group (preferably phenyl), (e) an aromatic heterocyclic group (preferably pyridyl), (f) a $C_{6-14}$ aryl group (preferably phenyl) optionally substituted with 1 to 3 substituents selected from a halogen atom (preferably fluorine), (g) a $C_{7-16}$ aralkyl group (preferably benzyl), (h) an amino group optionally substituted with 1 to 2 substituents selected from an $C_{6-14}$ aryl group (preferably phenyl), (i) a hydroxyl group optionally substituted with a halogenated $C_{6-14}$ aryl group (preferably 4-fluorophenyl).

Ring Q is preferably benzene, thiophene, thiazole, pyrazole, pyridine, indole, pyrazolothiazole, benzofuran, or dihydrobenzofuran, each of which optionally substituted.

Preferred specific examples of ring Q include:

(1) benzene optionally substituted with 1 to 4 (preferably 1 to 3) substituents selected from cyano, a halogen atom (preferably fluorine, chlorine, bromine, or iodine), an optionally substituted hydroxyl group, an optionally substituted $C_{1-6}$ alkyl group (preferably methyl, ethyl, propyl, trifluoromethyl, or pentafluoroethyl), an optionally substituted $C_{3-10}$ cycloalkyl group (preferably cyclopropyl or cyclobutyl), an optionally substituted $C_{1-5}$ alkoxy group (preferably methoxy, ethoxy, propoxy, or isopropoxy), an optionally substituted non-aromatic heterocyclic group (preferably morpholinyl, tetrahydropyranyl, thiomorpholinyl, pyrrolidinyl, piperidinyl, or azetidinyl), an optionally substituted $C_{6-14}$ aryloxy group (preferably phenoxy), an optionally substituted aromatic heterocyclic group (preferably pyrazolyl, thiazolyl, isoxazolyl, pyrimidinyl, pyridinyl, or thienyl), a $C_{3-10}$ cycloalkyloxy group (preferably cyclopentyloxy), an optionally substituted $C_{6-14}$ aryl group (preferably phenyl), and a $C_{3-10}$ cycloalkenyl group (preferably cyclohexenyl), or (2) thiophene, thiazole, pyrazole, pyridine, indole, pyrazolothiazole, benzofuran, or dihydrobenzofuran, each of which optionally substituted with 1 to 3 substituents selected from a halogen atom (preferably chlorine or bromine), a $C_1$ alkyl group (preferably methyl, ethyl, or isopropyl), a $C_{3-10}$ cycloalkyl group (preferably cyclopropyl), an optionally substituted $C_{1-6}$ alkoxy group (preferably methoxy or ethoxy), an aromatic heterocycle (preferably pyridine), an optionally substituted $C_{6-14}$ aryl group (preferably phenyl), a $C_{7-16}$ aralkyl group (preferably benzyl), an optionally substituted amino group.

More preferred specific examples of ring Q include benzene optionally substituted with 1 to 4 (preferably 1 to 3) substituents selected from (a) a halogen atom (preferably fluorine, chlorine, bromine, or iodine), (b) a $C_{3-10}$ cycloalkyl group (preferably cyclopropyl or cyclobutyl) optionally substituted with 1 to 3 halogen atoms, (c) a $C_{1-6}$ alkoxy group (preferably methoxy, ethoxy, propoxy, or isopropoxy) optionally substituted with an optionally halogenated $C_{3-10}$ cycloalkyl group, (d) a 3- to 8-membered monocyclic non-aromatic heterocyclic group (preferably morpholinyl, tetrahydropyranyl, thiomorpholinyl, pyrrolidinyl, piperidinyl, or azetidinyl) optionally substituted with 1 to 3 halogen atoms, and (e) a $C_{6-14}$ aryl group (preferably phenyl) optionally substituted with 1 to 3 halogen atoms.

More preferred specific examples of ring Q include benzene optionally substituted with 3 or 4 substituents selected from (a) a halogen atom (preferably fluorine or chlorine), (b) a $C_{3-10}$ cycloalkyl group (preferably cyclopropyl), (c) a $C_{1-6}$ alkoxy group (preferably methoxy or ethoxy), and (d) a $C_{6-14}$ aryl group (preferably phenyl) optionally substituted with 1 to 3 halogen atoms (preferably fluorine).

$R^1$ is $CO_2Ra$ (in which Ra is a hydrogen atom or a $C_{1-6}$ alkyl group). Here, Ra is preferably a hydrogen atom, methyl, or ethyl.

$R^1$ is preferably a $CO_2H$, $CO_2CH_3$, or $CO_2CH_2CH_3$.

$R^1$ is more preferably a $CO_2H$.

$R^2$ and $R^3$ are each independently a hydrogen atom, a halogen atom, or a $C_{1-6}$ alkyl group.

$R^2$ and $R^3$ are preferably a hydrogen atom.

$R^4$ and $R^5$ are each independently a hydrogen atom, a halogen atom, a $C_{1-6}$ alkyl group, or a $C_{3-10}$ cycloalkyl group. Here, the $C_{1-6}$ alkyl group is preferably methyl.

$R^4$ is preferably a hydrogen atom or methyl.

$R^5$ is preferably a hydrogen atom.

$R^6$, $R^7$, $R^8$ and $R^9$ are each independently a hydrogen atom, a halogen atom, or a $C_{1-6}$ alkyl group. Here, $C_{1-6}$ alkyl group is preferably methyl.

$R^6$ is preferably a hydrogen atom or methyl.

$R^7$ is preferably a hydrogen atom or methyl.

$R^8$ is preferably a hydrogen atom.

$R^9$ is preferably a hydrogen atom.

$R^{10}$ and $R^{11}$ are each independently a hydrogen atom, a halogen atom, or a $C_{1-6}$ alkyl group.

$R^{10}$ and $R^{11}$ are preferably a hydrogen atom.

n is an integer of 0 to 2.

n is preferably 0.

Preferred examples of the compound (I) include the following compounds.

[Compound A]

The compound (I), in which ring P is piperidine, cyclohexane, bicyclo[2.2.1]heptane, bicyclo[2.2.2]octane, azetidine or pyrrolidine, each of which optionally substituted with 1 to 3 substituents selected from a $C_{1-6}$ alkyl group (preferably methyl or ethyl), a halogen atom (preferably fluorine), a hydroxyl group, a $C_{1-6}$ alkoxy group (preferably methoxy), and a $C_{7-16}$ aralkyl group (preferably benzyl), ring Q is (1) benzene optionally substituted with 1 to 4 (preferably 1 to 3) substituents selected from cyano, a halogen atom (preferably fluorine, chlorine, bromine, or iodine), an optionally substituted hydroxyl group, an optionally substituted $C_{1-6}$ alkyl group (preferably methyl, ethyl, propyl, trifluoromethyl, or pentafluoroethyl), an optionally substituted $C_{3-10}$ cycloalkyl group (preferably cyclopropyl or cyclobutyl), an optionally substituted $C_{1-6}$ alkoxy group (preferably methoxy, ethoxy, propoxy, or isopropoxy), an optionally substituted non-aromatic heterocyclic group (preferably morpholinyl, tetrahydropyranyl, thiomorpholinyl, pyrrolidinyl, piperidinyl, or azetidinyl), an optionally substituted $C_{6-14}$ aryloxy group (preferably phenoxy), an optionally substituted aromatic heterocyclic group (preferably pyrazolyl, thiazolyl, isoxazolyl, pyrimidinyl, pyridinyl, or thienyl), a $C_{3-10}$ cycloalkyloxy group (preferably cyclopentyloxy), an optionally substituted $C_{6-14}$ aryl group (preferably phenyl), and a $C_{3-10}$ cycloalkenyl group (preferably cyclohexenyl), or (2) thiophene, thiazole, pyrazole, pyridine, indole, pyrazolothiazole, benzofuran, or dihydrobenzofuran, each of which optionally substituted with 1 to 3 substituents selected from a halogen atom (preferably chlorine or bromine), a $C_{1-6}$ alkyl group (preferably methyl, ethyl, or isopropyl), a $C_{3-10}$ cycloalkyl group (preferably cyclopropyl), an optionally substituted $C_{1-6}$ alkoxy group (preferably methoxy or ethoxy), an aromatic heterocyclic group (preferably pyridyl), an optionally substituted $C_{6-14}$ aryl group (preferably phenyl), a $C_{7-16}$ aralkyl group (preferably benzyl), an optionally substituted amino group, $R^1$ is $CO_2H$, $CO_2CH_3$ or $CO_2CH_2CH_3$, $R^4$ is a hydrogen atom or methyl, $R^5$ is a hydrogen atom, $R^6$ is a hydrogen atom or methyl, $R^7$ is a hydrogen atom or methyl, $R^8$ is a hydrogen atom, $R^9$ is a hydrogen atom, $R^{10}$ and $R^{11}$ are hydrogen atoms, and n is 0.

[Compound B]

The compound (I), in which ring P is piperidine or cyclohexane, each of which optionally substituted with a $C_{1-6}$ alkyl group (preferably methyl or ethyl), ring Q is benzene optionally substituted with 1 to 4 (preferably 1 to 3) substituents selected from (a) a halogen atom (preferably fluorine, chlorine, bromine, or iodine), (b) a $C_{3-10}$ cycloalkyl group (preferably cyclopropyl or cyclobutyl) optionally substituted with 1 to 3 halogen atoms, (c) a $C_{1-6}$ alkoxy group (preferably methoxy, ethoxy, propoxy, isopropoxy, or cyclopropylmethoxy) optionally substituted with an optionally halogenated $C_{3-10}$ cycloalkyl group, (d) a 3- to 8-membered monocyclic non-aromatic heterocyclic group (preferably morpholinyl, tetrahydropyranyl, thiomorpholinyl, pyrrolidinyl, piperidinyl, or azetidinyl) optionally substituted with 1 to 3 halogen atoms, and (e) a $C_{6-14}$ aryl group (preferably phenyl) optionally substituted with 1 to 3 halogen atoms, $R^1$ is $CO_2H$, $R^4$, $R^5$, $R^6$, $R^7$, $R^8$, $R^9$, $R^{10}$ and $R^{11}$ are hydrogen atoms, and n is 0.

[Compound C]

The compound (I), in which ring P is pyrrolidine, piperidine, cyclohexane or bicyclo[2.2.2]octane, each of which optionally substituted with a $C_{1-6}$ alkyl group (preferably methyl or ethyl) optionally substituted with an $C_{6-14}$ aryl group (preferably phenyl), an $C_{1-6}$ alkoxy group (preferably methoxy), or a hydroxyl group, ring Q is benzene optionally substituted with 1 to 4 substituents selected from the following (a) to (j):

(a) a halogen atom (preferably fluorine, chlorine, bromine, or iodine);

(b) a $C_{3-10}$ cycloalkyl group (preferably cyclopropyl, cyclobutyl, or cyclopentyl) optionally substituted with 1 to 3 substituents selected from a halogen atom (fluorine, chlorine, bromine, or iodine), an $C_{1-6}$ alkoxy group (preferably methoxy), a hydroxyl group, and an $C_{1-6}$ alkyl group (preferably methyl);

(c) a $C_{1-6}$ alkoxy group (preferably methoxy, ethoxy, propoxy, or isopropoxy) optionally substituted with 1 to 3 substituents selected from a halogen atom (preferably fluorine), an optionally halogenated $C_{3-10}$ cycloalkyl group (preferably cyclopropyl or difluorocyclopropyl), an $C_{1-6}$ alkoxy group (preferably methoxy or ethoxy), a $C_{6-14}$ aryl group (preferably phenyl), a 5- to 14-membered aromatic heterocyclic group optionally substituted with 1 to 3 substituents selected from a $C_{1-6}$ alkyl group and a $C_{6-14}$ aryl group (preferably 5-methyl-2-phenyl-1,3-oxazol-4-yl), and an $C_{1-6}$ alkylsulfonyl group (preferably methanesulfonyl);

(d) a 3- to 8-membered monocycle non-aromatic heterocyclic group (preferably morpholinyl, tetrahydropyranyl, thiomorpholinyl, pyrrolidinyl, piperidinyl, azetidinyl, or tetrahydropyranyl) optionally substituted with 1 to 3 substituents selected from a halogen atom (preferably fluorine), and a halogenated $C_{1-6}$ alkyl group (preferably pentafluoropropyl);

(e) a $C_{6-14}$ aryl group (preferably phenyl) optionally substituted with 1 to 3 substituents selected from a halogen atom (preferably fluorine, chlorine), an $C_{1-6}$ alkyl group (preferably methyl), a halogenated $C_{1-6}$ alkyl group (preferably trifluoromethyl), an amino group optionally substituted with 1 or 2 $C_{1-6}$ alkyl group (preferably dimethylamino), a cyano group, an $C_{1-6}$ alkylsulfonyl group (preferably methanesulfonyl); an $C_{1-6}$ alkoxy group (preferably methoxy) optionally substituted with a $C_{6-14}$ aryl group (preferably phenyl) or a halogen atom (preferably fluorine), and a $C_{3-6}$ cycloalkyl group (preferably cyclopropyl);

(f) a $C_{1-6}$ alkyl group (preferably methyl, ethyl, propyl, or isopropyl) optionally substituted with 1 to 3 substituents selected from a halogen atom (preferably fluorine), an optionally halogenated $C_{3-10}$ cycloalkyl group, and an $C_{1-6}$ alkoxy group (preferably methoxy);

(g) a $C_{6-14}$ aryloxy group (preferably phenoxy) optionally substituted with 1 to 3 substituents selected from a halogen atom (preferably fluorine);

(h) a 5- to 6-membered monocycle aromatic heterocyclic group (preferably pyridyl, pyrazolyl, oxazolyl, isoxazolyl, thiazolyl, thiophenyl, or pyrimidinyl) optionally substituted with 1 to 3 substituents selected from an optionally halogenated $C_{1-6}$ alkyl group (preferably methyl, or trifluoromethyl), a halogen atom (preferably fluorine or chlorine); and (i) a $C_{3-10}$ cycloalkyloxy group (preferably cyclopentyl), (j) a $C_{3-10}$ cycloalkenyl group (preferably cyclohex-1-en-1-yl), or 5- to 14-membered heterocycle optionally substituted with 1 to 4 substituents selected from the following (k) to (s):

(k) a halogen atom (preferably chlorine or bromine), (l) a $C_{1-6}$ alkyl group (preferably methyl, ethyl, or isopropyl), (m) a $C_{3-10}$ cycloalkyl group (preferably cyclopropyl), (n) a $C_{1-6}$ alkoxy group (preferably methoxy or ethoxy) optionally substituted with 1 to 3 substituents selected from a halogen atom (preferably fluorine), a $C_{6-14}$ aryl group (preferably phenyl), (o) a 5- to 6-membered monocyclic aromatic heterocyclic group (preferably pyridyl), (p) a $C_{6-14}$ aryl group (preferably phenyl) optionally substituted with 1 to 3 substituents selected from a halogen atom (preferably fluorine), (q) a $C_{7-16}$ aralkyl group (preferably benzyl), (r) an amino group optionally substituted with 1 to 2 substituents selected from an $C_{6-14}$ aryl group (preferably phenyl), (s) a hydroxyl group optionally substituted with a halogenated $C_{6-14}$ aryl group (preferably 4-fluorophenyl), $R^1$ is $CO_2H$, $CO_2CH_3$, or $CO_2CH_2CH_3$, $R^4$, $R^5$, $R^6$, $R^7$, $R^8$, $R^9$, $R^{10}$ and $R^{11}$ are each independently a hydrogen atom or a methyl group, and n is 0 to 2

[Compound D]

The compound (I), in which ring P is piperidine optionally substituted with a $C_{1-6}$ alkyl group (preferably methyl or ethyl), ring Q is benzene optionally substituted with 3 or 4 substituents selected from (a) a halogen atom (preferably fluorine or chlorine), (b) a $C_{3-10}$ cycloalkyl group (preferably cyclopropyl), (c) a $C_{1-6}$ alkoxy group (preferably methoxy or ethoxy), and (d) a $C_{6-14}$ aryl group (preferably phenyl) optionally substituted with 1 to 3 halogen atoms (preferably fluorine), $R^1$ is $CO_2H$, $R^4$, $R^5$, $R^6$, $R^7$, $R^8$, $R^9$, $R^{10}$ and $R^{11}$ are hydrogen atoms, and n is 0.

[Compound E]

1-(2-((2-Chloro-6-cyclopropyl-4'-fluoro-3-methoxybiphenyl-4-yl)methyl)-5-oxa-2,6-diazaspiro[3.4]octa-6-en-7-yl)-4-methylpiperidine-4-carboxylic acid or a salt thereof.

1-(2-((6-Cyclopropyl-2,4'-difluoro-3-methoxybiphenyl-4-yl)methyl)-5-oxa-2,6-diazaspiro[3. 4]octa-6-en-7-yl)-4-methylpiperidine-4-carboxylic acid or a salt thereof.

1-(2-((2,6-Diethoxy-4'-fluorobiphenyl-4-yl)methyl)-5-oxa-2,6-diazaspiro[3.4]octa-6-en-7-yl)-4-methylpiperidine-4-carboxylic acid or a salt thereof.

As a salt of the compound (I), a pharmacologically acceptable salt is preferable. Examples of such a salt include salts with inorganic bases, salts with organic bases, salts with inorganic acids, salts with organic acids, and salts with basic or acidic amino acids.

Preferred examples of the salts with inorganic bases include alkali metal salts such as a sodium salt and a potassium salt; alkaline earth metal salts such as a calcium salt and a magnesium salt; aluminum salts; and ammonium salts.

Preferred examples of the salts with organic bases include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine, and the like.

Preferred examples of the salts with inorganic acids include salts with hydrochloric acid, hydrobromic acid, nitric acid, sulfuric acid, phosphoric acid, and the like.

Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, and the like.

Preferred examples of the salts with basic amino acids include salts with arginine, lysine, ornithine, and the like.

Preferred examples of the salts with acidic amino acids include salts with aspartic acid, glutamic acid, and the like.

The compound (I) may also be used as a prodrug.

A prodrug of the compound (I) is a compound which is converted to the compound (I) with a reaction due to an enzyme, an gastric acid, or the like under the physiological condition in the living body, that is, a compound which is converted to the compound (I) by enzymatic oxidation, reduction, hydrolysis, or the like; or a compound which is converted to the compound (I) by hydrolysis or the like due to gastric acid or the like.

Examples of the prodrug of the compound (I) include:

a compound obtained by subjecting an amino group in the compound (I) to acylation, alkylation, or phosphorylation (e.g., a compound obtained by subjecting an amino group in the compound (I) to eicosanoylation, alanylation, pentylaminocarbonylation, (5-methyl-2-oxo-1,3-dioxolen-4-yl) methoxycarbonylation, tetrahydrofuranylation, pyrrolidylmethylation, pivaloyloxymethylation, or tert-butylation);

a compound obtained by subjecting a hydroxyl group in the compound (I) to acylation, alkylation, phosphorylation, or boration (e.g., a compound obtained by subjecting a hydroxyl group in the compound (I) to acetylation, palmitoylation, propanoylation, pivaloylation, succinylation, fumarylation, alanylation, or dimethylaminomethylcarbonylation); and a compound obtained by subjecting a carboxyl group in the compound (I) to esterification or amidation (e.g., a compound obtained by subjecting a carboxyl group in the compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methyl amidation). These compounds can be prepared from the compound (I) according to a method known per se.

Furthermore, a prodrug for compound (I) may also be one which is converted to the compound (I) under a physiological condition, such as those described in "Development of Pharmaceuticals", Vol. 7, Design of Molecules, pp. 163-198, Published by Hirokawa-Shoten Ltd., 1990.

In the present specification, the prodrug may form a salt, and examples of the salt include those exemplified as a salt of the compound of the formula (I) as described above.

Furthermore, the compound (I) may be labeled with an isotope (e.g., $^{3}H$, $^{13}C$, $^{14}C$, $^{18}F$, $^{35}S$, and $^{125}I$) and the like.

Incidentally, the compound (I) may be a hydrate or a non-hydrate, and may be a non-solvate or a solvate.

In addition, a deuterium-converted compound in which $^{1}H$ has been converted to $^{2}H$ (D) is also encompassed in the compound (I).

An isotope-labeled or substituted compound (I) can be used as, for example, a tracer used in Positron Emission Tomography (PET) (PET tracer), and is useful in the field of medical diagnosis.

Furthermore, the compound (I) may be a pharmaceutically acceptable cocrystal or cocrystal salt. Here, the cocrystal or cocrystal salt means a crystalline substance constituted by two or more kinds of special solids each having different physical properties (e.g., a structure, a melting point, a melting heat, hygroscopicity, solubility, and stability) at room temperature. The cocrystal or cocrystal salt can be prepared by a cocrystallization method known per se.

The compound (I) or a prodrug thereof (which may be sometimes simply referred to as the compound of the present invention) shows low toxicity and can be used as a prophylactic or therapeutic agent for various diseases as described later for mammals (e.g., humans, mice, rats, rabbits, dogs, cats, bovines, horses, pigs, and monkeys) as they are or by admixing with a pharmacologically acceptable carrier and the like to give a pharmaceutical composition.

Here, various organic or inorganic carriers commonly used as materials for preparations are used as a pharmacologically acceptable carrier, which are blended as an excipient, a lubricant, a binder, and a disintegrant for solid preparations; a solvent, a solubilizing agent, a suspending agent, an isotonicity agent, a buffer, and a soothing agent for liquid preparations, and the like. Where necessary, an additive for pharmaceutical preparations such as a preservative, an antioxidant, a colorant, and a sweetening agent can also be used.

Preferred examples of the excipient include lactose, sucrose, D-mannitol, D-sorbitol, starch, pregelatinized starch, dextrin, microcrystalline cellulose, low-substituted hydroxypropyl cellulose, sodium carboxymethylcellulose, gum arabic, pullulan, light anhydrous silicic acid, synthetic aluminum silicate, and magnesium aluminate metasilicate.

Preferred examples of the lubricant include magnesium stearate, calcium stearate, talc, and colloidal silica Preferred examples of the binder include pregelatinized starch, saccharose, gelatin, gum arabic, methylcellulose, carboxymethylcellulose, sodium carboxymethylcellulose, microcrystalline cellulose, sucrose, D-mannitol, trehalose, dextrin, pullulan, hydroxypropyl cellulose, hydroxypropyl methylcellulose, and polyvinylpyrrolidone.

Preferred examples of the disintegrant include lactose, sucrose, starch, carboxymethylcellulose, calcium carboxymethylcellulose, croscarmellose sodium, sodium carboxymethyl starch, light anhydrous silicic acid, and low-substituted hydroxypropyl cellulose.

Preferred examples of the solvent include water for injection, physiological saline, Ringer's solution, alcohol, propylene glycol, polyethylene glycol, sesame oil, corn oil, olive oil, and cottonseed oil.

Preferred examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, and sodium acetate.

Preferred examples of the suspending agent include surfactants such as stearyltriethanolamine, sodium lauryl sulfate, laurylaminopropionic acid, lecithin, benzalkonium chloride, benzethonium chloride, and glyceryl monostearate; hydrophilic polymers such as polyvinyl alcohol, polyvinylpyrrolidone, sodium carboxymethylcellulose, methylcellulose, hydroxymethyl cellulose, hydroxyethyl cellulose, and hydroxypropyl cellulose; polysorbates; and polyoxyethylene hydrogenated castor oil.

Preferred examples of the isotonicity agent include sodium chloride, glycerin, D-mannitol, D-sorbitol, and glucose.

Preferred examples of the buffer include buffers such as phosphates, acetates, carbonate, and citrates.

Preferred examples of the soothing agent include benzyl alcohol.

Preferred examples of the preservative include paraoxybenzoate, chlorobutanol, benzyl alcohol, phenethyl alcohol, dehydroacetic acid, and sorbic acid.

Preferred examples of the antioxidant include sulfites and ascorbates.

Preferred examples of the colorant include water-soluble edible tar pigments (e.g., foodcolors such as Food Color Red Nos. 2 and 3, Food Color Yellow Nos. 4 and 5, and Food Color Blue Nos. 1 and 2), water insoluble lake pigments (e.g., aluminum salts of the aforementioned water-soluble edible tar pigment), and natural pigments (e.g., β-carotene, chlorophyll, and red iron oxide).

Preferred examples of the sweetening agent include saccharin sodium, dipotassium glycyrrhizinate, aspartame, and stevia.

A pharmaceutical agent containing the compound of the present invention can be safely administered using the compound of the present invention solely or by mixing the compound of the present invention with a pharmacologically acceptable carrier, in the form of, for example, a tablet (including a sugar-coated tablet, a film-coated tablet, a sublingual tablet, an orally disintegrating tablet, and a buccal tablet), a pill, powder, a granule, a capsule (including a soft capsule and a microcapsule), a troche, a syrup, a liquid, an emulsion, a suspension, a release control preparation (e.g., immediate-release preparation, a sustained-release preparation, and a sustained-release microcapsule), an aerosol, a film (e.g., an orally disintegrating film and an oral mucosa-adhesive film), an injection (e.g., a subcutaneous injection, an intravenous injection, an intramuscular injection, and an intraperitoneal injection), a drip infusion, a transdermal absorption preparation, an ointment, a lotion, an adhesive preparation, a suppository (e.g., a rectal suppository and a vaginal suppository), a pellet, a nasal preparation, a pulmonary preparation (inhalation), and an eye drop to a mammal, orally or parenterally (e.g., intravenous, intramuscular, subcutaneous, intraorgan, intranasal, intradermal, instillation, intracerebral, intrarectal, intravaginal, intraperitoneal, and intratumor administrations, administration to the vicinity of tumor, and direct administration to the lesion).

These agents may be release control agents such as an immediate-release preparation and a sustained-release preparation (e.g., a sustained-release microcapsule).

A pharmaceutical composition can be prepared by a method commonly used in the technical field of preparations, for example, the method described in Japanese Pharmacopoeia, and the like.

Moreover, while the content of the compound of the present invention in the pharmaceutical composition varies depending on a dosage form, a dose of the compound of the present invention, or the like, it is, for example, about 0.1 to 100% by weight.

For the preparation of an oral agent, coating may be carried out, if necessary, for the purpose of masking of taste, enteric property, or durability.

Examples of the coating base used for coating include a sugar coating base, an aqueous film coating base, an enteric film coating base, and a sustained-release film coating base.

As the sugar coating base, sucrose is used, and further, one or more kinds selected from talc, precipitated calcium carbonate, gelatin, gum arabic, pullulan, camauba wax, and the like may be used in combination.

Examples of the aqueous film coating base include cellulose polymers such as hydroxypropyl cellulose, hydroxypropyl methyl cellulose, hydroxyethyl cellulose, and methylhydroxyethyl cellulose; synthetic polymers such as polyvinylacetal diethylaminoacetate, aminoalkyl methacrylate copolymer E [Eudragit E (trade name)], and polyvinylpyrrolidone; and polysaccharides such as pullulan.

Examples of the enteric film coating base include cellulose polymers such as hydroxypropyl methyl cellulose phthalate, hydroxypropyl methyl cellulose acetate succinate, a carboxymethylethyl cellulose, and cellulose acetate phthalate; acrylic polymers such as methacrylic acid copolymer L [Eudragit L (trade name)], methacrylic acid copolymer LD [Eudragit L-30D55 (trade name)], and methacrylic acid copolymer S [Eudragit S (trade name)]; and naturally occurring substances such as shellac.

Examples of the sustained-release film coating base include cellulose polymers such as ethyl cellulose; and acrylic polymers such as aminoalkyl methacrylate copolymer RS [Eudragit RS (trade name)] and ethyl acrylate-methyl methacrylate copolymer suspension [Eudragit NE (trade name)].

The above-described coating bases may be used after mixing with two or more kinds thereof at appropriate ratios. For coating, for example, a light shielding agent such as titanium oxide and iron sesquioxide may also be used.

The compound of the present invention shows low toxicity (e.g., cardiotoxicity (e.g., human ether-a-go-go related gene(hERG) inhibitory activity), acute toxicity, chronic toxicity, genetic toxicity, reproductive toxicity, pulmonary toxicity, and carcinogenicity) and a few side effects. Therefore, it can be used as a prophylactic, therapeutic or diagnostic agent for various diseases in a mammal.

The compound of the present invention has an excellent SSTR5 antagonistic action.

The compound of the present invention can be used as a prophylactic or therapeutic agent for diabetes mellitus (e.g., type 1 diabetes mellitus, type 2 diabetes mellitus, gestational diabetes mellitus, and obese diabetes mellitus), obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, and central obesity), hyperphagia, hyperlipemia/dyslipidemia (e.g., hypertriglyceridemia, hypercholesterolemia, hyper-LDL-cholesterolemia, hypo-HDL-cholesterolemia, and postprandial hyperlipemia), hypertension, cardiovascular diseases (e.g., heart failure, arrhythmias, ischemic heart disease, valvular heart disease, and arteriosclerosis), diabetic complications [for example, neuropathy disorder, nephropathy, retinopathy, diabetic cardiomyopathy, cataract, macroangiopathy, osteopenia, diabetic hyperosmolar coma, infections (e.g., respiratory infections, urinary tract infections, gastrointestinal infections, skin soft tissue infections, and lower limb infections), gangrene, xerostomia, hearing impairment, cerebrovascular disease, and peripheral blood circulation disorder], metabolic syndrome (disease conditions including at least three selected from hypertriglyceride (TG)-emia, hypo-HDL cholesterol(HDL-C)emia, hypertension, abdominal obesity, and impaired glucose tolerance), sarcopenia, affective disorder, sexual dysfunction, depression, anxiety, neurosis, arteriosclerosis, arthritis of the knee, or the like.

For criteria of diabetes mellitus, a "Report of the Committee on the Classification and Diagnostic Criteria of Diabetes Mellitus" has been reported from The Japan Diabetes Society in 2010.

According to this report, diabetes mellitus is a condition showing any of a fasting blood glucose level (glucose concentration of intravenous plasma) of 126 mg/dl or more, a 75 g oral glucose tolerance test (75 g OGTT) 2-h value (glucose concentration of intravenous plasma) of 200 mg/dl or more, a non-fasting blood glucose level (glucose concentration of intravenous plasma) of 200 mg/dl or more, an HbA1c (International Standard Value) of 6.5% or more. Here, the HbA1c (International Standard Value) (%) is expressed in a value obtained by adding 0.4% to an HbA1c (JDS value) (%) denoted as a JDS (Japan Diabetes Society) value in the related art corresponding to an NGSP (National Glycohemoglobin Standardization Program). Further, a condition not falling under the above-mentioned diabetes mellitus and different from "a condition showing a fasting blood glucose level (glucose concentration of intravenous plasma) of less than 110 mg/dl or a 75 g oral glucose tolerance test (75 g OGTT) 2-h value (glucose concentration of intravenous plasma) of less than 140 mg/dl" (normal type) is called a "borderline type".

In addition, for criteria of diabetes mellitus, a new criteria have been reported from World Health Organization (WHO) in 2006.

According to these reports, diabetes mellitus is a condition showing a fasting blood glucose level (glucose concentration of intravenous plasma) of 126 mg/dl or more, or a 75 g oral glucose tolerance test 2 h level (glucose concentration of intravenous plasma) of 200 mg/dl or more.

According to the reports as described above, impaired glucose tolerance (IGT) is a condition showing a fasting blood glucose level (glucose concentration of intravenous plasma) of less than 126 mg/dl, and a 75 g oral glucose tolerance test 2 h level (glucose concentration of intravenous plasma) of 140 mg/dl or more and less than 200 mg/dl. Further, According to the report of WHO, a condition showing a fasting blood glucose level (glucose concentration of intravenous plasma) of 110 mg/dl or more and less than 126 mg/dl, and if there is any measured value, showing a 75 g oral glucose tolerance test 2 h level (glucose concentration of intravenous plasma) of less than 140 mg/dl is called IFG (Impaired Fasting Glucose).

The compound of the present invention can also be used as a prophylactic or therapeutic agent for diabetes mellitus, borderline type, abnormal glucose tolerance, or impaired fasting glucose (IFG), as determined according to the above-mentioned diagnostic criteria. Further, the compound of the present invention can prevent progress of borderline type, abnormal glucose tolerance, or impaired fasting glucose (IFG) into diabetes mellitus.

The compound of the present invention can also be used as a prophylactic or therapeutic agent for metabolic syndrome. Since patients with metabolic syndrome have an extreme high incidence of cardiovascular diseases as compared to patients with single lifestyle-related disease, the prevention or treatment of metabolic syndrome is highly important to prevent cardiovascular diseases.

Criteria of metabolic syndrome have been announced by WHO in 1999 and by NCEP in 2001. According to the criteria of WHO, patients with at least two of abdominal obesity, dyslipidemia (high TG or low HDL) and hypertension in addition to hyperinsulinmia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criteria of Adult Treatment Panel III of National Cholesterol Education Program, that is an indicator for managing ischemic heart diseases in America, patients with at least three of abdominal obesity, high triglycerides, low HDL cholesterol, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compounds of the present invention can be used as a prophylactic or therapeutic agent for osteoporosis, cachexia (e.g., cancerous cachexia, tuberculous cachexia, diabetic cachexia, hemopathic cachexia, endocrinopathic cachexia, infectious cachexia, or acquired immunodeficiency syndrome-induced cachexia), fatty liver, polycystic ovary syndrome, renal diseases (e.g., diabetic nephropathy, glomerulonephritis, glomerulosclerosis, nephrotic syndrome, hypertensive nephrosclerosis, and end-stage renal diseases), muscular dystrophy, myocardial infarction, angina pectoris, cerebrovascular disorder (e.g., cerebral infarction and cerebral stroke), Alzheimer's disease, Parkinson's disease, dimential, insulin resistant syndrome, syndrome X, hyperinsulinmia, hyperinsulinmia-induced sensory disorder, acute/chronic diarrhea, inflammatory diseases (e.g., chronic rheumatoid arthritis, spondylitis deformans, arthritis deformans, lumbago, gout, postoperative or traumatic inflammation, swelling, neuralgia, pharyngitis, cystitis, hepatitis (including non-alcoholic fatty hepatitis), pneumonia, pancreatitis, enteritis, inflammatory bowel disease (including inflammatory colonic disease), ulcerative colitis, gastric mucosal colitis (including gastric mucosal colitis induced by aspirin)), intestinal mucosa colitis, malabsorption, testis dysfunction, abdominal obesity syndrome, or sarcopenia.

In addition, the compounds of the present invention can also be used as a prophylactic or therapeutic agent for various cancers (among these, breast cancer (e.g., invasive ductal carcinoma, non-invasive ductal carcinoma, and inflammatory breast cancer), prostate cancer (e.g., hormone-dependent prostate cancer and hormone-independent prostate cancer), pancreatic cancer (e.g., pancreatic ductal cancer), gastric cancer (e.g., papillary adenocarcinoma, mucinous carcinoma, and adenosquamous carcinoma), lung cancer (e.g., non-small cell lung cancer, small cell lung cancer, and malignant mesothelioma), colon cancer (e.g., gastrointestinal stromal tumor), rectal cancer (e.g., gastrointestinal stromal tumor), bowel cancer (e.g., familial bowel cancer, hereditary non-polyposis bowel cancer, and gastrointestinal stromal tumor), small intestine cancer (e.g., non-Hodgkin's lymphoma and gastrointestinal stromal tumor), esophageal cancer, duodenal cancer, tongue cancer, throat cancer (e.g., nasopharyngeal cancer; oropharyngeal cancer, and hypopharyngeal cancer), salivary gland cancer, brain tumor (e.g., pineal tumor stellate cells, hairy cell astrocytoma, diffuse astrocytoma, and anaplastic astrocytoma), schwannoma, liver cancer (e.g., primary liver cancer and extrahepatic bile duct cancer), renal cancer (e.g., renal cell cancer, and ureter-renal pelvis transitional cell carcinoma), bile duct cancer, endometrial cancer, cervical cancer, ovarian cancer (e.g., epithelial ovarian cancer, extragonadal germ cell tumor, ovarian germ cell tumor, and ovarian low-grade tumor), bladder cancer, urethral cancer, skin cancer (e.g., intraocular (eye) melanoma and Merkel cell carcinoma), hemangiorna, malignant lymphoma, malignant melanoma, thyroid cancer (e.g., medullary thyroid cancer), parathyroid cancer, nasal cancer, nasal sinus cancer, bone tumors (e.g., osteosarcoma, Ewing's tumor, uterine sarcoma, and soft tissue sarcoma), angiofibroma, retinal sarcoma, penile cancer, testicular tumor, pediatric solid cancers (e.g., Wilms' tumor and childhood kidney tumor), malignant skin cancer, AIDS-induced malignant skin cancer, maxillary sinus tumor, fibrous histiocytoma, leiomyosarcoma, rhabdomyosarcoma, leukemia (e.g., acute myeloid leukemia and acute lymphoblastic leukemia), The compound of the present invention can also be used in secondary prevention and suppression of progression of the above-mentioned various diseases (e.g., cardiovascular event such as myocardial infarction).

The dose of the compound of the present invention varies depending on an administration subject, an administration route, a target disease, a symptom, or the like, but the dose of the compound of the present invention for oral administration to an adult patient with obesity is generally about 0.01 to 100 mg/kg body weight, preferably 0.05 to 30 mg/kg body weight, and more preferably about 0.5 to 10 mg/kg, per dose. This amount is preferably administered 1 to 3 times per day.

The compound of the present invention may be used in combination with drugs such as a therapeutic agent for diabetes mellitus, a therapeutic agent for diabetic complications, a therapeutic agent for hyperlipemia, an antihypertensive agent, an antiobestic agent, a diuretic, and an antithrombotic agent (hereinafter sometimes to be abbreviated as a "combination drug") for the purpose of increasing the action of the compound and reducing the administration dose of the compound. Here, the timing of administration of the compound of the present invention and a combination drug is not limited, and these combination drugs may be low-molecular-weight compounds or high-molecular-weight proteins, polypeptides, antibodies, vaccines, or the like. These may be simultaneously administered to an administration subject or administered in a staggered manner. Further, the compound of the present invention and the combination drug may be administered as two kinds of preparations containing the active ingredients, respectively, or as a single preparation containing both active ingredients.

The administration dose of the combination drug can be appropriately selected based on the dose clinically employed. The blending proportion of the compound of the present invention and the combination drug can be appropriately selected depending on an administration subject, an administration route, a target disease, a condition, a combination, or the like. For example, in the case where the administration subject is human, the combination drug may be used in an amount of 0.01 to 100 parts by weight with respect to 1 part by weight of the compound of the present invention.

Examples of the therapeutic agents for diabetes mellitus include insulin preparations (e.g., animal insulin preparations extracted from pancreas of bovine or swine; human insulin preparations genetically synthesized using *Escherichia coli* or a yeast; insulin zinc; protamine insulin zinc; fragments or derivatives of insulin (e.g., INS-1), or oral insulin preparations), insulin resistance improving agents (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, or the compounds described in WO 2007/013694, WO 2007/018314, WO 2008/093639, or WO 2008/099794), α-glucosidase inhibitors (e.g., voglibose, acarbose, miglitol, and emiglitate), biguanides (e.g., metformin, and buformin or a salt thereof (e.g., hydrochloride, fumarate, and succinate)), insulin secretagogues [sulfonylurea preparations (e.g., tolbutamide, glibenclamide, gliclazide, chlorpropamide, tolazamide, acetohexamide, glyclopyramide, glimepiride, glipizide, and glybuzole), repaglinide, nateglinide, mitiglinide, or a calcium salt hydrate thereof], dipeptidyl peptidase IV inhibitors (e.g., Alogliptin, Vilclagiiptin, Sitagliptin, Saxagliptin, Teneligliptin, Linagliptin, Anagliptin, Melogliptin, Dutogliptin, PF-00734200, ALS2-0426, TA-6666, TS-021, KRP-104, and Trelagliptin), β3 agonists (e.g., N-5984), GPR40 agonists (e.g., the compound described in WO 2004/041266, WO 2004/106276, WO 2005/063729, WO 2005/063725, WO 2005/087710, WO 2005/095338, WO 2007/013689 or WO 2008/001931), GLP-1 receptor agonists [e.g., GLP-1, GLP-1MR preparation, Liraglutide, Exenatide, AVE-0010, BIM-51077, Aib(8,35)hGLP-1(7,37)$NH_2$, CJC-1131, and Albiglutide], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, and FBPase inhibitors), SGLT2 (sodium-glucose cotransporter 2) inhibitors (e.g., Depagliflozin, AVE2268, TS-033, YM543, TA-7284, Remogliflozin, and ASP1941), SGLT1 inhibitors, 11β-hydroxysteroid dehydrogenase inhibitors (e.g., BVT-3498), adiponectin or an agonist thereof, IKK inhibitors (e.g., AS-2868), leptin resistance improving drugs, somatostatin receptor agonists, glucokinase activating drugs (e.g., Piragliatin, AZD1656, AZD6370, TTP-355, and the compound described in WO 2006/112549, WO 2007/028135, WO 2008/047821, WO 2008/050821, WO 2008/136428, or WO 2008/156757), and GIP (Glucose-dependent insulinotropic peptide).

Examples of the therapeutic agents for diabetic complications include aldose reductase inhibitors (e.g., tolrestat, epalrestat, zopolrestat, fidarestat, CT-112, ranirestat (AS-3201), and lidorestat), a neurotrophic factor and an increasing drug thereof (e.g., NGF, NT-3, BDNF, and neurotrophin production/secretion promoters (e.g., 4-(4-chlorophenyl)-2-(2-methyl-1-imidazolyl)-5-[3-(2-methylphenoxy)propyl] oxazole) described in WO 01/14372, the compounds described in WO 2004/039365), agents for accelerating nerve regeneration (e.g., Y-128), PKC inhibitors (e.g., ruboxistaurin mesylate), AGE inhibitors (e.g., ALT946, pyratoxatin, N-phenacylthiazolium bromide (ALT766), ALT-711, EXO-226, Pyridorin, and pyridoxamine), GABA receptor agonists (e.g., gabapentin and Pregabalin), serotonin and noradrenaline reuptake inhibitors (e.g., duloxetine), sodium channel inhibitors (e.g., lacosamide), reactive oxygen scavengers (e.g., thioctic acid), cerebral vasodilators (e.g., tiapride and mexiletine), somatostatin receptor agonists (e.g., BIM23190), and apoptosis signal-regulating kinase-1 (ASK-1) inhibitors.

Examples of the therapeutic agent for hyperlipemia include statin-based compounds (e.g., pravastatin, simvastatin, lovastatin, atorvastatin, fluvastatin, rosuvastatin, pitavastatin, cerivastatin, or salts (e.g., a sodium salt and a calcium salt) thereof), squalene synthase inhibitors (e.g., the compounds described in WO 97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate-based compounds (e.g., bezafibrate, clofibrate, simfibrate, and clinofibrate), anion exchange resins (e.g., cholestyramine), probucol, nicotinic acid drugs (e.g., nicomol, niceritrol, and niaspan), ethyl icosapentate, phytosterols (e.g., soysterol and γ-oryzanol), cholesterol absorption inhibitors (e.g., zachia), CETP inhibitors (e.g., dalcetrapib and anacetrapib)), and ω-3 fatty acid preparations (e.g., ω-3-acid ethyl esters 90).

Examples of the antihypertensive agent include angiotensin converting enzyme inhibitors (e.g., captopril, enalapril, and delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, and azilsartan medoxomil), calcium antagonists (e.g., manidipine, nifedipine, amlodipine, efonidipine, nicardipine, amlodipine, and cilnidipine), β blockers (e.g., metoprolol, atenolol, propranolol, carvedilol, and pindolol), renin inhibitors (e.g., Aliskiren), and clonidine.

Examples of the anti-obestic agent include monoamine uptake inhibitors (e.g., phentermine, sibutramine, mazindol, fluoxetine, and tesofensine), serotonin 2C receptor agonists (e.g., lorcaserin), serotonin 6 receptor antagonists, histamine H3 receptor, GABA modulators (e.g., topiramate), MCH receptor antagonists (e.g., SB-568849; SNAP-7941; and the compounds described in WO 01/82925 or WO 01/87834), neuropeptide Y antagonists (e.g., velneperit), cannabinoid receptor antagonists (e.g., rimonabant, taranabant), ghrelin antagonists, ghrelin receptor antagonists, ghrelin acyltransferase inhibitors, opioid receptor antagonists (e.g., GSK-1521498), orexin receptor antagonists (e.g., Almorexant), melanocortin 4 receptor agonists, 11β-hydroxysteroid dehydrogenase inhibitors (e.g., AZD-4017), pancreatic lipase inhibitors (e.g., orlistat and cetilistat), β3 agonists (e.g., N-5984), diacylglycerol acyltransferase 1 (DGAT1) inhibitors, acetyl-CoA carboxylate (ACC) inhibitors, stearic acid-CoA desaturated enzyme inhibitors, microsomal triglyceride transfer protein inhibitors (e.g., R-256918), Na-glucose cotransporter inhibitors (e.g., JNJ-28431754, dapagliflozin, canagliflozin, and remogliflozin), NFκ inhibitors (e.g., HE-3286), PPAR agonists (e.g., GFT-505 and DRF-11605), phosphotyrosine phosphatase inhibitors (e.g., sodium vanadate and Trodusquemine), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine and swine; human GLP-1 preparations genetically synthesized using *Escherichia coli* or a yeast; fragments or derivatives of GLP-1 (e.g., exenatide and liraglutide)), amylin preparations (e.g., pramlintide and AC-2307), neuropeptide Y agonists (e.g., PYY3-36, derivatives of PYY3-36, obinepitide, TM-30339, and TM-30335), oxyntomodulin preparations: FGF21 preparations (e.g., animal FGF21 preparations extracted from the pancreas of bovine and swine; human FGF21 preparations genetically synthesized using *Escherichia coli* or a yeast; and fragments or derivatives of FGF21)), combination preparations of a bupropion hydrochloride sustained-release agent with a naltrexone hydrochloride sustained-release agent, and anorexigenic agents (e.g., P-57).

Examples of the diuretics include xanthine derivatives (e.g., theobromine sodium salicylate and theobromine calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, and methyclothiazide), antialdosterone preparations (e.g., spironolactone, triamterene, and potassium canrenoate), carbonic anhydrase inhibitors (e.g., acetazolamide), chlorobenzenesulfonamide preparations (e.g., chlorthalidone, mefruside, and indapamide), azosemide, isosorbide, ethacrynic acid, piretanide, bumetanide, and furosemide.

Examples of the antithrombotic agent include heparins (e.g., heparin sodium, heparin calcium, enoxaparin sodium, and dalteparin sodium), warfarin (e.g., warfarin potassium), antithrombin drugs (e.g., argatroban and dabigatran), thrombolytic agents (e.g., urokinase, tisokinase, alteplase, nateplase, monteplase, and pamiteplase), and antiplatelet aggregation drugs (e.g., ticlopidine hydrochloride, clopidogrel, E5555, SHC530348, cilostazol, ethyl icosapentate, beraprost sodium, sarpogrelate hydrochloride, prasugrel, and ticagrelor), FXa inhibition drugs (e.g., rivaroxaban, apixaban, edoxaban, YM150, and the compounds described in WO 02/06234, WO 2004/048363, WO 2005/030740, WO 2005/058823, or WO 2005/113504).

The administration time of the combination drug is not limited, and the compound of the present invention and the combination drug can be administered to an administration subject simultaneously or may be administered in a staggered manner. The administration dose of the combination drug may be determined based on the administration dose clinically employed, and can be appropriately selected depending on an administration subject, an administration route, a disease, a combination, or the like.

The administration mode of the combination drug is not particularly limited, and the compound of the present invention and the combination drug only need to be combined during the administration. Examples of such administration mode include:

(1) administration of a single preparation obtained by simultaneously formulating the compound of the present invention and the combination drug, (2) simultaneous administration of two kinds of preparations of the compound of the present invention and the combination drug, which have been separately formulated, by the same administration route, (3) administration of two kinds of preparations of the compound of the present invention and the combination drug, which have been separately formulated, by the same administration route in a staggered manner, (4) simultaneous administration of two kinds of preparations of the compound of the present invention and the combination drug, which have been separately formulated, by different administration routes, and (5) administration of two kinds of preparations of the compound of the present invention and the combination drug, which have been separately formulated, by different administration routes in a staggered manner (e.g., administration in the order of the compound of the present invention and the combination drug, or in the reverse order).

The blending proportion of the compound of the present invention and the combination drug can be appropriately selected depending on an administration subject, an administration route, a disease, or the like.

Hereinafter, the method for preparing the compound of the present invention will be described.

As examples of the method for preparing the compounds (I), (I-1), (I-2), (I-3), (I-4), (I-5), (I-6), (I-7), (I-8), and (I-9), the representative preparation methods are shown below, but the preparation methods are not limited thereto. The compounds (I), (I-1), (I-2), (I-3), (I-4), (I-5), (I-6), (I-7), (I-8) and (I-9) can be prepared by the methods described in the following reaction schemes 1, 2, 3, 4, and 5, or the methods analogous thereto. Further, the compounds (I-1), (I-2), (I-3), (I-4), (I-5), (I-6), (I-7), (I-8), and (I-9) are all included in the compound (I).

In the following reaction scheme, the respective starting compound may form a salt as long as it does not inhibit the reaction, and examples of such a salt include those exemplified as a salt of the compound (I).

Unless a specific production process of the starting material is indicated, a commercially available product may be used or a product prepared by a method analogous thereto may be used as the starting compound.

In each of the reactions in the following reaction schemes, the product may be used as a reaction liquid or as a crude product in the next reaction, but may be isolated from a reaction mixture by an ordinary method and may be easily purified by an ordinary separation means. Examples of the ordinary separation means include recrystallization, distillation, and chromatography.

In the following reaction scheme, in the case where an alkylation reaction, a hydrolysis reaction, an amination reaction, an esterification reaction, an amidation reaction, an etherification reaction, an oxidation reaction, a reduction reaction, or the like is carried out, these reactions are carried out according to methods known per se, for example, those described in Organic Functional Group Preparations, $2^{nd}$ Ed., Academic Press Inc., 1989; and Comprehensive Organic Transformations, VCH Publishers Inc., 1989.

The solvents shown by generic names which are used in the following reactions will be described.

Examples of the "nitrile solvent" include acetonitrile and propionitrile.

Examples of the "amide-based solvent" include N,N-dimethylformamide (DMF), N,N-dimethylacetamide, and N-methylpyrrolidone.

Examples of the "halogenated hydrocarbon-based solvent" include dichloromethane, chloroform, 1,2-dichloroethane, and carbon tetrachloride.

Examples of the "ether-based solvent" include diethylether, diisopropylether, tert-butylmethylether (TBME), cyclopentylmethylether (CPME), tetrahydrofuran (THF), 1,4-dioxane, and 1,2-dimethoxyethane.

Examples of the "aromatic solvent" include benzene, toluene, xylene, chlorobenzene, (trifluoromethyl)benzene, and pyridine.

Examples of the "aliphatichydrocarbon-based solvent" include hexane, pentane, and cyclohexane.

Examples of the "sulfoxide-based solvent" include dimethylsulfoxide (DMSO).

Examples of the "alcohol-based solvent" include methanol, ethanol, propanol, 2-propanol, butanol, isobutanol, and tert-butanol.

Examples of the "ester-based solvent" include methyl acetate, ethyl acetate, isopropyl acetate, n-butyl acetate, and tert-butyl acetate.

Examples of the "ketone-based solvent" include acetone and methyl ethyl ketone.

The bases shown by generic names which are used in the following reactions will be described.

Examples of the "inorganic bases" include sodium hydroxide, potassium hydroxide, lithium hydroxide, and barium hydroxide.

Examples of the "basic salts" include sodium carbonate, potassium carbonate, cesium carbonate, sodium hydrogen carbonate, potassium hydrogen carbonate, tripotassium phosphate, and cesium fluoride.

Examples of the "aromatic amines" include pyridine, imidazole, and 2,6-lutidine.

Examples of the "tertiary amines" include triethylamine, diisopropylethylamine, N-methylmorpholine, 1,8-diazabicyclo[5.4.0]undeca-7-ene (DBU), 1,5-diazabicyclo[4.3.0]nona-5-ene (DBN), and 1,1,3,3-tetramethyl guanidine.

Examples of the "hydrides of alkali metals or alkaline earth metals" include lithium hydride, sodium hydride, potassium hydride, and calcium hydride.

Examples of the "metal amides" include lithium amide, sodium amide, lithium diisopropylamide, lithium dicyclohexylamide, lithium hexamethyl disilazide, sodium hexamethyl disilazide, and potassium hexamethyl disilazide.

Examples of the "alkyl metals" include n-butyl lithium, sec-butyl lithium, tert-butyl lithium, and methylmagnesium bromide.

Examples of the "aryl metals" include phenyl lithium and phenylmagnesium bromide.

Examples of the "metal alkoxides" include sodium methoxide, sodium ethoxide, potassium tert-butoxide, and sodium tert-butoxide.

In each of the following reactions, in the case where the starting compound has an amino group, a carboxyl group, a hydroxyl group, a carbonyl group, or a sulfanyl group, a protecting group generally used in peptide chemistry or the like may be introduced into these groups, and a desired compound can be obtained by removing the protecting group as necessary after the reaction.

Examples of the amino group-protecting group include a formyl group, a $C_{1-6}$ alkyl-carbonyl group (e.g., acetyl), a $C_{1-6}$ alkoxy-carbonyl group (e.g., tert-butoxycarbonyl), a benzoyl group, a $C_{7-10}$ aralkyl-carbonyl group (e.g., benzylcarbonyl), a $C_{7-14}$ aralkyloxy-carbonyl group (e.g., benzyloxycarbonyl and 9-fluorenylmethoxycarbonyl), a $C_{2-6}$ alkenyloxy-carbonyl group (e.g., allyloxycarbonyl), a substituted silyl-$C_{1-6}$ alkoxy-carbonyl group (e.g., trimethylsilylethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl, and triisopropylsilyl), a $C_{2-6}$ alkenyl group (e.g., 1-allyl), and a substituted $C_{7-10}$ aralkyl group (e.g., 2,4-dimethoxybenzyl). These groups may be substituted with 1 to 3 substituents selected from a halogen atom, a $C_{1-6}$alkoxy group, and a nitro group.

Examples of the carboxyl group-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, and tert-butyldiethylsilyl), and a $C_{2-6}$ alkenyl group (e.g., 1-allyl). These protecting groups are optionally substituted with 1 to 3 substituents selected from a halogen atom, a $C_{1-6}$ alkoxy group, and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a $C_{1-6}$ alkoxy-$C_{1-6}$ alkyl group (e.g., a methoxymethyl group, a 2-tetrahydropyranyl group, and a 2-tetrahydrofuranyl group), a substituted silyl group (e.g., trimethylsilyl, triethylsilyl, dimethylphenylsilyl, tert-butyldimethylsilyl, tert-butyldiethylsilyl, and triisopropylsilyl), and a $C_{2-6}$ alkenyl group (e.g., 1-allyl). These groups may be substituted with 1 to 3 substituents selected from a halogen atom, a $C_{1-6}$ alkyl group, a $C_{1-6}$ alkoxy group, and a nitro group.

Examples of the carbonyl group-protecting group include a cyclic acetal (e.g., 1,3-dioxane), and a acyclic acetal (e.g., di-$C_{1-6}$ alkyl acetal).

Examples of the sulfanyl group-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl and 9-fluorenylmethoxycarbonyl), a 2-tetrahydropyranyl group, and a $C_{1-6}$ alkylamino-carbonyl group (e.g., methylaminocarbonyl and ethylaminocarbonyl). These groups may be substituted with 1 to 3 substituents selected from a halogen atom, a $C_{1-6}$ alkyl group, a $C_{1-6}$ alkoxy group, and a nitro group.

The method for removing the protecting group may be carried out according to a method known per se, for example, the method described in Protective Groups in Organic Synthesis, John Wiley and Sons (1980) or the like. Specifically, examples of the method include a method using an acid, a base, ultraviolet rays, hydrazine, phenylhydrazine, sodium N-methyldithiocarbamate, tetrabutylammonium fluoride, palladium acetate, trialkylsilyl halide (e.g., trimethylsilyl iodide and trimethylsilyl bromide), or the like, and a reduction method.

The compound (I) and a compound (I-1) that is the compound (I) in which $R^{10}$ and $R^{11}$ are both hydrogen atoms can be prepared by, for example, the method described in the following reaction scheme 1.

The compound (I) can be prepared by, for example, an alkylation reaction of the compound (2) with the compound (3). The present reaction is carried out by, for example, reacting the compound (2) with the compound (3) in an inert solvent in the presence of a base.

As the compound (3), a commercially available product may be used, or a product prepared according to a method known per se or a method analogous thereto may also be used. The amount of the compound (3) to be used is usually 1 equivalent to 10 equivalents, and preferably 1 equivalent to 5 equivalents, with respect to the compound (2).

<Reaction Scheme 1>

[Chem. 5]

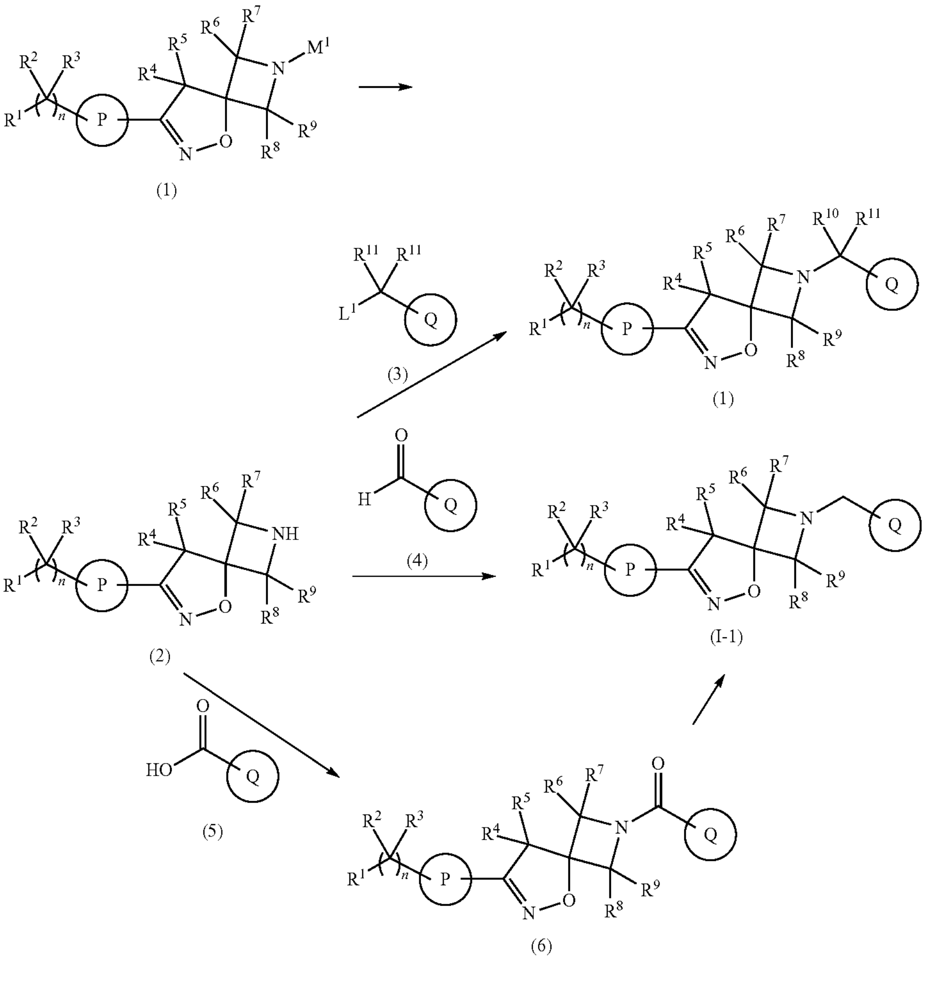

(in which each symbol has the same definition as above, $M^1$ is an amino group-protecting group, and $L^1$ is a sulfonate group or a halogen atom).

The compound (I) can be prepared by, for example, the method described in Reaction Schemes 6, 7, 8, and 14, or a method analogous thereto.

The compound (2) can be prepared, for example, a deprotection reaction of the compound (I). The deprotection reaction can be carried out according to a method known per se, for example, the method described in Protective Groups in Organic Synthesis, John Wiley and Sons (1980).

Examples of the "base" include "inorganic bases", "basic salts", "aromatic amines", "tertiary amines", "hydrides of alkali metals or alkali earth metals", and "metal alkoxides". The amount of the "base" to be used is usually 1 equivalent to 10 equivalents, and preferably 1 equivalent to 5 equivalents, with respect to the compound (2).

Examples of the "inert solvent" include a nitrile-based solvent, an amide-based solvent, a halogenated hydrocarbon-based solvent, an ether-based solvent, a sulfoxide-based solvent, an ester-based solvent, a ketone-based solvent, and an aromatic solvent. These may be used after mixing of two or more kinds thereof at appropriate ratios or may be mixed with water at appropriate ratios. Among these, THF, DMF, toluene, or the like is preferable.

The reaction temperature is usually −100° C. to 150° C., and preferably 0° C. to 100° C. The reaction time is usually 0.1 hours to 48 hours, and preferably 0.5 hours to 24 hours.

The compound (I-1) can be prepared by, for example, a reductive amination reaction of the compound (2) with the compound (4). The present reaction is carried out by, for example, reacting the compound (2) with the compound (4) in an inert solvent in the presence of a reducing agent. If necessary, the reaction may also be carried out in the presence of an acid or a base.

As the compound (4), a commercially available product may be used, or a product prepared according to a method known per se or a method analogous thereto may also be used. The amount of the compound (4) to be used is usually 1 equivalent to 10 equivalents, and preferably 1 equivalent to 5 equivalents, with respect to the compound (2).

Examples of the "reducing agent" include a borane-tetrahydrofuran complex, diisobutylaluminum hydride, sodium triacetoxyborohydride, sodium borohydride, sodium cyanoborohydride, lithium aluminum hydride, sodium aluminum hydride, and sodium bis(2-methoxyethoxy)aluminum hydride. The amount of "reducing agent" to be used is usually 0.1 equivalents to 20 equivalents, and preferably 1 equivalent to 5 equivalents, with respect to the compound (2).

Examples of the "acid" include formic acid, acetic acid, and hydrochloric acid. Examples of the "base" include "inorganic bases", "basic salts", "aromatic amines", and "tertiary amines".

The amount of the "acid" and "base" to be used is usually 0.01 equivalents to 20 equivalents, and preferably 0.1 equivalent to 5 equivalents, with respect to the compound (2).

Examples of the "inert solvent" include an ether-based solvent, a halogenated hydrocarbon-based solvent, an aromatic solvent, an aliphatichydrocarbon-based solvent, and an alcohol-based solvent. These may be used after mixing of two or more kinds thereof at appropriate ratios. Among these, THF, diethylether, 1,2-dimethoxyethane, dichloromethane, toluene, methanol, ethanol, and the like are preferable.

The reaction temperature is usually −70° C. to 150° C., and preferably 0° C. to 100° C. The reaction time is usually 0.1 hours to 100 hours, and preferably 0.5 hours to 60 hours.

The compound (6) can be prepared by, for example, an amidation reaction of the compound (2) with the compound (5).

Examples of the "amidation reaction" include a "method using a dehydration condensing agent" as described below, and a "method using a reactive derivative of a carboxylic acid".

As the compound (5), a commercially available product may be used, or a product prepared according to a method known per se or a method analogous thereto may also be used.

i) Method Using a Dehydration Condensing Agent

The "amidation reaction" is carried out by, for example, reacting the compound (2) with the compound (5) in an inert solvent in the presence of a dehydration condensing agent. If necessary, the reaction may also be carried out in the presence of 1-hydroxybenzotriazole (HOBt), a catalytic amount to 5 equivalents of a base, or the like.

The amount of the compound (5) to be used is usually 0.5 equivalents to 10 equivalents, and preferably 0.8 equivalents to 5 equivalents, with respect to the compound (2).

Examples of the "dehydration condensing agent" include dicyclohexylcarbodiimide (DCC), 1-ethyl-3-(3-dimethylaminopropyl) carbodiimide hydrochloride (WSC), and O-(7-azabenzotriazol-1-yl)-N,N,N',N'-tetramethyluronium hexafluorophosphate (HATU). Among these, WSC and HATU are preferable. The amount of the "dehydration condensing agent" to be used is usually 1 equivalent to 10 equivalents, and preferably 1 equivalent to 5 equivalents, with respect to the compound (2).

Examples of the "inert solvent" include a nitrile-based solvent, an amide-based solvent, a halogenated hydrocarbon-based solvent, and an ether-based solvent. These may be used after mixing of two or more kinds thereof at appropriate ratios. Among these, DMF, THF and acetonitrile are preferable.

Examples of the "base" include "aromatic amines" and "tertiary amines".

The reaction temperature is usually −70° C. to 150° C., and preferably −20° C. to 100° C. The reaction time is usually 0.1 hours to 100 hours, and preferably 1 hour to 48 hours.

ii) Method Using a Reactive Derivative of a Carboxylic Acid

The "amidation reaction" is carried out by, for example, a reactive derivative of the compound (5) with the compound (2) in an inert solvent. If necessary, the reaction may also be carried out in the presence of a base in 1 equivalent to a solvent amount, and preferably 1 equivalent to 3 equivalents.

Examples of the "reactive derivative of the compound (5)" include acid halides (e.g., acid chloride and acid bromide), mixed acid anhydrides (e.g., acid anhydrides with $C_{1-6}$ alkyl-carboxylic acid, $C_{6-10}$ aryl-carboxylic acid, $C_{1-6}$ alkylcarboxylic acid, and the like), and active esters (e.g., esters with phenol optionally having a substituent, HOBt, N-hydroxysuccinimide, and the like).

Examples of the "phenol optionally having a substituent" include phenol, pentachlorophenol, pentafluorophenol, and p-nitrophenol.

The "reactive derivative of the compound (5)" is preferably an acid halide. The amount of the "reactive derivative of the compound (5)" to be used is usually 0.5 equivalents to 10 equivalents, and preferably 0.8 equivalents to 5 equivalents, with respect to the compound (2).

Examples of the "inert solvent" include an ether-based solvent, a halogenated hydrocarbon-based solvent, an aromatic solvent, a nitrile-based solvent, an amide-based solvent, a ketone-based solvent, a sulfoxide-based solvent, and water. These may be used after mixing of two or more kinds thereof at appropriate ratios. Among these, acetonitrile, THF, toluene, dichloromethane, chloroform, and the like are preferable.

Examples of the "base" include "aromatic amines" and "tertiary amines".

The reaction temperature is usually −20° C. to 150° C., and preferably −20° C. to 100° C. The reaction time is usually 0.1 hours to 40 hours, and preferably 0.5 hours to 24 hours.

The compound (I-1) may also be prepared by, for example, a reduction reaction of the compound (6) as an alternative method. The present reaction is carried out by, for example, reacting the compound (6) with a reducing agent in an inert solvent.

Examples of the "reducing agent" include a borane-tetrahydrofuran complex, diisobutylaluminum hydride, sodium triacetoxyborohydride, sodium borohydride, sodium cyanoborohydride, lithium aluminum hydride, sodium aluminum hydride, and sodium bis(2-methoxyethoxy)aluminum hydride. The amount of the "reducing agent" to be used is usually 0.1 equivalents to 20 equivalents, and preferably 1 equivalent to 10 equivalents, with respect to the compound (6).

Examples of the "inert solvent" include an aromatic solvent, an aliphatic hydrocarbon-based solvent, an ether-based solvent, and a halogenated hydrocarbon-based solvent. These solvents may also be used after mixing of two or more kinds thereof at appropriate ratios. Among these, THF, toluene, and the like are preferable.

The reaction temperature is usually −78° C. to 150° C., and preferably −20° C. to 100° C. The reaction time is usually 0.1 hours to 48 hours, and preferably 0.5 hours to 24 hours.

A compound (I-2) that is the compound (I) in which ring P is ring $P^1$ bonded to an isoxazolone ring via a nitrogen atom, can be prepared by, for example, the method described in the following Reaction Scheme 2.

[Chem. 6]

<Reaction Scheme 2>

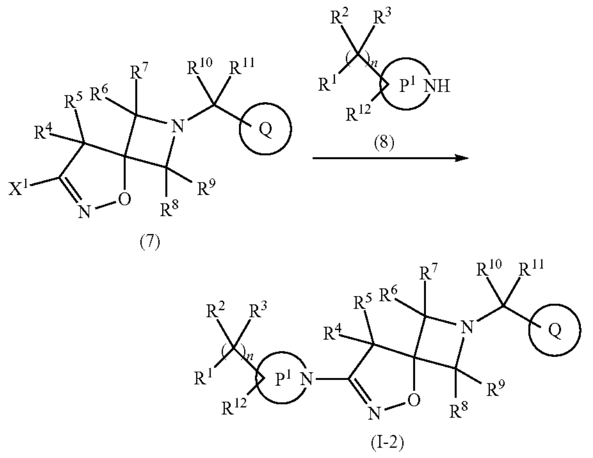

(8)

(7)

(I-2)

(in which each symbol has the same definition as above, $X^1$ is a halogen atom, ring $P^1$ is an optionally substituted nitrogen atom-containing non-aromatic ring, and $R^{12}$ is a $C_{1-6}$ alkyl group, a $C_{3-10}$ cycloalkyl group, a $C_{7-10}$ aralkyl group, a $C_{1-6}$ alkoxy group, a hydroxyl group, or a halogen atom.)

Here, examples of ring $P^1$ include ring P in which the "non-aromatic ring" contains a nitrogen atom.

The compound (7) can be prepared according to, for example, the method described in Reaction Scheme 15, a method known per se, or a method analogous thereto.

The compound (I-2) can be prepared by, for example, a substitution reaction of the compound (7) with the compound (8). The present reaction is carried out by, for example, reacting the compound (7) with the compound (8) in an inert solvent in the presence of a base. If necessary, the reaction may be carried out under the irradiation with microwaves.

As the compound (8), a commercially available product may be used, or a product prepared according to, for example, the method described in Reaction Schemes 11, 12, and 13, a method known per se, or a method analogous thereto may be carried out. The amount of the compound (8) to be used is usually 1 equivalent to 10 equivalents, and preferably 1 equivalent to 5 equivalents, with respect to the compound (7).

Examples of the "base" include "inorganic bases", "basic salts", "aromatic amines", and "tertiary amines". The amount of the "base" to be used is usually 1 equivalent to 10 equivalents, and preferably 1 equivalent to 5 equivalents, with respect to the compound (7).

Examples of the "inert solvent" include an alcohol-based solvent, a nitrile-based solvent, an amide-based solvent, a halogenated hydrocarbon-based solvent, an ether-based solvent, and an aromatic solvent. These may be used after mixing of two or more kinds thereof at appropriate ratios. Among these, methanol, ethanol, n-butanol, THF, DMF, toluene, and the like are preferable.

The reaction temperature is usually −100° C. to 300° C., and preferably 0° C. to 250° C. The reaction time is usually 0.1 hours to 60 hours, and preferably 0.5 hours to 24 hours.

A compound (I-4) that is the compound (I) which has a substituent $R^{13}$ in ring Q can be prepared by, for example, the method described in the following Reaction Scheme 3.

<Reaction Scheme 3>

[Chem. 7]

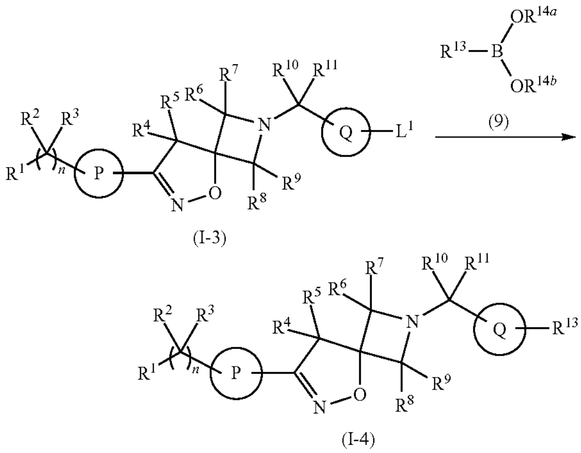

(9)

(I-3)

(I-4)

(in which each symbol has the same definition as above, $R^{13}$ is an optionally substituted $C_{1-6}$ alkyl group, or an optionally substituted $C_{6-14}$ aryl group, $R^{14a}$ and $R^{14b}$ are each independently a hydrogen atom or an optionally substituted $C_{1-6}$alkyl group, and they may be bonded to each other to form an optionally substituted ring (e.g., 1,3,2-dioxaborolane ring optionally substituted with 1 to 5 $C_{1-6}$ alkyl groups).)

The compound (I-3) can be prepared according to, for example, the method described in Reaction Schemes 1, 2, and 4, a method known per se, or a method analogous thereto.

The compound (I-4) can be prepared by, for example, a coupling reaction of the compound (I-3) with the compound (9). The present reaction is preferably carried out by, for example, reacting the compound (I-3) with the compound (9) in an inert solvent in the presence of a metal catalyst, a ligand, and a base. Further, the present reaction is preferably carried out under an inert gas atmosphere and if necessary, the reaction may be carried out under the irradiation with microwaves.

As the compound (9), a commercially available product may be used, or a product prepared according to a method known per se or a method analogous thereto may also be used. The amount of the compound (9) to be used is usually 0.5 equivalents to 10 equivalents, and preferably 0.8 equivalents to 5 equivalents, with respect to the compound (I-3).

Examples of the "metal catalyst" include bis(di-tert-butyl (4-dimethylaminophenyl)phosphine)dichloropalladium(II), palladium acetate(II), tetrakistriphenylphosphine palladium (0), tris(dibenzylideneacetone)dipalladium(0), and [1,1'-bis (diphenylphosphino)ferrocene]dichloropalladium(II) dichloromethane adduct. The amount of the "metal catalyst" to be used is usually 0.001 equivalents to 100 equivalents, and preferably 0.01 equivalents to 10 equivalents, with respect to the compound (I-3).

Examples of the "ligand" include dicyclohexyl(2',6'-dimethoxybiphenyl-2-yl)phosphine, tricyclohexylphosphine, and triphenylphosphine. The amount of the "ligand" to be used is usually 0.001 equivalents to 100 equivalents, and preferably 0.01 equivalents to 10 equivalents, with respect to the compound (I-3).

Examples of the "base" include "basic salts". Among these, tripotassium phosphate, cesium carbonate, cesium fluoride, and sodium carbonate are preferable. The amount of the "base" to be used is usually 1 equivalent to 20 equivalents, and preferably 1 equivalent to 10 equivalents, with respect to the compound (I-3).

Examples of the "inert solvent" include an amide-based solvent, an ether-based solvent, an aromatic solvent, and a halogenated hydrocarbon-based solvent. These may be used after mixing of two or more kinds thereof at appropriate ratios. Further, these may be used after mixing with water at appropriate ratios. Among these, DMF, THF, 1,2-dimethoxyethane, toluene, and the like are preferable.

Examples of the "inert gas" include an argon gas and a nitrogen gas.

The reaction temperature is usually −20° C. to 250° C., and preferably 0° C. to 200° C. The reaction time is usually 0.1 hours to 40 hours, and preferably 0.5 hours to 24 hours.

A compound (I-7) that is the compound (I) in which ring Q has a cyano group can be prepared by, for example, the following Reaction Scheme 4.

<Reaction Scheme 4>

[Chem. 8]

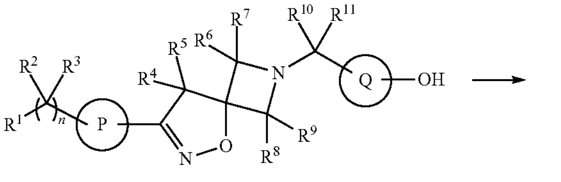

(I-5)

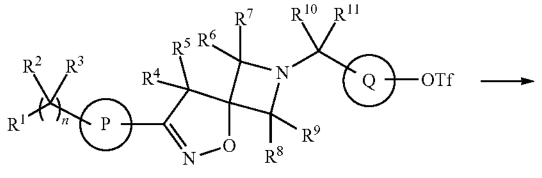

(I-6)

-continued

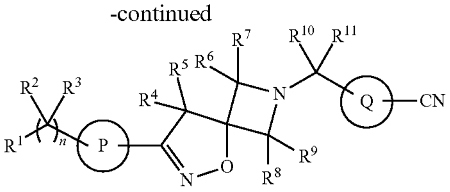

(I-7)

(in which each symbol has the same definition as above.)

The compound (I-5) can be prepared according to, for example, the methods described in Reaction Schemes 1, 2, and 3, a method known per se, or a method analogous thereto.

The compound (I-6) can be prepared by, for example, a trifluoromethane sulfonylation reaction of the compound (I-5). The present reaction is carried out by, for example, reacting the compound (I-5) with the trifluoromethane sulfonylating agent in an inert solvent in the presence of a base.

Examples of the "trifluoromethane sulfonylating agent" include trifluoromethane sulfonic anhydride, and N-phenyl bis(trifluoromethanesulfoneimide). The amount of the "trifluoromethane sulfonylating agent" to be used is usually 0.1 equivalents to 20 equivalents, and preferably 1 equivalent to 10 equivalents, with respect to the compound (I-5).

Examples of the "base" include "inorganic bases", "basic salts", "aromatic amines", "tertiary amines", and "metal alkoxides". The amount of the "base" to be used is usually 1 equivalent to 10 equivalents, and preferably 1 equivalent to 5 equivalents, with respect to the compound (I-5).

Examples of the "inert solvent" include a nitrile-based solvent, an amide-based solvent, a halogenated hydrocarbon-based solvent, an ether-based solvent, an aromatic solvent, a sulfoxide-based solvent, and an ester-based solvent. These may be used after mixing of two or more kinds thereof at appropriate ratios. Among these, DMF, THF, toluene, pyridine, and the like are preferable.

The reaction temperature is usually −78° C. to 150° C., and preferably −20° C. to 100° C. The reaction time is usually 0.1 hours to 100 hours, and preferably 0.5 hours to 48 hours.

The compound (I-7) can be prepared by, for example, a cyanidation reaction of the compound (I-6). The present reaction is carried out by reacting the compound (I-6) with a cyanidating agent in an inert solvent in the presence of a metal catalyst. Further, the present reaction is preferably carried out under an inert gas atmosphere. Further, the present reaction may be carried out in the presence of a ligand and a base, if necessary, or may be carried out under the irradiation of microwaves.

Examples of the "cyanidating agent" include zinc cyanide, copper cyanide, and sodium cyanide. The amount of the "cyanidating agent" to be used is usually 0.1 equivalents to 20 equivalents, and preferably 1 equivalent to 10 equivalents, with respect to the compound (I-8).

Examples of the "metal catalyst" include bis(di-tert-butyl (4-dimethylaminophenyl)phosphine)dichloropalladium(II), palladium(II) acetae, tetrakistriphenylphosphine palladium (0), tris(dibenzylideneacetone)dipalladium(0), and [1,1-bis (diphenylphosphino)ferrocene]dichloropalladium(II) dichloromethane adduct. The amount of the "metal catalyst" to be used is usually 0.001 equivalents to 100 equivalents, and preferably 0.01 equivalents to 10 equivalents, with respect to the compound (I-6).

Examples of the "ligand" include dicyclohexyl(2',6'-dimethoxybiphenyl-2-yl)phosphine, tricyclohexylphosphine, and triphenylphosphine. The amount of the "ligand" to be used is usually 0.001 equivalents to 100 equivalents, and preferably 0.01 equivalents to 10 equivalents, with respect to the compound (I-6).

Examples of the "base" include "basic salts". Among these, tripotassium phosphate, cesium carbonate, cesium fluoride, sodium carbonate, and the like are preferable. The amount of the "base" to be used is usually 1 equivalent to 20 equivalents, and preferably 1 equivalent to 10 equivalents, with respect to the compound (I-6).

Examples of the "inert solvent" include a nitrile-based solvent, an amide-based solvent, a halogenated hydrocarbon-based solvent, an ether-based solvent, an aromatic solvent, a sulfoxide-based solvent, and an ester-based solvent. These may be used after mixing of two or more kinds thereof at appropriate ratios. Among these, DMF, DMSO, THF, 1,2-dimethoxyethane, toluene, and the like are preferable.

Examples of the "inert gas" include an argon gas and a nitrogen gas.

The reaction temperature is usually −78° C. to 200° C., and preferably 0° C. to 150° C. The reaction time is usually 0.1 hours to 100 hours, and preferably 0.5 hours to 48 hours.

A compound (I-9) that is the compound (I) in which $R^1$ is COOH can be prepared by, for example, the method described in the following Reaction Scheme 5.

<Reaction Scheme 5>

[Chem. 9]

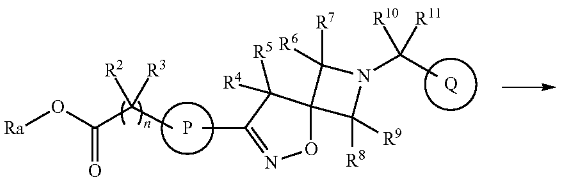

(I-8)

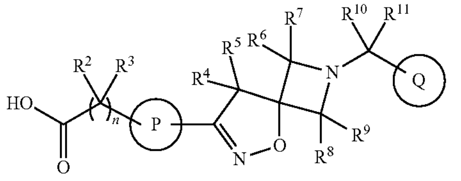

(I-9)

(in which each symbol has the same definition as above.)

A compound (I-8) that is the compound (I) in which $R^1$ is COORa can be prepared by, for example, the method described in the following Reaction Schemes 1, 2, 3, and 4.

The compound (I-9) can be prepared by, for example, a hydrolysis reaction of the compound (I-8). The present reaction is carried out by, for example, reacting the compound (I-8) with a base in an inert solvent Examples of the "base" include "inorganic bases". The amount of the "base" to be used is usually 1 equivalent to 30 equivalents, and preferably 1 equivalent to 20 equivalents, with respect to the compound (I-8).

Examples of the "inert solvent" include an alcohol-based solvent, a nitrile-based solvent, an aromatic solvent, an aliphatic hydrocarbon-based solvent, an ether-based solvent, an amide-based solvent, and a halogenated hydrocarbon-based solvent. These are preferably used as a mixture with water at appropriate ratios. Among these, a hydrated alcohol-based solvent is preferable.

The reaction temperature is usually −78° C. to 150° C., and preferably −20° C. to 100° C. The reaction time is usually 0.1 hours to 100 hours, and preferably 0.5 hours to 60 hours.

A compound (1-1) that is the compound (1) in which $R^4$ and $R^5$ are hydrogen atoms can be prepared by, for example, the method described in the following Reaction Scheme 6.

<Reaction Scheme 6>

[Chem. 10]

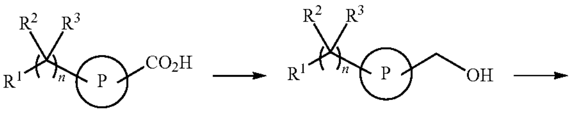

(10) (11)

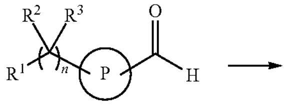

(12)

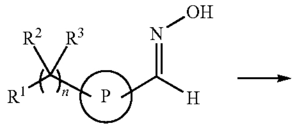

(13)

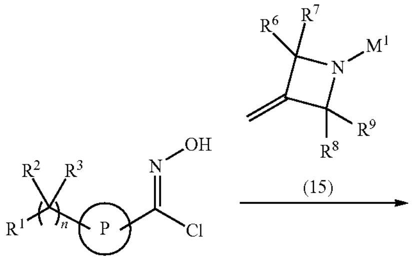

(14) (15)

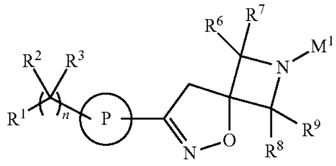

(1-1)

(in which each symbol has the same definition as above.)

As the compound (10), a commercially available product may be used, or a product prepared according to a method known per se or a method analogous thereto may also be used.

The compound (11) can be prepared by, for example, a reduction reaction of the compound (10). The present reaction is carried out by, for example, reacting the compound (10) with a reducing agent in an inert solvent Examples of the "reducing agent" include a borane-tetrahydrofuran complex, diisobutylaluminum hydride, sodium borohydride, sodium cyanoborohydride, lithium aluminum hydride, sodium aluminum hydride, and sodium bis(2-methoxyethoxy)aluminum hydride. The amount of the "reducing agent" to be used is usually 0.1 equivalents to 20 equivalents, and preferably 1 equivalent to 10 equivalents, with respect to the compound (10).

Examples of the "inert solvent" include an aromatic solvent, an aliphatic hydrocarbon-based solvent, an ether-based solvent, and a halogenated hydrocarbon-based solvent. These solvents may be used after mixing of two or more kinds thereof at appropriate ratios. Among these, THF, toluene, and the like are preferable.

The reaction temperature is usually −78° C. to 150° C., and preferably −20° C. to 100° C. The reaction time is usually 0.1 hours to 48 hours, and preferably 0.5 hours to 24 hours.

The compound (12) can be prepared by, for example, an oxidation compound (11).

The present reaction is carried out by, for example, reacting the compound (11) with an oxidant in an inert solvent. If necessary, the reaction may be carried out in the presence of a reoxidant Examples of the "oxidant" include a sulfur trioxide pyridine complex, manganese dioxide, tetrapropylammonium perruthenate, chromium trioxide, and Dess-Martin periodinane. The amount of the "oxidant" to be used is usually 0.01 equivalents to 30 equivalents, and preferably 0.05 equivalents to 20 equivalents, with respect to the compound (11).

Examples of the "reoxidant" include N-methylmorpholine-N-oxide (NMO). The amount of the "reoxidant" to be used is usually 0.01 equivalents to 30 equivalents, and preferably 0.1 equivalents to 20 equivalents, with respect to the compound (11).

Examples of the "inert solvent" include a nitrile-based solvent, an aromatic solvent, an aliphatic hydrocarbon-based solvent, an ether-based solvent, an amide-based solvent, a halogenated hydrocarbon-based solvent, a sulfoxide-based solvent, and an ester-based solvent. These solvents may be used after mixing of two or more kinds thereof at appropriate ratios. Among these, DMSO, THF, toluene, acetonitrile, ethyl acetate, dichloromethane, and the like are preferable.

The reaction temperature is usually −78° C. to 150° C., and preferably −20° C. to 100° C. The reaction time is usually 0.1 hours to 100 hours, and preferably 0.5 hours to 48 hours.

The compound (13) can be prepared by, for example, an oximation reaction of the compound (12). The present reaction is carried out by, for example, reacting the compound (12) with hydroxyamine hydrochloride in an inert solvent in the presence of a base.

The amount of the "hydroxyamine hydrochloride" to be used is usually 0.1 equivalents to 20 equivalents, and preferably 1 equivalent to 10 equivalents, with respect to the compound (12).

Examples of the "base" include "basic salts", "aromatic amines", and "tertiary amines". The amount of the "base" to be used is usually 0.1 equivalents to 20 equivalents, and preferably 1 equivalent to 10 equivalents, with respect to the compound (12).

Examples of the "inert solvent" include an alcohol-based solvent, a nitrile-based solvent, an aromatic solvent, an ether-based solvent, an amide-based solvent, a halogenated hydrocarbon-based solvent, and an ester-based solvent. These solvents may be used after mixing of two or more kinds thereof at appropriate ratios. Among these, methanol, ethanol, DMF, THF, toluene, and the like are preferable.

The reaction temperature is usually −78° C. to 150° C., and preferably −20° C. to 100° C. The reaction time is usually 0.1 hours to 100 hours, and preferably 0.5 hours to 48 hours.

The compound (14) can be prepared by, for example, a chlorination reaction of the compound (13). The present reaction is carried out by, for example, reacting the compound (13) with a chlorinating agent in an inert solvent Examples of the "chlorinating agent" include N-chlorosuccinimide, and benzyl trimethylammonium tetrachloroperiodate. The amount of the "chlorinating agent" to be used is usually 0.1 equivalents to 20 equivalents, and preferably 1 equivalent to 10 equivalents, with respect to the compound (13).

Examples of the "inert solvent" include an alcohol-based solvent, a nitrile-based solvent, an aromatic solvent, an ether-based solvent, an amide-based solvent, a halogenated hydrocarbon-based solvent, and an ester-based solvent. These solvents may be used after mixing of two or more kinds thereof at appropriate ratios. Among these, methanol, ethanol, acetonitrile, DMF, THF, toluene, and the like are preferable.

The reaction temperature is usually −78° C. to 150° C., and preferably −20° C. to 100° C. The reaction time is usually 0.1 hours to 100 hours, and preferably 0.5 hours to 48 hours.

The compound (1-1) can be prepared by, for example, a cyclization reaction of the compound (14) with the compound (15). The present reaction is carried out by, for example, reacting the compound (14) with the compound (15) in an inert solvent in the presence of a base.

The compound (15) can be prepared according to, for example, the method described in Reaction Scheme 9, a method known per se, or a method analogous thereto. The amount of the compound (15) to be used is usually 1 equivalent to 10 equivalents, and preferably 1 equivalent to 5 equivalents, with respect to the compound (14).

Examples of the "base" include "inorganic bases", "basic salts", "aromatic amines", and "tertiary amines". The amount of the "base" to be used is usually 1 equivalent to 10 equivalents, and preferably 1 equivalent to 5 equivalents, with respect to the compound (14).

Examples of the "inert solvent" include a nitrile-based solvent, an amide-based solvent, a halogenated hydrocarbon-based solvent, an ether-based solvent, an aromatic solvent, a sulfoxide-based solvent, and an ester-based solvent. These may be used after mixing of two or more kinds thereof at appropriate ratios. Among these, DMF, THF, toluene, and the like are preferable.

The reaction temperature is usually −100° C. to 250° C., and preferably 0° C. to 150° C. The reaction time is usually 0.1 hours to 72 hours, and preferably 0.5 hours to 48 hours.

A compound (I-2) that is the compound (I) in which $R^5$ is a hydrogen atom and $R^4$ is $R^{4a}$ can be prepared by, for example, the method described in the following Reaction Scheme 7.

[Chem. 11]

<Reaction Scheme 7>

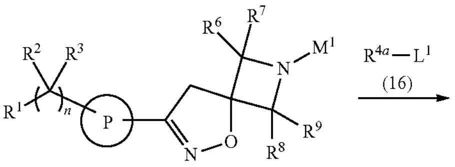

(1-1)

-continued

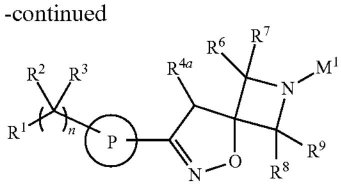

(1-2)

(in which each symbol has the same definition as above, and $R^{4a}$ is a $C_{1-6}$ alkyl group or a $C_{3-10}$ cycloalkyl group.)

The compound (1-1) can be prepared according to, for example, the method described in Reaction Schemes 6, 8, and 14, a method known per se, or a method analogous thereto.

The compound (1-2) can be prepared by, for example, an alkylation reaction of the compound (1-1). The present reaction is carried out by, for example, reacting the compound (1-1) with the compound (16) in an inert solvent in the presence of a base.

As the compound (16), a commercially available product may be used, or a product prepared according to a method known per se or a method analogous thereto may also be used. The amount of the compound (16) to be used is usually 1 equivalent to 10 equivalents, and preferably 1 equivalent to 5 equivalents, with respect to the compound (1-1).

Examples of the "base" include "inorganic bases", "basic salts", "tertiary amines", "hydrides of alkali metals or alkali earth metals", "metal amides", "alkyl metals", "aryl metals", and "metal alkoxides". The amount of the "base" to be used is usually 1 equivalent to 10 equivalents, and preferably 1 equivalent to 5 equivalents, with respect to the compound (1-1).

Examples of the "inert solvent" include a nitrile-based solvent, an amide-based solvent, a halogenated hydrocarbon-based solvent, an ether-based solvent, and an aromatic solvent. These may be used after mixing of two or more kinds thereof at appropriate ratios. Among these, THF, DMF, toluene, and the like are preferable.

The reaction temperature is usually −100° C. to 150° C., and preferably −70° C. to 100° C. The reaction time is usually 0.1 hours to 48 hours, and preferably 0.5 hours to 24 hours.

A compound (1-3) that is the compound (1) in which ring P is ring $P^1$ bonded to an isoxazolone ring via a nitrogen atom can be prepared by, for example, the method described in the following Reaction Scheme 8.

<Reaction Scheme 8>

[Chem. 12]

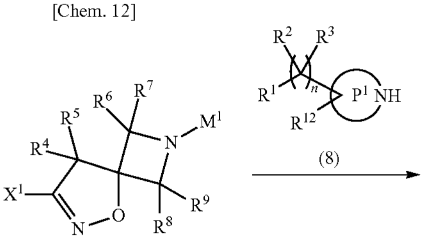

(8)

(17)

-continued

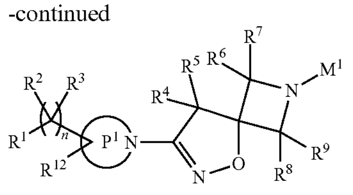

(1-3)

(in which each symbol has the same definition as above and $X^1$ is a halogen atom.)

The compound (17) can be prepared according to, for example, the method described in Reaction Scheme 9, a method known per se, or a method analogous thereto.

The compound (1-3) can be prepared by, for example, a substitution reaction of the compound (17) with the compound (8). The present reaction is carried out by, for example, reacting the compound (17) with the compound (8) in an inert solvent in the presence of a base.

The amount of the compound (8) to be used is usually 1 equivalent to 10 equivalents, and preferably 1 equivalent to 5 equivalents, with respect to the compound (17).

Examples of the "base" include "basic salts", "aromatic amines", "tertiary amines", and "metal alkoxides". The amount of the "base" to be used is usually 1 equivalent to 20 equivalents, and preferably 1 equivalent to 10 equivalents, with respect to the compound (17).

Examples of the "inert solvent" include a nitrile-based solvent, an amide-based solvent, a halogenated hydrocarbon-based solvent, an ether-based solvent, and an aromatic solvent. These may be used after mixing of two or more kinds thereof at appropriate ratios. Among these, THF, DMF, toluene, and the like are preferable.

The reaction temperature is usually −100° C. to 250° C., and preferably 0° C. to 200° C. The reaction time is usually 0.1 hours to 60 hours, and preferably 0.5 hours to 24 hours.

A compound (17-1) that is the compound (17) in which $R^4$ and $R^5$ are both hydrogen atoms can be prepared by, for example, the method described in the following Reaction Scheme 9.

[Chem. 13]

<Reaction Scheme 9>

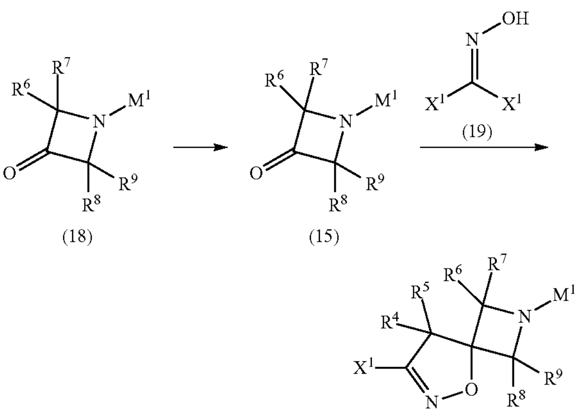

(18) (15) (19) (17-1)

(in which each symbol has the same definition as above.)

As the compound (18), a commercially available product may be used, or a product prepared by, for example, the method described in Reaction Scheme 10, a method known per se, or a method analogous thereto may be used.

The compound (15) can be prepared by, for example, an olefination reaction of the compound (18). The present reaction is carried out by, for example, reacting the compound (18) with an olefinating agent in an inert solvent in the presence of a base.

Examples of the "olefinating agent" include methyl(triphenyl)phosphonium bromide. The amount of the "olefinating agent" to be used is usually 1 equivalent to 10 equivalents, and preferably 1 equivalent to 5 equivalents, with respect to the compound (18).

Examples of the "base" include "inorganic bases", "basic salts", "aromatic amines", "tertiary amines", "hydrides of alkali metals or alkali earth metals", "metal amides", "alkyl metals", "aryl metals", and "metal alkoxides". The amount of the "base" to be used is usually 1 equivalent to 10 equivalents, and preferably 1 equivalent to 5 equivalents, with respect to the compound (18).

Examples of the "inert solvent" include amide-based solvent, a halogenated hydrocarbon-based solvent, an ether-based solvent, and an aromatic solvent. These may be used after mixing of two or more kinds thereof at appropriate ratios. Among these, THF, DMF, toluene, and the like are preferable.

The reaction temperature is usually −100° C. to 200° C., and preferably −80° C. to 100° C. The reaction time is usually 0.1 hours to 60 hours, and preferably 0.5 hours to 24 hours.

The compound (17-1) can be prepared by, for example, a cyclization reaction of the compound (15) with the compound (19). The present reaction is carried out by, for example, reacting the compound (15) with the compound (19) in an inert solvent in the presence of a base.

As the compound (19), a commercially available product may be used, or a product prepared according to a method known per se or a method analogous thereto may also be used. The amount of the compound (19) to be used is usually 1 equivalent to 10 equivalents, and preferably 1 equivalent to 5 equivalents, with respect to the compound (15).

Examples of the "base" include "basic salts", "tertiary amines", and "metal alkoxides". The amount of the "base" to be used is usually 1 equivalent to 30 equivalents, and preferably 1 equivalent to 20 equivalents, with respect to the compound (15).

Examples of the "inert solvent" include a nitrile-based solvent, an amide-based solvent, a halogenated hydrocarbon-based solvent, an ether-based solvent, an aromatic solvent, a sulfoxide-based solvent, and an ester-based solvent. These may be used after mixing of two or more kinds thereof at appropriate ratios. Among these, ethyl acetate, THF, DMF, toluene, and the like are preferable.

The reaction temperature is usually −100° C. to 200° C., and preferably 0° C. to 100° C. The reaction time is usually 0.1 hours to 60 hours, and preferably 0.5 hours to 24 hours.

A compound (18-1) that is the compound (18) in which $R^8$ and $R^9$ are both hydrogen atoms can be prepared by, for example, the method described in the following Reaction Scheme 10.

<Reaction Scheme 10>

[Chem. 14]

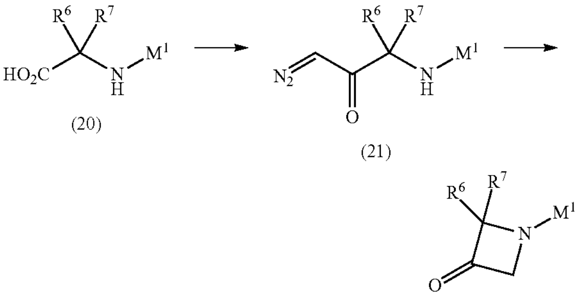

(20) (21) (18-1)

(in which each symbol has the same definition as above.)

As the compound (20), a commercially available product may be used, or a product prepared according to a method known per se or a method analogous thereto may also be used.

The compound (21) can be prepared by, for example, a diazoketonation reaction of the compound (20). The present reaction is carried out by, for example, reacting a reactive derivative of the compound (20) with diazomethane or an analogue to the diazomethane in an inert solvent.

Examples of the "reactive derivative of the compound (20)" include acid halides (e.g., acid chloride and acid bromide), mixed acid anhydrides (e.g., acid anhydrides with $C_{1-6}$ alkyl-carboxylic acid, $C_{6-10}$ aryl-carboxylic acid, $C_{1-6}$ alkylcarbonic acid, or the like), active esters (e.g., esters with phenol optionally having a substituent, HOBt, N-hydroxysuccinimide, or the like).

Examples of the "phenol optionally having a substituent" include phenol, pentachlorophenol, pentafluorophenol, and p-nitrophenol.

"The reactive derivative of the compound (20)" is preferably a mixed acid anhydride.

Examples of the "analogue to the diazomethane" include trimethylsilyldiazomethane. The amount of the "diazomethane or an analogue to the diazomethane" to be used is usually 1 equivalent to 20 equivalents, and preferably 1 equivalent to 10 equivalents, with respect to the compound (20).

Examples of the "inert solvent" include an ether-based solvent, a halogenated hydrocarbon-based solvent, an aromatic solvent, an aliphatic hydrocarbon-based solvent, a nitrile-based solvent, an amide-based solvent, a ketone-based solvent, and a sulfoxide-based solvent. These may be used after mixing of two or more kinds thereof at appropriate ratios. Among these, acetonitrile, THF, diethylether, toluene, dichloromethane, chloroform, and the like are preferable.

The reaction temperature is usually −20° C. to 150° C., and preferably −20° C. to 100° C. The reaction time is usually 0.1 hours to 40 hours, and preferably 0.5 hours to 24 hours.

The compound (18-1) can be prepared by, for example, a cyclization reaction of the compound (21). The present reaction is carried out by, for example, reacting the compound (21) with a metal catalyst in an inert solvent in the presence of a base.

Examples of the "metal catalyst" include rhodium(II) acetate. The amount of the "metal catalyst" to be used is usually 0.001 equivalents to 100 equivalents, and preferably 0.01 equivalents to 10 equivalents, with respect to the compound (21).

Examples of the "base" include "inorganic bases", "basic salts", "aromatic amines", "tertiary amines", and "metal alkoxides". The amount of the "base" to be used is usually 1 equivalent to 30 equivalents, and preferably 1 equivalent to 20 equivalents, with respect to the compound (21).

Examples of the "inert solvent" include a nitrile-based solvent, an amide-based solvent, a halogenated hydrocarbon-based solvent, an ether-based solvent, an aromatic solvent, and a sulfoxide-based solvent. These may be used after mixing of two or more kinds thereof at appropriate ratios. Among these, THF, toluene, dichloromethane, chloroform, and the like are preferable.

The reaction temperature is usually −100° C. to 250° C., and preferably 0° C. to 150° C. The reaction time is usually 0.1 hours to 60 hours, and preferably 0.5 hours to 24 hours.

A compound (8-1) that is the compound (8) in which $R^1$ is COORa and n is 0 can be prepared by, for example, the method described in the following Reaction Scheme 11.

<Reaction Scheme 11>

[Chem. 15]

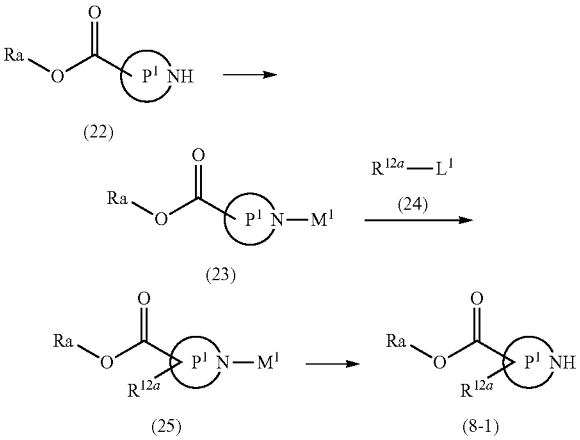

(22)

(23)

(24)

(25)

(8-1)

(in which each symbol has the same definition as above and $R^{12a}$ is a $C_{1-6}$ alkyl group, a $C_{3-10}$ cycloalkyl group, or a $C_{7-10}$ aralkyl group.)

In the present specification, examples of the "$C_{7-10}$ aralkyl group" include benzyl.

As the compound (22), a commercially available product may be used, or a product prepared according to a method known per se or a method analogous thereto may also be used.

The compound (23) can be prepared by, for example, a protection reaction of the compound (22).

The protection reaction can be carried out according to a method known per se, for example, the method described in Protective Groups in Organic Synthesis, John Wiley and Sons (1980).

The compound (25) can be prepared by, for example, an alkylation reaction of the compound (23).

The present reaction is carried out by, for example, reacting the compound (23) with the compound (24) in an inert solvent in the presence of a base.

As the compound (24), a commercially available product may be used, or a product prepared according to a method known per se or a method analogous thereto may also be used. The amount of the compound (24) to be used is usually 1 equivalent to 10 equivalents, and preferably 1 equivalent to 5 equivalents, with respect to the compound (23).

Examples of the "base" include "inorganic bases", "basic salts", "aromatic amines", "tertiary amines", "hydrides of alkali metals or alkali earth metals", "metal amides", "alkyl metals", "aryl metals", and "metal alkoxides". The amount of the "base" to be used is usually 1 equivalent to 10 equivalents, and preferably 1 equivalent to 5 equivalents, with respect to the compound (23).

Examples of the "inert solvent" include a nitrile-based solvent, an amide-based solvent, a halogenated hydrocarbon-based solvent, an ether-based solvent, and an aromatic solvent. These may be used after mixing of two or more kinds thereof at appropriate ratios. Among these, THF, DMF, toluene, and the like are preferable.

The reaction temperature is usually −100° C. to 150° C., and preferably −80° C. to 50° C. The reaction time is usually 0.5 hours to 48 hours, and preferably 1 hour to 24 hours.

The compound (8-1) can be prepared by, for example, a deprotection reaction of the compound (25).

The deprotection reaction can be carried out according to a method known per se, for example, the method described in Protective Groups in Organic Synthesis, John Wiley and Sons (1980).

A compound (8-2) that is the compound (8) in which $R^1$ is COORa, $R^2$ and $R^3$ are both hydrogen atoms, $R^1$ is a hydrogen atom, and n is 2 can be prepared by, for example, the method described in the following Reaction Scheme 12.

<Reaction Scheme 12>

[Chem. 16]

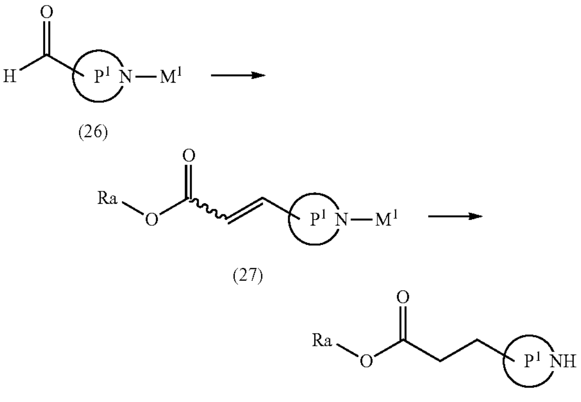

(26)

(27)

(8-2)

(in which each symbol has the same definition as above.)

As the compound (26), a commercially available product may be used, or a product prepared according to a method known per se or a method analogous thereto may also be used.

The compound (27) can be prepared by, for example, a Horner-Wadsworth-Emmons reaction of the compound (26).

The present reaction is carried out by, for example, reacting the compound (26) with ethyl(diethoxyphosphoryl) acetate in an inert solvent in the presence of a base.

The amount of the "ethyl(diethoxyphosphoryl)acetate" to be used is usually 1 equivalent to 10 equivalents, and preferably 1 equivalent to 5 equivalents, with respect to the compound (26).

Examples of the "base" include "basic salts", "aromatic amines", "tertiary amines", "hydrides of alkali metals or alkali earth metals", "metal amides", "alkyl metals", and "metal alkoxides". The amount of the "base" to be used is usually 1 equivalent to 10 equivalents, and preferably 1 equivalent to 5 equivalents, with respect to the compound (26).

Examples of the "inert solvent" include a nitrile-based solvent, an amide-based solvent, a halogenated hydrocarbon-based solvent, an ether-based solvent, an aromatic solvent, and a sulfoxide-based solvent. These may be used after mixing of two or more kinds thereof at appropriate ratios. Among these, THF, DMF, toluene, and the like are preferable.

The reaction temperature is usually −100° C. to 150° C., and preferably −70° C. to 100° C. The reaction time is usually 0.1 hours to 48 hours, and preferably 0.5 hours to 24 hours.

The compound (8-2) can be prepared by, for example, a reduction reaction of the compound (27). Further, if necessary, a deprotection reaction may be carried out after the reduction reaction.

The "reduction reaction" is carried out by, for example, reacting the compound (27) in the presence of a metal catalyst and a hydrogen source in an inert solvent. If necessary, the reaction may be carried out in the presence of a catalytic amount to a solvent amount of an organic acid or 1 equivalent to 50 equivalents of hydrogen chloride.

Examples of the "metal catalyst" include palladium-carbon, palladium black, palladium chloride, palladium hydroxide, rhodium carbon, platinum oxide, platinum black, platinum-palladium, Raney nickel, and Raney cobalt. The amount of the "metal catalyst" to be used is usually 0.001 equivalents to 1000 equivalents, and preferably 0.01 equivalents to 100 equivalents, with respect to the compound (27).

Examples of the "hydrogen source" include a hydrogen gas.

Examples of the "organic acid" include acetic acid.

Examples of the "inert solvent" include an alcohol-based solvent, a nitrile-based solvent, an aromatic solvent, an aliphatic hydrocarbon-based solvent, an ether-based solvent, an amide-based solvent, and a halogenated hydrocarbon-based solvent. These are preferably used after mixing with water at appropriate ratios or may be used after mixing of two or more kinds thereof at appropriate ratios. Among these, THF, methanol, ethanol, and the like are preferable.

The reaction temperature is usually −70° C. to 150° C., and preferably −20° C. to 100° C. The reaction time is usually 0.1 hours to 100 hours, and preferably 0.5 hours to 40 hours.

The deprotection reaction can be carried out according to a method known per se, for example, the method described in Protective Groups in Organic Synthesis, John Wiley and Sons (1980).

A compound (8-3) that is the compound (8) in which $R^1$ is COORa, $R^1$ is a hydroxyl group, and n is 0 can be prepared by, for example, the method described in the following Reaction Scheme 13.

<Reaction Scheme 13>

[Chem. 17]

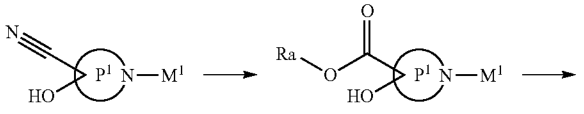

(28) (29)

-continued

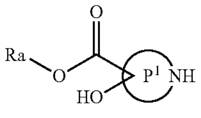

(8-3)

(in which each symbol has the same definition as above.)

As the compound (28), a commercially available product may be used, or a product prepared according to a method known per se or a method analogous thereto may also be used.

The compound (29) can be prepared by, for example, a hydrolysis reaction and a subsequent esterification reaction of the compound (28).

The "hydrolysis reaction" is carried out by, for example, reacting the compound (28) in an inert solvent in the presence of an acid or a base.

Examples of the "acid" include concentrated hydrochloric acid and concentrated sulfuric acid.

Examples of the "base" include "inorganic bases".

The amount of the "acid" and the "base" to be used is usually 0.1 equivalents to a solvent amount, and preferably 1 equivalent to a solvent amount, with respect to the compound (28).

Examples of the "inert solvent" include an alcohol-based solvent, an aromatic solvent, an aliphatic hydrocarbon-based solvent, an ether-based solvent, and a halogenated hydrocarbon-based solvent. These are preferably used after mixing with water at appropriate ratios or may also be used after mixing of two or more kinds thereof at appropriate ratios. Among these, THF, methanol, ethanol, and the like are preferable.

The reaction temperature is usually −78° C. to 250° C., and preferably 0° C. to 150° C.

The reaction time is usually 0.1 hours to 48 hours, and preferably 0.5 hours to 24 hours.

The "esterification reaction" can be carried out by a method known per se, for example, the method described in Protective Groups in Organic Synthesis, John Wiley and Sons (1980).

The compound (8-3) can be prepared by, for example, a deprotection reaction of the compound (29).

The deprotection reaction can be carried out by a method known per se, for example, the method described in Protective Groups in Organic Synthesis, John Wiley and Sons (1980).

A compound (1-3b) that is the compound (1-3) in which $R^{12}$ is $OR^{15}$ can be prepared by, for example, the method described in the following Reaction Scheme 14.

<Reaction Scheme 14>

[Chem. 18]

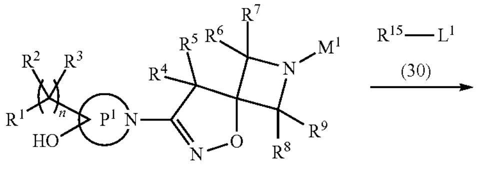

(1-3a)

-continued

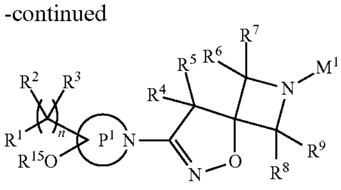

(1-3b)

(in which each symbol has the same definition as above, and $R^{15}$ is a $C_{1-6}$ alkyl group or a $C_{3-10}$cycloalkyl group.)

The compound (1-3a) can be prepared according to, for example, the method described in Reaction Scheme 8, a method known per se, or a method analogous thereto.

The compound (1-3b) can be prepared by, for example, an alkylation reaction of the compound (1-3a). The present reaction is carried out by, for example, reacting the compound (1-3a) with the compound (30) in an inert solvent in the presence of a base.

As the compound (30), a commercially available product may be used, or a product prepared according to a method known per se or a method analogous thereto may also be used. The amount of the compound (30) to be used is usually 1 equivalent to 10 equivalents, and preferably 1 equivalent to 5 equivalents, with respect to the compound (1-3a).

Examples of the "base" include "inorganic bases", "basic salts", "tertiary amines", "hydrides of alkali metals or alkali earth metals", "metal amides", and "metal alkoxides". The amount of the "base" to be used is usually 1 equivalent to 10 equivalents, and preferably 1 equivalent to 5 equivalents, with respect to the compound (1-3a).

Examples of the "inert solvent" include a nitrile-based solvent, an amide-based solvent, a halogenated hydrocarbon-based solvent, an ether-based solvent, and an aromatic solvent. These may be used after mixing of two or more kinds thereof at appropriate ratios. Among these, THF, DMF, toluene, and the like are preferable.

The reaction temperature is usually −100° C. to 150° C., and preferably −70° C. to 100° C. The reaction time is usually 0.1 hours to 48 hours, and preferably 0.5 hours to 24 hours.

A compound (7-1) that is the compound (7) in which $R^{10}$ and $R^{11}$ are both hydrogen atoms can be prepared by, for example, the method described in the following Reaction Scheme 15.

<Reaction Scheme 15>

[Chem. 19]

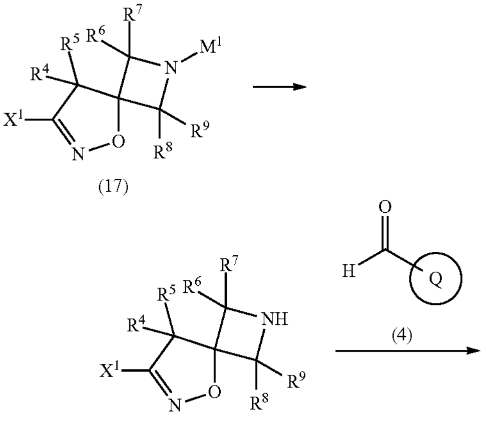

(17)

(4)

(31)

-continued

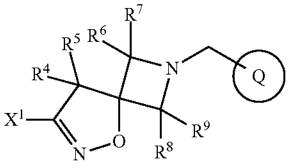

(7-1)

(in which each symbol has the same definition as above.)

The compound (17) can be prepared according to, for example, the method described in Reaction Scheme 9, a method known per se, or a method analogous thereto.

The compound (31) can be prepared by, for example, a deprotection reaction of the compound (17).

The deprotection reaction can be carried out according to a method known per se, for example, the method described in Protective Groups in Organic Synthesis, John Wiley and Sons (1980).

The compound (7-1) can be prepared by, for example, a reductive amination reaction of the compound (31) with the compound (4). The present reaction is carried out in the same manner as the method for preparing the compound (I-1) from the compound (2) in Reaction Scheme 1.

The present invention is further described in detail with respect to the following Examples, Test Examples, and Formulation Examples, but the present invention is not limited thereto and may be modified within a range not departing from the range of the present invention.

The "room temperature" in Examples below usually denotes about 10° C. to about 35° C. The ratio in the mixed solvent denotes a ratio by volume unless otherwise specified. % denotes % by weight unless otherwise specified.

In silica gel column chromatography, when NH was described, an aminopropylsilane-bonded silica gel was used. In HPLC (High Performance Liquid Chromatography), when C18 was described, an octadecyl-bonded silica gel was used. The ratio of the eluting solvents is denoted in a ratio by volume unless otherwise specified. Further, in the mobile phase, the description of "water/acetonitrile (system containing 0.1% TFA)" or the like means that water and acetonitrile containing 0.1% by volume TFA are used after mixing them at appropriate ratios. In SFC (Supercxritical Fluid Chromatography), the columns used are described, respectively. The ratio of the eluting solvents denotes a ratio by volume unless otherwise specified. Further, in the mobile phase, the description of "carbon dioxide/methanol/diethylamine" or the like means that carbon dioxide, methanol, and diethylamine are used after mixing them at appropriate ratios.

The following abbreviations are used in Examples below.

THF: tetrahydrofuran

DMF: dimethylformamide

DME: 1,2-dimethoxyethane

DMSO: dimethylsulfoxide $^1$H-NMR proton nuclear magnetic resonance (spectrum) was measured by Fourier-transform type NMR. The chemical shift in the $^1$H NMR spectrum is described in δ unit (ppm) when the peak of an internal standard material is set to 0 ppm using tetramethylsilane (TMS) as the internal standard material, and the coupling constant is described in Hertz (Hz). For the analysis, ACD/SpecManager (trade name) and the like were used. Proton such as a carboxyl group, a hydroxyl group, and an amino group may not be shown for the peak very loose.

The abbreviations used in other parts of the present specification have the following meanings.

s: singlet
d: doublet
t: triplet
q: quartet
quin: quintet
m: multiplet
br: broad
J: coupling constant
Hz: Hertz
$CDCl_3$: deuterated chloroform
DMSO-$d_6$: dimethylsulfoxide-$d_6$
$CD_3OD$: deuterated methanol
$^1$H-NMR: proton nuclear magnetic resonance
TFA: trifluoroacetic acid MS (mass spectrum) was measured by LC/MS (liquid chromatography mass spectrometer). As the ionization method, an ESI (ElectroSpray Ionization) method or an APCI (Atomospheric Pressure Chemical Ionization) method was used. For the ionization mode, several data items were described using both or either of a positive mode (ESI+) and a negative mode (ESI−). The data indicates the values found. Generally, a molecular ion peak is observed, but peaks derived from isotopes may be observed in some cases (e.g., compounds having bromine atoms). Further, in the case of a compound having a tert-butoxycarbonyl group (−Boc), a peak after elimination of a tert-butoxycarbonyl group or a tert-butyl group may be observed as a fragment ion in some cases. In addition, in the case of a compound having a hydroxyl group (—OH), a peak after elimination of $H_2O$ may be observed as a fragment ion. In the case of a salt, a molecular ion peak or fragment ion peak of free form is generally observed.

Example 1

Ethyl 1-(2-((2,6-diethoxy-4'-fluorobiphenyl-4-yl)methyl)-5-oxa-2,6-diazaspiro[3.4]oct-6-en-7-yl)piperidine-4-carboxylate

A) Ethyl 4-bromo-3,5-diethoxybenzoate

Potassium carbonate (89.0 g) and iodoethane (60.1 mL) was added to a solution of 4-bromo-3,5-dihydroxybenzoic acid (50.0 g) in DMF (300 mL), and the resultant was stirred for 2 hours at 60° C. After the reaction mixture was cooled to room temperature, water was added thereto, extraction thereof was performed using ethyl acetate, and the resultant was washed with a saturated saline solution. The obtained organic layer was passed through a silica gel column chromatography (NH, ethyl acetate), and then the solvent was distilled off under reduced pressure. The obtained solid was sequentially washed with diethyl ether and hexane, thereby obtaining the title compound (55.8 g).

$^1$H NMR (300 MHz, $CDCl_3$) δ 1.40 (3H, t, J=7.1 Hz), 1.49 (6H, t, J=7.0 Hz), 4.17 (4H, q, J=7.0 Hz), 4.38 (2H, q, J=7.1 Hz), 7.21 (2H, s).

B) Ethyl 2,6-diethoxy-4'-fluorobiphenyl-4-carboxylate

Palladium acetate (1.98 g), tripotassium phosphate (112 g), (4-fluorophenyl)boronic acid (43.1 g) and tricyclohexylphosphine (20% toluene solution, 31.2 mL) were added to a mixture of ethyl 4-bromo-3,5-diethoxybenzoate (55.8 g), toluene (300 mL) and water (150 mL), and the resultant was heated and stirred overnight at 90° C. in an argon atmosphere. After the reaction mixture was cooled to room temperature, water was added thereto, extraction thereof was performed using ethyl acetate, and the resultant was sequentially washed with water and a saturated saline solution. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (50.7 g).

$^1$H NMR (300 MHz, $CDCl_3$) δ 1.27 (6H, t, J=6.9 Hz), 1.41 (3H, t, J=7.1 Hz), 4.03 (4H, q, J=6.9 Hz), 4.40 (2H, q, J=7.1 Hz), 6.99-7.14 (2H, m), 7.28-7.41 (4H, m).

C) 2,6-Diethoxy-4'-fluorobiphenyl-4-carbaldehyde

A solution of ethyl 2,6-diethoxy-4'-fluorobiphenyl-4-carboxylate (50.7 g) in THF (200 mL) was added to a suspension of lithium aluminum hydride (4.34 g) in THF (200 mL) under ice-cooling. After stirring for 30 minutes at the same temperature, water (4.5 mL) and 1 M aqueous sodium hydroxide solution (4.5 mL) was added thereto, the resultant was stirred for 5 minutes, and water (13.5 mL) was further added thereto. After the reaction mixture was stirred for 1 hour, it was filtered using celite, and the filtrate was concentrated under reduced pressure. Sulfur trioxide-pyridine complex (48.6 g) was added to a solution of the obtained residue and triethylamine (63.8 mL) in DMSO (250 mL), and the resultant was stirred for 30 minutes at room temperature. Water (450 mL) was added to the reaction mixture, and the precipitated solids were collected by filtration. Recrystallization (ethanol/water) of the obtained solid was performed, thereby obtaining the title compound (36.9 g).

$^1$H NMR (300 MHz, $CDCl_3$) δ 1.29 (6H, t, J=7.0 Hz), 4.06 (4H, q, J=6.9 Hz), 7.08 (2H, t, J=8.9 Hz), 7.13 (2H, s), 7.34 (2H, dd, J=9.0, 5.6 Hz), 9.94 (1H, s).

D) tert-Butyl 3-methyleneazetidine-1-carboxylate

After potassium tert-butoxide (13.3 g) was added to a mixture of methyl(triphenyl)phosphonium bromide (38.7 g) and THF (150 mL) at 0° C., the resultant was stirred for 1 hour. A solution of tert-butyl 3-oxoazetidine-1-carboxylate (16.9 g) in THF (50 mL) was added to the reaction mixture, and the resultant was stirred for 2 hours at 50° C. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was dissolved into a solution in which ethyl acetate and hexane is mixed at a ratio of 1:3, the resultant was filtered using celite, and then the filtrate was concentrated under reduced pressure. The obtained residue was purified by a silica gel column chromatography (hexane/ethyl acetate), thereby obtaining the title compound (10.9 g).

$^1$H NMR (300 MHz, DMSO-$d_6$) δ 1.45 (9H, s), 4.46-4.51 (4H, m), 4.96-5.02 (2H, m).

E) tert-Butyl 7-bromo-5-oxa-2,6-diazaspiro[3.4]oct-6-ene-2-carboxylate

Sodium hydrogen carbonate (101 g) was added to a mixture of tert-butyl 3-methyleneazetidine-1-carboxylate (20.4 g), hydroxycarbonimidic dibromide (48.8 g) and ethyl acetate (400 mL), the resultant was stirred for 15 hours at room temperature, and was further stirred for 4 hours at 50°

C. After water was added to the reaction mixture at room temperature, the resultant was filtered using celite, and the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (27.8 g).

$^1$H NMR (400 MHz, $CDCl_3$) δ 1.44 (9H, s), 3.44 (2H, s), 4.02-4.07 (2H, m), 4.26-4.32 (2H, m).

F) tert-Butyl 7-(4-(ethoxycarbonyl)piperidin-1-yl)-5-oxa-2,6-diazaspiro[3.4]oct-6-ene-2-carboxylate tert-Butyl 7-bromo-5-oxa-2,6-diazaspiro[3.4]oct-6-ene-2-carboxylate (15.0 g), ethyl piperidine-4-carboxylate (11.3 g) and sodium carbonate (15.3 g) were added to DMF (60 mL), and the resultant was stirred for 4 hours at 130° C. After the reaction mixture was cooled to room temperature, water was added thereto, and extraction thereof was performed using ethyl acetate. The obtained organic layer was washed with a saturated saline solution, dried over anhydrous magnesium sulfate, and then the solvent was distilled off under reduced pressure. The obtained residue was crystallized (hexane/diisopropyl ether), thereby obtaining the title compound (15.1 g).

$^1$H NMR (400 MHz, DMSO-$d_6$) δ 1.18 (3H, t, J=7.1 Hz), 1.38 (9H, s), 1.52 (2H, d, J=10.2 Hz), 1.80 (2H, d, J=11.8 Hz), 2.50 (1H, brs), 2.84 (2H, t, J=11.6 Hz), 3.33 (2H, s), 3.43 (2H, d, J=12.9 Hz), 3.88 (2H, d, J=9.0 Hz), 3.98-4.12 (4H, m).

G) Ethyl 1-(2-((2,6-diethoxy-4'-fluorobiphenyl-4-yl)methyl)-5-oxa-2,6-diazaspiro[3.4]oct-6-en-7-yl)piperidine-4-carboxylate tert-Butyl 7-(4-(ethoxycarbonyl)piperidin-1-yl)-5-oxa-2,6-diazaspiro[3.4]oct-6-ene-2-carboxylate (3.50 g) was added to formic acid (14 mL), the resultant was stirred for 1 hour at 70° C., and the solvent was distilled off under reduced pressure. Sodium triacetoxyborohydride (3.03 g) was added to a solution of the obtained residue and 2,6-diethoxy-4'-fluorobiphenyl-4-carbaldehyde (2.75 g) in THF (20 mL), and the resultant was stirred for 1 hour at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. After the obtained residue was purified by a silica gel column chromatography (NH, hexane/ethyl acetate), crystallization (hexane/diisopropyl ether) was performed, thereby obtaining the title compound (4.04 g).

$^1$H NMR (400 MHz, DMSO-$d_6$) δ 1.07-1.22 (9H, m), 1.46-1.59 (2H, m), 1.80 (2H, d, J=11.8 Hz), 2.50 (1H, brs), 2.83 (2H, t, J=11.4 Hz), 3.17 (2H, d, J=7.7 Hz), 3.30 (2H, s), 3.41-3.49 (4H, m), 3.57 (2H, s), 3.95 (4H, q, J=6.8 Hz), 4.07 (2H, q, J=7.0 Hz), 6.61 (2H, s), 7.09-7.18 (2H, m), 7.23-7.31 (2H, m).

Example 2

1-(2-((2,6-Diethoxy-4'-fluorobiphenyl-4-yl)methyl)-5-oxa-2,6-diazaspiro[3.4]oct-6-en-7-yl)piperidine-4-carboxylic acid 2 M aqueous sodium hydroxide solution (46 mL) was added to a solution of ethyl 1-(2-((2,6-diethoxy-4'-fluorobiphenyl-4-yl)methyl)-5-oxa-2,6-diazaspiro[3.4]oct-6-en-7-yl)piperidine-4-carboxylate (8.20 g) in ethanol (30 mL) at room temperature, and the resultant was stirred for 1 hour at 70° C. After the reaction mixture was neutralized with 2 M hydrochloric acid at room temperature, the solvent was distilled off to half amount thereof under reduced pressure, and the precipitated solid was collected by filtration. Recrystallization (diisopropyl ether/ethanol) of the obtained solid was performed, thereby obtaining the title compound (6.06 g).

$^1$H NMR (400 MHz, $CD_3OD$) δ 1.24 (6H, t, J=7.0 Hz), 1.63-1.75 (2H, m), 1.88-1.98 (2H, m), 2.41-2.51 (1H, m), 2.89-3.00 (2H, m), 3.38 (2H, s), 3.55-3.66 (4H, m), 3.77 (2H, d, J=9.7 Hz), 3.85 (2H, s), 4.00 (4H, q, J=7.0 Hz), 6.69 (2H, s), 7.06 (2H, t, J=8.8 Hz), 7.28 (2H, dd, J=8.3, 5.8 Hz).

Example 3

Methyl trans-4-(2-((2,6-diethoxy-4'-fluorobiphenyl-4-yl)methyl)-5-oxa-2,6-diazaspiro[3.4]oct-6-en-7-yl)cyclohexanecarboxylate A) Methyl trans-4-(hydroxymethyl)cyclohexanecarboxylate Borane-tetrahydrofuran complex (1.1 M THF solution, 83 mL) was added dropwise to a solution of trans-4-(methoxycarbonyl)cyclohexanecarboxylic acid (12.2 g) in THF (300 mL) at −40° C., the resultant was stirred for 1 hours at the same temperature, and was stirred for 2 hour at 0° C. After water and an aqueous saturated sodium hydrogen carbonate solution were added to the reaction mixture at 0° C., extraction thereof was performed using ethyl acetate. The obtained organic layer was sequentially washed with water and a saturated saline solution, dried over anhydrous magnesium sulfate, and then the solvent was distilled off under reduced pressure. The residue was purified by a silica gel column chromatography (hexane/ethyl acetate), thereby obtaining the title compound (7.19 g).

$^1$H NMR (400 MHz, $CDCl_3$) δ 0.92-1.08 (2H, m), 1.39-1.52 (3H, m), 1.83-1.92 (2H, m), 1.98-2.08 (2H, m), 2.20-2.32 (1H, m), 3.47 (2H, d, J=6.1 Hz), 3.67 (3H, s).

B) Methyl trans-4-formylcyclohexanecarboxylate

Sulfur trioxide-pyridine complex (12.6 g) was added to a solution of methyl trans-4-(hydroxymethyl)cyclohexanecarboxylate (6.83 g) and triethylamine (12.0 g) in DMSO (200 mL) at 0° C., and the resultant was stirred for 2 hours at room temperature. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The residue was purified by a silica gel column chromatography (hexane/ethyl acetate), thereby obtaining the title compound (4.44 g).

$^1$H NMR (400 MHz, $CDCl_3$) δ 1.23-1.38 (2H, m), 1.44-1.56 (2H, m), 2.03-2.15 (4H, m), 2.17-2.33 (2H, m), 3.68 (3H, s), 9.63 (1H, s).

C) Methyl trans-4-((E)-(hydroxyimino)methyl)cyclohexanecarboxylate

Hydroxyamine hydrochloride was added to a mixture of methyl trans-4-formylcyclohexanecarboxylate (4.41 g), sodium hydrogen carbonate (2.39 g) and methanol (100 mL)

at room temperature, the resultant was stirred for 2 hours at the same temperature, and then the solvent was distilled off under reduced pressure. Water was added to the residue, and extraction thereof was performed using ethyl acetate. The obtained organic layer was sequentially washed with water and a saturated saline solution, dried over anhydrous magnesium sulfate, and then the solvent was distilled off under reduced pressure. The residue was purified by a silica gel column chromatography (hexane/ethyl acetate), thereby obtaining the title compound (3.69 g).

$^1$H NMR (300 MHz, $CDCl_3$) δ 1.17-1.35 (2H, m), 1.40-1.57 (2H, m), 1.88-1.99 (2H, m), 2.00-2.11 (2H, m), 2.15-2.35 (2H, m), 3.67 (3H, s), 7.33 (1H, d, J=5.9 Hz), 7.60 (1H, s).

D) tert-Butyl 7-(trans-4-(methoxycarbonyl)cyclohexyl)-5-oxa-2,6-diazaspiro[3.4]oct-6-ene-2-carboxylate N-chlorosuccinimide (2.88 g) was added to a solution of methyl trans-4-((E)-(hydroxyimino)methyl)cyclohexanecarboxylate (3.63 g) in DMF (70 mL) at room temperature, and the resultant was stirred for 2 hours at the same temperature. After water was added to the reaction mixture, extraction thereof was performed using diethyl ether. The obtained organic layer was sequentially washed with water and a saturated saline solution, dried over anhydrous magnesium sulfate, and then the solvent was distilled off under reduced pressure. Triethylamine (1.98 g) was added to a solution of tert-butyl 3-methyleneazetidine-1-carboxylate (3.32 g) in THF (80 mL), the resultant was stirred for 30 minutes at 80° C., a solution of the above-obtained residue in THF (20 mL) was added thereto, and the resultant was stirred for 16 hours at the same temperature. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The residue was purified by a silica gel column chromatography (hexane/ethyl acetate), thereby obtaining the title compound (2.40 g).

$^1$H NMR (400 MHz, $CDCl_3$) δ 1.29-1.57 (13H, m), 1.96-2.04 (2H, m), 2.04-2.14 (2H, m), 2.25-2.41 (2H, m), 3.15 (2H, s), 3.68 (3H, s), 3.96 (2H, d, J=9.8 Hz), 4.23 (2H, d, J=9.8 Hz).

E) Methyl trans-4-(5-oxa-2,6-diazaspiro[3.4]oct-6-en-7-yl)cyclohexanecarboxylate hydrochloride A solution of 4 M hydrogen chloride/ethyl acetate (30 mL) was added to a solution of tert-butyl 7-(trans-4-(methoxycarbonyl)cyclohexyl)-5-oxa-2,6-diazaspiro[3.4]oct-6-ene-2-carboxylate (2.58 g) in ethyl acetate (20 mL), and the resultant was stirred for 3 hours at room temperature. The precipitated solid was collected by filtration, thereby obtaining the title compound (1.53 g).

$^1$H NMR (400 MHz, DMSO-$d_6$) δ 1.24-1.47 (4H, m), 1.82-1.90 (2H, m), 1.91-2.00 (2H, m), 2.25-2.40 (2H, m), 3.37 (2H, s), 3.59 (3H, s), 4.07-4.14 (2H, m), 4.15-4.22 (2H, m), 9.22 (2H, brs).

F) Methyl trans-4-(2-((2,6-diethoxy-4'-fluorobiphenyl-4-yl)methyl)-5-oxa-2,6-diazaspiro[3.4]oct-6-en-7-yl)cyclohexanecarboxylate Triethylamine (211 mg) was added to a mixture of methyl trans-4-(5-oxa-2,6-diazaspiro[3.4]oct-6-en-7-yl)cyclohexanecarboxylate hydrochloride (301 mg), 2,6-diethoxy-4'-fluorobiphenyl-4-carbaldehyde (391 mg) and THF (10 mL), and the resultant was stirred for 20 minutes. Sodium triacetoxyborohydride (442 mg) was added thereto, and the resultant was stirred for 18 hours at room temperature. Furthermore, sodium triacetoxyborohydride (221 mg) was added to the reaction mixture, and the resultant was stirred for 3 hours at room temperature. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The residue was purified by a silica gel column chromatography (ethyl acetate/methanol), thereby obtaining the title compound (435 mg).

$^1$H NMR (400 MHz, $CDCl_3$) δ 1.24 (6H, t, J=6.9 Hz), 1.31-1.43 (2H, m), 1.44-1.57 (2H, m), 1.95-2.03 (2H, m), 2.04-2.13 (2H, m), 2.24-2.43 (2H, m), 3.20 (2H, s), 3.41 (2H, d, J=8.8 Hz), 3.51 (2H, d, J=8.7 Hz), 3.63-3.70 (5H, m), 3.96 (4H, q, J=6.9 Hz), 6.54 (2H, s), 7.04 (2H, t, J=8.8 Hz), 7.32 (2H, dd, J=8.5, 5.7 Hz).

Example 4

Trans-4-(2-((2,6-Diethoxy-4'-fluorobiphenyl-4-yl)methyl)-5-oxa-2,6-diazaspiro[3.4]oct-6-en-7-yl)cyclohexanecarboxylic acid 1 M aqueous sodium hydroxide solution (2 mL) was added to a mixture of methyl trans-4-(2-((2,6-diethoxy-4'-fluorobiphenyl-4-yl)methyl)-5-oxa-2,6-diazaspiro[3.4]oct-6-en-7-yl)cyclohexanecarboxylate (417 mg), THF (5 mL) and ethanol (5 mL), the resultant was stirred for 2 hours at 50° C., and then the solvent was distilled off under reduced pressure. Water was added to the residue, the resultant was neutralized with 1 M hydrochloric acid, and then the obtained solid was collected by filtration. After the obtained solid was dissolved in ethyl acetate and THF, it was dried over anhydrous magnesium sulfate, and the solvent was distilled off under reduced pressure. The residue was crystallized (hexane/ethanol), thereby obtaining the title compound (327 mg).

$^1$H NMR (400 MHz, DMSO-$d_6$) δ 1.15 (6H, t, J=7.0 Hz), 1.23-1.42 (4H, m), 1.82-1.89 (2H, m), 1.90-1.98 (2H, m), 2.12-2.22 (1H, m), 2.25-2.36 (1H, m), 3.20-3.27 (4H, m), 3.44 (2H, d, J=8.3 Hz), 3.58 (2H, s), 3.95 (4H, q, J=6.9 Hz), 6.61 (2H, s), 7.11-7.18 (2H, m), 7.23-7.31 (2H, m), 12.06 (1H, brs).

Example 5

(1-(2-((2,6-Diethoxy-4'-fluorobiphenyl-4-yl)methyl)-5-oxa-2,6-diazaspiro[3.4]oct-6-en-7-yl)piperidin-4-yl)acetic acid A) 7-bromo-5-oxa-2,6-diazaspiro[3.4]oct-6-en hydrochloride Using tert-butyl 7-bromo-5-oxa-2,6-diazaspiro[3.4]oct-6-ene-2-carboxylate, the title compound was obtained in the similar manner as in Step E of Example 3.

$^1$H NMR (400 MHz, DMSO-$d_6$) δ 3.67-3.77 (2H, m), 4.12-4.23 (2H, m), 4.25-4.34 (2H, m), 9.14 (2H, brs).

B) 7-Bromo-2-((2,6-diethoxy-4'-fluorobiphenyl-4-yl)methyl)-5-oxa-2,6-diazaspiro[3.4]oct-6-ene Using 7-bromo-5-oxa-2,6-diazaspiro[3.4]oct-6-en hydrochloride and 2,6-diethoxy-4'-fluorobiphenyl-4-carbaldehyde, the title compound was obtained in the similar manner as in Step F of Example 3.

$^1$H NMR (400 MHz, DMSO-$d_6$) δ 1.09-1.18 (6H, m), 3.32 (2H, d, J=8.4 Hz), 3.50-3.65 (6H, m), 3.95 (4H, q, J=6.9 Hz), 6.61 (2H, s), 7.10-7.19 (2H, m), 7.27 (2H, dd, J=8.3, 6.0 Hz).

C) (1-(2-((2,6-diethoxy-4'-fluorobiphenyl-4-yl)methyl)-5-oxa-2,6-diazaspiro[3.4]oct-6-en-7-yl) piperidin-4-yl)acetic acid A mixture of ethyl piperidin-4-ylacetate (222 mg), 7-bromo-2-((2,6-diethoxy-4'-fluorobiphenyl-4-yl)methyl)-5-oxa-2,6-diazaspiro[3.4]oct-6-ene (400 mg), sodium carbonate (229 mg) and n-butanol (3 mL) was stirred for 2 hours at 200° C. under microwave irradiation. After the reaction mixture was cooled to room temperature, insoluble matters were filtered, and the filtrate was concentrated under reduced pressure. The obtained residue was purified by a silica gel column chromatography (NH, hexane/ethyl acetate). 2 M aqueous sodium hydroxide solution was added to a solution of the obtained residue in ethanol (3.0 mL), and the resultant was stirred for 30 minutes at 70° C. After the reaction mixture was cooled to room temperature, it was neutralized with 2 M hydrochloric acid, and extraction thereof was performed using ethyl acetate. The organic layer was washed with a saturated saline solution, dried over anhydrous magnesium sulfate, and then the solvent was distilled off under reduced pressure. The obtained residue was crystallized (hexane/ethyl acetate), thereby obtaining the title compound (176 mg).

Example 6

1-(2-((2,6-Diethoxy-4'-fluorobiphenyl-4-yl)methyl)-5-oxa-2,6-diazaspiro[3.4]oct-6-en-7-yl)azetidine-3-carboxylic acid Using ethyl azetidine-3-carboxylate hydrochloride and 7-bromo-2-((2,6-diethoxy-4'-fluorobiphenyl-4-yl)methyl)-5-oxa-2,6-diazaspiro[3.4]oct-6-ene, the title compound was obtained in the similar manner as in Step C of Example 5.

Example 7

Ethyl 1-(2-((2,6-diethoxy-4'-fluorobiphenyl-4-yl)methyl)-5-oxa-2,6-diazaspiro[3.4]oct-6-en-7-yl)-4-methylpiperidine-4-carboxylate A) 1-benzyl 4-ethyl piperidine-1,4-dicarboxylate Benzyl chloroformate (29.5 mL) was added to a solution of ethyl piperidine-4-carboxylate (25.0 g) and diisopropylethylamine (55.5 mL) in THF (150 mL) at 0° C., and the resultant was stirred for 2 hours at 0° C. After an aqueous saturated sodium hydrogen carbonate solution was added to the reaction mixture at room temperature, extraction thereof was performed using ethyl acetate. The obtained organic layer was sequentially washed with an aqueous saturated sodium hydrogen carbonate solution, 1 M hydrochloric acid and a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (30.1 g).

$^1$H NMR (400 MHz, $CDCl_3$) δ 1.25 (3H, t, J=7.0 Hz), 1.58-1.73 (2H, m), 1.88 (2H, brs), 2.38-2.52 (1H, m), 2.93 (2H, t, J=11.6 Hz), 4.01-4.19 (4H, m), 5.13 (2H, s), 7.27-7.40 (5H, m).

B) 1-Benzyl 4-ethyl 4-methylpiperidine-1,4-dicarboxylate

Lithium bis(trimethylsilyl)amide (1.0 M THF solution, 233 mL) was added to a solution of 1-benzyl 4-ethyl piperidine-1,4-dicarboxylate (40.0 g) in THE (160 mL) at −40° C. After the reaction mixture was stirred for 1 hour at −40° C., iodomethane (39.0 g) was added thereto, and the resultant was stirred for 2 hours at room temperature. After an aqueous saturated sodium hydrogen carbonate solution was added to the reaction mixture, the resultant was filtered using celite, and the organic layer of the filtrate was separated. The obtained organic layer was sequentially washed with water and a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (34.0 g).

$^1$H NMR (400 MHz, $CDCl_3$) δ 1.20 (3H, s), 1.26 (3H, t, J=7.0 Hz), 1.31-1.44 (2H, m), 2.08 (2H, d, J=13.2 Hz), 2.99-3.13 (2H, m), 3.86 (2H, d, J=8.4 Hz), 4.16 (2H, q, J=7.0 Hz), 5.12 (2H, s), 7.28-7.39 (5H, m).

C) Ethyl 4-methylpiperidine-4-carboxylate

20% palladium hydroxide (50% water content, 4.00 g) was added to a solution of 1-benzyl 4-ethyl 4-methylpiperidine-1,4-dicarboxylate (34.0 g) in methanol (340 mL), and the resultant was stirred for 4 hours at room temperature in a hydrogen atmosphere. After the catalyst was filtered off, the filtrate was concentrated under reduced pressure, thereby obtaining the title compound (19.0 g).

$^1$H NMR (400 MHz, $CDCl_3$) δ 1.19 (3H, s), 1.26 (3H, t, J=7.1 Hz), 1.31-1.42 (2H, m), 2.08 (2H, d, J=13.6 Hz), 2.62-2.74 (2H, m), 2.87-2.96 (2H, m), 4.16 (2H, q, J=7.1 Hz).

D) tert-Butyl 7-(4-(ethoxycarbonyl)-4-methylpiperidin-1-yl)-5-oxa-2,6-diazaspiro[3.4]oct-6-ene-2-carboxylate tert-Butyl 7-bromo-5-oxa-2,6-diazaspiro[3.4]oct-6-ene-2-carboxylate (18.0 g), ethyl 4-methylpiperidine-4-carboxylate (14.8 g) and sodium carbonate (19.7 g) were added to DMF (90 mL), and the resultant was stirred overnight at 130° C. After the reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. The obtained residue was crystallized (hexane/ethyl acetate), thereby obtaining the title compound (18.1 g).

$^1$H NMR (400 MHz, DMSO-$d_6$) δ 1.15 (3H, s), 1.19 (3H, t, J=7.0 Hz), 1.31-1.46 (11H, m), 1.93 (2H, d, J=13.6 Hz), 2.87 (2H, t, J=10.4 Hz), 3.23-3.36 (4H, m), 3.88 (2H, d, J=9.3 Hz), 4.02 (2H, J=9.0 Hz), 4.11 (2H, q, J=6.9 Hz).

E) Ethyl 1-(2-((2,6-diethoxy-4'-fluorobiphenyl-4-yl)methyl)-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-5-oxa-2,6-diazaspiro[3.4]oct-6-ene-2-carboxylate (608 mg) was added to formic acid (3 mL), the resultant was stirred for 1 hour at 60° C., and the solvent was distilled off under reduced pressure. Sodium triacetoxyborohydride (507 mg) was added to a solution of the obtained residue and 2,6-diethoxy-4'-fluorobiphenyl-4-carbaldehyde (460 mg) in THF (10 mL), and the resultant was stirred for 1 hour at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (717 mg).

$^1$H NMR (400 MHz, DMSO-$d_6$) δ 1.05-1.24 (12H, m), 1.35-1.47 (2H, m), 1.93 (2H, d, J=13.6 Hz), 2.86 (2H, t, J=10.4 Hz), 3.16 (2H, d, J=8.2 Hz), 3.29 (4H, brs), 3.46 (2H, d, J=8.2 Hz), 3.57 (2H, s), 3.94 (4H, q, J=6.9 Hz), 4.10 (2H, q, J=7.1 Hz), 6.61 (2H, s), 7.09-7.19 (2H, m), 7.23-7.30 (2H, m).

Example 8

1-(2-((2,6-diethoxy-4'-fluorobiphenyl-4-yl)methyl)-5-oxa-2,6-diazaspiro[3.4]oct-6-en-7-yl)piperidine-4-carboxylic acid 2 M aqueous sodium hydroxide solution (3.5 mL) was added to a solution of ethyl 1-(2-((2,6-diethoxy-4'-fluorobiphenyl-4-yl)methyl)-5-oxa-2,6-diazaspiro[3.4]oct-6-en-7-yl)-4-methylpiperidine-4-carboxylate (658 mg) in ethanol (6 mL), and the resultant was stirred for 1 hour at 60° C. After the reaction mixture was cooled to room temperature, it was neutralized with 2 M hydrochloric acid, was stirred for 30 minutes, and then the precipitated solid was collected by filtration. After the obtained solid was stirred for 30 minutes at 70° C. in hydrous ethanol, the obtained solid was collected by filtration, and it was washed with hydrous ethanol, thereby obtaining the title compound (566 mg).

$^1$H NMR (400 MHz, DMSO-$d_6$) δ 1.09-1.19 (9H, m), 1.37 (2H, t, J=9.8 Hz), 1.91 (2H, d, J=13.3 Hz), 2.88 (2H, t, J=10.4 Hz), 3.16 (2H, d, J=8.2 Hz), 3.23-3.38 (4H, m), 3.46 (2H, d, J=7.9 Hz), 3.57 (2H, s), 3.95 (4H, q, J=7.0 Hz), 6.61 (2H, s), 7.10-7.19 (2H, m), 7.22-7.31 (2H, m).

Example 9

1-(2-((1-Ethyl-1H-indol-6-yl)methyl)-5-oxa-2,6-diazaspiro[3.4]oct-6-en-7-yl)piperidine-4-carboxylic acid A) 1-ethyl-1H-indole-6-carbaldehyde Potassium tert-butoxide (170 mg) was added to a solution of 1H-indole-6-carbaldehyde (200 mg) in THF (10 mL), the resultant was stirred for 20 minutes at room temperature, and iodoethane (236 mg) was added thereto, and the resultant was further stirred for 1 hour. The reaction mixture was diluted by ethyl acetate, the resultant was sequentially washed with water and a saturated saline solution. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (196 mg).

$^1$H NMR (400 MHz, DMSO-$d_6$) δ 1.41 (3H, t, J=7.2 Hz), 4.33 (2H, q, J=7.2 Hz), 6.58 (1H, d, J=3.0 Hz), 7.56 (1H, d, J=8.3 Hz), 7.66-7.79 (2H, m), 8.13 (1H, s), 10.02 (1H, s).

B) Ethyl 1-(2-((l-ethyl-1H-indol-6-yl)methyl)-5-oxa-2,6-diazaspiro[3.4]oct-6-en-7-yl)piperidine-4-carboxylate Using 1-ethyl-1H-indol-6-carbaldehyde and tert-butyl 7-(4-(ethoxycarbonyl)piperidin-1-yl)-5-oxa-2,6-diazaspiro[3.4]oct-6-ene-2-carboxylate, the title compound was obtained in the similar manner as in Step G of Example 1.

MS (ESI+): $[M+H]^+$ 425.4.

C) 1-(2-((1-Ethyl-1H-indol-6-yl)methyl)-5-oxa-2,6-diazaspiro[3.4]oct-6-en-7-yl)piperidine-4-carboxylic acid Using ethyl 1-(2-((1-ethyl-1H-indol-6-yl)methyl)-5-oxa-2,6-diazaspiro[3.4]oct-6-en-7-yl)piperidine-4-carboxylate, the title compound was obtained in the similar manner as in Example 2.

Example 10

1-(2-((3-Chloro-1-ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylic acid A) 4-(1-Ethyl-1H-pyrrol-2-yl)-3-(methoxycarbonyl)buta-3-enoic acid Potassium tert-butoxide (35.4 g) was added to a solution of 1H-pyrrole-2-carbaldehyde (25.0 g) in THF (300 mL), the resultant was stirred for 10 minutes at room temperature, iodoethane (49.2 g) was added thereto, and the resultant was stirred for 1 hour at 70° C. The reaction mixture was diluted by ethyl acetate, and was sequentially washed with water and a saturated saline solution. After the obtained organic layer was dried over anhydrous magnesium sulfate, the solvent was distilled off under reduced pressure. Potassium tert-butoxide (71.1 g) was added to a solution of the obtained residue and dimethylsuccinate (69.4 g) in THF (500 mL), and the resultant was heated to reflux for 1 hour. The solvent of the reaction mixture was distilled of to ⅓ amount under reduced pressure, and it was diluted by hexane and water. After a pH of the aqueous layer was adjusted to pH 1 with 6 M hydrochloric acid, extraction thereof was performed using ethyl acetate. After the obtained organic layer was dried over anhydrous magnesium sulfate, the solvent was distilled off under reduced pressure. The obtained residue was crystallized (hexane/ethyl acetate), thereby obtaining the title compound (50.5 g).

$^1$H NMR (400 MHz, DMSO-$d_6$) δ 1.27 (3H, t, J=7.2 Hz), 3.41-3.54 (2H, m), 3.73 (3H, s), 4.06 (2H, q, J=7.1 Hz), 6.15-6.24 (1H, m), 6.38-6.45 (1H, m), 7.05-7.15 (1H, m), 7.58-7.71 (1H, m), 12.40 (1H, brs).

B) Methyl 1-ethyl-4-hydroxy-1H-indole-6-carboxylate

A solution of 4-(1-ethyl-1H-pyrrol-2-yl)-3-(methoxycarbonyl)buta-3-enoic acid (50.0 g), acetic acid (10 mL) and acetic anhydride (199 mL) in toluene (400 mL) was heated to reflux overnight. After the reaction mixture was cooled at 0° C., it was neutralized with an aqueous saturated sodium hydrogen carbonate solution, and then the resultant was separated. Extraction was performed on the aqueous layer using ethyl acetate, the collected organic layer was washed with a saturated saline solution, and it was dried over anhydrous magnesium sulfate. After the obtained organic layer was passed through a silica gel pad, it was concentrated under reduced pressure. Sodium methoxide (45.5 g) was added to a solution in which the obtained residue was dissolved in methanol (400 mL), and the resultant was heated to reflux for 1 hour. The reaction mixture was cooled to room temperature, and it was concentrated to ⅓ amount thereof under reduced pressure. The obtained residue was added to a mixed solution of ethyl acetate and 2 M hydrochloric acid at 0° C., and the resultant was separated. Extraction was performed on the aqueous layer using ethyl acetate, the collected organic layer was washed with a saturated saline solution, and it was passed through a short column of a silica gel (NH), and was concentrated. The obtained residue was washed with hexane, thereby obtaining the title compound (33.0 g).

$^1$H NMR (400 MHz, DMSO-$d_6$) δ 1.35 (3H, t, J=7.2 Hz), 3.83 (3H, s), 4.22 (2H, q, J=7.2 Hz), 6.53 (1H, d, J=3.0 Hz), 7.02 (1H, s), 7.45 (1H, d, J=3.0 Hz), 7.60 (1H, s), 9.79 (1H, brs).

C) Methyl 1-ethyl-4-(2,2,2-trifluoroethoxy)-1H-indole-6-carboxylate

Potassium carbonate (958 mg), methyl 1-ethyl-4-hydroxy-1H-indole-6-carboxylate (760 mg) and 2,2,2-trifluoroethyl trifluoromethanesulfonate (1.21 g) were added to DMF (5.0 mL), and the resultant was stirred for 1 hour at 80° C.

After the reaction mixture was cooled to room temperature, it was diluted by ethyl acetate, and was sequentially washed with water and a saturated saline solution. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (695 mg).

$^1$H NMR (400 MHz, DMSO-$d_6$) δ 1.36 (3H, t, J=7.2 Hz), 3.88 (3H, s), 4.29 (2H, q, J=7.2 Hz), 4.94 (2H, q, J=8.9 Hz), 6.53 (1H, d, J=2.9 Hz), 7.22 (1H, s), 7.59 (1H, d, J=2.9 Hz), 7.89 (1H, s).

D) 1-Ethyl-4-(2,2,2-trifluoroethoxy)-1H-indole-6-carbaldehyde

Under ice-cooling, methyl 1-ethyl-4-(2,2,2-trifluoroethoxy)-1H-indole-6-carboxylate (690 mg) was added to a suspension of lithium aluminum hydride (174 mg) in THF (30 mL), and the resultant was stirred for 30 minutes. Sodium sulfate decahydrate was added to the reaction mixture, the resultant was stirred for 1 hour at room temperature, and then insoluble matter was separated by filtration. Manganese dioxide (1.99 g) was added to the obtained filtrate, and the resultant was stirred overnight at room temperature. After the catalyst was filtered of the filtrate was concentrated under reduced pressure. The obtained residue was washed with hexane, thereby obtaining the title compound (505 mg).

$^1$H NMR (400 MHz, DMSO-$d_6$) δ 1.40 (3H, t, J=7.2 Hz), 4.33 (2H, q, J=7.2 Hz), 4.96 (2H, q, 8.8 Hz), 6.56 (1H, d, J=2.9 Hz), 7.14 (1H, s), 7.67 (1H, d, J=2.8 Hz), 7.94 (1H, s), 9.98 (1H, s).

E) 3-Chloro-1-ethyl-4-(2,2,2-trifluoroethoxy)-1H-indole-6-carbaldehyde

N-chlorosuccinimide (269 mg) was added to a solution of 1-ethyl-4-(2,2,2-trifluoroethoxy)-1H-indole-6-carbaldehyde (496 mg) in acetonitrile (5.0 mL), and the resultant was stirred for 1 hour at room temperature. The reaction mixture was concentrated under reduced pressure, and the obtained residue was purified by a silica gel column chromatography (hexane/ethyl acetate), thereby obtaining the title compound (432 mg).

MS (ESI+): $[M+H]^+$ 306.0.

F) Ethyl 4-methyl-1-(5-oxa-2,6-diazaspiro[3.4]oct-6-en-7-yl)piperidine-4-carboxylate hydrochloride Using tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step E of Example 3.

$^1$H NMR (400 MHz, DMSO-$d_6$) δ 1.07-1.23 (6H, m), 1.36-1.47 (2H, m), 1.94 (2H, d, J=13.3 Hz), 2.88 (2H, t, J=10.5 Hz), 3.22-3.33 (2H, m), 3.42 (2H, s), 3.98-4.24 (6H, m), 9.26 (1H, brs), 9.42 (1H, brs).

G) Ethyl 1-(2-((3-chloro-1-ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylate Using ethyl 4-methyl-1-(5-oxa-2,6-diazaspiro[3.4]oct-6-en-7-yl)piperidine-4-carboxylate hydrochloride and 3-chloro-1-ethyl-4-(2,2,2-trifluoroethoxy)-1H-indole-6-carbaldehyde, the title compound was obtained in the similar manner as in Step F of Example 3.

MS (ESI+): $[M+H]^+$ 571.6.

H) 1-(2-((3-Chloro-1-ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylic acid Using ethyl 1-(2-((3-chloro-1-ethyl-4-(2,2,2-tifluoroethoxy)-1H-indol-6-yl)methyl)-5-oxa-2,6-diazaspiro[3.4]oct-6-en-7-yl)-4-methylpiperidine-4-carboxylate, the title compound was obtained in the similar manner as in Example 2.

Example 11

1-(2-((2,6-Diethoxy-4'-fluorobiphenyl-4-yl)methyl)-5-oxa-2,6-diazaspiro[3.4]oct-6-en-7-yl)pyrrolidine-3-carboxylic acid A) tert-Butyl 7-(3-(methoxycarbonyl)pyrrolidin-1-yl)-5-oxa-2,6-diazaspiro[3.4]oct-6-ene-2-carboxylate Using methylpyrrolidine 3-carboxylate hydrochloride and tert-butyl 7-bromo-5-oxa-2,6-diazaspiro[3.4]oct-6-ene-2-carboxylate, the title compound was obtained in the similar manner as in Step F of Example 1.

MS (ESI+): $[M+H]^+$ 340.3.

B) Methyl 1-(2-((2,6-diethoxy-4'-fluorobiphenyl-4-yl)methyl)-5-oxa-2,6-diazaspiro[3.4]oct-6-en-7-yl)pyrrolidine-3-carboxylate Using tert-butyl 7-(3-(methoxycarbonyl)pyrrolidin-1-yl)-5-oxa-2,6-diazaspiro[3.4]oct-6-ene-2-carboxylate and 2,6- diethoxy-4'-fluorobiphenyl-4-carbaldehyde, the title compound was obtained in the similar manner as in Step G of Example 1.

MS (ESI+): $[M+H]^+$ 512.5.

C) 1-(2-((2,6-Diethoxy-4'-fluorobiphenyl-4-yl) methyl)-5-oxa-2,6-diazaspiro[3.4]oct-6-en-7-yl) pyrrolidine-3-carboxylic acid Using methyl 1-(2-((2,6-diethoxy-4'-fluorobiphenyl-4-yl) methyl)-5-oxa-2,6-diazaspiro[3.4]oct-6-en-7-yl)pyrrolidine-3-carboxylate, the title compound was obtained in the similar manner as in Example 2.

$^1H$ NMR (400 MHz, DMSO-$d_6$) δ 1.15 (6H, t, J=6.9 Hz), 1.95-2.16 (2H, m), 3.01-3.12 (1H, m), 3.12-3.52 (10H, m), 3.58 (2H, s), 3.95 (4H, q, J=6.9 Hz), 6.61 (2H, s), 7.10-7.18 (2H, m), 7.23-7.31 (2H, m).

Example 12

1-(2-((2,6-Diethoxy-4'-fluorobiphenyl-4-yl)methyl)-8-methyl-5-oxa-2,6-diazaspiro[3.4]oct-6-en-7-yl)-4-methylpiperidine-4-carboxylic acid A) tert-Butyl 7-(4-(ethoxycarbonyl)-4-methylpiperidin-1-yl)-8-methyl-5-oxa-2,6-diazaspiro[3.4]oct-6-ene-2-carboxylate Lithium bis(timethylsilyl)amide (1 M THF solution, 5.44 mL) was added to a solution of tert-butyl 7-(4-(ethoxycarbonyl)piperidin-1-yl)-5-oxa-2,6-diazaspiro[3.4]oct-6-ene-2-carboxylate (1.00 g) in THE (10 mL) in the range of −15° C. to −5° C., the resultant was stirred for 1 hour in the range of −10° C. to 0° C., and then iodomethane (0.339 mL) was added thereto. After the reaction mixture was stirred for 1 hour at room temperature in a nitrogen atmosphere, an aqueous saturated sodium hydrogen carbonate solution was added thereto at 0° C., and extraction thereof was performed using ethyl acetate. The obtained organic layer was washed with a saturated saline solution, dried over anhydrous magnesium sulfate, and then the solvent was distilled off under reduced pressure. After the obtained residue was purified by a silica gel column chromatography (hexane/ethyl acetate), crystallization (hexane/ethyl acetate) was performed, thereby obtaining the title compound (320 mg).

$^1H$ NMR (400 MHz, DMSO-$d_6$) δ 1.02 (3H, d, J=7.2 Hz), 1.16 (3H, s), 1.19 (3H, t, J=7.1 Hz), 1.32-1.49 (11H, m), 1.88-2.01 (2H, m), 2.88 (2H, t, J=10.6 Hz), 3.26-3.40 (3H, m), 3.70 (1H, d, J=8.7 Hz), 3.75-3.91 (2H, m), 4.06-4.18 (3H, m).

B) Ethyl 1-(2-((2,6-diethoxy-4'-fluorobiphenyl-4-yl) methyl)-8-methyl-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-8-methyl-5-oxa-2,6-diazaspiro[3.4]oct-6-ene-2-carboxylate (320 mg) was added to formic acid (2 mL), the resultant was stirred for 1 hour at 60° C., and then the solvent was distilled off under reduced pressure. Sodium triacetoxyborohydride (257 mg) was added to a solution of the obtained residue and 2,6-diethoxy-4'-fluorobiphenyl-4-carbaldehyde (233 mg) in THF (5 mL), and the resultant was stirred for 1 hour at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (380 mg).

$^1H$ NMR (400 MHz, DMSO-$d_6$) δ 1.05 (3H, d, J=7.0 Hz), 1.09-1.21 (12H, m), 1.33-1.51 (2H, m), 1.88-2.01 (2H, m), 2.82-2.93 (2H, m), 3.02-3.17 (2H, m), 3.25-3.38 (4H, m), 3.53 (1H, d, J=8.2 Hz), 3.58 (2H, s), 3.95 (4H, q, J=6.9 Hz), 4.11 (2H, q, J=7.1 Hz), 6.61 (2H, s), 7.10-7.19 (2H, m), 7.23-7.32 (2H, m).

C) 1-(2-((2,6-Diethoxy-4'-fluorobiphenyl-4-yl) methyl)-8-methyl-5-oxa-2,6-diazaspiro[3.4]oct-6-en-7-yl)-4-methylpiperidine-4-carboxylate 2 M aqueous sodium hydroxide solution (3.0 mL) was added to a solution of ethyl 1-(2-((2,6-diethoxy-4'-fluorobiphenyl-4-yl)methyl)-8-methyl-5-oxa-2,6-diazaspiro[3.4]oct-6-en-7-yl)-4-methylpiperidine-4-carboxylate (360 mg) in ethanol (4 mL), and the resultant was Mined for 2 hours at 60° C. After the reaction mixture was cooled to room temperature, it was neutralized with 2 M hydrochloric acid and 1 M hydrochloric acid, and the resultant was stirred for 30 minutes. The precipitated solid was collected by filtration, and it was washed with water, thereby obtaining the title compound (290 mg).

$^1H$ NMR (400 MHz, DMSO-$d_6$) δ 1.05 (3H, d, J=7.0 Hz), 1.09-1.19 (9H, m), 1.27-1.45 (2H, m), 1.92 (2H, t, J=13.6 Hz), 2.89 (2H, t, J=10.5 Hz), 3.06 (1H, d, J=7.2 Hz), 3.13 (1H, d, J=8.3 Hz), 3.19-3.43 (4H, m), 3.53 (1H, d, J=8.2 Hz), 3.59 (2H, s), 3.95 (4H, q, J=6.9 Hz), 6.61 (2H, s), 7.10-7.19 (2H, m), 7.22-7.31 (2H, m), 12.44 (1H, brs).

Example 13

1-(2-((2,6-Diethoxy-4'-fluorobiphenyl-4-yl)methyl)-5-oxa-2,6-diazaspiro[3.4]oct-6-en-7-yl)piperidine-4-carboxylic acid A) tert-Butyl 7-(3-(ethoxycarbonyl)piperidin-1-yl)-5-oxa-2,6-diazaspiro[3.4]oct-6-ene-2-carboxylate Using ethylpiperidine-3-carboxylate and tert-butyl 7-bromo-5-oxa-2,6-diazaspiro[3.4]oct-6-ene-2-carboxylate, the title compound was obtained in the similar manner as in Step F of Example 1.

MS (ESI+): $[M+H]^+$ 368.4.

B) Ethyl 1-(2-((2,6-diethoxy-4'-fluorobiphenyl-4-yl) methyl)-5-oxa-2,6-diazaspiro[3.4]oct-6-en-7-yl)piperidine-3-carboxylate Using tert-butyl 7-(3-(ethoxycarbonyl)piperidin-1-yl)-5-oxa-2,6-diazaspiro[3.4]oct-6-ene-2-carboxylate and 2,6-diethoxy-4'-fluorobiphenyl-4-carbaldehyde, the title compound was obtained in the similar manner as in Step G of Example 1.

MS (ESI+): $[M+H]^+$ 540.6.

C) 1-(2-((2,6-Diethoxy-4'-fluorobiphenyl-4-yl) methyl)-5-oxa-2,6-diazaspiro[3.4]oct-6-en-7-yl) piperidine-3-carboxylic acid Using ethyl 1-(2-((2,6-diethoxy-4'-fluorobiphenyl-4-yl) methyl)-5-oxa-2,6-diazaspiro[3.4]oct-6-en-7-yl)piperidine-3-carboxylate, the title compound was obtained in the similar manner as in Example 2.

Example 14

1-(2-((2,6-Diethoxy-4'-fluorobiphenyl-4-yl)methyl)-5-oxa-2,6-diazaspiro[3.4]oct-6-en-7-yl)-4-fluoropiperidine-4-carboxylic acid

A) tert-Butyl 7-(4-(ethoxycarbonyl)-4-fluoropiperidin-1-yl)-5-oxa-2,6-diazaspiro[3.4]oct-6-ene-2-carboxylate Using ethyl 4-fluoropiperidine-4-carboxylate hydrochloride and tert-butyl 7-bromo-5-oxa-2,6-diazaspiro[3.4]oct-6-ene-2-carboxylate, the title compound was obtained in the similar manner as in Step F of Example 1.

MS (ESI+): $[M+H]^+$ 386.4.

B) Ethyl 1-(2-((2,6-diethoxy-4'-fluorobiphenyl-4-yl)methyl)-5-oxa-2,6-diazaspiro[3.4]oct-6-en-7-yl)-4-fluoropiperidine-4-carboxylate Using tert-butyl 7-(4-(ethoxycarbonyl)-4-fluoropiperidin-1-yl)-5-oxa-2,6-diazaspiro[3.4]oct-6-ene-2-carboxylate and 2,6-diethoxy-4'-fluorobiphenyl-4-carbaldehyde, the title compound was obtained in the similar manner as in Step G of Example 1.

MS (ESI+): $[M+H]^+$ 558.6.

C) 1-(2-((2,6-Diethoxy-4'-fluorobiphenyl-4-yl)methyl)-5-oxa-2,6-diazaspiro[3.4]oct-6-en-7-yl)-4-fluoropiperidine-4-carboxylic acid Using ethyl 1-(2-((2,6-diethoxy-4'-fluorobiphenyl-4-yl)methyl)-5-oxa-2,6-diazaspiro[3.4]oct-6-en-7-yl)-4-fluoropiperidine-4-carboxylate, the title compound was obtained in the similar manner as in Example 2.

Example 15

3-(1-(2-((2,6-Diethoxy-4'-fluorobiphenyl-4-yl)methyl)-5-oxa-2,6-diazaspiro[3.4]oct-6-en-7-yl)piperidin-4-yl)propionic acid

A) Benzyl 4-((1E)-3-ethoxy-3-oxoprop-1-en-1-yl)piperidine-1-carboxylate

Potassium tert-butoxide (2.04 g) was added to a solution of ethyl(diethoxyphosphoryl)acetate (3.54 g) in THE (40 mL), the resultant was stirred for 40 minutes at room temperature, and then benzyl 4-formylpiperidine-1-carboxylate (3.00 g) was added thereto. After 1-hour stirring at room temperature, the mixture was diluted by ethyl acetate and an aqueous ammonium chloride solution. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.50 g).

$^1$H NMR (400 MHz, $CDCl_3$) δ 1.29 (3H, t, J=7.2 Hz), 1.37 (2H, d, J=11.0 Hz), 1.75 (2H, d, J=11.9 Hz), 2.31 (1H, dd, J=7.0, 3.6 Hz), 2.85 (2H, brs), 4.13-4.26 (4H, m), 5.13 (2H, s), 5.80 (1H, dd, J=15.8, 1.1 Hz), 6.88 (1H, dd, J=15.8, 6.5 Hz), 7.28-7.41 (5H, m).

B) Ethyl 3-(piperidin-4-yl)propanoate

Using benzyl 4-((1E)-3-ethoxy-3-oxoprop-1-en-1-yl)piperidine-1-carboxylate, the title compound was obtained in the similar manner as in Step C of Example 7.

$^1$H NMR (400 MHz, $CDCl_3$) δ 1.09-1.29 (5H, m), 1.32-1.46 (1H, m), 1.58 (2H, q, J=7.3 Hz), 1.70 (2H, d, J=12.9 Hz), 2.32 (2H, t, J=7.8 Hz), 2.52-2.67 (2H, m), 3.10 (2H, d, J=12.3 Hz), 3.18 (1H, brs), 4.13 (2H, q, J=7.1 Hz).

C) tert-Butyl 7-(4-(3-ethoxy-3-oxopropyl)piperidin-1-yl)-5-oxa-2,6-diazaspiro[3.4]oct-6-ene-2-carboxylate Using ethyl 3-(piperidin-4-yl)propanoate and tert-butyl 7-bromo-5-oxa-2,6-diazaspiro[3.4]oct-6-ene-2-carboxylate, the title compound was obtained in the similar manner as in Step F of Example 1.

$^1$H NMR (400 MHz, $CDCl_3$) δ 1.13-1.29 (5H, m), 1.38-1.47 (10H, m), 1.55-1.64 (2H, m), 1.71 (2H, d, J=12.4 Hz), 2.32 (2H, t, J=7.6 Hz), 2.79 (2H, t, J=12.2 Hz), 3.19 (2H, s), 3.57 (2H, d, J=12.7 Hz), 3.98 (2H, d, J=9.5 Hz), 4.13 (2H, q, J=7.0 Hz), 4.20 (2H, d, J=9.5 Hz).

D) Ethyl 3-(1-(2-((2,6-diethoxy-4'-fluorobiphenyl-4-yl)methyl)-5-oxa-2,6-diazaspiro[3.4]oct-6-en-7-yl)piperidin-4-yl)propanoate Using tert-butyl 7-(4-(3-ethoxy-3-oxopropyl)piperidin-1-yl)-5-oxa-2,6-diazaspiro[3.4]oct-6-ene-2-carboxylate and 2,6-diethoxy-4'-fluorobiphenyl-4-carbaldehyde, the title compound was obtained in the similar manner as in Step G of Example 1.

MS (ESI+): $[M+H]^+$ 568.6.

E) 3-(1-(2-((2,6-Diethoxy-4'-fluorobiphenyl-4-yl)methyl)-5-oxa-2,6-diazaspiro[3.4]oct-6-en-7-yl)piperidin-4-yl)propionic acid Using ethyl 3-(1-(2-((2,6-diethoxy-4'-fluorobiphenyl-4-yl)methyl)-5-oxa-2,6-diazaspiro[3.4]oct-6-en-7-yl)piperidin-4-yl)propanoate, the title compound was obtained in the similar manner as in Example 2.

Example 16

1-(2-((2-Ethoxy-4'-fluoro-6-methylbiphenyl-4-yl)methyl)-5-oxa-2,6-diazaspiro[3.4]oct-6-en-7-yl)-4-methylpiperidine-4-carboxylic acid

A) Ethyl 4-bromo-3,5-dihydroxybenzoate

A mixture of 4-bromo-3,5-dihydroxybenzoic acid (150 g), concentrated sulfuric acid (5 mL) and ethanol (1000 mL) was heated to reflux for 24 hours, and the solvent was distilled off under reduced pressure. The residue was diluted by ethyl acetate, the resultant was sequentially washed with water, an aqueous saturated sodium hydrogen carbonate solution and a saturated saline solution. After the obtained organic layer was dried over anhydrous magnesium sulfate, the solvent was distilled off under reduced pressure. The obtained residue was washed with hexane, thereby obtaining the title compound (157 g).

$^1$H NMR (300 MHz, $CDCl_3$) δ 1.39 (3H, t, J=7.13 Hz), 4.37 (2H, q, J=7.18 Hz), 5.87 (2H, brs.), 7.32 (2H, s).

B) Ethyl 4-bromo-3-ethoxy-5-hydroxybenzoate

A mixture of iodoethane (15.3 mL), potassium carbonate (26.5 g), ethyl 4-bromo-3,5-dihydroxybenzoate (50.0 g) and DMF (250 mL) was stirred for 15 hours at 50° C. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (19.8 g).

$^1$H NMR (300 MHz, $CDCl_3$) δ 1.39 (3H, t, J=7.13 Hz), 1.48 (3H, t, J=6.99 Hz), 4.16 (2H, q, J=6.99 Hz), 4.37 (2H, q, J=7.08 Hz), 5.74 (1H, s), 7.13 (1H, d, J=1.79 Hz), 7.34 (1H, d, J=1.79 Hz).

C) Ethyl 4-bromo-3-ethoxy-5-((2-methoxyethoxy)methoxy)benzoate 1-(Chloromethoxy)-2-methoxyethane (7.64 mL) was added dropwise to a mixture of potassium carbonate (4.62 g), ethyl 4-bromo-3-ethoxy-5-hydroxybenzoate (9.67 g) and DMF (200 mL). The reaction mixture was stirred for 3 days at room temperature. Water was added to the reaction mixture, and extraction thereof was performed using ethyl acetate. The organic layer was sequentially washed with water and a saturated saline solution, dried over anhydrous magnesium sulfate, passed through a short column of a silica gel (NI-1), and then the solvent was distilled off under reduced pressure. The obtained residue was purified by a silica gel column chromatography (hexane/ethyl acetate), thereby obtaining the title compound (10.34 g).

$^1$H NMR (300 MHz, $CDCl_3$) δ 1.39 (3H, t, J=7.13 Hz), 1.49 (3H, t, J=6.99 Hz), 3.38 (3H, s), 3.53-3.64 (2H, m), 3.83-3.96 (2H, m), 4.17 (2H, q, J=6.99 Hz), 4.37 (2H, q, J=7.11 Hz), 5.39 (2H, s), 7.22-7.28 (1H, m), 7.45 (1H, d, J=1.70 Hz).

D) Ethyl 2-ethoxy-4'-fluoro-6-((2-methoxyethoxy)biphenyl-4-carboxylate

A mixture of ethyl 4-bromo-3-ethoxy-5-((2-methoxyethoxy)methoxy)benzoate (10.4 g), (4-fluorophenyl)boronic acid (4.63 g), tetrakistriphenylphosphine palladium(0) (1.59 g), sodium carbonate (7.01 g), DME (150 mL) and water (100 mL) was stirred for 15 hours at 80° C. in a nitrogen atmosphere. Water was added to the reaction mixture, and extraction thereof was performed using ethyl acetate. The organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (7.45 g).

$^1$H NMR (300 MHz, $CDCl_3$) δ 1.21-1.32 (3H, m), 1.36-1.43 (3H, m), 3.36 (3H, s), 3.43-3.50 (2H, m), 3.59-3.65 (2H, m), 4.04 (2H, q, J=6.99 Hz), 4.40 (2H, q, J=6.80 Hz), 5.17 (2H, s), 7.00-7.15 (2H, m), 7.28-7.40 (3H, m), 7.51 (1H, d, J=1.42 Hz).

E) (2-Ethoxy-4'-fluoro-6-((2-methoxyethoxy)methoxy)biphenyl-4-yl)methanol

Lithium aluminum hydride (721 mg) was added to a mixture of ethyl 2-ethoxy-4'-fluoro-6-((2-methoxyethoxy)methoxy)biphenyl-4-carboxylate (7.45 g) and THF (100 mL) at 0° C., and the resultant was stirred for 30 minutes at the same temperature. Sodium sulfate decahydrate (6.12 g) was added to the reaction mixture at room temperature, and the reaction mixture was stirred for 10 minutes at room temperature. The reaction mixture was diluted by ethyl acetate, was stirred for 1 hour at room temperature, and then it was filtered using celite. The filtrate was concentrated under reduced pressure, and the obtained residue was purified by a silica gel column chromatography (hexane/ethyl acetate), thereby obtaining the title compound (5.40 g).

$^1$H NMR (300 MHz, $CDCl_3$) δ 1.20-1.27 (3H, m), 3.34 (3H, s), 3.43-3.50 (2H, m), 3.60-3.67 (2H, m), 3.94-4.03 (2H, m), 4.66-4.72 (2H, m), 5.13 (2H, s), 6.72 (1H, s), 6.85-6.89 (1H, m), 7.02-7.10 (2H, m), 7.27-7.33 (2H, m).

F) 2-Ethoxy-4'-fluoro-6-((2-methoxyethoxy)methoxy)biphenyl-4-carbaldehyde

Sulfur trioxide-pyridine complex (7.36 g) was added to a mixture of (2-ethoxy-4'-fluoro-6-((2-methoxyethoxy)methoxy)biphenyl-4-yl)methanol (5.40 g), triethylamine (9.67 mL) and DMSO (100 mL) at room temperature, and the resultant was stirred for 1 hour at the same temperature. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (4.84 g).

$^1$H NMR (300 MHz, $CDCl_3$) δ 1.23-1.34 (3H, m), 3.35 (3H, s), 3.49 (2H, dd, J=5.52, 3.73 Hz), 3.67 (2H, dd, J=5.48, 3.78 Hz), 3.98-4.12 (2H, m), 5.21 (2H, s), 7.09 (2H, t, J=8.59 Hz), 7.20 (1H, s), 7.28-7.35 (2H, m), 7.39 (1H, s), 9.94 (1H, s).

G) 2-Ethoxy-4'-fluoro-6-hydroxybiphenyl-4-carbaldehyde

A mixture of 2-ethoxy-4'-fluoro-6-((2-methoxyethoxy)methoxy)biphenyl-4-carbaldehyde (4.84 g), 6 M hydrochloric acid (50 mL) and methanol (50 mL) was stirred for 1 hour at 80° C. Water was added to the reaction mixture, and extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining a solid. Fractionation was performed on the obtained solid using HPLC (C18, mobile phase: water/acetonitrile (5 mM ammonium acetate-containing system)), and the obtained fraction was concentrated. 1 M hydrochloric acid was added to the residue to acidify, and extraction thereof was performed using ethyl acetate. The organic layer was washed with a saturated saline solution, dried over anhydrous magnesium sulfate, and then the solvent was distilled off under reduced pressure. The obtained residue was washed with hexane, thereby obtaining the title compound (2.20 g).

$^1$H NMR (300 MHz, $CDCl_3$) δ 1.24-1.31 (3H, m), 4.06 (2H, q, J=7.02 Hz), 5.16 (1H, s), 7.07 (1H, d, J=1.32 Hz), 7.13 (1H, d, J=1.42 Hz), 7.16-7.24 (2H, m), 7.31-7.42 (2H, m), 9.92 (1H, s).

H) 6-Ethoxy-4'-fluoro-4-formylbiphenyl-2-yl trifluoromethanesulfonate

Sodium hydride (60% dispersion in oil, 1.29 g) was added to a mixture of 2-ethoxy-4'-fluoro-6-hydroxybiphenyl-4-carbaldehyde (4.20 g) and DMF (50 mL) at 0° C. After the reaction mixture was stirred for 30 minutes at the same temperature, N-phenyl bis(trifluoromethanesulfonimide) (6.92 g) was added thereto, and the resultant was stirred for 1 hour at room temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (4.03 g).

$^1$H NMR (300 MHz, $CDCl_3$) δ 1.33 (3H, t, J=6.99 Hz), 4.13 (2H, q, J=6.99 Hz), 7.04-7.22 (2H, m), 7.28-7.40 (2H, m), 7.45-7.58 (2H, m), 9.99 (1H, s).

I) 2-Ethoxy-4'-fluoro-6-methylbiphenyl-4-carbaldehyde

A mixture of 6-ethoxy-4'-fluoro-4-formylbiphenyl-2-yl trifluoromethanesulfonate (1.00 g), methyl borate (458 mg), tetrakistriphenylphosphine palladium (147 mg), sodium carbonate (1.35 g), DME (3 mL) and water (2 mL) was stirred for 1 hour at 100° C. under microwave irradiation in a nitrogen atmosphere. Water was added to the reaction mixture, and extraction thereof was performed using ethyl acetate. The obtained organic layer was washed with a saturated saline solution, dried over anhydrous magnesium sulfate, and then the solvent was distilled off. The obtained residue was purified by a silica gel column chromatography (hexane/ethyl acetate), thereby obtaining the title compound (440 mg).

$^1$H NMR (300 MHz, $CDCl_3$) δ 1.23 (3H, t, J=6.99 Hz), 2.16 (3H, s), 4.03 (2H, q, J=6.99 Hz), 7.02-7.21 (4H, m), 7.29 (1H, s), 7.38 (1H, dd, J=1.37, 0.61 Hz), 9.96 (1H, s).

J) Ethyl 1-(2-((2-ethoxy-4'-fluoro-6-methylbiphenyl-4-yl)methyl)-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-5-oxa-2,6-diazaspiro[3.4]oct-6-ene-2-carboxylate (650 mg) and formic acid (10 mL) was stirred for 1 hour at 60° C. The solvent of the reaction mixture was distilled off under reduced pressure, toluene was added to the residue, and then the solvent was distilled off under reduced pressure again. After a mixture of the obtained residue, 2-ethoxy-4'-fluoro-6-methylbiphenyl-4-carbaldehyde (440 mg) and THF (30 mL) was stirred for 15 minutes at room temperature, sodium triacetoxyborohydride (542 mg) was added thereto at room temperature, and the resultant was stirred for 4 hours at room temperature. Water was added to the reaction mixture, and the resultant was stirred for 10 minutes. After an aqueous saturated sodium hydrogen carbonate solution was added to the reaction mixture, extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (730 mg).

MS (ESI+): $[M+H]^+$ 524.5.

K) 1-(2-((2-Ethoxy-4'-fluoro-6-methylbiphenyl-4-yl)methyl)-5-oxa-2,6-diazaspiro[3.4]oct-6-en-7-yl)-4-methylpiperidine-4-carboxylic acid A mixture of ethyl 1-(2-((2-ethoxy-4'-fluoro-6-methylbiphenyl-4-yl)methyl)-5-oxa-2,6-diazaspiro[3.4]oct-6-en-7-yl)-4-methylpiperidine-4-carboxylate (730 mg), 2 M aqueous sodium hydroxide solution (5 mL), ethanol (5 mL) and THF (5 mL) was stirred for 5 hours at 60° C. The reaction mixture was cooled to mom temperature, 2 M hydrochloric acid (5 mL) and water were added thereto, and the resultant was stirred for 30 minutes at room temperature. After the precipitated solid was collected by filtration, recrystallization (acetone/methanol) of the obtained solid was performed, thereby obtaining the title compound (410 mg).

$^1$H NMR (300 MHz DMSO-$d_6$) δ 1.04-1.18 (6H, m), 1.37 (2H, ddd, J=13.50, 9.91, 3.97 Hz), 1.91 (2H, d, J=13.69 Hz), 1.98 (3H, s), 2.79-2.99 (2H, m), 3.14 (2H, d, J=8.50 Hz), 3.21-3.37 (4H, m), 3.45 (2H, d, J=8.50 Hz), 3.55 (2H, s), 3.92 (2H, q, J=6.99 Hz), 6.79 (2H, d, J=3.78 Hz), 7.13-7.25 (4H, m), 12.41 (1H, br. s.).

Example 17

1-(2-((2-Ethoxy-4'-fluoro-6-((2,2,2-trifluoroethoxy)biphenyl-4-yl)methyl)-5-oxa-2,6-diazaspiro[3.4]oct-6-en-7-yl)-4-methylpiperidine-4-carboxylic acid A) 2-Ethoxy-4'-fluoro-6-((2,2,2-trifluoroethoxy)biphenyl-4-carbaldehyde Sodium hydride (60% dispersion in oil, 50.7 mg) was added to a mixture of 2-ethoxy-4'-fluoro-6-hydroxybiphenyl-4-carbaldehyde (300 mg) and DMF (5 mL) at 0° C. After the reaction mixture was stirred for 10 minutes at the same temperature, 1,1,1-trifluoro-2-iodoethane (0.136 mL) was added thereto. The reaction mixture was stirred for 1 hour at room temperature. Potassium carbonate (319 mg) and 2,2,2-trifluoroethyl trifluoromethanesulfonate (0.249 mL) were added to the reaction mixture at room temperature, and the resultant was stirred for 2 hours at 80° C. Water was added to the reaction mixture, and extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (350 mg).

$^1$H NMR (300 MHz, $CDCl_3$) δ 1.31 (3H, t, J=6.99 Hz), 4.03-4.13 (2H, m), 4.28 (2H, q, J=8.03 Hz), 7.02-7.16 (3H, m), 7.23 (1H, d, J=1.32 Hz), 7.28-7.38 (2H, m), 9.95 (1H, s).

B) Ethyl 1-(2-((2-ethoxy-4'-fluoro-6-((2,2,2-trifluoroethoxy)biphenyl-4-yl)methyl)-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-5-oxa-2,6-diazaspiro[3.4]oct-6-ene-2-carboxylate (189 mg) and formic acid (2 mL) was stirred for 1 hour at 60° C. The solvent of the reaction mixture was distilled off under reduced pressure, toluene was added to the residue, and then the solvent was distilled off under reduced pressure again. A mixture of the obtained residue, 2-ethoxy-4'-fluoro-6-((2,2,2-trifluoroethoxy)biphenyl-4-carbaldehyde (170 mg) and THF (10 mL) was stirred for 15 minutes at room temperature. Sodium triacetoxyborohydride (158 mg) was added to the reaction mixture, and the resultant was stirred for 2 hours at the same temperature. Water was added to the reaction mixture, and the resultant was stirred for 10 minutes. After an aqueous saturated sodium hydrogen carbonate solution was added to the reaction mixture, extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (NH, hexane/ethyl acetate), crystallization (hexane) was performed, thereby obtaining the title compound (170 mg).

MS (ESI+): $[M+H]^+$ 608.1.

C) 1-(2-((2-Ethoxy-4'-fluoro-6-((2,2,2-trifluoroethoxy)biphenyl-4-yl)methyl)-5-oxa-2,6-diazaspiro[3.4]oct-6-en-7-yl)-4-methylpiperidine-4-carboxylic acid A mixture of ethyl 1-(2-((2-ethoxy-4'-fluoro-6-((2,2,2-trifluoroethoxy)biphenyl-4-yl)methyl)-5-oxa-2,6-diazaspiro[3.4]oct-6-en-7-yl)-4-methylpiperidine-4-carboxylate (155 mg), 1 M aqueous sodium hydroxide solution (3 mL), ethanol (2 mL) and THF (2 mL) was stirred for 3 hours at 60° C. The reaction mixture was cooled to room temperature, 1 M hydrochloric acid (3 mL) and water were added thereto, and the resultant was stirred for 30 minutes at room temperature. After the precipitated solid was collected by filtration, recrystallization (acetone/methanol) of the obtained solid was performed, thereby obtaining the title compound (125 mg).

$^1$H NMR (300 MHz, DMSO-$d_6$) δ 1.09-1.21 (6H, m), 1.28-1.45 (2H, m), 1.91 (2H, d, J=13.50 Hz), 2.81-2.97 (2H, m), 3.18 (2H, d, J=8.50 Hz), 3.22-3.36 (4H, m), 3.47 (2H, d, J=8.59 Hz), 3.59 (2H, s), 3.98 (2H, q, J=6.99 Hz), 4.63 (2H, q, J=8.94 Hz), 6.73 (2H, s), 7.08-7.20 (2H, m), 7.22-7.35 (2H, m), 12.40 (1H, br. s.).

Example 18

4-Benzyl-1-(2-((2,6-diethoxy-4'-fluorobiphenyl-4-yl)methyl)-5-oxa-2,6-diazaspiro[3.4]oct-6-en-7-yl)piperidine-4-carboxylic acid A) 1-Benzyl 4-ethyl 4-benzylpiperidine-1,4-dicarboxylate Using (bromomethyl)benzene and 1-benzyl 4-ethyl piperidine-1,4-dicarboxylate, the title compound was obtained in the similar manner as in Step B of Example 7.

$^1$H NMR (400 MHz, DMSO-$d_6$) δ 1.13 (3H, t, J=7.1 Hz), 1.44 (2H, t, J=10.7 Hz), 1.93 (2H, d, J=13.3 Hz), 2.73-2.94 (4H, m), 3.87 (2H, d, J=13.6 Hz), 4.05 (2H, q, J=7.1 Hz), 5.06 (2H, s), 7.05 (2H, d, J=7.2 Hz), 7.17-7.40 (8H, m).

B) Ethyl 4-benzylpiperidine-4-carboxylate

Using 1-benzyl 4-ethyl 4-benzylpiperidine-1,4-dicarboxylate, the title compound was obtained in the similar manner as in Step C of Example 7.

$^1$H NMR (400 MHz, DMSO-$d_6$) δ 1.12 (3H, t, J=7.1 Hz), 1.29-1.41 (2H, m), 1.87 (2H, d, J=12.9 Hz), 2.42 (2H, t, J=11.2 Hz), 2.68-2.86 (4H, m), 3.12 (1H, brs), 4.03 (2H, q, J=7.0 Hz), 7.04 (2H, d, J=7.0 Hz), 7.16-7.29 (3H, m).

C) tert-Butyl 7-(4-benzyl-4-(ethoxycarbonyl)piperidin-1-yl)-5-oxa-2,6-diazaspiro[3.4]oct-6-ene-2-carboxylate Using ethyl 4-benzylpiperidine-4-carboxylate and tert-butyl 7-bromo-5-oxa-2,6-diazaspiro[3.4]oct-6-ene-2-carboxylate, the title compound was obtained in the similar manner as in Step F of Example 1.

MS (ESI+): $[M+H]^+$ 458.5.

D) Ethyl 4-benzyl-1-(2-((2,6-diethoxy-4'-fluorobiphenyl-4-yl)methyl)-5-oxa-2,6-diazaspiro[3.4]oct-6-en-7-yl)piperidine-4-carboxylate Using tert-butyl 7-(4-benzyl-4-(ethoxycarbonyl)piperidin-1-yl)-5-oxa-2,6-diazaspiro[3.4]oct-6-ene-2-carboxylate and 2,6-diethoxy-4'-fluorobiphenyl-4-carbaldehyde, the title compound was obtained in the similar manner as in Step G of Example 1.

$^1$H NMR (400 MHz, DMSO-$d_6$) δ 1.08-1.21 (9H, m), 1.51 (2H, t, J=10.6 Hz), 1.92 (2H, d, J=13.4 Hz), 2.74 (2H, t, J=11.9 Hz), 2.80 (2H, s), 3.15 (2H, d, J=7.4 Hz), 3.28 (2H, s), 3.36-3.49 (4H, m), 3.57 (2H, s), 3.94 (4H, q, J=6.8 Hz), 3.99-4.11 (2H, m), 6.61 (2H, s), 7.05 (2H, d, J=7.2 Hz), 7.10-7.18 (2H, m), 7.18-7.31 (5H, m).

E) 4-Benzyl-1-(2-((2,6-diethoxy-4'-fluorobiphenyl-4-yl)methyl)-5-oxa-2,6-diazaspiro[3.4]oct-6-en-7-yl)piperidine-4-carboxylic acid Using ethyl 4-benzyl-1-(2-((2,6-diethoxy-4'-fluorobiphenyl-4-yl)methyl)-5-oxa-2,6-diazaspiro[3.4]oct-6-en-7-yl)piperidine-4-carboxylate, the title compound was obtained in the similar manner as in Example 2.

Example 19

1-(2-((2,6-Diethoxy-4'-fluorobiphenyl-4-yl)methyl)-5-oxa-2,6-diazaspiro[3.4]oct-6-en-7-yl)-4-ethylpiperidine-4-carboxylic acid A) Ethyl 4-ethylpiperidine-4-carboxylate A solution of 1-benzyl 4-ethyl piperidine-1,4-dicarboxylate (10.0 g) in THF (100 mL) was cooled to −10° C., and lithium bistrimethylsilylamide (1 M THF solution, 62 mL) was added thereto. After the reaction mixture was stirred for 1 hour at −10° C., iodoethane (10.7 g) was added thereto, and the resultant was stirred overnight at room temperature in a nitrogen atmosphere. After an aqueous saturated sodium hydrogen carbonate solution was added to the reaction mixture at 0° C., extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining an oily matter. 20% palladium hydroxide (50% water content, 1.00 g) was added to a solution of the obtained oily matter in methanol (100 mL), and the resultant was stirred for 2 hours at room temperature in a hydrogen atmosphere. After the catalyst was filtered off, the filtrate was concentrated under reduced pressure, thereby obtaining the title compound (4.50 g).

$^1$H NMR (300 MHz, $CDCl_3$) δ 0.81 (3H, t, J=7.6 Hz), 1.27 (3H, t, J=7.1 Hz), 1.30-1.42 (2H, m), 1.55 (2H, q, J=7.6 Hz), 2.06-2.18 (2H, m), 2.60-2.73 (2H, m), 2.91-3.02 (2H, m), 4.18 (2H, q, J=7.1 Hz).

B) tert-Butyl 7-(4-(ethoxycarbonyl)-4-ethylpiperidin-1-yl)-5-oxa-2,6-diazaspiro[3.4]oct-6-ene-2-carboxylate tert-Butyl 7-bromo-5-oxa-2,6-diazaspiro[3.4]oct-6-ene-2-carboxylate (5.00 g), ethyl 4-ethylpiperidine-4-carboxylate (4.45 g) and sodium carbonate (5.46 g) were added to DMF (5 mL), and the resultant was stirred for 2 hours at 130° C. After the reaction mixture was cooled to room temperature, water was added thereto, and extraction thereof was performed using ethyl acetate. The obtained organic layer was washed with a saturated saline solution, dried over anhydrous magnesium sulfate, and then the solvent was distilled off under reduced pressure. After the obtained residue was purified by a silica gel column chromatography (hexane/ethyl acetate), crystallization (hexane/diisopropyl ether) was performed, thereby obtaining the title compound (5.14 g).

$^1$H NMR (300 MHz, DMSO-$d_6$) δ 0.75 (3H, t, J=7.5 Hz), 1.19 (3H, t, J=7.1 Hz), 1.30-1.44 (11H, m), 1.45-1.57 (2H, m), 1.97 (2H, d, J=13.5 Hz), 2.78 (2H, t, J=11.3 Hz), 3.25-3.41 (4H, m), 3.87 (2H, d, J=9.2 Hz), 4.02 (2H, d, J=9.4 Hz), 4.12 (2H, q, J=7.1 Hz).

C) Ethyl 1-(2-((2,6-diethoxy-4'-fluorobiphenyl-4-yl) methyl)-5-oxa-2,6-diazaspiro[3.4]oct-6-en-7-yl)-4-ethylpiperidine-4-carboxylate tert-Butyl 7-(4-(ethoxycarbonyl)-4-ethylpiperidin-1-yl)-5-oxa-2,6-diazaspiro[3.4]oct-6-ene-2-carboxylate (440 mg) was added to formic acid (2 mL), the resultant was stirred for 30 minutes at 60° C., and the solvent was distilled off under reduced pressure. Sodium triacetoxyborohydride (354 mg) was added to a solution of the obtained residue and 2,6-diethoxy-4'-fluorobiphenyl-4-carbaldehyde (321 mg) in THF (5.0 mL), and the resultant was stirred for 1 hour at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (500 mg).

MS (ESI+): $[M+14]^+$ 568.6.

D) 1-(2-((2,6-Diethoxy-4'-fluorobiphenyl-4-yl) methyl)-5-oxa-2,6-diazaspiro[3.4]oct-6-en-7-yl)-4-ethylpiperidine-4-carboxylic acid 2 M aqueous sodium hydroxide solution (3.0 mL) was added to a solution of ethyl 1-(2-((2,6-diethoxy-4'-fluorobiphenyl-4-yl)methyl)-5-oxa-2,6-diazaspiro[3.4]oct-6-en-7-yl)-4-ethylpiperidine-4-carboxylate (450 mg) in ethanol (6.0 mL). After the resultant was stirred for 1 hour at 60° C., 8 M aqueous sodium hydroxide solution (4.0 mL) was added thereto, and the resultant was stirred overnight at 80° C. After the reaction mixture was cooled to room temperature, it was neutralized with 6 M hydrochloric acid, and the precipitated solid was collected by filtration. The obtained solid was washed with ethanol and ethyl acetate, thereby obtaining the title compound (402 mg).

$^1$H NMR (400 MHz, DMSO-$d_6$) δ 0.78 (3H, t, J=7.3 Hz), 1.15 (6H, t, J=6.8 Hz), 1.34 (2H, t, J=10.4 Hz), 1.44-1.54 (2H, m), 1.93 (2H, d, J=12.8 Hz), 2.81 (2H, t, J=11.2 Hz), 3.16 (2H, d, J=7.3 Hz), 3.21-3.39 (4H, m), 3.46 (2H, d, J=7.5 Hz), 3.57 (2H, s), 3.90-3.99 (4H, m), 6.61 (2H, s), 7.14 (2H, t, J=8.5 Hz), 7.22-7.32 (2H, m).

Example 20

1-(2-((2-Ethoxy-4'-fluorobiphenyl-4-yl)methyl)-5-oxa-2,6-diazaspiro[3.4]oct-6-en-7-yl)-4-methylpiperidine-4-carboxylic acid A) Methyl 3-hydroxy-4-iodobenzoate 2 M hydrochloric acid (90 mL) was added to a solution of methyl 4-amino-3-hydroxybenzoate (6.00 g) in acetonitrile (30 mL), and the resultant was stirred for 30 minutes at 0° C. An aqueous solution (15 mL) of sodium nitrite (2.97 g) was added thereto, and the resultant was stirred for 30 minutes at 0° C. An aqueous solution of potassium iodide (23.8 g) was added to the reaction mixture, the resultant was stirred for 1 hour at 0° C., and then extraction thereof was performed using ethyl acetate. The obtained organic layer was washed with an aqueous saturated sodium carbonate solution and an aqueous saturated sodium thiosulfate solution, dried over anhydrous magnesium sulfate, and then the solvent was distilled off under reduced pressure. The obtained residue was purified by a silica gel column chromatography (hexane/ethyl acetate), thereby obtaining the title compound (8.10 g).

$^1$H NMR (400 MHz, DMSO-$d_6$) δ 3.82 (3H, s), 7.14 (1H, dd, J=8.0, 1.6 Hz), 7.43 (1H, d, J=1.6 Hz), 7.83 (1H, d, J=8.2 Hz), 10.80 (1H, brs).

B) Methyl 3-ethoxy-4-iodobenzoate

Using methyl 3-hydroxy-4-iodobenzoate and iodoethane, the title compound was obtained in the similar manner as in Step A of Example 1.

$^1$H NMR (400 MHz, $CDCl_3$) δ 1.50 (3H, t, J=7.0 Hz), 3.91 (3H, s), 4.16 (2H, q, J=6.9 Hz), 7.35 (1H, dd, J=8.2, 1.6 Hz), 7.42 (1H, d, J=1.3 Hz), 7.85 (1H, d, 8.0 Hz).

C) Methyl 2-ethoxy-4'-fluorobiphenyl-4-carboxylate

Using methyl 3-ethoxy-4-iodobenzoate and (4-fluorophenyl)boronic acid, the title compound was obtained in the similar manner as in Step B of Example 1.

$^1$H NMR (300 MHz, $CDCl_3$) δ 1.37 (3H, t, J=7.0 Hz), 3.94 (3H, s), 4.11 (2H, q, J=7.0 Hz), 7.06-7.14 (2H, m), 7.35 (1H, d, J=7.8 Hz), 7.51-7.57 (2H, m), 7.62 (1H, d, J 1.5 Hz), 7.69 (1H, dd, J=7.9, 1.6 Hz).

D) (2-ethoxy-4'-fluorobiphenyl-4-yl)methanol

A solution of methyl 2-ethoxy-4'-fluorobiphenyl-4-carboxylate (981 mg) in THF (10 mL) was added dropwise to a mixture of lithium aluminum hydride (285 mg) and THF (20 mL) at 0° C., and the resultant was stirred for 1 hour at room temperature. Water (0.5 mL), 1 M aqueous sodium hydroxide solution (0.5 mL) and water (1.5 mL) were sequentially added to the reaction mixture at 0° C., the resultant was filtered using celite, and then the filtrate was concentrated under reduced pressure. The obtained residue was purified by a silica gel column chromatography (hexane/ethyl acetate), thereby obtaining the title compound (880 mg).

$^1$H NMR (400 MHz, $CDCl_3$) δ 1.35 (3H, t, J=7.0 Hz), 1.74 (1H, brs), 4.06 (2H, q, J=6.9 Hz), 4.71 (2H, brs), 6.96-7.02 (2H, m), 7.08 (2H, t, J=8.7 Hz), 7.28 (1H, d, J=7.5 Hz), 7.51 (2H, dd, J=8.5, 5.5 Hz).

E) 2-Ethoxy-4'-fluorobiphenyl-4-carbaldehyde

Tetrapropylammonium perruthenate (62.8 mg) was added to a mixture of (2-ethoxy-4'-fluorobiphenyl-4-yl)methanol (880 mg), 4-methylmorpholine N-oxide (628 mg), a molecular sieve 4A (1.7 g) and acetonitrile (30 mL), and the resultant was stirred for 1 hour at room temperature. The reaction mixture was filtered using celite, and the filtrate was concentrated under reduced pressure. The obtained residue was purified by a silica gel column chromatography (hexane/ethyl acetate), thereby obtaining the title compound (647 mg).

$^1$H NMR (400 MHz, $CDCl_3$) δ 1.39 (3H, t, J=7.0 Hz), 4.13 (2H, q, J=6.9 Hz), 7.12 (2H, t, J=8.7 Hz), 7.43-7.59 (5H, m), 9.99 (1H, s).

F) Ethyl 1-(2-((2-ethoxy-4'-fluorobiphenyl-4-yl)methyl)-5-oxa-2,6-diazaspiro[3.4]oct-6-en-7-yl)-4-methylpiperidine-4-carboxylate Using ethyl 4-methyl-1-(5-oxa-2,6-diazaspiro[3.4]oct-6-en-7-yl)piperidine-4-carboxylate hydrochloride and 2-ethoxy-4'-fluorobiphenyl-4-carbaldehyde, the title compound was obtained in the similar manner as in Step F of Example 3.

MS (ESI+): $[M+H]^+$ 510.3.

G) 1-(2-((2-Ethoxy-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((2-ethoxy-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 21

1-(2-((1-(4-Fluorophenyl)-5-isopropyl-1H-pyrazolo[3,4-d][1,3]thiazole-3-yl)methy 1)-5-oxa-2,6-diazaspiro[3.4]oct-6-en-7-yl)-4-methylpiperidine-4-carboxylic acid A) Methyl 5-amino-1-(4-fluorophenyl)-1H-pyrazole-3-carboxylate Sulfuric acid (16 mL) was added to a mixture of potassium (1Z)-1-cyano-3-methoxy-3-oxoprop-1-ene-2-olate (41.0 g), (4-fluorophenyl)hydrazine hydrochloride (40.0 g) and THF (500 mL) at 0° C., and the resultant was stirred overnight at room temperature. The solvent was distilled off under reduced pressure, water was added to the obtained residue. The resultant was neutralized with sodium carbonate, and extraction thereof was performed using ethyl acetate. The organic layer was washed with a saturated saline solution, dried over anhydrous sodium sulfate, and then the solvent was distilled off under reduced pressure. The residue was purified by a silica gel column chromatography (hexane/ethyl acetate), thereby obtaining the title compound (7.50 g).

$^1$H NMR (400 MHz, $CDCl_3$) δ 3.82 (2H, brs), 3.91 (3H, s), 6.15 (1H, s), 7.16-7.21 (2H, m), 7.55-7.58 (2H, m).

B) Methyl 1-(4-fluorophenyl)-5-(isobutyrylamino)-1H-pyrazole-3-carboxylate

2-Methylpropanoyl chloride (3.30 g) was slowly added dropwise to a solution of methyl 5-amino-1-(4-fluorophenyl)-1H-pyrazole-3-carboxylate (7.50 g) and triethylamine (9.10 g) in dichloromethane (100 mL) at 0° C., and the resultant was stirred for 3 hours at 15° C. Water and ethyl acetate were added to the reaction mixture, and the organic layer was separated. The obtained organic layer was washed with a saturated saline solution, dried over anhydrous sodium sulfate, and then the solvent was distilled off under reduced pressure. The residue was purified by a silica gel column chromatography (hexane/ethyl acetate), thereby obtaining the title compound (7.60 g).

$^1$H NMR (400 MHz, $CDCl_3$) δ 1.15-1.20 (6H, m), 2.43-2.50 (1H, m), 3.92 (3H, s), 7.09 (1H, s), 7.10-7.20 (2H, m), 7.28 (1H, brs), 7.43-7.46 (2H, m).

C) Methyl 4-bromo-1-(4-fluorophenyl)-5-(isobutyrylamino)-1H-pyrazole-3-carboxylate N-bromosuccinimide (4.45 g) was added to a solution of methyl 1-(4-fluorophenyl)-5-(isobutyrylamino)-1H-pyrazole-3-carboxylate (7.60 g) in dichloromethane (100 mL), and the resultant was stirred for 3 hours at 20° C. After the reaction mixture was filtered, the solvent was distilled off, thereby obtaining the title compound (7.2 g).

$^1$H NMR (400 MHz, $CDCl_3$) δ 1.17 (6H, d, J=6.8 Hz), 2.43-2.50 (1H, m), 3.96 (3H, s), 6.83 (1H, brs), 7.11-7.15 (2H, m), 7.44-7.47 (2H, m).

D) Methyl 1-(4-fluorophenyl)-5-isopropyl-1H-pyrazolo[3,4-d][1,3]thiazole-3-carboxylate Lawessson's reagent (15.0 g) was added to a solution of methyl 4-bromo-1-(4-fluorophenyl)-5-(isobutyrylamino)-1H-pyrazole-3-carboxylate (7.20 g) in toluene (100 mL), and the resultant was stirred overnight at 100° C. After the reaction mixture was filtered, the solvent was distilled off under reduced pressure. Cesium carbonate (8.20 g), N,N'-dimethylethylenediamine (500 mg) and copper iodide (500 mg) were added to a solution of the obtained residue in diethyl ether (50 mL), and the resultant was stirred for 3 hours at 40° C. in a nitrogen atmosphere. After the reaction mixture was filtered, the filtrate was distilled off under reduced pressure, and the obtained residue was purified by a silica gel column chromatography (hexane/ethyl acetate), thereby obtaining the title compound (1.30 g).

$^1$H NMR (400 MHz, $CDCl_3$) δ 1.49 (6H, d, J=6.8 Hz), 3.38-3.44 (1H, m), 4.02 (3H, s), 7.18-7.22 (2H, m), 8.25-8.29 (2H, m).

E) (1-(4-Fluorophenyl)-5-isopropyl-1H-pyrazolo[3,4-d][1,3]thiazole-3-yl)methanol Sodium borohydride (1.37 g) was slowly added to a mixture of methyl 1-(4-fluorophenyl)-5-isopropyl-1H-pyrazolo[3,4-d][1,3]thiazole-3-carboxylate (1.30 g), calcium chloride (451 mg), THF (10 mL) and methanol (10 mL) at −30° C., and the resultant was stirred for 2 hours at 25° C. Water was added to the reaction mixture, the resultant was neutralized with 1 M hydrochloric acid, and extraction thereof was performed using ethyl acetate. The organic layer was washed with a saturated saline solution, dried over anhydrous sodium sulfate, and then the solvent was distilled off under reduced pressure. The residue was purified by a silica gel column chromatography (hexane/ethyl acetate), thereby obtaining the title compound (741 mg).

MS (ESI+): $[M+H]^+$ 292.0.

F) 1-(4-Fluorophenyl)-5-isopropyl-1H-pyrazolo[3,4-d][1,3]thiazole-3-carbaldehyde Triethylamine (0.574 mL) and sulfur trioxide-pyridine complex (437 mg) was added to a solution of (1-(4-fluorophenyl)-5-isopropyl-1H-pyrazolo[3,4-d][1,3]thiazole-3-yl) methanol (400 mg) in DMSO (10 mL), and the resultant was stirred for 30 minutes at room temperature. The reaction mixture was diluted by ethyl acetate, and was washed with a saturated saline solution. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (317 mg).

$^1$H NMR (400 MHz, $CDCl_3$) δ 1.50 (6H, d, J=6.9 Hz), 320-3.62 (1H, m), 7.17-7.31 (2H, m), 8.18-8.38 (2H, m), 10.08 (1H, s).

G) 1-(2-((1-(4-Fluorophenyl)-5-isopropyl-1H-pyrazolo[3,4-d][1,3]thiazole-3-yl)methyl)-5-oxa-2,6-diazaspiro[3.4]oct-6-en-7-yl)-4-methylpiperidine-4-carboxylic acid Using ethyl 4-methyl-1-(5-oxa-2,6-diazaspiro[3.4]oct-6-en-7-yl)piperidine-4-carboxylate hydrochloride and 1-(4-fluorophenyl)-5-isopropyl-1H-pyrazolo[3,4-d][1,3]thiazole-3-carbaldehyde, the title compound was obtained in the similar manner as in Step F of Example 3 and Example 2.

Example 22

4-Methyl-1-(2-(3-methyl-5-(1-phenylethoxy)benzyl)-5-oxa-2,6-diazaspiro[3.4]oct-6-en-7-yl)piperidine-4-carboxylic acid Using 3-hydroxy-5-methyl benzoic acid, (1-bromoethyl) benzene and ethyl 4-methyl-1-(5-oxa-2,6-diazaspiro[3.4] oct-6-en-7-yl)piperidine-4-carboxylate hydrochloride, the title compound was obtained in the similar manner as in Step A and Step C of Example 1, Step F of Example 3, and Example 2.

Example 23

Ethyl 1-(2-((2-cyclopropyl-6-ethoxy-4'-fluorobiphenyl-4-yl)methyl)-5-oxa-2,6-diazaspiro[3.4]oct-6-en-7-yl)-4-methylpiperidine-4-carboxylate A) Ethyl 4-bromo-3-ethoxy-5-hydroxybenzoate Sodium hydride (60% dispersion in oil, 3.86 g) was added to a solution of ethyl 4-bromo-3,5-dihydroxybenzoate (12.3 g) in DMF (100 mL), and the resultant was stirred for 30 minutes at 0° C. in a nitrogen atmosphere. Iodoethane (4.15 mL) was added to the reaction mixture, and the resultant was stirred for 2 hours at room temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (8.87 g).

$^1$H NMR (300 MHz, $CDCl_3$) δ 1.35-1.43 (3H, m), 1.49 (3H, t, J=7.0 Hz), 4.13-4.22 (2H, m), 4.37 (2H, q, J=7.2 Hz), 5.75 (1H, s), 7.13 (1H, d, J=1.7 Hz), 7.34 (1H, d, J=1.8 Hz).

B) Ethyl 2-ethoxy-4'-fluoro-6-hydroxybiphenyl-4-carboxylate

Palladium acetate (344 mg) was added to a mixture of ethyl 4-bromo-3-ethoxy-5-hydroxybenzoate (8.87 g), tripotassium phosphate (19.5 g), (4-fluorophenyl)boronic acid (10.7 g), tricyclohexylphosphine (20% toluene solution, 5.45 mL), toluene (80 mL) and water (40 mL), and the resultant was stirred overnight at 90° C. in an argon atmosphere. After the reaction mixture was cooled to room temperature, it was diluted by ethyl acetate, and was sequentially washed with water and a saturated saline solution. After the organic layer was dried over anhydrous magnesium sulfate, the solvent was distilled off under reduced pressure. The obtained residue was purified by a silica gel column chromatography (hexane/ethyl acetate), thereby obtaining the title compound (9.34 g).

$^1$H NMR (300 MHz, $CDCl_3$) δ 1.26 (3H, t, J=7.1 Hz), 1.40 (3H, t, J=7.1 Hz), 4.04 (2H, q, J=7.0 Hz), 4.39 (2H, q, J=7.2 Hz), 5.06 (1H, s), 7.14-7.23 (3H, m), 7.30-7.39 (3H, m).

C) Ethyl 2-ethoxy-4'-fluoro-6-(((trifluoromethyl) sulfonyl)oxy)biphenyl-4-carboxylate Trifluoromethanesulfonic anhydride (8.66 mL) was added to a mixture of ethyl 2-ethoxy-4'-fluoro-6-hydroxybiphenyl-4-carboxylate (13.0 g) and pyridine (80 mL) at 0° C., and the resultant was stirred for 20 minutes at the same temperature. The reaction mixture was passed through a short column of a silica gel (NH), and the solvent was distilled off under reduced pressure. The obtained residue was purified by a silica gel column chromatography (hexane/ethyl acetate), thereby obtaining the title compound (15.6 g).

$^1$H NMR (300 MHz, $CDCl_3$) δ 1.31 (3H, t, J=7.0 Hz), 1.42 (3H, t, J=7.1 Hz), 4.10 (2H, q, J=7.0 Hz), 4.43 (2H, q, J=7.2 Hz), 7.10-7.19 (2H, m), 7.28-7.38 (2H, m), 7.64 (2H, s).

D) Ethyl 2-cyclopropyl-6-ethoxy-4'-fluorobiphenyl-4-carboxylate

A mixture of ethyl 2-ethoxy-4'-fluoro-6-(((trifluoromethyl)sulfonyl)oxy)biphenyl-4-carboxylate (15.6 g), cyclopropylboronic acid (7.67 g), dicyclohexyl(2',6'-dimethoxybiphenyl-2-yl)phosphine (2.20 g), 2 M aqueous sodium carbonate solution (53.6 mL), tris(dibenzylideneacetone) dipalladium(0) (2.29 g) and toluene (60 mL) was stirred for 2 hours at 100° C. in an argon atmosphere. After the reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (10.5 g).

$^1$H NMR (300 MHz, $CDCl_3$) δ 0.65-0.73 (2H, m), 0.73-0.83 (2H, m), 1.18-1.26 (3H, m), 1.40 (3H, t, J=7.1 Hz), 1.56-1.67 (1H, m), 4.01 (2H, q, J=7.0 Hz), 4.39 (2H, q, J=7.2 Hz), 7.05-7.16 (2H, m), 7.20-7.31 (3H, m), 7.42 (1H, d, J=1.4 Hz).

E) 2-Cyclopropyl-6-ethoxy-4'-fluorobiphenyl-4-carbaldehyde

A solution of ethyl 2-cyclopropyl-6-ethoxy-4'-fluorobiphenyl-4-carboxylate (10.5 g) in THF (50 mL) was added to a suspension of lithium aluminum hydride (1.21 g) in THF (50 mL) under ice-cooling in a nitrogen atmosphere. After stirring for 30 minutes at the same temperature, water (1.2 mL), 15% aqueous sodium hydroxide solution (1.2 mL)

were added thereto, and the resultant was stirred for 5 minutes. Water (3.6 mL) was added to the reaction mixture, the resultant was stirred for 30 minutes, filtered, and then the filtrate was concentrated under reduced pressure. Manganese dioxide (13.9 g) was added to a solution of the obtained residue in toluene (60 mL), and the resultant was stirred for 1 hour at 60° C. in a nitrogen atmosphere. After the reaction mixture was filtered, the solvent was distilled off under reduced pressure. The obtained residue was purified by a silica gel column chromatography (hexane/ethyl acetate), thereby obtaining the title compound (7.79 g).

$^1$H NMR (300 MHz, $CDCl_3$) δ 0.66-0.77 (2H, m), 0.80-0.91 (2H, m), 1.24 (3H, t, 0.1=6.9 Hz), 1.60-1.74 (1H, m), 4.03 (2H, q, J=6.9 Hz), 7.03 (1H, d, J=1.1 Hz), 7.08-7.18 (2H, m), 7.22-7.31 (3H, m), 9.94 (1H, s).

F) Ethyl 1-(2-((2-cyclopropyl-6-ethoxy-4'-fluorobiphenyl-4-yl)methyl)-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-5-oxa-2,6-diazaspiro[3.4]oct-6-ene-2-carboxylate (1.05 g) was added to formic acid (5 mL), the resultant was stirred for 1 hour at 60° C., and then the solvent was distilled off under reduced pressure. Sodium triacetoxyborohydride (872 mg) was added to a solution of the obtained residue and 2-cyclopropyl-6-ethoxy-4'-fluorobiphenyl-4-carbaldehyde (780 mg) in THF (10 mL), and the resultant was stirred for 1 hour at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (1.37 g).

$^1$H NMR (400 MHz, DMSO-$d_6$) δ 0.57 (2H, d, J=4.1 Hz), 0.71 (2H, d, J=7.5 Hz), 1.06-1.22 (9H, m), 1.34-1.53 (3H, m), 1.93 (2H, d, J=13.4 Hz), 2.86 (2H, t, J=10.4 Hz), 3.13 (2H, d, J=7.7 Hz), 3.28 (4H, brs), 3.43 (2H, d, J=7.7 Hz), 3.54 (2H, s), 3.92 (2H, q, J=6.9 Hz), 4.10 (2H, q, J=6.9 Hz), 6.42 (1H, s), 6.76 (1H, s), 7.13-7.32 (4H, m).

Example 24

1-(2-((2-Cyclopropyl-6-ethoxy-4'-fluorobiphenyl-4-yl)methyl)-5-oxa-2,6-diazaspiro[3.4]oct-6-en-7-yl)-4-methylpiperidine-4-carboxylic acid 4 M aqueous sodium hydroxide solution (4 mL) was added to a solution of ethyl 1-(2-((2-cyclopropyl-6-ethoxy-4'-fluorobiphenyl-4-yl)methyl)-5-oxa-2,6-diazaspiro[3.4]oct-6-en-7-yl)-4-methylpiperidine-4-carboxylate (1.15 g) in ethanol (10 mL), and the resultant was stirred for 1 hour at 60° C. After the reaction mixture was cooled to room temperature, it was neutralized with 2 M hydrochloric acid, the precipitated solid was collected by filtration, and was washed with water. The obtained solid was washed with hydrous ethanol, thereby obtaining the title compound (880 mg).

$^1$H NMR (400 MHz, DMSO-$d_6$) δ 0.57 (2H, d, J=4.0 Hz), 0.71 (2H, d, J=7.5 Hz), 1.02-1.20 (6H, m), 1.37 (2H, t, J=10.0 Hz), 1.43-1.53 (1H, m), 1.91 (2H, d, J=13.3 Hz), 2.88 (2H, t, J=10.7 Hz), 3.14 (2H, d, J=7.5 Hz), 3.20-3.33 (4H, m), 3.43 (2H, d, J=7.5 Hz), 3.54 (2H, s), 3.92 (2H, q, J=6.8 Hz), 6.42 (1H, s), 6.76 (1H, s), 7.14-7.32 (4H, m).

Example 25

1-(2-((2-Ethoxy-4'-fluoro-6-methoxylbiphenyl-4-yl)methyl)-5-oxa-2,6-diazaspiro[3.4]oct-6-en-7-yl)-4-methylpiperidine-4-carboxylic acid A) 2-Ethoxy-4'-fluoro-6'-methoxybiphenyl-4-carbaldehyde Sodium hydride (60% dispersion in oil, 30.4 mg) was added to a mixture of 2-ethoxy-4'-fluoro-6-hydroxybiphenyl-4-carbaldehyde (300 mg) and DMF (10 mL) at 0° C. After the reaction mixture was stirred for 15 minutes at the same temperature, iodomethane (0.215 mL) was added thereto. The reaction mixture was stirred for 15 hours at room temperature. Sodium hydride (60% dispersion in oil, 13.8 mg) was added to the reaction mixture, and the resultant was stirred for 1 hour at the same temperature. Water was added to the reaction mixture, and extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (195 mg).

$^1$H NMR (300 MHz, $CDCl_3$) δ 1.28 (3H, t, J=7.0 Hz), 3.82 (3H, s), 4.06 (2H, q, J=6.9 Hz), 6.97-7.17 (4H, m), 7.29-7.38 (2H, m), 9.96 (1H, s).

B) Ethyl 1-(2-((2-ethoxy-4'-fluoro-6-methoxybiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-ethoxy-4'-fluoro-6-methoxybiphenyl-4-carbaldehyde, the title compound was obtained in the similar manner as in Step G of Example 1.

MS (ESI+): $[M+H]^+$ 540.5.

C) 1-(2-((2-Ethoxy-4'-fluoro-6-methoxylbiphenyl-4-yl)methyl)-5-oxa-2,6-diazaspiro[3.4]oct-6-en-7-yl)-4-methylpiperidine-4-carboxylic acid Using ethyl 1-(2-((2-ethoxy-4'-fluoro-6-methoxybiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 26

1-(2-((4'-Fluoro-2-propylbiphenyl-4-yl)methyl)-5-oxa-2,6-diazaspiro[3.4]oct-6-en-7-yl)-4-methylpiperidine-4-carboxylic acid A) 2-Allyl-4-formylphenyl trifluoromethanesulfonate Using 3-allyl-4-hydroxybenzaldehyde, the title compound was obtained in the similar manner as in Step H of Example 16.

$^1$H NMR (300 MHz, $CDCl_3$) δ 3.55 (2H, d, J=6.5 Hz), 5.12-5.27 (2H, m), 5.94 (1H, ddt, J=16.9, 10.2, 6.6 Hz), 7.47 (1H, d, J=8.4 Hz), 7.79-7.93 (2H, m), 10.02 (1H, s).

B) (4'-Fluoro-2-propylbiphenyl-4-yl)methanol

A mixture of tripotassium phosphate (3.61 g), (4-fluorophenyl)boronic acid (1.19 g), palladium(II) acetate (0.064 g), tricyclohexylphosphine (20% toluene solution, 0.796 g), 2-allyl-4-formylphenyl trifluoromethanesulfonate (1.67 g), toluene (40 mL) and water (20 mL) was stirred for 15 hours at 90° C. in a nitrogen atmosphere. Ethyl acetate and water were added to the reaction mixture, and insoluble matters were filtered. The filtrate was extracted using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining an oily matter (1.16 g). A mixture of the obtained oily matter (1.16 g), 10% palladium on carbon (55% water content, 100 mg) and ethyl acetate (20 mL) was stirred for 2 hours at room temperature in a hydrogen atmosphere. After the catalyst was filtered off, the obtained filtrate was concentrated under reduced pressure, and the obtained residue was purified by a silica gel column chromatography (hexane/ethyl acetate), thereby obtaining the title compound (850 mg).

$^1H$ NMR (300 MHz, $CDCl_3$) δ 0.81 (3H, t, J=7.32 Hz), 1.36-1.55 (2H, m), 1.68 (1H, t, J=5.90 Hz), 2.47-2.61 (2H, m), 4.72 (2H, d, J=5.67 Hz), 6.97-7.37 (7H, m).

C) 4'-Fluoro-2-propylbiphenyl-4-carbaldehyde

Using (4'-fluoro-2-propylbiphenyl-4-yl)methanol, the title compound was obtained in the similar manner as in Step B of Example 3.

$^1H$ NMR (300 MHz, $CDCl_3$) δ 0.83 (3H, t, J=7.32 Hz), 1.41-1.61 (2H, m), 2.55-2.70 (2H, m), 7.07-7.18 (2H, m), 7.21-7.30 (2H, m), 7.34 (1H, d, J=7.84 Hz), 7.73 (1H, dd, J=7.84, 1.70 Hz), 7.81 (1H, d, J=1.42 Hz), 10.04 (1H, s).

D) Ethyl 1-(2-((4'-fluoro-2-propylbiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 4'-fluoro-2-propylbiphenyl-4-carbaldehyde, the title compound was obtained in the similar manner as in Step G of Example 1.

MS (ESI+): $[M+H]^+$ 508.5.

E) 1-(2-((4'-Fluoro-2-propylbiphenyl-4-yl)methyl)-5-oxa-2,6-diazaspiro[3.4]oct-6-en-7-yl)-4-methylpiperidine-4-carboxylic acid Using ethyl 1-(2-((4'-fluoro-2-propylbiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 27

1-(2-(3,5-Dichlorobenzyl)-5-oxa-2,6-diazaspiro[3.4]oct-6-en-7-yl)-4-methylpiperidine-4-carboxylic acid 3,5-dichlorobezaldehyde (35.0 mg) and triethylamine (10.1 mg) was added to a mixture of ethyl 4-methyl-1-(5-oxa-2,6-diazaspiro[3.4]oct-6-en-7-yl)piperidine-4-carboxylate hydrochloride (31.8 mg) and THF (0.5 mL). After the resultant was stirred for 5 hours at room temperature, sodium triacetoxyborohydride (42.4 mg) was added thereto, and the resultant was stirred overnight at room temperature. After an aqueous saturated sodium hydrogen carbonate solution (1 mL) and ethyl acetate (3 mL) were added to the reaction mixture, the resultant was stirred, extraction was performed on the organic layer, and the solvent was evaporated using an air spay apparatus. The residue was purified using HPLC (column: YMCTriartC18, mobile phase: acetonitrile/10 mM aqueous ammonium bicarbonate solution), and the solvent was evaporated using an air spay apparatus. Ethanol (0.5 mL), THF (0.5 mL) and 2 M aqueous sodium hydroxide solution (0.50 mL) were added to the obtained residue, the resultant was stirred overnight at 60° C., and the solvent was evaporated using an air spay apparatus. The obtained residue was purified using HPLC (column: YMCTriartC18, mobile phase: acetonitrile/10 mM aqueous ammonium bicarbonate solution), and the solvent was evaporated using an air spay apparatus, thereby obtaining the title compound (2.80 mg).

Example 28

1-(2-(3,5-Bis(trifluoromethyl)benzyl)-5-oxa-2,6-diazaspiro[3.4]oct-6-en-7-yl)-4-methylpiperidine-4-carboxylic acid Using ethyl 4-methyl-1-(5-oxa-2,6-diazaspiro[3.4]oct-6-en-7-yl)piperidine-4-carboxylate hydrochloride and 3,5-bis(trifluoromethyl)benzaldehyde, the title compound was obtained in the similar manner as in Example 27.

Example 29

1-(2-((4,5-Dibromo-2-thienyl)methyl)-5-oxa-2,6-diazaspiro[3.4]oct-6-en-7-yl)-4-methylpiperidine-4-carboxylic acid Using ethyl 4-methyl-1-(5-oxa-2,6-diazaspiro[3.4]oct-6-en-7-yl)piperidine-4-carboxylate hydrochloride and 4,5-dibromothiophene-2-carbaldehyde, the title compound was obtained in the similar manner as in Example 27.

Example 30

4-Methyl-1-(2-((1-phenyl-3-(pyridin-3-yl)-1H-pyrazol-4-yl)methyl)-5-oxa-2,6-diazaspiro[3.4]oct-6-en-7-yl)piperidine-4-carboxylic acid Using ethyl 4-methyl-1-(5-oxa-2,6-diazaspiro[3.4]oct-6-en-7-yl)piperidine carboxylate hydrochloride and 3-phenyl-1-(pyridin-3-yl)-1H-pyrazole-4-carbaldehyde, the title compound was obtained in the similar manner as in Example 27.

Example 31

1-(2-((2-Bromo-5-ethoxybenzyl)-5-oxa-2,6-diazaspiro[3.4]oct-6-en-7-yl)-4-methyl piperidine-4-carboxylic acid Using ethyl 4-methyl-1-(5-oxa-2,6-diazaspiro[3.4]oct-6-en-7-yl)piperidine-4-carboxylate hydrochloride and 2-bromo-5-ethoxybenzaldehyde, the title compound was obtained in the similar manner as in Example 27.

Example 32

1-(2-((4-(4-Fluorophenoxy)benzyl)-5-oxa-2,6-diazaspiro[3.4]oct-6-en-7-yl)-4-methylpiperidine-4-carboxylic acid Using ethyl 4-methyl-1-(5-oxa-2,6-diazaspiro[3.4]oct-6-en-7-yl)piperidine-4-carboxylate hydrochloride and 4-(4-fluorophenoxy)benzaldehyde, the title compound was obtained in the similar manner as in Example 27.

Example 33

1-(2-(4-(Benzyloxy)-3-ethoxybenzyl)-5-oxa-2,6-diazaspiro[3.4]oct-6-en-7-yl)-4-methylpiperidine-4-carboxylic acid Using ethyl 4-methyl-1-(5-oxa-2,6-diazaspiro[3.4]oct-6-en-7-yl)piperidine-4-carboxylate hydrochloride and 4-(benzyloxy)-3-ethoxybenzaldehyde, the title compound was obtained in the similar manner as in Example 27.

Example 34

1-(2-((7-Ethoxy-2,2-dimethyl-2,3-dihydro-1-benzofuran-5-yl)methyl)-5-oxa-2,6-diazaspiro[3.4]oct-6-en-7-yl)-4-methylpiperidine-4-carboxylic acid Using ethyl 4-methyl-1-(5-oxa-2,6-diazaspiro[3.4]oct-6-en-7-yl)piperidine-4-carboxylate hydrochloride and 7-ethoxy-2,2-dimethyl-2,3-dihydro-1-benzofuran-5-carbaldehyde, the title compound was obtained in the similar manner as in Example 27.

Example 35

1-(2-(3,5-Dibromobenzyl)-5-oxa-2,6-diazaspiro[3.4]oct-6-en-7-yl)-4-methylpiperidine-4-carboxylic acid Using ethyl 4-methyl-1-(5-oxa-2,6-diazaspiro[3.4]oct-6-en-7-yl)piperidine-4-carboxylate hydrochloride and 3,5-dibromobenzaldehyde, the title compound was obtained in the similar manner as in Example 27.

Example 36

1-(2-(4-Chloro-5-methoxybenzyl)-5-oxa-2,6-diazaspiro[3.4]oct-6-en-7-yl)-4-methylpiperidine-4-carboxylic acid Using ethyl 4-methyl-1-(5-oxa-2,6-diazaspiro[3.4]oct-6-en-7-yl)piperidine-4-carboxylate hydrochloride and 4-chloro-2-methoxybenzaldehyde, the title compound was obtained in the similar manner as in Example 27.

Example 37

1-(2-(3-Bromobenzyl)-5-oxa-2,6-diazaspiro[3.4]oct-6-en-7-yl)-4-methylpiperidine-4-carboxylic acid Using ethyl 4-methyl-1-(5-oxa-2,6-diazaspiro[3.4]oct-6-en-7-yl)piperidine-4-carboxylate hydrochloride and 3-bromobenzaldehyde, the title compound was obtained in the similar manner as in Example 27.

Example 38

1-(2-((2-Anilino-4-chloro-1,3-thiazol-5-yl)methyl)-5-oxa-2,6-diazaspiro[3.4]oct-6-en-7-yl)-4-methylpiperidine-4-carboxylic acid Using ethyl 4-methyl-1-(5-oxa-2,6-diazaspiro[3.4]oct-6-en-7-yl)piperidine-4-carboxylate hydrochloride and 2-anilino-4-chloro-1,3-thiazole-5-carbaldehyde, the title compound was obtained in the similar manner as in Example 27.

Example 39

1-(2-(3-Ethoxy-4-((5-methyl-2-phenyl-1,3-oxazol-4-yl)methoxy)benzyl)-5-oxa-2,6-diazaspiro[3.4]oct-6-en-7-yl)-4-methylpiperidine-4-carboxylic acid Using ethyl 4-methyl-1-(5-oxa-2,6-diazaspiro[3.4]oct-6-en-7-yl)piperidine-4-carboxylate hydrochloride and 3-ethoxy-4-((5-methyl-2-phenyl-1,3-oxazol-4-yl)methoxy) benzaldehyde, the title compound was obtained in the similar manner as in Example 27.

Example 40

1-(2-((2-Cyclopropyl-7-ethoxy-1-benzofuran-5-yl)methyl)-5-oxa-2,6-diazaspiro[3.4]oct-6-en-7-yl)-4-methylpiperidine-4-carboxylic acid A) 3-Ethoxy-4-hydroxy-5-iodobenzaldehyde After sodium iodide (19.84 g) was added to a mixture of 3-ethoxy-4-hydroxybenzadehyde (20.0 g), acetonitrile (300 mL) and water (60 mL), tert-butyl hypochlorite (14.9 mL) was added dropwise thereto at 0° C., and the resultant was stirred for 20 minutes at the same temperature. The reaction mixture was diluted by ethyl acetate and water, and the organic layer was separated. The obtained organic layer was washed with an aqueous saturated sodium thiosulfate solution and a saturated saline solution, dried over anhydrous magnesium sulfate, and then the solvent was distilled of under reduced pressure. The obtained residue was crystallized (acetonitrile/water), thereby obtaining the title compound (20.3 g).

$^1$H NMR (400 MHz, DMSO-$d_6$) δ 1.38 (3H, t, J=6.8 Hz), 4.16 (2H, q, J=6.7 Hz), 7.40 (1H, s), 7.87 (1H, s), 9.74 (1H, s), 10.48 (1H, brs).

B) (2-Cyclopropyl-7-ethoxy-1-benzofuran-5-yl)methanol

Sodium tetrahydroborate (433 mg) was added to a mixture of 3-ethoxy-4-hydroxy-5-iodobenzaldehyde (1.52 g), THF (40 mL) and methanol (10 mL), the resultant was stirred for 2 hours at room temperature. Sodium tetrahydroborate (197 mg) was further added thereto, and the resultant was stirred for 1 hour at room temperature. After an aqueous saturated ammonium chloride solution was added to the reaction mixture at room temperature, extraction thereof was performed using ethyl acetate. The obtained organic layer was washed with a saturated saline solution, dried over anhydrous magnesium sulfate, and then the solvent was distilled off under reduced pressure. 1,1,3,3-Tetramethylguanidine (1.80 g) was added to a mixture of the obtained residue, ethynylcyclopropane (516 mg), bis(triphenylphosphine)palladium(II) dichloride (365 mg), copper(I) iodide (99.0 mg), THF (40 mL) and DMF (20 mL), and the resultant was stirred for 16 hours at 70° C. in an argon atmosphere. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (661 mg).

$^1$H NMR (300 MHz, $CDCl_3$) δ 0.88-1.03 (4H, m), 1.50 (3H, t, J=7.0 Hz), 1.67 (1H, brs), 2.04 (1H, s), 4.25 (2H, q, J=7.0 Hz), 4.68 (2H, s), 6.26 (1H, d, J=0.7 Hz), 6.75 (1H, d, J=1.3 Hz), 6.99-7.02 (1H, m).

C) 2-Cyclopropyl-7-ethoxy-1-benzofuran-5-carbaldehyde

Using (2-cyclopropyl-7-ethoxy-1-benzofuran-5-yl) methanol, the title compound was obtained in the similar manner as in Step B of Example 3.

MS (ESI+): $[M+H]^+$ 231.1.

D) Ethyl 1-(2-((2-cyclopropyl-7-ethoxy-1-benzofuran-5-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-7-ethoxy-1-benzofuran-5-carbaldehyde, the title compound was obtained in the similar manner as in Step G of Example 1.

MS (ESI+): $[M+H]^+$ 496.3.

E) 1-(2-((2-Cyclopropyl-7-ethoxy-1-benzofuran-5-yl)methyl)-5-oxa-2,6-diazaspiro[3.4]oct-6-en-7-yl)-4-methylpiperidine-4-carboxylic acid Using ethyl 1-(2-((2-cyclopropyl-7-ethoxy-1-benzofuran-5-yl)methyl)-5-oxa-2,6-diazaspiro[3.4]oct-6-en-7-yl)-4-methylpiperidine-4-carboxylate, the title compound was obtained in the similar manner as in Example 2.

Example 41

1-(2-(3-Chloro-5-ethoxy-4-(2,2,2-trifluoroethoxy)benzyl)-5-oxa-2,6-diazaspiro[3.4]oct-6-en-7-yl)-4-methylpiperidine-4-carboxylic acid A) 3-chloro-5-ethoxy-4-hydroxybenzaldehyde Sodium hydroxide (60% dispersion in oil, 1.43 g) was added to a solution of 3-ethoxy-4-hydroxybenzaldehyde (5.41 g) in THF (100 mL) at 0° C., the resultant was stirred for 30 minutes at the same temperature. A solution of N-chlorosuccinimide (4.56 g) in THF (100 mL) was added dropwise thereto, and the resultant was stirred for 48 hours at room temperature. An aqueous saturated ammonium chloride solution was added to the reaction mixture, and the precipitated solid was washed with a mixed solution in which ethyl acetate and hexane was mixed at a ratio of 1:1. Extraction was performed on the obtained washing solution using a mixed solution in which ethyl acetate and hexane was mixed at a ratio of 1:1. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.59 g).

$^1$H NMR (400 MHz, DMSO-$d_6$) δ 1.38 (3H, t, J=6.8 Hz), 4.17 (2H, q, J=6.8 Hz), 7.39 (1H, s), 7.58 (1H, s), 9.77 (1H, s), 10.44 (1H, brs).

B) 3-Chloro-5-ethoxy-4-(2,2,2-trifluoroethoxy)benzaldehyde

Using 3-chloro-5-ethoxy-4-hydroxybenzaldehyde, 1,1,1-trifluoro-2-iodoethane and 2,2,2-trifluoroethyl trifluoromethanesulfonate, the title compound was obtained in the similar manner as in Step A of Example 17.

$^1$H NMR (400 MHz, $CDCl_3$) δ 1.50 (3H, t, J=7.0 Hz), 4.17 (2H, q, J=6.9 Hz), 4.51 (2H, q, J=8.3 Hz), 7.36 (1H, s), 7.51 (1H, s), 9.85 (1H, s).

C) Ethyl 1-(2-(3-chloro-5-ethoxy-4-(2,2,2-trifluoroethoxy)benzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 3-chloro-5-ethoxy-4-(2,2,2-trifluoroethoxy)benzaldehyde, the title compound was obtained in the similar manner as in Step G of Example 1.

MS (ESI+): $[M+H]^+$ 548.2.

D) 1-(2-(3-Chloro-5-ethoxy-4-(2,2,2-trifluoroethoxy)benzyl)-5-oxa-2,6-diazaspiro[3.4]oct-6-en-7-yl)-4-methylpiperidine-4-carboxylic acid Using ethyl 1-(2-(3-chloro-5-ethoxy-4-(2,2,2-trifluoroethoxy)benzyl)-5-oxa-2,6-diazaspiro[3.4]oct-6-en-7-yl)-4-methylpiperidine-4-carboxylate, the title compound was obtained in the similar manner as in Example 2.

Example 42

1-(2-((2-Ethoxy-6-ethyl-4'-fluorobiphenyl-4-yl)methyl)-5-oxa-2,6-diazaspiro[3.4]oct-6-en-7-yl)-4-methylpiperidine-4-carboxylic acid A) 2-Ethoxy-4'-fluoro-6-vinylbiphenyl-4-carbaldehyde A mixture of 6-ethoxy-4'-fluoro-4-formylbiphenyl-2-yl trifluoromethanesulfonate (1.23 g), 4,4,5,5-tetramethyl-2-vinyl-1,3,2-dioxaborolane (1.21 g), dicyclohexyl(2',6'-dimethoxybiphenyl-2-yl)phosphine (257 mg), tris(dibenzylideneacetone)dipalladium(0) (287 mg), 2 M aqueous sodium carbonate solution (6.27 mL) and toluene (20 mL) was stirred for 2 hours at 100° C. in an argon atmosphere. After the reaction mixture was cooled to room temperature, it was poured into water, and extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (463 mg).

$^1$H NMR (400 MHz, DMSO-$d_6$) δ 1.17 (3H, t, J=6.8 Hz), 4.07 (2H, q, J=7.0 Hz), 5.29 (1H, d, J=11.2 Hz), 5.87 (1H, d, J=17.4 Hz), 6.36 (1H, dd, J=17.5, 11.1 Hz), 7.17-7.33 (4H, m), 7.46 (1H, s), 7.89 (1H, s), 10.05 (1H, s).

B) 2-Ethoxy-6-ethyl-4'-fluorobiphenyl-4-carbaldehyde

A mixture of 2-ethoxy-4'-fluoro-6-vinylbiphenyl-4-carbaldehyde (450 mg), 20% palladium hydroxide (50% water content, 50 mg) and ethyl acetate (20 mL) (50% dispersion in oil, 50 mg) was stirred for 1 hour at room temperature in a hydrogen atmosphere. The catalyst was filtered off, the obtained filtrate was concentrated under reduced pressure, and the residue was purified by a silica gel column chromatography (hexane/ethyl acetate), thereby obtaining the title compound (285 mg).

$^1$H NMR (400 MHz, DMSO-$d_6$) δ 1.00 (3H, t, J=7.5 Hz), 1.14 (3H, t, J=6.9 Hz), 2.41 (2H, q, J=7.4 Hz), 4.03 (2H, q, J=6.9 Hz), 7.16-7.30 (4H, m), 7.38 (1H, s), 7.52 (1H, s), 10.00 (1H, s).

C) Ethyl 1-(2-((2-ethoxy-6-ethyl-4'-fluorobiphenyl-4-yl)methyl)-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-5-oxa-2,6-diazaspiro[3.4]oct-6-ene-2-carboxylate (392 mg) was added to formic acid (3 mL), the resultant was stirred for 1 hour at 60° C., and then the solvent was distilled off under reduced pressure. Sodium triacetoxyborohydride (327 mg) was added to a solution of the obtained residue and 2-diethoxy-6-ethyl-4'-fluorobiphenyl-4-carbaldehyde (280 mg) in THF (10 mL), and the resultant was stirred for 1 hour at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (481 mg).

$^1$H NMR (400 MHz, DMSO-$d_6$) δ 0.93 (3H, t, J=7.5 Hz), 1.09 (3H, t, J=6.9 Hz), 1.12-1.22 (6H, m), 1.41 (2H, t, J=10.1 Hz), 1.93 (2H, d, J=13.4 Hz), 2.30 (2H, q, J=7.4 Hz), 2.87 (2H, t, J=10.5 Hz), 3.15 (2H, d, J=7.7 Hz), 3.29 (4H, brs), 3.45 (2H, d, J=7.5 Hz), 3.57 (2H, s), 3.91 (2H, q, J=6.9 Hz), 4.11 (2H, q, J=7.0 Hz), 6.79 (2H, d, J=4.8 Hz), 7.10-7.26 (4H, m).

D) 1-(2-((2-Ethoxy-6-ethyl-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (2.73 mL) was added to a solution of ethyl 1-(2-((2-ethoxy-6-ethyl-4'-fluorobiphenyl-4-yl)methyl)-5-oxa-2,6-diazaspiro[3.4]oct-6-en-7-yl)-4-methylpiperidine-4-carboxylate (420 mg) in ethanol (5 mL), and the resultant was stirred for 1 hour at 70° C. After the reaction mixture was cooled to room temperature, it was neutralized with 2 M hydrochloric acid and 1 M hydrochloric acid, and the resultant was stirred for 20 minutes. After the precipitated solid was collected by filtration, recrystallization (hydrous methanol) of the obtained solid was performed, thereby obtaining the title compound (325 mg).

$^1$H NMR (400 MHz, DMSO-$d_6$) δ 0.93 (3H, t, J=7.4 Hz), 1.03-1.18 (6H, m), 1.36 (2H, t, J=10.2 Hz), 1.91 (2H, d, J=13.1 Hz), 2.30 (2H, q, J=7.2 Hz), 2.89 (2H, t, J=10.8 Hz), 3.15 (2H, d, J=7.7 Hz), 3.20-3.37 (4H, m), 3.45 (2H, d, J=7.4 Hz), 3.57 (2H, s), 3.91 (2H, q, J=6.7 Hz), 6.79 (2H, d, J=4.6 Hz), 7.05-7.35 (4H, m), 12.40 (1H, brs).

Example 43

1-(2-((2-Chloro-6-ethoxy-4'-fluorobiphenyl-4-yl)methyl)-5-oxa-2,6-diazaspiro[3.4]oct-6-en-7-yl)-4-methylpiperidine-4-carboxylic acid A) Ethyl 3-ethoxy-4-nitrobenzoate Iodoethane (38.9 g) was added to a mixture of 3-hydroxy-4-nitrobenzoic acid (15.2 g), potassium carbonate (45.9 g) and DMF (250 mL) at room temperature, and the resultant was stirred for 15 hours at the same temperature. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The residue was purified by a silica gel column chromatography (hexane/ethyl acetate), thereby obtaining the title compound (7.55 g).

$^1$H NMR (300 MHz, $CDCl_3$) δ 1.42 (3H, t, J=7.1 Hz), 1.49 (3H, t, J=7.0 Hz), 4.25 (2H, q, J=7.0 Hz), 4.42 (2H, q, J=7.1 Hz), 7.65-7.69 (1H, m), 7.73 (1H, d, J=1.5 Hz), 7.77-7.82 (1H, m).

B) Ethyl 4-amino-3-ethoxybenzoate

10% palladium on carbon (55% water content, 1.00 g) was added to a mixture of ethyl 3-ethoxy-4-nitrobenzoate (7.55 g), THF (100 ml) and ethanol (100 mL), and the resultant was stirred for 2 hours at room temperature in a hydrogen atmosphere. The reaction mixture was filtered using celite, and the filtrate was concentrated under reduced pressure. The obtained residue was purified by a silica gel column chromatography (NH, ethyl acetate), thereby obtaining the title compound (6.60 g).

$^1$H NMR (400 MHz, $CDCl_3$) δ 1.36 (3H, t, J=7.1 Hz), 1.45 (3H, t, J=6.9 Hz), 4.13 (2H, q, J=6.7 Hz), 4.21 (2H, brs), 4.32 (2H, q, J=6.9 Hz), 6.66 (1H, d, J=8.2 Hz), 7.45 (1H, s), 7.54 (1H, d, J=8.0 Hz).

C) Ethyl 4-amino-3-chloro-5-ethoxybenzoate

A solution of N-chlorosuccinimide (1.43 g) in acetonitrile (20 mL) was added dropwise to a solution of ethyl 4-amino-3-ethoxybenzoate (2.04 g) in acetonitrile (40 mL) at room temperature, the resultant was stirred for 3 hours at 60° C., and then the solvent was distilled off under reduced pressure. The residue was diluted by ethyl acetate and water, and after the organic layer was separated, the obtained organic layer sequentially washed with water and a saturated saline solution, dried over anhydrous magnesium sulfate, and then the solvent was distilled off under reduced pressure. The residue was purified by a silica gel column chromatography (hexane/ethyl acetate), thereby obtaining the title compound (1.82 g).

$^1$H NMR (400 MHz, $CDCl_3$) δ 1.37 (3H, t, J=7.1 Hz), 1.45 (3H, t, J=7.0 Hz), 4.13 (2H, q, J=6.9 Hz), 4.33 (2H, q, J=7.0 Hz), 4.58 (2H, brs), 7.35 (1H, s), 7.65 (1H, s).

D) Ethyl 3-chloro-5-ethoxy-4-iodobenzoate

Isoamyl nitrite (1.49 mL) was added dropwise to a mixture of ethyl 4-amino-3-chloro-5-ethoxybenzoate (1.81 g), diiodomethane (2.39 mL) and acetonitrile (50 mL) at room temperature, the resultant was stirred for 1 hour at 70° C., and then the solvent was distilled off under reduced pressure. The residue was purified by a silica gel column chromatography (hexane/ethyl acetate), thereby obtaining the title compound (1.42 g).

$^1$H NMR (400 MHz, $CDCl_3$) δ 1.40 (3H, t, J=7.0 Hz), 1.49-1.53 (3H, m), 4.17 (2H, q, J=6.8 Hz), 4.38 (2H, q, J=7.0 Hz), 7.28 (1H, brs), 7.73 (1H, s).

E) Ethyl 2-chloro-6-ethoxy-4'-fluorobiphenyl-4-carboxylate (1,1'-Bis(diphenylphosphino)ferrocene)dichloropalladium(II) (223 mg) was added to a mixture of ethyl 3-chloro-5-ethoxy-4-iodobenzoate (539 mg), (4-fluorophenyl)boronic acid (319 mg), cesium fluoride (639 mg) and DME (15 mL), and the resultant was stirred for 16 hours at 100° C. in an argon atmosphere. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The residue was purified by a silica gel column chromatography (hexane/ethyl acetate), thereby obtaining the title compound (396 mg).

$^1$H NMR (400 MHz, $CDCl_3$) δ 1.25 (3H, t, J=6.9 Hz), 1.41 (3H, t, J=7.0 Hz), 4.04 (2H, q, J=6.8 Hz), 4.40 (2H, q, J=7.0 Hz), 7.12 (2H, t, J=8.5 Hz), 7.22-7.30 (2H, m), 7.51 (1H, s), 7.76 (1H, s).

F) (2-Chloro-6-ethoxy-4'-fluorobiphenyl-4-yl)methanol

Diisobutylaluminum hydride (1.5 M toluene solution, 2 mL) was added dropwise to a solution of ethyl 2-chloro-6-ethoxy-4'-fluorobiphenyl-4-carboxylate (378 mg) in THF (8 mL) at 0° C., and the resultant was stirred for 1 hour at the same temperature. Sodium sulfate decahydrate was added to the reaction mixture at 0° C., the resultant was filtered using celite, and then the filtrate was concentrated under reduced pressure. The residue was purified by a silica gel column chromatography (hexane/ethyl acetate), thereby obtaining the title compound (314 mg).

$^1$H NMR (400 MHz, $CDCl_3$) δ 1.23 (3H, t, J=6.9 Hz), 1.75 (1H, brs), 3.98 (2H, q, J=6.8 Hz), 4.70 (2H, d, J=4.6 Hz), 6.89 (1H, s), 7.06-7.13 (3H, m), 7.21-7.28 (2H, m).

G) 2-Chloro-6-ethoxy-4'-fluorobiphenyl-4-carbaldehyde

Sulfur trioxide-pyridine complex (479 mg) was added to a mixture of (2-chloro-6-ethoxy-4'-fluorobiphenyl-4-yl)methanol (422 mg), triethylamine (457 mg) and DMSO (15 mL), and the resultant was stirred for 2 hours at room temperature. Sulfur trioxide-pyridine complex (479 mg) and triethylamine (457 mg) was further added thereto, and the resultant was stirred for 1 hour at room temperature. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The residue was purified by a silica gel column chromatography (hexane/ethyl acetate), thereby obtaining the title compound (388 mg).

$^1$H NMR (300 MHz, $CDCl_3$) δ 1.27 (3H, t, J=6.9 Hz), 4.06 (2H, q, J=7.0 Hz), 7.10-7.17 (2H, m), 7.24-7.30 (2H, m), 7.36 (1H, d, J=1.3 Hz), 7.58 (1H, d, J=1.4 Hz), 9.94 (1H, s).

H) Ethyl 1-(2-((2-chloro-6-ethoxy-4'-fluorobiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (375 mg) and formic acid (5 mL) was stirred for 1 hour at 60° C., the solvent was distilled off under reduced pressure. 2-Chloro-6-ethoxy-4'-fluorobiphenyl-4-carbaldehyde (384 mg) and sodium triacetoxyborohydride (417 mg) were added to a solution of the residue in THF (10 mL), and the resultant was stirred for 15 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The residue was purified by a silica gel column chromatography (hexane/ethyl acetate), thereby obtaining the title compound (443 mg).

$^1$H NMR (400 MHz, $CDCl_3$) δ 1.19-1.29 (9H, m), 1.40-1.51 (2H, m), 2.07-2.16 (2H, m), 2.92-3.04 (2H, m), 3.26 (2H, s), 3.32-3.43 (4H, m), 3.55 (2H, d, J=8.0 Hz), 3.63 (2H, s), 3.95 (2H, q, J=6.9 Hz), 4.16 (2H, q, J=7.0 Hz), 6.77 (1H, s), 7.01 (1H, s), 7.09 (2H, t, J=8.6 Hz), 7.21-7.25 (2H, m).

I) 1-(2-((2-Chloro-6-ethoxy-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (1.5 mL) was added to a solution of ethyl 1-(2-((2-chloro-6-ethoxy-4'-fluorobiphenyl-4-yl)methyl)-5-oxa-2,6-diazaspiro[3.4]oct-6-en-7-yl)-4-methylpiperidine-4-carboxylate (401 mg) in ethanol (15 mL), the resultant was stirred for 2 hours at 60° C. 2 M aqueous sodium hydroxide solution (2 mL) was added thereto, and the resultant was stirred 1 hour at 70° C. Furthermore, 2 M aqueous sodium hydroxide solution (1 mL) was added to the reaction mixture, the resultant was stirred for 2 hours at 70° C., and the solvent was distilled off under reduced pressure. Water was added to the residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The residue was crystallized (hexane/ethanol), thereby obtaining the title compound (174 mg).

$^1$H NMR (400 MHz, DMSO-$d_6$) δ 1.10-1.18 (6H, m), 1.32-1.43 (2H, m), 1.86-1.95 (2H, m), 2.83-2.94 (2H, m), 3.17 (2H, d, J=7.5 Hz), 3.31 (4H, brs), 3.47 (2H, d, J=7.5 Hz), 3.61 (2H, s), 3.99 (2H, q, J=6.9 Hz), 6.97 (1H, s), 7.03 (1H, s), 7.18-7.30 (4H, m), 12.39 (1H, brs).

Example 44

1-(2-(4-(Benzyloxy)-3-chloro-5-ethoxybenzyl)-5-oxa-2,6-diazaspiro[3.4]oct-6-en-7-yl)-4-methylpiperidine-4-carboxylic acid

A) 4-(Benzyloxy)-3-chloro-5-ethoxybenzaldehyde

Using 3-chloro-5-ethoxy-4-hydroxybenzaldehyde and (bromomethyl)benzene, the title compound was obtained in the similar manner as in Step A of Example 1.

$^1H$ NMR (400 MHz, $CDCl_3$) δ 1.49 (3H, t, J=6.9 Hz), 4.15 (2H, q, J=6.9 Hz), 5.18 (2H, s), 7.30-7.40 (4H, m), 7.46-7.54 (3H, m), 9.83 (1H, s).

B) Ethyl 1-(2-(4-(benzyloxy)-3-chloro-5-ethoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 4-(benzyloxy)-3-chloro-5-ethoxybenzaldehyde, the title compound was obtained in the similar manner as in Step G of Example 1.

MS (ESI+): $[M+H]^+$ 556.3.

C) 1-(2-(4-(Benzyloxy)-3-chloro-5-ethoxybenzyl)-5-oxa-2,6-diazaspiro[3.4]oct-6-en-7-yl)-4-methylpiperidine-4-carboxylic acid Using ethyl 1-(2-(4-(benzyloxy)-3-chloro-5-ethoxybenzyl)-5-oxa-2,6-diazaspiro[3.4]oct-6-en-7-yl)-4-methylpiperidine-4-carboxylate, the title compound was obtained in the similar manner as in Example 2.

Example 45

1-(2-(3,5-Diethoxy-4-(morpholin-4-yl)benzyl)-5-oxa-2,6-diazaspiro[3.4]oct-6-en-7-yl)-4-methylpiperidine-4-carboxylic acid A) Ethyl 3,5-diethoxy-4-iodobenzoate A solution of iodine (139 g) in THF (350 mL) was added dropwise to a mixture of ethyl 3,5-dihydroxybenzoate (50 g), sodium hydrogen carbonate (69.2 g), THF (150 mL) and water (50 mL), and the resultant was stirred for 1 hour at room temperature. The reaction mixture was diluted by ethyl acetate (250 mL), an aqueous sodium thiosulfate solution was added thereto, and the resultant was stirred for 30 minutes. The organic layer was washed with a saturated saline solution, dried over anhydrous magnesium sulfate, and then the solvent was distilled off under reduced pressure. Iodoethane (55.3 mL) and potassium carbonate (114 g) were added to a solution of the obtained residue in DMF (500 mL), and the resultant was stirred for 2 hours at 60° C. After the reaction mixture was cooled to room temperature, water (500 mL) was added thereto, and the resultant was stirred for 30 minutes. The precipitated solid was collected by filtration, thereby obtaining the title compound (90.0 g).

$^1H$ NMR (300 MHz, DMSO-$d_6$) δ 1.18-1.45 (9H, m), 4.14 (4H, q, J=7.0 Hz), 4.32 (2H, q, J=7.1 Hz), 7.08 (2H, s).

B) Ethyl 3,5-diethoxy-4-(morpholin-4-yl)benzoate

Morpholine (1.08 g), tris(dibenzylideneacetone)dipalladium(0) (189 mg), dicyclohexyl(2',6'-diisopropoxybiphenyl-2-yl)phosphine (192 mg) and cesium carbonate (5.37 g) were added to a solution of ethyl 3,5-diethoxy-4-iodobenzoate (1.50 g) in DMF (10 mL), and the resultant was stirred 1 hour at 130° C. The reaction mixture was cooled to room temperature, and it was diluted by ethyl acetate and water. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (720 mg).

MS (ESI+): $[M+H]^+$ 324.3.

C) 3,5-Diethoxy-4-(morpholin-4-yl)benzaldehyde

Using ethyl 3,5-diethoxy-4-(morpholin-4-yl)benzoate, the title compound was obtained in the similar manner as in Step D of Example 10.

MS (ESI+): $[M+H]^+$ 280.1.

D) Ethyl 1-(2-(3,5-diethoxy-4-(morpholin-4-yl)benzyl)-5-oxa-2,6-diazaspiro[3.4]oct-6-en-7-yl)-4-methylpiperidine-4-carboxylate Using 3,5-diethoxy-4-(morpholin-4-yl)benzaldehyde and tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step G of Example 1.

MS (ESI+): $[M+H]^+$ 545.5.

E) 1-(2-(3,5-Diethoxy-4-(morpholin-4-yl)benzyl)-5-oxa-2,6-diazaspiro[3.4]oct-6-en-7-yl)-4-methylpiperidine-4-carboxylic acid Using ethyl 1-(2-(3,5-diethoxy-4-(morpholin-4-yl)benzyl)-5-oxa-2,6-diazaspiro[3.4]oct-6-en-7-yl)-4-methylpiperidine-4-carboxylate, the title compound was obtained in the similar manner as in Example 2.

Example 46

1-(2-((7-(4-Fluorophenyl)-2,2-dimethyl-2,3-dihydro-1-benzofuran-4-yl)methyl)-5-oxa-2,6-diazaspiro[3.4]oct-6-en-7-yl)-4-methylpiperidine-4-carboxylic acid A) Ethyl 4-bromo-3-((2-methylprop-2-en-1-yl)oxy)benzoate Sodium hydride (60% dispersion in oil, 1.55 g) was added to a mixture of ethyl 4-bromo-3-hydroxybenzoate (7.90 g) and DMF (100 mL) at 0° C. After the resultant was stirred for 10 minutes at the same temperature, 3-chloro-2-methylprop-1-ene (8.76 g) was added dropwise thereto. The reaction mixture was stirred for 15 hours at room temperature. Water was added to the reaction mixture, and extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (9.02 g).

$^1H$ NMR (300 MHz, $CDCl_3$) δ 1.39 (3H, t, J=7.13 Hz), 1.87 (3H, d, J=0.47 Hz), 4.37 (2H, q, J=7.08 Hz), 4.56 (2H, s), 5.00-5.10 (1H, m), 5.14-5.24 (1H, m), 7.45-7.56 (2H, m), 7.57-7.67 (1H, m).

B) Ethyl 4-bromo-3-hydroxy-2-(2-methylprop-2-en-1-yl)benzoate

After a mixture of ethyl 4-bromo-3-((2-methylprop-2-en-1-yl)oxy)benzoate (4.00 g) and N,N-diethylaniline (20 mL) was stirred for 3 hours at 200° C. under microwave irradiation, the solvent was distilled off under reduced pressure. The residue was diluted by ethyl acetate, sequentially washed with 1 M hydrochloric acid and a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (3.63 g).

$^1$H NMR (300 MHz, $CDCl_3$) δ 1.32-1.40 (3H, m), 1.81 (3H, d, J=0.57 Hz), 3.80 (2H, s), 4.32 (2H, q, J=7.18 Hz), 4.41 (1H, dd, J=1.70, 0.85 Hz), 4.77 (1H, dt, J=2.97, 1.44 Hz), 5.77 (1H, s), 7.29-7.34 (1H, m), 7.39-7.44 (1H, m).

C) Ethyl 7-bromo-2,2-dimethyl-2,3-dihydro-1-benzofuran-4-carboxylate

A mixture of ethyl 4-bromo-3-hydroxy-2-(2-methylprop-2-en-1-yl)benzoate (480 mg) and formic acid (3 mL) was heated to reflux for 30 minutes. Water was added to the reaction mixture, and extraction thereof was performed using ethyl acetate. The organic layer was sequentially washed with water, an aqueous saturated sodium hydrogen carbonate solution and a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (330 mg).

$^1$H NMR (300 MHz, $CDCl_3$) δ 1.39 (3H, t, J=7.13 Hz), 1.53 (6H, s), 3.43 (2H, s), 4.34 (2H, q, J=7.18 Hz), 7.31-7.41 (2H, m).

D) (7-Bromo-2,2-dimethyl-2,3-dihydro-1-benzofuran-4-yl)methanol

Using ethyl 7-bromo-2,2-dimethyl-2,3-dihydro-1-benzofuran-4-carboxylate, the title compound was obtained in the similar manner as in Step E of Example 16.

$^1$H NMR (300 MHz, $CDCl_3$) δ 1.50-1.55 (6H, m), 3.07-3.14 (2H, m), 4.57 (2H, d, J=5.85 Hz), 6.71-6.76 (1H, m), 7.24-7.31 (1H, m).

E) 7-Bromo-2,2-dimethyl-2,3-dihydro-1-benzofuran-4-carbaldehyde

Using (7-bromo-2,2-dimethyl-2,3-dihydro-1-benzofuran-4-yl)methanol, the title compound was obtained in the similar manner as in Step B of Example 3.

$^1$H NMR (300 MHz, $CDCl_3$) δ 1.55 (6H, s), 3.44 (2H, s), 7.16 (1H, d, J=8.12 Hz), 7.49 (1H, d, J=8.12 Hz), 9.99 (1H, s).

F) 7-(4-Fluorophenyl)-2,2-dimethyl-2,3-dihydro-1-benzofuran-4-carbaldehyde

Using 7-bromo-2,2-dimethyl-2,3-dihydro-1-benzofuran-4-carbaldehyde and (4-fluorophenyl)boronic acid, the title compound was obtained in the similar manner as in Step D of Example 16.

$^1$H NMR (300 MHz, $CDCl_3$) δ 1.53 (6H, s), 3.41 (2H, s), 7.13 (2H, t, J=8.73 Hz), 7.33-7.48 (2H, m), 7.74 (2H, dd, J=8.73, 5.52 Hz), 10.05 (1H, s).

G) Ethyl 1-(2-((7-(4-fluorophenyl)-2,2-dimethyl-2,3-dihydro-1-benzofuran-4-yl)methyl)-5-oxa-2,6-diazaspiro[3.4]oct-6-en-7-yl)-4-methylpiperidine-4-carboxylate Using 7-(4-fluorophenyl)-2,2-dimethyl-2,3-dihydro-1-benzofuran-4-carbaldehyde and tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step G of Example 1.

MS (ESI+): $[M+H]^+$ 536.6.

H) 1-(2-((7-(4-Fluorophenyl)-2,2-dimethyl-2,3-dihydro-1-benzofuran-4-yl)methyl)-5-oxa-2,6-diazaspiro[3.4]oct-6-en-7-yl)-4-methylpiperidine-4-carboxylic acid Using ethyl 1-(2-((7-(4-fluorophenyl)-2,2-dimethyl-2,3-dihydro-1-benzo furan-4-yl)methyl)-5-oxa-2,6-diazospiro[3.4]oct-6-en-7-yl)-4-methylpiperidine-4-carboxylate, the title compound was obtained in the similar manner as in Example 2.

Example 47

Cis-4-(2-((2,6-Diethoxy-4'-fluorobiphenyl-4-yl)methyl)-5-oxa-2,6-diazaspiro[3.4]oct-6-en-7-yl)cyclohexanecarboxylic acid A) Methyl cis-4-(hydroxymethyl)cyclohexanecarboxylate Using cis-4-(methoxycarbonyl)cyclohexanecarboxylic acid, the title compound was obtained in the similar manner as in Step A of Example 3.

$^1$H NMR (400 MHz, $CDCl_3$) δ 123-1.36 (2H, m), 1.52-1.66 (5H, m), 1.96-2.06 (2H, m), 2.54-2.62 (1H, m), 3.50 (2H, d, J=6.1 Hz), 3.68 (3H, s).

B) Methyl cis-4-formylcyclohexanecarboxylate

Using methyl cis-4-(hydroxymethyl)cyclohexanecarboxylate, the title compound was obtained in the similar manner as in Step B of Example 3.

$^1$H NMR (400 MHz, $CDCl_3$) δ 1.62-1.82 (6H, m), 1.90-2.00 (2H, m), 2.32-2.40 (1H, m), 2.41-2.51 (1H, m), 3.67 (3H, s), 9.66 (1H, s).

C) Methyl cis-4-((E)-(hydroxyimino)methyl)cyclohexanecarboxylate

Using methyl cis-4-formylcyclohexanecarboxylate, the title compound was obtained in the similar manner as in Step C of Example 3.

$^1$H NMR (400 MHz, $CDCl_3$) δ 1.57-1.75 (6H, m), 1.92-2.07 (2H, m), 2.32-2.43 (1H, m), 2.54 (1H, brs), 3.68 (3H, s), 7.37 (1H, d, J=5.6 Hz), 7.67 (1H, s).

D) tert-Butyl 7-(cis-4-(methoxycarbonyl)cyclohexyl)-5-oxa-2,6-diazaspiro[3.4]oct-6-ene-2-carboxylate Using methyl cis-4-((E)-(hydroxyimino)methyl)cyclohexanecarboxylate and tert-butyl 3-methyleneazetidine-1-carboxylate, the title compound was obtained in the similar manner as in Step D of Example 3.

$^1$H NMR (400 MHz, $CDCl_3$) δ 1.44 (9H, s), 1.59-1.76 (6H, m), 2.00-2.10 (2H, m), 2.46-2.54 (1H, m), 2.59 (1H, brs), 3.13 (2H, s), 3.68 (3H, s), 3.96 (2H, d, J=9.7 Hz), 4.23 (2H, d, J=9.7 Hz).

E) Methyl cis-4-(5-oxa-2,6-diazaspiro[3.4]oct-6-en-7-yl)cyclohexanecarboxylate hydrochloride Using tert-butyl 7-(cis-4-(methoxycarbonyl)cyclohexyl)-5-oxa-2,6-diazaspiro[3.4]oct-6-ene-2-carboxylate, the title compound was obtained in the similar manner as in Step E of Example 3.

$^1$H NMR (300 MHz, DMSO-$d_6$) δ 1.52-1.72 (6H, m), 1.75-1.93 (2H, m), 2.48-2.53 (1H, m), 2.57 (1H, brs), 3.37 (2H, s), 3.60 (3H, s), 4.08-4.14 (2H, m), 4.16-4.22 (2H, m), 9.26 (2H, brs).

F) Methyl cis-4-(2-((2,6-diethoxy-4'-fluorobiphenyl-4-yl)methyl)-5-oxa-2,6-diazaspiro[3.4]oct-6-en-7-yl) cyclohexanecarboxylate Using methyl cis-4-(5-oxa-2,6-diazaspiro[3.4]oct-6-en-7-yl)cyclohexanecarboxylate hydrochloride and 2,6-diethoxy-4'-fluorobiphenyl-4-carbaldehyde, the title compound was obtained in the similar manner as in Step F of Example 3.

MS (ESI+): $[M+H]^+$ 525.6.

G) cis-4-(2-((2,6-Diethoxy-4'-fluorobiphenyl-4-yl) methyl)-5-oxa-2,6-diazaspiro[3.4]oct-6-en-7-yl)cyclohexanecarboxylic acid Using methyl cis-4-(2-((2,6-diethoxy-4'-fluorobiphenyl-4-yl)methyl)-5-oxa-2,6-diazaspiro[3.4]oct-6-en-7-yl)cyclohexanecarboxylate, the title compound was obtained in the similar manner as in Example 2.

Example 48

Trans-4-(2-((2-Chloro-6-ethoxy-4'-fluorobiphenyl-4-yl)methyl)-5-oxa-2,6-diazaspiro[3.4]oct-6-en-7-yl) cyclohexanecarboxylic acid A) Methyl trans-4-(2-((2-chloro-6-ethoxy-4'-fluorobiphenyl-4-yl)methyl)-5-oxa-2,6-diazaspiro[3.4]oct-6-en-7-yl)cyclohexanecarboxylate Using methyl trans-4-(5-oxa-2,6-diazaspiro[3.4]oct-6-en-7-yl)cyclohexanecarboxylate hydrochloride and 2-chloro-6-ethoxy-4'-fluorobiphenyl-4-carbaldehyde, the title compound was obtained in the similar manner as in Step F of Example 3.

MS (ESI+): $[M+H]^+$ 515.2.

B) trans-4-(2-((2-Chloro-6-ethoxy-4'-fluorobiphenyl-4-yl)methyl)-5-oxa-2,6-diazaspiro[3.4]oct-6-en-7-yl)cyclohexanecarboxylic acid Using methyl trans-4-(2-((2-chloro-6-ethoxy-4'-fluorobiphenyl-4-yl)methyl)-5-oxa-2,6-diazaspiro[3.4]oct-6-en-7-yl)cyclohexanecarboxylate, the title compound was obtained in the similar manner as in Example 2.

Example 49

1-(2-(3,5-Diethoxy-4-(1-methyl-1H-pyrazol-4-yl) benzyl)-5-oxa-2,6-diazaspiro[3.4]oct-6-en-7-yl)-4-methylpiperidine-4-carboxylic acid A) 3,5-Diethoxy-4-iodobenzaldehyde Diisobutylaluminium hydride (1.5 M toluene solution, 68.6 mL) was added dropwise to a solution of ethyl 3,5-diethoxy-4-iodobenzoate (15.0 g) in THF (120 mL) at 0° C. in an argon atmosphere, and the resultant was stirred for 30 minutes at the same temperature. Sodium sulfate decahydrate was added to the reaction mixture, the resultant was filtered using celite, washed with ethyl acetate and THF, and then the filtrate was concentrated under reduced pressure. The obtained residue was mixed with manganese dioxide (17.90 g), toluene (150 mL) and THF (100 mL), and the mixture was stirred overnight at mom temperature, and further stirred for 5 hours at 70° C. The reaction mixture was filtered using celite, and the filtrate was concentrated under reduced pressure. The residue was purified by a silica gel column chromatography (hexane/ethyl acetate), thereby obtaining the title compound (10.7 g).

$^1$H NMR (400 MHz, $CDCl_3$) δ 1.52 (6H, t, J=7.0 Hz), 4.19 (4H, q, J=6.9 Hz), 6.93 (2H, s), 9.92 (1H, s).

B) Ethyl 1-(2-(3,5-diethoxy-4-iodobenzyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (1.80 g) and formic acid (5 mL) was stirred for 1 hour at 60° C., the solvent was distilled of under reduced pressure. 3,5-diethoxy-4-iodobenzaldehyde (1.51 g) and sodium triacetoxyborohydride (1.50 g) were added to a mixture of the obtained residue and THF (10 mL), and the resultant was stirred for 1 hour at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The residue was purified by a silica gel column chromatography (NH, hexane/ethyl acetate), thereby obtaining the title compound (1.98 g).

$^1$H NMR (400 MHz, DMSO-$d_6$) δ 1.14 (3H, s), 1.18 (3H, t, J=7.1 Hz), 1.28-1.46 (8H, m), 1.93 (2H, d, J=13.3 Hz), 2.85 (2H, t, J=10.6 Hz), 3.13 (2, d, J=7.8 Hz), 3.27 (4H, s), 3.41 (2H, d, J=7.8 Hz), 3.54 (2H, s), 3.98-4.19 (6H, m), 6.51 (2H, s).

C) 1-(2-(3,5-Diethoxy-4-(1-methyl-1H-pyrazol-4-yl) benzyl)-5-oxa-2,6-diazaspiro[3.4]oct-6-en-7-yl)-4-methylpiperidine-4-carboxylic acid 1-Methyl-4-(4,4,5,5-tetramethyl-1,3,2-dioxaborolan-2-yl)-1H-pyrazole (33.3 mg), potassium carbonate (22.1 mg) and bis(di-tert-butyl(4-dimethylaminophenyl)phosphine)dichloropalladium(II) (5.66 mg) were added to a mixture of ethyl 1-(2-(3,5-diethoxy-4-iodobenzyl)-5-oxa-2,6-diazaspiro[3.4]oct-6-en-7-yl)-4-methylpiperidine-4-carboxylate (46.8 mg), DME (0.9 mL) and water (0.1 mL), and the resultant was stirred for 30 minutes at 130° C. under microwave irradiation. After an aqueous saturated sodium hydrogen carbonate solution and ethyl acetate (3 mL) were added to the reaction mixture, the resultant was stirred, extraction was performed on the organic layer, and the solvent was evaporated using an air spay apparatus. The residue was purified using HPLC (column: YMCTriartC18, mobile phase: acetonitrile/10 mM aqueous ammonium bicarbonate solution), and the solvent was evaporated using an air spay apparatus. Ethanol (0.5 mL), THF (0.5 mL) and 2 M aqueous sodium hydroxide solution (0.5 mL) were added to the residue, the resultant was stirred overnight at 60° C., and the solvent was evaporated using an air spay apparatus. The residue was purified using HPLC (column: YMCTriartC18, mobile phase: acetonitrile/10 mM aqueous ammonium bicarbonate solution), and the solvent was evaporated using an air spay apparatus, thereby obtaining the title compound (6.18 mg).

Example 50

1-2-(4-(1,3-Dimethyl-1H-pyrazol-4-yl)-3,5-diethoxybenzyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and 1,3-dimethyl-4-(4,4,5,5-tetramethyl-1,3,2-dioxaborolan-2-yl)-1H-pyrazole, the title compound was obtained in the similar manner as in Step C of Example 49.

Example 51

1-2-(4-(1,5-Dimethyl-1H-pyrazol-4-yl)-3,5-diethoxybenzyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (1,5-dimethyl-1H-pyrazol-4-yl)boronic acid, the title compound was obtained in the similar manner as in Step C of Example 49.

Example 52

1-(2-(3,5-Diethoxy-4-(1-methyl-1H-pyrazol-3-yl)benzyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and 1-methyl-3-(4,4,5,5-tetramethyl-1,3,2-dioxaborolan-2-yl)-1H-pyrazole, the title compound was obtained in the similar manner as in Step C of Example 49.

Example 53

1-2-(4-(3,5-Dimethyl-1,2-oxazole-4-yl)-3,5-diethoxybenzyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and 3,5-dimethyl-4-(4,4,5,5-tetramethyl-1,3,2-dioxaborolan-2-yl)-1,2-oxazole, the title compound was obtained in the similar manner as in Step C of Example 49.

Example 54

1-2-(4-(2,4-Dimethyl-1,3-thiazol-5-yl)-3,5-diethoxybenzyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and 2,4-dimethyl-5-(4,4,5,5-tetramethyl-1,3,2-dioxaborolan-2-yl)-1,3-thiazole, the title compound was obtained in the similar manner as in Step C of Example 49.

Example 55

1-(2-((4'-Chloro-2,6-dimethoxybiphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and 2-(4-chlorophenyl)-4,4,5,5-tetramethyl-1,3,2-dioxaborolane, the title compound was obtained in the similar manner as in Step C of Example 49.

Example 56

1-(2-((4'-Cyclopropyl-2,6-diethoxybiphenyl-4-yl)methyl)-5-oxa-2,6-diaza spiro[3.4]oct-6-en-7-yl)-4-methylpiperidine-4-carboxylic acid Using ethyl 1-(2-(3,5-diethoxy-4-iodobenzyl)-5-oxa-2,6-diaza spiro[3.4]oct-6-en-7-yl)-4-methylpiperidine-4-carboxylate and (4-cyclopropylphenyl)boronic acid, the title compound was obtained in the similar manner as in Step C of Example 49.

Example 57

1-(2-((2,6-Diethoxy-4'-(trifluoromethyl)biphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (4-(trifluoromethyl)phenyl)boronic acid, the title compound was obtained in the similar manner as in Step C of Example 49.

Example 58

1-(2-((2,6-Diethoxy-4'-methoxybiphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (4-methoxyphenyl)boronic acid, the title compound was obtained in the similar manner as in Step C of Example 49.

Example 59

1-(2-((4'-(Dimethylamino)-2,6-diethoxybiphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (4-(dimethylamino)phenyl)boronic acid, the title compound was obtained in the similar manner as in Step C of Example 49.

Example 60

1-(2-((4'-Cyano-2,6-diethoxybiphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (4-cyanophenyl)boronic acid, the title compound was obtained in the similar manner as in Step C of Example 49.

Example 61

1-(2-((2,6-Diethoxy-4'-(methylsulfonyl)biphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (4-(methylsulfonyl)phenyl)boronic acid, the title compound was obtained in the similar manner as in Step C of Example 49.

Example 62

1-(2-((2,6-Diethoxy-3'-fluorobiphenyl-4-yl)methyl)-5-oxa-2,6-diazaspiro[3.4]oct-6-en-7-yl)-4-piperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (3-fluorophenyl)boronic acid, the title compound was obtained in the similar manner as in Step C of Example 49.

Example 63

1-(2-((2,6-Diethoxy-3'-(trifluoromethyl)biphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (3-(trifluoromethyl)phenyl)boronic acid, the title compound was obtained in the similar manner as in Step C of Example 49.

Example 64

1-(2-((2,6-Diethoxy-3'-methoxybiphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (3-methoxyphenyl)boronic acid, the title compound was obtained in the similar manner as in Step C of Example 49.

Example 65

1-(2-((2,6-Diethoxy-2'-(trifluoromethyl)biphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (2-(trifluoromethyl)phenyl)boronic acid, the title compound was obtained in the similar manner as in Step C of Example 49.

Example 66

1-(2-((3',5'-Dichloro-2,6-diethoxybiphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (3,5-dichlorophenyl)boronic acid, the title compound was obtained in the similar manner as in Step C of Example 49.

Example 67

1-(2-((2,6-Diethoxy-3',5'-dimethoxybiphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (3,5-dimethoxyphenyl)boronic acid, the title compound was obtained in the similar manner as in Step C of Example 49.

Example 68

1-(2-(3,5-Diethoxy-4-(pyrimidin-5-yl)benzyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and pyrimidin-5-yl boronic acid, the title compound was obtained in the similar manner as in Step C of Example 49.

Example 69

1-(2-(3,5-Diethoxy-4-(pyridin-3-yl)benzyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and pyridin-3-yl boronic acid, the title compound was obtained in the similar manner as in Step C of Example 49.

Example 70

1-(2-((2,6-Diethoxy-2'-methoxybiphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (2-methoxyphenyl)boronic acid, the title compound was obtained in the similar manner as in Step C of Example 49.

Example 71

1-(2-(3,5-Diethoxy-4-(1H-pyrazol-4-yl)benzyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and tert-butyl 4-(4,4,5,5-tetramethyl-1,3,2-dioxaborolan-2-yl)-1H-pyrazole-1-carboxylate, the title compound was obtained in the similar manner as in Step C of Example 49.

Example 72

1-(2-((2,6-Diethoxy-2'-fluorobiphenyl-4-yl)methyl)-5-oxa-2,6-diazaspiro[3.4]oct-6-en-7-yl)-4-piperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (2-fluorophenyl)boronic acid, the title compound was obtained in the similar manner as in Step C of Example 49.

Example 73

1-(2-(4-Cyclopropyl-3,5-diethoxybenzyl)-5-oxa-2,6-diazaspiro[3.4]oct-6-en-7-yl)-4-methylpiperidin-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and cyclopropyl boronic acid, the title compound was obtained in the similar manner as in Step C of Example 49.

Example 74

1-(2-(3,5-Diethoxy-4-((5-methyl-2-thienyl)benzyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (5-methyl-2-thieny)boronic acid, the title compound was obtained in the similar manner as in Step C of Example 49.

Example 75

1-(2-((2,6-Diethoxy-2',4'-difluorobiphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (2,4-difluorophenyl)boronic acid, the title compound was obtained in the similar manner as in Step C of Example 49.

Example 76

1-(2-((2,6-Diethoxy-2',3',4'-trifluorobiphenyl-4-yl)methyl)-5-oxa-2,6-diazaspiro[3.4]oct-6-en-7-yl)-4-methylpiperidine-4-carboxylic acid Using ethyl 1-(2-(3,5-diethoxy-4-iodobenzyl)-5-oxa-2,6-diazaspiro[3.4]oct-6-en-7-yl)-4-methylpiperidine-4-carboxylate and (2,3,4-trifluorophenyl)boronic acid, the title compound was obtained in the similar manner as in Step C of Example 49.

Example 77

1-(2-((2,6-Diethoxy-3',4'-difluorobiphenyl-4-yl)methyl)-5-oxa-2,6-diazaspiro[3.4]oct-6-en-7-yl)-4-methylpiperidine-4-carboxylic acid A) Ethyl 4-bromo-3,5-diethoxybenzoate A mixture of 4-bromo-3,5-dihydroxybenzoic acid (75.0 g) and DMF (100 mL) was added to a mixture of potassium carbonate (177 g) and DMF (200 mL) at 0° C., iodoethane (129 mL) was further added thereto, and then the resultant was stirred for 16 hours at room temperature. After the reaction mixture was filtered using celite, water was added to the filtrate, and extraction thereof was performed using ethyl acetate. The obtained organic layer was sequentially washed with water and a saturated saline solution, dried over anhydrous sodium sulfate, and then the solvent was distilled off under reduced pressure, thereby obtaining the title compound (90.0 g).

$^1$H NMR (400 MHz, DMSO-$d_6$) δ 1.32 (3H, t, J=7.04 Hz), 1.37 (6H, t, J=6.9 Hz), 4.15 (4H, q, J=6.9 Hz), 4.32 (2H, q, J=7.0 Hz), 7.18 (2H, s).

B) (4-Bromo-3,5-diethoxyphenyl)methanol

Diisobutylaluminium hydride (1 M toluene solution, 79 mL) was added to a solution of ethyl 4-bromo-3,5-diethoxybenzoate (10.0 g) in THF (250 mL) at 0° C. in an argon atmosphere, and the resultant was stirred for 2 hours at room temperature. Sodium sulfate decahydrate was added to the reaction mixture at 0° C., the resultant was filtered using celite, dried over anhydrous sodium sulfate, and then the filtrate was concentrated under reduced pressure, thereby obtaining the title compound (8.20 g).

$^1$H NMR (400 MHz, DMSO-$d_6$) δ 1.34 (6H, t, J=6.9 Hz), 4.06 (4H, q, J=6.9 Hz), 4.45 (2H, d, J=5.7 Hz), 5.26 (1H, t, J=5.8 Hz), 6.65 (2H, s).

C) 4-Bromo-3,5-diethoxybenzaldehyde

Manganese dioxide (25.9 g) was added to a solution of (4-bromo-3,5-diethoxyphenyl)methanol (8.20 g) in dichloromethane (60 mL), and the resultant was stirred for 16 hours at room temperature. After the reaction mixture was filtered using celite, the filtrate was concentrated, thereby obtaining the title compound (7.60 g).

$^1$H NMR (400 MHz, DMSO-$d_6$) δ 1.41 (6H, t, J=6.9 Hz), 4.21 (4H, q, J=6.9 Hz), 7.25 (2H, s), 9.97 (1H, s).

D) 2,6-Diethoxy-3',4'-difluorobiphenyl-4-carbaldehyde

A mixture of 4-bromo-3,5-diethoxybenzaldehyde (5.00 g), (3,4-difluorophenyl)boronic acid (7.23 g), tripotassium phosphate (15.6 g), DMF (75 mL) and dioxane (75 mL) was stirred for 45 minutes at room temperature while degassing. Palladium acetate (206 mg) and tricyclohexylphosphine (514 mg) were added to the reaction mixture, and the resultant was heated to reflux for 14 hours in an argon atmosphere. After the reaction mixture was cooled to mom temperature, ethyl acetate was added thereto, the organic layer was sequentially washed with water and a saturated saline solution, dried over anhydrous sodium sulfate, and then the solvent was distilled off under reduced pressure. The obtained residue was purified by a silica gel column chromatography (hexane/ethyl acetate), thereby obtaining the title compound (2.70 g).

$^1$H NMR (400 MHz, DMSO-$d_6$) δ 1.22 (6H, t, J=6.9 Hz), 4.08 (4H, q, J=6.8 Hz), 7.14-7.17 (1H, m), 7.27 (2H, s), 7.34-7.44 (2H, m), 9.97 (1H, s).

E) Ethyl 1-(2-((2,6-diethoxy-3',4'-difluorobiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (304 mg) and formic acid (6 mL) was stirred for 1 hour at 60° C., the solvent was distilled off under reduced pressure. The obtained residue was mixed with 2,6-diethoxy-3',4'-difluorobiphenyl-4-carbaldehyde (293 mg) and THF (10 mL), sodium triacetoxyborohydride (338 mg) was added to the mixture, and the resultant was stirred for 15 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (405 mg).

$^1$H NMR (300 MHz, $CDCl_3$) δ 1.20-1.29 (12H, m), 1.39-1.51 (2H, m), 2.11 (2H, d, J=13.5 Hz), 2.90-3.03 (2H, m), 3.26 (2H, s), 3.34-3.44 (4H, m), 3.56 (2H, d, J=8.9 Hz), 3.65 (2H, s), 3.97 (4H, q, J=7.0 Hz), 4.16 (2H, q, J=7.1 Hz), 6.53 (2H, s), 7.04-7.24 (3H, m).

F) 1-(2-((2,6-Diethoxy-3',4'-difluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (2 mL) was added to a solution of ethyl 1-(2-((2,6-diethoxy-3',4'-difluorobiphenyl-4-yl)methyl)-5-oxa-2,6-diazaspiro[3.4]oct-6-en-7-yl)-4-methylpiperidine-4-carboxylate (397 mg) in ethanol (10 mL), the resultant was stirred for 15 hours at 70° C., and then the solvent was distilled off under reduced pressure. Water was added to the residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The residue was crystallized (hexane/ethanol), thereby obtaining the title compound (252 mg).

$^1$H NMR (300 MHz, DMSO-$d_6$) δ 1.12-1.22 (9H, m), 1.31-1.44 (2H, m), 1.91 (2H, d, J=13.6 Hz), 2.82-2.97 (2H, m), 3.24-3.40 (6H, m), 3.42-3.82 (4H, m), 3.98 (4H, q, J=7.0 Hz), 6.69 (2H, brs), 7.06-7.13 (1H, m), 7.24-7.33 (1H, m), 7.33-7.45 (1H, m), 12.45 (1H, brs).

Example 78

1-(2-((2,6-Diethoxy-4'-fluorobiphenyl-4-yl)methyl)-5-oxa-2,6-diazaspiro[3.4]oct-6-en-7-yl)-4-hydroxypiperidine-4-carboxylic acid A) Methyl 1-benzyl-4-hydroxypiperidine-4-carboxylate 1-Benzyl-4-hydroxypiperidine-4-carbonitrile (10.0 g) was added to concentrated hydrochloric acid (25 mL), and the resultant was stirred for 1 hour at 90° C. The reaction mixture was cooled to room temperature, and it was concentrated under reduced pressure. Toluene was added to the residue, and the resultant was again concentrated. Concentrated sulfuric acid (4.00 mL) was added to a solution of the obtained residue in methanol (100 mL), and the resultant was stirred for 1 hour at 50° C. The reaction mixture was cooled to room temperature, it was neutralized by the addition of sodium hydrogen carbonate, and then insoluble matter was separated by filtration. The filtrate was concentrated under reduced pressure, and the obtained residue was purified by a silica gel column chromatography (NH, hexane/ethyl acetate), thereby obtaining the title compound (6.20 g).

MS (ESI+): $[M+H]^+$ 250.2.

B) Ethyl 4-hydroxypiperidine-4-carboxylate

Using methyl 1-benzyl-4-hydroxypiperidine-4-carboxylate, the title compound was obtained in the similar manner as in Step C of Example 7.

$^1$H NMR (400 MHz, DMSO-$d_6$) δ 1.46 (2H, d, J=12.8 Hz), 1.67-1.81 (2H, m), 2.54-2.65 (2H, m), 2.69-2.82 (2H, m), 3.63 (3H, s), 5.22 (1H, brs).

C) tert-Butyl 7-(4-hydroxy-4-(methoxycarbonyl)piperidin-1-yl)-5-oxa-2,6-diazaspiro[3.4]oct-6-ene-2-carboxylate Using methyl 4-hydroxypiperidine-4-carboxylate and tert-butyl 7-bromo-5-oxa-2,6-diazaspiro[3.4]oct-6-ene-2-carboxylate, the title compound was obtained in the similar manner as in Step F of Example 1.

MS (ESI+): $[M+H]^+$ 370.3.

D) Methyl 1-(2-((2,6-diethoxy-4'-fluorobiphenyl-4-yl)methyl)-5-oxa-2,6-diazaspiro[3.4]oct-6-en-7-yl)-4-hydroxypiperidine-4-carboxylate Using tert-butyl 7-(4-hydroxy-4-(methoxycarbonyl)piperidin-1-yl)-5-oxa-2,6-diazaspiro[3.4]oct-6-ene-2-carboxylate and 2,6-diethoxy-4'-fluorobiphenyl-4-carbaldehyde, the title compound was obtained in the similar manner as in Step G of Example 1.

MS (ESI+): $[M+H]^+$ 542.5.

E) 1-(2-((2,6-Diethoxy-4'-fluorobiphenyl-4-yl)methyl)-5-oxa-2,6-diazaspiro[3.4]oct-6-en-7-yl)-4-hydroxypiperidine-4-carboxylic acid Using methyl 1-(2-((2,6-diethoxy-4'-fluorobiphenyl-4-yl)methyl)-5-oxa-2,6-diazaspiro[3.4]oct-6-en-7-yl)-4-hydroxypiperidine-4-carboxylate, the title compound was obtained in the similar manner as in Example 2.

Example 79

1-(2-((4'-Fluoro-2,6-dimethylbiphenyl-4-yl)methyl)-5-oxa-2,6-diazaspiro[3.4]oct-6-en-7-yl)-4-methylpiperidine-4-carboxylic acid A) Methyl 4'-fluoro-2,6-dimethylbiphenyl-4-carboxylate Using methyl 4-bromo-3,5-dimethylbenzoate and (4-fluorophenyl)boronic acid, the title compound was obtained in the similar manner as in Step D of Example 23.

$^1$H NMR (400 MHz, DMSO-$d_6$) δ 2.03 (6H, s), 3.86 (3H, s), 7.16-7.25 (2H, m), 7.27-7.35 (2H, m), 7.73 (2H, s).

B) 4'-Fluoro-2,6-dimethylbiphenyl-4-carbaldehyde

Using methyl 4'-fluoro-2,6-dimethylbiphenyl-4-carboxylate, the title compound was obtained in the similar manner as in Step D of Example 10.

$^1$H NMR (400 MHz, DMSO-$d_6$) δ 2.05 (6H, s), 7.18-7.26 (2H, m), 7.28-7.36 (2H, m), 7.68 (2H, s), 9.98 (1H, s).

C) Ethyl 1-(2-((4'-fluoro-2,6-dimethylbiphenyl-4-yl)methyl)-5-oxa-2,6-diazaspiro[3.4]oct-6-en-7-yl)-4-methylpiperidine-4-carboxylate Using 4'-fluoro-2,6-dimethylbiphenyl-4-carbaldehyde and tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step G of Example 1.

MS (ESI+): $[M+H]^+$ 494.4.

D) 1-(2-((4'-Fluoro-2,6-dimethylbiphenyl-4-yl)methyl)-5-oxa-2,6-diazaspiro[3.4]oct-6-en-7-yl)-4-methylpiperidine-4-carboxylic acid Using ethyl 1-(2-((4'-fluoro-2,6-dimethylbiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 80

4-Methyl-1-(2-((2,2,4-trimethyl-2,3-dihydro-1-benzofuran-6-yl)methyl)-5-oxa-2,6-diazaspiro[3.4]oct-6-en-7-yl)piperidine-4-carboxylic acid A) Ethyl 3-bromo-5-((2-methylprop-2-en-1-yl)oxy)benzoate Using ethyl 3-bromo-5-hydroxybenzoate and 3-chloro-2-methylprop-1-ene, the title compound was obtained in the similar manner as in Step A of Example 46.

$^1$H NMR (300 MHz, $CDCl_3$) δ 1.39 (3H, t, J=7.18 Hz), 1.83 (3H, d, J=0.47 Hz), 4.37 (2H, q, J=7.08 Hz), 4.46 (2H, s), 4.95-5.03 (1H, m), 5.10 (1H, t, J=1.18 Hz), 7.22-7.31 (1H, m), 7.51 (1H, dd, J=2.45, 1.32 Hz), 7.69-7.78 (1H, m).

B) (3-Bromo-5-((2-methylprop-2-en-1-yl)oxy)phenyl)methanol

Diisobutylaluminium hydride (1.5 M toluene solution, 46.8 mL) was added to a mixture of ethyl 3-bromo-5-((2-methylprop-2-en-1-yl)oxy)benzoate (7.00 g) and toluene (150 mL) at 0° C., and the resultant was stirred for 2 hours at room temperature. 1 M hydrochloric acid was added to the reaction mixture, and extraction thereof was performed using ethyl acetate. The organic layer was washed with a saturated saline solution, dried over anhydrous magnesium sulfate, and then the solvent was distilled off under reduced pressure, thereby obtaining the title compound (5.98 g).

$^1$H NMR (300 MHz, $CDCl_3$) δ 1.69 (1H, t, J=6.04 Hz), 1.82 (3H, s), 4.42 (2H, s), 4.64 (2H, d, J=6.04 Hz), 5.00 (1H, s), 5.08 (1H, s), 6.87 (1H, s), 6.99 (1H, t, J 1.98 Hz), 7.10 (1H, s).

C) 3-Bromo-5-((2-methylprop-2-en-1-yl)oxy)benzaldehyde

Using (3-bromo-5-((2-methylprop-2-en-1-yl)oxy)phenyl)methanol, the title compound was obtained in the similar manner as in Step B of Example 3.

$^1$H NMR (300 MHz, $CDCl_3$) δ 1.83 (3H, d, J=0.57 Hz), 4.48 (2H, s), 5.03 (1H, tt, J=1.58, 0.87 Hz), 5.10 (1H, t, J=1.18 Hz), 7.28-7.38 (2H, m), 7.58 (1H, t, J=1.51 Hz), 9.89 (1H, s).

D) 3-Bromo-5-hydroxy-4-(2-methylprop-2-en-1-yl)benzaldehyde

Using 3-bromo-5-((2-methylprop-2-en-1-yl)oxy)benzaldehyde, the title compound was obtained in the similar manner as in Step B of Example 46.

$^1$H NMR (300 MHz, $CDCl_3$) δ 1.82 (3H, d, J=0.57 Hz), 3.66 (2H, s), 4.70 (1H, s), 4.93 (1H, dt, J=2.64, 1.32 Hz), 5.68 (1H, brs), 7.30 (1H, s), 7.69 (1H, d, J=1.51 Hz), 9.87 (1H, s).

E) 4-Bromo-2,2-dimethyl-2,3-dihydro-1-benzofuran-4-carbaldehyde

Using 3-bromo-5-hydroxy-4-(2-methylprop-2-en-1-yl)benzaldehyde, the title compound was obtained in the similar manner as in Step C of Example 46.

$^1$H NMR (300 MHz, $CDCl_3$) δ 1.52 (6H, s), 3.07 (2H, s), 7.12 (1H, d, J=1.13 Hz), 7.49 (1H, d, J=1.13 Hz), 9.84 (1H, s).

F) 4-Bromo-6-(1,3-dioxolan-2-yl)-2,2-dimethyl-2,3-dihydro-1-benzofuran

A mixture of 4-bromo-2,2-dimethyl-2,3-dihydro-1-benzofuran-6-carbaldehyde (680 mg), p-toluenesulfonic acid monohydrate (50.7 mg), ethylene glycol (0.45 mL) and toluene (30 mL) was heated to reflux for 14 hours while performing an azeotropic dehydration. The reaction mixture was diluted by ethyl acetate, it was sequentially washed with an aqueous saturated sodium hydrogen carbonate solution, water and a saturated saline solution, dried over anhydrous magnesium sulfate, passed through a short column of a silica gel (NH), and then the solvent was distilled off under reduced pressure. The obtained residue was purified by a silica gel column chromatography (hexane/ethyl acetate), thereby obtaining the title compound (620 mg).

$^1$H NMR (300 MHz, $CDCl_3$) δ 1.48 (6H, s), 3.00 (2H, s), 3.87-4.31 (4H, m), 5.72 (1H, s), 6.76 (1H, dd, J=1.23, 0.38 Hz), 7.10 (1H, d, J=1.04 Hz).

G) 2,2,4-Trimethyl-2,3-dihydro-1-benzofuran-6-carbaldehyde

Chloromethyl zinc (2 M THF solution, 1.24 mL) was added to a mixture of 4-bromo-6-(1,3-dioxolan-2-yl)-2,2- dimethyl-2,3-dihydro-1-benzofuran (620 mg), tris(dibenzylideneacetone)dipalladium(0) (95 mg), 1,2,3,4,5-pentaphenyl-1'-(di-tert-butylphosphino)ferrocene (73.6 mg) and THF (20 mL) at room temperature in a nitrogen atmosphere, and the resultant was stirred for 15 hours at the same temperature. Water was added to the reaction mixture, and extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining an oily matter (560 mg). A mixture of the obtained oily matter (560 mg), 6M hydrochloric acid (10 mL) and THF (20 mL) was stirred for 15 hours at 60° C. Water was added to the reaction mixture, and extraction thereof was performed using ethyl acetate. The organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (250 mg).

$^1$H NMR (300 MHz, $CDCl_3$) δ 1.50 (6H, s), 2.28 (3H, s), 2.97 (2H, s), 7.04 (1H, s), 7.18 (1H, s), 9.87 (1H, s).

H) Ethyl 4-methyl-1-(2-((2,2,4-trimethyl-2,3-dihydro-1-benzofuran-6-yl)methyl)-5-oxa-2,6-diazaspiro[3.4]oct-6-en-7-yl)piperidine-4-carboxylate Using 2,2,4-trimethyl-2,3-dihydro-1-benzofuran-6-carbaldehyde and tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step G of Example 1.

MS (ESI+): $[M+H]^+$ 456.5.

I) 4-Methyl-1-(2-((2,2,4-trimethyl-2,3-dihydro-1-benzofuran-6-yl)methyl)-5-oxa-2,6-diazaspiro[3.4]oct-6-en-7-yl)piperidine-4-carboxylic acid Using ethyl 4-methyl-1-(2-((2,2,4-trimethyl-2,3-dihydro-1-benzofuran-4-yl)methyl)-5-oxa-2,6-diazaspiro[3.4]oct-6-en-7-yl)piperidine-4-carboxylate, the title compound was obtained in the similar manner as in Example 2.

Example 81

1-(2-((2,6-Diethoxy-4'-fluorobiphenyl-4-yl)methyl)-5-oxa-2,6-diazaspiro[3.4]oct-6-en-7-yl)-4-methylpiperidine-4-carboxylic acid A) tert-Butyl 7-(4-methoxy-4-(methoxycarbonyl)piperidin-1-yl)-5-oxa-2,6-diazaspiro[3.4]oct-6-ene-2-carboxylate Sodium hydride (60% dispersion in oil, 52 mg) was added to a solution of tert-butyl 7-(4-hydroxy-4-(methoxycarbonyl)piperidin-1-yl)-5-oxa-2,6-diazaspiro[3.4]oct-6-ene-2-carboxylate (320 mg) in DMF (3 mL), the resultant was stirred for 1 hour at room temperature. Iodomethane (184 mg) was added to the reaction mixture, the resultant was stirred for 1 hour at room temperature, and then an aqueous saturated ammonium chloride solution and ethyl acetate were added thereto. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (210 mg).

MS (ESI+): $[M+H]^+$ 384.3.

B) Methyl 1-(2-((2,6-diethoxy-4'-fluorobiphenyl-4-yl)methyl)-5-oxa-2,6-diazaspiro[3.4]oct-6-en-7-yl)-4-methoxypiperidine-4-carboxylate Using tert-butyl 7-(4-methoxy-4-(methoxycarbonyl)piperidin-1-yl)-5-oxa-2,6-diazaspiro[3.4]oct-6-ene-2-carboxylate and 2,6-diethoxy-4'-fluorobiphenyl-4-carbaldehyde, the title compound was obtained in the similar manner as in Step G of Example 1.

MS (ESI+): $[M+H]^+$ 556.5.

C) 1-(2-((2,6-Diethoxy-4'-fluorobiphenyl-4-yl)methyl)-5-oxa-2,6-diazaspiro[3.4]oct-6-en-7-yl)-4-methylpiperidine-4-carboxylic acid Using methyl 1-(2-((2,6-diethoxy-4'-fluorobiphenyl-4-yl)methyl)-5-oxa-2,6-diazaspiro[3.4]oct-6-en-7-yl)-4-methoxypiperidine-4-carboxylate, the title compound was obtained in the similar manner as in Example 2.

Example 82

1-(2-((4-(4-Fluorophenyl)-1-isopropyl-1H-indol-3-yl)methyl)-5-oxa-2,6-diazaspiro[3.4]oct-6-en-7-yl)-4-methylpiperidine-4-carboxylic acid A) 4-Bromo-1-isopropyl-1H-indole-3-carbaldehyde Potassium tert-butoxide (2.88 g) was added to a solution of 4-bromo-1H-indole-3-carbaldehyde (5.22 g) in THF (50 mL), the resultant was stirred for 20 minutes at room temperature. 2-Iodopropane (4.75 g) was added thereto, and the resultant was stirred for 1 hour at 80° C. The reaction mixture was cooled to room temperature, water and ethyl acetate were added thereto, and the organic layer was separated. The obtained organic layer was washed with a saturated saline solution, dried over anhydrous magnesium sulfate, and then the solvent was distilled off under reduced pressure. The obtained residue was crystallized (hexane/ethyl acetate), thereby obtaining the title compound (4.23 g).

$^1$H NMR (400 MHz, DMSO-$d_6$) δ 1.51 (6H, d, J=6.5 Hz), 4.78-4.99 (1H, m), 7.23 (1H, t, J=8.0 Hz), 7.52 (1H, d, J=7.7 Hz), 7.79 (1H, d, J=8.3 Hz), 8.45 (1H, s), 10.70 (1H, s).

B) 4-(4-Fluorophenyl)-1-isopropyl-1H-indole-3-carbaldehyde

Using 4-bromo-1-isopropyl-1H-indole-3-carbaldehyde and (4-fluorophenyl)boronic acid, the title compound was obtained in the similar manner as in Step D of Example 23.

$^1$H NMR (400 MHz, DMSO-$d_6$) δ 1.54 (6H, d, J=6.7 Hz), 4.86-4.96 (1H, m), 7.11 (1H, d, J=7.2 Hz), 728 (2H, t, J=8.8 Hz), 7.36 (1H, t, J=7.8 Hz), 7.48 (2H, dd, J=8.2, 5.7 Hz), 7.73 (1H, d, J=8.4 Hz), 8.38 (1H, s), 9.36 (1H, s).

C) Ethyl 1-(2-((4-(4-fluorophenyl)-1-isopropyl-1H-indol-3-yl)methyl)-5-oxa-2,6-diazaspiro[3.4]oct-6-en-7-yl)-4-methylpiperidine-4-carboxylic acid Using tert-butyl 7-(4-(ethoxycarbonyl)-4-methylpiperidin-1-yl)-5-oxa-2,6-diazaspiro[3.4]oct-6-ene-2-carboxylate and 4-(4-fluorophenyl)-1-isopropyl-1H-indole-3-carbaldehyde, the title compound was obtained in the similar manner as in Step G of Example 1.

MS (ESI+): $[M+H]^+$ 547.6.

D) 1-(2-((4-(4-Fluorophenyl)-1-isopropyl-1H-indol-3-yl)methyl)-5-oxa-2,6-diazaspiro[3.4]oct-6-en-7-yl)-4-methylpiperidine-4-carboxylic acid Using ethyl 1-(2-((4-(4-fluorophenyl)-1-isopropyl-1H-indol-3-yl)methyl)-5-oxa-2,6-diazaspiro[3.4]oct-6-en-7-yl)-4-methylpiperidine-4-carboxylate, the title compound was obtained in the similar manner as in Example 2.

Example 83

1-(2-(3-Chloro-4-(cyclopentyloxy)-5-ethoxybenzyl)-5-oxa-2,6-diazaspiro[3.4]oct-6-en-7-yl)-4-methylpiperidine-4-carboxylic acid A) 3-Chloro-4-(cyclopentyloxy)-5-ethoxybenzaldehyde Using 3-chloro-5-ethoxy-4-hydroxybenzaldehyde and bromocyclopentane, the title compound was obtained in the similar manner as in Step A of Example 1.

$^1$H NMR (400 MHz, $CDCl_3$) δ 1.48 (3H, t, J=6.9 Hz), 1.62 (2H, brs), 1.72 (2H, brs), 1.87-2.01 (4H, m), 4.13 (2H, q, J=6.9 Hz), 5.11 (1H, brs), 7.32 (1H, s), 7.48 (1H, s), 9.82 (1H, s).

B) Ethyl 1-(2-(3-chloro-4-(cyclopentyloxy)-5-ethoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 3-chloro-4-(cyclopentyloxy)-5-ethoxybenzaldehyde, the title compound was obtained in the similar manner as in Step G of Example 1.

MS (ESI+): $[M+H]^+$ 534.3.

C) 1-(2-(3-Chloro-4-(cyclopentyloxy)-5-ethoxybenzyl)-5-oxa-2,6-diazaspiro[3.4]oct-6-en-7-yl)-4-methylpiperidine-4-carboxylic acid Using ethyl 1-(2-(3-chloro-4-(cyclopentyloxy)-5-ethoxybenzyl)-5-oxa-2,6-diazaspiro[3.4]oct-6-en-7-yl)-4-methylpiperidine-4-carboxylate, the title compound was obtained in the similar manner as in Example 2.

Example 84

1-(2-((5-Cyclopropyl-2-ethoxy-4'-fluorobiphenyl-4-yl)methyl)-5-oxa-2,6-diazaspiro[3.4]oct-6-en-7-yl)-4-methylpiperidine-4-carboxylic acid A) Methyl 2-(benzyloxy)-4'-fluorobiphenyl-4-carboxylate Methyl 3-(benzyloxy)-4-bromobenzoate (10.0 g), (4-fluorophenyl)boronic acid (6.53 g), dicyclohexyl(2',6'-dimethoxybiphenyl-2-yl)phosphine (1.92 g), tris(dibenzylideneacetone)dipalladium(0) (1.43 g) and 2 M aqueous sodium carbonate solution (46.7 mL) was added to toluene (100 mL) in an argon atmosphere, the resultant was stirred 2 hours at 100° C. The reaction mixture was cooled to room temperature, it was poured into water, and extraction thereof was performed using ethyl acetate. After the obtained organic layer was dried over anhydrous magnesium sulfate, the solvent was distilled off under reduced pressure. The obtained residue was purified by a silica gel column chromatography (NH, hexane/ethyl acetate), thereby obtaining the title compound (10.0 g).

$^1$H NMR (400 MHz, DMSO-$d_6$) δ 3.88 (3H, s), 5.22 (2H, s), 7.22-7.32 (3H, m), 7.33-7.40 (4H, m), 7.48 (1H, d, J=7.9 Hz), 7.59-7.68 (3H, m), 7.71 (1H, s).

B) Methyl 5-bromo-2-ethoxy-4'-fluorobiphenyl-4-carboxylate

20% palladium hydroxide (50% water content, 600 mg) was added to a solution of methyl 2-(benzyloxy)-4'-fluorobiphenyl-4-carboxylate (6.00 g) in methanol (120 mL), and the resultant was stirred for 1 hours at room temperature in a hydrogen atmosphere. The catalyst was filtered off, and the obtained filtrate was concentrated under reduced pressure. Potassium tert-butoxide (2.20 g) was added to a solution of the obtained residue in THF (100 mL), the resultant was stirred for 30 minutes at room temperature. Iodoethane (3.34 g) was added thereto, and the resultant was stirred for 2 hours at 60° C. The reaction mixture was cooled to room temperature, water was added thereto, and extraction thereof was performed using ethyl acetate. The obtained organic layer was sequentially washed with an aqueous saturated ammonium chloride solution and a saturated saline solution, dried over anhydrous magnesium sulfate, and then the solvent was distilled off under reduced pressure. The obtained residue was washed with hexane, thereby obtaining a solid. After a solution of bromine (1.17 g) in ethyl acetate was added dropwise to a solution of the obtained solid (1.34 g) in acetic acid (6 mL), the resultant was stirred for 4 hours in the range of 60° C. to 70° C. The reaction mixture was cooled to room temperature, 28% aqueous ammonia was added thereto, and extraction thereof was performed using ethyl acetate. After the solvent of the obtained organic layer was distilled off under reduced pressure, the obtained residue was purified by a silica gel column chromatography (hexane/ethyl acetate), thereby obtaining the title compound (850 mg).

$^1$H NMR (400 MHz, DMSO-$d_6$) δ 1.27 (3H, t, J=6.8 Hz), 3.88 (3H, s), 4.10 (2H, q, J=6.8 Hz), 7.27 (2H, t, J=8.6 Hz), 7.44 (1H, s), 7.56-7.65 (3H, m).

C) 5-Bromo-2-ethoxy-4'-fluorobiphenyl-4-carbaldehyde

Methyl 5-bromo-2-ethoxy-4'-fluorobiphenyl-4-carboxylate (3.16 g) was added to a suspension of lithium aluminum hydride (679 mg) in THF (50 mL) at 0° C., and the resultant was stirred for 10 minutes. Sodium sulfate decahydrate was added to the reaction mixture, the resultant was stirred for 1 hour at room temperature, and was filtered using celite. Manganese dioxide (11.7 g) was added to the obtained filtrate, and the resultant was stirred overnight at room temperature. After the reaction mixture was filtered using celite, the filtrate was concentrated under reduced pressure, and the obtained residue was purified by a silica gel column chromatography (hexane/ethyl acetate), thereby obtaining the title compound (2.40 g).

$^1$H NMR (300 MHz, DMSO-$d_6$) δ 1.25-1.33 (3H, m), 4.09-4.19 (2H, m), 7.24-7.34 (2H, m), 7.47 (1H, s), 7.61-7.69 (2H, m), 7.71 (1H, s), 10.19 (1H, s).

D) 5-Cyclopropyl-2-ethoxy-4'-fluorobiphenyl-4-carbaldehyde

5-Bromo-2-ethoxy-4'-fluorobiphenyl-4-carbaldehyde (600 mg), cyclopropyl boronic acid (239 mg), dicyclohexyl (2',6'-dimethoxybiphenyl-2-yl)phosphine (114 mg), tris (dibenzylideneacetone)dipalladium(0) (119 mg) and 2 M aqueous sodium carbonate solution (2.79 mL) was added to toluene (12 mL) in an argon atmosphere, the resultant was stirred overnight at 100° C. The reaction mixture was cooled to room temperature, it was poured into water, and extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (320 mg).

$^1$H NMR (400 MHz, DMSO-d$_6$) δ 0.79 (2H, q, J=5.0 Hz), 0.95-1.03 (2H, m), 1.28 (3H, t, J=6.9 Hz), 2.60-2.70 (1H, m), 4.10 (2H, q, J=7.0 Hz), 7.05 (1H, s), 7.25 (2H, t, J=8.8 Hz), 7.43 (1H, s), 7.57-7.64 (2H, m), 10.56 (1H, s).

E) Ethyl 1-(2-((5-cyclopropyl-2-ethoxy-4'-fluorobiphenyl-4-yl)methyl)-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-5-oxa-2,6-diazaspiro[3.4]oct-6-ene-2-carboxylate (300 mg) was added to formic acid (3 mL), the resultant was stirred for 1 hour at 60° C., and then the solvent was distilled off under reduced pressure. Sodium triacetoxyborohydride (250 mg) was added to a solution of the obtained residue and 5-cyclopropyl-2-ethoxy-4'-fluorobiphenyl-4-carbaldehyde (224 mg) in THF (10 mL), and the resultant was stirred for 1 hour at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. After the obtained residue was purified by a silica gel column chromatography (NH, hexane/ethyl acetate), the obtained residue was further purified by a silica gel column chromatography (hexane/ethyl acetate), thereby obtaining the title compound (360 mg).

$^1$H NMR (400 MHz, DMSO-d$_6$) δ 0.59 (2H, d, J=5.0 Hz), 0.85 (2H, d, J=8.3 Hz), 1.11-1.21 (6H, m), 1.25 (3H, t, J=6.8 Hz), 1.35-1.46 (2H, m), 1.89-1.97 (3H, m), 2.80-2.92 (2H, m), 3.21 (2H, d, J=8.0 Hz), 3.31 (4H, s), 3.51 (2H, d, J=7.9 Hz), 3.77 (2H, s), 4.01 (2H, q, J=6.8 Hz), 4.11 (2H, q, J=7.0 Hz), 6.84 (1H, s), 7.00 (1H, s), 7.19 (2H, t, J=8.7 Hz), 7.51 (2H, dd, J=8.2, 5.8 Hz).

F) 1-(2-((5-Cyclopropyl-5-ethoxy-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (2.4 mL) was added to a solution of ethyl 1-(2-((5-cyclopropyl-2-ethoxy-4'-fluorobiphenyl-4-yl)methyl)-5-oxa-2,6-diazaspiro[3.4]oct-6-en-7-yl)-4-methylpiperidine-4-carboxylate (330 mg) in ethanol (3.0 mL), and the resultant was stirred for 1 hour at 60° C. After the reaction mixture was neutralized with 2 M hydrochloric acid, it was stirred for 30 minutes, the precipitated solid was collected by filtration, and it was washed with water, thereby obtaining the title compound (280 mg).

$^1$H NMR (400 MHz, DMSO-d$_6$) δ 0.55-0.63 (2H, m), 0.82-0.89 (2H, m), 1.14 (3H, s), 1.25 (3H, t, J=6.9 Hz), 1.32-1.42 (2H, m), 1.86-2.00 (3H, m), 2.89 (2H, t, J=10.3 Hz), 3.21 (2H, d, J=8.0 Hz), 3.24-3.38 (4H, m), 3.51 (2H, d, J=8.0 Hz), 3.77 (2H, s), 4.01 (2H, q, J=7.0 Hz), 6.84 (1H, s), 7.00 (1H, s), 7.19 (2H, t, J=8.9 Hz), 7.51 (2H, dd, J=8.5, 5.7 Hz), 12.43 (1H, brs).

Example 85

1-(2-((3-Cyclopropyl-1-ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylic acid A) 3-Bromo-1-ethyl-4-(2,2,2-trifluoroethoxy)-1H-indole-6-carbaldehyde N-bromosuccinimide (2.17 g) was added to a solution of 1-ethyl-4-(2,2,2-trifluoroethoxy)-1H-indole-6-carbaldehyde (3.00 g) in DMF (12 mL) at 0° C., and the resultant was stirred for 10 minutes at the same temperature. Water (10 mL) was added to the reaction mixture, the resultant was stirred for 20 minutes, and then the precipitated solid was collected by filtration, thereby obtaining the title compound (3.64 g).

MS (ESI+): [M+H]$^+$ 351.0.

B) 3-Cyclopropyl-1-ethyl-4-(2,2,2-trifluoroethoxy)-1H-indole-6-carbaldehyde

Using 3-bromo-1-ethyl-4-(2,2,2-trifluoroethoxy)-1H-indole-6-carbaldehyde and cyclopropyl boronic acid, the title compound was obtained in the similar manner as in Step D of Example 23.

MS (ESI+): [M+H]$^+$ 312.1.

C) Ethyl 1-(2-((3-cyclopropyl-1-ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 3-cyclopropyl-1-ethyl-4-(2,2,2-trifluoroethoxy)-1H-indole-6-carbaldehyde, the title compound was obtained in the similar manner as in Step G of Example 1.

MS (ESI+): [M+H]$^+$ 577.5.

D) 1-(2-((3-Cyclopropyl-1-ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylic acid Using ethyl 1-(2-((3-cyclopropyl-1-ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylate, the title compound was obtained in the similar manner as in Example 2.

Example 86

1-(2-((5-Bromo-2-ethoxy-4'-fluorobiphenyl-4-yl)methyl)-5-oxa-2,6-diazaspiro[3.4]oct-6-en-7-yl)-4-methylpiperidine-4-carboxylic acid A) Ethyl 1-(2-((5-bromo-2-ethoxy-4'-fluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 5-bromo-2-ethoxy-4'-fluorobiphenyl-4-carbaldehyde, the title compound was obtained in the similar manner as in Step G of Example 1.

MS (ESI+): $[M+H]^+$ 589.4.

B) 1-(2-((5-Bromo-2-ethoxy-4'-fluorobiphenyl-4-yl) methyl)-5-oxa-2,6-diazaspiro[3.4]oct-6-en-7-yl)-4-methylpiperidine-4-carboxylic acid Using ethyl 1-(2-((5-bromo-2-ethoxy-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 87

1-(2-((2-Ethoxy-4'-fluoro-6-(trifluoromethyl)biphenyl-4-yl)methyl)-5-oxa-2,6-diazaspiro[3.4]oct-6-en-7-yl)-4-methylpiperidine-4-carboxylic acid A) 3-Ethoxy-4-hydroxy-5-iodobenzaldehyde tert-Butyl hypochlorite (3.73 mL) was added dropwise to a mixture of 3-ethoxy-4-hydroxybenzadehyde (5.00 g), sodium iodide (4.96 g), acetonitrile (100 mL) and water (20 mL) at 0° C., and the resultant was stirred for 20 minutes at the same temperature. Ethyl acetate and water were added to the reaction mixture, and the organic layer was separated. The obtained organic layer was sequentially washed with an aqueous sodium thiosulfate solution and a saturated saline solution, dried over anhydrous magnesium sulfate, and then the solvent was distilled off under reduced pressure. The obtained residue was crystallized (hexane/ethanol), thereby obtaining the title compound (7.70 g).

$^1H$ NMR (300 MHz, DMSO-$d_6$) δ 1.37 (3H, t, J=6.9 Hz), 4.16 (2H, q, J=7.0 Hz), 7.40 (1H, d, J=1.7 Hz), 7.87 (1H, d, J=1.7 Hz), 9.74 (1H, s), 10.48 (1H, brs).

B) 3-Ethoxy-4-hydroxy-5-iodobenzoic acid

After sodium dihydrogen phosphate (11.1 g) was added to a mixture of 3-ethoxy-4-hydroxy-5-iodobenzaldehyde (12.0 g), 2-methyl-2-butene (26.1 mL), tert-butanol (60 mL), THF (60 mL) and water (40 mL), sodium chlorite (16.7 g) was added thereto under ice-cooling, the resultant was stirred for 30 minutes at 20° C. The reaction mixture was added to ice water, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was washed with hexane, thereby obtaining the title compound (11.0 g).

$^1H$ NMR (400 MHz, DMSO-$d_6$) δ 1.36 (3H, t, J=6.8 Hz), 4.12 (2H, q, J=6.7 Hz), 7.43 (1H, s), 7.84 (1H, s), 10.11 (1H, brs), 12.75 (1H, brs).

C) Methyl 3-ethoxy-4-hydroxy-5-iodobenzoate

Concentrated sulfuric acid (2.85 mL) was added to a solution of 3-ethoxy-4-hydroxy-5-iodobenzoic acid (11.0 g) in methanol (80 mL) at room temperature, the resultant was stirred overnight at the same temperature, and stirred for 3 hours at 60° C. The reaction mixture was neutralized with sodium hydrogen carbonate at 0° C., ethyl acetate and water were added thereto, and then the organic layer was separated. The obtained organic layer was washed with a saturated saline solution, dried over anhydrous magnesium sulfate, and then the solvent was distilled off under reduced pressure. The obtained residue was washed with hexane, thereby obtaining the title compound (10.7 g).

$^1H$ NMR (400 MHz, DMSO-$d_6$) δ 1.36 (3H, t, J=6.8 Hz), 3.80 (3H, s), 4.13 (2H, q, J=6.8 Hz), 7.43 (1H, s), 7.86 (1H, s), 10.24 (1H, brs).

D) Methyl 4-(benzyloxy)-3-ethoxy-5-iodobenzoate

A mixture of methyl 3-ethoxy-4-hydroxy-5-iodobenzoate (3.00 g), bromomethyl benzene (1.75 g), potassium carbonate (1.55 g) and DMF (15 mL) was stirred for 1 hour at 70° C. The reaction mixture was added to water, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (3.50 g).

$^1H$ NMR (400 MHz, DMSO-$d_6$) δ 1.40 (3H, t, J=6.8 Hz), 3.84 (3H, s), 4.16 (2H, q, J=6.8 Hz), 5.07 (2H, s), 7.31-7.44 (3H, m), 7.49-7.56 (3H, m), 7.90 (1H, s).

E) Methyl 4-(benzyloxy)-3-ethoxy-5-(trifluoromethyl)benzoate

Methyldifluoro(fluorosulfonyl)acetate (3.28 g) was added to a mixture of methyl 4-(benzyloxy)-3-ethoxy-5-iodobenzoate (1.41 g), copper(I) iodide (1.30 g), N,N,N',N',N'',N''-hexamethylphosphoric triamide (3.06 g) and DMF (25 mL) was stirred for 18 hours at 90° C. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (745 mg).

$^1H$ NMR (400 MHz, $CDCl_3$) δ 1.50 (3H, t, J=7.0 Hz), 3.93 (3H, s), 4.19 (2H, q, J=6.7 Hz), 5.19 (2H, s), 7.31-7.43 (3H, m), 7.46-7.53 (2H, m), 7.78 (1H, s), 7.90 (1H, s).

F) Methyl 3-ethoxy-4-hydroxy-5-(trifluoromethyl)benzoate

10% palladium on carbon (55% water content, 330 mg) was added to a mixed solution of methyl 4-(benzyloxy)-3-ethoxy-5-(trifluoromethyl)benzoate (934 mg) in ethanol (20 mL) and THF (5 mL), and the resultant was stirred for 3 hours at room temperature in a hydrogen atmosphere. The reaction mixture was filtered using celite, and the filtrate was concentrated. 10% palladium on carbon (55% water content, 300 mg) was added to a solution of the obtained residue in ethanol (30 mL), and the resultant was stirred for 3 hours at room temperature in a hydrogen atmosphere. After the reaction mixture was filtered using celite, the filtrate was concentrated, thereby obtaining the title compound (690 mg).

$^1H$ NMR (300 MHz, $CDCl_3$) δ 1.50 (3H, t, J=7.0 Hz), 3.91 (3H, s), 4.23 (2H, q, J=7.1 Hz), 6.54 (1H, s), 7.67 (1H, d, J=1.7 Hz), 7.90 (1H, dd, J=1.8, 0.5 Hz).

G) Methyl 3-ethoxy-5-(trifluoromethyl)-4-(((trifluoromethyl)sulfonyl)oxy)benzoate Trifluoromethanesulfonic anhydride (1.10 g) was added to a solution of methyl 3-ethoxy-4-hydroxy-5-(trifluoromethyl)benzoate (687 mg) in pyridine (10 mL), the resultant was stirred for 2 hours at room temperature, and then the solvent was distilled off under reduced pressure. 1 M hydrochloric acid was added to the obtained residue, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (939 mg).

$^1$H NMR (400 MHz, $CDCl_3$) δ 1.50-1.55 (3H, m), 3.97 (3H, s), 4.28 (2H, q, J=7.0 Hz), 7.89 (1H, s), 7.96 (1H, s).

H) Methyl 2-ethoxy-4'-fluoro-6-(trifluoromethyl)biphenyl-4-carboxylate (1,1'-Bis(diphenylphosphino)ferrocene)dichloropalladium(II) (103 mg) was added to a mixture of methyl 3-ethoxy-5-(trifluoromethyl)-4-(((trifluoromethyl)sulfonyl)oxy)benzoate (279 mg), (4-fluorophenyl)boronic acid (148 mg), cesium fluoride (321 mg) and DME (10 mL), and the resultant was stirred for 5 hours at 100° C. in an argon atmosphere. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (184 mg).

$^1$H NMR (400 MHz, $CDCl_3$) δ 1.22 (3H, t, J=6.9 Hz), 3.97 (3H, s), 4.04 (2H, q, J=7.0 Hz), 7.06-7.12 (2H, m), 7.14-7.20 (2H, m), 7.76 (1H, s), 8.02 (1H, s).

I) (2-Ethoxy-4'-fluoro-6-(trifluoromethyl)biphenyl-4-yl)methanol

A solution of methyl 2-ethoxy-4'-fluoro-6-(trifluoromethyl)biphenyl-4-carboxylate (313 mg) in THF (5 mL) was added to a mixture of lithium aluminum hydride (72.9 mg) and THF (5 mL) at 0° C., and the resultant was stirred for 1 hour at room temperature. Water (0.2 mL), 1 M aqueous sodium hydroxide solution (0.2 mL) and water (0.6 mL) were sequentially added to the reaction mixture at 0° C., the resultant was filtered using celite, and then the filtrate was concentrated under reduced pressure. The obtained residue was purified by a silica gel column chromatography (hexane/ethyl acetate), thereby obtaining the title compound (270 mg).

$^1$H NMR (400 MHz, $CDCl_3$) δ 1.19 (3H, t, J=6.9 Hz), 1.83 (1H, brs), 3.98 (2H, q, J=6.9 Hz), 4.78 (2H, d, J=3.8 Hz), 7.03-7.10 (2H, m), 7.13-7.19 (3H, m), 7.31 (1H, s).

J) 2-Ethoxy-4'-fluoro-6-(trifluoromethyl)biphenyl-4-carbaldehyde

Sulfur trioxide-pyridine complex (405 mg) was added to a mixture of (2-ethoxy-4'-fluoro-6-(trifluoromethyl)biphenyl-4-yl)methanol (267 mg), triethylamine (343 mg) and DMSO (10 mL), and the resultant was stirred for 2 hours at room temperature. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (252 mg).

$^1$H NMR (400 MHz, $CDCl_3$) δ 1.23 (3H, t, J=6.9 Hz), 4.07 (2H, q, J=6.9 Hz), 7.07-7.14 (2H, m), 7.15-7.22 (2H, m), 7.61 (1H, s), 7.83 (1H, s), 10.04 (1H, s).

K) Ethyl 1-(2-((2-ethoxy-4'-fluoro-6-(trifluoromethyl)biphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (280 mg) and formic acid (5 mL) was stirred for 1 hour at 60° C., the solvent was distilled off under reduced pressure. Sodium triacetoxyborohydride (311 mg) was added to a mixture of the obtained residue, 2-ethoxy-4'-fluoro-6-(trifluoromethyl)biphenyl-4-carbaldehyde (252 mg) and THF (10 mL), and the resultant was stirred for 15 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (293 mg).

$^1$H NMR (400 MHz, $CDCl_3$) δ 1.18 (3H, t, J=7.0 Hz), 1.21 (3H, s), 1.26 (3H, t, J=7.1 Hz), 1.41-1.50 (2H, m), 2.11 (2H, d, J=13.6 Hz), 2.93-3.03 (2H, m), 3.27 (2H, s), 3.34-3.43 (4H, m), 3.56 (2H, d, J=8.7 Hz), 3.71 (2H, s), 3.96 (2H, q, J=7.0 Hz), 4.17 (2H, q, J=7.1 Hz), 7.03-7.09 (3H, m), 7.13-7.19 (2H, m), 7.24 (1H, s).

L) 1-(2-((2-Ethoxy-4'-fluoro-6-(trifluoromethyl)biphenyl-4-yl)methyl)-5-oxa-2,6-diazaspiro[3.4]oct-6-en-7-yl)-4-methylpiperidine-4-carboxylic acid 2 M aqueous sodium hydroxide solution (1.5 mL) was added to a solution of ethyl 1-(2-((2-ethoxy-4'-fluoro-6-(trifluoromethyl)biphenyl-4-yl)methyl)-5-oxa-2,6-diazaspiro[3.4]oct-6-en-7-yl)-4-methylpiperidine-4-carboxylate (276 mg) in ethanol (10 mL), and the resultant was stirred for 2 hours at 70° C. 2 M aqueous sodium hydroxide solution (1.5 mL) was added to the reaction mixture, the resultant was stirred for 2 hours at 70° C., and then the solvent was distilled off under reduced pressure. Water was added to the obtained residue, the resultant was neutralized with 2 M hydrochloric acid, and then the precipitated solid was collected by filtration. After the obtained solid was dissolved in ethyl acetate and THF, it was dried over anhydrous magnesium sulfate, and the solvent was distilled off under reduced pressure. The residue was crystallized (hexane/ethanol), thereby obtaining the title compound (175 mg).

$^1$H NMR (400 MHz, $CDCl_3$) δ 1.18 (3H, t, J=7.0 Hz), 1.26 (3H, s), 1.42-1.52 (2H, m), 2.14 (2H, d, J=13.4 Hz), 2.96-3.06 (2H, m), 3.30 (2H, brs), 3.38-3.45 (2H, m), 3.54 (2H, brs), 3.65-3.80 (2H, m), 3.89 (2H, brs), 3.94-4.01 (2H, m), 7.03-7.09 (2H, m), 7.12-7.17 (2H, m), 7.26 (2H, s).

Example 88

1-(2-((2-Cyclopropyl-4'-fluoro-6-((2,2,2-trifluoroethoxy)biphenyl-4-yl)methyl)-5-oxa-2,6-diazaspiro[3.4]oct-6-en-7-yl)-4-methylpiperidine-4-carboxylic acid A) Ethyl 3-hydroxy-4-nitrobenzoate Concentrated sulfuric acid (5 mL) was added to a solution of 3-hydroxy-4-nitrobenzoic acid (50.0 g) in ethanol (400 mL), and the resultant was heated to reflux for 15 hours. The reaction mixture was neutralized with an aqueous saturated sodium hydrogen carbonate solution at 0° C., and extraction thereof was performed using ethyl acetate. The obtained organic layer was sequentially washed with water and a saturated saline solution, dried over anhydrous sodium sulfate, and then the solvent was distilled off under reduced pressure, thereby obtaining the title compound (55.2 g).

$^1$H NMR (400 MHz, $CDCl_3$) δ 1.42 (3H, t, J=7.1 Hz), 4.42 (2H, q, J=7.0 Hz), 7.62 (1H, d, J=8.8 Hz), 7.83 (1H, s), 8.17 (1H, d, J=8.8 Hz), 10.50 (1H, s).

B) Ethyl 3-(methoxymethoxy)-4-nitrobenzoate

Chloro(methoxy)methane (31.6 g) was added to a mixture of ethyl 3-hydroxy-4-nitrobenzoate (55.2 g), potassium carbonate (72.2 g) and DMF (300 mL), and the resultant was stirred for 48 hours at room temperature. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (65.8 g).

$^1$H NMR (300 MHz, $CDCl_3$) δ 1.41 (3H, t, J=7.1 Hz), 3.54 (3H, s), 4.42 (2H, q, J=7.2 Hz), 5.35 (2H, s), 7.73-7.77 (1H, m), 7.78-7.82 (1H, m), 7.96 (1H, d, J=1.4 Hz).

C) Ethyl 4-amino-3-(methoxymethoxy)benzoate

10% palladium on carbon (55% water content, 6.00 g) was added to a mixture of ethyl 3-(methoxymethoxy)-4-nitrobenzoate (65.8 g), THF (200 ml) and ethanol (200 mL), and the resultant was stirred for 6 hours at room temperature in a hydrogen atmosphere. The reaction mixture was filtered using celite, and the filtrate was concentrated under reduced pressure. The obtained residue was dissolved in ethanol (400 mL), 10% palladium on carbon (55% water content, 4.00 g) was added thereto, and the resultant was stirred for 5 hours at room temperature in a hydrogen atmosphere. The reaction mixture was filtered using celite, and the filtrate was concentrated under reduced pressure. The obtained residue was purified by a silica gel column chromatography (NH, ethyl acetate), thereby obtaining the title compound (57.4 g).

$^1$H NMR (400 MHz, $CDCl_3$) δ 1.36 (3H, t, J=7.1 Hz), 3.51 (3H, s), 4.23 (2H, brs), 4.32 (2H, q, J=7.1 Hz), 5.24 (2H, s), 6.68 (1H, d, J=8.2 Hz), 7.60 (1H, d, J=8.2 Hz), 7.66 (1H, s).

D) Ethyl 4-amino-3-iodo-5-(methoxymethoxy)benzoate

A mixed solution of iodine (31.9 g) in acetonitrile (150 mL) and THF (20 mL) was added dropwise to a mixture of ethyl 4-amino-3-(methoxymethoxy)benzoate (27.0 g), silver (I) nitrate (24.4 g) and acetonitrile (450 mL) at 0° C., and the resultant was stirred for 16 hours at room temperature. The reaction mixture was filtered using celite, and the filtrate was concentrated under reduced pressure. Ethyl acetate and an aqueous sodium thiosulfate solution were added to the residue, and the organic layer was separated. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (26.0 g).

$^1$H NMR (400 MHz, $CDCl_3$) δ 1.36 (3H, t, J=7.1 Hz), 3.50 (3H, s), 4.32 (2H, q, J=7.1 Hz), 4.70 (2H, hrs), 5.24 (2H, s), 7.62 (1H, s), 8.05 (1H, s).

E) Ethyl 4-amino-3-cyclopropyl-5-(methoxymethoxy)benzoate

Cyclopropyl boronic acid (9.95 g), 2 M sodium carbonate (116 mL), tris(dibenzylideneacetone)dipalladium(0) (7.95 and dicyclohexyl(2',6'-dimethoxybiphenyl-2-yl)phosphine (3.57 g) were added to a solution of ethyl 4-amino-3-iodo-5-(methoxymethoxy)benzoate (20.3 g) in toluene (400 mL), the resultant was stirred 18 hours at 100° C. in an argon atmosphere. Water was added to the reaction mixture, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (14.3 g).

$^1$H NMR (400 MHz, $CDCl_3$) δ 0.61-0.67 (2H, m), 0.89-0.96 (2H, m), 1.36 (3H, t, J=7.2 Hz), 1.62-1.70 (1H, m), 3.51 (3H, s), 4.31 (2H, q, J=7.1 Hz), 4.54 (2H, brs), 5.24 (2H, s), 7.50 (1H, s), 7.57 (1H, s).

F) Ethyl 4-amino-3-cyclopropyl-5-hydroxybenzoate

6 M hydrochloric acid (70 mL) was added to a solution of ethyl 4-amino-3-cyclopropyl-5-(methoxymethoxy)benzoate (10.8 g) in ethanol (150 mL), the resultant was stirred for 3 hours at 70° C., and then the solvent was distilled off under reduced pressure. The obtained residue was neutralized with an aqueous saturated sodium hydrogen carbonate solution at 0° C., and extraction thereof was performed using ethyl acetate. The obtained organic layer was sequentially washed with water and a saturated saline solution, dried over anhydrous sodium sulfate, and then the solvent was distilled off under reduced pressure, thereby obtaining the title compound (8.93 g).

$^1$H NMR (400 MHz, $CDCl_3$) δ 0.60-0.67 (2H, m), 0.89-0.96 (2H, m), 1.36 (3H, t, J=7.2 Hz), 1.62-1.72 (1H, m), 4.32 (2H, q, J=7.2 Hz), 7.40 (1H, s), 7.49 (1H, s).

G) Ethyl 3-cyclopropyl-5-hydroxy-4-iodobenzoate

2 M hydrochloric acid (101 mL) was added to a solution of ethyl 4-amino-3-cyclopropyl-5-hydroxybenzoate (8.91 g) in acetonitrile (130 mL) at 0° C., and the resultant was stirred for 30 minutes at the same temperature. An aqueous solution (65 mL) of sodium nitrite (3.61 g) was added to the reaction mixture, and the resultant was stirred for 30 minutes at 0° C. An aqueous solution (65 mL) of potassium iodide (26.7 g) was added dropwise thereto, and the resultant was stirred for 2 hours at 70° C. The reaction mixture was neutralized with an aqueous saturated sodium hydrogen carbonate solution at 0° C., and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (8.76 g).

$^1$H NMR (400 MHz, $CDCl_3$) δ 0.69-0.75 (2H, m), 1.03-1.10 (2H, m), 1.38 (3H, t, J=7.2 Hz), 1.95-2.04 (1H, m), 4.35 (2H, q, J=7.2 Hz), 5.62 (1H, s), 7.19 (1H, d, J=1.4 Hz), 7.48 (1H, d, J=1.6 Hz).

H) 3-Cyclopropyl-5-(hydroxymethyl)-2-iodophenol

Diisobutylaluminium hydride (1.5 M toluene solution, 32 mL) was added to a solution of ethyl 3-cyclopropyl-5-hydroxy-4-iodobenzoate (4.56 g) in THF (150 mL) at 0° C., and the resultant was stirred for 1 hour at room temperature. Diisobutylaluminium hydride (1.5 M toluene solution, 9.15 mL) was further added to the reaction mixture, the resultant was stirred for 1 hour at room temperature. Sodium sulfate decahydrate was added thereto 0° C., the resultant was filtered using celite. After the obtained filtrate was dried over anhydrous magnesium sulfate, it was concentrated under reduced pressure, thereby obtaining the title compound (3.86 g).

$^1$H NMR (400 MHz, $CDCl_3$) δ 0.63-0.70 (2H, m), 0.98-1.07 (2H, m), 1.65 (1H, t, J=6.0 Hz), 1.92-2.03 (1H, m), 4.60 (2H, d, J=5.8 Hz), 5.53 (1H, s), 6.55 (1H, s), 6.87 (1H, s).

I) 3-Cyclopropyl-5-hydroxy-4-iodobenzaldehyde

Sulfur trioxide-pyridine complex (6.35 g) was added to a mixture of 3-cyclopropyl-5-(hydroxymethyl)-2-iodophenol (3.86 g), triethylamine (5.39 g) and DMSO (100 mL), and the resultant was stirred for 3 hours at room temperature. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (3.39 g).

$^1$H NMR (400 MHz, $CDCl_3$) δ 0.70-0.78 (2H, m), 1.06-1.14 (2H, m), 1.98-2.08 (1H, m), 5.74 (1H, s), 7.04 (1H, d, J=1.4 Hz), 7.30 (1H, d, J=1.6 Hz), 9.91 (1H, s).

J) 3-Cyclopropyl-4-iodo-5-((2,2,2-trifluoroethoxy) benzaldehyde 2,2,2-Trifluoroethyl trifluoromethanesulfonate (304 mg) was added to a mixture of 3-cyclopropyl-5-hydroxy-4-iodobenzaldehyde (251 mg), cesium carbonate (568 mg) and DMF (10 mL), and the resultant was stirred for 14 hours at 60° C. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (299 mg).

$^1$H NMR (400 MHz, $CDCl_3$) δ 0.71-0.78 (2H, m), 1.10-1.18 (2H, m), 2.13-2.24 (1H, m), 4.47 (2H, q, J=8.0 Hz), 7.12 (2H, s), 9.92 (1H, s).

K) 2-Cyclopropyl-4'-fluoro-6-((2,2,2-trifluoroethoxy)biphenyl-4-carbaldehyde (1,1'-Bis(diphenylphosphino)ferrocene)dichloropalladium(II) (117 mg) was added to a mixture of 3-cyclopropyl-4-iodo-5-((2,2,2-trifluoroethoxy)benzaldehyde (296 mg), (4-fluorophenyl)boronic acid (168 mg), cesium fluoride (364 mg) and DME (10 mL), and the resultant was stirred for 14 hours at 100° C. in an argon atmosphere. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (245 mg).

$^1$H NMR (400 MHz, $CDCl_3$) δ 0.70-0.77 (2H, m), 0.85-0.92 (2H, m), 1.64-1.74 (1H, m), 4.29 (2H, q, J=8.0 Hz), 7.11-7.18 (3H, m), 7.25-7.31 (3H, m), 9.95 (1H, s).

L) Ethyl 1-(2-((2-cyclopropyl-4'-fluoro-6-((2,2,2-trifluoroethoxy)biphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (251 mg) and formic acid (6 mL) was stirred for 1 hour at 60° C., the solvent was distilled off under reduced pressure. Sodium triacetoxyborohydride (279 mg) was added to a mixture of the obtained residue, 2-cyclopropyl-4'-fluoro-6-((2,2,2-trifluoroethoxy)biphenyl-4-carbaldehyde (245 mg) and THF (10 mL), and the resultant was stirred for 2 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (307 mg).

$^1$H NMR (400 MHz, $CDCl_3$) δ 0.60-0.67 (2H, m), 0.74-0.81 (2H, m), 1.19-1.30 (6H, m), 1.40-1.51 (2H, m), 1.56-1.65 (1H, m), 2.11 (2H, d, J=13.6 Hz), 2.92-3.02 (2H, m), 3.26 (2H, s), 3.30-3.43 (4H, m), 3.52 (2H, d, J=8.8 Hz), 3.62 (2H, s), 4.12-4.21 (4H, m), 6.52 (1H, s), 6.72 (1H, s), 7.06-7.13 (2H, m), 7.23-7.29 (2H, m).

M) 1-(2-((2-Cyclopropyl-4'-fluoro-6-((2,2,2-trifluoroethoxy)biphenyl-4-yl)methyl)-5-oxa-2,6-diazaspiro[3.4]oct-6-en-7-yl)-4-methylpiperidine-4-carboxylic acid 2 M aqueous sodium hydroxide solution (1.5 mL) was added to a solution of ethyl 1-(2-((2-cyclopropyl-4'-fluoro-6-((2,2,2-trifluoroethoxy)biphenyl-4-yl)methyl)-5-oxa-2,6-diazaspiro[3.4]oct-6-en-7-yl)-4-methylpiperidine-4-carboxylate (292 mg) in ethanol (10 mL), the resultant was stirred for 15 hours at 70° C., and then the solvent was distilled off under reduced pressure. Water was added to the residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The residue was crystallized (hexane/ethanol), thereby obtaining the title compound (130 mg).

$^1$H NMR (400 MHz, $CDCl_3$) δ 0.61-0.67 (2H, m), 0.76-0.84 (2H, m), 1.26 (3H, s), 1.41-1.52 (2H, m), 1.57-1.67 (1H, m), 2.14 (2H, d, J=13.4 Hz), 3.01 (2H, t, J=10.7 Hz), 3.30 (2H, brs), 3.37-3.46 (2H, m), 3.57 (2H, brs), 3.88 (4H, brs), 4.18 (2H, q, J=8.1 Hz), 6.56 (1H, s), 6.85 (1H, brs), 7.07-7.14 (2H, m), 7.22-7.25 (2H, m).

Example 89

1-(2-((1-Ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylic acid A) Ethyl 1-(2-((1-ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 1-ethyl-4-(2,2,2-trifluoroethoxy)-1H-indole-6-carbaldehyde, the title compound was obtained in the similar manner as in Step G of Example 1.

MS (ESI+): $[M+H]^+$ 537.5.

B) 1-(2-((1-Ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylic acid Using ethyl 1-(2-((1-ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylate, the title compound was obtained in the similar manner as in Example 2.

Example 90

1-(2-((2,2'-Diethoxy-4'-fluorobiphenyl-4-yl)methyl)-5-oxa-2,6-diazaspiro[3.4]oct-6-en-7-yl)-4-piperidine-4-carboxylic acid A) 2-Ethoxy-4-formylphenyl trifluoromethanesulfonate Using 3-ethoxy-4-hydroxybenzaldehyde and N-phenyl bis(trifluoromethanesulfonimide), the title compound was obtained in the similar manner as in Step H of Example 16.

$^1H$ NMR (300 MHz, $CDCl_3$) δ 1.50 (3H, t, J=7.0 Hz), 4.23 (2H, q, J=7.0 Hz), 7.38-7.42 (1H, m), 7.46-7.52 (1H, m), 7.54 (1H, d, J=1.7 Hz), 9.98 (1H, s).

B) 2,2'-Diethoxy-4'-fluorobiphenyl-4-carbaldehyde

Using 2-ethoxy-4-formylphenyl trifluoromethanesulfonate and (2-ethoxy-4-fluorophenyl)boronic acid, the title compound was obtained in the similar manner as in Step D of Example 16.

$^1H$ NMR (300 MHz, $CDCl_3$) δ 1.24-1.34 (6H, m), 3.99 (2H, q, J=7.0 Hz), 4.05-4.13 (2H, m), 6.64-6.75 (2H, m), 7.14-7.23 (1H, m), 7.36-7.50 (3H, m), 9.99 (1H, s).

C) Ethyl 1-(2-((2,2'-diethoxy-4'-fluorobiphenyl-4-yl)methyl)-5-oxa-2,6-diazaspiro[3.4]oct-6-en-7-yl)-4-methylpiperidine-4-carboxylate Using 2,2'-diethoxy-4'-fluorobiphenyl-4-carbaldehyde and tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step G of Example 1.

MS (ESI+): $[M+H]^+$ 554.5.

D) 1-(2-((2,2'-Diethoxy-4'-fluorobiphenyl-4-yl)methyl)-5-oxa-2,6-diazaspiro[3.4]oct-6-en-7-yl)-4-piperidine-4-carboxylic acid Using ethyl 1-(2-((2,2'-ethoxy-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 91

1-(2-((2,6-Diethoxy-4'-fluoro-3-iodobiphenyl-4-yl)methyl)-5-oxa-2,6-diazaspiro[3.4]oct-6-en-7-yl)-4-methylpiperidine-4-carboxylic acid A) 2,6-Diethoxy-4'-fluoro-3-iodobiphenyl-4-carbaldehyde N-iodosuccinimide (0.86 g) was added to a solution of 2,6-diethoxy-4-fluorobiphenyl-4-carbaldehyde (1.00 g) in acetonitrile (10 mL), and the resultant was stirred for 8 hours at 65° C. The reaction mixture was cooled to room temperature, and water (3.0 mL) was added thereto. The precipitated solid was collected by filtration, thereby obtaining the title compound (1.10 g).

MS (ESI+): $[M+H]^+$ 415.0.

B) Ethyl 1-(2-((2,6-diethoxy-4'-fluoro-3-iodobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2,6-diethoxy-4'-fluoro-3-iodobiphenyl-4-carbaldehyde, the title compound was obtained in the similar manner as in Step G of Example 1.

MS (ESI+): $[M+H]^+$ 680.4.

C) 1-(2-((2,6-Diethoxy-4'-fluoro-3-iodobiphenyl-4-yl)methyl)-5-oxa-2,6-diazaspiro[3.4]oct-6-en-7-yl)-4-methylpiperidine-4-carboxylic acid Using ethyl 1-(2-((2,6-diethoxy-4'-fluoro-3-iodobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 92

1-(2-((3-Cyclopropyl-2,6-diethoxy-4'-fluorobiphenyl-4-yl)methyl)-5-oxa-2,6-diazaspiro[3.4]oct-6-en-7-yl)-4-methylpiperidine-4-carboxylic acid A) 3-Cyclopropyl-2,6-diethoxy-4'-fluorobiphenyl-4-carbaldehyde Using 2,6-diethoxy-4'-fluoro-3-iodobiphenyl-4-carbaldehyde and cyclopropyl boronic acid, the title compound was obtained in the similar manner as in Step D of Example 23.

MS (ESI+): $[M+H]^+$ 329.1.

B) Ethyl 1-(2-((3-cyclopropyl-2,6-diethoxy-4'-fluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 3-cyclopropyl-2,6-diethoxy-4'-fluorobiphenyl-4-carbaldehyde, the title compound was obtained in the similar manner as in Step G of Example 1.

MS (ESI+): $[M+H]^+$ 594.5.

C) 1-(2-((3-Cyclopropyl-2,6-diethoxy-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((3-cyclopropyl-2,6-diethoxy-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 93

1-(2-((2-Cyclopropyl-6-(cyclopropylmethoxy)-4'-fluorobiphenyl-4-yl)methyl)-5-oxa-2,6-diazaspiro[3.4]oct-6-en-7-yl)-4-methylpiperidine-4-carboxylic acid A) 3-Cyclopropyl-5-(cyclopropylmethoxy)-4-iodobenzaldehyde (Bromomethyl)cyclopropane (248 mg) was added to a mixture of 3-cyclopropyl-5-hydroxy-4-iodobenzaldehyde (352 mg), potassium carbonate (338 mg) and DMF (10 mL), and the resultant was stirred for 15 hours at 60° C. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (408 mg).

$^1H$ NMR (400 MHz, $CDCl_3$) δ 0.42-0.49 (2H, m), 0.62-0.77 (4H, m), 1.06-1.14 (2H, m), 1.29-1.41 (1H, m), 2.12-2.22 (1H, m), 3.98 (2H, d, J=6.5 Hz), 7.01 (1H, s), 7.08 (1H, s), 9.90 (1H, s).

B) 2-Cyclopropyl-6-(cyclopropylmethoxy)-4'-fluorobiphenyl-4-carbaldehyde (1,1'-Bis(diphenylphosphino)ferrocene)dichloropalladium(II) (169 mg) was added to a mixture of 3-cyclopropyl-5-(cyclopropylmethoxy)-4-iodobenaldehyde (394 mg), (4-fluorophenyl)boronic acid (242 mg), cesium fluoride (525 mg) and DME (10 mL), and the resultant was stirred for 14 hours at 100° C. in an argon atmosphere. Water was added to the reaction mixture, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (333 mg).

$^1H$ NMR (400 MHz, $CDCl_3$) δ 0.14-0.21 (2H, m), 0.43-0.51 (2H, m), 0.68-0.74 (2H, m), 0.80-0.88 (2H, m), 1.02-1.13 (1H, m), 1.61-1.70 (1H, m), 3.83 (2H, d, J=6.4 Hz), 7.04 (1H, s), 7.13 (2H, t, J=8.8 Hz), 7.25-7.31 (3H, m), 9.93 (1H, s).

C) Ethyl 1-(2-((2-cyclopropyl-6-(cyclopropylmethoxy)-4'-fluorobiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (330 mg) and formic acid (6 mL) was stirred for 1 hour at 60° C., the solvent was distilled off under reduced pressure. Sodium triacetoxyborohydride (367 mg) was added to a mixture of the obtained residue, 2-cyclopropyl-6-(cyclopropylmethoxy)-4'-fluorobiphenyl-4-carbaldehyde (323 mg) and THE (10 mL), and the resultant was stirred for 4 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (380 mg).

$^1H$ NMR (400 MHz, $CDCl_3$) δ 0.09-0.16 (2H, m), 0.39-0.46 (2H, m), 0.59-0.65 (2H, m), 0.71-0.78 (2H, m), 0.97-1.08 (1H, m), 1.19-1.30 (6H, m), 1.40-1.51 (2H, m), 1.55-1.63 (1H, m), 2.11 (2H, d, J=13.6 Hz), 2.91-3.02 (2H, m), 3.25 (2H, s), 3.31-3.42 (4H, m), 3.52 (2H, d, J=8.8 Hz), 3.61 (2H, s), 3.72 (2H, d, J=6.3 Hz), 4.16 (2H, q, J=7.1 Hz), 6.42 (1H, s), 6.69 (1H, s), 7.05-7.12 (2H, m), 7.23-7.30 (2H, m).

D) 1-(2-((2-Cyclopropyl-6-(cyclopropylmethoxy)-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (2 mL) was added to a solution of ethyl 1-(2-((2-cyclopropyl-6-(cyclopropylmethoxy)-4'-fluorobiphenyl-4-yl)methyl)-5-oxa-2,6-diazaspiro[3.4]oct-6-en-7-yl)-4-methylpiperidine-4-carboxylate (365 mg) in ethanol (8 mL), the resultant was stirred for 13 hours at 70° C., and then the solvent was distilled off under reduced pressure. Water was added to the residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The residue was crystallized (hexane/ethanol), thereby obtaining the title compound (181 mg).

$^1H$ NMR (400 MHz, DMSO-$d_6$) δ 0.10-0.17 (2H, m), 0.35-0.42 (2H, m), 0.54-0.60 (2H, m), 0.67-0.75 (2H, m), 0.94-1.04 (1H, m), 1.14 (3H, s), 1.32-1.41 (2H, m), 1.45-1.54 (1H, m), 1.90 (2H, d, J=13.7 Hz), 2.83-2.94 (2H, m), 3.13 (2H, d, J=8.0 Hz), 3.25-3.35 (4H, m), 3.42 (2H, d, J=8.2 Hz), 3.53 (2H, s), 3.74 (2H, d, J=6.4 Hz), 6.42 (1H, s), 6.76 (1H, s), 7.17-7.31 (4H, m).

Example 94

1-(2-((2-Cyclopropyl-4'-fluoro-6-propoxybiphenyl-4-yl)methyl)-5-oxa-2,6-diazaspiro[3.4]oct-6-en-7-yl)-4-methylpiperidine-4-carboxylic acid A) Ethyl 4-fluoro-3,5-dihydroxybenzoate A mixture of 4-bromo-3,5-dihydroxybenzoic acid (45.0 g), concentrated sulfuric acid (5 mL) and ethanol (300 mL)

was heated to reflux for 24 hours, and the solvent was distilled off under reduced pressure. The residue was diluted by ethyl acetate, the resultant was sequentially washed with water, an aqueous saturated sodium hydrogen carbonate solution and a saturated saline solution. After the obtained organic layer was dried over anhydrous magnesium sulfate, the solvent was distilled off under reduced pressure. The obtained solid was washed with hexane, thereby obtaining the title compound (48.3 g).

$^1$H NMR (300 MHz, $CDCl_3$) δ 1.39 (3H, t, J=7.1 Hz), 4.37 (2H, q, J=7.1 Hz), 5.82 (2H, brs), 7.31 (2H, s).

B) Ethyl 4-bromo-3-hydroxy-5-propoxybenzoate

Sodium hydride (60% dispersion in oil, 10.1 g) was added to a mixture of ethyl 4-bromo-3,5-dihydroxybenzoate (30.0 g) and DMF (200 mL), the resultant was stirred for 30 minutes at 0° C. in a nitrogen atmosphere. 1-Iodopropane (11.2 mL) was added to the reaction mixture, and the resultant was stirred for 2 hours at room temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (14.1 g).

$^1$H NMR (300 MHz, $CDCl_3$) δ 1.08 (3H, t, J=7.4 Hz), 1.39 (3H, t, J=7.1 Hz), 1.78-1.95 (2H, m), 4.05 (2H, t, J=6.4 Hz), 4.37 (2H, q, J=7.1 Hz), 5.74 (1H, s), 7.13 (1H, d, J=1.8 Hz), 7.34 (1H, d, J=1.8 Hz).

C) Ethyl 4'-fluoro-2-hydroxy-6-propoxybiphenyl-4-carboxylate

Palladium acetate (1.11 g) was added to a mixture of ethyl 4-bromo-3-hydroxy-5-propoxybenzoate (30.0 g), tripotassium phosphate (63.0 g), (4-fluorophenyl)boronic acid (34.6 g), tricyclohexylphosphine (20% toluene solution, 17.6 mL), toluene (200 mL) and water (100 mL), and the resultant was heated and stirred overnight at 90° C. in an argon atmosphere. After the reaction mixture was cooled to room temperature, it was diluted by ethyl acetate, and was sequentially washed with water and a saturated saline solution. After the organic layer was dried over anhydrous magnesium sulfate, the solvent was distilled off under reduced pressure. The obtained residue was purified by a silica gel column chromatography (hexane/ethyl acetate), thereby obtaining the title compound (31.5 g).

$^1$H NMR (300 MHz, $CDCl_3$) δ 0.86 (3H, t, J=7.4 Hz), 1.40 (3H, t, J=7.1 Hz), 1.58-1.71 (2H, m), 3.92 (2H, t, J=6.4 Hz), 4.39 (2H, q, J=7.1 Hz), 5.03 (1H, s), 7.10-7.23 (3H, m), 7.30-7.41 (3H, m).

D) Ethyl 4'-fluoro-2-propoxy-6-(((trifluoromethyl)sulfonyl)oxy)biphenyl-4-carboxylate Trifluoromethanesulfonic anhydride (20.1 mL) was added to a mixture of ethyl 4'-fluoro-2-hydroxy-6-propoxybiphenyl-4-carboxylate (31.5 g) and pyridine (200 mL) at 0° C., and the resultant was stirred for 20 minutes at the same temperature. The reaction mixture was passed through a short column of a silica gel (NH), and the solvent was distilled off under reduced pressure. The obtained residue was purified by a silica gel column chromatography (hexane/ethyl acetate), thereby obtaining the title compound (44.6 g).

$^1$H NMR (300 MHz, $CDCl_3$) δ 0.81-0.96 (3H, m), 1.43 (3H, t, J=7.1 Hz), 1.62-1.76 (2H, m), 3.99 (2H, t, J=6.3 Hz), 4.43 (2H, q, J=7.2 Hz), 7.09-7.18 (2H, m), 7.28-7.38 (2H, m), 7.63 (2H, s).

E) (2-Cyclopropyl-4'-fluoro-6-propoxybiphenyl-4-yl)methanol

Tris(dibenzylideneacetone)dipalladium(0) (6.65 g) was added to a mixture of ethyl-4'-fluoro-2-propoxy-6-(((trifluoromethyl)sulfonyl)oxy)biphenyl-4-carboxyalte (44.6 g), cyclopropylboronic acid (22.3 g), dicyclohexyl(2',6'-dimethoxybiphenyl-2-yl)phosphine (6.38 g), 2 M aqueous sodium carbonate solution (156 mL) and toluene (250 mL), and the resultant was stirred for 4 hours at 100° C. in an argon atmosphere. The reaction mixture was cooled to room temperature, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate). A solution of the obtained product in THF (150 mL) was added to a suspension of lithium aluminum hydride (3.50 g) in THF (150 mL) under ice-cooling in a nitrogen atmosphere. After stirring for 30 minutes at the same temperature, water (3.5 mL) and 15% aqueous sodium hydroxide solution (3.5 mL) were added thereto, and the resultant was stirred for 15 minutes. Water (10.5 mL) was further added thereto, and the resultant was stirred for 30 minutes. The reaction mixture was filtered, and the filtrate was concentrated under reduced pressure. The obtained residue was purified by a silica gel column chromatography (hexane/ethyl acetate), thereby obtaining the title compound (29.8 g).

$^1$H NMR (300 MHz, $CDCl_3$) δ 0.58-0.69 (2H, m), 0.72-0.78 (2H, m), 0.82 (3H, t, J=7.4 Hz), 1.50-1.76 (3H, m), 3.84 (2H, t, J=6.3 Hz), 4.66 (2H, d, J=5.9 Hz), 6.51 (1H, s), 6.80 (1H, s), 7.03-7.13 (2H, m), 7.20-7.31 (2H, m).

F) 2-Cyclopropyl-4'-fluoro-6-propoxybiphenyl-4-carbaldehyde

Manganese dioxide (60.4 g) was added to a mixture of (2-cyclopropyl-4'-fluoro-6-propylbiphenyl-4-yl)methanol (29.8 g) and toluene (200 mL), and the resultant was stirred for 1 hour at 60° C. in a nitrogen atmosphere. The reaction mixture was filtered, and the filtrate was concentrated. The obtained residue was purified by a silica gel column chromatography (hexane/ethyl acetate), thereby obtaining the title compound (22.1 g).

$^1$H NMR (300 MHz, $CDCl_3$) δ 0.67-0.76 (2H, m), 0.78-0.93 (5H, m), 1.57-1.73 (3H, m), 3.91 (2H, t, J=6.3 Hz), 7.03 (1H, d, J=1.2 Hz), 7.07-7.18 (2H, m), 7.22-7.33 (3H, m), 9.94 (1H, s).

G) Ethyl 1-(2-((2-cyclopropyl-4'-fluoro-6-propoxybiphenyl-4-yl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)methyl-5-oxa-2,6-diazaspiro[3.4]oct-6-ene-2-carboxylate (20.3 g) and formic acid (50 mL) was stirred for 1 hour at 70° C., the solvent was distilled off under reduced pressure. The obtained residue was mixed with 2-cyclopropyl-4'-fluoro-6-propoxybiphenyl-4-carbaldehyde (17.4 g) and THF (200 mL), sodium triacetoxyborohydride (16.9 g) was added to the mixture, and the resultant was stirred for 16 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (25.5 g).

$^1$H NMR (300 MHz, $CDCl_3$) δ 0.59-0.65 (2H, m), 0.70-0.78 (2H, m), 0.81 (3H, t, J=7.4 Hz), 1.21 (3H, s), 1.26 (3H, t, J=7.1 Hz), 1.40-1.51 (2H, m), 1.52-1.65 (3H, m), 2.11 (2H, d, J=13.5 Hz), 2.90-3.03 (2H, m), 3.26 (2H, s), 3.31-3.44 (4H, m), 3.55 (2H, d, J=8.9 Hz), 3.63 (2H, s), 3.82 (2H, t, J=6.3 Hz), 4.16 (2H, q, J=7.1 Hz), 6.40 (1H, s), 6.68 (1H, s), 7.03-7.11 (2H, m), 7.22-7.29 (2H, m).

H) 1-(2-((2-Cyclopropyl-4'-fluoro-6-propoxybiphenyl-4-yl)methyl)-5-oxa-2,6-diazaspiro[3.4]oct-6-en-7-yl)-4-methylpiperidine-4-carboxylic acid 2 M aqueous sodium hydroxide solution (150 mL) was added to a solution of ethyl 1-(2-((2-cyclopropyl-4'-fluoro-6-propoxybiphenyl-4-yl)methyl)-5-oxa-2,6-diazaspiro[3.4] oct-6-en-7-yl)-4-methylpiperidine-4-carboxylate (25.5 g) in ethanol (300 mL), and the resultant was stirred for 5 hours at 70° C., and the solvent was distilled off under reduced pressure. Water was added to the obtained residue, the resultant was neutralized with 2 M hydrochloric acid, and then the obtained solid was collected by filtration, and was dried under reduced pressure. The obtained residue was crystallized (ethanol), thereby obtaining the title compound (11.9 g).

$^1$H NMR (300 MHz, DMSO-$d_6$) δ 0.54-0.62 (2H, m), 0.67-0.80 (5H, m), 1.14 (3H, s), 1.30-1.42 (2H, m), 1.43-1.56 (3H, m), 1.90 (2H, d, J=13.7 Hz), 2.82-2.95 (2H, m), 3.13 (2H, d, J=8.3 Hz), 3.25-3.34 (4H, m), 3.43 (2H, d, J=8.3 Hz), 3.54 (2H, s), 3.81 (2H, t, J=6.2 Hz), 6.41 (1H, s), 6.75 (1H, s), 7.16-7.29 (4H, m).

Example 95

1-(2-((2-Cyclopropyl-6-((2,2-difluoroethoxy)-4'-fluorobiphenyl-4-yl)methyl)-5-oxa-2,6-diazaspiro [3.4]oct-6-en-7-yl)-4-methylpiperidine-4-carboxylic acid

A) 3-Cyclopropyl-5-((2,2-difluoroethoxy)-4-iodo-benzaldehyde 2,2-Difluoroethyl trifluoromethanesulfonate (416 mg) was added to a mixture of 3-cyclopropyl-5-hydroxy-4-iodobenzaldehyde (373 mg), potassium carbonate (358 mg) and DMF (10 mL), and the resultant was stirred for 16 hours at 60° C. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (438 mg).

$^1$H NMR (400 MHz, $CDCl_3$) δ 0.70-0.78 (2H, m), 1.09-1.16 (2H, m), 2.12-2.21 (1H, m), 4.31 (2H, td, J=12.7, 4.1 Hz), 6.04-6.37 (1H, m), 7.07-7.13 (2H, m), 9.92 (1H, s).

B) 2-Cyclopropyl-6-((2,2-difluoroethoxy)-4'-fluoro-biphenyl-4-carbaldehyde (1,1% Bis(diphenylphosphino)ferrocene)dichloropalladium(II) (176 mg) was added to a mixture of 3-cyclopropyl-5-((2,2-difluoroethoxy)-4-iodobenaldehyde (424 mg), (4-fluorophenyl)boronic acid (253 mg), cesium fluoride (549 mg) and DME (10 mL), and the resultant was stirred for 8 hours at 100° C. in an argon atmosphere. Water was added to the reaction mixture, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (284 mg).

$^1$H NMR (400 MHz, $CDCl_3$) δ 0.70-0.76 (2H, m), 0.83-0.91 (2H, m), 1.62-1.71 (1H, m), 4.14 (2H, td, J=12.9, 4.0 Hz), 5.68-5.99 (1H, m), 7.10-7.17 (3H, m), 7.24-7.30 (3H, m), 9.95 (1H, s).

C) Ethyl 1-(2-((2-cyclopropyl-6-((2,2-difluoroethoxy)-4'-fluorobiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (300 mg) and formic acid (6 mL) was stirred for 1 hour at 60° C., the solvent was distilled off under reduced pressure. Sodium triacetoxyborohydride (333 mg) was added to a mixture of the obtained residue, 2-cyclopropyl-6-((2,2-difluoroethoxy)-4'-fluorobiphenyl-4-carbaldehyde (277 mg) and THF (10 mL), and the resultant was stirred for 2 hours at mom temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (353 mg).

$^1$H NMR (400 MHz, $CDCl_3$) δ 0.60-0.65 (2H, m), 0.73-0.80 (2H, m), 1.21 (3H, s), 1.26 (3H, t, J=7.1 Hz), 1.41-1.50 (2H, m), 1.54-1.64 (1H, m), 2.11 (2H, d, J=13.4 Hz), 2.93-3.02 (2H, m), 3.26 (2H, s), 3.31-3.43 (4H, m), 3.53 (2H, d, J=8.7 Hz), 3.63 (2H, s), 4.04 (2H, td, J=13.1, 4.2 Hz), 4.16 (2H, q, J=7.2 Hz), 5.62-5.94 (1H, m), 6.49 (1H, s), 6.71 (1H, s), 7.06-7.12 (2H, m), 7.22-7.26 (2H, m).

D) 1-(2-((2-Cyclopropyl-6-((2,2-di fluoroethoxy)-4'-fluorobiphenyl-4-yl)methyl)-5-oxa-2,6-diazaspiro [3.4]oct-6-en-7-yl)-4-methylpiperidine-4-carboxylic acid 2 M aqueous sodium hydroxide solution (2 mL) was added to a solution of ethyl 1-(2-((2-cyclopropyl-6-((2,2-difluoroethoxy)-4'-fluorobiphenyl-4-yl)methyl)-5-oxa-2,6-diaza spiro[3.4]oct-6-en-7-yl)-4-methylpiperidine-4-carboxylate (338 mg) in ethanol (8 mL), the resultant was stirred for 16 hours at 70° C., and then the solvent was distilled off under reduced pressure. Water was added to the obtained residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The obtained residue was crystallized (hexane/ethanol), thereby obtaining the title compound (182 mg).

$^1$H NMR (400 MHz, DMSO-$d_6$) δ 0.56-0.64 (2H, m), 0.69-0.78 (2H, m), 1.14 (3H, s), 1.32-1.42 (2H, m), 1.46-1.55 (1H, m), 1.91 (2H, d, J=13.7 Hz), 2.84-2.94 (2H, m), 3.17 (2H, brs), 3.26-3.34 (4H, m), 3.45 (2H, brs), 3.57 (2H, brs), 4.19 (2H, td, J=14.5, 3.5 Hz), 5.95-6.27 (1H, m), 6.51 (1H, s), 6.86 (1H, s), 7.18-7.30 (4H, m), 12.42 (1H, brs).

Example 96

1-(2-((2'-(Benzyloxy)-2-ethoxy-4'-fluorobiphenyl-4-yl)methyl)-5-oxa-2,6-diazaspiro[3.4]oct-6-en-7-yl)-4-methylpiperidine-4-carboxylic acid

A) 2'-(Benzyloxy)-2-ethoxy-4'-fluorobiphenyl-4-carbaldehyde

Using 2-ethoxy-4-formylphenyl trifluoromethanesulfonate and (2-benzyloxy-4-fluorophenyl)boronic acid, the title compound was obtained in the similar manner as in Step D of Example 16.

$^1$H NMR (300 MHz, $CDCl_3$) δ 1.18-1.29 (3H, m), 4.04 (2H, q, J=7.0 Hz), 5.04 (2H, s), 6.68-6.80 (2H, m), 7.11-7.33 (6H, m), 7.36-7.53 (3H, m), 10.00 (1H, s).

B) Ethyl 1-(2-((2'-(benzyloxy)-2-ethoxy-4'-fluorobiphenyl-4-yl)methyl)-5-oxa-2,6-diazaspiro[3.4]oct-6-en-7-yl)-4-methylpiperidine-4-carboxylate Using 2'-(benzyloxy)-2-ethoxy-4'-fluorobiphenyl-4-carbaldehyde and tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step G of Example 1.

MS (ESI+): $[M+H]^+$ 616.5.

C) 1-(2-((2'-(Benzyloxy)-2-ethoxy-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((2'-(benzyloxy)-2-ethoxy-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 97

1-(2-((2-Cyano-6-ethoxy-4'-fluorobiphenyl-4-yl)methyl)-5-oxa-2,6-diazaspiro[3.4]oct-6-en-7-yl)-4-methylpiperidine-4-carboxylic acid

A) 6-Ethoxy-4'-fluoro-4-(hydroxymethyl)biphenyl-2-yl trifluoromethane sulfonate Sodium borohydride (58.1 mg) was added to a mixture of 6-ethoxy-4'-fluoro-4-formylbiphenyl-2-yl trifluoromethanesulfonate (1.20 g), THF (10 mL) and methanol (10 mL), and the resultant was stirred for 1 hour at room temperature. An aqueous ammonium chloride solution was added to the reaction mixture, and extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (940 mg).

$^1$H NMR (300 MHz, $CDCl_3$) δ 1.21-1.29 (3H, m), 4.04 (2H, q, J=7.0 Hz), 4.76 (2H, s), 6.99 (2H, d, J=7.4 Hz), 7.04-7.18 (2H, m), 7.30 (2H, dd, J=8.9, 5.4 Hz).

B) 4-(((tert-Butyl(dimethyl)silyl)oxy)methyl)-6-ethoxy-4'-fluorobiphenyl-2-yl trifluoromethanesulfonate tert-Butyldimethylchlorosilane (539 mg) was added to a mixture of 6-ethoxy-4'-fluoro-4-(hydroxymethyl)biphenyl-2-yl trifluoromethanesulfonate (940 mg), imidazole (325 mg) and DMF (10 mL), and the resultant was stirred for 1 hour at room temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.11 g).

$^1$H NMR (300 MHz, $CDCl_3$) δ 0.15 (6H, s), 0.98 (9H, s), 1.29 (3H, t, J=7.0 Hz), 4.03 (2H, q, J=7.0 Hz), 4.78 (2H, s), 6.96 (2H, s), 7.06-7.16 (2H, m), 7.31 (2H, dd, J=8.9, 5.4 Hz).

C) 6-Ethoxy-4'-fluoro-4-(hydroxymethyl)biphenyl-2-carbonitrile

Tetrakis(triphenylphosphine)palladium (252 mg) was added to a mixture of 4-(((tert-butyl(dimethyl)silyl)oxy)methyl)-6-ethoxy-4'-fluorobiphenyl-2-yl trifluoromethanesulfonate (1.11 g), zinc cyanide (0.769 g) and DMF (10 mL), and the resultant was stirred overnight at 100° C. in an argon atmosphere. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. Tetrabutylammonium fluoride (1.0 M THF solution 3.27 mL) was added to a mixture of the obtained residue and THF (10 mL), and the resultant was stirred for 20 minutes at room temperature. An aqueous ammonium chloride solution was added to the reaction mixture, and extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (571 mg).

$^1$H NMR (300 MHz, $CDCl_3$) δ 1.29 (3H, t, J=7.0 Hz), 4.04 (2H, q, J=7.0 Hz), 4.75 (2H, brs), 7.06-7.17 (2H, m), 7.21 (1H, s), 7.28-7.34 (1H, m), 7.40 (2H, dd, J=9.0, 5.4 Hz).

D) 6-Ethoxy-4'-fluoro-4-formylbiphenyl-2-carbonitrile

Sulfur trioxide-pyridine complex (1.00 g) was added to a mixture of 6-ethoxy-4'-fluoro-4-(hydroxymethyl)biphenyl-2-carbonitrile (571 mg), triethylamine (0.880 mL) and DMSO (10 mL), and the resultant was stirred for 20 minutes at room temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (176 mg).

$^1$H NMR (300 MHz, $CDCl_3$) δ 1.34 (3H, t, J=6.9 Hz), 4.12 (2H, q, J=7.2 Hz), 7.18 (2H, t, J=8.7 Hz), 7.45 (2H, dd, J=9.0, 5.3 Hz), 7.64 (1H, d, J=1.4 Hz), 7.81 (1H, d, J=1.4 Hz), 10.00 (1H, s).

E) Ethyl 1-(2-((2-cyano-6-ethoxy-4'-fluorobiphenyl-4-yl)methyl)-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-5-oxa-2,6-diazaspiro[3.4]oct-6-ene-2-carboxylate (374 mg) and formic acid (5 mL) was stirred for 1 hour at 60° C. The solvent of the reaction mixture was distilled off under reduced pressure, toluene was added to the residue, and then the solvent was distilled off under further reduced pressure. The obtained residue was mixed with 6-ethoxy-4'-fluoro-6-formylbiphenyl-2-carbonitrile (176 mg) and THF (5 mL), the mixture was stirred for 15 minutes at room temperature, sodium triacetoxyborohydride (208 mg) was added thereto at room temperature, and then the resultant was stirred for 2 hours at room temperature. Water was added to the reaction mixture, and the resultant was stirred for 10 minutes. After an aqueous saturated sodium hydrogen carbonate solution was added to the reaction mixture, extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (240 mg).

MS (ESI+): $[M+H]^+$ 535.3.

F) 1-(2-((2-Cyano-6-ethoxy-4'-fluorobiphenyl-4-yl)methyl)-5-oxa-2,6-diazaspiro[3.4]oct-6-en-7-yl)-4-methylpiperidine-4-carboxylic acid A mixture of ethyl 1-(2-((2-cyano-6-ethoxy-4'-fluorobiphenyl-4-yl)methyl)-5-oxa-2,6-diazaspiro[3.4]oct-6-en-7-yl)-4-methylpiperidine-4-carboxylate (230 mg), 2 M aqueous sodium hydroxide solution (1.3 mL), methanol (5 mL) and THF (3 mL) was stirred for 2 hours at 60° C. The reaction mixture was cooled to room temperature, and it was neutralized with 6 M hydrochloric acid. Extraction thereof was performed using ethyl acetate, the filtrate was dried over anhydrous magnesium sulfate, and then the solvent was distilled off under reduced pressure. The obtained solid was washed with ethyl acetate, thereby obtaining the title compound (195 mg).

$^1$H NMR (300 MHz, DMSO-$d_6$) δ 1.15 (3H, s), 1.23 (3H, t, J=6.9 Hz), 1.32-1.48 (2H, m, J=3.9 Hz), 1.77-2.00 (2H, m), 2.92 (2H, t, J=10.3 Hz), 3.15-3.30 (2H, m), 3.46 (2H, s), 4.12 (2H, q, J=7.0 Hz), 4.20-4.56 (6H, m), 7.24-7.38 (2H, m), 7.42-7.52 (2H, m), 7.60-7.84 (2H, m), 12.43 (1H, brs).

Example 98

1-(2-((4-(3,5-Difluoropyridin-2-yl)-3,5-diethoxybenzyl)-5-oxa-2,6-diazaspiro[3.4]oct-6-en-7-yl)-4-methylpiperidine-4-carboxylic acid A) (3,5-Diethoxy-4-iodophenyl)methanol Diisobutylaluminium hydride (1.5 M toluene solution, 8.05 mL) was added to a solution of ethyl 3,5-diethoxy-4-iodobenzoate (2.0 g) in diethyl ether (20 mL) at 0° C., and the resultant was stirred for 30 minutes at 0° C. 1 M hydrochloric acid was added to the reaction mixture, and extraction thereof was performed using ethyl acetate. The obtained organic layer was washed with a saturated saline solution, dried over anhydrous magnesium sulfate, and then the solvent was distilled off under reduced pressure, thereby obtaining the title compound (1.86 g).

$^1$H NMR (300 MHz, $CDCl_3$) δ 1.50 (6H, t, J=7.0 Hz), 1.70 (1H, t, J=6.0 Hz), 4.13 (4H, q, J=7.0 Hz), 4.68 (2H, d, J=6.0 Hz), 6.51 (2H, s).

B) tert-Butyl((3,5-diethoxy-4-iodobenzyl)oxy)dimethylsilane

Using (3,5-diethoxy-4-iodophenyl)methanol, the title compound was obtained in the similar manner as in Step B of Example 97.

$^1$H NMR (300 MHz, $CDCl_3$) δ 0.10 (6H, s), 0.94 (9H, s), 1.47 (6H, t, J=7.0 Hz), 4.09 (4H, q, J=7.0 Hz), 4.69 (2H, t, J=0.8 Hz), 6.47 (2H, s).

C) (4-(((tert-Butyl(dimethyl)silyl)oxy)methyl)-2,6-diethoxyphenyl)boronic acid n-Butyllithium (1.6 M hexane solution, 1.07 mL) was added to a solution of tert-butyl((3,5-diethoxy-4-iodobenzyl)oxy)dimethylsilane (500 mg) in THF (4.0 mL) at −78° C., and the resultant was stirred for 10 minutes at −78° C. Tris(trimethylsilyl)borate (0.576 mL) was added to the reaction mixture at −78° C., and the resultant was stirred for 50 minutes at room temperature. After an aqueous saturated sodium hydrogen carbonate solution and 1 M hydrochloric acid were added to the reaction mixture, extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (300 mg).

MS (ESI+): $[M+H]^+$ 355.2.

D) 2-(4-(((tert-Butyl(dimethyl)silyl)oxy)methyl)-2,6-diethoxyphenyl)-3,5-difluoropyridine Using (4-(((tert-butyl(dimethyl)silyl)oxy)methyl)-2,6-diethoxyphenyl)boronic acid and 2-bromo-3,5-difluoropyridine, the title compound was obtained in the similar manner as in Step D of Example 16.

MS (ESI+): $[M+H]^+$ 424.1.

E) (4-(3,5-Difluoropyridin-2-yl)-3,5-diethoxyphenyl)methanol

Tetrabutylammonium fluoride (1.0 M THF solution, 1.02 mL) was added to a solution of 2-(4-(((tert-butyl(dimethyl)silyl)oxy)methyl)-2,6-diethoxyphenyl)-3,5-difluoropyridine (288 mg) in THF (5 mL) at 0° C., and the resultant was stirred for 1 hour at room temperature. After water was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (202 mg).

MS (ESI+): $[M+H]^+$ 310.1.

F) 4-(3,5-Difluoropyridin-2-yl)-3,5-diethoxybenzaldehyde

Using (4-(3,5-difluoropyridin-2-yl)-3,5-diethoxyphenyl) methanol, the title compound was obtained in the similar manner as in Step B of Example 3.

MS (ESI+): $[M+H]^+$ 308.0.

G) Ethyl 1-(2-((4-(3,5-difluoropyridin-2-yl)-3,5-diethoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 4-(3,5-difluoropyridin-2-yl)-3,5-diethoxybenzaldehyde, the title compound was obtained in the similar manner as in Step G of Example 1.

MS (ESI+): $[M+H]^+$ 573.3.

H) 1-(2-(4-(3,5-Difluoropyridin-2-yl)-3,5-diethoxybenzyl)-5-oxa-2,6-diazaspiro[3.4]oct-6-en-7-yl)-4-methylpiperidine-4-carboxylic acid Using ethyl 1-(2-((4-(3,5-difluoropyridin-2-yl)-3,5-diethoxybenzyl)-5-oxa-2,6-diazaspiro[3.4]oct-6-en-7-yl)-4-methylpiperidine-4-carboxylate, the title compound was obtained in the similar manner as in Example 2.

Example 99

1-(2-(3,5-Diethoxy-4-(pentafluoroethyl)benzyl)-5-oxa-2,6-diazaspiro[3.4]oct-6-en-7-yl)-4-methylpiperidine-4-carboxylic acid A) Ethyl 3,5-diethoxy-4-(pentafluoroethyl)benzoate A mixture of ethyl 3,5-diethoxy-4-iodobenzoate (500 mg), trimethyl(pentafluoroethyl)silane (317 mg), potassium fluoride (96 mg), copper(I) iodide (392 mg) and DMF (5 mL) was stirred for 12 hours at 60° C. under microwave irradiation. The reaction mixture was diluted by ethyl acetate (20 mL), an aqueous saturated ammonium chloride solution was added thereto, and then extraction thereof was performed using ethyl acetate. The organic layer was sequentially washed with water and a saturated saline solution, dried over anhydrous sodium sulfate, and then the solvent was distilled off under reduced pressure, thereby obtaining the title compound.

MS (ESI+): $[M+H]^+$ 357.1.

B) 3,5-Diethoxy-4-(pentafluoroethyl)benzaldehyde

Using ethyl 3,5-diethoxy-4-(pentafluoroethyl)benzoate (479 mg), the title compound was obtained in the similar manner as in Step C of Example 1.

$^1H$ NMR (300 MHz, $CDCl_3$) δ 1.43 (6H, t, J=7.0 Hz), 4.11-4.17 (4H, m), 7.06 (2H, s), 9.94 (1H, s).

C) Ethyl 1-(2-(3,5-diethoxy-4-(pentafluoroethyl) benzyl)-5-oxa-2,6-diazaspiro[3.4]oct-6-en-7-yl)-4-methylpiperidine-4-carboxylate Using 3,5-diethoxy-4-(pentafluoroethyl)benzaldehyde and tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step G of Example 1.

MS (ESI+): $[M+H]^+$ 578.3.

D) 1-(2-(3,5-Diethoxy-4-(pentafluoroethyl)benzyl)-5-oxa-2,6-diazaspiro[3.4]oct-6-en-7-yl)-4-methylpiperidine-4-carboxylic acid Using ethyl 1-(2-(3,5-diethoxy-4-(pentafluoroethyl)benzyl)-5-oxa-2,6-diazaspiro[3.4]oct-6-en-7-yl)-4-methylpiperidine-4-carboxylate, the title compound was obtained in the similar manner as in Example 2.

Example 100

1-(2-(4-Cyclobutyl-3,5-diethoxybenzyl)-5-oxa-2,6-diazaspiro[3.4]oct-6-en-7-yl)-4-methylpiperidine-4-carboxylic acid A) Ethyl 4-cyclobutyl-3,5-diethoxybenzoate (1,1'-Bis(diphenylphosphino)ferrocene)dichloropalladium(II) dichloromethane adduct (669 mg) was added to a mixture of ethyl 3,5-diethoxy-4-iodobenzoate (2.87 g), copper iodide (234 mg), cyclobutylzinc bromide (0.5 M THF solution, 24.6 mL) and THF (20 mL), and the resultant was stirred for 3 hours at 60° C. in an argon atmosphere. An aqueous ammonium chloride solution was added to the reaction mixture, and extraction thereof was performed using ethyl acetate. The organic layer was passed through a short column of a silica gel (NH), and the solvent was distilled off under reduced pressure. The obtained residue was purified by a silica gel column chromatography (hexane/ethyl acetate), thereby obtaining the title compound (1.48 g).

$^1H$ NMR (300 MHz, $CDCl_3$) δ 1.38 (3H, t, J=7.1 Hz), 1.44 (6H, t, J=6.9 Hz), 1.78-2.07 (2H, m), 2.16-2.35 (2H, m), 2.49-2.71 (2H, m), 3.86-4.02 (1H, m), 4.06 (4H, q, J=6.9 Hz), 4.35 (2H, q, J=7.1 Hz), 7.17 (2H, s).

B) 4-Cyclobutyl-3,5-diethoxybenzaldehyde

A solution of ethyl 4-cyclobutyl-3,5-diethoxybenzoate (1.48 g) in THF (20 mL) was added to a mixture of lithium aluminum hydride (144 mg) and THF (20 mL) at 0° C., and the resultant was stirred for 30 minutes at the same temperature. Water (0.2 mL) and 15% aqueous sodium hydroxide solution (0.2 mL) were added the reaction mixture, the resultant was stirred for 5 minutes, water (0.2 mL) was further added thereto, and then the reaction mixture was stirred for 1 hour at room temperature. The reaction mixture was filtered using celite, and the filtrate was concentrated under reduced pressure. The obtained residue was mixed with triethylamine (2.11 mL) and DMSO (10 mL), sulfur trioxide-pyridine complex (1.61 g) was added to the mixture, and the resultant was stirred for 20 minutes at room temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.02 g).

$^1$H NMR (300 MHz, $CDCl_3$) δ 1.46 (6H, t, J=7.0 Hz), 1.77-2.03 (2H, m), 2.21-2.36 (2H, m), 2.49-2.70 (2H, m), 3.90-4.04 (1H, m), 4.08 (4H, q, J=7.0 Hz), 7.00 (2H, s), 9.85 (1H, s).

C) Ethyl 1-(2-(4-cyclobutyl-3,5-diethoxybenzyl)-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-5-oxa-2,6-diazaspiro[3.4]oct-6-ene-2-carboxylate (750 mg) and formic acid (10 mL) was stirred for 1 hour at 60° C. The solvent of the reaction mixture was distilled off under reduced pressure, toluene was added to the residue, and then the solvent was distilled off under further reduced pressure. After a mixture of the obtained residue, 4-cyclobutyl-3,5-diethoxybenzaldehyde (488 mg) and THF (5 mL) was stirred for 15 minutes at room temperature, sodium triacetoxyborohydride (625 mg) was added thereto at room temperature, and the resultant was stirred for 2 hours at room temperature. Water was added to the reaction mixture, and the resultant was stirred for 10 minutes. An aqueous saturated sodium hydrogen carbonate solution was added to the reaction mixture, and extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (929 mg).

MS (ESI+): $[M+H]^+$ 514.3.

D) 1-(2-(4-Cyclobutyl-3,5-diethoxybenzyl)-5-oxa-2,6-diazaspiro[3.4]oct-6-en-7-yl)-4-methylpiperidine-4-carboxylic acid A mixture of ethyl 1-(2-(4-cyclobutyl-3,5-diethoxybenzyl)-5-oxa-2,6-diazaspiro[3.4]oct-6-en-7-yl)-4-methylpiperidine-4-carboxylate (926 mg), 2 M aqueous sodium hydroxide solution (5.41 mL), methanol (5 mL) and THF (5 mL) was stirred for 2 hours at 60° C. The reaction mixture was cooled to room temperature, and it was neutralized with 6 M hydrochloric acid. Extraction thereof was performed using ethyl acetate, the filtrate was dried over anhydrous magnesium sulfate, and then the solvent was distilled off under reduced pressure. After the obtained solid was washed with ethyl acetate, fractionation was performed thereon using HPLC (C18, mobile phase: water/acetonitrile (10 mM ammonium carbonate-containing system), and the obtained fraction was concentrated. After the residue was dissolved in ethyl acetate, it was dried over anhydrous magnesium sulfate, and the solvent was distilled off under reduced pressure. The obtained solid was sequentially washed with diethyl ether and hexane, thereby obtaining the title compound (407 mg).

$^1$H NMR (300 MHz, DMSO-$d_6$) δ 1.23 (3H, s), 1.35-1.53 (8H, m), 1.78-1.99 (2H, m), 2.10-2.29 (4H, m), 2.47-2.69 (2H, m), 2.90-3.05 (2H, m), 3.25 (2H, s), 3.34-3.46 (2H, m), 3.52 (2H, d, J=9.9 Hz), 3.71 (2H, d, J=10.1 Hz), 3.80 (2H, s), 3.85-4.03 (5H, m), 6.45 (2H, s).

Example 101

1-(2-((1-Benzyl-5-isopropyl-1H-pyrazolo[3,4-d][1,3]thiazole-3-yl)methyl)-5-oxa-2,6-diazaspiro[3.4]oct-6-en-7-yl)-4-methylpiperidine-4-carboxylic acid Using benzylhydrazine dihydrochloride, the title compound was obtained in the similar manner as in Step A, Step B, Step C, Step D, Step E, Step F and Step G of Example 21, and Example 2.

Example 102

1-(2-((2'-(Cyclopropylmethoxy)-2-ethoxy-4'-fluorobiphenyl-4-yl)methyl)-5-oxa-2,6-diazaspiro[3.4]oct-6-en-7-yl)-4-methylpiperidine-4-carboxylic acid A) 2-ethoxy-4'-fluoro-2'-hydroxybiphenyl carbaldehyde A mixture of 2'-(benzyloxy)-2-ethoxy-4'-fluorobiphenyl-4-carbaldehyde (2.45 g), 6 M hydrochloric acid (30 mL) and acetic acid (100 mL) was stirred for 4 hours at 100° C. The reaction mixture was concentrated under reduced pressure. Ethyl acetate was added to the obtained residue, was sequentially washed with water and a saturated saline solution, was dried over anhydrous magnesium sulfate, and then the solvent was distilled off under reduced pressure. The obtained residue was washed with hexane, thereby obtaining the title compound (1.50 g).

$^1$H NMR (300 MHz, $CDCl_3$) δ 1.44 (3H, t, J=7.0 Hz), 4.26 (2H, q, J=7.0 Hz), 6.65 (1H, d, J=0.9 Hz), 6.71-6.83 (2H, m), 7.18-725 (1H, m), 7.46-7.52 (1H, m), 7.54-7.63 (2H, m), 10.03 (1H, s).

B) 2'-(Cyclopropylmethoxy)-2-ethoxy-4'-fluorobiphenyl-4-carbaldehyde

Using 2-ethoxy-4'-fluoro-2'-hydroxybiphenyl-4-carbaldehyde and (bromomethyl)cyclopropane, the title compound was obtained in the similar manner as in Step B of Example 16.

$^1$H NMR (300 MHz, $CDCl_3$) δ 0.14-0.26 (2H, m), 0.45-0.57 (2H, m), 1.00-1.15 (1H, m), 1.31 (3H, t, J=7.0 Hz), 3.78 (2H, d, J=6.5 Hz), 4.02-4.15 (2H, m), 6.57-6.81 (2H, m), 7.20 (1H, dd, J=8.4, 6.8 Hz), 7.35-7.55 (3H, m), 10.00 (1H, s).

C) Ethyl 1-(2-((2'-(cyclopropylmethoxy)-2-ethoxy-4'-fluorobiphenyl-4-yl)methyl)-5-oxa-2,6-diazaspiro[3.4]oct-6-en-7-yl)-4-methylpiperidine-4-carboxylate Using 2'-(cyclopropylmethoxy)-2-ethoxy-4'-fluorobiphenyl-4-carbaldehyde and tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step G of Example 1.

MS (ESI+): $[M+H]^+$ 580.5.

D) 1-(2-((2'-(Cyclopropylmethoxy)-2-ethoxy-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((2'-(cyclopropylmethoxy)-2-ethoxy-4'-fluorobiphenyl-4-yl)methyl)-5-oxa-2,6-diazaspiro[3.4]oct- 6-en-7-yl)-4-methylpiperidine-4-carboxylate, the title compound was obtained in the similar manner as in Example 2.

Example 103

1-(2-((2-Ethoxy-4'-fluoro-2'-(2-methoxyethoxy)biphenyl-4-yl)methyl)-5-oxa-2,6-diazaspiro[3.4]oct-6-en-7-yl)-4-methylpiperidine-4-carboxylic acid A) 2-ethoxy-4'-fluoro-2'-(2-methoxyethoxy)biphenyl-4-carbaldehyde Using 2-ethoxy-4'-fluoro-2'-hydroxybiphenyl-4-carbaldehyde and 1-bromo-2-methoxyethane, the title compound was obtained in the similar manner as in Step B of Example 16.

MS (ESI+): $[M+H]^+$ 319.1.

B) Ethyl 1-(2-((2-ethoxy-4'-fluoro-2'-(2-methoxyethoxy)biphenyl-4-yl)methyl)-5-oxa-2,6-diazaspiro[3.4]oct-6-en-7-yl)-4-methylpiperidine-4-carboxylate Using 2-ethoxy-4'-fluoro-2'-(2-methoxyethoxy)biphenyl-4-carbaldehyde and tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step G of Example 1.

MS (ESI+): $[M+H]^+$ 584.5.

C) 1-(2-((2-Ethoxy-4'-fluoro-2'-(2-methoxyl)dioxy)biphenyl-4-yl)methyl)-5-oxa-2,6-diazaspiro[3.4]oct-6-en-7-yl)-4-methylpiperidine-4-carboxylic acid Using ethyl 1-(2-((2-ethoxy-4'-fluoro-2'-(2-methoxyethoxy)biphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 104

1-(2-((2-Cyclopropyl-6-((2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylic acid A) 3-Cyclopropyl-5-((2,2-difluorocyclopropyl)methoxy)-4-iodobenzaldehyde 2-(Bromomethyl)-1,1-difluorocyclopropane (322 mg) was added to a mixture of 3-cyclopropyl-5-hydroxy-4-iodobenzaldehyde (361 mg), potassium carbonate (347 mg) and DMF (10 mL), and the resultant was stirred for 2 hours at 70° C.

After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (461 mg).

$^1$H NMR (400 MHz, $CDCl_3$) δ 0.69-0.77 (2H, m), 1.07-1.15 (2H, m), 1.35-1.45 (1H, m), 1.59-1.70 (1H, m), 2.11-2.23 (2H, m), 4.11-4.18 (1H, m), 4.20-4.28 (1H, m), 7.05 (1H, d, J=1.1 Hz), 7.09 (1H, d, J=1.4 Hz), 9.91 (1H, s).

B) 2-Cyclopropyl-6-((2,2-difluorocyclopropyl)methoxy)-4'-fluorobiphenyl 4 carbaldehyde (4-Fluorophenyl)boronic acid (248 mg), cesium fluoride (539 mg), and (1,1'-bis(diphenylphosphino)ferrocene)dichloropalladium(II) (173 mg) were added to a solution of 3-cyclopropyl-5-((2,2-difluorocyclopropyl)methoxy)-4-iodobenaldehyde (448 mg) in DME (10 mL), and the resultant was stirred for 15 hours at 100° C. in an argon atmosphere. Water was added to the reaction mixture, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (390 mg).

$^1$H NMR (400 MHz, $CDCl_3$) δ 0.70-0.75 (2H, m), 0.83-0.90 (2H, m), 1.03-1.14 (1H, m), 1.37-1.48 (1H, m), 1.62-1.71 (1H, m), 1.80-1.94 (1H, m), 4.03 (2H, d, J=7.3 Hz), 7.07 (1H, s), 7.10-7.17 (2H, m), 7.24-7.30 (3H, m), 9.94 (1H, s).

C) Ethyl 1-(2-((2-cyclopropyl-6-((2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (379 mg) and formic acid (6 mL) was stirred for 1 hour at 60° C., the solvent was distilled off under reduced pressure. The obtained residue was mixed with 2-cyclopropyl-6-((2,2-difluorocyclopropyl)methoxy)-4'-fluorobiphenyl-4-carbaldehyde (378 mg) and THF (10 mL), sodium triacetoxyborohydride (421 mg) was added thereto, and the resultant was stirred for 16 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (490 mg).

$^1$H NMR (400 MHz, $CDCl_3$) δ 0.60-0.66 (2H, m), 0.72-0.79 (2H, m), 0.98-1.09 (1H, m), 1.21 (3H, s), 1.26 (3H, t, J=7.2 Hz), 1.33-1.50 (3H, m), 1.55-1.64 (1H, m), 1.77-1.87 (1H, m), 2.11 (2H, d, J=13.6 Hz), 2.92-3.01 (2H, m), 3.25 (2H, s), 3.31-3.43 (4H, m), 3.53 (2H, d, J=8.7 Hz), 3.62 (2H, s), 3.85-3.92 (1H, m), 3.93-4.00 (1H, m), 4.16 (2H, q, J=7.2 Hz), 6.45 (1H, s), 6.70 (1H, s), 7.05-7.12 (2H, m), 7.23-7.29 (2H, m).

D) 1-(2-((2-Cyclopropyl-6-((2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (2 mL) was added to a solution of ethyl 1-(2-((2-cyclopropyl-6-((2,2-difluorocyclopropyl)methoxy)-4'-fluorobiphenyl-4-yl)

methyl)-5-oxa-2,6-diazaspiro[3.4]oct-6-en-7-yl)-4-methylpiperidine-4-carboxylate (467 mg) in ethanol (8 mL), the resultant was stirred for 3 hours at 70° C., and then the solvent was distilled off under reduced pressure. Water was added to the obtained residue, the resultant was neutralized with 2 M hydrochloric acid, and then the precipitated solid was collected by filtration. After the obtained solid was dissolved in ethyl acetate and THF, it was dried over anhydrous magnesium sulfate, and the solvent was distilled off under reduced pressure, thereby obtaining the title compound (407 mg).

$^1$H NMR (300 MHz, $CDCl_3$) δ 0.59-0.67 (2H, m), 0.74-0.82 (2H, m), 0.98-1.12 (1H, m), 1.25 (3H, s), 1.33-1.51 (3H, m), 1.54-1.66 (1H, m), 1.75-1.92 (1H, m), 2.13 (2H, d, J=13.5 Hz), 2.94-3.08 (2H, m), 3.32 (2H, s), 3.36-3.46 (2H, m), 3.64 (2H, brs), 3.84-4.03 (6H, m), 6.51 (1H, s), 6.83 (1H, brs), 7.06-7.13 (2H, m), 7.20-7.25 (2H, m).

Example 105

1-(2-(3,5-Diethoxy-4-(5-fluoropyridin-2-yl)benzyl)-5-oxa-2,6-diazaspiro[3.4]oct-6-en-7-yl)-4-methylpiperidine-4-carboxylic acid A) 2-(4-(((tert-Butyl(dimethyl)silyl)oxy)methyl)-2,6-diethoxyphenyl)-5-fluoropyridine Using (4-(((tert-butyl(dimethyl)silyl)oxy)methyl)-2,6-diethoxyphenyl)boronic acid and 2-bromo-5-fluoropyridine, the title compound was obtained in the similar manner as in Step D of Example 16.

MS (ESI+): $[M+H]^+$ 406.2.

B) (3,5-Diethoxy-4-(5-fluoropyridin-2-yl)phenyl)methanol

Using 2-(4-(((tert-butyl(dimethyl)silyl)oxy)methyl)-2,6-diethoxyphenyl)-5-fluoropyridine, the title compound was obtained in the similar manner as in Step E of Example 98.

MS (ESI+): $[M+H]^+$ 292.1.

C) 3,5-Diethoxy-4-(5-fluoropyridin-2-yl)benzaldehyde

Using (3,5-diethoxy-4-(5-fluoropyridin-2-yl)phenyl)methanol, the title compound was obtained in the similar manner as in Step B of Example 3.

MS (ESI+): $[M+H]^+$ 290.1.

D) Ethyl 1-(2-(3,5-diethoxy-4-(5-fluoropyridin-2-yl)benzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 3,5-diethoxy-4-(5-fluoropyridin-2-yl)benzaldehyde, the title compound was obtained in the similar manner as in Step G of Example 1.

MS (ESI+): $[M+H]^+$ 555.3.

E) 1-(2-(3,5-Diethoxy-4-(5-fluoropyridin-2-yl)benzyl)-5-oxa-2,6-diazaspiro[3.4]oct-6-en-7-yl)-4-methylpiperidine-4-carboxylic acid Using ethyl 1-(2-(3,5-diethoxy-4-(5-fluoropyridin-2-yl)benzyl)-5-oxa-2,6-diazaspiro[3.4]oct-6-en-7-yl)-4-methylpiperidine-4-carboxylate, the title compound was obtained in the similar manner as in Example 2.

Example 106

1-(2-((2-Cyclopropyl-4'-fluoro-6-(3,3,3-trifluoropropoxy)biphenyl-4-yl)methyl)-5-oxa-2,6-diazaspiro[3.4]oct-6-en-7-yl)-4-methylpiperidine-4-carboxylic acid

A) 3-Cyclopropyl-4-iodo-5-(3,3,3-trifluoropropoxy)benzaldehyde 1,1,1-Trifluoro-3-iodopropane (531 mg) was added to a mixture of 3-cyclopropyl-5-hydroxy-4-iodobenzaldehyde (342 mg), potassium carbonate (491 mg) and DMF (10 mL), and the resultant was stirred for 4 hours at 70° C. 1,1,1-trifluoro-3-iodopropane (2.66 g) and potassium carbonate (1.64 g) were added to the reaction mixture, and the resultant was stirred for 15 hours at 70° C. 1,1,1-trifluoro-3-iodopropane (2.66 g) and potassium carbonate (1.64 g) were further added thereto, and the resultant was stirred for 6 hours at 70° C. 1,1,1-trifluoro-3-iodopropane (2.66 g) and potassium carbonate (1.64 g) were added to the reaction mixture, and the resultant was stirred for 15 hours at 70° C. 1,1,1-Trifluoro-3-iodopropane (2.66 g) and potassium carbonate (1.64 g) were further added thereto, and the resultant was stirred for 7 hours at 70° C. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (382 mg).

$^1$H NMR (400 MHz, $CDCl_3$) δ 0.70-0.76 (2H, m), 1.08-1.15 (2H, m), 2.12-2.22 (1H, m), 2.70-2.83 (2H, m), 4.32 (2H, t, J=6.5 Hz), 7.06 (1H, s), 7.10 (1H, s), 9.92 (1H, s).

B) 2-Cyclopropyl-4'-fluoro-6-(3,3,3-trifluoropropoxy)biphenyl-4-carbaldehyde (4-Fluorophenyl)boronic acid (201 mg), cesium fluoride (436 mg), and (1,1'-bis(diphenylphosphino)ferrocene)dichloropalladium(II) (140 mg) were added to a solution of 3-cyclopropyl-4-iodo-5-(3,3,3-trifluoropropoxy)benzaldehyde (368 mg) in DME (10 mL), and the resultant was stirred for 18 hours at 100° C. in an argon atmosphere. Water was added to the reaction mixture, the resultant was filtered using celite, and then the filtrate was extracted using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (283 mg).

$^1$H NMR (400 MHz, $CDCl_3$) δ 0.69-0.75 (2H, m), 0.82-0.91 (2H, m), 1.60-1.70 (1H, m), 2.36-2.51 (2H, m), 4.17 (2H, t, J=6.4 Hz), 7.07-7.15 (3H, m), 7.22-7.27 (3H, m), 9.95 (1H, s).

C) Ethyl 1-(2-((2-cyclopropyl-4'-fluoro-6-(3,3,3-trifluoropropoxy)biphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene- 2-carboxylate (266 mg) and formic acid (5 mL) was stirred for 1 hour at 60° C., the solvent was distilled off under reduced pressure. The obtained residue was mixed with 2-cyclopropyl-4'-fluoro-6-(3,3,3-trifluoropropoxy)biphenyl-4-carbaldehyde (270 mg) and THF (10 mL), sodium triacetoxyborohydride (295 mg) was added to the mixture, and the resultant was stirred for 18 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (324 mg).

$^1$H NMR (400 MHz, $CDCl_3$) δ 0.59-0.66 (2H, m), 0.72-0.78 (2H, m), 1.21 (3H, s), 1.26 (3H, t, J=7.2 Hz), 1.40-1.51 (2H, m), 1.53-1.63 (1H, m), 2.11 (2H, d, J=13.6 Hz), 2.31-2.45 (2H, m), 2.92-3.03 (2H, m), 3.26 (2H, s), 3.31-3.42 (4H, m), 3.53 (2H, d, J=8.8 Hz), 3.63 (2H, s), 4.07 (2H, t, J=6.6 Hz), 4.16 (2H, q, J=7.1 Hz), 6.45 (1H, s), 6.69 (1H, s), 7.04-7.11 (2H, m), 7.23 (2H, dd, J=8.5, 5.6 Hz).

D) 1-(2-((2-Cyclopropyl-4'-fluoro-6-(3,3,3-trifluoropropoxy)biphenyl-4-yl)methyl)-5-oxa-2,6-diazaspiro[3.4]oct-6-en-7-yl)-4-methylpiperidine-4-carboxylic acid 2 M aqueous sodium hydroxide solution (2 mL) was added to a solution of ethyl 1-(2-((2-cyclopropyl-4'-fluoro-6-(3,3,3-trifluoropropoxy)biphenyl-4-yl)methyl)-5-oxa-2,6-diazaspiro[3.4]oct-6-en-7-yl)-4-methylpiperidine-4-carboxylate (314 mg) in ethanol (8 mL), the resultant was stirred for 3 hours at 70° C., and then the solvent was distilled off under reduced pressure. Water was added to the residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The residue was crystallized (diisopropyl ether/ethyl acetate), thereby obtaining the title compound (193 mg).

$^1$H NMR (400 MHz, $CDCl_3$) δ 0.60-0.68 (2H, m), 0.75-0.82 (2H, m), 1.25 (3H, s), 1.40-1.51 (2H, m), 1.55-1.64 (1H, m), 2.12 (2H, d, J=13.4 Hz), 2.32-2.46 (2H, m), 2.95-3.08 (2H, m), 3.31-3.47 (4H, m), 3.58-3.82 (2H, m), 3.86-4.18 (6H, m), 6.52 (1H, s), 6.89 (1H, brs), 7.05-7.11 (2H, m), 7.21 (2H, dd, J=8.4, 5.5 Hz).

Example 107

1-(2-((2-Cyclobutyl-6-ethoxy-4'-fluorobiphenyl-4-yl)methyl)-5-oxa-2,6-diazaspiro[3.4]oct-6-en-7-yl)-4-methylpiperidine-4-carboxylic acid A) Ethyl 3-(benzyloxy)-4-bromo-5-ethoxybenzoate A mixture of bromomethyl benzene (9.03 mL), potassium carbonate (14.3 g), ethyl 4-bromo-3-ethoxy-5-hyroxybenzoate (20.0 g) and DMF (200 mL) was stifled for 2 hours at 60° C. Water was added to the reaction mixture, and extraction thereof was performed using ethyl acetate. The obtained organic layer was washed with a saturated saline solution, it was passed through a short column of a silica gel (NH), and the solvent was distilled off under reduced pressure. The obtained solid was washed with diethyl ether and hexane, thereby obtaining the title compound (22.5 g).

$^1$H NMR (300 MHz, $CDCl_3$) δ 1.40 (3H, t, J=7.1 Hz), 1.49 (3H, t, J=7.0 Hz), 4.17 (2H, q, J=7.0 Hz), 4.37 (2H, q, J=7.2 Hz), 5.21 (2H, s), 7.23 (1H, d, J=1.7 Hz), 7.30 (1H, d, J=1.6 Hz), 7.32-7.44 (3H, m), 7.46-7.54 (2H, m).

B) Ethyl 2-(benzyloxy)-6-ethoxy-4'-fluorobiphenyl-4-carboxylate

Palladium acetate (666 mg) was added to a mixture of ethyl 3-(benzyloxy)-4-bromo-5-ethoxybenzoate (22.5 g), tripotassium phosphate (37.8 g), (4-fluorophenyl)boronic acid (24.9 g), tricyclohexylphosphine (20% toluene solution, 10.5 mL), toluene (150 mL) and water (75 mL), and the resultant was heated and stirred overnight at 90° C. in an argon atmosphere. After the reaction mixture was cooled to room temperature, water was added thereto, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (23.1 g).

$^1$H NMR (300 MHz, $CDCl_3$) δ 1.27 (3H, t, J=7.0 Hz), 1.41 (3H, t, J=7.1 Hz), 4.05 (2H, q, J=7.0 Hz), 4.40 (2H, q, J=7.2 Hz), 5.07 (2H, s), 7.08 (2H, t, J=8.9 Hz), 7.15-7.43 (9H, m).

C) Ethyl 2-ethoxy-4'-fluoro-6-hydroxybiphenyl-4-carboxylate

A mixture of ethyl 2-(benzyloxy)-6-ethoxy-4'-fluorobiphenyl-4-carboxylate (15.0 g), 10% palladium on carbon (55% water content, 4.05 g) and THF (150 mL) was stirred for 1 hour at room temperature in a hydrogen atmosphere. After the catalyst was removed by filtration, the obtained filtrate was concentrated under reduced pressure. The obtained residue was purified by a silica gel column chromatography (hexane/ethyl acetate), thereby obtaining the title compound (11.7 g).

$^1$H NMR (300 MHz, $CDCl_3$) δ 1.26 (3H, t, J=6.9 Hz), 1.40 (3H, t, J=7.1 Hz), 4.04 (2H, q, J=6.9 Hz), 4.38 (2H, q, J=7.1 Hz), 5.07 (1H, t, J=10.6 Hz), 7.10-7.24 (3H, m), 7.29-7.40 (3H, m).

D) Ethyl 2-ethoxy-4'-fluoro-6-(((trifluoromethyl)sulfonyl)oxy)biphenyl-4-carboxylate Sodium hydride (60% dispersion in oil, 434 mg) was added to a mixture of ethyl 2-ethoxy-4'-fluoro-6-hydroxybiphenyl-4-carboxylate (2.20 g) and THF (15 mL) at 0° C., and the resultant was stirred for 30 minutes at the same temperature. N-phenyl bis(trifluoromethane sulfonimide) (3.87 g) was added to the reaction mixture, and the resultant was stirred for 1 hour at room temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.41 g).

$^1$H NMR (300 MHz, $CDCl_3$) δ 1.31 (3H, t, J=7.0 Hz), 1.42 (3H, t, J=7.1 Hz), 4.03-4.14 (2H, m), 4.43 (2H, q, J=7.1 Hz), 7.07-7.19 (2H, m), 7.28-7.36 (2H, m), 7.64 (2H, s).

E) Ethyl 2-cyclobutyl-6-ethoxy-4'-fluorobiphenyl-4-carboxylate

Cyclobutylzinc bromide (0.5 M THF solution, 22.1 mL) was added to a mixture of ethyl 2-ethoxy-4'-fluoro-6-(((trifluoromethyl)sulfonyl)oxy)biphenyl-4-carboxylate (2.41 mg), copper iodide (158 mg), (1,1'-bis(diphenylphosphino) ferrocene)dichloropalladium(II) dichloromethane adduct (451 mg) and THF (5 mL), and the resultant was stirred for 3 hours at 60° C. in an argon atmosphere. An aqueous ammonium chloride solution was added to the reaction mixture, and extraction thereof was performed using ethyl acetate. After being dried over anhydrous magnesium sulfate, the solvent was distilled off under reduced pressure. The obtained residue was purified by a silica gel column chromatography (hexane/ethyl acetate), thereby obtaining the title compound (1.05 g).

$^1$H NMR (300 MHz, $CDCl_3$) δ 1.20 (3H, t, J=7.0 Hz), 1.42 (3H, t, J=7.1 Hz), 1.64-2.16 (6H, m), 3.25-3.57 (1H, m), 4.00 (2H, q, J=7.0 Hz), 4.42 (2H, q, J=7.1 Hz), 6.99-7.16 (4H, m), 7.45 (1H, d, J=1.4 Hz), 7.74 (1H, d, J=0.9 Hz).

F) 2-Cyclobutyl-6-ethoxy-4'-fluorobiphenyl-4-carbaldehyde

A solution of ethyl 2-cyclobutyl-6-ethoxy-4'-fluorobiphenyl-4-carboxylate (1.05 g) in THF (50 mL) was added to a suspension of lithium aluminum hydride (87.0 mg) in THF (20 mL) at 0° C. in a nitrogen atmosphere. After stirring for 30 minutes at the same temperature, water (0.2 mL) and 15% aqueous sodium hydroxide solution (0.2 mL) were sequentially added thereto. After the resultant was stirred for 5 minutes, water (0.2 mL) was further added thereto. After the reaction mixture was stirred for 1 hour, the reaction mixture was filtered, and the filtrate was concentrated under reduced pressure. The obtained residue was dissolved in DMSO (10 mL), triethylamine (1.28 mL) and sulfur trioxide-pyridine complex (977 mg) were added to the solution, and the resultant was stirred for 20 minutes at room temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (581 mg).

$^1$H NMR (300 MHz, $CDCl_3$) δ 1.22 (3H, t, J=6.9 Hz), 1.66-2.20 (6H, m), 3.24-3.56 (1H, m), 4.02 (2H, q, J=7.0 Hz), 7.04-7.18 (4H, m), 7.29 (1H, d, J=1.3 Hz), 7.48-7.61 (1H, m), 10.02 (1H, s).

G) Ethyl 1-(2-((2-cyclobutyl-6-ethoxy-4'-fluorobiphenyl-4-yl)methyl)-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-5-oxa-2,6-diazaspiro[3.4]oct-6-ene-2-carboxylate (966 mg) and formic acid (10 mL) was stirred for 1 hour at 60° C. The solvent of the reaction mixture was distilled off under reduced pressure, toluene was added to the obtained residue, and then the solvent was distilled off under reduced pressure. The obtained residue was mixed with 2-cyclobutyl-6-ethoxy-4'-fluorobiphenyl-4-carbaldehyde (581 mg) and THF (5 mL), the mixture was stirred for 15 minutes at room temperature, sodium triacetoxyborohydride (619 mg) was added thereto at room temperature, and then the resultant was stirred for 2 hours at room temperature. Water was added to the reaction mixture, and the resultant was stirred for 10 minutes. An aqueous saturated sodium hydrogen carbonate solution was added to the reaction mixture, and extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (1.06 g).

$^1$H NMR (300 MHz, $CDCl_3$) δ 1.17 (3H, t, J=7.0 Hz), 1.21 (3H, s), 1.22-1.30 (3H, m), 1.38-1.56 (2H, m), 1.66-2.21 (8H, m), 2.89-3.05 (2H, m), 3.27 (2H, s), 3.32-3.46 (5H, m), 3.53-3.63 (2H, m), 3.69 (2H, s), 3.92 (2H, q, J=7.0 Hz), 4.11-4.24 (2H, m), 6.72 (1H, d, J=1.2 Hz), 6.92 (1H, d, J=0.8 Hz), 7.01-7.15 (4H, m).

H) 1-(2-((2-Cyclobutyl-6-ethoxy-4'-fluorobiphenyl-4-yl)methyl)-5-oxa-2,6-diazaspiro[3.4]oct-6-en-7-yl)-4-methylpiperidine-4-carboxylic acid A mixture of ethyl 1-(2-((2-cyclobutyl-6-ethoxy-4'-fluorobiphenyl-4-yl)methyl)-5-oxa-2,6-diazaspiro[3.4]oct-6-en-7-yl)-4-methylpiperidine-4-carboxylate (1.00 g), 2 M aqueous sodium hydroxide solution (5.32 mL), methanol (5 mL) and THF (5 mL) was stirred for 2 hours at 60° C. After the reaction mixture was cooled to room temperature, it was neutralized with 6 M hydrochloric acid, and extraction thereof was performed using ethyl acetate. After the obtained organic layer was dried over anhydrous magnesium sulfate, the solvent was distilled off under reduced pressure. The obtained solid was washed with ethyl acetate, thereby obtaining the title compound (756 mg).

$^1$H NMR (300 MHz, DMSO-$d_6$) δ 1.09-1.17 (6H, m), 1.30-1.47 (2H, m), 1.59-2.05 (8H, m), 2.82-3.02 (2H, m), 3.19-3.51 (7H, m), 3.96 (2H, q, J=6.8 Hz), 4.10-4.52 (4H, m), 7.06-7.26 (6H, m).

Example 108

1-(2-(3,5-Diethoxy-4-(1-(2,2,3,3,3-pentafluoropropyl)piperidin-4-yl)benzyl)-5-oxa-2,6-diazaspiro[3.4]oct-6-en-7-yl)-4-methylpiperidine-4-carboxylic acid A) tert-Butyl 4-(2,6-diethoxy-4-(ethoxycarbonyl)phenyl)-3,6-dihydropyridine-1(2H)-carboxylate Ethyl 3,5-diethoxy-4-iodobenzoate (1.00 g), tert-butyl 4-(4,4,5,5-tetramethyl-1,3,2-dioxaborolan-2-yl)-3,6-dihydropyridine-1(2H)-carboxylate (849 mg), cesium carbonate (1.34 g), (1,1'-bis(diphenylphosphino)ferrocene)dichloropalladium(II) dichloromethane adduct (112 mg), THF (5 mL) and water (1 mL) were mixed, and the mixture was stirred for 0.5 hours at 130° C. under microwave irradiation. The reaction mixture was diluted by ethyl acetate (20 mL), an aqueous saturated ammonium chloride solution was added thereto, and then extraction thereof was performed using ethyl acetate. The organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (900 mg).

MS (ESI+): $[M+H-(Boc)]^+$ 320.1.

B) tert-Butyl 4-(2,6-diethoxy-4-(ethoxycarbonyl)phenyl)piperidine-1-carboxylate

Using tert-butyl 4-(2,6-diethoxy-4-(ethoxycarbonyl)phenyl)-3,6-dihydropyridine-1(2H)-carboxylate, the title compound was obtained in the similar manner as in Step F of Example 87.

MS (ESI+): $[M+H-(Boc)]^+$ 322.2.

C) Ethyl 3,5-diethoxy-4-(piperidin-4-yl)benzoate hydrochloride

Using tert-butyl 4-(2,6-diethoxy-4-(ethoxycarbonyl)phenyl)piperidine-1-carboxylate, the title compound was obtained in the similar manner as in Step E of Example 3.

MS (ESI+): $[M+H]^+$ 322.3.

D) Ethyl 3,5-diethoxy-4-(1-(2,2,3,3,3-pentafluoropropyl)piperidin-4-yl)benzoate

Triethylamine (297 mg) and 2,2,3,3,3-pentafluoropropyltrifluoromethanesulfonate (552 mg) were added to a solution of ethyl 3,5-diethoxy-4-(piperidin-4-yl)benzoate hydrochloride (350 mg) in THF (3 mL), and the resultant was stirred for 4 hours at 60° C. The reaction mixture was diluted by ethyl acetate (20 mL), an aqueous saturated ammonium chloride solution was added thereto, and then extraction thereof was performed using ethyl acetate. The organic layer was sequentially washed with water and a saturated saline solution, dried over anhydrous sodium sulfate, and then the solvent was distilled off under reduced pressure, thereby obtaining the title compound (450 mg).

MS (ESI+): $[M+H]^+$ 454.1.

E) 3,5-Diethoxy-4-(1-(2,2,3,3,3-pentafluoropropyl)piperidin-4-yl)benzaldehyde

Using ethyl 3,5-diethoxy-4-(1-(2,2,3,3,3-pentafluoropropyl)piperidin-4-yl)benzoate, the title compound was obtained in the similar manner as in Step C of Example 1.

MS (ESI+): $[M+H]^+$ 410.1.

F) Ethyl 1-(2-(3,5-diethoxy-4-(1-(2,2,3,3,3-pentafluoropropyl)piperidin-4-yl)benzyl)-5-oxa-2,6-diazaspiro[3.4]oct-6-en-7-yl)-4-methylpiperidine-4-carboxylate Using 3,5-diethoxy-4-(1-(2,2,3,3,3-pentafluoropropyl)piperidin-4-yl)benzaldehyde and tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step G of Example 1.

MS (ESI+): $[M+H]^+$ 675.3.

G) 1-(2-(3,5-Diethoxy-4-(1-(2,2,3,3,3-pentafluoropropyl)piperidin-4-yl)benzyl)-5-oxa-2,6-diazaspiro[3.4]oct-6-en-7-yl)-4-methylpiperidine-4-carboxylic acid Using ethyl 1-(2-(3,5-diethoxy-4-(1-(2,2,3,3,3-pentafluoropropyl)piperidin-4-yl)benzyl)-5-oxa-2,6-diazaspiro[3.4]oct-6-en-7-yl)-4-methylpiperidine-4-carboxylate, the title compound was obtained in the similar manner as in Example 2.

Example 109

An optically active substance of 1-(2-((2,6-diethoxy-4'-fluorobiphenyl-4-yl)methyl)-8-methyl-5-oxa-2,6-diazaspiro[3.4]oct-6-en-7-yl)-4-methylpiperidine-4-carboxylic acid Fractionation was performed on a racemate (260 mg) of 1-(2-((2,6-diethoxy-4'-fluorobiphenyl-4-yl)methyl)-8-methyl-5-oxa-2,6-diazaspiro[3.4]oct-6-en-7-yl)-4-methylpiperidine-4-carboxylic acid using SFC (column: CHIRALPAK IA (LG021) 46 mmID×150 mmL, manufactured by Daicel Chemical Industries, Ltd., mobile phase: carbon dioxide/methanol/diethylamine=700/300/3), thereby obtaining a compound with a short retention time as a title compound (101 mg).

$^1H$ NMR (400 MHz, DMSO-$d_6$) δ 1.05 (3H, d, J=7.0 Hz), 1.09-1.19 (9H, m), 1.27-1.45 (2H, m), 1.92 (2H, t, J=13.6 Hz), 2.89 (2H, t, J=10.5 Hz), 3.06 (1H, d, J=7.2 Hz), 3.13 (1H, d, J=8.3 Hz), 3.19-3.43 (4H, m), 3.53 (1H, d, J=8.2 Hz), 3.59 (2H, s), 3.95 (4H, q, J=6.9 Hz), 6.61 (2H, s), 7.10-7.19 (2H, m), 7.22-7.31 (2H, m), 12.44 (1H, brs).

Retention time (IA) was 4.73 minutes.

Example 110

An optically active substance of 1-(2-((2,6-diethoxy-4'-fluorobiphenyl-4-yl)methyl)-8-methyl-5-oxa-2,6-diazaspiro[3.4]oct-6-en-7-yl)-4-methylpiperidine-4-carboxylic acid Fractionation was performed on a racemate (260 mg) of 1-(2-((2,6-diethoxy-4'-fluorobiphenyl-4-yl)methyl)-8-methyl-5-oxa-2,6-diazaspiro[3.4]oct-6-en-7-yl)-4-methylpiperidine-4-carboxylic acid using SFC (column: CHIRALPAK IA (LG021) 46 mmID×150 mmL, manufactured by Daicel Chemical Industries, Ltd., mobile phase: carbon dioxide/methanol/diethylamine=700/300/3), thereby obtaining a compound with a short retention time as a title compound (101 mg).

Retention time (IA) was 7.63 minutes.

Example 111

1-(2-((2-Cyclopropyl-4'-fluoro-6-(2-methoxyethoxy)biphenyl-4-yl)methyl)-5-oxa-2,6-diazaspiro[3.4]oct-6-en-7-yl)-4-methylpiperidine-4-carboxylic acid A) 3-Cyclopropyl-4-iodo-5-(2-methoxyethoxy)benzaldehyde Using 3-cyclopropyl-5-hydroxy-4-iodobenzaldehyde and 1-bromo-2-methoxyethane, the title compound was obtained in the similar manner as in Step A of Example 93.

$^1H$ NMR (400 MHz, $CDCl_3$) δ 0.69-0.76 (2H, m), 1.06-1.13 (2H, m), 2.11-2.22 (1H, m), 3.51 (3H, s), 3.86 (2H, t, J=4.7 Hz), 4.25 (2H, t, J=4.7 Hz), 7.03 (1H, s), 7.13 (1H, s), 9.91 (1H, s).

B) 2-Cyclopropyl-4'-fluoro-6-((2-methoxyethoxy)biphenyl-4-carbaldehyde

Using 3-cyclopropyl-4-iodo-5-(2-methoxyethoxy)benzaldehyde and (4-fluorophenyl)boronic acid, the title compound was obtained in the similar manner as in Step B of Example 93.

$^1H$ NMR (400 MHz, $CDCl_3$) δ 0.69-0.75 (2H, m), 0.81-0.87 (2H, m), 1.61-1.70 (1H, m), 3.24 (3H, s), 3.54-3.60 (2H, m), 4.06-4.12 (2H, m), 7.06 (1H, s), 7.09-7.15 (2H, m), 7.25-7.32 (3H, m), 9.93 (1H, s).

C) Ethyl 1-(2-((2-cyclopropyl-4'-fluoro-6-((2-methoxyethoxy)biphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-6-((2-methoxyethoxy)biphenyl-4-carbaldehyde, the title compound was obtained in the similar manner as in Step C of Example 93.

MS (ESI+): $[M+H]^+$ 580.3.

D) 1-(2-((2-Cyclopropyl-4'-fluoro-6-((2-methoxyethoxy)biphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-6-((2-methoxyethoxy)biphenyl-4-yl)methyl)-5-oxa-2,6-diazaspiro[3.4]oct-6-en-7-yl)-4-methylpiperidine-4-carboxylate, the title compound was obtained in the similar manner as in Step D of Example 93.

Example 112

1-(2-((2-(2,2-Difluorocyclopropyl)-6-ethoxy-4'-fluorobiphenyl-4-yl)methyl)-5-oxa-2,6-diazaspiro[3.4]oct-6-en-7-yl)-4-methylpiperidine-4-carboxylic acid A) Ethyl 2-ethoxy-4'-fluoro-6-vinylbiphenyl-4-carboxylate Ethyl 2-ethoxy-4'-fluoro-6-(((trifluoromethyl)sulfonyl)oxy)biphenyl-4-carboxylate (3.50 g), 4,4,5,5-tetramethyl-2-vinyl-1,3,2-dioxaborolane (3.09 g), dicyclohexyl(2',6'-dimethoxybiphenyl-2-yl)phosphine (461 mg), tris(dibenzylideneacetone)dipalladium(0) (514 mg) and 2 M aqueous sodium carbonate solution (16 mL) were stirred to toluene (40 mL) in an argon atmosphere, the resultant was stirred for 4 hours at 100° C. After the reaction mixture was cooled to room temperature, water was added thereto, and extraction thereof was performed using ethyl acetate. After the obtained organic layer was dried over anhydrous magnesium sulfate, the solvent was distilled off under reduced pressure. The obtained residue was purified by a silica gel column chromatography (NH, hexane/ethyl acetate), thereby obtaining the title compound (2.45 g).

$^1$H NMR (400 MHz, DMSO-$d_6$) δ 1.16 (3H, t, J=7.0 Hz), 1.35 (3H, t, J=7.1 Hz), 4.03 (2H, q, J=6.9 Hz), 4.36 (2H, q, J=7.1 Hz), 5.25 (1H, d, J=11.2 Hz), 5.76 (1H, d, J=17.6 Hz), 6.34 (1H, dd, J=17.5, 11.0 Hz), 7.16-7.33 (4H, m), 7.49 (1H, s), 7.84 (1H, s).

B) Ethyl 2-(2,2-difluorocyclopropyl)-6-ethoxy-4'-fluorobiphenyl-4-carboxylate

Trimethyl(trifluoromethyl)silane (4.03 mL) was added to a mixture of ethyl 2-ethoxy-4'-fluoro-6-vinylbiphenyl-4-carboxylate (2.45 g), sodium iodide (1.17 g) and THF (25 mL), and the resultant was stirred overnight at 70° C. in a nitrogen atmosphere. After water was added to the reaction mixture, extraction thereof was performed using ethyl acetate. The obtained organic layer was washed with a saturated saline solution, and was dried over anhydrous magnesium sulfate. The solvent was distilled off under reduced pressure, and the obtained residue was purified by a silica gel column chromatography (hexane/ethyl acetate), thereby obtaining the title compound (2.66 g).

$^1$H NMR (400 MHz, DMSO-$d_6$) δ 1.16 (3H, t, J=7.0 Hz), 1.34 (3H, t, J=7.1 Hz), 1.72-1.87 (2H, m), 2.59-2.70 (1H, m), 4.05 (2H, q, J=6.8 Hz), 4.31-4.40 (2H, m), 7.21-7.35 (4H, m), 7.47 (1H, s), 7.53 (1H, d, J 0.9 Hz).

C) 2-(2,2-difluorocyclopropyl)-6-ethoxy-4'-fluorobiphenyl-4-carbaldehyde

Ethyl 2-(2,2-difluorocyclopropyl)-6-ethoxy-4'-fluorobiphenyl-4-carboxylate (2.50 g) was added to a suspension of lithium aluminum hydride (521 mg) in THF (50 mL) under ice-cooling, and the resultant was stirred for 20 minutes. Sodium sulfate decahydrate was added to the reaction mixture, the resultant was stirred for 1 hour at room temperature, and then insoluble matter was separated by filtration. The obtained filtrate was passed through a silica gel, and was concentrated under reduced pressure. Manganese dioxide (5.97 g) was added to a solution of the obtained residue in THF (50 mL), and the resultant was stirred for 1 hour at room temperature. After the reaction mixture was filtered, and the filtrate was concentrated under reduced pressure. The obtained residue was purified by a silica gel column chromatography (hexane/ethyl acetate), thereby obtaining the title compound (1.94 g).

$^1$H NMR (400 MHz, DMSO-$d_6$) δ 1.17 (3H, t, J=7.0 Hz), 1.77-1.96 (2H, m), 2.64 (1H, td, J=12.2, 8.8 Hz), 4.08 (2H, q, J=6.9 Hz), 7.19-7.37 (4H, m), 7.52 (2H, d, J=1.8 Hz), 10.01 (1H, d, J=0.8 Hz).

D) Ethyl 1-(2-((2-(2,2-difluorocyclopropyl)-6-ethoxy-4'-fluorobiphenyl-4-yl)methyl)-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-5-oxa-2,6-diazaspiro[3.4]oct-6-ene-2-carboxylate (715 mg) was added to formic acid (3 mL), the resultant was stirred for 30 hour at 70° C., and then the solvent was distilled off under reduced pressure. Sodium triacetoxyborohydride (596 mg) was added to a solution of the obtained residue and 2-(2,2-difluorocyclopropyl)-6-ethoxy-4'-fluorobiphenyl-4-carbaldehyde (600 mg) in THF (10 mL), and the resultant was stirred for 1 hour at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (960m g).

$^1$H NMR (400 MHz, DMSO-$d_6$) δ 1.10-1.21 (9H, m), 1.36-1.45 (2H, m), 1.68-1.79 (2H, m), 1.93 (2H, d, J=13.6 Hz), 2.48-2.52 (1H, m), 2.82-2.91 (2H, m), 3.16 (2H, d, J=7.9 Hz), 3.27-3.30 (4H, m), 3.42-3.46 (2H, m), 3.57-3.61 (2H, m), 3.92-4.00 (2H, m), 4.10 (2H, q, J=7.1 Hz), 6.78 (1H, s), 6.93 (1H, s), 7.19-7.26 (4H, m).

E) 1-(2-((2-(2,2-difluorocyclopropyl)-6-ethoxy-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (5.9 mL) was added to a solution of ethyl 1-(2-((2-(2,2-difluorocyclopropyl)-6-ethoxy-4'-fluorobiphenyl-4-yl)methyl)-5-oxa-2,6-diaza spiro[3.4]oct-6-en-7-yl)-4-methylpiperidine-4-carboxylate (9150 mg) in ethanol (11 mL), and the resultant was stirred for 2 hours at 60° C. After the reaction mixture was neutralized with 2 M hydrochloric acid, it was concentrated to half amount thereof under reduced pressure, and the precipitated solid was collected by filtration, thereby obtaining the title compound (270 mg).

$^1$H NMR (400 MHz, DMSO-$d_6$) δ 1.09-1.17 (6H, m), 1.32-1.43 (2H, m), 1.68-1.79 (2H, m), 1.90 (2H, d, J=13.8 Hz), 2.47-2.57 (1H, m), 2.88 (2H, t, J=10.4 Hz), 3.12-3.21 (2H, m), 3.22-3.40 (4H, m), 3.43-3.50 (2H, m), 3.60 (2H, brs), 3.97 (2H, q, J=6.6 Hz), 6.78 (1H, s), 6.94 (1H, s), 7.17-7.28 (4H, m).

Example 113

Trans-4-(2-((2-Cyclopropyl-4'-fluoro-5-methoxybiphenyl-4-yl)methyl)-5-oxa-2,6-diazaspiro[3.4]oct-6-en-7-yl)cyclohexanecarboxylic acid

A) Methyl 4'-fluoro-3-hydroxybiphenyl-4-carboxylate

Palladium acetate (1.45 g) was added to a mixture of methyl 2-hydroxy-4-iodobenzoate (18.0 g), tripotassium phosphate (41.2 g), (4-fluorophenyl)boronic acid (18.1 g), tricyclohexylphosphine (20% toluene solution, 23.0 mL), toluene (200 mL) and water (100 mL), and the resultant was stirred for 1.5 hours at 90° C. in an argon atmosphere. The reaction mixture was cooled to room temperature, and the organic layer was separated. After the aqueous layer was acidified with 2 M hydrochloric acid, extraction thereof was performed using ethyl acetate. The collected organic layer was washed with a saturated saline solution, dried over anhydrous magnesium sulfate, and then distilled off under reduced pressure. The obtained residue was crystallized (methanol), thereby obtaining the title compound (16.4 g).

$^1$H NMR (300 MHz, DMSO-$d_6$) δ 3.92 (3H, s), 7.23-7.36 (4H, m), 7.73-7.82 (2H, m), 7.86 (1H, d, J=8.9 Hz), 10.60 (1H, brs).

B) Methyl 2-bromo-4'-fluoro-5-hydroxybiphenyl-4-carboxylate

Bromine (13.8 g) was added dropwise to a solution of methyl 4'-fluoro-3-hydroxybiphenyl-4-carboxylate (16.4 g) in ethyl acetate (200 mL), and the resultant was stirred for 2 hours at 50° C. The reaction mixture was cooled to room temperature, water was added thereto, and extraction thereof was performed using ethyl acetate. The obtained organic layer was sequentially washed with an aqueous sodium thiosulfate solution and a saturated saline solution, dried over anhydrous magnesium sulfate, and then the solvent was distilled off under reduced pressure. The obtained residue was crystallized (methanol), thereby obtaining the title compound (11.4 g).

MS (ESI−): [M−H]$^-$ 323.0, 325.0.

C) Methyl 2-cyclopropyl-4'-fluoro-5-hydroxybiphenyl-4-carboxylate

Methyl 2-bromo-4'-fluoro-5-hydroxybiphenyl-4-carboxylate (10.5 g), cyclopropyl boronic acid (5.55 g), dicyclohexyl(2',6'-dimethoxybiphenyl-2-yl)phosphine (1.33 g), tris(dibenzylideneacetone)dipalladium(0) (1.48 g) and 2 M aqueous sodium carbonate solution (48.4 mL) were added to toluene (100 mL) in an argon atmosphere, the resultant was stirred for 1 hour at 100° C. The reaction mixture was cooled to room temperature, and the organic layer was separated. After 2 M hydrochloric acid was added to the aqueous layer, and extraction thereof was performed using ethyl acetate. The collected organic layer was washed with a saturated saline solution, dried over anhydrous magnesium sulfate, and then the solvent was distilled off under reduced pressure. The obtained residue was crystallized (methanol), thereby obtaining the title compound (9.65 g).

$^1$H NMR (300 MHz, DMSO-$d_6$) δ 0.48-0.56 (2H, m), 0.72-0.81 (2H, m), 1.65-1.78 (1H, m), 3.90 (3H, s), 6.82 (1H, s), 7.25-7.35 (2H, m), 7.38-7.43 (1H, m), 7.45-7.54 (2H, m), 10.35 (1H, s).

D) Methyl 2-cyclopropyl-4'-fluoro-5-(methoxymethoxy)biphenyl-4-carboxylate

Chloro(methoxy)methane (1.75 g) was added to a mixture of methyl 2-cyclopropyl-4'-fluoro-5-hydroxybiphenyl-4-carboxylate (4.14 g), potassium carbonate (4.00 g) and DMF (70 mL), and the resultant was stirred for 3 hours at room temperature. Chloro(methoxy)methane (1.75 g) and potassium carbonate (4.00 g) were added to the reaction mixture, and the resultant was stirred for 15 hours at 60° C. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (4.06 g).

$^1$H NMR (300 MHz, $CDCl_3$) δ 0.61-0.69 (2H, m), 0.77-0.86 (2H, m), 1.70-1.83 (1H, m), 3.51 (3H, s), 3.90 (3H, s), 5.23 (2H, s), 7.04 (1H, s), 7.08-7.16 (2H, m), 7.37-7.44 (3H, m).

E) (2-Cyclopropyl-4'-fluoro-5-(methoxymethoxy)biphenyl-4-yl)methanol

Methyl 2-cyclopropyl-5-(methoxymethoxy)-4'-fluorobiphenyl-4-carboxylate (4.04 g) was added to a suspension of lithium aluminum hydride (975 mg) in THE (5 mL) at 0° C., and the resultant was stirred for 1 hour at room temperature. Water (1 mL), 1 M aqueous sodium hydroxide solution (1 mL) and water (3 mL) were sequentially added to the reaction mixture, the resultant was filtered using celite, and then the filtrate was concentrated under reduced pressure. The obtained residue was purified by a silica gel column chromatography (hexane/ethyl acetate), thereby obtaining the title compound (3.65 g).

$^1$H NMR (300 MHz, $CDCl_3$) δ 0.59-0.66 (2H, m), 0.75-0.83 (2H, m), 1.72-1.83 (1H, m), 2.24 (1H, t, J=6.5 Hz), 3.49 (3H, s), 4.70 (2H, d, J=6.4 Hz), 5.22 (2H, s), 6.91 (1H, s), 6.96 (1H, s), 7.06-7.14 (2H, m), 7.35-7.43 (2H, m).

F) 2-Cyclopropyl-4'-fluoro-5-(methoxymethoxy)biphenyl-4-carbaldehyde

Sulfur trioxide-pyridine complex (3.82 g) was added to a mixture of (2-cyclopropyl-4'-fluoro-5-(methoxymethoxy)biphenyl-4-yl)methanol (3.63 g), triethylamine (3.64 g) and DMSO (70 mL), and the resultant was stirred for 3 hours at room temperature. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (3.26 g).

$^1H$ NMR (300 MHz, $CDCl_3$) δ 0.65-0.72 (2H, m), 0.78-0.87 (2H, m), 1.69-1.80 (1H, m), 3.52 (3H, s), 5.29 (2H, s), 7.06 (1H, s), 7.09-7.17 (2H, m), 7.39-7.47 (3H, m), 10.48 (1H, s).

G) 2-Cyclopropyl-4'-fluoro-5-hydroxybiphenyl-4-carbaldehyde

6 M hydrochloric acid (25 mL) was added to a solution of 2-cyclopropyl-4'-fluoro-5-(methoxymethoxy)biphenyl-4-carbaldehyde (3.22 g) in methanol (60 mL) at room temperature, the resultant was stirred for 3 hours at 70° C., and then the solvent was distilled off under reduced pressure. The obtained residue was neutralized with an 8 M aqueous sodium hydroxide solution at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.67 g).

$^1H$ NMR (300 MHz, $CDCl_3$) δ 0.58-0.65 (2H, m), 0.79-0.87 (2H, m), 1.71-1.82 (1H, m), 6.87 (1H, s), 7.09-7.21 (3H, m), 7.38-7.46 (2H, m), 9.88 (1H, s), 10.85 (1H, s).

H) 2-Cyclopropyl-4'-fluoro-5-methoxybiphenyl-4-carbaldehyde

Iodomethane (213 mg) was added to a mixture of 2-cyclopropyl-4'-fluoro-5-hydroxybiphenyl-4-carboxylate (256 mg), potassium carbonate (276 mg) and DMF (10 mL) at room temperature, and the resultant was stirred for 3 hours at 70° C. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (263 mg).

$^1H$ NMR (300 MHz, $CDCl_3$) δ 0.62-0.70 (2H, m), 0.76-0.85 (2H, m), 1.67-1.79 (1H, m), 3.91 (3H, s), 6.82 (1H, s), 7.10-7.19 (2H, m), 7.39-7.47 (3H, m), 10.45 (1H, s).

I) Methyl trans-4-(2-((2-cyclopropyl-4'-fluoro-5-methoxybiphenyl-4-yl)methyl)-5-oxa-2,6-diazaspiro[3.4]oct-6-en-7-yl)cyclohexanecarboxylate Sodium triacetoxyborohydride (341 mg) was added to a mixture of methyl trans-4-(5-oxa-2,6-diazaspiro[3.4]oct-6-en-7-yl)cyclohexanecarboxylate hydrochloride (232 mg), 2-cyclopropyl-4'-fluoro-5-methoxybiphenyl-4-carbaldehyde (261 mg), triethylamine (163 mg) and THF (10 mL), and the resultant was stirred for 18 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The residue was purified by a silica gel column chromatography (hexane/ethyl acetate), thereby obtaining the title compound (370 mg).

$^1H$ NMR (300 MHz, $CDCl_3$) δ 0.55-0.62 (2H, m), 0.72-0.81 (2H, m), 1.30-1.58 (4H, m), 1.70-1.82 (1H, m), 1.93-2.13 (4H, m), 2.23-2.44 (2H, m), 3.20 (2H, s), 3.42-3.48 (2H, m), 3.49-3.55 (2H, m), 3.66-3.71 (5H, m), 3.79 (3H, s), 6.69 (1H, s), 6.84 (1H, s), 7.06-7.15 (2H, m), 7.36-7.44 (2H, m).

J) trans-4-(2-((2-Cyclopropyl-4'-fluoro-5-methoxybiphenyl-4-yl)methyl)-5-oxa-2,6-diazaspiro[3.4]oct-6-en-7-yl)cyclohexanecarboxylic acid 2 M aqueous sodium hydroxide solution (2 mL) was added to a solution of methyl trans-4-(2-((2-cyclopropyl-4'-fluoro-5-methoxybiphenyl-4-yl)methyl)-5-oxa-2,6-diazaspiro[3.4]oct-6-en-7-yl)cyclohexanecarboxylate (362 mg) in ethanol (8 mL), and the resultant was stirred for 15 hours at 70° C., and then the solvent was distilled off under reduced pressure. Water was added to the residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The residue was crystallized (hexane/ethanol), thereby obtaining the title compound (268 mg).

$^1H$ NMR (300 MHz, DMSO-$d_6$) δ 0.49-0.57 (2H, m), 0.72-0.81 (2H, m), 1.21-1.44 (4H, m), 1.68-1.80 (1H, m), 1.82-1.99 (4H, m), 2.11-2.23 (1H, m), 2.24-2.37 (1H, m), 3.18-3.27 (4H, m), 3.42 (2H, d, J=7.9 Hz), 3.56 (2H, s), 3.76 (3H, s), 6.75 (1H, s), 6.84 (1H, s), 7.22-7.31 (2H, m), 7.43-7.53 (2H, m), 12.08 (1H, brs).

Example 114

1-(2-((2-Cyclopropyl-4'-fluoro-5-methoxybiphenyl-4-yl)methyl)-5-oxa-2,6-diazaspiro[3.4]oct-6-en-7-yl)-4-methylpiperidine-4-carboxylic acid A) 4'-Fluoro-3-methoxybiphenyl-4-carbaldehyde Palladium acetate (2.61 g) was added to a mixture of 4-bromo-2-methoxybenzaldehyde (25.0 g), tripotassium phosphate (74.0 g), (4-fluorophenyl)boronic acid (24.4 g), tricyclohexylphosphine (20% toluene solution, 41.3 mL), toluene (250 mL) and water (125 mL), and the resultant was stirred for 3 hours at 90° C. in an argon atmosphere. The reaction mixture was cooled to room temperature, the organic layer was separated, and extraction was performed on the aqueous layer using ethyl acetate. The collected organic layer was sequentially washed with water and a saturated saline solution, dried over anhydrous magnesium sulfate, and then the solvent was distilled off under reduced pressure. The obtained residue was crystallized using methanol (150 mL), thereby obtaining the title compound (16.0 g).

$^1H$ NMR (300 MHz, DMSO-$d_6$) δ 4.03 (3H, s), 7.31-7.41 (3H, m), 7.45 (1H, d, J=1.3 Hz), 7.77 (1H, d, J=8.0 Hz), 7.82-7.91 (2H, m), 10.37 (1H, s).

H) 2-Bromo-4'-fluoro-5-methoxybiphenyl-4-carbaldehyde 1,3-Dibromo-1,3,5-triazine-2,4,6-trione (10.6 g) was added to a solution of 4'-fluoro-3-methoxybiphenyl-4-carbaldehyde (16.0 g) in DMF (90 mL) in the range of 15° C. to 30° C., the resultant was stirred for 40 minutes. Water (3 mL) was added thereto, and the resultant was further stirred for 1 hour. The precipitated solid was collected by filtration, it was sequentially washed with a mixed solution of DMF (15 mL) and water (15 mL), and water (30 mL), thereby obtaining the title compound (20.6 g).

$^1$H NMR (300 MHz, DMSO-$d_6$) δ 3.96 (3H, s), 7.25 (1H, s), 7.29-7.40 (2H, m), 7.54 (2H, dd, J=8.4, 5.6 Hz), 7.91 (1H, s), 10.30 (1H, s).

C) 2-Cyclopropyl-4'-fluoro-5-methoxybiphenyl-4-carbaldehyde

2-Bromo-4'-fluoro-5-methoxybiphenyl-4-carboxylate (20.6 g), cyclopropyl boronic acid (10.3 g), dicyclohexyl(2',6'-dimethoxybiphenyl-2-yl)phosphine (4.10 g), tris(dibenzylideneacetone)dipalladium(0) (427 g) and 2 M aqueous sodium carbonate solution (100 mL) were added to toluene (250 mL) in an argon atmosphere, and the resultant was stirred for 2 hours at 100° C. The reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. After the obtained residue was passed through a short column (hexane/ethyl acetate) of a silica gel, the filtrate was concentrated under reduced pressure. The obtained residue was crystallized using a mixed solution of ethanol (50 mL) and water (10 mL), and the obtained crystals were washed with ethanol (85 mL), thereby obtaining the title compound (9.70 g).

$^1$H NMR (300 MHz, $CDCl_3$) δ 0.62-0.71 (2H, m), 0.77-0.86 (2H, m), 1.66-1.79 (1H, m), 3.91 (3H, s), 6.82 (1H, s), 7.09-7.19 (2H, m), 7.38-7.48 (3H, m), 10.45 (1H, s).

D) Ethyl 1-(2-((2-cyclopropyl-4'-fluoro-5-methoxybiphenyl-4-yl)methyl)-5-oxa-2,6-diazaspiro[3.4]oct-6-en-7-yl)-4-methylpiperidine-4-carboxylate oxalate tert-Butyl 7-(4-(ethoxycarbonyl)-4-methylpiperidin-1-yl)-5-oxa-2,6-diazaspiro[3.4]oct-6-ene-2-carboxylate (13.0 g) was added to formic acid (26 mL), the resultant was stirred for 1 hour at 70° C., and then the solvent was distilled off under reduced pressure. The obtained residue was mixed with 2-cyclopropyl-4'-fluoro-5-methoxybiphenyl-4-carbaldehyde (9.21 g) and THF (78 mL), sodium triacetoxyborohydride (10.8 g) was added to the mixture, and the resultant was stirred for 3 hours at room temperature. After an aqueous saturated sodium hydrogen carbonate solution was added to the reaction mixture, extraction thereof was performed using ethyl acetate. The obtained organic layer was washed with a 5% saline solution, and the solvent was distilled off under reduced pressure. The obtained residue was dissolved in ethyl acetate (130 mL), oxalic acid (3.38 g) was added to the solution at 70° C., and the resultant was stirred for 30 minutes at the same temperature. Furthermore, after stirring overnight at room temperature, the solid was collected by filtration, and it was washed with ethyl acetate (39 mL), thereby obtaining the title compound (19.2 g).

$^1$H NMR (300 MHz, $CD_3OD$) δ 0.58-0.71 (2H, m), 0.75-0.89 (2H, m), 1.23 (3H, s), 1.27 (3H, t, J=7.1 Hz), 1.43-1.57 (2H, m), 1.73-1.85 (1H, m), 2.11 (2H, d, J=14.1 Hz), 3.00 (2H, t, J=10.7 Hz), 3.36-3.50 (4H, m), 3.91 (3H, s), 4.18 (2H, q, J=7.1 Hz), 4.28-4.50 (6H, m), 6.92 (1H, s), 7.07 (1H, s), 7.20 (2H, t, J=8.7 Hz), 7.46 (2H, dd, J 8.5, 5.5 Hz).

E) 1-(2-((2-Cyclopropyl-4'-fluoro-5-methoxybiphenyl-4-yl)methyl)-5-oxa-2,6-diazaspiro[3.4]oct-6-en-7-yl)-4-methylpiperidine-4-carboxylic acid Ethyl 1-(2-((2-cyclopropyl-4'-fluoro-5-methoxybiphenyl-4-yl)methyl)-5-oxa-2,6-diazaspiro[3.4]oct-6-en-7-yl)-4-methylpiperidine-4-carboxylate oxalate (19.2 g) was added to a mixed solution of ethyl acetate (200 mL) and an aqueous saturated sodium hydrogen carbonate solution (200 mL), the resultant was stirred for 30 minutes at room temperature, and then the organic layer was concentrated under reduced pressure. 4 M aqueous sodium hydroxide solution (50 mL) was added to a solution of the obtained residue in ethanol (150 mL), and the resultant was stirred for 2 hours at 70° C. The reaction mixture was cooled to room temperature, it was neutralized with 2 M hydrochloric acid (100 mL). The resultant was stirred for 30 minutes at room temperature and for 30 minutes at 0° C., and the precipitated solid was collected by filtration. Recrystallization (dimethylsulfoxide/ethanol) of the obtained solid was performed, thereby obtaining the title compound (12.3 g).

$^1$H NMR (300 MHz, DMSO-$d_6$) δ 0.49-0.57 (2H, m), 0.71-0.81 (2H, m), 1.14 (3H, s), 1.29-1.44 (2H, m), 1.68-1.80 (1H, m), 1.90 (2H, d, J=13.4 Hz), 2.88 (2H, t, J=10.5 Hz), 3.15 (2H, d, J=6.2 Hz), 3.23-3.39 (4H, m), 3.45 (2H, d, J=7.1 Hz), 3.55 (2H, brs), 3.76 (3H, s), 6.75 (1H, s), 6.84 (1H, s), 7.22-7.32 (2H, m), 7.48 (2H, dd, J=8.6, 5.6 Hz).

Example 115

1-(2-((2-Ethoxy-4'-fluoro-2'-(3,3,3-trifluoropropoxy)biphenyl-4-yl)methyl)-5-oxa-2,6-diazaspiro[3.4]oct-6-en-7-yl)-4-methylpiperidine-4-carboxylic acid A) 2-Ethoxy-4'-fluoro-2'-(3,3,3-trifluoropropoxy)biphenyl-4-carbaldehyde Using 2-ethoxy-4'-fluoro-2'-hydroxybiphenyl-4-carbaldehyde and 1,1,1-trifluoro-3-iodopropane, the title compound was obtained in the similar manner as in Step A of Example 106.

$^1$H NMR (300 MHz, $CDCl_3$) δ 1.29 (3H, t, J=7.0 Hz), 2.45 (2H, qt, J=10.5, 6.5 Hz), 4.07 (2H, q, J=7.0 Hz), 4.14 (2H, t, J=6.5 Hz), 6.69 (1H, dd, J=10.6, 2.5 Hz), 6.77 (1H, td, J=8.3, 2.4 Hz), 7.22 (1H, dd, J=8.3, 6.7 Hz), 7.34-7.39 (1H, m), 7.43 (1H, d, J=1.3 Hz), 7.45-7.49 (1H, m), 10.00 (1H, s).

B) Ethyl 1-(2-((2-ethoxy-4'-fluoro-2'-(3,3,3-trifluoropropoxy)biphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-ethoxy-4'-fluoro-2'-(3,3,3-trifluoropropoxy)biphenyl-4-carbaldehyde, the title compound was obtained in the similar manner as in Step G of Example 1.

MS (ESI+): $[M+H]^+$ 622.3.

C) 1-(2-((2-Ethoxy-4'-fluoro-2'-(3,3,3-trifluoropropoxy)biphenyl-4-yl)methyl)-5-oxa-2,6-diazaspiro[3.4]oct-6-en-7-yl)-4-methylpiperidine-4-carboxylic acid Using ethyl 1-(2-((2-ethoxy-4'-fluoro-2'-(3,3,3-trifluoropropoxy)biphenyl-4-yl)methyl)-5-oxa-2,6-diazaspiro[3.4]

oct-6-en-7-yl)-4-methylpiperidine-4-carboxylate, the title compound was obtained in the similar manner as in Example 2.

Example 116

1-(2-((2-Ethoxy-4'-fluoro-6-(pyrrolidin-1-yl)biphenyl-4-yl)methyl)-5-oxa-2,6-diazaspiro[3.4]oct-6-en-7-yl)-4-methylpiperidine-4-carboxylic acid A) Ethyl 2-ethoxy-4'-fluoro-6-((2-oxopyrrolidin-1-yl)biphenyl-4-carboxylate A mixture of ethyl 2-ethoxy-4'-fluoro-6-(((trifluoromethyl)sulfonyl)oxy)biphenyl-4-carboxylate (900 mg), cesium carbonate (941 mg), (9,9-dimethyl-9H-xanthen-4,5-diyl)bis(diphenylphosphine) (72 mg), pyrrolidine-2-one (211 mg), tris(dibenzylideneacetone)dipalladium(0) (19 mg) and toluene (10 mL) was stirred overnight at 100° C. in an argon atmosphere. The reaction mixture was diluted by ethyl acetate (20 mL), water was added thereto, and then extraction thereof was performed using ethyl acetate. The organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound.

MS (ESI+): $[M+H]^+$ 372.1.

B) (2-Ethoxy-4'-fluoro-6-(pyrrolidin-1-yl)biphenyl-4-yl)methanol

Using ethyl 2-ethoxy-4'-fluoro-6-((2-oxopyrrolidin-1-yl) biphenyl-4-carboxylate, and toluene instead of THF, the title compound was obtained in the similar manner as in Step F of Example 43.

MS (ESI+): $[M+14]^+$ 316.1.

C) 2-Ethoxy-4'-fluoro-6-(pyrrolidin-1-yl)biphenyl 4 carbaldehyde

Using (2-ethoxy-4'-fluoro-6-(pyrrolidin-1-yl)biphenyl-4-yl)methanol, the title compound was obtained in the similar manner as in Step B of Example 3.

MS (ESI+): $[M+H]^+$ 314.1.

D) 1-(2-((2-Ethoxy-4'-fluoro-6-(pyrrolidin-1-yl) biphenyl-4-yl)methyl)-5-oxa-2,6-diazaspiro[3.4]oct-6-en-7-yl)-4-methylpiperidine-4-carboxylic acid Using 2-ethoxy-4'-fluoro-6-(pyrrolidin-1-yl)biphenyl-4-carbaldehyde tert-butyl 7-(4-(ethoxycarbonyl)-4-methylpiperidin-1-yl)-5-oxa-2,6-diazaspiro[3.4]oct-6-ene-2-carboxylate, the title compound was obtained in the similar manner as in Step G of Example 1 and Example 2.

Example 117

1-(2-((2-Cyclopropyl-4'-fluoro-6-(3-methoxypropoxy)biphenyl-4-yl)methyl)-5-oxa-2,6-diazaspiro[3.4]oct-6-en-7-yl)-4-methylpiperidine-4-carboxylic acid A) 3-Cyclopropyl-4-iodo-5-(3-methoxypropoxy) benzaldehyde Using 3-cyclopropyl-5-hydroxy-4-iodobenzaldehyde and 1-bromo-3-methoxypropane, the title compound was obtained in the similar manner as in Step A of Example 93.

$^1$H NMR (400 MHz, $CDCl_3$) δ 0.70-0.77 (2H, m), 1.06-1.14 (2H, m), 2.09-2.21 (3H, m), 3.37 (3H, s), 3.66 (2H, t, J=6.1 Hz), 4.20 (2H, t, J=6.1 Hz), 7.02 (1H, d, J=1.0 Hz), 7.12 (1H, d, J=1.3 Hz), 9.91 (1H, s).

B) 2-Cyclopropyl-4'-fluoro-6-(3-methoxypropoxy) biphenyl-4-carbaldehyde

Using 3-cyclopropyl-4-iodo-5-(3-methoxypropoxy)benzaldehyde and (4-fluorophenyl)boronic acid, the title compound was obtained in the similar manner as in Step B of Example 93.

$^1$H NMR (400 MHz, $CDCl_3$) δ 0.69-0.75 (2H, m), 0.80-0.87 (2H, m), 1.60-1.69 (1H, m), 1.81-1.91 (2H, m), 3.24-3.31 (5H, m), 4.04 (2H, t, J=6.1 Hz), 7.04 (1H, s), 7.09-7.16 (2H, m), 7.23-7.29 (3H, m), 9.94 (1H, s).

C) Ethyl 1-(2-((2-cyclopropyl-4'-fluoro-6-(3-methoxypropoxy)biphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-6-(3-methoxypropoxy)biphenyl-4-carbaldehyde, the title compound was obtained in the similar manner as in Step C of Example 93.

MS (ESI+): $[M+H]^+$ 594.3.

D) 1-(2-((2-Cyclopropyl-4'-fluoro-6-(3-methoxypropoxy)biphenyl-4-yl)methyl)-5-oxa-2,6-diazaspiro [3.4]oct-6-en-7-yl)-4-methylpiperidine-4-carboxylic acid Using ethyl 1-(2-((2-cyclopropyl-4'-fluoro-6-(3-methoxypropoxy)biphenyl-4-yl)methyl)-5-oxa-2,6-diazaspiro[3.4]oct-6-en-7-yl)-4-methylpiperidine-4-carboxylate, the title compound was obtained in the similar manner as in Step D of Example 93.

Example 118

1-(2-((2-Cyclopropyl-6-ethoxy-2',4'-difluorobiphenyl-4-yl)methyl)-5-oxa-2,6-diazaspiro[3.4]oct-6-en-7-yl)-4-methylpiperidine-4-carboxylic acid A) Methyl 3-cyclopropyl-5-hydroxy-4-iodobenzoate 6 M hydrochloric acid (60 mL) was added to a solution of ethyl 4-amino-3-cyclopropyl-5-(methoxymethoxy)benzoate (8.89 g) in methanol (150 mL), the resultant was stirred for 3 hours at 70° C., and then the solvent was distilled off under reduced pressure. The obtained residue was neutralized with aqueous saturated sodium hydrogen carbonate solution at 0° C., and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining a purified product 2 M hydrochloric acid (68 mL) was added to a solution of the obtained residue in acetonitrile (100 mL) at 0° C., and the resultant was stirred for 30 minutes at the same temperature. An aqueous solution (50 mL) of sodium nitrite (2.45 g) was added to the reaction mixture, and the resultant was stirred for 30 minutes at 0° C. An aqueous solution (50 mL) of potassium iodide (18.1 g) was added dropwise thereto, and the resultant was stirred for 3 hours at 70° C. The reaction mixture was neutralized with an aqueous saturated sodium hydrogen carbonate solution at 0° C., and extraction thereof was performed using ethyl acetate. The obtained organic layer was sequentially washed with an aqueous sodium thiosulfate solution and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (3.68 g).

$^1$H NMR (400 MHz, $CDCl_3$) δ 0.69-0.76 (2H, m), 1.03-1.10 (2H, m), 1.95-2.04 (1H, m), 3.90 (3H, s), 5.61 (1H, s), 7.19 (1H, d, J=1.8 Hz), 7.47 (1H, d, J=1.9 Hz).

B) Methyl 3-cyclopropyl-5-ethoxy-4-iodobenzoate

Iodoethane (2.35 g) was added to a mixture of methyl 3-cyclopropyl-5-hydroxy-4-iodobenzoate (3.68 g), potassium carbonate (2.40 g) and DMF (70 mL), and the resultant was stirred for 5 hours at 60° C. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (3.92 g).

$^1$H NMR (400 MHz, $CDCl_3$) δ 0.68-0.74 (2H, m), 1.02-1.09 (2H, m), 1.51 (3H, t, J=7.0 Hz), 2.08-2.17 (1H, m), 3.90 (3H, s), 4.16 (2H, q, J=7.0 Hz), 7.21 (1H, s), 7.26 (1H, s).

C) (3-Cyclopropyl-5-ethoxy-4-iodophenol)methanol

Diisobutylaluminium hydride (1.5 M toluene solution, 15 mL) was added to a solution of methyl 3-cyclopropyl-5-ethoxy-4-iodobenzoate (3.14 g) in THF (50 mL) at 0° C., and the resultant was stirred for 2 hours at room temperature. Diisobutylaluminium hydride (1.5 M toluene solution, 15 mL) was further added to the reaction mixture, the resultant was stirred for 2 hours at room temperature. Sodium sulfate decahydrate was added thereto 0° C., the resultant was stirred for 30 minutes at room temperature, and it was filtered using celite. The obtained filtrate was concentrated under reduced pressure, thereby obtaining the title compound (2.89 g).

$^1$H NMR (400 MHz, $CDCl_3$) δ 0.61-0.70 (2H, m), 0.98-1.06 (2H, m), 1.49 (3H, t, J=7.0 Hz), 1.65-1.72 (1H, m), 2.06-2.15 (1H, m), 4.10 (2H, q, J=6.9 Hz), 4.61 (2H, d, J=4.6 Hz), 6.54 (1H, s), 6.68 (1H, s).

D) 3-Cyclopropyl-5-ethoxy-4-iodobenzaldehyde

Sulfur trioxide-pyridine complex (2.89 g) was added to a mixture of (3-cyclopropyl-5-ethoxy-4-iodophenyl)methanol (2.89 g), triethylamine (2.75 g) and DMSO (50 mL), and the resultant was stirred for 1 hour at room temperature. Sulfur trioxide-pyridine complex (1.44 g) and triethylamine (1.38 g) were added to the reaction mixture, the resultant was stirred for 2 hours at room temperature, water was added thereto, and then extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.76 g).

$^1$H NMR (300 MHz, $CDCl_3$) δ 0.69-0.76 (2H, m), 1.05-1.14 (2H, m), 1.52 (3H, t, J=7.0 Hz), 2.10-2.23 (1H, m), 4.18 (2H, q, J=7.0 Hz), 7.01 (1H, d, J=1.3 Hz), 7.09 (1H, d, J=1.7 Hz), 9.91 (1H, s).

E) Ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (3.03 g) and formic acid (10 mL) was stirred for 1 hour at 60° C., the solvent was distilled off under reduced pressure. The obtained residue was mixed with 3-cyclopropyl-5-ethoxy-4-iodobenzaldehyde (2.76 g) and THF (50 mL), sodium triacetoxyborohydride (3.36 g) was added to the mixture, and the resultant was stirred for 15 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (3.91 g).

$^1$H NMR (400 MHz, $CDCl_3$) δ 0.60-0.68 (2H, m), 0.96-1.04 (2H, m), 1.20 (3H, s), 1.26 (3H, t, J=7.2 Hz), 1.41-1.53 (5H, m), 2.05-2.14 (3H, m), 2.91-3.01 (2H, m), 3.23 (2H, s), 3.29 (2H, d, J=8.8 Hz), 3.33-3.41 (2H, m), 3.48 (2H, d, J=8.7 Hz), 3.56 (2H, s), 4.09 (2H, q, J=7.0 Hz), 4.16 (2H, q, J=7.2 Hz), 6.45 (1H, s), 6.58 (1H, s).

F) Ethyl 1-(2-((2-cyclopropyl-6-ethoxy-2',4'-difluorobiphenyl-4-yl)methyl)-5-oxa-2,6-diazaspiro[3.4]oct-6-en-7-yl)-4-methylpiperidine-4-carboxylate (1,1% Bis(diphenylphosphino)ferrocene)dichloropalladium(II) (96 mg) was added to a mixture of ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate (380 mg), (2,4-difluorophenyl)boronic acid (207 mg), cesium fluoride (298 mg) and DME (10 mL), and the resultant was stirred for 17 hours at 100° C. in an argon atmosphere. Water was added to the reaction mixture, the resultant was filtered using celite, and then the filtrate was extracted using ethyl acetate. The obtained organic layer was washed with a saturated saline solution, dried over anhydrous magnesium sulfate, and then the solvent was distilled off under reduced pressure. The obtained residue was purified by a silica gel chromatography (NH, hexane/ethyl acetate), and fractionation was performed thereon using HPLC (C18, mobile phase: water/acetonitrile (0.1% TFA-containing system)). The obtained fraction was concentrated, an aqueous saturated sodium hydrogen carbonate solution was added to the residue, and extraction thereof was performed using ethyl acetate. The obtained organic layer was washed with a saturated saline solution, dried over anhydrous magnesium sulfate, and then the solvent was distilled off under reduced pressure, thereby obtaining the title compound (214 mg).

$^1$H NMR (300 MHz, $CDCl_3$) δ 0.54-0.69 (2H, m), 0.70-0.77 (2H, m), 1.17-1.29 (9H, m), 1.39-1.61 (3H, m), 2.11 (2H, d, J=13.5 Hz), 2.91-3.03 (2H, m), 3.26 (2H, s), 3.33-3.44 (4H, m), 3.52-3.61 (2H, m), 3.65 (2H, s), 3.96 (2H, q,

J=6.9 Hz), 4.16 (2H, q, J=7.1 Hz), 6.46 (1H, s), 6.71 (1H, s), 6.83-6.96 (2H, m), 7.17-7.26 (1H, m).

G) 1-(2-((2-Cyclopropyl-6-ethoxy-2',4'-difluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (1.5 mL) was added to a solution of ethyl 1-(2-((2-cyclopropyl-6-ethoxy)-2',4'-difluorobiphenyl-4-yl)methyl)-5-oxa-2,6-diazaspiro[3.4]oct-6-en-7-yl)-4-methylpiperidine-4-carboxylate (214 mg) in ethanol (6 mL), the resultant was stirred for 15 hours at 70° C., and then the solvent was distilled off under reduced pressure. Water was added to the residue, the resultant was neutralized with 2 M hydrochloric acid, and then the obtained solid was collected by filtration. After the obtained solid was dissolved in ethyl acetate and THE, it was dried over anhydrous magnesium sulfate, and the solvent was distilled off under reduced pressure. The residue was crystallized (hexane/ethanol), thereby obtaining the title compound (106 mg).

$^1$H NMR (300 MHz, DMSO-$d_6$) δ 0.53-0.60 (2H, m), 0.66-0.75 (2H, m), 1.07-1.17 (6H, m), 1.30-1.50 (3H, m), 1.91 (2H, d, J=13.7 Hz), 2.83-2.94 (2H, m), 3.14 (2H, d, J=8.3 Hz), 3.25-3.36 (4H, m), 3.44 (2H, d, J=8.3 Hz), 3.55 (2H, s), 3.94 (2H, q, J=7.0 Hz), 6.45 (1H, s), 6.78 (1H, s), 7.07-7.16 (1H, m), 7.22-7.35 (2H, m).

Example 119

1-(2-((2-Cyclopropyl-6-ethoxy-3',4',5'-trifluorobiphenyl-4-yl)methyl)-5-oxa-2,6-diazaspiro[3.4]oct-6-en-7-yl)-4-methylpiperidine-4-carboxylic acid (3,4,5-Trifluorophenyl)boronic acid (28.1 mg), bis(di-tert-butyl(4-dimethylaminophenyl)phosphine)dichloropalladium(II) (5.66 mg) and 1.6 M aqueous potassium carbonate solution (0.1 mL) were added to a solution of ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate (46.5 mg) in DME (0.9 mL), and the resultant was stirred for 30 minutes at 130° C. under microwave irradiation. After an aqueous saturated sodium hydrogen carbonate solution (1 mL) and ethyl acetate (3 mL) were added to the reaction mixture, the resultant was stirred, extraction was performed on the organic layer, and the solvent was evaporated using an air spay apparatus. The obtained residue was purified using HPLC (column: YMC Triart C18, mobile phase: acetonitrile/10 mM aqueous ammonium bicarbonate solution), and the solvent was evaporated using an air spay apparatus. Ethanol (0.5 mL), THF (0.5 mL) and 2 M aqueous sodium hydroxide solution (0.5 mL) were added to the obtained residue, the resultant was stirred overnight at 60° C., and the solvent was evaporated using an air spay apparatus. The obtained residue was purified using HPLC (column: YMC Triart C18, mobile phase: acetonitrile/10 mM aqueous ammonium bicarbonate solution), and the solvent was evaporated using an air spay apparatus, thereby obtaining the title compound (15.2 mg).

Example 120

1-(2-((2-Cyclopropyl-6-ethoxy-2',3',4',5'-tetrafluorobiphenyl-4-yl)methyl)-5-oxa-2,6-diazaspiro[3.4]oct-6-en-7-yl)-4-methylpiperidine-4-carboxylic acid Using ethyl 1-(2-((3-cyclopropyl-5-ethoxy-4-iodobenzyl)-5-oxa-2,6-diazaspiro[3.4]oct-6-en-7-yl)-4-meth ylpiperidine-4-carboxylate and (2,3,4,5-tetrafluorophenyl)boronic acid, the title compound was obtained in the similar manner as in Example 119.

Example 121

1-(2-((2-Cyclopropyl-6-ethoxy-2',6'-difluorobiphenyl-4-yl)methyl)-5-oxa-2,6-diazaspiro[3.4]oct-6-en-7-yl)-4-methylpiperidine-4-carboxylic acid Using ethyl 1-(2-((3-cyclopropyl-5-ethoxy-4-iodobenzyl)-5-oxa-2,6-diazaspiro[3.4]oct-6-en-7-yl)-4-meth ylpiperidine-4-carboxylate and (2,6-difluorophenyl)boronic acid, the title compound was obtained in the similar manner as in Example 119.

Example 122

1-(2-((2-Cyclopropyl-6-ethoxy-2',4',5'-trifluorobiphenyl-4-yl)methyl)-5-oxa-2,6-diazaspiro[3.4]oct-6-en-7-yl)-4-methylpiperidine-4-carboxylic acid Using ethyl 1-(2-((3-cyclopropyl-5-ethoxy-4-iodobenzyl)-5-oxa-2,6-diazaspiro[3.4]oct-6-en-7-yl)-4-methylpiperidine-4-carboxylate and (2,4,5-trifluorophenyl)boronic acid, the title compound was obtained in the similar manner as in Example 119.

Example 123

1-(2-((2-Cyclopropyl-6-ethoxybiphenyl-4-yl)methyl)-5-oxa-2,6-diazaspiro[3.4]oct-6-en-7-yl)-4-methylpiperidine-4-carboxylic acid Using ethyl 1-(2-((3-cyclopropyl-5-ethoxy-4-iodobenzyl)-5-oxa-2,6-diazaspiro[3.4]oct-6-en-7-yl)-4-methylpiperidine-4-carboxylate and phenylboronic acid, the title compound was obtained in the similar manner as in Example 119.

Example 124

1-(2-((2-Cyclopropyl-6-ethoxy-4'-methylbiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (4-methylphenyl)boronic acid, the title compound was obtained in the similar manner as in Example 119.

Example 125

1-(2-((3'-Chloro-2-cyclopropyl-6-ethoxy-4'-fluorobiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (3-chloro-4-fluorophenyl)boronic acid, the title compound was obtained in the similar manner as in Example 119.

Example 126

1-(2-((2-Cyclopropyl-6-ethoxy-4'-fluoro-3'-methyl-biphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate and (4-fluoro-3-methylphenyl)boronic acid, the title compound was obtained in the similar manner as in Example 119.

Example 127

1-(2-((2'-Chloro-2-cyclopropyl-6-ethoxy-4'-fluorobiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate and (2-chloro-4-fluorophenyl)boronic acid, the title compound was obtained in the similar manner as in Example 119.

Example 128

1-(2-((2-Cyclopropyl-6-ethoxy-4'-fluoro-2'-methyl-biphenyl-4-yl)methyl)-5-oxa-2,6-diazaspiro[3.4]oct-6-en-7-yl)-4-methylpiperidine-4-carboxylic acid Using ethyl 1-(2-((3-cyclopropyl-5-ethoxy-4-iodobenzyl)-5-oxa-2,6-diazaspiro[3.4]oct-6-en-7-yl)-4-meth ylpiperidine-4-carboxylate and (4-fluoro-2-methylphenyl)boronic acid, the title compound was obtained in the similar manner as in Example 119.

Example 129

1-(2-((2-Cyclopropyl-6-ethoxy-4'-fluoro-2'-(trifluoromethyl)biphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (4-fluoro-2-(trifluoromethyl)phenyl) boronic acid, the title compound was obtained in the similar manner as in Example 119.

Example 130

1-(2-((2-Cyclopropyl-6-ethoxy-2',4'-methylbiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (2,4-difluoro-5-methylphenyl)boronic acid, the title compound was obtained in the similar manner as in Example 119.

Example 131

1-(2-((2-Cyclopropyl-6-ethoxy-2'-fluorobiphenyl-4-yl)methyl)-5-oxa-2,6-diazaspiro[3.4]oct-6-en-7-yl)-4-methylpiperidine-4-carboxylic acid Using ethyl 1-(2-((3-cyclopropyl-5-ethoxy-4-iodobenzyl)-5-oxa-2,6-diazaspiro[3.4]oct-6-en-7-yl)-4-methylpiperidine-4-carboxylate and (2-fluorophenyl)boronic acid, the title compound was obtained in the similar manner as in Example 119.

Example 132

1-(2-((2-Cyclopropyl-6-ethoxy-2',3',4'-trifluorobiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate and (2,3,4-trifluorophenyl)boronic acid, the title compound was obtained in the similar manner as in Example 119.

Example 133

1-(2-((4'-Cyano-2-cyclopropyl-6-ethoxy-2'-methyl-biphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate and (4-cyano-2-methylphenyl)boronic acid, the title compound was obtained in the similar manner as in Example 119.

Example 134

1-(2-((2'-Cyano-2-cyclopropyl-6-ethoxybiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate and (2-cyanophenyl)boronic acid, the title compound was obtained in the similar manner as in Example 119.

Example 135

1-(2-((2-Cyclopropyl-2',6-diethoxy-4'-fluorobiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (2-ethoxy-4-fluorophenyl)boronic acid, the title compound was obtained in the similar manner as in Example 119.

Example 136

1-(2-((2-Cyclopropyl-6-ethoxy-4'-(methoxymethyl) biphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (4-(methoxymethyl)phenyl)boronic acid, the title compound was obtained in the similar manner as in Example 119.

Example 137

1-(2-((2-Cyclopropyl-6-ethoxy-2'-fluoro-4'-methyl-biphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate and (2-fluoro-4-methylphenyl)boronic acid, the title compound was obtained in the similar manner as in Example 119.

Example 138

1-(2-((2-Cyclopropyl-6-ethoxy-3'-fluorobiphenyl-4-yl)methyl)-5-oxa-2,6-diazaspiro[3.4]oct-6-en-7-yl)-3-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (3-fluorophenyl)boronic acid, the title compound was obtained in the similar manner as in Example 119.

Example 139

1-(2-((2-Cyclopropyl-6-ethoxy-2'-methylbiphenyl-4-yl)methyl)-5-oxa-2,6-diazaspiro[3.4]oct-6-en-7-yl)-2-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (2-methylphenyl)boronic acid, the title compound was obtained in the similar manner as in Example 119.

Example 140

1-(2-((2'-Chloro-2-cyclopropyl-6-ethoxybiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (2-chlorophenyl)boronic acid, the title compound was obtained in the similar manner as in Example 119.

Example 141

1-(2-((2-Cyclopropyl-6-ethoxy-2'-(trifluoromethyl) biphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate and (2-(trifluoromethyl)phenyl)boronic acid, the title compound was obtained in the similar manner as in Example 119.

Example 142

1-(2-((3-Cyclopropyl-5-ethoxy-4-(6-fluoropyridin-3-yl)benzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (6-fluoropyridin-3-yl)boronic acid, the title compound was obtained in the similar manner as in Example 119.

Example 143

1-(2-(3-Cyclopropyl-5-ethoxy-4-(6-methoxypyridin-3-yl)benzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate and (6-methoxypyridin-3-yl)boronic acid, the title compound was obtained in the similar manner as in Example 119.

Example 144

1-(2-(3-Cyclopropyl-5-ethoxy-4-(6-(trifluoromethyl-3-yl)benzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate and (6-(trifluoromethyl)pyridin-3-yl)boronic acid, the title compound was obtained in the similar manner as in Example 119.

Example 145

1-(2-((3-Cyclopropyl-5-ethoxy-4-(6-methylpyridin-3-yl)benzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (6-methylpyridin-3-yl)boronic acid, the title compound was obtained in the similar manner as in Example 119.

Example 146

1-(2-(3-Cyclopropyl-5-ethoxy-4-(pyridin-3-yl)benzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and pyridin-3-yl boronic acid, the title compound was obtained in the similar manner as in Example 119.

Example 147

1-(2-(3-Cyclopropyl-5-ethoxy-4-(5-fluoropyridin-3-yl)benzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (5-fluoropyridin-3-yl)boronic acid, the title compound was obtained in the similar manner as in Example 119.

Example 148

1-(2-(3-Cyclopropyl-5-ethoxy-4-(2-fluoropyridin-3-yl)benzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate and (2-fluoropyridin-3-yl)boronic acid, the title compound was obtained in the similar manner as in Example 119.

Example 149

1-(2-(3-Cyclopropyl-5-ethoxy-4-((5-methylpyridin-3-yl)benzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (5-methylpyridin-3-yl)boronic acid, the title compound was obtained in the similar manner as in Example 119.

Example 150

1-(2-((4-(5-Chloro-2-thienyl)-3-cyclopropyl-5-ethoxybenzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (5-chloro-2-thienyl)boronic acid, the title compound was obtained in the similar manner as in Example 119.

Example 151

1-(2-(3-Cyclopropyl-5-ethoxy-4-((5-methyl-2-thienyl)benzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (5-methyl-2-thienyl)boronic acid, the title compound was obtained in the similar manner as in Example 119.

Example 152

1-(2-(3,4-Dicyclopropyl-5-ethoxybenzyl)-5-oxa-2,6-diazaspiro[3.4]oct-6-en-7-yl)-4-methylpiperidine-4-carboxylic acid Using ethyl 1-(2-((3-cyclopropyl-5-ethoxy-4-iodobenzyl)-5-oxa-2,6-diazaspiro[3.4]oct-6-en-7-yl)-4-methylpiperidine-4-carboxylate and cyclopropylboronic acid, the title compound was obtained in the similar manner as in Example 119.

Example 153

1-(2-((4'-Cyano-2-cyclopropyl-6-ethoxy-2'-fluorobiphenyl-4-yl)methyl)-5-oxa-2,6-diazaspiro[3.4]oct-6-en-7-yl)-4-methylpiperidine-4-carboxylic acid (4-Cyano-2-fluorophenyl)boronic acid (26.4 mg), bis(di-tert-butyl(4-dimethylaminophenyl)phosphine)dichloropalladium(II) (5.66 mg) and 1.6 M aqueous potassium carbonate solution were added to a solution of ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate (46.5 mg) in DME (0.9 mL), and the resultant was stirred for 30 minutes at 130° C. under microwave irradiation. After an aqueous saturated sodium hydrogen carbonate solution (1 mL) and ethyl acetate (3 mL) were added to the reaction mixture, the resultant was stirred, extraction was performed on the organic layer, and the solvent was evaporated using an air spay apparatus. The residue was purified using HPLC (column: YMC Triart C18, mobile phase: acetonitrile/10 mM aqueous ammonium bicarbonate solution), and the solvent was evaporated using an air spay apparatus. Ethanol (0.5 mL), THF (0.5 mL) and 1 M aqueous sodium hydroxide solution (0.5 mL) were added to the obtained residue, the resultant was stirred for 1 hour at 40° C., and the solvent was evaporated using an air spay apparatus. The residue was purified using HPLC (column: YMC Triart C18, mobile phase: acetonitrile/10 mM aqueous ammonium bicarbonate solution), and the solvent was evaporated using an air spay apparatus, thereby obtaining the title compound (5.29 mg).

Example 154

1-(2-((4'-Cyano-2-cyclopropyl-6-ethoxy-3'-fluorobiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-meth ylpiperidine-4-carboxylate and (4-cyano-3-fluorophenyl)boronic acid, the title compound was obtained in the similar manner as in Example 153.

Example 155

1-(2-((3'-Chloro-4'-cyano-2-cyclopropyl-6-ethoxybiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (3-chloro-4-cyanophenyl)boronic acid, the title compound was obtained in the similar manner as in Example 153.

Example 156

1-(2-((3'-Cyano-2-cyclopropyl-6-ethoxybiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (3-cyanophenyl)boronic acid, the title compound was obtained in the similar manner as in Example 153.

Example 157

1-(2-((3'-Cyano-2-cyclopropyl-6-ethoxy-4'-fluorobiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (3-cyano-4-fluorophenyl)boronic acid, the title compound was obtained in the similar manner as in Example 153.

Example 158

1-(2-((5'-Cyano-2-cyclopropyl-6-ethoxy-2'-fluorobiphenyl-4-yl)methyl)-5-oxa-2,6-diazaspiro[3.4]oct-6-en-7-yl)-2-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (5-cyano-2-fluorophenyl)boronic acid, the title compound was obtained in the similar manner as in Example 153.

Example 159

1-(2-((4'-Cyano-2-cyclopropyl-6-ethoxybiphenyl-4-yl)methyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (4-cyanophenyl)boronic acid, the title compound was obtained in the similar manner as in Example 153.

Example 160

1-(2-((3-Cyclopropyl-4-(5,6-difluoropyridin-3-yl)-5-ethoxybenzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (5,6-difluoropyridin-3-yl)boronic acid, the title compound was obtained in the similar manner as in Example 153.

Example 161

1-(2-(3-Cyclopropyl-4-(2,6-difluoropyridin-3-yl)-5-ethoxybenzyl)-5-oxa-2,6-diazaspiro[3.4]oct-6-en-7-yl)-4-methylpiperidine-4-carboxylic acid Using ethyl 1-(2-(3-cyclopropyl-5-ethoxy-4-iodobenzyl)-5-oxa-2,6-diazaspiro[3.4]oct-6-en-7-yl)-4-methylpiperidine-4-carboxylate and (2,6-difluoropyridin-3-yl)boronic acid, the title compound was obtained in the similar manner as in Example 153.

Example 162

1-(2-((2-Cyclopropyl-6-ethoxy-3',4'-difluorobiphenyl-4-yl)methyl)-5-oxa-2,6-diazaspiro[3.4]oct-6-en-7-yl)-4-methylpiperidine-4-carboxylic acid A) 3-Ethoxy-5-iodo-4-(methoxymethoxy)benzaldehyde Chloro(methoxy)methane (3.89 g) was added to a mixture of 3-ethoxy-4-hydroxy-5-iodobenzaldehyde (9.41 g), potassium carbonate (8.90 g) and DMF (120 mL), and the resultant was stirred for 3 hours at room temperature. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (9.20 g).

$^1$H NMR (300 MHz, $CDCl_3$) δ 1.47 (3H, t, J=7.0 Hz), 3.67 (3H, s), 4.13 (2H, q, J=7.0 Hz), 5.33 (2H, s), 7.39 (1H, d, J=1.7 Hz), 7.86 (1H, d, J=1.8 Hz), 9.81 (1H, s).

B) 3-Cyclopropyl-5-ethoxy-4-hydroxybenzaldehyde

Tris(dibenzylideneacetone)dipalladium(0) (1.75 g) and dicyclohexyl(2',6'-dimethoxybiphenyl-2-yl)phosphine (1.66 g) were added to a mixture of 3-ethoxy-5-iodo-4-(methoxymethoxy)benzaldehyde (9.20 g), cyclopropyl boronic acid (3.53 g), 2 M aqueous sodium carbonate solution (41 mL) and toluene (150 mL), the resultant was stirred 15 hours at 100° C. in an argon atmosphere. Water was added to the reaction mixture, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining a purified product 6 M hydrochloric acid (50 mL) was added to a solution of the obtained purified product in methanol (100 mL), the resultant was stirred for 3 hours at 70° C., the solvent was distilled off under reduced pressure, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (5.21 g).

$^1$H NMR (300 MHz, $CDCl_3$) δ 0.71-0.79 (2H, m), 0.97-1.05 (2H, m), 1.48 (3H, t, J=7.0 Hz), 2.12-2.24 (1H, m), 4.20 (2H, q, J=7.0 Hz), 6.38 (1H, s), 7.02 (1H, d, J=1.7 Hz), 7.23 (1H, d, J=1.7 Hz), 9.76 (1H, s).

C) 2-Cyclopropyl-6-ethoxy-4-formylphenyl trifluoromethanesulfonate

Trifluoromethanesulfonic anhydride (11.5 g) was added to a solution of 3-cyclopropyl-5-ethoxy-4-hydroxybenzaldehyde (5.59 g) in pyridine (100 mL), the resultant was stirred for 2 hours at room temperature, and then the solvent was distilled off under reduced pressure. Ethyl acetate and 1 M hydrochloric acid were added to the obtained residue, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (4.24 g).

$^1$H NMR (300 MHz, $CDCl_3$) δ 0.79-0.87 (2H, m), 1.10-1.19 (2H, m), 1.49 (3H, t, J 7.0 Hz), 2.07-2.21 (1H, m), 4.20 (2H, q, J=7.0 Hz), 7.05 (1H, d, J=1.7 Hz), 7.32 (1H, d, J=1.8 Hz), 9.90 (1H, s).

D) 2-Cyclopropyl-6-ethoxy-3',4'-difluorobiphenyl-4-carbaldehyde (1,1'-Bis(diphenylphosphino)ferrocene)dichloropalladium(II) (350 mg) was added to a mixture of 2-cyclopropyl-6-ethoxy-4-formylphenyl trifluoromethanesulfonate (810 mg), (3,4-difluorophenyl)boronic acid (756 mg), cesium fluoride (1.09 g) and DME (15 mL), and the resultant was stirred for 15 hours at 100° C. in an argon atmosphere. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (257 mg).

$^1$H NMR (300 MHz, DMSO-$d_6$) δ 0.67-0.74 (2H, m), 0.78-0.86 (2H, m), 1.16 (3H, t, J=6.9 Hz), 1.52-1.64 (1H, m), 4.05 (2H, q, J=6.9 Hz), 7.08-7.16 (1H, m), 7.18 (1H, d, J=1.0 Hz), 7.33-7.42 (2H, m), 7.45-7.56 (1H, m), 9.96 (1H, s).

E) Ethyl 1-(2-((2-cyclopropyl-6-ethoxy-3',4'-difluorobiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (257 mg) and formic acid (6 mL) was stirred for 1 hour at 60° C., the solvent was distilled off under reduced pressure. The obtained residue was mixed with 2-cyclopropyl-6-ethoxy-3',4'-difluorobiphenyl-4-carbaldehyde (244 mg) and THF (10 mL), sodium triacetoxyborohydride (285 mg) was added to the mixture, and the resultant was stirred for 15 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (332 mg).

$^1$H NMR (300 MHz, $CDCl_3$) δ 0.58-0.67 (2H, m), 0.71-0.80 (2H, m), 1.17-1.31 (9H, m), 1.39-1.63 (3H, m), 2.11 (2H, d, J=13.6 Hz), 2.90-3.02 (2H, m), 3.26 (2H, s), 3.31-3.44 (4H, m), 3.50-3.56 (2H, m), 3.62 (2H, s), 3.94 (2H, q, J=7.0 Hz), 4.16 (2H, q, J=7.1 Hz), 6.41 (1H, s), 6.69 (1H, s), 6.97-7.04 (1H, m), 7.07-7.23 (2H, m).

F) 1-(2-((2-Cyclopropyl-6-ethoxy-3',4'-difluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (2 mL) was added to a solution of ethyl 1-(2-((2-cyclopropyl-6-ethoxy)-3',4'-difluorobiphenyl-4-yl)methyl)-5-oxa-2,6-diazaspiro[3.4]oct-6-en-7-yl)-4-methylpiperidine-4-carboxylate (320 mg) in ethanol (8 mL), the resultant was stirred for 15 hours at 70° C., and then the solvent was distilled off under reduced pressure. Water was added to the obtained residue, the resultant was neutralized with 2 M hydrochloric acid, and then the precipitated solid was collected by filtration. After the obtained solid was dissolved in ethyl acetate and THF, dried over anhydrous magnesium sulfate, and the solvent was distilled off under reduced pressure. The obtained residue was crystallized (hexane/ethanol), thereby obtaining the title compound (233 mg).

$^1$H NMR (300 MHz, DMSO-$d_6$) δ 0.57-0.65 (2H, m), 0.70-0.80 (2H, m), 1.10-1.19 (6H, m), 1.32-1.43 (2H, m), 1.45-1.57 (1H, m), 1.91 (2H, d, J=13.8 Hz), 2.83-2.97 (2H, m), 3.20-3.57 (8H, m), 3.61-3.87 (2H, m), 3.96 (2H, q, J=7.0 Hz), 6.55 (1H, brs), 6.90 (1H, brs), 7.02-7.10 (1H, m), 7.23-7.34 (1H, m), 7.40-7.51 (1H, m).

Example 163

1-(2-((2-(2,2-Difluoro-1-methylcyclopropyl)-6-ethoxy-4'-fluorobiphenyl-4-yl)methyl)-5-oxa-2,6-diazaspiro[3.4]oct-6-en-7-yl)-4-methylpiperidine-4-carboxylic acid

A) Ethyl 2-ethoxy-4'-fluoro-6-(prop-1-en-2-yl)biphenyl-4-carboxylate

Ethyl 2-ethoxy-4'-fluoro-6-(((trifluoromethyl)sulfonyl)oxy)biphenyl-4-carboxylate (2.50 g), 4,4,5,5-tetramethyl-2-(prop-1-en-2-yl)-1,3,2-dioxaborolane (2.41 g), dicyclohexyl (2',6'-dimethoxybiphenyl-2-yl)phosphine (329 mg), tris (dibenzylideneacetone)dipalladium(0) (367 mg) and 2 M aqueous sodium carbonate solution (11.5 mL) were stirred to toluene (40 mL) in an argon atmosphere, the resultant was stirred for 3 hours at 100° C. The reaction mixture was cooled to room temperature, it was poured into water, and extraction thereof was performed using ethyl acetate. After the obtained organic layer was dried over anhydrous magnesium sulfate, the solvent was distilled off under reduced pressure. The obtained residue was purified by a silica gel column chromatography (NH, hexane/ethyl acetate), thereby obtaining the title compound (1.10 g).

$^1$H NMR (400 MHz, $CDCl_3$) δ 1.23-1.29 (6H, m), 1.41 (3H, t, J=7.1 Hz), 4.03 (2H, q, J=7.0 Hz), 4.40 (2H, q, J=7.1 Hz), 4.93 (1H, s), 5.03 (1H, s), 7.04 (2H, t, J=8.8 Hz), 7.23-7.29 (2H, m), 7.53 (1H, d, J=1.0 Hz), 7.59 (1H, d, J=1.3 Hz).

B) Ethyl 2-(2,2-difluoro-1-methylcyclopropyl)-6-ethoxy-4'-fluorobiphenyl-4-carboxylate Ethyl 2-ethoxy-4'-fluoro-6-(prop-1-en-2-yl)biphenyl-4-carboxylate (500 mg), trimethyl(trifluoromethyl)silane (0.79 mL) and sodium iodide (228 mg) were added to THF (10 mL), and the resultant was stirred overnight at 70° C. After the reaction mixture was cooled to room temperature, water was added thereto, and extraction thereof was performed using ethyl acetate. The obtained organic layer was washed with a saturated saline solution, and was dried over anhydrous magnesium sulfate. The solvent was distilled off under reduced pressure, and the obtained residue was purified by a silica gel column chromatography (hexane/ethyl acetate), thereby obtaining the title compound (540 mg).

MS (ESI+): $[M+H]^+$ 379.1.

C) 2-(2,2-Difluoro-1-methylcyclopropyl)-6-ethoxy-4'-fluorobiphenyl-4-carbaldehyde Ethyl 2-(2,2-difluoro-1-methylcyclopropyl)-6-ethoxy-4'-fluorobiphenyl-4-carboxylate (540 mg) was added to a suspension of lithium aluminum hydride (108 mg) in THF (50 mL) under ice-cooling, and the resultant was stirred for 20 minutes. Sodium sulfate decahydrate was added to the reaction mixture, the resultant was stirred for 1 hour at room temperature, and then insoluble matter was separated by filtration. The obtained filtrate was passed through a silica gel pad, and was concentrated under reduced pressure. The obtained residue was dissolved in THF (50 mL), manganese dioxide (1.24 g) was added to the solution, and the resultant was stirred for 1 hour at room temperature. After the reaction mixture was filtered, the filtrate was concentrated under reduced pressure, and the obtained residue was purified by a silica gel column chromatography (hexane/ethyl acetate), thereby obtaining the title compound (395 mg).

$^1$H NMR (400 MHz, $CDCl_3$) δ 1.09-1.18 (1H, m), 1.23 (3H, t, J=7.0 Hz), 1.28 (3H, s), 1.35-1.44 (1H, m), 3.97-4.09 (2H, m), 7.13 (2H, t, J=8.3 Hz), 7.20-7.30 (2H, m), 7.38 (1H, s), 7.47 (1H, s), 9.99 (1H, s).

D) Ethyl 1-(2-((2-(2,2-difluoro-1-methylcyclopropyl)-6-ethoxy-4'-fluorobiphenyl-4-yl)methyl)-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-5-oxa-2,6-diazaspiro[3.4]oct-6-ene-2-carboxylate (445 mg) was added to formic acid (3 mL), the resultant was stirred for 1 hour at 70° C., and then the solvent was distilled off under reduced pressure. The obtained residue was mixed with 2-(2,2-difluoro-1-methylcyclopropyl)-6-ethoxy-4'-fluorobiphenyl-4-carbaldehyde (390 mg) and THF (10 mL), sodium triacetoxyborohydride (371 mg) was added the mixture, and the resultant was stirred for 5 hours at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (610 mg).

$^1$H NMR (400 MHz, $CDCl_3$) δ 0.98-1.07 (1H, m), 1.17 (3H, t, J=7.0 Hz), 1.21 (3H, s), 1.23-1.29 (7H, m), 1.41-1.50 (2H, m), 2.11 (2H, d, J=13.7 Hz), 2.92-3.02 (2H, m), 3.26 (2H, s), 3.32-3.43 (4H, m), 3.55 (2H, d, J=8.8 Hz), 3.66 (2H, d, J=3.3 Hz), 3.88-3.99 (2H, m), 4.16 (2H, q, J=7.1 Hz), 6.80 (1H, s), 6.86 (1H, s), 7.04-7.12 (2H, m), 7.18-7.31 (2H, m).

E) 1-(2-((2-(2,2-Difluoro-1-methylcyclopropyl)-6-ethoxy-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (3.5 mL) was added to a solution of ethyl 1-(2-((2-(2,2-difluoro-1-methylcyclopropyl)-6-ethoxy-4'-fluorobiphenyl-4-yl)methyl)-5-oxa-2,6-diazaspiro[3.4]oct-6-en-7-yl)-4-methylpiperidine-4-carboxylate (600 mg) in ethanol (7 mL), and the resultant was stirred for 2 hours at 60° C. After the reaction mixture was neutralized with 2 M hydrochloric acid, it was stirred for 30 minutes, and the precipitated solid was collected by filtration. Recrystallization (methanol) of the obtained solid was performed, thereby obtaining the title compound (353 mg).

$^1$H NMR (400 MHz, DMSO-$d_6$) δ 1.10 (3H, t, J=6.9 Hz), 1.14 (3H, s), 1.17 (3H, s), 1.23-1.49 (4H, m), 1.91 (2H, d, J=13.8 Hz), 2.89 (2H, t, J=10.2 Hz), 3.09-3.23 (2H, m), 3.24-3.40 (4H, m), 3.43-3.51 (2H, m), 3.61 (2H, brs), 3.93 (2H, d, J=7.0 Hz), 6.84-6.94 (2H, m), 7.16-7.32 (4H, m).

Example 164

1-(2-((3-Cyclopropyl-5-ethoxy-4-(piperidin-1-yl)benzyl)-5-oxa-2,6-diazaspiro[3.4]oct-6-en-7-yl)-4-methylpiperidine-4-carboxylic acid A) Ethyl 3-cyclopropyl-5-(methoxymethoxy)-4-(piperidin-1-yl)benzoate Sodium hydride (273 mg) was added to a solution of ethyl 4-amino-3-cyclopropyl-5-(methoxymethoxy)benzoate (603 mg) in DMSO (8 mL) at 0° C., and the resultant was stirred for 30 minutes at room temperature. 1,5-dibromopentane (0.929 mL) was added to the reaction mixture, and the resultant was stirred overnight at room temperature. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (487 mg).

$^1$H NMR (300 MHz, $CDCl_3$) δ 0.63-0.73 (2H, m), 0.91-1.01 (2H, m), 1.36 (3H, t, J=7.1 Hz), 1.58-1.69 (6H, m), 2.40-2.52 (1H, m), 3.05-3.20 (4H, m), 3.52 (3H, s), 4.33 (2H, q, J=7.1 Hz), 5.21 (2H, s), 7.17 (1H, d, J=1.9 Hz), 7.50 (1H, d, J=1.9 Hz).

B) Ethyl 3-cyclopropyl-5-hydroxy-4-(piperidin-1-yl)benzoate

6 M hydrochloric acid (2.88 mL) was added to a solution of ethyl 3-cyclopropyl-5-(methoxymethoxy)-4-(piperidin-1-yl)benzoate (577 mg) in ethanol (10 mL) at room temperature, then the resultant was stirred for 3 hours at 70° C. The solvent of the reaction mixture was distilled off under reduced pressure. After the obtained residue was neutralized with an aqueous saturated sodium hydrogen carbonate solution, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (292 mg).

$^1$H NMR (300 MHz, $CDCl_3$) δ 0.77-0.85 (2H, m), 0.96-1.05 (2H, m), 1.36 (3H, t, J=7.1 Hz), 1.58-1.97 (6H, m), 1.99-2.13 (1H, m), 2.95 (2H, brs), 3.37 (2H, brs), 4.32 (2H, q, J=7.1 Hz), 7.08 (1H, d, J=2.1 Hz), 7.43 (1H, d, J=2.1 Hz), 8.07 (1H, s).

C) Ethyl 3-cyclopropyl-5-ethoxy-4-(piperidin-1-yl)benzoate

Potassium carbonate (209 mg) and iodoethane (0.105 mL) were added to a solution of ethyl 3-cyclopropyl-5-hydroxy-4-(piperidin-1-yl)benzoate (292 mg) in DMF (6 mL), the resultant was stirred overnight at 60° C. After the reaction mixture was cooled to room temperature, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (251 mg).

$^1$H NMR (300 MHz, $CDCl_3$) δ 0.63-0.70 (2H, m), 0.89-0.99 (2H, m), 1.36 (3H, t, J=7.2 Hz), 1.45 (3H, t, J=7.0 Hz), 1.58-1.69 (6H, m), 2.43-2.54 (1H, m), 3.13 (4H, brs), 4.05 (2H, q, J=7.0 Hz), 4.33 (2H, q, J=7.1 Hz), 7.10 (1H, d, J=1.9 Hz), 7.32 (1H, d, J=1.9 Hz).

D) (3-Cyclopropyl-5-ethoxy-4-(piperidin-1-yl)phenyl)methanol

Lithium aluminum hydride (60.0 mg) was added to a solution of ethyl 3-cyclopropyl-5-ethoxy-4-(piperidin-1-yl) benzoate (251 mg) in THF (8 mL) at 0° C., and the resultant was stirred for 15 minutes at the same temperature. Sodium sulfate decahydrate was added to the reaction mixture at 0° C., and the resultant was stirred overnight at room temperature. After the reaction mixture was filtered using celite, the filtrate was concentrated under reduced pressure, thereby obtaining the title compound (221 mg).

$^1$H NMR (300 MHz, $CDCl_3$) δ 0.56-0.63 (2H, m), 0.85-0.95 (2H, m), 1.41-1.47 (4H, m), 1.50 (1H, t, J=6.0 Hz), 1.56-1.69 (5H, m), 2.54-2.65 (1H, m), 3.08 (4H, brs), 4.02 (2H, q, J=7.0 Hz), 4.56 (2H, d, J=6.0 Hz), 6.33 (1H, d, J=1.7 Hz), 6.69 (1H, d, J=1.9 Hz).

E) 3-Cyclopropyl-5-ethoxy-4-(piperidin-1-yl)benzaldehyde

Sulfur trioxide-pyridine complex (251 mg) was added to a mixture of (3-cyclopropyl-5-ethoxy-4-(piperidin-1-yl)phenyl)methanol (217 mg), triethylamine (0.329 mg) and DMSO (5 mL) at room temperature, and the resultant was stirred for 1 hour at the same temperature. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (76.0 mg).

$^1$H NMR (300 MHz, $CDCl_3$) δ 0.64-0.72 (2H, m), 0.94-1.05 (2H, m), 1.47 (3H, t, J=7.0 Hz), 1.58-1.69 (6H, m), 2.37-2.51 (1H, m), 3.11-3.22 (4H, m), 4.07 (2H, q, J=7.0 Hz), 6.92 (1H, d, J=1.7 Hz), 7.17 (1H, d, J=1.9 Hz), 9.80 (1H, s).

F) Ethyl 1-(2-(3-cyclopropyl-5-ethoxy-4-(piperidin-1-yl)benzyl)-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-5-oxa-2,6-diazaspiro[3.4]oct-6-ene-2-carboxylate (158 mg) and formic acid (2 mL) was stirred for 1 hour at 60° C. The solvent of the reaction mixture was distilled off under reduced pressure, toluene was added to the residue, and furthermore the solvent was distilled off under reduced pressure. The obtained residue was mixed with 3-cyclopropyl-5-ethoxy-4-(piperidin-1-yl)benzaldehyde (75.7 mg) and THF (3 mL), the mixture was stirred for 2 hours at room temperature, sodium triacetoxyborohydride (88.0 mg) was added thereto at room temperature, and then the resultant was stirred overnight at room temperature. Water was added to the reaction mixture, and the resultant was stirred for 10 minutes. After an aqueous saturated sodium hydrogen carbonate solution was added to the reaction mixture, extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (121 mg).

$^1$H NMR (300 MHz, $CDCl_3$) δ 0.53-0.61 (2H, m), 0.86-0.91 (2H, m), 1.20 (3H, s), 1.25 (4H, t, J=7.2 Hz), 1.38-1.50 (5H, m), 1.58 (8H, brs), 2.05-2.16 (2H, m), 2.51-2.63 (1H, m), 2.88-3.02 (3H, m), 3.23 (2H, s), 3.25-3.30 (2H, m), 3.32-3.43 (2H, m), 3.45-3.50 (2H, m), 3.52 (2H, s), 3.99 (2H, q, J=7.0 Hz), 4.16 (2H, q, J=7.2 Hz), 6.22 (1H, d, J=2.1 Hz), 6.57 (1H, d, J=1.7 Hz).

G) 1-(2-((3-Cyclopropyl-5-ethoxy-4-(piperidin-1-yl) benzyl)-5-oxa-2,6-diazaspiro[3.4]oct-6-en-7-yl)-4-methylpiperidine-4-carboxylic acid A mixture of ethyl 1-(2-(3-cyclopropyl-5-ethoxy-4-(piperidin-1-yl)benzyl)-5-oxa-2,6-diazaspiro[3.4]oct-6-en-7-yl)-4-methylpiperidine-4-carboxylate (112 mg), 1 M aqueous sodium hydroxide solution (0.624 mL), methanol (2 mL) and THF (2 mL) was stirred for 5 hours at 60° C. The reaction mixture was cooled to room temperature, and the solvent was distilled off under reduced pressure. The obtained residue was neutralized with 1 M hydrochloric acid, and the solvent was distilled off under reduced pressure. The obtained residue was diluted by water, and extraction was performed using ethyl acetate. The obtained organic layer was washed with a saturated saline solution, dried over anhydrous magnesium sulfate, and then the solvent was distilled off under reduced pressure. The obtained residue was crystallized (hexane/ethyl acetate), thereby obtaining the title compound (64.0 mg).

$^1$H NMR (300 MHz, $CDCl_3$) δ 0.52-0.63 (2H, m), 0.87-0.97 (2H, m), 1.27 (3H, s), 1.37-1.51 (5H, m), 1.63 (4H, brs), 2.09-2.24 (5H, m), 2.47-2.65 (1H, m), 2.86-3.20 (5H, m), 3.26 (2H, s), 3.37-3.47 (2H, m), 3.48-3.55 (2H, m), 3.66-3.74 (2H, m), 3.78 (2H, s), 3.92-4.03 (2H, m), 6.27 (1H, d, J=1.9 Hz), 6.64 (1H, d, J=2.1 Hz).

Example 165

1-(2-((2-Cyclopropyl-2'-ethoxy-4'-fluorobiphenyl-4-yl)methyl)-5-oxa-2,6-diazaspiro[3.4]oct-6-en-7-yl)-4-methylpiperidine-4-carboxylic acid A) 3-Cyclopropyl-4-hydroxybenzaldehyde Using 3-bromo-4-hydroxybenzaldehyde and cyclopropylboronic acid, the title compound was obtained in the similar manner as in Step D of Example 23.

MS (ESI+): $[M+H]^+$ 163.1.

B) 2-Cyclopropyl-4-formylphenyl trifluoromethanesulfonate

Using 3-cyclopropyl-4-hydroxybenzaldehyde, the title compound was obtained in the similar manner as in Step H of Example 16.

$^1$H NMR (300 MHz, $CDCl_3$) δ 0.81-0.89 (2H, m), 1.12-1.20 (2H, m), 2.10-2.20 (1H, m), 7.42 (1H, d, J=8.5 Hz), 7.55 (1H, d, J=2.1 Hz), 7.76 (1H, dd, J=8.5, 2.1 Hz), 9.98 (1H, s).

C) 2'-(Benzyloxy)-2-cyclopropyl-4'-fluorobiphenyl-4-carbaldehyde

Using 2-cyclopropyl-4-formylphenyl trifluoromethanesulfonate and (2-(benzyloxy)-4-fluorophenyl)boronic acid, the title compound was obtained in the similar manner as in Step D of Example 16.

MS (ESI+): $[M+H]^+$ 347.1.

D) 2-Cyclopropyl-4'-fluoro-2'-hydroxybiphenyl-4-carbaldehyde

Using 2'-(benzyloxy)-2-cyclopropyl-4'-fluorobiphenyl-4-carbaldehyde, the title compound was obtained in the similar manner as in Step A of Example 102.

$^1$H NMR (300 MHz, $CDCl_3$) δ 0.79 (2H, d, J=4.7 Hz), 0.89-1.03 (2H, m), 1.70-1.82 (1H, m), 6.70-6.80 (2H, m), 7.11-7.19 (1H, m), 7.39 (1H, d, J=7.9 Hz), 7.46 (1H, d, J=1.7 Hz), 7.75 (1H, dd, J=7.7, 1.7 Hz), 10.01 (1H, s).

E) 2-Cyclopropyl-2'-ethoxy-4'-fluorobiphenyl-4-carbaldehyde

Using 2-cyclopropyl-4'-fluoro-2'-hydroxybiphenyl-4-carbaldehyde and iodoethane, the title compound was obtained in the similar manner as in Step B of Example 16.

MS (ESI+): $[M+H]^+$ 285.1.

F) Ethyl 1-(2-((2-cyclopropyl-2'-ethoxy-4'-fluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-2'-ethoxy-4'-fluorobiphenyl-4-carbaldehyde, the title compound was obtained in the similar manner as in Step G of Example 1.

MS (ESI+): $[M+H]^+$ 550.3.

G) 1-(2-((2-Cyclopropyl-2'-ethoxy-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-2-ethoxy-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 166

1-(2-((2-Cyclopropyl-4'-fluoro-6-((1-fluorocyclopropyl)methoxy)biphenyl-4-yl)methyl)-5-oxa-2,6-diazaspiro[3.4]oct-6-en-7-yl)-4-methylpiperidine-4-carboxylic acid A) Ethyl 3-cyclopropyl-4-iodo-5-(methoxymethoxy)benzoate Chloro(methoxy)methane (1.25 g) was added to a mixture of ethyl 3-cyclopropyl-5-hydroxy-4-iodobenzoate (3.42 g), potassium carbonate (2.85 g) and DMF (60 mL), and the resultant was stirred for 60 hours at room temperature. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (3.69 g).

$^1$H NMR (400 MHz, $CDCl_3$) δ 0.69-0.75 (2H, m), 1.03-1.10 (2H, m), 1.38 (3H, t, J=7.1 Hz), 2.07-2.17 (1H, m), 3.53 (3H, s), 4.36 (2H, q, J=7.2 Hz), 5.30 (2H, s), 7.27 (1H, d, J=1.4 Hz), 7.49 (1H, d, J=1.5 Hz).

B) Ethyl 2-cyclopropyl-4'-fluoro-6-(methoxymethoxy)biphenyl-4-carboxylate (1,1'-Bis(diphenylphosphino)ferrocene)dichloropalladium(II) (1.43 g) was added to a mixture of ethyl 3-cyclopropyl-4-iodo-5-(methoxymethoxy)benzoate (3.68 g), (4-fluorophenyl)boronic acid (2.05 g), cesium fluoride (4.46 g) and DME (80 mL), and the resultant was stirred for 16 hours at 100° C. in an argon atmosphere. Water was added to the reaction mixture, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (3.37 g).

$^1$H NMR (400 MHz, $CDCl_3$) δ 0.67-0.74 (2H, m), 0.76-0.83 (2H, m), 1.40 (3H, t, J=7.1 Hz), 1.56-1.63 (1H, m), 3.29 (3H, s), 4.38 (2H, q, J=7.1 Hz), 5.08 (2H, s), 7.09-7.16 (2H, m), 7.25-7.32 (3H, m), 7.62 (1H, s).

C) (2-Cyclopropyl-4'-fluoro-6-(methoxymethoxy)biphenyl-4-yl)methanol

A solution of ethyl 2-cyclopropyl-4'-fluoro-6-(methoxymethoxy)biphenyl-4-carboxylate (3.37 g) in THF (10 mL) was added to a suspension of lithium aluminum hydride (780 mg) in THF (70 mL) at 0° C., and the resultant was stirred for 1 hour at the same temperature. Water (1 mL), 1 M aqueous sodium hydroxide solution (1 mL) and water (3 mL) were sequentially added to the reaction mixture, the resultant was filtered using celite, and then the filtrate was concentrated under reduced pressure. The obtained residue was purified by a silica gel column chromatography (hexane/ethyl acetate), thereby obtaining the title compound (2.83 g).

$^1$H NMR (400 MHz, $CDCl_3$) δ 0.62-0.67 (2H, m), 0.72-0.79 (2H, m), 1.55-1.62 (1H, m), 1.69 (1H, t, J=5.9 Hz), 3.30 (3H, s), 4.66 (2H, d, J=5.6 Hz), 5.03 (2H, s), 6.61 (1H, s), 7.01 (1H, s), 7.07-7.13 (2H, m), 7.24-7.29 (2H, m).

D) 2-Cyclopropyl-4'-fluoro-6-(methoxymethoxy) biphenyl-4-carbaldehyde

Sulfur trioxide-pyridine complex (2.96 g) was added to a mixture of (2-cyclopropyl-4'-fluoro-6-(methoxymethoxy) biphenyl-4-yl)methanol (2.81 g), triethylamine (2.83 g) and DMSO (80 mL), and the resultant was stirred for 1 hour at the same temperature. Sulfur trioxide-pyridine complex (1.48 g) and triethylamine (1.41 g) were added to the reaction mixture, the resultant was stirred for 1 hour at room temperature, water was added thereto, and then extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.65 g).

$^1$H NMR (300 MHz, $CDCl_3$) δ 0.69-0.75 (2H, m), 0.80-0.87 (2H, m), 1.57-1.67 (1H, m), 3.32 (3H, s), 5.10 (2H, s), 7.11-7.18 (3H, m), 7.25-7.31 (2H, m), 7.48 (1H, d, J=1.4 Hz), 9.95 (1H, s).

E) 2-Cyclopropyl-4'-fluoro-6-hydroxybiphenyl-4-carbaldehyde

6 M hydrochloric acid (30 mL) was added to a solution of 2-cyclopropyl-4'-fluoro-6-(methoxymethoxy)biphenyl-4-carbaldehyde (2.65 g) in methanol (70 mL), the resultant was stirred for 2 hours at 70° C., and then the solvent was distilled off under reduced pressure. The obtained residue was neutralized with 8 M aqueous sodium hydroxide solution at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.14 g).

$^1$H NMR (400 MHz, $CDCl_3$) δ 0.68-0.75 (2H, m), 0.79-0.86 (2H, m), 1.50-1.59 (1H, m), 4.92 (1H, s), 7.05 (1H, s), 7.22-7.31 (3H, m), 7.33-7.40 (2H, m), 9.93 (1H, s).

F) 2-Cyclopropyl-4'-fluoro-6-(1-fluorocyclopropyl) methoxy)biphenyl-4-carbaldehyde Methanesulfonyl chloride (552 mg) was added to a mixture of (1-fluorocyclopropyl)methanol (289 mg), triethylamine (650 mg) and THF (10 mL), and the resultant was stirred for 1 hour at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was added to a mixture of 2-cyclopropyl-4'-fluoro-6-hydroxybiphenyl-4-carbaldehyde (400 mg), potassium carbonate (431 mg) and DMF (10 mL), and the resultant was stirred for 72 hours at 70° C. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (391 mg).

$^1$H NMR (300 MHz, $CDCl_3$) δ 0.52-0.62 (2H, m), 0.69-0.78 (2H, m), 0.81-0.91 (2H, m), 0.93-1.08 (2H, m), 1.62-1.74 (1H, m), 4.22 (2H, d, J=18.1 Hz), 7.07-7.17 (3H, m), 7.26-7.32 (3H, m), 9.94 (1H, s).

G) Ethyl 1-(2-((2-cyclopropyl-4'-fluoro-6-(1-fluoro-cyclopropyl)methoxy)biphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (406 mg) and formic acid (6 mL) was stirred for 1 hour at 60° C., the solvent was distilled off under reduced pressure. The obtained residue was mixed with 2-cyclopropyl-4'-fluoro-6-((1-fluorocyclopropyl)methoxy) biphenyl-4-carbaldehyde (384 mg) and THF (10 mL), sodium triacetoxyborohydride (451 mg) was added the mixture, and the resultant was stirred for 5 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (488 mg).

$^1$H NMR (300 MHz, $CDCl_3$) δ 0.46-0.56 (2H, m), 0.59-0.66 (2H, m), 0.71-0.80 (2H, m), 0.88-1.02 (2H, m), 1.21 (3H, s), 1.26 (3H, t, J=7.1 Hz), 1.39-1.52 (2H, m), 1.55-1.67 (1H, m), 2.11 (2H, d, J=13.5 Hz), 2.90-3.03 (2H, m), 3.26 (2H, s), 3.30-3.44 (4H, m), 3.53 (2H, d, J=9.0 Hz), 3.62 (2H, s), 4.06-4.21 (4H, m), 6.45 (1H, s), 6.75 (1H, s), 7.04-7.12 (2H, m), 7.23-7.29 (2H, m).

H) 1-(2-((2-Cyclopropyl-4'-fluoro-6-((1-fluorocyclo-propyl)methoxy)biphenyl-4-yl)methyl)-5-oxa-2,6-diazaspiro[3.4]oct-6-en-7-yl)-4-methylpiperidine-4-carboxylic acid 2 M aqueous sodium hydroxide solution (2 mL) was added to a solution of ethyl 1-(2-((2-cyclopropyl-4'-fluoro-6-((1-fluorocyclopropyl)methoxy)biphenyl-4-yl)methyl)-5-oxa-2,6-diazaspiro[3.4]oct-6-en-7-yl)-4-methylpiperidine-4-carboxylate (480 mg) in ethanol (8 mL), the resultant was stirred for 4 hours at 70° C., and then the solvent was distilled off under reduced pressure. Water was added to the residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The residue was crystallized (hexane/ethyl acetate), thereby obtaining the title compound (300 mg).

$^1$H NMR (300 MHz, DMSO-$d_6$) δ 0.55-0.77 (6H, m), 0.87-0.99 (2H, m), 1.14 (3H, s), 1.31-1.43 (2H, m), 1.45-1.57 (1H, m), 1.91 (2H, d, J=13.7 Hz), 2.81-2.95 (2H, m), 3.15 (2H, d, J=7.0 Hz), 3.26-3.36 (4H, m), 3.44 (2H, d, J=7.6 Hz), 3.54 (2H, s), 4.12-4.25 (2H, m), 6.47 (1H, s), 6.83 (1H, s), 7.18-7.32 (4H, m).

Example 167

1-(2-((2-Ethoxy-4'-fluoro-6-(pentafluoroethyl)biphenyl-4-yl)methyl)-5-oxa-2,6-diazaspiro[3.4]oct-6-en-7-yl)-4-methylpiperidine-4-carboxylic acid

A) Methyl 4-(benzyloxy)-3-ethoxy-5-(pentafluoroethyl)benzoate

A mixture of methyl 4-(benzyloxy)-3-ethoxy-5-iodobenzoate (980 mg), trimethyl(pentafluoroethyl)silane (914 mg), potassium fluoride (249 mg), copper(I) iodide (996 mg) and DMF (5 mL) was stirred for 6 hours at 80° C. under microwave irradiation. After an aqueous saturated ammonium chloride solution was added to the reaction mixture, extraction thereof was performed using ethyl acetate. The organic layer was sequentially washed with water and a saturated saline solution, dried over anhydrous magnesium sulfate, and then the solvent was distilled off under reduced pressure. The obtained residue was passed through a short column (ethyl acetate) of a silica gel, the solvent was distilled off under reduced pressure, and the obtained residue was purified by a silica gel column chromatography (hexane/ethyl acetate), thereby obtaining the title compound (961 mg).

$^1$H NMR (300 MHz, $CDCl_3$) δ 1.49 (3H, t, J=7.0 Hz), 3.93 (3H, s), 4.19 (2H, q, J=6.9 Hz), 5.15 (2H, s), 7.31-7.42 (3H, m), 7.48 (2H, d, J=7.2 Hz), 7.79 (1H, s), 7.85 (1H, d, J=1.5 Hz).

B) Methyl 3-ethoxy-5-(pentafluoroethyl)-4-(((trifluoromethyl)sulfonyl)oxy)benzoate 20% palladium hydroxide (50% water content, 800 mg) was added to a mixed solution of methyl 4-(benzyloxy)-3-ethoxy-5-(pentafluoroethyl)benzoate (1.00 g) in methanol (20 mL) and THF (4 mL), and the resultant was stirred for 2 hours at 50° C. in a hydrogen atmosphere. After the catalyst was filtered, the obtained filtrate was concentrated under reduced pressure. The obtained residue was dissolved in pyridine (10 mL), trifluoromethanesulfonic anhydride (698 mg) was added to the solution at 0° C., and the resultant was stirred for 1 hour at room temperature. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (300 mg).

$^1$H NMR (300 MHz, $CDCl_3$) δ 1.51-1.55 (3H, m), 3.97 (3H, s), 4.29 (2H, q, J=7.0 Hz), 7.91 (2H, s).

C) Methyl 2-ethoxy-4'-fluoro-6-(pentafluoroethyl)biphenyl-4-carboxylate

A mixture of methyl 3-ethoxy-5-(pentafluoroethyl)-4-(((trifluoromethyl)sulfonyl)oxy)benzoate (300 mg), (4-fluorophenyl)boronic acid (113 mg), cesium carbonate (329 mg), (1,1'-bis(diphenylphosphino)ferrocene)dichloropalladium(II) dichloromethane adduct (27.0 mg), THF (5 mL) and water (1 mL) was stirred for 30 minutes at 130° C. under microwave irradiation. The reaction mixture was cooled to room temperature, an aqueous saturated ammonium chloride solution was added thereto, and then extraction thereof was performed using ethyl acetate. The organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (264 mg).

$^1$H NMR (300 MHz, $CDCl_3$) δ 1.18 (3H, t, J=7.0 Hz), 3.97 (3H, s), 4.01 (2H, q, J=7.0 Hz), 7.02-7.15 (4H, m), 7.75 (1H, s), 7.93 (1H, s).

D) 2-Ethoxy-4'-fluoro-6-(pentafluoroethyl)biphenyl-4-carbaldehyde

Lithium aluminum hydride (25 mg) was added to a mixture of methyl 2-ethoxy-4'-fluoro-6-(pentafluoroethyl)biphenyl-4-carboxylate (264 mg) and THF (15 mL) under ice-cooling in a nitrogen atmosphere. After stirring for 30 minutes at the same temperature, water (1 mL) and 1 M aqueous sodium hydroxide solution (1 mL) were added thereto, the resultant was stirred for 30 minutes, and then water (3 mL) was further added thereto. After the reaction mixture was stirred for 1 hour, it was filtered, and the solvent of the filtrate was distilled off under reduced pressure. Triethylamine (0.28 mL) and sulfur trioxide-pyridine complex (214 mg) were added to a solution of the obtained residue in DMSO (5 mL), and the resultant was stirred for 1 hour at room temperature in a nitrogen atmosphere. After an aqueous saturated ammonium chloride solution was added to the reaction mixture, extraction thereof was performed using ethyl acetate. The organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (244 mg).

$^1$H NMR (400 MHz, $CDCl_3$) δ 1.19 (3H, t, J=6.9 Hz), 4.03 (2H, q, J=7.0 Hz), 7.02-7.16 (4H, m), 7.60 (1H, s), 7.73 (1H, s), 10.04 (1H, s).

E) 1-(2-((2-Ethoxy-4'-fluoro-6-(pentafluoroethyl)biphenyl-4-yl)methyl)-5-oxa-2,6-diazaspiro[3.4]oct-6-en-7-yl)-4-methylpiperidine-4-carboxylic acid tert-Butyl 7-(4-(ethoxycarbonyl)-4-methylpiperidin-1-yl)-5-oxa-2,6-diazaspiro[3.4]oct-6-ene-2-carboxylate (385 mg) was added to formic acid (5 mL), the resultant was stirred for 30 minutes at 60° C., and then the solvent was distilled off under reduced pressure. The obtained residue was dissolved in 2-ethoxy-4'-fluoro-6-(pentafluoroethyl)biphenyl-4-carbaldehyde (244 mg) and THF (10 mL), sodium triacetoxyborohydride (214 mg) was added to the solution, and the resultant was stirred overnight at room temperature in a nitrogen atmosphere. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off off under reduced pressure. The obtained residue was purified by a silica gel column chromatography (NH, hexane/ethyl acetate), and it was once more purified by a silica gel column chromatography (hexane/ethyl acetate), thereby obtaining a purified product 8 M aqueous sodium hydroxide solution (0.07 mL) was added to a solution of the obtained purified product in ethanol (10 mL), and the resultant was stirred for 2 hours at 60° C. After the reaction mixture was neutralized with 6 M hydrochloric acid, the resultant was concentrated to half amount thereof under reduced pressure, and the precipitated solid was collected by filtration. Fractionation was performed on the obtained solid using HPLC (C18, mobile phase: water/acetonitrile (0.1% TFA-containing system)), and the obtained fraction was concentrated. An aqueous saturated sodium hydrogen carbonate solution was added to the obtained residue, and extraction thereof was performed using ethyl acetate. The obtained organic layer was washed with a saturated saline solution, dried over anhydrous magnesium sulfate, and then the solvent was distilled off under reduced pressure, thereby obtaining the title compound (62.0 mg).

$^1$H NMR (300 MHz, DMSO-$d_6$) δ 1.06 (3H, t, J=6.8 Hz), 1.14 (3H, s), 1.37 (2H, t, J=9.7 Hz), 1.91 (2H, d, J=13.2 Hz), 2.89 (2H, t, J=10.4 Hz), 3.20 (2H, brs), 3.25-3.33 (4H, m), 3.47 (2H, brs), 3.71 (2H, brs), 3.98 (2H, q, J=6.8 Hz), 7.08-7.33 (6H, m), 12.42 (1H, brs).

Example 168

1-(2-((2-Cyclopropyl-6-((2,2-difluoropropoxy)-4'-fluorobiphenyl-4-yl)methyl)-5-oxa-2,6-diazaspiro[3.4]oct-6-en-7-yl)-4-methylpiperidine-4-carboxylic acid

A) Ethyl 3-cyclopropyl-4-iodo-5-(2-oxopropoxy)benzoate

1-Bromoacetone (499 mg) was added to a mixture of ethyl 3-cyclopropyl-5-hydroxy-4-iodobenzoate (606 mg), potassium carbonate (504 mg) and DMF (10 mL), and the resultant was stirred for 2 hours at 60° C. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (651 mg).

$^1$H NMR (400 MHz, $CDCl_3$) δ 0.71-0.76 (2H, m), 1.05-1.13 (2H, m), 1.39 (3H, t, J=7.2 Hz), 2.10-2.19 (1H, m), 2.46 (3H, s), 4.37 (2H, q, J=7.1 Hz), 4.60 (2H, s), 7.15 (1H, d, J=1.3 Hz), 7.28 (1H, d, J=1.1 Hz).

B) Ethyl 3-cyclopropyl-5-((2,2-difluoropropoxy)-4-iodobenzoate

Bis(2-methoxyethyl)aminosulfur trifluoride (647 mg) was added to a solution of ethyl 3-cyclopropyl-4-iodo-5-(2-oxopropoxy)benzoate (325 mg) in toluene (10 mL), and the resultant was stirred for 3 hours at 80° C. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (311 mg).

$^1$H NMR (400 MHz, $CDCl_3$) δ 0.69-0.76 (2H, m), 1.04-1.11 (2H, m), 1.40 (3H, t, J=7.2 Hz), 1.91 (3H, t, J=18.9 Hz), 2.08-2.18 (1H, m), 4.21 (2H, t, J=11.0 Hz), 4.38 (2H, q, J=7.1 Hz), 7.24 (1H, d, J=1.4 Hz), 7.28 (1H, d, J=1.4 Hz).

C) Ethyl 2-cyclopropyl-6-((2,2-difluoropropoxy)-4'-fluorobiphenyl-4-carboxylate (1,1'-Bis(diphenylphosphino)ferrocene)dichloropalladium(II) (193 mg) was added to a mixture of ethyl 3-cyclopropyl-5-((2,2-difluoropropoxy)-4-iodobenzoate (541 mg), (4-fluorophenyl)boronic acid (277 mg), cesium fluoride (601 mg) and DME (10 mL), and the resultant was stirred for 15 hours at 100° C. in an argon atmosphere. Water was added to the reaction mixture, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (475 mg).

$^1$H NMR (300 MHz, $CDCl_3$) δ 0.68-0.76 (2H, m), 0.78-0.85 (2H, m), 1.37-1.48 (6H, m), 1.58-1.70 (1H, m), 4.05 (2H, t, J=11.2 Hz), 4.40 (2H, q, J=7.1 Hz), 7.08-7.16 (2H, m), 7.23-7.31 (3H, m), 7.38 (1H, d, J=1.4 Hz).

D) (2-Cyclopropyl-6-((2,2-difluoropropoxy)-4'-fluorobiphenyl-4-yl)methanol

A solution of ethyl 2-cyclopropyl-6-((2,2-difluoropropoxy)-4'-fluorobiphenyl-4-carboxylate (468 mg) in THF (3 mL) was added to a suspension of lithium aluminum hydride (98.0 mg) in THF (7 mL) at 0° C., and the resultant was stirred for 30 minutes at room temperature. Water (0.2 mL), 1 M aqueous sodium hydroxide solution (0.2 mL) and water (0.6 mL) were sequentially added to the reaction mixture at 0° C., the resultant was filtered using celite, and then the filtrate was concentrated under reduced pressure. The obtained residue was purified by a silica gel column chromatography (hexane/ethyl acetate), thereby obtaining the title compound (401 mg).

$^1$H NMR (300 MHz, $CDCl_3$) δ 0.62-0.70 (2H, m), 0.75-0.83 (2H, m), 1.38 (3H, t, J=18.9 Hz), 1.58-1.72 (2H, m), 3.99 (2H, t, J=11.2 Hz), 4.68 (2H, d, J=5.7 Hz), 6.58 (1H, s), 6.78 (1H, s), 7.06-7.14 (2H, m), 7.22-7.30 (2H, m).

E) 2-Cyclopropyl-6-((2,2-difluoropropoxy)-4'-fluorobiphenyl-4-carbaldehyde

Sulfur trioxide-pyridine complex (366 mg) was added to a mixture of (2-cyclopropyl-6-((2,2-difluoropropoxy)-4'-fluorobiphenyl-4-yl)methanol (387 mg), triethylamine (349 mg) and DMSO (10 mL), and the resultant was stirred for 1 hour at room temperature. Sulfur trioxide-pyridine complex (366 mg) and triethylamine (349 mg) were added to the reaction mixture, the resultant was stirred for 2 hours at 60° C. Sulfur trioxide-pyridine complex (366 mg) and triethylamine (349 mg) were further added thereto, and the resultant was stirred for 1 hour at 60° C. Sulfur trioxide-pyridine complex (366 mg) and triethylamine (349 mg) were added to the reaction mixture, the resultant was stirred for 1 hour at 60° C., water was added thereto, and then extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (240 mg).

$^1$H NMR (300 MHz, $CDCl_3$) δ 0.70-0.77 (2H, m), 0.83-0.92 (2H, m), 1.41 (3H, t, J=18.8 Hz), 1.62-1.74 (1H, m), 4.07 (2H, t, J=11.1 Hz), 7.09-7.18 (3H, m), 7.22-7.31 (3H, m), 9.95 (1H, s).

F) Ethyl 1-(2-((2-cyclopropyl-6-((2,2-difluoro-propoxy)-4'-fluorobiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (241 mg) and formic acid (6 mL) was stirred for 1 hour at 60° C., the solvent was distilled off under reduced pressure. The obtained residue was mixed with 2-cyclopropyl-6-((2,2-difluorocyclopropoxy)-4'-fluorobiphenyl-4-carbaldehyde (232 mg) and THF (10 mL), sodium triacetoxyborohydride (268 mg) was added the mixture, and the resultant was stirred for 5 hours at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (281 mg).

$^1$H NMR (300 MHz, $CDCl_3$) δ 0.59-0.67 (2H, m), 0.72-0.81 (2H, m), 1.21 (3H, s), 1.26 (3H, t, J=7.1 Hz), 1.30-1.52 (5H, m), 1.55-1.66 (1H, m), 2.11 (2H, d, J=13.4 Hz), 2.91-3.03 (2H, m), 3.27 (2H, s), 3.31-3.44 (4H, m), 3.53 (2H, d, J=9.0 Hz), 3.63 (2H, s), 3.97 (2H, t, J=11.3 Hz), 4.16 (2H, q, J=7.1 Hz), 6.47 (1H, s), 6.68 (1H, s), 7.05-7.13 (2H, m), 7.22-7.29 (2H, m).

G) 1-(2-((2-Cyclopropyl-6-((2,2-difluoropropoxy)-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (1.5 mL) was added to a solution of ethyl 1-(2-((2-cyclopropyl-6-((2,2-difluoropropoxy)-4'-fluorobiphenyl-4-yl)methyl)-5-oxa-2,6-diazaspiro[3.4]oct-6-en-7-yl)-4-methylpiperidine-4-carboxylate (272 mg) in ethanol (8 mL), the resultant was stirred for 4 hours at 60° C., and then the solvent was distilled off under reduced pressure. Water was added to the residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The obtained residue was crystallized (hexane/ethyl acetate), thereby obtaining the title compound (192 mg).

$^1$H NMR (300 MHz, DMSO-$d_6$) δ 0.56-0.65 (2H, m), 0.69-0.79 (2H, m), 1.14 (3H, s), 1.30-1.57 (6H, m), 1.91 (2H, d, J=13.2 Hz), 2.82-2.94 (2H, m), 3.14 (2H, d, J=8.2 Hz), 3.25-3.35 (4H, m), 3.44 (2H, d, J=8.0 Hz), 3.55 (2H, s), 4.13 (2H, t, J=12.1 Hz), 6.50 (1H, s), 6.83 (1H, s), 7.19-7.30 (4H, m).

Example 169

1-(2-((2-Cyclopropyl-2',4'-difluoro-6-propoxybiphenyl-4-yl)methyl)-5-oxa-2,6-diazaspiro[3.4]oct-6-en-7-yl)-4-methylpiperidine-4-carboxylic acid

A) 3-Cyclopropyl-4-iodo-5-propoxybenzaldehyde

3-Cyclopropyl-5-hydroxy-4-iodobenzaldehyde (330 mg), 1-iodopropane (389 mg) and potassium carbonate (317 mg) were added to DMF (3.0 mL), and the resultant was stirred for 30 minutes at 80° C. The reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (300 mg).

$^1$H NMR (300 MHz, DMSO-$d_6$) δ 0.69-0.76 (2H, m), 1.02-1.10 (5H, m), 1.73-1.85 (2H, m), 2.09-2.19 (1H, m), 4.08 (2H, t, J=6.2 Hz), 7.11 (1H, d, J=1.5 Hz), 7.20 (1H, d, J=1.5 Hz), 9.94 (1H, s).

B) 2-Cyclopropyl-2',4'-difluoro-6-propoxybiphenyl-4-carbaldehyde

3-Cyclopropyl-4-iodo-5-propoxybenzaldehyde (290 mg), (2,4-difluorophenyl)boronic acid (277 mg), dicyclohexyl(2',6'-dimethoxybiphenyl-2-yl)phosphine (54.1 mg), tris(dibenzylideneacetone)dipalladium(0) (56.3 mg) and 2 M aqueous sodium carbonate solution (1.3 mL) were added to toluene (5.0 mL) in an argon atmosphere, and the resultant was stirred overnight at 100° C. The reaction mixture was cooled to room temperature, it was poured into water, and extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (250 mg).

MS (ESI+): $[M+H]^+$ 317.1.

C) Ethyl 1-(2-((2-cyclopropyl-2',4'-difluoro-6-propoxybiphenyl-4-yl)methyl)-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-5-oxa-2,6-diazaspiro[3.4]oct-6-ene-2-carboxylate (301 mg) was added to formic acid (3 mL), the resultant was stirred for 1 hour at 70° C., and then the solvent was distilled off under reduced pressure. Sodium triacetoxyborohydride (251 mg) was added to a solution of the obtained residue and 2-cyclopropyl-2',4'-difluoro-6-propoxybiphenyl-4-carbaldehyde (250 mg) in THF (10 mL), and the resultant was stirred for 5 hours at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (350 mg).

$^1$H NMR (300 MHz, $CDCl_3$) δ 0.54-0.76 (4H, m), 0.81 (3H, t, J=7.4 Hz), 1.21 (3H, s), 1.26 (3H, t, J=7.1 Hz), 1.39-1.63 (5H, m), 2.11 (2H, d, J=13.7 Hz), 2.90-3.03 (2H, m), 3.26 (2H, s), 3.31-3.44 (4H, m), 3.54 (2H, d, J=9.0 Hz), 3.62 (2H, s), 3.84 (2H, t, J=6.3 Hz), 4.12-4.21 (2H, m), 6.45 (1H, s), 6.69 (1H, s), 6.82-6.96 (2H, m), 7.16-7.24 (1H, m).

D) 1-(2-((2-Cyclopropyl-2',4'-difluoro-6-propoxybiphenyl-4-yl)methyl)-5-oxa-2,6-diazaspiro[3.4]oct-6-en-7-yl)-4-methylpiperidine-4-carboxylic acid 2 M aqueous sodium hydroxide solution (2.1 mL) was added to a solution of ethyl 1-(2-((2-cyclopropyl-2',4'-difluoro-6-propoxybiphenyl-4-yl)methyl)-5-oxa-2,6-diazaspiro[3.4]oct-6-en-7-yl)-4-methylpiperidine-4-carboxylate (327 mg) in ethanol (3.0 mL), and the resultant was stirred for 2 hours at 60° C. After the reaction mixture was neutralized with 2 M hydrochloric acid, it was stirred for 30 minutes, and the precipitated solid was collected by filtration. Recrystallization (ethanol/water) of the obtained solid was performed, thereby obtaining the title compound (192 mg).

$^1$H NMR (300 MHz, $CDCl_3$) δ 0.51-0.69 (2H, m), 0.74 (2H, dd, J=8.5, 3.2 Hz), 0.81 (3H, t, J=7.4 Hz), 1.26 (3H, s), 1.38-1.63 (5H, m), 2.12-2.21 (2H, m), 2.99 (2H, t, J=10.9 Hz), 3.27 (2H, s), 3.42 (2H, d, J=12.7 Hz), 3.54 (2H, d, J=9.9 Hz), 3.74 (2H, d, J=10.0 Hz), 3.79-3.87 (4H, m), 6.47 (1H, s), 6.73 (1H, s), 6.82-6.96 (2H, m), 7.15-7.25 (1H, m).

Example 170

1-(2-((2-Cyclopropyl-6-(2-((2,2-difluorocyclopropyl)ethoxy)-4'-fluorobiphenyl-4-yl)methyl)-5-oxa-2,6-diazaspiro[3.4]oct-6-en-7-yl)-4-methylpiperidine-4-carboxylic acid A) 2-Cyclopropyl-6-(2-((2,2-difluorocyclopropyl)ethoxy)-4'-fluorobiphenyl-4-carbaldehyde Using 2-cyclopropyl-4'-fluoro-6-hydroxybiphenyl-4-carbaldehyde and 2-(2,2-difluorocyclopropyl)ethyl methanesulfonate, the title compound was obtained in the similar manner as in Step F of Example 166.

MS (ESI+): $[M+H]^+$ 361.2.

B) Ethyl 1-(2-((2-cyclopropyl-6-(2-((2,2-difluorocyclopropyl)ethoxy)-4'-fluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-6-(2-((2,2-difluorocyclopropyl)ethoxy)-4'-fluorobiphenyl-4-carbaldehyde, the title compound was obtained in the similar manner as in Step G of Example 166.

MS (ESI+): $[M+H]^+$ 626.5.

C) 1-(2-((2-Cyclopropyl-6-(2-((2,2-difluorocyclopropyl)ethoxy)-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-6-(2-((2,2-difluorocyclopropyl)ethoxy)-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Step H of Example 166.

Example 171

An optically active isomer of 1-(2-((2-(2,2-difluorocyclopropyl)-6-ethoxy-4'-fluorobiphenyl-4-yl)methyl)-5-oxa-2,6-diazaspiro[3.4]oct-6-en-7-yl)-4-methylpiperidine-4-carboxylic acid Fractionation was performed on a racemate (350 mg) of 1-(2-((2-(2,2-difluorocyclopropyl)-6-ethoxy-4'-fluorobiphenyl-4-yl)methyl)-5-oxa-2,6-diazaspiro[3.4]oct-6-en-7-yl)-4-methylpiperidine-4-carboxylic acid using SFC (column: CHIRALPAK ADH (LA145) 46 mmID×250 mmL, manufactured by Daicel Chemical Industries, Ltd., mobile phase: carbon dioxide/methanol/diethylamine=700/700/150), thereby obtaining a compound with a short retention time as a title compound (126 mg). Retention time (ADH) was 3.61 minutes.

Example 172

An optically active isomer of 1-(2-((2-(2,2-difluorocyclopropyl)-6-ethoxy-4'-fluorobiphenyl-4-yl)methyl)-5-oxa-2,6-diazaspiro[3.4]oct-6-en-7-yl)-4-methylpiperidine-4-carboxylic acid Fractionation was performed on a racemate (350 mg) of 1-(2-((2-(2,2-difluorocyclopropyl)-6-ethoxy-4'-fluorobiphenyl-4-yl)methyl)-5-oxa-2,6-diaza spiro[3.4]oct-6-en-7-yl)-4-methylpiperidine-4-carboxylic acid using SFC (column: CHIRALPAK ADH (LA145) 46 mmID×250 mmL, manufactured by Daicel Chemical Industries, Ltd., mobile phase: carbon dioxide/methanol/diethylamine=700/700/150), thereby obtaining a compound with a long retention time as a title compound (136 mg). Retention time (ADH) was 4.96 minutes.

Example 173

1-(2-((2-Cyclopropyl-4'-fluoro-6-(3-(methylsulfonyl)propoxy)biphenyl-4-yl)methyl)-5-oxa-2,6-diazaspiro[3.4]oct-6-en-7-yl)-4-methylpiperidine-4-carboxylic acid A) 2-Cyclopropyl-4'-fluoro-6-(3-(methylsulfonyl)propoxy)biphenyl-4-carbaldehyde Using 2-cyclopropyl-4'-fluoro-6-hydroxybiphenyl-4-carbaldehyde and 3-(methylsulfonyl)propyl 4-methylbenzenesulfonate, the title compound was obtained in the similar manner as in Step F of Example 166.

MS (ESI+): $[M+H]^+$ 377.1.

B) Ethyl 1-(2-((2-cyclopropyl-4'-fluoro-6-(3-(methylsulfonyl)propoxy)biphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-6-(3-methylsulfonyl)propoxy)biphenyl-4-carbaldehyde, the title compound was obtained in the similar manner as in Step G of Example 166.

MS (ESI+): $[M+H]^+$ 642.5.

C) 1-(2-((2-Cyclopropyl-4'-fluoro-6-(3-(methylsulfonyl)propoxy)biphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-6-(3-(methylsulfonyl)propoxy)biphenyl-4-yl)methyl)-5-oxa-2,6-diazaspiro[3.4]oct-6-en-7-yl)-4-methylpiperidine-4-carboxylate, the title compound was obtained in the similar manner as in Step H of Example 166.

Example 174

1-(2-((2-Cyclopropyl-6-ethoxy-4'-fluorobiphenyl-4-yl)methyl)-5-oxa-2,6-diazaspiro[3.4]oct-6-en-7-yl)-4-ethylpiperidine-4-carboxylic acid A) Ethyl 1-(2-((2-cyclopropyl-6-ethoxy-4'-fluorobiphenyl-4-yl)methyl)-5-oxa-2,6-diazaspiro[3.4]oct-6-en-7-yl)-4-ethylpiperidine-4-carboxylate tert-Butyl 7-(4-(ethoxycarbonyl)-4-ethylpiperidin-1-yl)-5-oxa-2,6-diazaspiro[3.4]oct-6-ene-2-carboxylate (417 mg) was added to formic acid (3 mL), the resultant was stirred for 1 hour at 70° C., and then the solvent was distilled off under reduced pressure. Sodium triacetoxyborohydride (335 mg) was added to a solution of the obtained residue and cyclopropyl-6-ethoxy-4'-fluorobiphenyl-4-carbaldehyde (300 mg) in THF (10 mL), and the resultant was stirred for 5 hours at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (200 mg).

MS (ESI+): $[M+H]^+$ 564.2.

B) 1-(2-((2-Cyclopropyl-6-ethoxy-4'-fluorobiphenyl-4-yl)methyl)-5-oxa-2,6-diazaspiro[3.4]oct-6-en-7-yl)-4-ethylpiperidine-4-carboxylic acid 2 M aqueous sodium hydroxide solution (1.4 mL) was added to a solution of ethyl 1-(2-((2-cyclopropyl-6-ethoxy-4'-fluorobiphenyl-4-yl)methyl)-5-oxa-2,6-diazaspiro[3.4]oct-6-en-7-yl)-4-ethylpiperidine-4-carboxylate (200 mg) in methanol (3 mL), and the resultant was stirred for 2 days at 60° C. After the reaction mixture was neutralized with 2 M hydrochloric acid, it was stirred for 30 minutes, and the precipitated solid was collected by filtration. Recrystallization (methanol) of the obtained solid was performed, thereby obtaining the title compound (65.0 mg).

$^1$H NMR (300 MHz, DMSO-$d_6$) δ 0.54-0.61 (2H, m), 0.67-0.82 (5H, m), 1.11 (3H, t, J=6.9 Hz), −1.35 (2H, d, J=9.8 Hz), 1.43-1.55 (3H, m), 1.93 (2H, d, J=13.1 Hz), 2.81 (2H, t, J=11.0 Hz), 3.14 (2H, brs), 3.26-3.39 (4H, m), 3.40-3.59 (4H, m), 3.92 (2H, q, J=6.8 Hz), 6.42 (1H, s), 6.77 (1H, s), 7.15-7.29 (4H, m).

Example 175

1-(2-((2-Cyclopropyl-6-(2-ethoxyethoxy)-4'-fluorobiphenyl-4-yl)methyl)-5-oxa-2,6-diazaspiro[3.4]oct-6-en-7-yl)-4-methylpiperidine-4-carboxylic acid A) 2-Cyclopropyl-6-(2-ethoxyethoxy)-4'-fluorobiphenyl-4-carbaldehyde Using 2-cyclopropyl-4'-fluoro-6-hydroxybiphenyl-4-carbaldehyde and 1-bromo-2-ethoxyethane, the title compound was obtained in the similar manner as in Step F of Example 166.

MS (ESI+): $[M+H]^+$ 329.2.

B) Ethyl 1-(2-((2-cyclopropyl-6-(2-ethoxyethoxy)-4'-fluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-6-(2-ethoxyethoxy)-4'-fluorobiphenyl-4-carbaldehyde, the title compound was obtained in the similar manner as in Step G of Example 166.

MS (ESI+): $[M+H]^+$ 594.5.

C) 1-(2-((2-Cyclopropyl-6-(2-ethoxyethoxy)-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-6-(2-ethoxyethoxy)-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Step H of Example 166.

Example 176

1-(2-(3,5-Diethoxy-4-(1-methoxycyclobutyl)benzyl)-5-oxa-2,6-diazaspiro[3.4]oct-6-en-7-yl)-4-methylpiperidine-4-carboxylic acid A) tert-Butyl ((3,5-diethoxy-4-iodobenzyl)oxy)dimethylsilane tert-Butyldimethylchlorosilane (2.06 g) was added to a mixture of (3,5-diethoxy-4-iodophenyl)methanol (3.67 g), imidazole (1.16 g) and DMF (10 mL), and the resultant was stirred for 1 hour at room temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (4.56 g).

$^1$H NMR (300 MHz, $CDCl_3$) δ 0.11 (6H, s), 0.95 (9H, s), 1.48 (6H, t, J=7.0 Hz), 4.10 (4H, q, J=6.9 Hz), 4.70 (2H, s), 6.47 (2H, s).

B) 1-(4-(((tert-Butyl(dimethyl)silyl)oxy)methyl)-2,6-diethoxyphenyl)cyclobutanol n-Butyllithium (1.6 M hexane solution, 9.80 mL) was added to a mixture of tert-butyl((3,5-diethoxy-4-iodobenzyl)oxy)dimethylsilane (4.56 g) and THF (30 mL) at −78° C., and the resultant was stirred for 10 minutes at the same temperature. Cyclobutanone (1.17 mL) was added to the reaction mixture at −78° C., the resultant was warmed to mom temperature, and it was stirred for 50 minutes. After an aqueous saturated sodium hydrogen carbonate solution and 1 M hydrochloric acid were sequentially added to the reaction mixture, extraction thereof was performed using ethyl acetate. The extract was washed with a saturated saline solution, dried over magnesium sulfate, and then concentrated under reduced pressure. The obtained residue was purified by a silica gel column chromatography (hexane/ethyl acetate), thereby obtaining the title compound (1.94 g).

$^1$H NMR (300 MHz, $CDCl_3$) δ 0.10 (6H, s), 0.95 (9H, s), 1.41 (6H, t, J=7.0 Hz), 1.68-1.85 (1H, m), 2.15-2.39 (1H, m), 2.39-2.50 (2H, m), 2.61 (1H, s), 2.65-2.83 (2H, m), 4.02 (4H, q, J=7.0 Hz), 4.68 (2H, s), 6.49 (2H, s).

C) tert-Butyl ((3,5-diethoxy-4-(1-methoxycyclobutyl)benzyl)oxy)dimethylsilane

Sodium hydride (60% dispersion in oil, 0245 g) was added to a mixture of 1-(4-(((tert-butyl(dimethyl)silyl)oxy)methyl)-2,6-diethoxyphenyl)cyclobutanol (1.94 g) and DMF (25 mL), and the resultant was stirred for 30 minutes at 0° C. Iodomethane (0.478 mL) was added to the reaction mixture, and the resultant was stirred for 2 hours at room temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.63 g).

$^1$H NMR (300 MHz, $CDCl_3$) δ 0.11 (6H, s), 0.96 (9H, s), 1.40 (6H, t, J=7.0 Hz), 1.68-1.86 (1H, m), 2.08-2.29 (1H, m), 2.34-2.67 (4H, m), 3.15 (3H, s), 4.01 (4H, q, J=7.0 Hz), 4.69 (2H, s), 6.49 (2H, s).

D) (3,5-Diethoxy-4-(1-methoxycyclobutyl)phenyl)methanol

Tetrabutylammonium fluoride (1.0 M THF solution, 6.20 mL) was added to a mixture of tert-butyl((3,5-diethoxy-4-(1-methoxycyclobutyl)benzyl)oxy)dimethylsilane (1.63 g) and THF (25 mL) at room temperature, and the resultant was stirred for 30 minutes. An aqueous ammonium chloride solution was added to the reaction mixture, and extraction thereof was performed using ethyl acetate. After being dried over anhydrous magnesium sulfate, the solvent was distilled off under reduced pressure. The obtained residue was purified by a silica gel column chromatography (hexane/ethyl acetate), thereby obtaining the title compound (1.05 g).

$^1$H NMR (300 MHz, $CDCl_3$) δ 1.40 (6H, t, J=7.0 Hz), 1.67-1.85 (2H, m), 2.06-2.29 (1H, m), 2.39-2.69 (4H, m), 3.14 (3H, s), 4.02 (4H, q, J=7.0 Hz), 4.63 (2H, d, J=5.5 Hz), 6.52 (2H, s).

E) 3,5-Diethoxy-4-(1-methoxycyclobutyl)benzaldehyde

Using (3,5-diethoxy-4-(1-methoxycyclobutyl)phenyl)methanol, the title compound was obtained in the similar manner as in Step F of Example 16.

$^1$H NMR (300 MHz, $CDCl_3$) δ 1.44 (6H, t, J=7.0 Hz), 1.68-1.87 (1H, m), 2.08-2.28 (1H, m), 2.43-2.67 (4H, m), 3.15 (3H, s), 4.09 (4H, q, J=7.0 Hz), 7.01 (2H, s), 9.89 (1H, s).

F) Ethyl 1-(2-(3,5-diethoxy-4-(1-methoxycyclobutyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 3,5-diethoxy-4-(1-methoxycyclobutyl)benzaldehyde, the title compound was obtained in the similar manner as in Step G of Example 1.

MS (ESI+): $[M+H]^+$ 544.5.

G) 1-(2-(3,5-Diethoxy-4-(1-methoxycyclobutyl)benzyl)-5-oxa-2,6-diazaspiro[3.4]oct-6-en-7-yl)-4-methylpiperidine-4-carboxylic acid Using ethyl 1-(2-(3,5-diethoxy-4-(1-methoxycyclobutyl)benzyl)-5-oxa-2,6-diazaspiro[3.4]oct-6-en-7-yl)-4-methylpiperidine-4-carboxylate, the title compound was obtained in the similar manner as in Example 2.

Example 177

1-(2-((2-Cyclopropyl-4'-fluoro-5-propoxybiphenyl-4-yl)methyl)-5-oxa-2,6-diazaspiro[3.4]oct-6-en-7-yl)-4-methylpiperidine-4-carboxylic acid A) 2-Cyclopropyl-4'-fluoro-5-propoxybiphenyl-4-carbaldehyde Using 2-cyclopropyl-4'-fluoro-5-hydroxybiphenyl-4-carbaldehyde and 1-iodopropane, the title compound was obtained in the similar manner as in Step H of Example 113.

$^1$H NMR (300 MHz, DMSO-$d_6$) δ 0.52-0.62 (2H, m), 0.73-0.85 (2H, m), 1.00 (3H, t, J=7.4 Hz), 1.68-1.85 (3H, m), 4.11 (2H, t, J=6.4 Hz), 7.02 (1H, s), 7.27-7.38 (3H, m), 7.50-7.59 (2H, m), 10.37 (1H, s).

B) Ethyl 1-(2-((2-cyclopropyl-4'-fluoro-5-propoxybiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-5-propoxybiphenyl-4-carbaldehyde, the title compound was obtained in the similar manner as in Step G of Example 1.

MS (ESI+): $[M+H]^+$ 564.3.

C) 1-(2-((2-Cyclopropyl-4'-fluoro-5-propoxybiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-5-propoxybiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 178

1-(2-((2,6-Diethoxy-3',4'-difluorobiphenyl-4-yl)methyl)-5-oxa-2,6-diazaspiro[3.4]oct-6-en-7-yl)-4-ethylpiperidine-4-carboxylic acid A) Ethyl 1-(2-((2,6-diethoxy-3',4'-difluorobiphenyl-4-yl)methyl)-5-oxa-2,6-diazaspiro[3.4]oct-6-en-7-yl)-4-piperidine-4-carboxylate After a mixture of tert-butyl 7-(4-(ethoxycarbonyl)-4-ethylpiperidin-1-yl)-5-oxa-2,6-diazaspiro[3.4]oct-6-ene-2-carboxylate (352 mg) and formic acid (6 mL) was stirred for 1 hour at 60° C., the solvent was distilled off under reduced pressure. The obtained residue was mixed with 2,6-diethoxy-3',4'-difluorobiphenyl-4-carbaldehyde (327 mg) and THF (10 mL), sodium triacetoxyborohydride (377 mg) was added to the mixture, and the resultant was stirred for 5 hours at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (445 mg).

$^1$H NMR (300 MHz, $CDCl_3$) δ 0.82 (3H, t, J=7.6 Hz), 1.22-1.30 (9H, m), 1.36-1.48 (2H, m), 1.56 (2H, q, J=7.6 Hz), 2.14 (2H, d, J=13.0 Hz), 2.85-2.97 (2H, m), 3.26 (2H, s), 3.33-3.38 (2H, m), 3.39-3.49 (2H, m), 3.52-3.58 (2H, m), 3.64 (2H, s), 3.97 (4H, q, J=7.0 Hz), 4.18 (2H, q, J=7.1 Hz), 6.53 (2H, s), 7.04-7.24 (3H, m).

B) 1-(2-((2,6-Diethoxy-3',4'-difluorobiphenyl-4-yl)methyl)-5-oxa-2,6-diazaspiro[3.4]oct-6-en-7-yl)-4-ethylpiperidine-4-carboxylic acid 2 M aqueous sodium hydroxide solution (2.5 mL) was added to a solution of ethyl 1-(2-((2,6-diethoxy-3',4'-difluorobiphenyl-4-yl)methyl)-5-oxa-2,6-diazaspiro[3.4]oct-6-en-7-yl)-4-ethylpiperidine-4-carboxylate (428 mg) in methanol (8 mL), the resultant was stirred for 15 hours at 70° C. 2 M aqueous sodium hydroxide solution (2 mL) was added thereto, and the resultant was stirred for 8 hours at 80° C. 2 M aqueous sodium hydroxide solution (1 mL) was added to the reaction mixture, the resultant was stirred for 15 hours at 80° C., and then the solvent was distilled off under reduced pressure. Water was added to the obtained residue, the resultant was neutralized with 2 M hydrochloric acid, and then the precipitated solid was collected by filtration. After the obtained solid was dissolved in ethyl acetate and THF, it was dried over anhydrous magnesium sulfate, and the solvent was distilled off under reduced pressure. The residue was crystallized (hexane/ethyl acetate), thereby obtaining the title compound (340 mg).

$^1$H NMR (300 MHz, DMSO-$d_6$) δ 0.78 (3H, t, J=7.5 Hz), 1.18 (6H, t, J=6.9 Hz), 1.29-1.41 (2H, m), 1.50 (2H, q, J=7.3 Hz), 1.88-2.00 (2H, m), 2.75-2.90 (2H, m), 3.27-3.50 (8H, m), 3.70 (2H, brs), 3.98 (4H, q, J=6.9 Hz), 6.72 (2H, brs), 7.06-7.14 (1H, m), 723-7.33 (1H, m), 7.33-7.44 (1H, m).

Example 179

1-(2-((2-Cyclopropyl-4'-fluoro-5-(2-methoxyethoxy)biphenyl-4-yl)methyl)-5-oxa-2,6-diazaspiro[3.4]oct-6-en-7-yl)-4-methylpiperidine 4 carboxylic acid A) 2-Cyclopropyl-4'-fluoro-5-(2-methoxyethoxy)biphenyl-4-carbaldehyde Using 2-cyclopropyl-4'-fluoro-5-hydroxybiphenyl-4-carbaldehyde and 1-bromo-2-methoxyethane, the title compound was obtained in the similar manner as in Step H of Example 113.

MS (ESI+): $[M+H]^+$ 315.2.

B) Ethyl 1-(2-((2-cyclopropyl-4'-fluoro-5-(2-methoxyethoxy)biphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-5-(2-methoxyethoxy)biphenyl-4-carbaldehyde, the title compound was obtained in the similar manner as in Step G of Example 1.

MS (ESI+): $[M+H]^+$ 580.3.

C) 1-(2-((2-Cyclopropyl-4'-fluoro-5-(2-methoxyethoxy)biphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-5-(2-methoxyethoxy)biphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 180

1-(2-((2,5-Dicyclopropyl-4'-fluorobiphenyl-4-yl)methyl)-5-oxa-2,6-diazaspiro[3.4]oct-6-en-7-yl)-4-methylpiperidine-4-carboxylic acid A) 6-Cyclopropyl-4'-fluoro-4-formylbiphenyl-3-yl trifluoromethanesulfonate A solution of 2-cyclopropyl-4'-fluoro-5-hydroxybiphenyl-4-carbaldehyde (600 mg) and N,N-diisopropylethylamine (0.82 mL), N-phenyl bis(trifluoromethanesulfonimide) (1.00 g) and 4-dimethylaminopyridine (28.6 mg) in THF (15 mL) was stirred for 5 hours at 70° C. The reaction mixture was cooled to room temperature, 1 M hydrochloric acid was added thereto, and then extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (647 mg).

$^1$H NMR (300 MHz, DMSO-$d_6$) δ 0.80-1.02 (4H, m), 1.83-1.95 (1H, m), 7.31-7.41 (3H, m), 7.52-7.61 (2H, m), 7.74 (1H, s), 10.07 (1H, s).

B) 2,5-Dicyclopropyl-4'-fluorobiphenyl-4-carbaldehyde

Using 6-cyclopropyl-4'-fluoro-4-formylbiphenyl-3-yl trifluoromethanesulfonate and cyclopropylboronic acid, the title compound was obtained in the similar manner as in Step D of Example 23.

$^1$H NMR (300 MHz, DMSO-$d_6$) δ 0.64-0.72 (2H, m), 0.75-0.90 (4H, m), 0.96-1.05 (2H, m), 1.72-1.85 (1H, m), 2.69-2.80 (1H, m), 6.91 (1H, s), 7.25-7.35 (2H, m), 7.41 (1H, s), 7.46-7.54 (2H, m), 10.47 (1H, s).

C) Ethyl 1-(2-((2,5-dicyclopropyl-4'-fluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2,5-dicyclopropyl-4'-fluorobiphenyl-4-carbaldehyde, the title compound was obtained in the similar manner as in Step G of Example 1.

MS (ESI+): $[M+H]^+$ 546.2.

D) 1-(2-((2,5-Dicyclopropyl-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((2,5-dicyclopropyl-4'-fluorobiphenyl-4-yl)methyl)-5-oxa-2,6-diazaspiro[3.4]oct-6-en-7-yl)-4-methylpiperidine-4-carboxylate, the title compound was obtained hi the similar manner as in Example 2.

Example 181

1-(2-((2-Cyclopropyl-4'-fluoro-5-isopropoxybiphenyl-4-yl)methyl)-5-oxa-2,6-diazaspiro[3.4]oct-6-en-7-yl)-4-methylpiperidine-4-carboxylic acid A) 2-Cyclopropyl-4'-fluoro-5-isopropoxybiphenyl-4-carbaldehyde Using 2-cyclopropyl-4'-fluoro-5-hydroxybiphenyl-4-carbaldehyde, 2-iodopropane, and cesium carbonate instead of potassium carbonate, the title compound was obtained in the similar manner as in Step H of Example 113.

$^1$H NMR (300 MHz, DMSO-$d_6$) δ 0.53-0.61 (2H, m), 0.75-0.83 (2H, m), 1.32 (6H, d, J=5.9 Hz), 1.73 (1H, tt, J=8.4, 5.3 Hz), 4.77-4.88 (1H, m), 7.04 (1H, s), 7.27-7.37 (3H, m), 7.49-7.58 (2H, m), 10.34 (1H, s).

B) Ethyl 1-(2-((2-cyclopropyl-4'-fluoro-5-isopropoxybiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-5-isopropoxybiphenyl-4-carbaldehyde, the title compound was obtained in the similar manner as in Step G of Example 1.

MS (ESI+): $[M+H]^+$ 564.2.

C) 1-(2-((2-Cyclopropyl-4'-fluoro-5-isopropoxybiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-5-isopropoxybiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 182

1-(2-((2,6-Diethoxy-2',4'-difluorobiphenyl-4-yl)methyl)-5-oxa-2,6-diazaspiro[3.4]oct-6-en-7-yl)-4-ethylpiperidine-4-carboxylic acid A) 2,6-Diethoxy-2',4'-difluorobiphenyl-4-carbaldehyde A mixture of 4-bromo-3,5-diethoxybenzaldehyde (4.0 g), (2,4-difluorophenyl)boronic acid (5.80 g), tripotassium phosphate (12.5 g) and dioxane (50 mL) was degassed for 45 minutes, (1,1'-bis(diphenylphosphino)ferrocene)dichloropalladium(II) (1.20 g) and tetrabutylammonium bromide (945 mg) were added thereto, and the resultant was heated to reflux for 14 hours in an argon atmosphere. After the reaction mixture was cooled to room temperature, ethyl acetate was added thereto, and the resultant was filtered using celite. The obtained filtrate was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.30 g).

$^1$H NMR (400 MHz, DMSO-$d_6$) δ 1.17 (6H, t, J=6.96 Hz), 4.02-4.13 (4H, m), 7.10 (1H, td, J=8.1, 2.4 Hz), 7.22-7.28 (3H, m), 7.33 (1H, q, J=8.3 Hz), 9.98 (1H, s).

B) Ethyl 1-(2-((2,6-diethoxy-2',4'-difluorobiphenyl-4-yl)methyl)-5-oxa-2,6-diazaspiro[3.4]oct-6-en-7-yl)-4-ethylpiperidine-4-carboxylate After a mixture of tert-butyl 7-(4-(ethoxycarbonyl)-4-ethylpiperidin-1-yl)-5-oxa-2,6-diazaspiro[3.4]oct-6-ene-2-carboxylate (351 mg) and formic acid (6 mL) was stirred for 1 hour at 60° C., the solvent was distilled off under reduced pressure. The obtained residue was mixed with 2,6-diethoxy-2',4'-difluorobiphenyl-4-carbaldehyde (327 mg) and THF (10 mL), sodium triacetoxyborohydride (377 mg) was added to the mixture, and the resultant was stirred for 5 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (442 mg).

$^1$H NMR (300 MHz, $CDCl_3$) δ 0.82 (3H, t, J=7.6 Hz), 1.20-1.29 (9H, m), 1.36-1.48 (2H, m), 1.56 (2H, q, J=7.5 Hz), 2.14 (2H, d, J=13.1 Hz), 2.85-2.97 (2H, m), 3.26 (2H, s), 3.32-3.38 (2H, m), 3.39-3.49 (2H, m), 3.53-3.59 (2H, m), 3.65 (2H, s), 3.93-4.03 (4H, m), 4.18 (2H, q, J=7.1 Hz), 6.53 (2H, s), 6.79-6.91 (2H, m), 7.19-7.27 (1H, m).

C) 1-(2-((2,6-Diethoxy-2',4'-difluorobiphenyl-4-yl)methyl)-5-oxa-2,6-diazaspiro[3.4]oct-6-en-7-yl)-4-ethylpiperidine-4-carboxylic acid 2 M aqueous sodium hydroxide solution (2.5 mL) was added to a solution of ethyl 1-(2-((2,6-diethoxy-2',4'-difluorobiphenyl-4-yl)methyl)-5-oxa-2,6-diazaspiro[3.4]oct-6-en-7-yl)-4-ethylpiperidine-4-carboxylate (423 mg) in methanol (8 mL), and the resultant was stirred for 7 hours at 70° C. 2 M aqueous sodium hydroxide solution (2.5 mL) was added thereto, and the resultant was stirred for 15 hours at 70° C. 2 M aqueous sodium hydroxide solution (2.5 mL) was further added thereto, the resultant was stirred for 15 hours at 70° C., and then the solvent was distilled off under reduced pressure. Water was added to the obtained residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The obtained residue was crystallized (hexane/ethanol), thereby obtaining the title compound (338 mg).

$^1$H NMR (300 MHz, DMSO-d$_6$) δ 0.78 (3H, t, J=7.4 Hz), 1.16 (6H, t, J=6.9 Hz), 1.29-1.41 (2H, m), 1.50 (2H, q, J=7.4 Hz), 1.95 (2H, d, J=13.4 Hz), 2.76-2.93 (2H, m), 3.20-3.53 (10H, m), 3.94-4.06 (4H, m), 6.79 (2H, brs), 7.02-7.12 (1H, m), 7.15-7.32 (2H, m).

Example 183

1-(2-((2-Cyclopropyl-6-(((1R)-2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylic acid

A) 3-Cyclopropyl-5-(((1R)-2,2-difluorocyclopropyl)methoxy)-4-iodobenzaldehyde ((1R)-2,2-difluorocyclopropyl)methyl 4-methylbenzenesulfonate (460 mg) was added to a mixture of 3-cyclopropyl-5-hydroxy-4-iodobenzaldehyde (301 mg), potassium carbonate (289 mg) and DMF (10 mL), and the resultant was stirred for 2 hours at 60° C. After water was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (392 mg).

$^1$H NMR (300 MHz, CDCl$_3$) δ 0.69-0.77 (2H, m), 1.07-1.16 (2H, m), 1.34-1.47 (1H, m), 1.58-1.72 (1H, m), 2.10-2.25 (2H, m), 4.10-4.28 (2H, m), 7.05 (1H, d, J=1.5 Hz), 7.09 (1H, d, J=1.6 Hz), 9.91 (1H, s).

B) 2-Cyclopropyl-6-(((1R)-2,2-difluorocyclopropyl)methoxy)-4'-fluorobiphenyl-4-carbaldehyde (1,1% Bis(diphenylphosphino)ferrocene)dichloropalladium(II) (148 mg) was added to a mixture of 3-cyclopropyl-5-(((1R)-2,2-difluorocyclopropyl)methoxy)-4-iodobenzaldehyde (383 mg), (4-fluorophenyl)boronic acid (212 mg), cesium fluoride (461 mg) and DME (10 mL), and the resultant was stirred for 20 hours at 100° C. in an argon atmosphere. Water was added to the reaction mixture, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (170 mg).

$^1$H NMR (300 MHz, CDCl$_3$) δ 0.68-0.76 (2H, m), 0.82-0.89 (2H, m), 1.02-1.16 (1H, m), 1.36-1:50 (1H, m), 1.61-1.72 (1H, m), 1.79-1.96 (1H, m), 4.00-4.06 (2H, m), 7.07 (1H, d, J=1.3 Hz), 7.10-7.18 (2H, m), 7.24-7.31 (3H, m), 9.94 (1H, s).

C) Ethyl 1-(2-((2-cyclopropyl-6-(((1R)-2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (170 mg) and formic acid (6 mL) was stirred for 1 hour at 60° C., the solvent was distilled off under reduced pressure. The obtained residue was mixed with 2-cyclopropyl-6-(((1R)-2,2-difluorocyclopropyl)methoxy)-4'-fluorobiphenyl-4-carbaldehyde (170 mg) and THF (10 mL), sodium triacetoxyborohydride (189 mg) was added to the mixture, and the resultant was stirred for 15 hours at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (205 mg).

$^1$H NMR (300 MHz, CDCl$_3$) δ 0.59-0.66 (2H, m), 0.71-0.80 (2H, m), 0.97-1.10 (1H, m), 1.21 (3H, s), 1.26 (3H, t, J=7.1 Hz), 1.33-1.51 (3H, m), 1.54-1.65 (1H, m), 1.80-1.91 (1H, m), 2.11 (2H, d, J=13.6 Hz), 2.91-3.03 (2H, m), 3.26 (2H, s), 3.30-3.43 (4H, m), 3.50-3.56 (2H, m), 3.62 (2H, s), 3.84-4.01 (2H, m), 4.16 (2H, q, J=7.1 Hz), 6.45 (1H, s), 6.70 (1H, d, J=1.0 Hz), 7.05-7.13 (2H, m), 7.22-7.29 (2H, m).

D) 1-(2-((2-Cyclopropyl-6-(((1R)-2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (1.5 mL) was added to a solution of ethyl 1-(2-((2-cyclopropyl-6-(((1R)-2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylate (205 mg) in ethanol (8 mL), the resultant was stirred for 5 hours at 70° C., and then the solvent was distilled off under reduced pressure. Water was added to the residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The residue was crystallized (hexane/ethanol), thereby obtaining the title compound (110 mg).

$^1$H NMR (400 MHz, DMSO-d$_6$) δ 0.55-0.63 (2H, m), 0.68-0.77 (2H, m), 1.14 (3H, s), 1.21-1.43 (3H, m), 1.45-1.64 (2H, m), 1.85-2.05 (3H, m), 2.82-2.95 (2H, m), 3.18 (2H, brs), 3.25-3.38 (4H, m), 3.45 (2H, brs), 3.57 (2H, brs), 3.84-3.95 (1H, m), 3.98-4.08 (1H, m), 6.48 (1H, s), 6.82 (1H, s), 7.17-7.30 (4H, m).

Example 184

1-(2-((2-Cyclopropyl-4'-fluoro-5-(2,2,2-trifluoroethoxy)biphenyl-4-yl)methyl)-5-oxa-2,6-diazaspiro[3.4]oct-6-en-7-yl)-4-methylpiperidine-4-carboxylic acid

A) 2-Cyclopropyl-4'-fluoro-5-((2,2,2-trifluoroethoxy)biphenyl-4-carbaldehyde Using 2-cyclopropyl-4'-fluoro-5-hydroxybiphenyl-4-carbaldehyde and 2,2,2-trifluoroethyl trifluoromethanesulfonate, the title compound was obtained in the similar manner as in Step H of Example 113.

$^{1}H$ NMR (300 MHz, DMSO-$d_6$) δ 0.57-0.66 (2H, m), 0.79-0.88 (2H, m), 1.73-1.85 (1H, m), 4.98 (2H, q, J=8.9 Hz), 7.21 (1H, s), 7.30-7.40 (3H, m), 7.53-7.62 (2H, m), 10.31 (1H, s).

B) Ethyl 1-(2-((2-cyclopropyl-4'-fluoro-5-((2,2,2-trifluoroethoxy)biphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-5-((2,2,2-trifluoroethoxy)biphenyl-4-carbaldehyde, the title compound was obtained in the similar manner as in Step G of Example 1.

MS (ESI+): $[M+H]^+$ 604.3.

C) 1-(2-((2-Cyclopropyl-4'-fluoro-5-((2,2,2-trifluoroethoxy)biphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-5-((2,2,2-trifluoroethoxy)biphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 185

1-(2-((5-Cyclopropyl-4-(3,3-difluorocyclobutyl)-2-methoxybenzyl)-5-oxa-2,6-diazaspiro[3.4]oct-6-en-7-yl)-4-methylpiperidine-4-carboxylic acid A) Methyl 2-methoxy-4-vinylbenzoate (1,1'-Bis(diphenylphosphino)ferrocene)dichloropalladium(II) dichloromethane adduct (1.50 g) was added to a mixture of methyl 4-bromo-2-methoxybenzoate (4.50 g), potassium vinyltrifluoroborate (4.92 g), triethylamine (5.12 mL) and ethanol (30 mL), and the resultant was stirred overnight at 100° C. in an argon atmosphere. Water was added to the reaction mixture, extraction thereof was performed using ethyl acetate, the organic layer was dried over anhydrous magnesium sulfate, and then the solvent was distilled off under reduced pressure. The obtained residue was purified by a silica gel column chromatography (hexane/ethyl acetate), thereby obtaining the title compound (3.53 g).

$^{1}H$ NMR (300 MHz, $CDCl_3$) δ 3.88 (3H, s), 3.93 (3H, s), 5.38 (1H, d, J=10.9 Hz), 5.84 (1H, d, J=17.6 Hz), 6.71 (1H, dd, J=17.6, 10.9 Hz), 6.98 (1H, s), 7.03 (1H, dd, J=8.0, 1.4 Hz), 7.78 (1H, d, J=8.0 Hz).

B) Methyl 2-methoxy-4-(3-oxocyclobutyl)benzoate

A solution of phosphorus oxychloride (1.76 mL) and trichloroacetyl chloride (6.32 mL) in DME (5 mL) was added to a mixture of methyl 2-methoxy-4-vinylbenzoate (3.63 g), zinc copper couple (9.12 g) and DME (10 mL) at 0° C. over 20 minutes. After the reaction mixture was stirred for 4 hours at room temperature in a nitrogen atmosphere, an aqueous saturated sodium hydrogen carbonate solution was added to the reaction mixture, and the resultant was filtered using celite. The filtrate was extracted using ethyl acetate, the organic layer was dried over anhydrous magnesium sulfate, and then the solvent was distilled off under reduced pressure. Zinc powder (4.94 g) was added to a mixture of the obtained residue and acetic acid (30 mL), and the resultant was stirred for 20 minutes at room temperature. An aqueous saturated sodium hydrogen carbonate solution was added to the reaction mixture, the resultant was filtered using celite, and extraction was performed on the obtained filtrate using ethyl acetate. After the organic layer was dried over anhydrous magnesium sulfate, the solvent was distilled off under reduced pressure. The obtained residue was purified by a silica gel column chromatography (hexane/ethyl acetate), thereby obtaining the title compound (2.40 g).

$^{1}H$ NMR (300 MHz, $CDCl_3$) δ 3.15-3.37 (2H, m), 3.44-3.61 (2H, m), 3.63-3.79 (1H, m), 3.89 (3H, s), 3.93 (3H, s), 6.88 (1H, s), 6.90-6.96 (1H, m), 7.81 (1H, d, J=7.9 Hz).

C) Methyl 4-(3,3-difluorocyclobutyl)-2-methoxybenzoate

Bis(2-methoxyethyl)aminosulfur trifluoride (3.78 mL) was added to a mixture of methyl 2-methoxy-4-(3-oxocyclobutyl)benzoate (2.40 g) and toluene (30 mL) at room temperature under a nitrogen flow, and the resultant was stirred for 2 hours at the same temperature. After an aqueous saturated sodium hydrogen carbonate solution was added to the reaction mixture, extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (1.66 g).

$^{1}H$ NMR (300 MHz, $CDCl_3$) δ 2.54-2.83 (2H, m), 2.94-3.14 (2H, m), 3.32-3.48 (1H, m), 3.88 (3H, s), 3.92 (3H, s), 6.81 (1H, s), 6.86 (1H, dd, J=8.0, 1.1 Hz), 7.79 (1H, d, J=7.9 Hz).

D) Methyl 5-bromo-4-(3,3-difluorocyclobutyl)-2-methoxybenzoate

Bromine (0.531 mL) was added to a mixture of methyl 4-(3,3-difluorocyclobutyl)-2-methoxybenzoate (1.66 g) and acetic acid (15 mL), and the resultant was stirred for 2 hours at room temperature. An aqueous saturated sodium hydrogen carbonate solution and an aqueous saturated sodium thiosulfate solution was added to the reaction mixture, the resultant was extracted using ethyl acetate. After the organic layer was dried over anhydrous magnesium sulfate, the solvent was distilled off under reduced pressure. The obtained residue was purified by a silica gel column chromatography (hexane/ethyl acetate), thereby obtaining the title compound (1.80 g).

$^{1}H$ NMR (300 MHz, $CDCl_3$) δ 2.53-2.79 (2H, m), 3.00-3.21 (2H, m), 3.53-3.74 (1H, m), 3.89 (3H, s), 3.94 (3H, s), 6.87 (1H, s), 7.99 (1H, s).

E) Methyl 5-cyclopropyl-4-(3,3-difluorocyclobutyl)-2-methoxybenzoate

Tris(dibenzylideneacetone)dipalladium(0) (344 mg) was added to a mixture of methyl 5-bromo-4-(3,3-difluorocyclobutyl)-2-methoxybenzoate (1.80 g), cyclopropylboronic acid (1.15 g), dicyclohexyl(2',6'-dimethoxybiphenyl-2-yl)phosphine (331 mg), 2 M aqueous sodium carbonate solution (8.06 mL) and toluene (30 mL), and the resultant was stirred for 2 hours at 100° C. in an argon atmosphere. The reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.47 g).

$^1$H NMR (300 MHz, $CDCl_3$) δ 0.56-0.66 (2H, m), 0.84-0.98 (2H, m), 1.62-1.81 (1H, m), 2.56-2.83 (2H, m), 2.97-3.18 (2H, m), 3.75-3.90 (4H, m), 3.92 (3H, s), 6.82 (1H, s), 7.51 (1H, s).

F) 5-Cyclopropyl-4-(3,3-difluorocyclobutyl)-2-methoxybenzaldehyde

A solution of methyl 5-cyclopropyl-4-(3,3-difluorocyclobutyl)-2-methoxybenzoate (1.47 g) in THF (20 mL) was added to a suspension of lithium aluminum hydride (188 mg) in THF (20 mL) under ice-cooling in a nitrogen atmosphere. After stirring for 30 minutes at the same temperature, 15% aqueous sodium hydroxide solution (0.20 mL) was added thereto, and the resultant was stirred for 30 minutes at 0° C. Water (0.60 mL) was added to the reaction mixture, the resultant was stirred for 30 minutes, filtered, and then the filtrate was concentrated under reduced pressure. Manganese dioxide (4.31 g) was added to a solution of the obtained residue in toluene (10 mL), and the resultant was stirred for 1 hour at 60° C. After the reaction mixture was filtered, the solvent was distilled off under reduced pressure. The obtained residue was purified by a silica gel column chromatography (hexane/ethyl acetate), thereby obtaining the title compound (1.24 g).

$^1$H NMR (300 MHz, $CDCl_3$) δ 0.58-0.69 (2H, m), 0.89-0.97 (2H, m), 1.62-1.79 (1H, m), 2.59-2.84 (2H, m), 2.96-3.19 (2H, m), 3.77-3.92 (1H, m), 3.95 (3H, s), 6.83 (1H, s), 7.52 (1H, s), 10.40 (1H, s).

G) Ethyl 1-(2-((5-cyclopropyl-4-(3,3-difluorocyclobutyl)-2-methoxybenzyl)-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-5-oxa-2,6-diazaspiro[3.4]oct-6-ene-2-carboxylate (824 mg) and formic acid (10 mL) was stirred for 1 hour at 60° C. The solvent of the reaction mixture was distilled off under reduced pressure, toluene was added to the residue, and furthermore the solvent was distilled off under reduced pressure. The obtained residue was mixed with 5-cyclopropyl-4-(3,3-difluorocyclobutyl)-2-methoxybenzaldehyde (500 mg) and THF (5 mL), the mixture was stirred for 15 minutes at room temperature. Sodium triacetoxyborohydride (597 mg) was added thereto at room temperature, and the resultant was stirred for 2 hours at room temperature. Water was added to the reaction mixture, and the resultant was stirred for 10 minutes. After an aqueous saturated sodium hydrogen carbonate solution was added to the reaction mixture, extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (748 mg).

$^1$H NMR (300 MHz, $CDCl_3$) δ 0.47-0.66 (2H, m), 0.80-0.93 (2H, m), 1.20 (3H, s), 1.26 (3H, t, J=7.1 Hz), 1.37-1.53 (2H, m), 1.67-1.79 (1H, m), 2.05-2.18 (2H, m), 2.56-2.80 (2H, m), 2.88-3.10 (4H, m), 3.24 (2H, s), 3.31-3.43 (4H, m), 3.47-3.57 (2H, m), 3.63 (2H, s), 3.72-3.90 (4H, m), 4.10-4.22 (2H, m), 6.70 (1H, s), 6.93 (1H, s).

H) 1-(2-((5-Cyclopropyl-4-(3,3-difluorocyclobutyl)-2-methoxybenzyl)-5-oxa-2,6-diazaspiro[3.4]oct-6-en-7-yl)-4-methylpiperidine-4-carboxylic acid A mixture of ethyl 1-(2-((5-cyclopropyl-4-(3,3-difluorocyclobutyl)-2-methoxybenzyl)-5-oxa-2,6-diazaspiro[3.4]oct-6-en-7-yl)-4-methylpiperidine-4-carboxylate (740 mg), 2 M aqueous sodium hydroxide solution (4.18 mL), methanol (5 mL) and THF (5 mL) was stirred for 2 hours at 60° C. The reaction mixture was cooled to room temperature, and it was neutralized with 6 M hydrochloric acid. Ethyl acetate was added thereto, the solvent was distilled off. After the obtained solid was washed with ether, recrystallization (hexane/ethanol) of the washed solid was performed, thereby obtaining the title compound (400 mg).

$^1$H NMR (300 MHz, DMSO-$d_6$) δ 0.45-0.55 (2H, m), 0.79-0.92 (2H, m), 1.13 (3H, s), 1.29-1.43 (2H, m), 1.72-1.84 (1H, m), 1.90 (2H, d, J=13.7 Hz), 2.62-3.14 (8H, m), 3.17-3.56 (8H, m), 3.61-3.84 (4H, m), 6.81 (1H, s), 6.86 (1H, s).

Example 186

1-(2-((2-(3,3-Difluorocyclobutyl)-6-ethoxy-4'-fluorobiphenyl-4-yl)methyl)-5-oxa-2,6-diazaspiro[3.4]oct-6-en-7-yl)-4-methylpiperidine-4-carboxylic acid A) Ethyl 2-ethoxy-4'-fluoro-6-vinylbiphenyl-4-carboxylate (1,1'-Bis(diphenylphosphino)ferrocene)dichloropalladium(II) dichloromethane adduct (1.35 g) was added to a mixture of ethyl 2-ethoxy-4'-fluoro-6-(((trifluoromethyl)sulfonyl)oxy)biphenyl-4-carboxylate (7.19 g), potassium vinyltrifluoroborate (3.31 g), triethylamine (4.59 mL) and ethanol (10 mL), and the resultant was stirred for 1 hour at 90° C. in an argon atmosphere. Water was added to the reaction mixture, and extraction thereof was performed using ethyl acetate. The obtained organic layer was passed through a short column of a silica gel (NH), and the solvent was distilled off under reduced pressure. The obtained residue was purified by a silica gel column chromatography (hexane/ethyl acetate), thereby obtaining the title compound (5.19 g).

$^1$H NMR (300 MHz, $CDCl_3$) δ 1.19-1.28 (3H, m), 1.42 (3H, t, J=7.1 Hz), 4.03 (2H, q, J=7.0 Hz), 4.42 (2H, q, J=7.1 Hz), 5.19 (1H, d, J=12.0 Hz), 5.74 (1H, d, J=16.5 Hz), 6.43 (1H, dd, J=17.5, 11.0 Hz), 7.04-7.14 (2H, m), 7.15-7.24 (2H, m), 7.51 (1H, d, J=1.3 Hz), 7.94 (1H, d, J=1.4 Hz).

B) Ethyl 2-ethoxy-4'-fluoro-6-(3-oxocyclobutyl)biphenyl-4-carboxylate

A solution of phosphorus oxychloride (1.85 mL) and trichloroacetyl chloride (5.53 mL) in DME (5 mL) was added to a mixture of ethyl 2-ethoxy-4'-fluoro-6-vinylbiphenyl-4-carboxylate (5.19 g), zinc copper couple (15.9 g) and DME (40 mL) at 0° C. over 20 minutes. After the reaction mixture was stirred overnight at room temperature in a nitrogen atmosphere, an aqueous saturated sodium hydrogen carbonate solution was added to the reaction mixture, and the resultant was filtered using celite. Extraction was performed on the obtained filtrate using ethyl acetate, the organic layer was dried over anhydrous magnesium sulfate, and then the solvent was distilled off under reduced pressure. The obtained residue was mixed with acetic acid (30 mL), Zinc powder (4.32 g) was added to the mixture at 0° C., and the resultant was stirred for 20 minutes at room temperature. An aqueous saturated sodium hydrogen carbonate solution was added to the reaction mixture, the resultant was filtered using celite, and the filtrate was extracted using ethyl acetate. After the organic layer was dried over anhydrous magnesium sulfate, the solvent was distilled off under reduced pressure. The obtained residue was purified by a silica gel column chromatography (hexane/ethyl acetate), thereby obtaining the title compound (3.69 g).

$^1$H NMR (300 MHz, $CDCl_3$) δ 1.18-1.27 (3H, m), 1.43 (3H, t, J=7.1 Hz), 2.99-3.25 (4H, m), 3.41-3.61 (1H, m), 4.04 (2H, q, J=7.0 Hz), 4.42 (2H, q, J=7.1 Hz), 7.02-7.23 (4H, m), 7.53 (1H, d, J=1.2 Hz), 7.73 (1H, d, J=1.1 Hz).

C) Ethyl 2-(3,3-difluorocyclobutyl)-6-ethoxy-4'-fluorobiphenyl-4-carboxylate

Bis(2-methoxyethyl)aminosulfur trifluoride (5.73 mL) was added to a mixture of ethyl 2-ethoxy-4'-fluoro-6-(3-oxocyclobutyl)biphenyl-4-carboxylate (3.69 g) and toluene (30 mL) at room temperature under a nitrogen flow, and the resultant was stirred for 3 hours at the same temperature. An aqueous saturated sodium hydrogen carbonate solution was added to the reaction mixture, extraction was performed on the resultant using ethyl acetate. After the organic layer was dried over anhydrous magnesium sulfate, the solvent was distilled off under reduced pressure. The obtained residue was purified by a silica gel column chromatography (hexane/ethyl acetate), thereby obtaining the title compound (2.44 g).

$^1$H NMR (300 MHz, $CDCl_3$) δ 1.22 (3H, t, J=7.0 Hz), 1.43 (3H, t, J=7.1 Hz), 2.45-2.63 (4H, m), 3.18-3.38 (1H, m), 4.02 (2H, q, J=7.0 Hz), 4.42 (2H, q, J=7.2 Hz), 7.05-7.19 (4H, m), 7.51 (1H, d, J=1.2 Hz), 7.64 (1H, s).

D) 2-(3,3-Difluorocyclobutyl)-6-ethoxy-4'-fluorobiphenyl-4-carbaldehyde

A solution of ethyl 2-(3,3-difluorocyclobutyl)-6-ethoxy-4'-fluorobiphenyl-4-carboxylate (2.44 g) in THF (20 mL) was added to a suspension of lithium aluminum hydride (245 mg) in THF (20 mL) under ice-cooling in a nitrogen atmosphere. After stirring for 30 minutes at the same temperature, water (0.25 mL) and 15% aqueous sodium hydroxide solution (0.25 mL) were added thereto, the resultant was stirred for 5 minutes, and then water (0.75 mL) was further added thereto. After the reaction mixture was stirred for 1 hour, it was filtered, and the obtained filtrate was concentrated under reduced pressure. Manganese dioxide (5.61 g) was added to a solution of the obtained residue in toluene (10 mL), and the resultant was stirred for 1 hour at 60° C. in a nitrogen atmosphere. After the reaction mixture was filtered, the solvent of the obtained filtrate was distilled off under reduced pressure. The obtained residue was purified by a silica gel column chromatography (hexane/ethyl acetate), thereby obtaining the title compound (1.98 g).

$^1$H NMR (300 MHz, $CDCl_3$) δ 1.18-1.26 (3H, m), 2.44-2.72 (4H, m), 3.18-3.42 (1H, m), 4.04 (2H, q, J=6.9 Hz), 7.06-7.19 (4H, m), 7.36 (1H, d, J=1.1 Hz), 7.47 (1H, s), 10.02 (1H, s).

E) Ethyl 1-(2-((2-(3,3-difluorocyclobutyl)-6-ethoxy-4'-fluorobiphenyl-4-yl)methyl)-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-5-oxa-2,6-diazaspiro[3.4]oct-6-ene-2-carboxylate (628 mg) and formic acid (10 mL) was stirred for 1 hour at 60° C. The solvent of the reaction mixture was distilled off under reduced pressure, toluene was added to the residue, and furthermore the solvent was distilled off under reduced pressure. The obtained residue was mixed with 2-(3,3-difluorocyclobutyl)-6-ethoxy-4'-fluorobiphenyl-4-carbaldehyde (500 mg) and THE (5 mL), the mixture was stirred for 15 minutes at room temperature, sodium triacetoxyborohydride (475 mg) was added thereto at room temperature, and then the resultant was stirred for 2 hours at room temperature. Water was added to the reaction mixture, and the resultant was stirred for 10 minutes. After an aqueous saturated sodium hydrogen carbonate solution was added to the reaction mixture, extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (846 mg).

$^1$H NMR (300 MHz, $CDCl_3$) δ 1.13-1.22 (6H, m), 1.26 (3H, t, J=7.1 Hz), 1.39-1.54 (2H, m), 2.11 (2H, d, J=13.5 Hz), 2.37-2.61 (4H, m), 2.90-3.04 (2H, m), 3.13-3.45 (7H, m), 3.56 (2H, d, J=8.9 Hz), 3.69 (2H, s), 3.94 (2H, q, J=7.0 Hz), 4.07-4.16 (2H, m), 6.78 (1H, s), 6.84 (1H, s), 7.02-7.16 (4H, m).

F) 1-(2-((2-(3,3-Difluorocyclobutyl)-6-ethoxy-4'-fluorobiphenyl-4-yl)methyl)-5-oxa-2,6-diazaspiro[3.4]oct-6-en-7-yl)-4-methylpiperidine-4-carboxylic acid A mixture of ethyl 1-(2-((2-(3,3-difluorocyclobutyl)-6-ethoxy-4'-fluorobiphenyl-4-yl)methyl)-5-oxa-2,6-diazaspiro[3.4]oct-6-en-7-yl)-4-methylpiperidine-4-carboxylate (840 mg), 2 M aqueous sodium hydroxide solution (4.2 mL), ethanol (5 mL) and THF (5 mL) was stirred for 1 hour at 70° C. The reaction mixture was cooled to room temperature, and it was neutralized with 6 M hydrochloric acid. Ethyl acetate was added thereto, the solvent was distilled off under reduced pressure. The obtained solid was collected by filtration, washed with diethyl ether, and it was crystallized (hexane/ethyl acetate), thereby obtaining the title compound (345 mg).

$^1$H NMR (300 MHz, DMSO-$d_6$) δ 1.07-1.19 (6H, m), 1.28-1.45 (2H, m), 1.80-2.02 (2H, m), 2.41-2.48 (2H, m), 2.80-2.96 (2H, m), 3.07-3.22 (3H, m), 3.24-3.39 (6H, m), 3.46 (2H, d, J=8.4 Hz), 3.62 (2H, s), 3.94 (2H, q, J=7.0 Hz), 6.89 (2H, d, J=4.2 Hz), 7.12-7.29 (4H, m).

Example 187

1-(2-((2-Cyclopropyl-6-(((1S)-2,2-difluorocyclopropyl)methoxy)-4'-fluorobipheny 1-4-yl)methyl)-5-oxa-2,6-diazaspiro[3.4]oct-6-en-7-yl)-4-methylpiperidine-4-carboxylic acid A) 3-Cyclopropyl-5-(((1S)-2,2-difluorocyclopropyl)methoxy)-4-iodobenzaldehyde ((1S)-2,2-difluorocyclopropyl)methyl 4-methylbenzenesulfonate (465 mg) was added to a mixture of 3-cyclopropyl-5-hydroxy-4-iodobenzaldehyde (304 mg), potassium carbonate (292 mg) and DMF (10 mL), and the resultant was stirred for 2 hours at 70° C. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (389 mg).

$^1$H NMR (300 MHz, $CDCl_3$) δ 0.69-0.77 (2H, m), 1.06-1.16 (2H, m), 1.34-1.47 (1H, m), 1.57-1.72 (1H, m), 2.10-2.24 (2H, m), 4.10-4.19 (1H, m), 4.20-4.29 (1H, m), 7.05 (1H, d, J=1.5 Hz), 7.09 (1H, d, J=1.6 Hz), 9.91 (1H, s).

B) 2-Cyclopropyl-6-(((1S)-2,2-difluorocyclopropyl) methoxy)-4'-fluorobiphenyl-4-carbaldehyde (1,1'-Bis(diphenylphosphino)ferrocene)dichloropalladium(II) (144 mg) was added to a mixture of 3-cyclopropyl-5-(((1S)-2,2-difluorocyclopropyl)methoxy)-4-iodobenzaldehyde (373 mg), (4-fluorophenyl)boronic acid (207 mg), cesium fluoride (450 mg) and DME (10 mL), the resultant was stirred for 11 hours at 100° C., and for 6 hours at room temperature in an argon atmosphere. Water was added to the reaction mixture, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (261 mg).

$^1$H NMR (300 MHz, $CDCl_3$) δ 0.68-0.76 (2H, m), 0.81-0.91 (2H, m), 1.01-1.15 (1H, m), 1.36-1.50 (1H, m), 1.61-1.72 (1H, m), 1.79-1.96 (1H, m), 4.00-4.06 (2H, m), 7.07 (1H, d, J=1.3 Hz), 7.10-7.18 (2H, m), 7.24-7.30 (3H, m), 9.94 (1H, s).

C) Ethyl 1-(2-((2-cyclopropyl-6-(((1S)-2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (254 mg) and formic acid (6 mL) was stirred for 1 hour at 60° C., the solvent was distilled off under reduced pressure. The obtained residue was mixed with 2-cyclopropyl-6-(((1S)-2,2-difluorocyclopropyl)methoxy)-4'-fluorobiphenyl-4-carbaldehyde (254 mg) and THF (10 mL), sodium triacetoxyborohydride (282 mg) was added to the mixture, and the resultant was stirred for 15 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (304 mg).

$^1$H NMR (300 MHz, $CDCl_3$) δ 0.59-0.66 (2H, m), 0.72-0.80 (2H, m), 0.97-1.10 (1H, m), 1.19-1.29 (6H, m), 1.32-1.51 (3H, m), 1.54-1.65 (1H, m), 1.78-1.92 (1H, m), 2.11 (2H, d, J=13.6 Hz), 2.91-3.03 (2H, m), 3.26 (2H, s), 3.30-3.44 (4H, m), 3.50-3.56 (2H, m), 3.62 (2H, s), 3.84-4.02 (2H, m), 4.16 (2H, q, J=7.1 Hz), 6.45 (1H, d, J=0.8 Hz), 6.70 (1H, d, J=1.0 Hz), 7.05-7.13 (2H, m), 7.22-7.29 (2H, m).

D) 1-(2-((2-Cyclopropyl-6-(((1S)-2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (1.5 mL) was added to a solution of ethyl 1-(2-((2-cyclopropyl-6-(((1S)-2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylate (295 mg) in ethanol (8 mL), the resultant was stirred for 5 hours at 70° C., and then the solvent was distilled off under reduced pressure. Water was added to the residue, the resultant was neutralized with 2 M hydrochloric acid, and then the precipitated solid was collected by filtration. After the obtained solid was dissolved in a mixed solution of ethyl acetate and THF, it was dried over anhydrous magnesium sulfate, and the solvent was distilled off under reduced pressure. The residue was crystallized (hexane/ethanol), thereby obtaining the title compound (180 mg).

$^1$H NMR (300 MHz, DMSO-$d_6$) δ 0.55-0.62 (2H, m), 0.68-0.77 (2H, m), 1.14 (3H, s), 1.21-1.43 (3H, m), 1.45-1.64 (2H, m), 1.85-2.05 (3H, m), 2.82-2.94 (2H, m), 3.14 (2H, d, J=8.3 Hz), 3.25-3.37 (4H, m), 3.43 (2H, d, J=8.4 Hz), 3.54 (2H, s), 3.84-3.93 (1H, m), 3.98-4.08 (1H, m), 6.46 (1H, s), 6.80 (1H, s), 7.17-7.30 (4H, m).

Example 188

1-(2-((2-Cyclopropyl-2'-fluoro-6-propoxybiphenyl-4-yl)methyl)-5-oxa-2,6-diazaspiro[3.4]oct-6-en-7-yl)-4-methylpiperidine-4-carboxylic acid A) 3-Cyclopropyl-4-iodo-5-propoxybenzaldehyde 1-Iodopropane (810 mg) was added to a mixture of 3-cyclopropyl-5-hydroxy-4-iodobenzaldehyde (915 mg), potassium carbonate (878 mg) and DMF (20 mL), and the resultant was stirred for 2 hours at 70° C. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.02 g).

$^1$H NMR (300 MHz, $CDCl_3$) δ 0.68-0.77 (2H, m), 1.03-1.17 (5H, m), 1.85-1.97 (2H, m), 2.11-2.23 (1H, m), 4.06 (2H, t, J=6.3 Hz), 7.01 (1H, d, J=1.5 Hz), 7.09 (1H, d, J=1.6 Hz), 9.91 (1H, s).

B) 2-Cyclopropyl-2'-fluoro-6-propoxybiphenyl-4-carbaldehyde (1,1% Bis(diphenylphosphino)ferrocene)dichloropalladium(II) (227 mg) was added to a mixture of 3-cyclopropyl-4-iodo-5-propoxybenzaldehyde (511 mg), (2-fluorophenyl) boronic acid (325 mg), cesium fluoride (706 mg) and DME (15 mL), and the resultant was stirred for 15 hours at 100° C. in an argon atmosphere. Water was added to the reaction mixture, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (425 mg).

$^1$H NMR (300 MHz, $CDCl_3$) δ 0.65-0.92 (7H, m), 1.57-1.72 (3H, m), 3.94 (2H, t, J=6.3 Hz), 7.07 (1H, d, J=1.1 Hz), 7.11-7.29 (4H, m), 7.32-7.41 (1H, m), 9.95 (1H, s).

C) Ethyl 1-(2-((2-cyclopropyl-2'-fluoro-6-propoxy-biphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (228 mg) and formic acid (6 mL) was stirred for 1 hour at 60° C., the solvent was distilled off under reduced pressure. The obtained residue was mixed with 2-cyclopropyl-2'-fluoro-6-propoxybiphenyl-4-carbaldehyde (196 mg) and THF (10 mL), sodium triacetoxyborohydride (253 mg) was added to the mixture, and the resultant was stirred for 18 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), and fractionation was performed on the obtained purified product using HPLC (C18, mobile phase: water/acetonitrile (0.1% TFA-containing system)). The obtained fraction was concentrated under reduced pressure, an aqueous saturated sodium hydrogen carbonate solution was added to the obtained residue, and extraction thereof was performed using ethyl acetate. The obtained organic layer was washed with a saturated saline solution, dried over anhydrous magnesium sulfate, and then the solvent was distilled off under reduced pressure, thereby obtaining the title compound (216 mg).

$^1$H NMR (300 MHz, $CDCl_3$) δ 0.54-0.75 (4H, m), 0.80 (3H, t, J=7.4 Hz), 1.19-1.29 (6H, m), 1.38-1.64 (5H, m), 2.11 (2H, d, J=13.7 Hz), 2.90-3.04 (2H, m), 3.27 (2H, s), 3.33-3.44 (4H, m), 3.55-3.72 (4H, m), 3.84 (2H, t, J=6.3 Hz), 4.16 (2H, q, J=7.1 Hz), 6.45 (1H, s), 6.71 (1H, s), 7.07-7.20 (2H, m), 7.22-7.36 (2H, m).

D) 1-(2-((2-Cyclopropyl-2'-fluoro-6-propoxybiphenyl-4-yl)methyl)-5-oxa-2,6-diazaspiro[3.4]oct-6-en-7-yl)-4-methylpiperidine-4-carboxylic acid 2 M aqueous sodium hydroxide solution (1.5 mL) was added to a solution of ethyl 1-(2-((2-cyclopropyl-2'-fluoro-6-propoxybiphenyl-4-yl)methyl)-5-oxa-2,6-diazaspiro[3.4]oct-6-en-7-yl)-4-methylpiperidine-4-carboxylate (213 mg) in ethanol (8 mL), and the resultant was stirred for 15 hours at 60° C., and the solvent was distilled off under reduced pressure. Water was added to the obtained residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The obtained residue was crystallized (hexane/ethyl acetate), thereby obtaining the title compound (151 mg).

$^1$H NMR (300 MHz, DMSO-$d_6$) δ 0.53-0.61 (2H, m), 0.66-0.78 (5H, m), 1.14 (3H, s), 1.31-1.54 (5H, m), 1.91 (2H, d, J=13.9 Hz), 2.81-2.94 (2H, m), 3.15 (2H, d, J=8.2 Hz), 3.25-3.37 (4H, m), 3.45 (2H, d, J=8.0 Hz), 3.55 (2H, s), 3.83 (2H, t, J=6.1 Hz), 6.43 (1H, s), 6.77 (1H, s), 7.18-7.29 (3H, m), 7.33-7.44 (1H, m).

Example 189

1-(2-((5-Cyclopropyl-4-(4,4-difluoropiperidin-1-yl)-2-methoxybenzyl)-5-oxa-2,6-diazaspiro[3.4]oct-6-en-7-yl)-4-methylpiperidine-4-carboxylic acid A) Methyl 4-(4,4-difluoropiperidin-1-yl)-2-methoxybenzoate A mixture of methyl 4-fluoro-2-methoxybenzoate (2.17 g), potassium carbonate (3.25 g), 4,4-difluoropiperidine hydrochloride (3.71 g) and DMF (30 mL) was stirred overnight at 120° C. Water was added to the reaction mixture, and extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.24 g).

$^1$H NMR (300 MHz, $CDCl_3$) δ 1.87-2.21 (4H, m), 3.43-3.56 (4H, m), 3.84 (3H, s), 3.90 (3H, s), 6.40 (1H, d, J=2.3 Hz), 6.48 (1H, dd, J=8.8, 2.4 Hz), 7.81 (1H, d, J=8.8 Hz).

B) Methyl 5-bromo-4-(4,4-difluoropiperidin-1-yl)-2-methoxybenzoate

N-bromosuccinimide (812 mg) was added to a mixture of methyl 4-(4,4-difluoropiperidin-1-yl)-2-methoxybenzoate (1.24 g) and acetonitrile (15 mL), and the resultant was stirred for 10 minutes at room temperature. An aqueous saturated sodium hydrogen carbonate solution and an aqueous saturated sodium thiosulfate solution was added to the reaction mixture, the resultant was extracted using ethyl acetate. After the organic layer was dried over anhydrous magnesium sulfate, the solvent was distilled off under reduced pressure. The obtained residue was purified by a silica gel column chromatography (hexane/ethyl acetate), thereby obtaining the title compound (1.36 g).

$^1$H NMR (300 MHz, $CDCl_3$) δ 2.09-2.32 (4H, m), 3.13-3.27 (4H, m), 3.86 (3H, s), 3.90 (3H, s), 6.59 (1H, s), 8.05 (1H, s).

C) Methyl 5-cyclopropyl-4-(4,4-difluoropiperidin-1-yl)-2-methoxybenzoate

Tris(dibenzylideneacetone)dipalladium(0) (239 mg) was added to a mixture of methyl 5-bromo-4-(4,4-difluoropiperidin-1-yl)-2-methoxybenzoate (1.36 g), cyclopropylboronic acid (962 mg), dicyclohexyl(2',6'-dimethoxybiphenyl-2-yl)phosphine (230 mg), 2 M aqueous sodium carbonate solution (5.60 mL) and toluene (30 mL), and the resultant was stirred for 2 hours at 100° C. in an argon atmosphere. The reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.32 g).

$^{1}H$ NMR (300 MHz, $CDCl_3$) δ 0.68-0.77 (2H, m), 0.91-1.02 (2H, m), 1.94-2.07 (1H, m), 2.09-2.27 (4H, m), 3.14-3.28 (4H, m), 3.85 (3H, s), 3.88 (3H, s), 6.56 (1H, s), 7.35 (1H, s).

D) 5-Cyclopropyl-4-(4,4-difluoropiperidin-1-yl)-2-methoxybenzaldehyde

A solution of methyl 5-cyclopropyl-4-(4,4-difluoropiperidin-1-yl)-2-methoxybenzoate (1.32 g) in THF (20 mL) was added to a suspension of lithium aluminum hydride (154 mg) in THF (20 mL) under ice-cooling in a nitrogen atmosphere. After stirring for 30 minutes at the same temperature, water (0.20 mL) and 15% aqueous sodium hydroxide solution (0.20 mL) were added thereto, the resultant was stirred for 5 minutes, and then water (0.60 mL) was further added thereto. After the reaction mixture was stirred for 30 minutes, it was filtered, and the obtained filtrate was concentrated under reduced pressure. Manganese dioxide (3.53 g) was added to a solution of the obtained residue in toluene (10 mL), and the resultant was stirred for 1 hour at 60° C. in a nitrogen atmosphere. After the reaction mixture was filtered, the filtrate was concentrated under reduced pressure. The obtained residue was purified by a silica gel column chromatography (hexane/ethyl acetate), thereby obtaining the title compound (610 mg).

$^{1}H$ NMR (300 MHz, $CDCl_3$) δ 0.72-0.80 (2H, m), 0.92-1.03 (2H, m), 1.89-2.03 (1H, m), 2.08-2.30 (4H, m), 3.23-3.34 (4H, m), 3.90 (3H, s), 6.51 (1H, s), 7.34 (1H, s), 10.30 (1H, s).

E) Ethyl 1-(2-((5-cyclopropyl-4-(4,4-difluoropiperidin-1-yl)-2-methoxybenzyl)-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-5-oxa-2,6-diazaspiro[3.4]oct-6-ene-2-carboxylate (570 mg) and formic acid (10 mL) was stirred for 1 hour at 60° C. The solvent of the reaction mixture was distilled off under reduced pressure, toluene was added to the obtained residue, and then the solvent was distilled off under reduced pressure. The obtained residue was mixed with 5-cyclopropyl-4-(4,4-difluoropiperidin-1-yl)-2-methoxybenzaldehyde (485 mg) and THF (5 mL), and the mixture was stirred for 15 minutes at room temperature. Sodium triacetoxyborohydride (475 mg) was added thereto at room temperature, and the resultant was stirred for 2 hours at room temperature. Water was added to the reaction mixture, and the resultant was stirred for 10 minutes. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (706 mg).

$^{1}H$ NMR (300 MHz, $CDCl_3$) δ 0.60-0.70 (2H, m), 0.88-0.97 (2H, m), 1.20 (3H, s), 1.25 (3H, t, J=7.1 Hz), 1.35-1.51 (2H, m), 1.94-2.27 (7H, m), 2.86-3.02 (2H, m), 3.13 (4H, t, J=5.5 Hz), 3.27 (2H, s), 3.37 (2H, dt, J=13.4, 4.1 Hz), 3.45-3.60 (2H, m), 3.67-3.91 (7H, m), 4.16 (2H, q, J=7.2 Hz), 6.54 (1H, s), 6.69 (1H, s).

F) 1-(2-((5-Cyclopropyl-4-(4,4-difluoropiperidin-1-yl)-2-methoxybenzyl)-5-oxa-2,6-diazaspiro[3.4]oct-6-en-7-yl)-4-methylpiperidine-4-carboxylic acid A mixture of ethyl 1-(2-((5-cyclopropyl-4-(4,4-difluoropiperidin-1-yl)-2-methoxybenzyl)-5-oxa-2,6-diazaspiro[3.4]oct-6-en-7-yl)-4-methylpiperidine-4-carboxylate (700 mg), 2 M aqueous sodium hydroxide solution (3.75 mL), ethanol (5 mL) and THF (5 mL) was stirred for 1 hour at 70° C. The reaction mixture was cooled to room temperature, and it was neutralized with 6 M hydrochloric acid. Ethyl acetate was added thereto, the solvent was distilled off under reduced pressure, and the obtained solid was washed with diethyl ether. Furthermore, recrystallization (hexane/ethanol) of the washed solid was performed, thereby obtaining the title compound (275 mg).

$^{1}H$ NMR (300 MHz, DMSO-$d_6$) δ 0.52-0.62 (2H, m), 0.86-0.96 (2H, m), 1.13 (3H, s), 1.28-1.42 (2H, m), 1.90 (2H, d, J=13.7 Hz), 2.02-2.22 (5H, m), 2.79-2.96 (2H, m), 3.01-3.14 (6H, m), 3.20-3.51 (8H, m), 3.74 (3H, s), 6.61 (1H, s), 6.63 (1H, s).

Example 190

1-(2-((5-Cyano-2-cyclopropyl-4'-fluorobiphenyl-4-yl)methyl)-5-oxa-2,6-diazaspiro[3.4]oct-6-en-7-yl)-4-methylpiperidine-4-carboxylic acid A) Ethyl 1-(2-((2-cyclopropyl-4'-fluoro-5-hydroxybiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-5-hydroxybiphenyl-4-carbaldehyde, the title compound was obtained in the similar manner as in Step G of Example 1.

MS (ESI+): $[M+H]^+$ 522.3.

B) Ethyl 1-(2-((2-cyclopropyl-4'-fluoro-5-(((trifluoromethyl)sulfonyl)oxy)biphenyl-4-yl)methyl)-5-oxa-2,6-diazaspiro[3.4]oct-6-en-7-yl)-4-methylpiperidine-4-carboxylate Using ethyl 1-(2-((2-cyclopropyl-4'-fluoro-5-hydroxybiphenyl-4-yl)methyl)-5-oxa-2,6-diazaspiro[3.4]oct-6-en-7-yl)-4-methylpiperidine-4-carboxylate, and potassium tert-butoxide instead of sodium hydride, the title compound was obtained in the similar manner as in Step H of Example 16.

$^{1}H$ NMR (300 MHz, DMSO-$d_6$) δ 0.68-0.78 (2H, m), 0.84-0.95 (2H, m), 1.13-1.22 (6H, m), 1.34-1.49 (2H, m), 1.81 (1H, s), 1.93 (2H, d, J=13.4 Hz), 2.78-2.92 (2H, m), 3.18 (2H, d, J=8.3 Hz), 3.23-3.30 (4H, m), 3.42 (2H, d, J=8.3 Hz), 3.65 (2H, s), 4.10 (2H, q, J=7.1 Hz), 7.11 (2H, d, J=4.6 Hz), 7.27-7.36 (2H, m), 7.45-7.53 (2H, m).

C) Ethyl 1-(2-((5-cyano-2-cyclopropyl-4'-fluorobiphenyl-4-yl)methyl)-5-oxa-2,6-diazaspiro[3.4]oct-6-en-7-yl)-4-methylpiperidine-4-carboxylate A solution of ethyl 1-(2-((2-cyclopropyl-4'-fluoro-5-(((trifluoromethyl)sulfonyl)oxy)biphenyl-4-yl)methyl)-5-oxa-2,6-diazaspiro[3.4]oct-6-en-7-yl)-4-methylpiperidine-4-carboxylate (700 mg), zinc cyanide (377 mg) and tetrakistriphenylphosphine palladium(0) (124 mg) in DMF (10 mL) was stirred for 5 hours at 90° C. The reaction mixture was cooled to room temperature, water was added thereto, and extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (490 mg).

MS (ESI+): $[M+H]^+$ 531.2.

D) 1-(2-((5-Cyano-2-cyclopropyl-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((5-cyano-2-cyclopropyl-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 191

1-(2-((2-Cyclopropyl-6-(cyclopropylmethoxy)-2',4'-difluorobiphenyl-4-yl)methyl)-5-oxa-2,6-diazaspiro[3.4]oct-6-en-7-yl)-4-methylpiperidine-4-carboxylic acid A) 2-Cyclopropyl-6-(cyclopropylmethoxy)-2',4'-difluorobiphenyl-4-carbaldehyde (1,1% Bis(diphenylphosphino)ferrocene)dichloropalladium(II) (159 mg) was added to a mixture of 3-cyclopropyl-5-(cyclopropylmethoxy)-4-iodobenzaldehyde (373 mg), (2,4-difluorophenyl)boronic acid (344 mg), cesium fluoride (497 mg) and DME (10 mL), and the resultant was stirred for 15 hours at 100° C. in an argon atmosphere. Water was added to the reaction mixture, the resultant was filtered using celite, and then extraction was performed on the obtained filtrate using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (300 mg).

$^1$H NMR (300 MHz, $CDCl_3$) δ 0.15-0.23 (2H, m), 0.43-0.52 (2H, m), 0.62-0.79 (2H, m), 0.81-0.90 (2H, m), 1.01-1.15 (1H, m), 1.59-1.70 (1H, m), 3.78-3.93 (2H, m), 6.88-7.01 (2H, m), 7.07 (1H, d, J=1.1 Hz), 7.19-7.29 (2H, m), 9.94 (1H, s).

B) Ethyl 1-(2-((2-cyclopropyl-6-(cyclopropylmethoxy)-2',4'-difluorobiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (313 mg) and formic acid (6 mL) was stirred for 1 hour at 60° C., the solvent was distilled off under reduced pressure. The obtained residue was mixed with 2-cyclopropyl-6-(cyclopropylmethoxy)-2',4'-difluorobiphenyl-4-carbaldehyde (296 mg) and THF (10 mL), sodium triacetoxyborohydride (347 mg) was added to the mixture, and the resultant was stirred for 15 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (385 mg).

$^1$H NMR (300 MHz, $CDCl_3$) δ 0.11-0.18 (2H, m), 0.39-0.47 (2H, m), 0.53-0.69 (2H, m), 0.70-0.77 (2H, m), 0.98-1.09 (1H, m), 1.19-1.29 (6H, m), 1.39-1.62 (3H, m), 2.11 (2H, d, J=13.5 Hz), 2.90-3.03 (2H, m), 3.25 (2H, s), 3.31-3.43 (4H, m), 3.53 (2H, d, J=8.9 Hz), 3.62 (2H, s), 3.69-3.83 (2H, m), 4.16 (2H, q, J=7.1 Hz), 6.46 (1H, s), 6.69 (1H, s), 6.83-6.96 (2H, m), 7.18-7.25 (1H, m).

C) 1-(2-((2-Cyclopropyl-6-(cyclopropylmethoxy)-2',4'-difluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (2 mL) was added to a solution of ethyl 1-(2-((2-cyclopropyl-6-(cyclopropylmethoxy)-2',4'-difluorobiphenyl-4-yl)methyl)-5-oxa-2,6-diazaspiro[3.4]oct-6-en-7-yl)-4-methylpiperidine-4-carboxylate (371 mg) in ethanol (8 mL), the resultant was stirred for 15 hours at 70° C., and then the solvent was distilled off under reduced pressure. Water was added to the obtained residue, the resultant was neutralized with 2 M hydrochloric acid, and then the precipitated solid was collected by filtration. After the obtained solid was dissolved in ethyl acetate and THF, it was dried over anhydrous magnesium sulfate, and the solvent was distilled off under reduced pressure. The residue was crystallized (hexane/ethyl acetate), thereby obtaining the title compound (203 mg).

$^1$H NMR (300 MHz, DMSO-$d_6$) δ 0.10-0.18 (2H, m), 0.35-0.42 (2H, m), 0.52-0.61 (2H, m), 0.67-0.76 (2H, m), 0.93-1.05 (1H, m), 1.14 (3H, s), 1.30-1.52 (3H, m), 1.90 (2H, d, J=13.8 Hz), 2.82-2.94 (2H, m), 3.14 (2H, d, J=8.2 Hz), 3.26-3.37 (4H, m), 3.44 (2H, d, J=8.3 Hz), 3.54 (2H, s), 3.69-3.84 (2H, m), 6.46 (1H, s), 6.77 (1H, s), 7.07-7.17 (1H, m), 7.23-7.35 (2H, m), 12.44 (1H, brs).

Example 192

1-(2-((2-Cyclopropyl-4'-fluoro-5-methoxybiphenyl-4-yl)methyl)-5-oxa-2,6-diazaspiro[3.4]oct-6-en-7-yl)-4-ethylpiperidine-4-carboxylic acid A) Ethyl 1-(2-((2-cyclopropyl-4'-fluoro-5-methoxybiphenyl-4-yl)methyl)-5-oxa-2,6-diazaspiro[3.4]oct-6-en-7-yl)-4-ethylpiperidine-4-carboxylate tert-Butyl 7-(4-(ethoxycarbonyl)-4-ethylpiperidin-1-yl)-5-oxa-2,6-diazaspiro[3.4]oct-6-ene-2-carboxylate (420 mg) was added to formic acid (3 mL), the resultant was stirred for 30 minutes at 70° C., and the solvent was distilled off under reduced pressure. The obtained residue was mixed with 2-cyclopropyl-4'-fluoro-5-methoxybiphenyl-4-carbaldehyde (287 mg) and THF (10 mL), sodium triacetoxyborohydride (338 mg) was added to the mixture, and the resultant was stirred for 3 hours at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (570 mg).

$^1$H NMR (300 MHz, DMSO-$d_6$) δ 0.48-0.56 (2H, m), 0.70-0.80 (5H, m), 1.15-1.22 (3H, m), 1.31-1.44 (2H, m), 1.51 (2H, q, J=7.5 Hz), 1.68-1.79 (1H, m), 1.91-2.01 (2H, m), 2.71-2.84 (2H, m), 3.13 (2H, d, J=8.3 Hz), 3.26-3.30 (2H, m), 3.33-3.45 (4H, m), 3.53 (2H, s), 3.76 (3H, s), 4.12 (2H, q, J=7.1 Hz), 6.74 (1H, s), 6.83 (1H, s), 7.26 (2H, t, J=8.9 Hz), 7.44-7.52 (2H, m).

B) 1-(2-((2-Cyclopropyl-4'-fluoro-5-methoxybiphenyl-4-yl)methyl)-5-oxa-2,6-diazaspiro[3.4]oct-6-en-7-yl)-4-ethylpiperidine-4-carboxylic acid 2 M aqueous sodium hydroxide solution (3.6 mL) was added to a solution of ethyl 1-(2-((2-cyclopropyl-4'-fluoro-5-methoxybiphenyl-4-yl)methyl)-5-oxa-2,6-diazaspiro[3.4]oct-6-en-7-yl)-4-ethylpiperidine-4-carboxylate (570 mg) in ethanol (5.0 mL), and the resultant was stirred for 2 hours at 60° C. After the reaction mixture was neutralized with 2 M hydrochloric acid, it was stirred for 30 minutes. The precipitated solid was collected by filtration. Recrystallization (hydrous methanol) of the obtained solid was performed, thereby obtaining the title compound (335 mg).

$^1$H NMR (300 MHz, DMSO-$d_6$) δ 0.48-0.56 (2H, m), 0.71-0.82 (5H, m), 1.26-1.40 (2H, m), 1.49 (2H, q, J=7.2 Hz), 1.68-1.80 (1H, m), 1.93 (2H, d, J=13.7 Hz), 2.81 (2H, t, J=11.0 Hz), 3.13 (2H, d, J=8.2 Hz), 3.22-3.39 (4H, m), 3.43 (2H, d, J=8.2 Hz), 3.54 (2H, s), 3.76 (3H, s), 6.74 (1H, s), 6.84 (1H, s), 7.26 (2H, t, J=8.9 Hz), 7.48 (2H, dd, J=8.6, 5.6 Hz).

Example 193

1-(2-((2-Cyclopropyl-2'-fluoro-6-propoxybiphenyl-4-yl)methyl)-5-oxa-2,6-diazaspiro[3.4]oct-6-en-7-yl)-4-ethylpiperidine-4-carboxylic acid A) Ethyl 1-(2-((2-cyclopropyl-2'-fluoro-6-propoxybiphenyl-4-yl)methyl)-5-oxa-2,6-diazaspiro[3.4]oct-6-en-7-yl)-4-ethylpiperidine-4-carboxylate After a mixture of tert-butyl 7-(4-(ethoxycarbonyl)-4-ethylpiperidin-1-yl)-5-oxa-2,6-diazaspiro[3.4]oct-6-ene-2-carboxylate (235 mg) and formic acid (6 mL) was stirred for 1 hour at 60° C., the solvent was distilled of under reduced pressure. Sodium triacetoxyborohydride (252 mg) was added to a mixture of the obtained residue, 2-cyclopropyl-2'-fluoro-6-propoxybiphenyl-4-carbaldehyde (195 mg) and THF (10 mL), and the resultant was stirred for 18 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), and fractionation was performed thereon using HPLC (C18, mobile phase: water/acetonitrile (0.1% TFA-containing system)). The obtained fraction was concentrated, an aqueous saturated sodium hydrogen carbonate solution was added to the obtained residue, and extraction thereof was performed using ethyl acetate. The obtained organic layer was washed with a saturated saline solution, dried over anhydrous magnesium sulfate, and then the solvent was distilled off under reduced pressure, thereby obtaining the title compound (258 mg).

$^1$H NMR (300 MHz, $CDCl_3$) δ 0.54-0.75 (4H, m), 0.76-0.85 (6H, m), 1.26 (3H, t, J=7.1 Hz), 1.36-1.48 (2H, m), 1.51-1.65 (5H, m), 2.14 (2H, d, J=13.5 Hz), 2.85-2.97 (2H, m), 3.27 (2H, s), 3.32-3.50 (4H, m), 3.53-3.72 (4H, m), 3.84 (2H, t, J=6.4 Hz), 4.18 (2H, q, J=7.1 Hz), 6.45 (1H, s), 6.71 (1H, s), 7.07-7.20 (2H, m), 7.22-7.35 (2H, m).

B) 1-(2-((2-Cyclopropyl-2'-fluoro-6-propoxybiphenyl-4-yl)methyl)-5-oxa-2,6-diazaspiro[3.4]oct-6-en-7-yl)-4-ethylpiperidine-4-carboxylic acid 2 M aqueous sodium hydroxide solution (1.5 mL) was added to a mixture of ethyl 1-(2-((2-cyclopropyl-2'-fluoro-6-propoxybiphenyl-4-yl)methyl)-5-oxa-2,6-diazaspiro[3.4]oct-6-en-7-yl)-4-ethylpiperidine-4-carboxylate (245 mg), ethanol (6 mL) and methanol (2 mL), the resultant was stirred for 5 hours at 70° C. 2 M aqueous sodium hydroxide solution (1.5 mL) was added thereto, and the resultant was stirred 15 hours at 70° C. 2 M aqueous sodium hydroxide solution (1.5 mL) was added to the reaction mixture, and the resultant was stirred for 20 hours at 80° C. 2 M aqueous sodium hydroxide solution (1 mL) was added thereto, the resultant was stirred for 5 hours at 80° C., and the solvent was distilled off under reduced pressure. Water was added to the obtained residue, the resultant was neutralized with 2 M hydrochloric acid, and then the precipitated solid was collected by filtration. After the obtained solid was dissolved in ethyl acetate and THF, it was dried over anhydrous magnesium sulfate, and the solvent was distilled off under reduced pressure. The residue was crystallized (hexane/ethanol), thereby obtaining the title compound (135 mg).

$^1$H NMR (300 MHz, DMSO-$d_6$) δ 0.53-0.63 (2H, m), 0.68-0.89 (8H, m), 1.28-1.40 (2H, m), 1.42-1.56 (5H, m), 1.93 (2H, d, J=13.5 Hz), 2.74-2.88 (2H, m), 3.17 (2H, brs), 3.28-3.40 (4H, m), 3.46 (2H, brs), 3.58 (2H, brs), 3.83 (2H, t, J=6.1 Hz), 6.44 (1H, s), 6.78 (1H, s), 7.18-7.28 (3H, m), 7.33-7.44 (1H, m), 12.47 (1H, brs).

Example 194

Trans-4-(2-((2-Cyclopropyl-5-ethoxy-4'-fluorobiphenyl-4-yl)methyl)-5-oxa-2,6-diazaspiro[3.4]oct-6-en-7-yl)cyclohexanecarboxylic acid A) 2-Cyclopropyl-5-ethoxy-4'-fluorobiphenyl-4-carbaldehyde Iodoethane (235 mg) was added to a mixture of 2-cyclopropyl-4'-fluoro-5-hydroxybiphenyl-4-carbaldehyde (257 mg), potassium carbonate (278 mg) and DMF (10 mL), and the resultant was stirred for 1 hour at 60° C. After water was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (280 mg).

$^1$H NMR (300 MHz, $CDCl_3$) δ 0.63-0.70 (2H, m), 0.76-0.84 (2H, m), 1.46 (3H, t, J=7.0 Hz), 1.66-1.78 (1H, m), 4.14 (2H, q, J=7.0 Hz), 6.81 (1H, s), 7.10-7.18 (2H, m), 7.37-7.47 (3H, m), 10.48 (1H, s).

B) Methyl trans-4-(2-((2-cyclopropyl-5-ethoxy-4'-fluorobiphenyl-4-yl)methyl)-5-oxa-2,6-diazaspiro[3.4]oct-6-en-7-yl)cyclohexanecarboxylate Triethylamine (163 mg) was added to a mixture of methyl trans-4-(5-oxa-2,6-diazaspiro[3.4]oct-6-en-7-yl)cyclohexanecarboxylate hydrochloride (233 mg), 2-cyclopropyl-5-ethoxy-4'-fluorobiphenyl-4-carbaldehyde (276 mg) and THF (10 mL), and the resultant was stirred for 10 minutes at room temperature. Sodium triacetoxyborohydride (342 mg) was added thereto, and the resultant was stirred for 15 hours at the same temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The residue was purified by a silica gel column chromatography (hexane/ethyl acetate), thereby obtaining the title compound (398 mg).

$^1$H NMR (300 MHz, $CDCl_3$) δ 0.55-0.62 (2H, m), 0.72-0.80 (2H, m), 1.34-1.58 (7H, m), 1.70-1.81 (1H, m), 1.95-2.13 (4H, m), 2.23-2.44 (2H, m), 3.21 (2H, s), 3.42-3.48 (2H, m), 3.50-3.55 (2H, m), 3.66-3.72 (5H, m), 4.01 (2H, q, J=7.0 Hz), 6.67 (1H, s), 6.84 (1H, s), 7.06-7.13 (2H, m), 7.36-7.42 (2H, m).

C) trans-4-(2-((2-Cyclopropyl-5-ethoxy-4'-fluorobiphenyl-4-yl)methyl)-5-oxa-2,6-diazaspiro[3.4]oct-6-en-7-yl)cyclohexanecarboxylic acid 2 M aqueous sodium hydroxide solution (2 mL) was added to a solution of methyl trans-4-(2-((2-cyclopropyl-5-ethoxy-4'-fluorobiphenyl-4-yl)methyl)-5-oxa-2,6-diazaspiro[3.4]oct-6-en-7-yl)cyclohexanecarboxylate (387 mg) in ethanol (8 mL), the resultant was stirred for 5 hours at 70° C., and then the solvent was distilled off under reduced pressure. Water was added to the obtained residue, the resultant was neutralized with 2 M hydrochloric acid, and then the precipitated solid was collected by filtration. After the obtained solid was dissolved in ethyl acetate and THF, it was dried over anhydrous magnesium sulfate, and the solvent was distilled off under reduced pressure. The obtained residue was crystallized (hexane/ethanol), thereby obtaining the title compound (247 mg).

$^1$H NMR (300 MHz, DMSO-$d_6$) δ 0.48-0.57 (2H, m), 0.70-0.80 (2H, m), 1.21-1.45 (7H, m), 1.68-1.79 (1H, m), 1.82-1.98 (4H, m), 2.11-2.23 (1H, m), 2.25-2.37 (1H, m), 3.18-3.26 (4H, m), 3.42 (2H, d, J=8.0 Hz), 3.56 (2H, s), 4.02 (2H, q, J=6.9 Hz), 6.73 (1H, s), 6.84 (1H, s), 7.21-7.31 (2H, m), 7.47 (2H, dd, J=8.5, 5.7 Hz), 12.07 (1H, brs).

Example 195

1-(2-((6-Cyclopropyl-4'-fluoro-4-methoxybiphenyl-3-yl)methyl)-5-oxa-2,6-diazaspiro[3.4]oct-6-en-7-yl)-4-methylpiperidine-4-carboxylic acid A) Methyl 4-cyclopropyl-2-methoxybenzoate Using methyl 4-bromo-2-methoxybenzoate and cyclopropylboronic acid, the title compound was obtained in the similar manner as in Step D of Example 23.

$^1$H NMR (300 MHz, $CDCl_3$) δ 0.72-0.81 (2H, m), 0.96-1.11 (2H, m), 1.80-1.98 (1H, m), 3.86 (3H, s), 3.90 (3H, s), 6.62 (1H, dd, J=8.1, 1.5 Hz), 6.69 (1H, d, J=1.4 Hz), 7.72 (1H, d, J=8.1 Hz).

B) Methyl 5-bromo-4-cyclopropyl-2-methoxybenzoate

Using methyl 4-cyclopropyl-2-methoxybenzoate, the title compound was obtained in the similar manner as in Step D of Example 185.

$^1$H NMR (300 MHz, $CDCl_3$) δ 0.63-0.81 (2H, m), 1.04-1.16 (2H, m), 2.13-2.28 (1H, m), 3.86 (3H, s), 3.87 (3H, s), 6.49 (1H, s), 7.99 (1H, s).

C) Methyl 6-cyclopropyl-4'-fluoro-4-methoxybiphenyl-3-carboxylate

Using methyl 5-bromo-4-cyclopropyl-2-methoxybenzoate and (4-fluorophenyl)boronic acid, the title compound was obtained in the similar manner as in Step K of Example 88.

$^1$H NMR (300 MHz, $CDCl_3$) δ 0.69-0.79 (2H, m), 0.89-0.98 (2H, m), 1.81-1.95 (1H, m), 3.86 (3H, s), 3.91 (3H, s), 6.48 (1H, s), 7.10 (2H, t, J=8.7 Hz), 7.31-7.42 (2H, m), 7.68 (1H, s).

D) 6-Cyclopropyl-4'-fluoro-4-methoxybiphenyl-3-carbaldehyde

Using methyl 6-cyclopropyl-4'-fluoro-4-methoxybiphenyl-3-carboxylate, the title compound was obtained in the similar manner as in Step D of Example 10.

$^1$H NMR (300 MHz, $CDCl_3$) δ 0.74-0.84 (2H, m), 0.93-1.04 (2H, m), 1.84-1.98 (1H, m), 3.93 (3H, s), 6.46 (1H, s), 7.10 (2H, t, J=8.7 Hz), 7.35 (2H, dd, J=8.7, 5.4 Hz), 7.67 (1H, s), 10.41 (1H, s).

E) Ethyl 1-(2-((6-cyclopropyl-4'-fluoro-4-methoxybiphenyl-3-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 6-cyclopropyl-4'-fluoro-4-methoxybiphenyl-3-carbaldehyde, the title compound was obtained in the similar manner as in Step G of Example 1.

MS (ESI+): $[M+H]^+$ 536.5.

F) 1-(2-((6-Cyclopropyl-4'-fluoro-4-methoxybiphenyl-3-yl)methyl)-5-oxa-2,6-diazaspiro[3.4]oct-6-en-7-yl)-4-methylpiperidine-4-carboxylic acid Using ethyl 1-(2-((6-cyclopropyl-4'-fluoro-4-methoxybiphenyl-3-yl)methyl)-5-oxa-2,6-diazaspiro[3.4]oct-6-en-7-yl)-4-methylpiperidine-4-carboxylate, the title compound was obtained in the similar manner as in Example 2.

Example 196

1-(2-((2-Cyclopropyl-4'-fluoro-5-(oxetane-3-yloxy)biphenyl-4-yl)methyl)-5-oxa-2,6-diazaspiro[3.4]oct-6-en-7-yl)-4-methylpiperidine-4-carboxylic acid A) 2-Cyclopropyl-4'-fluoro-5-(oxetane-3-yloxy)biphenyl-4-carbaldehyde Using 2-cyclopropyl-4'-fluoro-5-hydroxybiphenyl-4-carbaldehyde, 3-iodooxetane, and cesium carbonate instead of potassium carbonate, the title compound was obtained in the similar manner as in Step H of Example 113.

$^1$H NMR (300 MHz, DMSO-$d_6$) δ 0.52-0.64 (2H, m), 0.74-0.85 (2H, m), 1.68-1.82 (1H, m), 4.64 (2H, dd, J=7.6, 4.9 Hz), 4.93 (2H, t, J=6.8 Hz), 5.44-5.54 (1H, m), 6.62 (1H, s), 7.26-7.37 (3H, m), 7.47-7.57 (2H, m), 10.42 (1H, s).

B) Ethyl 1-(2-((2-cyclopropyl-4'-fluoro-5-(oxetane-3-yloxy)biphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-5-(oxetane-3-yloxy)biphenyl-4-carbaldehyde, the title compound was obtained in the similar manner as in Step G of Example 1.

MS (ESI+): $[M+H]^+$ 578.1.

C) 1-(2-((2-Cyclopropyl-4'-fluoro-5-(oxetane-3-yloxy)biphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-5-(oxetane-3-yloxy)biphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 197

1-(2-((2-Cyclopropyl-4'-fluoro-5-hydroxybiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-5-hydroxybiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 198

1-(2-((5-Cyclopropyl-4-(3,3-difluoropyrrolidin-1-yl)-2-methoxybenzyl)-5-oxa-2,6-diazaspiro[3.4]oct-6-en-7-yl)-4-methylpiperidine-4-carboxylic acid A) Methyl 4-(3,3-difluoropyrrolidin-1-yl)-2-methoxybenzoate Using methyl 4-fluoro-2-methoxybenzoate and 3,3-difluoropyrrolidine hydrochloride, the title compound was obtained in the similar manner as in Step A of Example 189.

$^1H$ NMR (300 MHz, $CDCl_3$) δ 2.43-2.60 (2H, m), 3.61 (2H, t, J=7.2 Hz), 3.68-3.80 (2H, m), 3.84 (3H, s), 3.91 (3H, s), 5.99 (1H, d, J=2.2 Hz), 6.12 (1H, dd, J=8.7, 2.3 Hz), 7.83 (1H, d, J=8.8 Hz).

B) Methyl 5-bromo-4-(3,3-difluoropyrrolidin-1-yl)-2-methoxybenzoate

Using methyl 4-(3,3-difluoropyrrolidin-1-yl)-2-methoxybenzoate, the title compound was obtained in the similar manner as in Step B of Example 189.

$^1H$ NMR (300 MHz, $CDCl_3$) δ 2.31-2.57 (2H, m), 3.62 (2H, t, J=6.9 Hz), 3.85 (3H, s), 3.88-4.00 (5H, m), 6.34 (1H, s), 8.04 (1H, s).

C) Methyl 5-cyclopropyl-4-(3,3-difluoropyrrolidin-1-yl)-2-methoxybenzoate

Using methyl 5-bromo-4-(3,3-difluoropyrrolidin-1-yl)-2-methoxybenzoate and cyclopropylboronic acid, the title compound was obtained in the similar manner as in Step C of Example 189.

$^1H$ NMR (300 MHz, $CDCl_3$) δ 0.63-0.77 (2H, m), 0.88-1.01 (2H, m), 1.80-1.95 (1H, m), 2.35-2.57 (2H, m), 3.60 (2H, t, J=7.0 Hz), 3.84 (3H, s), 3.87-3.96 (5H, m), 6.27 (1H, s), 7.61 (1H, s).

D) 5-Cyclopropyl-4-(3,3-difluoropyrrolidin-1-yl)-2-methoxybenzaldehyde

Using methyl 5-cyclopropyl-4-(3,3-difluoropyrrolidin-1-yl)-2-methoxybenzoate, the title compound was obtained in the similar manner as in Step D of Example 189.

$^1H$ NMR (300 MHz, $CDCl_3$) δ 0.65-0.78 (2H, m), 0.86-1.00 (2H, m), 1.76-1.95 (1H, m), 2.48 (2H, tt, J=13.7, 6.9 Hz), 3.69 (2H, t, J=7.0 Hz), 3.89 (3H, s), 3.98 (2H, t, J=13.4 Hz), 6.18 (1H, s), 7.58 (1H, s), 10.22 (1H, s).

E) Ethyl 1-(2-((5-cyclopropyl-4-(3,3-difluoropyrrolidin-1-yl)-2-methoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 5-cyclopropyl-4-(3,3-difluoropyrrolidin-1-yl)-2-methoxybenzaldehyde, the title compound was obtained in the similar manner as in Step E of Example 189.

MS (ESI+): $[M+H]^+$ 547.5.

F) 1-(2-((5-Cyclopropyl-4-(3,3-difluoropyrrolidin-1-yl)-2-methoxybenzyl)-5-oxa-2,6-diazaspiro[3.4]oct-6-en-7-yl)-4-methylpiperidine-4-carboxylic acid Using ethyl 1-(2-((5-cyclopropyl-4-(3,3-difluoropyrrolidin-1-yl)-2-methoxybenzyl)-5-oxa-2,6-diazaspiro[3.4]oct-6-en-7-yl)-4-methylpiperidine-4-carboxylate, the title compound was obtained in the similar manner as in Step F of Example 189.

Example 199

1-(2-(5-Cyclopropyl-2-ethoxybenzyl)-5-oxa-2,6-diazaspiro[3.4]oct-6-en-7-yl)-4-methylpiperidine-4-carboxylic acid A) 5-Bromo-2-ethoxybenzaldehyde Using 5-bromo-2-hydroxybenzaldehyde and iodoethane, the title compound was obtained in the similar manner as in Step A of Example 1.

$^1H$ NMR (300 MHz, $CDCl_3$) δ 1.48 (3H, t, J=7.0 Hz), 4.14 (2H, q, J=7.0 Hz), 6.88 (1H, d, J=9.0 Hz), 7.60 (1H, dd, J=8.9, 2.6 Hz), 7.92 (1H, d, J=2.6 Hz), 10.42 (1H, s).

B) 5-Cyclopropyl-2-ethoxybenzaldehyde

Using 5-bromo-2-ethoxybenzaldehyde and cyclopropylboronic acid, the title compound was obtained in the similar manner as in Step K of Example 88.

MS (ESI+): $[M+H]^+$ 191.2.

C) Ethyl 1-(2-(5-cyclopropyl-2-ethoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 5-cyclopropyl-2-ethoxybenzaldehyde, the title compound was obtained in the similar manner as in Step G of Example 1.

MS (ESI+): $[M+H]^+$ 456.4.

D) 1-(2-(5-Cyclopropyl-2-ethoxybenzyl)-5-oxa-2,6-diazaspiro[3.4]oct-6-en-7-yl)-4-methylpiperidine-4-carboxylic acid Using ethyl 1-(2-(5-cyclopropyl-2-ethoxybenzyl)-5-oxa-2,6-diazaspiro[3.4]oct-6-en-7-yl)-4-methylpiperidine-4-carboxylate, the title compound was obtained in the similar manner as in Example 2.

Example 200

1-(2-(5-Cyclopropyl-4-(4-fluoropiperidin-1-yl)-2-methoxybenzyl)-5-oxa-2,6-diazaspiro[3.4]oct-6-en-7-yl)-4-methylpiperidine-4-carboxylic acid A) Methyl 4-(4-hydroxypiperidin-1-yl)-2-methoxybenzoate Using methyl 4-fluoro-2-methoxybenzoate and 4-hydroxypiperidine, the title compound was obtained in the similar manner as in Step A of Example 189.

$^1$H NMR (300 MHz, $CDCl_3$) δ 1.53-1.74 (3H, m), 1.91-2.08 (2H, m), 3.00-3.17 (2H, m), 3.64-3.76 (2H, m), 3.83 (3H, s), 3.86-3.99 (4H, m), 6.38 (1H, d, J=2.3 Hz), 6.46 (1H, dd, J=8.9, 2.3 Hz), 7.79 (1H, d, J=8.9 Hz).

B) Methyl 4-(4-((tert-butyl(dimethyl)silyl)oxy)piperidin-1-yl)-2-methoxybenzoate Using methyl 4-(4-hydroxypiperidin-1-yl)-2-methoxybenzoate, the title compound was obtained in the similar manner as in Step B of Example 97.

$^1$H NMR (300 MHz, $CDCl_3$) δ 0.09 (6H, s), 0.80-1.02 (9H, m), 1.59-1.72 (2H, m), 1.80-1.95 (2H, m), 3.17-3.28 (2H, m), 3.48-3.63 (2H, m), 3.84 (3H, s), 3.90 (3H, s), 3.91-4.00 (1H, m), 6.38 (1H, d, J=2.3 Hz), 6.42-6.53 (1H, m), 7.79 (1H, d, J=8.9 Hz).

C) Methyl 5-bromo-4-(4-((tert-butyl(dimethyl)silyl)oxy)piperidin-1-yl)-2-methoxybenzoate Using methyl 4-(4-((tert-butyl(dimethyl)silyl)oxy)piperidin-1-yl)-2-methoxybenzoate, the title compound was obtained in the similar manner as in Step B of Example 189.

$^1$H NMR (300 MHz, $CDCl_3$) δ 0.09 (6H, s), 0.92 (9H, s), 1.68-1.84 (2H, m), 1.86-2.01 (2H, m), 2.90-3.04 (2H, m), 3.24-3.38 (2H, m), 3.86 (3H, s), 3.88-3.98 (4H, m), 6.58 (1H, s), 8.04 (1H, s).

D) Methyl 4-(4-((tert-butyl(dimethyl)silyl)oxy)piperidin-1-yl)-5-cyclopropyl-2-methoxybenzoate Using methyl 5-bromo-4-(4-((tert-butyl(dimethyl)silyl)oxy)piperidin-1-yl)-2-methoxybenzoate and cyclopropylboronic acid, the title compound was obtained in the similar manner as in Step C of Example 189.

$^1$H NMR (300 MHz, $CDCl_3$) δ 0.10 (6H, s), 0.65-0.76 (2H, m), 0.83-1.02 (11H, m), 1.67-1.82 (2H, m), 1.86-1.99 (2H, m), 1.99-2.10 (1H, m), 2.85-2.99 (2H, m), 3.24-3.51 (2H, m), 3.85 (3H, s), 3.87-3.95 (4H, m), 6.54 (1H, s), 7.34 (1H, s).

E) 4-(4-((tert-Butyl(dimethyl)silyl)oxy)piperidin-1-yl)-5-cyclopropyl-2-methoxybenzyl acetate A solution of methyl 4-(4-((tert-butyl(dimethyl)silyl)oxy)piperidin-1-yl)-5-cyclopropyl-2-methoxybenzoate (2.49 g) in THF (20 mL) was added to a suspension of lithium aluminum hydride (255 mg) in THF (20 mL) under ice-cooling in a nitrogen atmosphere. After stirring for 30 minutes at the same temperature, water (0.25 mL), 15% aqueous sodium hydroxide solution (0.25 mL) and water (0.75 mL) were sequentially added thereto. After the reaction mixture was stirred for 30 minutes, it was filtered, and the obtained filtrate was concentrated under reduced pressure. Acetic anhydride (5.00 mL) was added to a solution of the obtained residue in pyridine (20 mL), and the resultant was stirred for 30 minutes at room temperature. The solvent of the reaction mixture was distilled off under reduced pressure. The obtained residue was purified by a silica gel column chromatography (hexane/ethyl acetate), thereby obtaining the title compound (2.05 g).

$^1$H NMR (300 MHz, $CDCl_3$) δ 0.10 (6H, s), 0.60-0.73 (2H, m), 0.85-1.00 (11H, m), 1.66-1.83 (2H, m), 1.86-1.99 (2H, m), 2.01-2.21 (4H, m), 2.77-2.92 (2H, m), 3.21-3.36 (2H, m), 3.76-3.91 (4H, m), 5.06 (2H, s), 6.58 (1H, s), 6.74 (1H, s).

F) 5-Cyclopropyl-4-(4-hydroxypiperidin-1-yl)-2-methoxybenzyl acetate

Using 4-(4-((tert-butyl(dimethyl)silyl)oxy)piperidin-1-yl)-5-cyclopropyl-2-methoxybenzyl acetate, the title compound was obtained in the similar manner as in Step D of Example 176.

$^1$H NMR (300 MHz, $CDCl_3$) δ 0.52-0.72 (2H, m), 0.86-1.02 (2H, m), 1.64-1.85 (2H, m), 1.97-2.21 (6H, m), 2.76-2.90 (2H, m), 3.24-3.39 (2H, m), 3.81 (3H, s), 3.83-3.92 (1H, m), 5.05 (2H, s), 6.57 (1H, s), 6.74 (1H, s).

G) 5-Cyclopropyl-4-(4-fluoropiperidin-1-yl)-2-methoxybenzyl acetate

Using 5-cyclopropyl-4-(4-hydroxypiperidin-1-yl)-2-methoxybenzyl acetate, the title compound was obtained in the similar manner as in Step B of Example 168.

$^1$H NMR (300 MHz, $CDCl_3$) δ 0.59-0.73 (2H, m), 0.87-1.03 (2H, m), 1.94-2.20 (8H, m), 2.91-3.04 (2H, m), 3.11-3.26 (2H, m), 3.81 (3H, s), 4.68-4.97 (1H, m), 5.05 (2H, s), 6.58 (1H, s), 6.75 (1H, s).

H) (5-Cyclopropyl-4-(4-fluoropiperidin-1-yl)-2-methoxyphenyl)methanol

Potassium carbonate (499 mg) was added to a mixture of 5-cyclopropyl-4-(4-fluoropiperidin-1-yl)-2-methoxybenzyl acetate (580 mg) and methanol (15 mL), and the resultant was stirred for 30 minutes at room temperature. Water was added to the reaction mixture, extraction thereof was performed using ethyl acetate, the obtained organic layer was dried over anhydrous magnesium sulfate, and then the solvent was distilled off under reduced pressure. The obtained residue was purified by a silica gel column chromatography (hexane/ethyl acetate), thereby obtaining the title compound (458 mg).

$^1$H NMR (300 MHz, $CDCl_3$) δ 0.62-0.71 (2H, m), 0.88-1.00 (2H, m), 1.92-2.24 (5H, m), 2.89-3.04 (2H, m), 3.11-

3.26 (2H, m), 3.84 (3H, s), 4.58 (2H, d, J=6.3 Hz), 4.67-4.97 (1H, m), 6.59 (1H, s), 6.68 (1H, s).

I) 5-Cyclopropyl-4-(4-fluoropiperidin-1-yl)-2-methoxybenzaldehyde

Manganese dioxide (1.42 g) was added to a solution of (5-cyclopropyl-4-(4-fluoropiperidin-1-yl)-2-methoxyphenyl)methanol (458 mg) in toluene (10 mL), and the resultant was stirred for 1 hour at 60° C. After the reaction mixture was filtered, the solvent was distilled off under reduced pressure. The obtained residue was purified by a silica gel column chromatography (hexane/ethyl acetate), thereby obtaining the title compound (124 mg).

$^1$H NMR (300 MHz, $CDCl_3$) δ 0.65-0.83 (2H, m), 0.90-1.05 (2H, m), 1.84-2.24 (5H, m), 3.07-3.20 (2H, m), 3.22-3.42 (2H, m), 3.90 (3H, s), 4.69-5.02 (1H, m), 6.51 (1H, s), 7.33 (1H, s), 10.29 (1H, s).

J) Ethyl 1-(2-((5-cyclopropyl-4-(4-fluoropiperidin-1-yl)-2-methoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 5-cyclopropyl-4-(4-fluoropiperidin-1-yl)-2-methoxybenzaldehyde, the title compound was obtained in the similar manner as in Step G of Example 1.

MS (ESI+): $[M+H]^+$ 543.5.

K) 1-(2-((5-Cyclopropyl-4-(4-fluoropiperidin-1-yl)-2-methoxybenzyl)-5-oxa-2,6-diazaspiro[3.4]oct-6-en-7-yl)-4-methylpiperidine-4-carboxylic acid Using ethyl 1-(2-((5-cyclopropyl-4-(4-fluoropiperidin-1-yl)-2-methoxybenzyl)-5-oxa-2,6-diazaspiro[3.4]oct-6-en-7-yl)-4-methylpiperidine-4-carboxylate, the title compound was obtained in the similar manner as in Example 2.

Example 201

1-(2-((2-Cyclopropyl-4'-fluoro-5-(morpholin-4-yl)biphenyl-4-yl)methyl)-5-oxa-2,6-diazaspiro[3.4]oct-6-en-7-yl)-4-methylpiperidine-4-carboxylic acid A) Methyl 4-(benzyloxy)-2-(morpholin-5-yl)benzoate Methyl 2-fluoro-4-hydroxybenzoate (4.90 g), benzylbromide (5.91 g) and potassium carbonate (5.97 g) were added to DMF (30 mL), and the resultant was stirred for 1 hour at 50° C. The reaction mixture was cooled to room temperature, water was added thereto, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining a solid. Morpholine (9.37 g) and potassium carbonate (14.9 g) were added to a solution of the obtained solid in DMF (21 mL), and the resultant was stirred for 3 hours at 140° C. The reaction mixture was cooled to room temperature, water was added thereto, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel chromatography (hexane/ethyl acetate), thereby obtaining the title compound.

MS (ESI+): $[M+H]^+$ 328.1.

B) Methyl 4-(benzyloxy)-5-bromo-2-(morpholin-4-yl)benzoate

Using methyl 4-(benzyloxy)-2-(morpholin-4-yl)benzoate, the title compound was obtained in the similar manner as in Step B of Example 189.

$^1$H NMR (300 MHz, DMSO-$d_6$) δ 2.95-3.02 (4H, m), 3.68-3.73 (4H, m), 3.77 (3H, s), 5.31 (2H, s), 6.78 (1H, s), 7.30-7.55 (5H, m), 7.88 (1H, s).

C) Methyl 5-cyclopropyl-4-hydroxy-2-(morpholin-4-yl)benzoate

Methyl 4-(benzyloxy)-5-bromo-2-(morpholin-4-yl)benzoate (3.70 g), cyclopropylboronic acid (1.57 g), dicyclohexyl(2',6'-dimethoxybiphenyl-2-yl)phosphine (374 mg), tris(dibenzylideneacetone)dipalladium(0) (417 mg) and 2 M aqueous sodium carbonate solution (13.7 mL) were added to toluene (100 mL) in an argon atmosphere, and the resultant was stirred for 1 hour at 100° C. The reaction mixture was cooled to room temperature, and extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining a solid. The obtained solid was dissolved in methanol, 20% palladium hydroxide (50% water content 1.28 g) was added to the solution, and the resultant was stirred for 2 hours at room temperature in a hydrogen atmosphere. The catalyst was filtered off, the obtained filtrate was concentrated under reduced pressure, and the residue was purified by a silica gel column chromatography (hexane/ethyl acetate), thereby obtaining the title compound (1.90 g).

$^1$H NMR (300 MHz, DMSO-$d_6$) δ 0.46-0.62 (2H, m), 0.77-0.90 (2H, m), 1.87-1.99 (1H, m), 2.81-2.94 (4H, m), 3.58-3.82 (7H, m), 6.49 (1H, s), 7.21 (1H, s), 10.06 (1H, brs).

D) Methyl 5-cyclopropyl-2-(morpholin-4-yl)-4-(((trifluoromethyl)sulfonyl)oxy)benzoate Using methyl 5-cyclopropyl-4-hydroxy-2-(morpholin-4-yl)benzoate, the title compound was obtained in the similar manner as in Step A of Example 180.

$^1$H NMR (300 MHz, DMSO-$d_6$) δ 0.68-0.76 (2H, m), 0.96-1.04 (2H, m), 1.86-1.97 (1H, m), 2.88-2.99 (4H, m), 3.64-3.73 (4H, m), 3.81 (3H, s), 6.98 (1H, s), 7.34 (1H, s).

E) Methyl 2-cyclopropyl-4'-fluoro-5-(morpholin-4-yl)biphenyl-4-carboxylate

Using methyl 5-cyclopropyl-2-(morpholin-4-yl)-4-(((trifluoromethyl)sulfonyl)oxy)benzoate and (4-fluorophenyl)boronic acid, the title compound was obtained in the similar manner as in Step B of Example 1.

MS (ESI+): $[M+H]^+$ 356.2.

F) 2-Cyclopropyl-4'-fluoro-5-(morpholin-4-yl)biphenyl-4-carbaldehyde

Using methyl 2-cyclopropyl-4'-fluoro-5-(morpholin-4-yl)biphenyl-4-carboxylate, the title compound was obtained in the similar manner as in Step C of Example 1.

$^1H$ NMR (300 MHz, DMSO-$d_6$) δ 0.55-0.68 (2H, m), 0.77-0.88 (2H, m), 1.71-1.84 (1H, m), 2.97-3.07 (4H, m), 3.71-3.81 (4H, m), 6.99 (1H, s), 7.25-7.38 (3H, m), 7.49-7.59 (2H, m), 10.22 (1H, s).

G) Ethyl 1-(2-((2-cyclopropyl-4'-fluoro-5-(morpholin-4-yl)biphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-5-(morpholin-4-yl)biphenyl-4-carbaldehyde, the title compound was obtained in the similar manner as in Step G of Example 1.

MS (ESI+): $[M+H]^+$ 591.2.

H) 1-(2-((2-Cyclopropyl-4'-fluoro-5-(morpholin-4-yl)biphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-5-(morpholin-4-yl)biphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 202

1-(2-((5-Cyclopropyl-2-ethoxy-6-(4-fluorophenyl)pyridin-3-yl)methyl)-5-oxa-2,6-diazaspiro[3.4]oct-6-en-7-yl)-4-methylpiperidine-4-carboxylic acid A) 6-(4-Fluorophenyl)-2-hydroxynicotinonitrile 2-Cyanoacetamide (1.44 and 3-(dimethylamino)-1-(4-fluorophenyl)prop-2-en-1-one (3.00 g) were sequentially added to a mixture of sodium hydride (60% dispersion in oil, 1.37 g) and DMF (30 mL), the resultant was stirred for 2 hours at 105° C., and then the solvent was distilled off under reduced pressure. After water was added to the obtained residue, acetic acid was added thereto to make it acidic, and the resultant was stirred for 15 minutes at 70° C. Methanol was added to the reaction mixture to suspend, the precipitated solid was collected by filtration, and the obtained solid was washed with ethyl acetate, thereby obtaining the title compound (3.01 g).

$^1H$ NMR (300 MHz, DMSO-$d_6$) δ 6.78 (1H, brs), 7.38 (2H, t, J=8.9 Hz), 7.89 (2H, dd, J 8.6, 5.4 Hz), 8.20 (1H, d, J=7.6 Hz), 12.76 (1H, brs).

B) 5-Bromo-6-(4-fluorophenyl)-2-hydroxynicotinonitrile

N-bromosuccinimide (2.66 g) was added to a mixture of 6-(4-fluorophenyl)-2-hydroxynicotinonitrile (2.91 g), THF (30 mL) and methanol (30 mL), the resultant was stirred for 10 minutes at room temperature, and then the solvent was distilled off under reduced pressure. After the obtained residue was suspended in water, ethyl acetate and hexane, the obtained solid was washed with hexane, thereby obtaining the title compound (3.98 g).

$^1H$ NMR (300 MHz, DMSO-$d_6$) δ 7.37 (2H, t, J=8.9 Hz), 7.63 (2H, dd, J=8.7, 5.4 Hz), 8.54 (1H, s).

C) 5-Bromo-2-ethoxy-6-(4-fluorophenyl)nicotinonitrile

Iodoethane (1.43 mL) was added to a mixture of 5-bromo-6-(4-fluorophenyl)-2-hydroxynicotinonitrile (3.49 g), potassium carbonate (3.29 g) and DMF (30 mL), and the resultant was stirred for 30 minutes at 80° C. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (3.00 g).

$^1H$ NMR (300 MHz, $CDCl_3$) δ 1.45 (3H, t, J=7.1 Hz), 4.51 (2H, q, J=7.0 Hz), 7.16 (2H, t, J=8.7 Hz), 7.77 (2H, dd, J=8.9, 5.3 Hz), 8.10 (1H, s).

D) Ethyl 5-bromo-2-ethoxy-6-(4-fluorophenyl)nicotinate

8 M aqueous potassium hydroxide solution (14.6 mL) was added to a mixture of 5-bromo-2-ethoxy-6-(4-fluorophenyl)nicotinonitrile (3.75 g), THF (10 mL) and ethanol (10 mL), and the resultant was stirred overnight at 100° C. After the reaction mixture was neutralized with 6 M hydrochloric acid, extraction thereof was performed using ethyl acetate, the organic layer was dried over anhydrous magnesium sulfate, and then the solvent was distilled off under reduced pressure. The obtained residue was dissolved in DMF (10 mL), potassium carbonate (3.23 g) and iodoethane (1.40 mL) were added to the solution, and the resultant was stirred for 30 minutes at 60° C. Water was added to the reaction mixture, and extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.40 g).

$^1H$ NMR (300 MHz, $CDCl_3$) δ 1.33-1.50 (6H, m), 4.38 (2H, q, J=7.1 Hz), 4.49 (2H, q, J=7.0 Hz), 7.14 (2H, t, J=8.8 Hz), 7.79 (2H, dd, J=8.9, 5.4 Hz), 8.38 (1H, s).

E) Ethyl 5-cyclopropyl-2-ethoxy-6-(4-fluorophenyl)nicotinate

Tris(dibenzylideneacetone)dipalladium(0) (418 mg) was added to a mixture of ethyl 5-bromo-2-ethoxy-6-(4-fluorophenyl)nicotinate (2.40 g), cyclopropylboronic acid (1.68 g), dicyclohexyl(2',6'-dimethoxybiphenyl-2-yl)phosphine (401 mg), 2 M aqueous sodium carbonate solution (9.78 mL) and toluene (25 mL), and the resultant was stirred for 2 hours at 100° C. in an argon atmosphere. The reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.06 g).

$^1H$ NMR (300 MHz, $CDCl_3$) δ 0.60-0.68 (2H, m), 0.84-0.96 (2H, m), 1.33-1.47 (6H, m), 1.89-2.00 (1H, m), 4.37 (2H, q, J=7.2 Hz), 4.50 (2H, q, J=7.0 Hz), 7.14 (2H, t, J=8.7 Hz), 7.77 (2H, dd, J=8.8, 5.5 Hz), 7.82 (1H, s).

F) 5-Cyclopropyl-2-ethoxy-6-(4-fluorophenyl)nicotinaldehyde

A solution of ethyl 5-cyclopropyl-2-ethoxy-6-(4-fluorophenyl)nicotinate (2.06 g) in THF (20 mL) was added to a suspension of lithium aluminum hydride (237 mg) in THF (20 mL) under ice-cooling in a nitrogen atmosphere. After stirring for 30 minutes at the same temperature, water (0.20 mL) and 15% aqueous sodium hydroxide solution (0.20 mL) were added thereto, the resultant was stirred for 5 minutes, and then water (0.60 mL) was further added thereto. After the reaction mixture was stirred for 1 hour, it was filtered, and the filtrate was concentrated under reduced pressure. The obtained residue was dissolved in toluene (10 mL), manganese dioxide (5.43 g) was added to the solution, and the resultant was stirred for 1 hour at 60° C. in a nitrogen atmosphere. After the reaction mixture was filtered, the obtained filtrate was concentrated under reduced pressure. The obtained residue was purified by a silica gel column chromatography (hexane/ethyl acetate), thereby obtaining the title compound (1.47 g).

$^1$H NMR (300 MHz, $CDCl_3$) δ 0.64-0.71 (2H, m), 0.88-0.99 (2H, m), 1.44 (3H, t, J=7.1 Hz), 1.86-2.01 (1H, m), 4.54 (2H, q, J=7.1 Hz), 7.15 (2H, t, J=8.8 Hz), 7.75-7.83 (3H, m), 10.38 (1H, s).

G) Ethyl 1-(2-((5-cyclopropyl-2-ethoxy-6-(4-fluorophenyl)pyridin-3-yl)methyl)-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-5-oxa-2,6-diazaspiro[3.4]oct-6-ene-2-carboxylate (809 mg) and formic acid (10 mL) was stirred for 1 hour at 60° C. The solvent of the reaction mixture was distilled off under reduced pressure, toluene was added to the obtained residue, and furthermore the solvent was distilled off under reduced pressure. The obtained residue was mixed with 5-cyclopropyl-2-ethoxy-6-(4-fluorophenyl)nicotinaldehyde (550 mg) and THF (5 mL), and the mixture was stirred for 15 minutes at room temperature. Sodium triacetoxyborohydride (613 mg) was added thereto at room temperature, and the resultant was stirred for 2 hours at room temperature. Water was added to the reaction mixture, and the resultant was stirred for 10 minutes. After an aqueous saturated sodium hydrogen carbonate solution was added to the reaction mixture, extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (866 mg).

$^1$H NMR (300 MHz, $CDCl_3$) δ 0.50-0.64 (2H, m), 0.79-0.95 (2H, m), 1.21 (3H, s), 1.26 (3H, t, J=7.1 Hz), 1.33-1.54 (5H, m), 1.85-1.97 (1H, m), 2.11 (2H, d, J=13.5 Hz), 2.87-3.06 (2H, m), 3.29 (2H, s), 3.32-3.44 (2H, m), 3.44-3.90 (6H, m), 4.12 (2H, q, J=7.1 Hz), 4.40 (2H, q, J=7.1 Hz), 7.11 (2H, t, J=8.8 Hz), 7.19 (1H, s), 7.71 (2H, dd, J=8.8, 5.6 Hz).

H) 1-(2-((5-Cyclopropyl-2-ethoxy-6-(4-fluorophenyl)pyridin-3-yl)methyl)-5-oxa-2,6-diazaspiro[3.4]oct-6-en-7-yl)-4-methylpiperidine-4-carboxylic acid A mixture of ethyl 1-(2-((5-cyclopropyl-2-ethoxy-6-(4-fluorophenyl)pyridin-3-yl)methyl)-5-oxa-2,6-diazaspiro[3.4]oct-6-en-7-yl)-4-methylpiperidine-4-carboxylate (860 mg), 2 M aqueous sodium hydroxide solution (4.69 mL), ethanol (2 mL) and THF (2 mL) was stirred for 1 hour at 70° C. The reaction mixture was cooled to room temperature, it was neutralized with 6 M hydrochloric acid. Ethyl acetate was added the reaction mixture, the solvent was distilled off under reduced pressure, the precipitated solid was collected by filtration, and it was washed with diethyl ether. The obtained solid was recrystallized (hexane/ethyl acetate), thereby obtaining the title compound (512 mg).

$^1$H NMR (300 MHz, DMSO-$d_6$) δ 0.56 (2H, q, J=5.4 Hz), 0.77-0.94 (2H, m), 1.14 (3H, s), 1.23-1.47 (5H, m), 1.75-1.98 (3H, m), 2.81-2.98 (2H, m), 3.09-3.39 (6H, m), 3.41-3.65 (4H, m), 4.32 (2H, q, J=7.0 Hz), 7.20-7.36 (3H, m), 7.73 (2H, dd, J=8.4, 6.1 Hz), 12.43 (1H, brs).

Example 203

1-(2-((5-Cyclopropyl-2-methoxy-4-(piperidin-1-yl)benzyl)-5-oxa-2,6-diazaspiro[3.4]oct-6-en-7-yl)-4-methylpiperidine-4-carboxylic acid A) Methyl 2-methoxy-4-(piperidin-1-yl)benzoate Using methyl 4-fluoro-2-methoxybenzoate and piperidine, the title compound was obtained in the similar manner as in Step A of Example 189.

$^1$H NMR (300 MHz, $CDCl_3$) δ 1.55-1.76 (6H, m), 3.27-3.38 (4H, m), 3.83 (3H, s), 3.89 (3H, s), 6.36 (1H, d, J=2.3 Hz), 6.45 (1H, dd, J=8.9, 2.4 Hz), 7.79 (1H, d, J=8.8 Hz).

C) Methyl 5-bromo-2-methoxy-4-(piperidin-1-yl)benzoate

Using methyl 2-methoxy-4-(piperidin-1-yl)benzoate, the title compound was obtained in the similar manner as in Step B of Example 189.

$^1$H NMR (300 MHz, $CDCl_3$) δ 1.58-1.66 (2H, m), 1.70-1.82 (4H, m), 3.01-3.11 (4H, m), 3.85 (3H, s), 3.90 (3H, s), 6.55 (1H, s), 8.04 (1H, s).

C) Methyl 5-cyclopropyl-2-methoxy-4-(piperidin-1-yl)benzoate

Using methyl 5-bromo-2-methoxy-4-(piperidin-1-yl)benzoate and cyclopropylboronic acid, the title compound was obtained in the similar manner as in Step C of Example 189.

$^1$H NMR (300 MHz, $CDCl_3$) δ 0.64-0.78 (2H, m), 0.90-1.03 (2H, m), 1.56-1.66 (2H, m), 1.68-1.78 (4H, m), 1.94-2.11 (1H, m), 2.97-3.13 (4H, m), 3.84 (3H, s), 3.88 (3H, s), 6.53 (1H, s), 7.32 (1H, s).

D) 5-Cyclopropyl-2-methoxy-4-(piperidin-1-yl)benzaldehyde

Using methyl 5-cyclopropyl-2-methoxy-4-(piperidin-1-yl)benzoate and Dess-Martin periodinane instead of manganese dioxide, the title compound was obtained in the similar manner as in Step D of Example 189.

$^1$H NMR (300 MHz, $CDCl_3$) δ 0.69-0.79 (2H, m), 0.92-1.04 (2H, m), 1.54-1.67 (2H, m), 1.70-1.81 (4H, m), 1.92-2.04 (1H, m), 3.05-3.17 (4H, m), 3.89 (3H, s), 6.46 (1H, s), 7.30 (1H, s), 10.27 (1H, s).

E) Ethyl 1-(2-((5-cyclopropyl-2-methoxy-4-(piperidin-1-yl)benzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 5-cyclopropyl-2-methoxy-4-(piperidin-1-yl)benzaldehyde, the title compound was obtained in the similar manner as in Step E of Example 189.

MS (ESI+): $[M+H]^+$ 525.5.

F) 1-(2-((5-Cyclopropyl-2-methoxy-4-(piperidin-1-yl)benzyl)-5-oxa-2,6-diazaspiro[3.4]oct-6-en-7-yl)-4-methylpiperidine-4-carboxylic acid Using ethyl 1-(2-(5-cyclopropyl-2-methoxy-4-(piperidin-1-yl)benzyl)-5-oxa-2,6-diazaspiro[3.4]oct-6-en-7-yl)-4-methylpiperidine-4-carboxylate, the title compound was obtained in the similar manner as in Step F of Example 189.

Example 204

1-(2-((5-Cyclopropyl-2-ethoxybiphenyl-3-yl)methyl)-5-oxa-2,6-diazaspiro[3.4]oct-6-en-7-yl)-4-methylpiperidine-4-carboxylic acid A) 5-Bromo-2-(methoxymethoxy)benzaldehyde Using 5-bromo-2-hydroxybenzaldehyde and chloro(methoxy)methane, the title compound was obtained in the similar manner as in Step A of Example 1.

$^1$H NMR (300 MHz, $CDCl_3$) δ 3.52 (3H, s), 5.29 (2H, s), 7.15 (1H, d, J=8.9 Hz), 7.61 (1H, dd, J=8.9, 2.6 Hz), 7.94 (1H, d, J=2.5 Hz), 10.42 (1H, s).

B) 5-Cyclopropyl-2-hydroxybenzaldehyde

Using 5-bromo-2-(methoxymethoxy)benzaldehyde and cyclopropylboronic acid, the title compound was obtained in the similar manner as in Step D of Example 23 and Step F of Example 88.

$^1$H NMR (300 MHz, $CDCl_3$) δ 0.60-0.68 (2H, m), 0.91-1.00 (2H, m), 1.84-1.95 (1H, m), 6.87-6.93 (1H, m), 7.24-7.30 (2H, m), 9.86 (1H, s), 10.82 (1H, s).

C) 5-Cyclopropyl-2-hydroxy-3-iodobenzaldehyde

Using 5-cyclopropyl-2-hydroxybenzaldehyde, the title compound was obtained in the similar manner as in Step A of Example 87.

$^1$H NMR (300 MHz, $CDCl_3$) δ 0.62-0.70 (2H, m), 0.93-1.03 (2H, m), 1.83-1.93 (1H, m), 7.28 (1H, d, J=2.2 Hz), 7.75 (1H, d, J=2.2 Hz), 9.72 (1H, s), 11.59 (1H, s).

D) 5-Cyclopropyl-2-ethoxy-3-iodobenzaldehyde

Using 5-cyclopropyl-2-hydroxy-3-iodobenzaldehyde and iodoethane, the title compound was obtained in the similar manner as in Step A of Example 1.

MS (ESI+): $[M+H]^+$ 317.1.

E) 5-Cyclopropyl-2-ethoxybiphenyl-3-carbaldehyde

Using 5-cyclopropyl-2-ethoxy-3-iodobenzaldehyde and phenylboronic acid, the title compound was obtained in the similar manner as in Step K of Example 88.

MS (ESI+): $[M+H]^+$ 267.2.

F) Ethyl 1-(2-((5-cyclopropyl-2-ethoxybiphenyl-3-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 5-cyclopropyl-2-ethoxybiphenyl-3-carbaldehyde, the title compound was obtained in the similar manner as in Step G of Example 1.

MS (ESI+): $[M+H]^+$ 532.5.

G) 1-(2-((5-Cyclopropyl-2-ethoxybiphenyl-3-yl)methyl)-5-oxa-2,6-diazaspiro[3.4]oct-6-en-7-yl)-4-methylpiperidine-4-carboxylic acid Using ethyl 1-(2-((5-cyclopropyl-2-ethoxybiphenyl-3-yl)methyl)-5-oxa-2,6-diazaspiro[3.4]oct-6-en-7-yl)-4-methylpiperidine-4-carboxylate, the title compound was obtained in the similar manner as in Example 2.

Example 205

1-(2-((2-Cyclopropyl-5-ethoxy-4'-fluorobiphenyl-4-yl)methyl)-5-oxa-2,6-diazaspiro[3.4]oct-6-en-7-yl)-4-methylpiperidine 1 carboxylic acid A) 2-Cyclopropyl-5-ethoxy-4'-fluorobiphenyl-4-carbaldehyde 2-Cyclopropyl-4'-fluoro-5-hydroxybiphenyl-4-carbaldehyde (250 mg), iodoethane (228 mg) and potassium carbonate (270 mg) were added to DMF (1.0 mL), and the resultant was stirred for 30 minutes at 70° C. The reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (230 mg).

$^1$H NMR (400 MHz, $CDCl_3$) δ 0.63-0.71 (2H, m), 0.76-0.84 (2H, m), 1.46 (3H, t, J=7.0 Hz), 1.67-1.77 (1H, m), 4.14 (2H, q, J=6.9 Hz), 6.81 (1H, s), 7.08-7.18 (2H, m), 7.37-7.47 (3H, m), 10.48 (1H, s).

B) Ethyl 1-(2-((2-cyclopropyl-5-ethoxy-4'-fluorobiphenyl-4-yl)methyl)-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-5-oxa-2,6-diazaspiro[3.4]oct-6-ene-2-carboxylate (295 mg) was added to formic acid (2 mL), the resultant was stirred for 30 minutes at 70° C., and then the solvent was distilled off under reduced pressure. The obtained residue was mixed with 2-cyclopropyl-5-ethoxy-4'-fluorobiphenyl-4-carbaldehyde (220 mg) and THF (10 mL), sodium triacetoxyborohydride (246 mg) was added to the mixture, and the resultant was stirred for 3 hours at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (370 mg).

$^1$H NMR (400 MHz, $CDCl_3$) δ 0.54-0.61 (2H, m), 0.72-0.78 (2H, m), 1.21 (3H, s), 1.26 (3H, t, J=7.1 Hz), 1.37-1.50 (5H, m), 1.70-1.80 (1H, m), 2.11 (2H, d, J=13.6 Hz), 2.92-3.01 (2H, m), 3.27 (2H, s), 3.35-3.43 (4H, m), 3.56 (2H, d, J=8.8 Hz), 3.69 (2H, s), 4.00 (2H, q, J=7.0 Hz), 4.16

(2H, q, J=7.1 Hz), 6.67 (1H, s), 6.84 (1H, s), 7.05-7.13 (2H, m), 7.39 (2H, dd, J=8.5, 5.5 Hz).

C) 1-(2-((2-Cyclopropyl-5-ethoxy-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (2.2 mL) was added to a solution of ethyl 1-(2-((2-cyclopropyl-5-ethoxy-4'-fluorobiphenyl-4-yl)methyl)-5-oxa-2,6-diazaspiro[3.4]oct-6-en-7-yl)-4-methylpiperidine-4-carboxylate (350 mg) in ethanol (4.0 mL), and the resultant was stirred for 2 hours at 60° C. The reaction mixture was cooled to room temperature, it was neutralized with 2 M hydrochloric acid, and the resultant was stirred for 30 minutes. The precipitated solid was collected by filtration, thereby obtaining the title compound (276 mg).

$^1$H NMR (400 MHz, DMSO-$d_6$) δ 0.49-0.56 (2H, m), 0.75 (2H, d, J=8.4 Hz), 1.14 (3H, s), 1.28-1.42 (5H, m), 1.69-1.78 (1H, m), 1.91 (2H, d, J=13.7 Hz), 2.89 (2H, t, J=10.2 Hz), 3.16 (2H, brs), 3.31 (4H, brs), 3.41-3.60 (4H, m), 4.02 (2H, q, J=6.9 Hz), 6.73 (1H, s), 6.84 (1H, s), 7.26 (2H, t, J=8.7 Hz), 7.47 (2H, dd, J=8.3, 5.8 Hz), 12.37 (1H, brs).

Example 206

1-(2-((2-Cyclopropyl-4'-fluoro-6-isopropoxybiphenyl-4-yl)methyl)-5-oxa-2,6-diazaspiro[3.4]oct-6-en-7-yl)-4-methylpiperidine-4-carboxylic acid A) 2-Cyclopropyl-4'-fluoro-6-isopropoxybiphenyl-4-carbaldehyde 2-Bromopropane (204 mg) was added to a mixture of 2-cyclopropyl-4'-fluoro-6-hydroxybiphenyl-4-carbaldehyde (283 mg), potassium carbonate (306 mg) and DMF (8 mL), and the resultant was stirred for 3 hours at 70° C. 2-Bromopropane (204 mg) and potassium carbonate (306 mg) were added thereto, and the resultant was stirred for 2 hours at 70° C. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (298 mg).

$^1$H NMR (300 MHz, $CDCl_3$) δ 0.67-0.75 (2H, m), 0.79-0.87 (2H, m), 1.18 (6H, d, J=6.0 Hz), 1.59-1.69 (1H, m), 4.44-4.55 (1H, m), 7.02 (1H, d, J=1.1 Hz), 7.08-7.16 (2H, m), 7.22-7.29 (3H, m), 9.93 (1H, s).

B) Ethyl 1-(2-((2-cyclopropyl-4'-fluoro-6-isopropoxybiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (309 mg) and formic acid (8 mL) was stirred for 1 hour at 60° C., the solvent was distilled off under reduced pressure. The obtained residue was mixed with 2-cyclopropyl-4'-fluoro-6-isopropoxybiphenyl-4-carbaldehyde (290 mg) and THF (10 mL), sodium triacetoxyborohydride (343 mg) was added to the mixture, and the resultant was stirred for 15 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (394 mg).

$^1$H NMR (300 MHz, $CDCl_3$) δ 0.58-0.66 (2H, m), 0.69-0.78 (2H, m), 1.11 (6H, d, J=6.1 Hz), 1.19-1.29 (6H, m), 1.39-1.51 (2H, m), 1.53-1.64 (1H, m), 2.11 (2H, d, J=13.6 Hz), 2.91-3.02 (2H, m), 3.26 (2H, s), 3.31-3.44 (4H, m), 3.54 (2H, d, J=9.0 Hz), 3.62 (2H, s), 4.16 (2H, q, J=7.1 Hz), 4.28-4.38 (1H, m), 6.41 (1H, d, J=0.8 Hz), 6.72 (1H, d, J=0.8 Hz), 7.03-7.11 (2H, m), 7.21-7.28 (2H, m).

C) 1-(2-((2-Cyclopropyl-4'-fluoro-6-isopropoxybiphenyl-4-yl)methyl)-5-oxa-2,6-diazaspiro[3.4]oct-6-en-7-yl)-4-methylpiperidine-4-carboxylic acid 2 M aqueous sodium hydroxide solution (2 mL) was added to a solution of ethyl 1-(2-((2-cyclopropyl-4'-fluoro-6-isopropoxybiphenyl-4-yl)methyl)-5-oxa-2,6-diazaspiro[3.4]oct-6-en-7-yl)-4-methylpiperidine-4-carboxylate (373 mg) in ethanol (8 mL), the resultant was stirred for 15 hours at 70° C., and the solvent was distilled off under reduced pressure. Water was added to the residue, the resultant was neutralized with 2 M hydrochloric acid, and then the precipitated solid was collected by filtration. After the obtained solid was dissolved in ethyl acetate and THF, it was dried over anhydrous magnesium sulfate, and the solvent was distilled off under reduced pressure. The obtained residue was crystallized (hexane/ethanol), thereby obtaining the title compound (258 mg).

$^1$H NMR (300 MHz, DMSO-$d_6$) δ 0.54-0.62 (2H, m), 0.66-0.75 (2H, m), 1.07 (611, d, J=6.0 Hz), 1.13 (3H, s), 1.29-1.53 (3H, m), 1.90 (2H, d, J=13.9 Hz), 2.82-2.94 (2H, m), 3.13 (2H, J=8.2 Hz), 3.25-3.37 (4H, m), 3.43 (2H, d, J=8.2 Hz), 3.53 (2H, s), 4.34-4.45 (1H, m), 6.41 (1H, s), 6.77 (1H, s), 7.16-7.27 (4H, m).

Example 207

1-(2-((2-Cyclopropyl-4'-fluoro-5-(tetrahydro-2H-pyran-4-yl)biphenyl-4-yl)methyl)-5-oxa-2,6-diazaspiro[3.4]oct-6-en-7-yl)-4-methylpiperidine-4-carboxylic acid A) Methyl 2-cyclopropyl-4'-fluoro-5-(((trifluoromethyl)sulfonyl)oxy)biphenyl-4-carboxylate Trifluoromethanesulfonic anhydride (3.3 mL) was added to a solution of methyl 2-cyclopropyl-4'-fluoro-5-hydroxybiphenyl-4-carboxylate (5.50 g) in pyridine (15 mL) under ice-cooling, and the resultant was stirred for 30 minutes at 0° C. The reaction mixture was concentrated, and the obtained residue was diluted by ethyl acetate. The organic layer was sequentially washed with 1 M hydrochloric acid and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (6.00 g).

$^1$H NMR (300 MHz, DMSO-$d_6$) δ 0.72-0.80 (2H, m), 0.89-0.98 (2H, m), 1.82-1.93 (1H, m), 3.90 (3H, s), 7.31-7.40 (3H, m), 7.51-7.60 (3H, m).

B) Methyl 2-cyclopropyl-4'-fluoro-5-(tetrahydro-2H-pyran-4-yl)biphenyl-4-carboxylate Using methyl 2-cyclopropyl-4'-fluoro-5-(((trifluoromethyl)sulfonyl)oxy)biphenyl-4-carboxylate and 4-(4,4,5,5-tetramethyl-1,3,2-dioxaborolan-2-yl)-3,6-dihydro-2H-pyran, the title compound was obtained in the similar manner as in Step D of Example 23.

$^1$H NMR (300 MHz, DMSO-$d_6$) δ 0.60-0.67 (2H, m), 0.80-0.88 (2H, m), 1.60-1.86 (5H, m), 3.35-3.50 (3H, m), 3.82-3.87 (3H, m), 3.88-3.97 (2H, m), 7.23 (1H, s), 7.25-7.35 (3H, m), 7.47-7.55 (2H, m).

C) 2-Cyclopropyl-4'-fluoro-5-(tetrahydro-2H-pyran-4-yl)biphenyl-4-carbaldehyde

Using methyl 2-cyclopropyl-4'-fluoro-5-(tetrahydro-2H-pyran-4-yl)biphenyl-4-carboxylate, the title compound was obtained in the similar manner as in Step D of Example 10.

$^1$H NMR (300 MHz, DMSO-$d_6$) δ 0.67-0.75 (2H, m), 0.83-0.92 (2H, m), 1.61-1.89 (5H, m), 3.41-3.54 (2H, m), 3.77-3.98 (3H, m), 7.25-7.36 (3H, m), 7.48 (1H, s), 7.50-7.58 (2H, m), 10.28 (1H, s).

D) Ethyl 1-(2-((2-cyclopropyl-4'-fluoro-5-(tetrahydro-2H-pyran-4-yl)biphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-5-(tetrahydro-2H-pyran-4-yl) biphenyl-4-carbaldehyde, the title compound was obtained in the similar manner as in Step G of Example 1.

MS (ESI+): $[M+H]^+$ 590.3.

E) 1-(2-((2-Cyclopropyl-4'-fluoro-5-(tetrahydro-2H-pyran-4-yl)biphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-5-(tetrahydro-2H-pyran-4-yl)biphenyl-4-yl)methyl)-5-oxa-2,6-diazaspiro [3.4]oct-6-en-7-yl)-4-methylpiperidine-4-carboxylate, the title compound was obtained in the similar manner as in Example 2.

Example 208

Trans-4-(2-((2-Cyclopropyl-4'-fluoro-6-propoxybiphenyl-4-yl)methyl)-5-oxa-2,6-diazaspiro[3.4]oct-6-en-7-yl)cyclohexane carboxylic acid A) Methyl trans-4-(2-((2-cyclopropyl-4'-fluoro-6-propoxybiphenyl-4-yl)methyl)-5-oxa-2,6-diazaspiro [3.4]oct-6-en-7-yl)cyclohexanecarboxylate Sodium triacetoxyborohydride (243 mg) was added to a mixture of methyl trans-4-(5-oxa-2,6-diazaspiro[3.4]oct-6-en-7-yl)cyclohexanecarboxylate hydrochloride (166 mg), 2-cyclopropyl-4'-fluoro-6-propoxybiphenyl-4-carbaldehyde (188 mg), triethylamine (116 mg) and THF (8 mL), and the resultant was stirred for 15 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (284 mg).

$^1$H NMR (300 MHz, $CDCl_3$) δ 0.59-0.66 (2H, m), 0.70-0.84 (5H, m), 1.30-1.65 (7H, m), 1.95-2.12 (4H, m), 2.23-2.43 (2H, m), 3.20 (2H, s), 3.36-3.42 (2H, m), 3.46-3.53 (2H, m), 3.63 (2H, s), 3.67 (3H, s), 3.82 (2H, t, J=6.3 Hz), 6.41 (1H, d, J=0.8 Hz), 6.69 (1H, d, J=0.9 Hz), 7.03-7.11 (2H, m), 7.22-7.29 (2H, m).

B) trans-4-(2-((2-Cyclopropyl-4'-fluoro-6-propoxybiphenyl-4-yl)methyl)-5-oxa-2,6-diazaspiro[3.4]oct-6-en-7-yl)cyclohexanecarboxylic acid 2 M aqueous sodium hydroxide solution (1.5 mL) was added to a solution of methyl trans-4-(2-((2-cyclopropyl-4'-fluoro-6-propoxybiphenyl-4-yl)methyl)-5-oxa-2,6-diazaspiro[3.4]oct-6-en-7-yl)cyclohexanecarboxylate (269 mg) in ethanol (8 mL), the resultant was stirred for 3 hours at 70° C., and then the solvent was distilled off under reduced pressure. Water was added to the obtained residue, the resultant was neutralized with 2 M hydrochloric acid, and then the precipitated solid was collected by filtration. After the obtained solid was dissolved in ethyl acetate and THF, it was dried over anhydrous magnesium sulfate, and the solvent was distilled off under reduced pressure. The residue was crystallized (hexane/ethanol), thereby obtaining the title compound (198 mg).

$^1$H NMR (300 MHz, DMSO-$d_6$) δ 0.55-0.62 (2H, m), 0.67-0.80 (5H, m), 1.23-1.39 (4H, m), 1.42-1.57 (3H, m), 1.79-1.99 (4H, m), 2.11-2.23 (1H, m), 2.24-2.36 (1H, m), 3.17-3.25 (4H, m), 3.41 (2H, d, J=8.4 Hz), 3.54 (2H, s), 3.81 (2H, t, J=6.2 Hz), 6.42 (1H, s), 6.76 (1H, s), 7.16-7.29 (4H, m), 12.11 (1H, brs).

Example 209

1-(2-((2-Cyclopropyl-4'-fluoro-6-propoxybiphenyl-4-yl)methyl)-5-oxa-2,6-diazaspiro[3.4]oct-6-en-7-yl) piperidine-4-carboxylic acid A) Ethyl 1-(2-((2-cyclopropyl-4'-fluoro-6-propoxybiphenyl-4-yl)methyl)-5-oxa-2,6-diazaspiro[3.4]oct-6-en-7-yl)piperidine-4-carboxylate After a mixture of tert-butyl 7-(4-(ethoxycarbonyl)piperidin-1-yl)-5-oxa-2,6-diazaspiro[3.4]oct-6-ene-2-carboxylate (207 mg) and formic acid (6 mL) was stirred for 1 hour at 60° C., the solvent was distilled off under reduced pressure. The obtained residue was mixed with 2-cyclopropyl-4'-fluoro-6-propoxybiphenyl-4-carbaldehyde (185 mg) and THF (10 mL), sodium triacetoxyborohydride (239 mg) was added to the mixture, and the resultant was stirred for 15 hours at mom temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (243 mg).

$^1$H NMR (300 MHz, $CDCl_3$) δ 0.59-0.66 (2H, m), 0.70-0.85 (5H, m), 1.26 (3H, t, J=7.1 Hz), 1.51-1.64 (3H, m), 1.66-1.81 (2H, m), 1.88-1.99 (2H, m), 2.37-2.51 (1H, m), 2.82-2.95 (2H, m), 3.27 (2H, s), 3.32-3.38 (2H, m), 3.52-3.65 (6H, m), 3.82 (2H, t, J=6.3 Hz), 4.15 (2H, q, J=7.2 Hz), 6.41 (1H, s), 6.68 (1H, s), 7.03-7.12 (2H, m), 7.21-7.30 (2H, m).

B) 1-(2-((2-Cyclopropyl-4'-fluoro-6-propoxybiphenyl-4-yl)methyl)-5-oxa-2,6-diazaspiro[3.4]oct-6-en-7-yl)piperidine-4-carboxylic acid 2 M aqueous sodium hydroxide solution (1.5 mL) was added to a solution of ethyl 1-(2-((2-cyclopropyl-4'-fluoro-6-propoxybiphenyl-4-yl)methyl)-5-oxa-2,6-diazaspiro[3.4]oct-6-en-7-yl)piperidine-4-carboxylate (241 mg) in ethanol (8 mL), and the resultant was stirred for 3 hours at 70° C., and the solvent was distilled off under reduced pressure. Water was added to the obtained residue, the resultant was neutralized with 2M hydrochloric acid, and then the precipitated solid was collected by filtration. After the obtained solid was dissolved in ethyl acetate and THF, it was dried over anhydrous magnesium sulfate, and the solvent was distilled off under reduced pressure. The obtained residue was crystallized (hexane/ethanol), thereby obtaining the title compound (150 mg).

$^1$H NMR (300 MHz, DMSO-$d_6$) δ 0.55-0.64 (2H, m), 0.68-0.80 (5H, m), 1.42-1.60 (5H, m), 1.74-1.86 (2H, m), 2.35-2.47 (1H, m), 2.76-2.90 (2H, m), 3.21-3.54 (8H, m), 3.65 (2H, brs), 3.82 (2H, t, J=6.2 Hz), 6.46 (1H, brs), 6.80 (1H, brs), 7.17-7.29 (4H, m).

Example 210

1-(2-((4-Cyclopropyl-6-ethoxy-5-(4-fluorophenyl)pyridin-2-yl)methyl)-5-oxa-2,6-diazaspiro[3.4]oct-6-en-7-yl)-4-methylpiperidine-4-carboxylic acid A) 3-(Benzyloxy)-2-chloro-6-(((triisopropylsilyl)oxy)methyl)pyridine Chloro(triisopropyl)silane (9.82 g) was added to a mixture of (5-(benzyloxy)-6-chloropyridin-2-yl)methanol (10.6 g), 1H-imidazole (3.76 g) and DMF (50 mL), and the resultant was stirred for 1 hour at mom temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (16.1 g).

$^1$H NMR (300 MHz, $CDCl_3$) δ 1.02-1.12 (18H, m), 1.24-1.34 (3H, m), 4.84 (2H, s), 5.18 (2H, s), 7.26 (1H, d, J=8.3 Hz), 7.30-7.51 (6H, m).

B) 3-(Benzyloxy)-2-ethoxy-6-(((triisopropylsilyl)oxy)methyl)pyridine

A mixture of 3-(benzyloxy)-2-chloro-6-(((triisopropylsilyl)oxy)methyl)pyridine (15.0 g), sodium ethoxide (7.54 g) and ethanol (90 mL) was stirred for 50 minutes at 150° C. under microwave irradiation. After water was added to the reaction mixture, extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (11.3 g).

$^1$H NMR (300 MHz, $CDCl_3$) δ 0.97-1.33 (21H, m), 1.42 (3H, t, J=7.1 Hz), 4.44 (2H, q, J=7.1 Hz), 4.73 (2H, s), 5.14 (2H, s), 6.87-6.97 (1H, m), 7.00-7.09 (1H, m), 7.29-7.47 (5H, m).

C) 2-Ethoxy-6-(((triisopropylsilyl)oxy)methyl)pyridin-3-ol

A mixture of 3-(benzyloxy)-2-ethoxy-6-(((triisopropylsilyl)oxy)methyl)pyridine (11.4 g), 10% palladium on carbon (55% water content, 5.00 g) and ethyl acetate (90 mL) was stirred for 30 minutes at room temperature in a hydrogen atmosphere. After the catalyst was filtered of the obtained filtrate was concentrated under reduced pressure. The obtained residue was purified by a silica gel column chromatography (hexane/ethyl acetate), thereby obtaining the title compound (7.78 g).

$^1$H NMR (300 MHz, $CDCl_3$) δ 1.01-1.34 (21H, m), 1.40 (3H, t, J=7.0 Hz), 4.41 (2H, q, J=7.1 Hz), 4.73 (2H, s), 5.30 (1H, s), 6.96-7.04 (1H, m), 7.09-7.15 (1H, m).

D) 2-Ethoxy-3-(methoxymethoxy)-6-(((triisopropylsilyl)oxy)methyl)pyridine

Chloro(methoxy)methane (2.72 mL) was added to a mixture of 2-ethoxy-6-(((triisopropylsilyl)oxy)methyl)pyridin-3-ol (7.78 g), potassium carbonate (6.61 g) and DMF (50 mL), and the resultant was stirred for 30 minutes at 0° C. in a nitrogen atmosphere. After water was added to the reaction mixture, extraction thereof was performed using ethyl acetate. After the obtained organic layer was dried over anhydrous magnesium sulfate, the solvent was distilled off under reduced pressure. The obtained residue was purified by a silica gel column chromatography (NH, hexane/ethyl acetate), thereby obtaining the title compound (6.91 g).

$^1$H NMR (300 MHz, $CDCl_3$) δ 1.03-1.34 (21H, m), 1.40 (3H, t, J=7.1 Hz), 3.51 (3H, s), 4.43 (2H, q, J=7.1 Hz), 4.74 (2H, s), 5.20 (2H, s), 7.02 (1H, d, J=7.9 Hz), 7.36 (1H, d, J=7.9 Hz).

E) 2-Ethoxy-4-iodo-3-(methoxymethoxy)-6-(((triisopropylsilyl)oxy)methyl)pyridine n-Butyllithium (1.6 M hexane solution, 15.2 mL) was added to a mixture of 2-ethoxy-3-(methoxymethoxy)-6-(((triisopropylsilyl)oxy)methyl)pyridine (6.91 g) and THF (50 mL) at −78° C., and the resultant was stirred for 1 hour at the same temperature. Iodine (6.17 g) was added to the reaction mixture at −78° C., and the resultant was warmed to room temperature. After an aqueous saturated ammonium chloride solution and an aqueous saturated sodium thiosulfate solution were added to the reaction mixture, extraction thereof was performed using ethyl acetate. The obtained organic layer was dried over anhydrous magnesium sulfate, and concentrated under reduced pressure. The obtained residue was purified by a silica gel column chromatography (hexane/ethyl acetate), thereby obtaining the title compound (7.90 g).

$^1$H NMR (300 MHz, $CDCl_3$) δ 1.04-1.32 (21H, m), 1.38 (3H, t, J=7.0 Hz), 3.67 (3H, s), 4.35 (2H, q, J=7.1 Hz), 4.70 (2H, s), 5.19 (2H, s), 7.47 (1H, s).

F) 4-Cyclopropyl-2-ethoxy-3-(methoxymethoxy)-6-(((triisopropylsilyl)oxy)methyl)pyridine Tris(dibenzylideneacetone)dipalladium(0) (1.02 g) was added to a mixture of 2-ethoxy-4-iodo-3-

(methoxymethoxy)-6-(((triisopropylsilyl)oxy)methyl)pyridine (7.90 g), cyclopropylboronic acid (4.11 g), dicyclohexyl(2',6'-dimethoxybiphenyl-2-yl)phosphine (982 mg), 2 M aqueous sodium carbonate solution (23.9 mL) and toluene (25 mL), and the resultant was stirred for 2 hours at 100° C. in an argon atmosphere. The reaction mixture was cooled to room temperature, and extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (6.39 g).

$^1$H NMR (300 MHz, $CDCl_3$) δ 0.69-0.80 (2H, m), 0.98-1.31 (23H, m), 1.38 (3H, t, J=7.1 Hz), 2.23-2.42 (1H, m), 3.61 (3H, s), 4.35 (2H, q, J=7.1 Hz), 4.68 (2H, s), 5.14 (2H, s), 6.52 (1H, s).

G) (4-Cyclopropyl-6-ethoxy-5-(methoxymethoxy)pyridin-2-yl)methanol

Tetrabutylammonium fluoride (1.0 M THF solution, 23.4 mL) was added to a mixture of 4-cyclopropyl-2-ethoxy-3-(methoxymethoxy)-6-(((triisopropylsilyl)oxy)methyl)pyridine (6.39 g) and THF (50 mL) at room temperature, and the resultant was stirred for 10 minutes. An aqueous ammonium chloride solution was added to the reaction mixture, and extraction thereof was performed using ethyl acetate. After the obtained organic layer was dried over anhydrous magnesium sulfate, the solvent was distilled off under reduced pressure. The obtained residue was purified by a silica gel column chromatography (hexane/ethyl acetate), thereby obtaining the title compound (4.11 g).

$^1$H NMR (300 MHz, $CDCl_3$) δ 0.68-0.79 (2H, m), 0.98-1.12 (2H, m), 1.41 (3H, t, J=7.1 Hz), 2.27-2.43 (1H, m), 3.22 (1H, t, J=5.2 Hz), 3.61 (3H, s), 4.42 (2H, q, J=7.1 Hz), 4.53 (2H, d, J=5.2 Hz), 5.16 (2H, s), 6.16 (1H, s).

H) 4-Cyclopropyl-6-ethoxy-5-(methoxymethoxy)pyridine-2-carbaldehyde

Manganese dioxide (7.05 g) was added to a mixture of (4-cyclopropyl-6-ethoxy-5-(methoxymethoxy)pyridin-2-yl)methanol (4.11 g) and toluene (10 mL), and the resultant was stirred for 10 minutes at 60° C. After the reaction mixture was filtered, the obtained filtrate was concentrated under reduced pressure. The obtained residue was purified by a silica gel column chromatography (hexane/ethyl acetate), thereby obtaining the title compound (3.45 g).

$^1$H NMR (300 MHz, $CDCl_3$) δ 0.75-0.86 (2H, m), 1.05-1.17 (2H, m), 1.45 (3H, t, J=7.1 Hz), 2.29-2.47 (1H, m), 3.60 (3H, s), 4.51 (2H, q, J=7.1 Hz), 5.29 (2H, s), 7.01 (1H, s), 9.81 (1H, s).

I) 4-Cyclopropyl-6-ethoxy-5-hydroxypyridine-2-carbaldehyde

A mixture of 4-cyclopropyl-6-ethoxy-5-(methoxymethoxy)pyridine-2-carbaldehyde (3.15 g) and formic acid (5 mL) was stirred for 30 minutes at 60° C. The formic acid was distilled off under reduced pressure, and the obtained residue was washed with diethyl ether and hexane, thereby obtaining the title compound (2.38 g).

$^1$H NMR (300 MHz, $CDCl_3$) δ 0.73-0.91 (2H, m), 1.00-1.15 (2H, m), 1.46 (3H, t, J=7.1 Hz), 2.09-2.32 (1H, m), 4.55 (2H, q, J=7.1 Hz), 6.11 (1H, brs), 7.11 (1H, s), 9.78 (1H, s).

J) 4-Cyclopropyl-6-ethoxy-5-(4-fluorophenyl)pyridine-2-carbaldehyde

Sodium hydride (60% dispersion in oil, 352 mg) was added to a mixture of 4-cyclopropyl-6-ethoxy-5-hydroxypyridine-2-carbaldehyde (1.52 g) and THF (20 mL), and the resultant was stirred for 30 minutes at room temperature. N-phenyl bis(trifluoromethanesulfonimide) (3.41 g) and DMF (1 mL) were added to the reaction mixture, and the resultant was stirred for 30 minutes at room temperature. A saturated saline solution was added to the reaction mixture, extraction thereof was performed using ethyl acetate. The obtained organic layer was dried over anhydrous magnesium sulfate, and then distilled off under reduced pressure. The obtained residue was purified by a silica gel column chromatography (hexane/ethyl acetate). The obtained solid was mixed with (4-fluorophenyl)boronic acid (3.08 g), cesium fluoride (3.34 g) and DME (20 mL), (1,1'-bis(diphenylphosphino)ferrocene)dichloropalladium(II) dichloromethane adduct (1.07 g) was added to the mixture, and the resultant was stirred for 15 hours at 100° C. in an argon atmosphere. Water was added to the reaction mixture, and extraction thereof was performed using ethyl acetate. After the obtained organic layer was dried over anhydrous magnesium sulfate, it was concentrated under reduced pressure. The obtained residue was purified by a silica gel column chromatography (hexane/ethyl acetate), thereby obtaining the title compound (1.59 g).

$^1$H NMR (300 MHz, $CDCl_3$) δ 0.77-1.03 (4H, m), 1.25-1.32 (3H, m), 1.62-1.79 (1H, m), 4.43 (2H, q, J=7.1 Hz), 7.05 (1H, s), 7.09-7.20 (2H, m), 7.31 (2H, dd, J=8.8, 5.5 Hz), 9.91 (1H, s).

K) Ethyl 1-(2-((4-cyclopropyl-6-ethoxy-5-(4-fluorophenyl)pyridin-2-yl)methyl)-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-5-oxa-2,6-diazaspiro[3.4]oct-6-ene-2-carboxylate (809 mg) and formic acid (5 mL) was stirred for 1 hour at 60° C. The solvent of the reaction mixture was distilled off under reduced pressure, toluene was added to the obtained residue, and then the solvent was distilled off under reduced pressure. The obtained residue was mixed with 4-cyclopropyl-6-ethoxy-5-(4-fluorophenyl)pyridine-2-carbaldehyde (550 mg) and THF (5 mL), and the mixture was stirred for 15 minutes at mom temperature. Sodium triacetoxyborohydride (613 mg) was added thereto at room temperature, and the resultant was stirred for 2 hours at room temperature. Water was added to the reaction mixture, and the resultant was stirred for 10 minutes. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel chromatography (hexane/ethyl acetate/methanol), thereby obtaining the title compound (1.02 g).

$^1$H NMR (300 MHz, $CDCl_3$) δ 0.68-0.77 (2H, m), 0.83-0.94 (2H, m), 1.16-1.33 (9H, m), 1.37-1.52 (2H, m), 1.54-1.71 (1H, m), 2.11 (2H, d, J=13.5 Hz), 2.86-3.08 (2H, m), 3.26-3.50 (4H, m), 3.58-4.04 (6H, m), 4.12-4.21 (2H, m), 4.28 (2H, d, J=7.1 Hz), 6.28 (1H, s), 7.04-7.15 (2H, m), 7.21-7.31 (2H, m).

L) 1-(2-((4-Cyclopropyl-6-ethoxy-5-(4-fluorophenyl)pyridin-2-yl)methyl)-5-oxa-2,6-diazaspiro[3.4]oct-6-en-7-yl)-4-methylpiperidine-4-carboxylic acid A mixture of ethyl 1-(2-((4-cyclopropyl-6-ethoxy-5-(4-fluorophenyl)pyridin-2-yl)methyl)-5-oxa-2,6-diazaspiro[3.4]oct-6-en-7-yl)-4-methylpiperidine-4-carboxylate (1.00 g), 2 M aqueous sodium hydroxide solution (5.45 mL), ethanol (2 mL) and THF (2 mL) was stirred for 1 hour at 70° C. The reaction mixture was cooled to room temperature, and it was neutralized with 6 M hydrochloric acid. Ethyl acetate was added thereto, the solvent was distilled off to ⅓ amount thereof under reduced pressure, and the precipitated solid was collected by filtration. The obtained solid was recrystallized (hexane/ethyl acetate), thereby obtaining the title compound (487 mg).

$^1$H NMR (300 MHz, DMSO-$d_6$) δ 0.64-0.78 (2H, m), 0.80-0.94 (2H, m), 1.09-1.20 (6H, m), 1.30-1.45 (2H, m), 1.45-1.62 (1H, m), 1.91 (2H, d, J=13.8 Hz), 2.78-2.95 (2H, m), 3.14-3.41 (6H, m), 3.44-3.63 (4H, m), 4.22 (2H, q, J=7.0 Hz), 6.39 (1H, s), 7.11-7.45 (4H, m), 12.45 (1H, brs).

Example 211

1-(2-((2-Cyclopropyl-4'-fluoro-5-(thiomorpholin-4-yl)biphenyl-4-yl)methyl)-5-oxa-2,6-diazaspiro[3.4]oct-6-en-7-yl)-4-methylpiperidine-4-carboxylic acid A) Methyl 2-fluoro-4-(((trifluoromethyl)sulfonyl)oxy)benzoate Using methyl 2-fluoro-4-hydroxybenzoate, the title compound was obtained in the similar manner as in Step D of Example 94.

$^1$H NMR (300 MHz, DMSO-$d_6$) δ 3.89 (3H, s), 7.54 (1H, dd, J=8.8, 1.7 Hz), 7.83 (1H, dd, J=10.7, 2.5 Hz), 8.10 (1H, t, J=8.5 Hz).

B) Methyl 3,4'-difluorobiphenyl-4-carboxylate

Using methyl 2-fluoro-4-(((trifluoromethyl)sulfonyl)oxy)benzoate and (4-fluorophenyl)boronic acid, the title compound was obtained in the similar manner as in Step B of Example 1.

$^1$H NMR (300 MHz, DMSO-$d_6$) δ 3.88 (3H, s), 7.35 (2H, t, J=8.8 Hz), 7.63-7.75 (2H, m), 7.81-7.91 (2H, m), 7.96 (1H, t, J=8.0 Hz).

C) Methyl 4'-fluoro-3-(thiomorpholin-4-yl)biphenyl-4-carboxylate

Methyl 3,4'-difluorobiphenyl-4-carboxylate (3.10 g), thiomorpholine (5.15 g) and potassium carbonate (6.90 g) were added to DMF (10 mL), and the resultant was stirred for 3 hours at 140° C. The reaction mixture was cooled to room temperature, water was added thereto, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound.

MS (ESI+): $[M+H]^+$ 332.2.

D) Methyl 2-bromo-4'-fluoro-5-(thiomorpholin-4-yl)biphenyl-4-carboxylate

Using methyl 4'-fluoro-3-(thiomorpholin-4-yl)biphenyl-4-carboxylate, the title compound was obtained in the similar manner as in Step D of Example 185.

MS (ESI+): $[M+H]^+$ 410.0.

E) Methyl 2-cyclopropyl-4'-fluoro-5-(thiomorpholin-4-yl)biphenyl-4-carboxylate

Using methyl 2-bromo-4'-fluoro-5-(thiomorpholin-4-yl)biphenyl-4-carboxylate and cyclopropylboronic acid, the title compound was obtained in the similar manner as in Step D of Example 23.

MS (ESI+): $[M+H]^+$ 372.1.

F) 2-Cyclopropyl-4'-fluoro-5-(thiomorpholin-4-yl)biphenyl-4-carbaldehyde

Using methyl 2-cyclopropyl-4'-fluoro-5-(thiomorpholin-4-yl)biphenyl-4-carboxylate, the title compound was obtained in the similar manner as in Step C of Example 1.

MS (ESI+): $[M+H]^+$ 342.2.

G) Ethyl 1-(2-((2-cyclopropyl-4'-fluoro-5-(thiomorpholin-4-yl)biphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-5-(thiomorpholin-4-yl)biphenyl-4-carbaldehyde, the title compound was obtained in the similar manner as in Step G of Example 1.

MS (ESI+): $[M+H]^+$ 607.4.

H) 1-(2-((2-Cyclopropyl-4'-fluoro-5-(thiomorpholin-4-yl)biphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-5-(thiomorpholin-4-yl)biphenyl-4-yl)methyl)-5-oxa-2,6-diazaspiro[3.4]oct-6-en-7-yl)-4-methylpiperidine 4 carboxylate, the title compound was obtained in the similar manner as in Example 2.

Example 212

1-(2-(5-Cyclopropyl-4-(4,4-difluoropiperidin-1-yl)-2-isopropoxybenzyl)-5-oxa-2,6-diazaspiro[3.4]oct-6-en-7-yl)-4-methylpiperidine-4-carboxylic acid A) Methyl 4-(1,4-dioxa-8-azaspiro[4.5]deca-8-yl)-2-isopropoxybenzoate Tris(dibenzylideneacetone)dipalladium(0) (1.17 g) was added to a mixture of methyl 4-bromo-2-isopropoxybenzoate (5.00 g), 1,4-dioxa-8-azaspiro[4.5]decane (4.69 mL), cesium carbonate (8.95 g), (±)-2,2'-bis(diphenylphosphino)-1,1'-binaphthyl (1.60 g) and 1-methyl-2-pyrrolidone (50 mL), and the resultant was stirred for 3 days at 110° C. in an argon atmosphere. Water was added to the reaction mixture, and extraction thereof was performed using ethyl acetate.

The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (3.00 g).

$^1$H NMR (300 MHz, $CDCl_3$) δ 1.37 (6H, d, J=6.0 Hz), 1.72-1.87 (4H, m), 3.31-3.53 (4H, m), 3.82 (3H, s), 4.00 (4H, s), 4.40-4.63 (1H, m), 6.42 (1H, d, J=2.4 Hz), 6.50 (1H, dd, J=8.9, 2.4 Hz), 7.77 (1H, d, J=8.9 Hz).

B) Methyl 2-isopropoxy-4-(4-oxopiperidin-1-yl)benzoate

A mixture of methyl 4-(1,4-dioxa-8-azaspiro[4.5]deca-8-yl)-2-isopropoxybenzoate (8.04 g), acetic acid (20 mL), THF (20 mL) and water (20 mL) was stirred for 5 hours at 80° C. The solvent was distilled off under reduced pressure, and the obtained residue was purified by a silica gel column chromatography (hexane/ethyl acetate), thereby obtaining the title compound (6.09 g).

$^1$H NMR (300 MHz, $CDCl_3$) δ 1.39 (6H, d, J=6.0 Hz), 2.57 (4H, t, J=6.1 Hz), 3.71 (4H, t, J=6.1 Hz), 3.84 (3H, s), 4.43-4.61 (1H, m), 6.45 (1H, d, J=2.5 Hz), 6.52 (1H, dd, J=8.8, 2.5 Hz), 7.83 (1H, d, J=8.8 Hz).

C) Methyl 4-(4,4-difluoropiperidin-1-yl)-2-isopropoxybenzoate

Using methyl 2-isopropoxy-4-(4-oxopiperidin-1-yl)benzoate, the title compound was obtained in the similar manner as in Step B of Example 168.

$^1$H NMR (300 MHz, $CDCl_3$) δ 1.38 (6H, d, J=6.0 Hz), 1.86-2.19 (4H, m), 3.31-3.55 (4H, m), 3.84 (3H, s), 4.37-4.64 (1H, m), 6.43 (1H, d, J=2.5 Hz), 6.50 (1H, dd, J=8.8, 2.5 Hz), 7.79 (1H, d, J=8.8 Hz).

D) Methyl 5-bromo-4-(4,4-difluoropiperidin-1-yl)-2-isopropoxybenzoate

Using methyl 4-(4,4-difluoropiperidin-1-yl)-2-isopropoxybenzoate, the title compound was obtained in the similar manner as in Step D of Example 185.

$^1$H NMR (300 MHz, $CDCl_3$) δ 1.37 (6H, d, J=6.0 Hz), 2.19 (4H, ddd, J=19.5, 13.7, 5.7 Hz), 3.06-3.28 (4H, m), 3.85 (3H, s), 4.42-4.60 (1H, m), 6.61 (1H, s), 8.03 (1H, s).

E) Methyl 5-cyclopropyl-4-(4,4-difluoropiperidin-1-yl)-2-isopropoxybenzoate

Using methyl 5-bromo-4-(4,4-difluoropiperidin-1-yl)-2-isopropoxybenzoate and cyclopropylboronic acid, the title compound was obtained in the similar manner as in Step D of Example 23.

$^1$H NMR (300 MHz, $CDCl_3$) δ 0.67-0.78 (2H, m), 0.92-1.01 (2H, m), 1.35 (6H, d, J=6.1 Hz), 1.91-2.08 (1H, m), 2.08-2.27 (4H, m), 3.12-3.26 (4H, m), 3.84 (3H, s), 4.29-4.55 (1H, m), 6.58 (1H, s), 7.31 (1H, s).

F) 5-Cyclopropyl-4-(4,4-difluoropiperidin-1-yl)-2-isopropoxybenzoic acid

Using methyl 5-cyclopropyl-4-(4,4-difluoropiperidin-1-yl)-2-isopropoxybenzoate, the title compound was obtained in the similar manner as in Example 2.

$^1$H NMR (300 MHz, $CDCl_3$) δ 0.76-0.83 (2H, m), 0.92-1.04 (2H, m), 1.47 (6H, d, J=6.1 Hz), 1.92-2.08 (1H, m), 2.09-2.29 (4H, m), 3.06-3.31 (4H, m), 4.72-4.89 (1H, m), 6.59 (1H, s), 7.63 (1H, s).

G) 5-Cyclopropyl-4-(4,4-difluoropiperidin-1-yl)-2-isopropoxybenzaldehyde

O-(7-azabenzotriazol-1-yl)-N,N,N',N'-tetramethyluronium hexafluorophosphate (5.82 g) was added to a mixture of 5-cyclopropyl-4-(4,4-difluoropiperidin-1-yl)-2-isopropoxybenzoic acid (4.33 g), N,O-dimethylhydroxyamine hydrochloride (1.88 g), N-ethyldiisopropylamine (3.34 mL) and DMF (30 mL), and the resultant was stirred overnight at 60° C. Water was added to the reaction mixture, and extraction thereof was performed using ethyl acetate. The organic layer was washed with a saturated saline solution, dried over anhydrous magnesium sulfate, and then the solvent was distilled off under reduced pressure. The obtained residue was purified by a silica gel column chromatography (hexane/ethyl acetate). A solution of the obtained oily matter in THF (20 mL) was added to a suspension of lithium aluminum hydride (516 mg) in THF (20 mL) under ice-cooling in a nitrogen atmosphere. After stirring for 30 minutes at the same temperature, water (0.50 mL), 15% aqueous sodium hydroxide solution (0.50 mL) and water (1.5 mL) were sequentially added thereto. After the reaction mixture was stirred for 30 minutes, it was filtered, and the filtrate was concentrated under reduced pressure. The obtained residue was purified by a silica gel column chromatography (hexane/ethyl acetate), thereby obtaining the title compound (2.05 g).

$^1$H NMR (300 MHz, $CDCl_3$) δ 0.69-0.81 (2H, m), 0.88-1.05 (2H, m), 1.38 (6H, d, J=6.0 Hz), 1.87-2.03 (1H, m), 2.08-2.29 (4H, m), 3.13-3.32 (4H, m), 4.52-4.72 (1H, m), 6.53 (1H, s), 7.33 (1H, s), 10.31 (1H, s).

H) Ethyl 1-(2-(5-cyclopropyl-4-(4,4-difluoropiperidin-1-yl)-2-isopropoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 5-cyclopropyl-4-(4,4-fluoropiperidin-1-yl)-2-isopropoxybenzaldehyde, the title compound was obtained in the similar manner as in Step G of Example 1.

MS (ESI+): $[M+H]^+$ 589.6.

I) 1-(2-(5-Cyclopropyl-4-(4,4-difluoropiperidin-1-yl)-2-isopropoxybenzyl)-5-oxa-2,6-diazaspiro[3.4]oct-6-en-7-yl)-4-methylpiperidine-4-carboxylic acid Using ethyl 1-(2-(5-cyclopropyl-4-(4,4-difluoropiperidin-1-yl)-2-isopropoxybenzyl)-5-oxa-2,6-diazaspiro[3.4]oct-6-en-7-yl)-4-methylpiperidine-4-carboxylate, the title compound was obtained in the similar manner as in Example 2.

Example 213

1-(2-(5-Cyclopropyl-4-(4,4-difluoropiperidin-1-yl)-2-isopropoxybenzyl)-5-oxa-2,6-diazaspiro[3.4]oct-6-en-7-yl)-4-ethylpiperidine-4-carboxylic acid A) Ethyl 1-(2-((5-cyclopropyl-4-(4,4-difluoropiperidin-1-yl)-2-isopropoxybenzyl)-5-oxa-2,6-diazaspiro[3.4]oct-6-en-7-yl)-4-ethylpiperidine-4-carboxylate Using tert-butyl 7-(4-(ethoxycarbonyl)-4-ethylpiperidin-1-yl)-5-oxa-2,6-diazaspiro[3.4]oct-6-ene-2-carboxylate and 5-cyclopropyl-4-(4,4-difluoropiperidin-1-yl)-2-isopropoxybenzaldehyde, the title compound was obtained in the similar manner as in Step G of Example 1.

MS (ESI+): $[M+H]^+$ 603.6.

B) 1-(2-(5-Cyclopropyl-4-(4,4-difluoropiperidin-1-yl)-2-isopropoxybenzyl)-5-oxa-2,6-diazaspiro[3.4]oct-6-en-7-yl)-4-ethylpiperidine-4-carboxylic acid Using ethyl 1-(2-((5-cyclopropyl-4-(4,4-difluoropiperidin-1-yl)-2-isopropoxybenzyl)-5-oxa-2,6-diazaspiro[3.4]oct-6-en-7-yl)-4-ethylpiperidine-4-carboxylate, the title compound was obtained in the similar manner as in Example 2.

Example 214

1-(2-((2-Cyclopropyl-4'-fluoro-5-methoxybiphenyl-4-yl)methyl)-5-oxa-2,6-diazaspiro[3.4]oct-6-en-7-yl)piperidine-4-carboxylic acid A) Ethyl 1-(2-((2-cyclopropyl-4'-fluoro-5-methoxybiphenyl-4-yl)methyl)-5-oxa-2,6-diazaspiro[3.4]oct-6-en-7-yl)piperidine-4-carboxylate tert-Butyl 7-(4-(ethoxycarbonyl)piperidin-1-yl)-5-oxa-2,6-diazaspiro[3.4]oct-6-ene-2-carboxylate (421 mg) was added to formic acid (3 mL), the resultant was stirred for 1 hour at 70° C., and the solvent was distilled off under reduced pressure. The obtained residue was mixed with 2-cyclopropyl-4'-fluoro-5-methoxybiphenyl-4-carbaldehyde (310 mg) and THF (10 mL), sodium triacetoxyborohydride (368 mg) was added to the mixture, and the resultant was stirred for 3 hours at mom temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (587 mg).

MS (ESI+): $[M+H]^+$ 522.2.

B) 1-(2-((2-Cyclopropyl-4'-fluoro-5-methoxybiphenyl-4-yl)methyl)-5-oxa-2,6-diazaspiro[3.4]oct-6-en-7-yl)piperidine-4-carboxylic acid 2 M aqueous sodium hydroxide solution (3.8 mL) was added to a solution of ethyl 1-(2-((2-cyclopropyl-4'-fluoro-5-methoxybiphenyl-4-yl)methyl)-5-oxa-2,6-diazaspiro[3.4]oct-6-en-7-yl)piperidine-4-carboxylate (570 mg) in ethanol (3 mL), and the resultant was stirred for 1 hour at 60° C. After the reaction mixture was neutralized with 2 M hydrochloric acid, the precipitated solid was collected by filtration. Recrystallization (hydrous methanol) of the obtained solid was performed, thereby obtaining the title compound (265 mg).

$^1H$ NMR (300 MHz, DMSO-$d_6$) δ 0.53 (2H, d, J=4.2 Hz), 0.76 (2H, d, J=8.1 Hz), 1.41-1.59 (2H, m), 1.68-1.86 (3H, m), 2.34-2.46 (1H, m), 2.81 (2H, t, J=11.2 Hz), 3.17 (2H, brs), 3.23-3.38 (2H, m), 3.45 (4H, d, J=8.6 Hz), 3.55 (2H, brs), 3.76 (3H, s), 6.75 (1H, s), 6.84 (1H, s), 7.20-7.33 (2H, m), 7.42-7.53 (2H, m), 12.23 (1H, brs).

Example 215

1-(2-((2-Cyclopropyl-5-ethoxy-4'-fluorobiphenyl-4-yl)methyl)-5-oxa-2,6-diazaspiro[3.4]oct-6-en-7-yl)piperidine-4-carboxylic acid A) Ethyl 1-(2-((2-cyclopropyl-5-ethoxy-4'-fluorobiphenyl-4-yl)methyl)-5-oxa-2,6-diazaspiro[3.4]oct-6-en-7-yl)piperidine-4-carboxylate tert-Butyl 7-(4-(ethoxycarbonyl)piperidin-1-yl)-5-oxa-2,6-diazaspiro[3.4]oct-6-ene-2-carboxylate (345 mg) was added to formic acid (3 mL), the resultant was stirred for 30 minutes at 70° C., and the solvent was distilled off under reduced pressure. The obtained residue was mixed with 2-cyclopropyl-5-ethoxy-4'-fluorobiphenyl-4-carbaldehyde (267 mg) and THF (10 mL), sodium triacetoxyborohydride (299 mg) was added to the mixture, and the resultant was stirred for 3 hours at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (470 mg).

MS (ESI+): $[M+H]^+$ 536.1

B) 1-(2-((2-Cyclopropyl-5-ethoxy-4'-fluorobiphenyl-4-yl)methyl)-5-oxa-2,6-diazaspiro[3.4]oct-6-en-7-yl)piperidine-4-carboxylic acid 2 M aqueous sodium hydroxide solution (3.1 mL) was added to a solution of ethyl 1-(2-((2-cyclopropyl-5-ethoxy-4'-fluorobiphenyl-4-yl)methyl)-5-oxa-2,6-diazaspiro[3.4]oct-6-en-7-yl)piperidine-4-carboxylate (470 mg) in ethanol (3.1 mL), and the resultant was stirred for 1 hour at 60° C. After the reaction mixture was neutralized with 2 M hydrochloric acid, it was stirred for 30 minutes, and the precipitated solid was collected by filtration. Recrystallization (hydrous methanol) of the obtained solid was performed, thereby obtaining the title compound (265 mg).

$^1H$ NMR (300 MHz, DMSO-$d_6$) δ 0.48-0.57 (2H, m), 0.71-0.80 (2H, m), 1.31 (3H, t, J=6.9 Hz), 1.42-1.58 (2H, m), 1.68-1.84 (3H, m), 2.34-2.46 (1H, m), 2.81 (2H, t, J=11.0 Hz), 3.14 (2H, d, J=8.3 Hz), 3.25-3.37 (2H, m), 3.40-3.50 (4H, m), 3.55 (2H, s), 4.01 (2H, q, J=7.0 Hz), 6.73 (1H, s), 6.83 (1H, s), 7.21-7.31 (2H, m), 7.42-7.51 (2H, m), 12.27 (1H, brs).

Example 216

1-(2-((2,6-Diethoxy-4'-fluorobiphenyl-4-yl)methyl)-1,1-dimethyl-5-oxa-2,6-diazaspiro[3.4]oct-6-en-7-yl)-4-methylpiperidine-4-carboxylic acid A) tert-Butyl (4-diazo-2-methyl-3-oxobutan-2-yl)carbamate 50% aqueous potassium hydroxide solution (100 mL) was added to a mixture of N-methyl-N-nitrosourea (47.9 g) and diethyl ether (200 mL), and the resultant was stirred until color of the organic layer becomes yellow. The organic layer was separated, and dried over potassium hydroxide. 4-Methylmorpholine (5.48 mL) and isobutyl chloroformate (7.40 g) was sequentially added to a mixture of N-(tert-butoxycarbonyl)-2-methylalanine (10.0 g) and dichloromethane (150 mL) at 0° C., and the resultant was stirred for 1 hour at the same temperature. A solution (100 mL) of diazomethane in ether which was prepared in advance was added to the reaction mixture, and the resultant was stirred overnight at room temperature. The solvent of the reaction mixture was distilled off under reduced pressure. The obtained residue was purified by a silica gel column chromatography (hexane/ethyl acetate), thereby obtaining the title compound (7.30 g).

$^1$H NMR (400 MHz, $CDCl_3$) δ 1.42 (15H, s), 5.10 (1H, brs), 5.55 (1H, s).

B) tert-Butyl 2,2-dimethyl-3-oxoazetidine-1-carboxylate

Triethylamine (0.3 mL) was added to a mixture of tert-butyl (4-diazo-2-methyl-3-oxobutan-2-yl)carbamate and dichloromethane (60 mL) at 0° C., and the resultant was stirred for 10 minutes at the same temperature. Rhodium(II) acetate (285 mg) was added to the reaction mixture, and the resultant was stirred overnight at room temperature. The solvent of the reaction mixture was distilled off under reduced pressure. The obtained residue was purified by a silica gel column chromatography (hexane/ethyl acetate), thereby obtaining the title compound (3.70 g).

$^1$H NMR (400 MHz, $CDCl_3$) δ 1.47 (15H, s), 4.60 (2H, s).

C) tert-Butyl 2,2-dimethyl-3-methyleneazetidine-1-carboxylate

Using tert-butyl 2,2-dimethyl-3-oxoazetidine-1-carboxylate, the title compound was obtained in the similar manner as in Step D of Example 1.

$^1$H NMR (400 MHz, $CDCl_3$) δ 1.45 (15H, s), 4.36 (2H, s), 4.87-4.92 (2H, m).

D) tert-Butyl 7-bromo-1,1-dimethyl-5-oxa-2,6-diazaspiro[3.4]oct-6-en-2-carboxylate Using tert-butyl 2,2-dimethyl-3-methyleneazetidine-1-carboxylate, the title compound was obtained in the similar manner as in Step E of Example 1.

MS (ESI+): $[M+H]^+$ 319.0.

E) tert-Butyl 7-(4-(ethoxycarbonyl)-4-methylpiperidin-1-yl)-1,1-dimethyl-5-oxa-2,6-diazaspiro[3.4]oct-6-ene-2-carboxylate Using tert-butyl 7-bromo-1,1-dimethyl-5-oxa-2,6-diazaspiro[3.4]oct-6-en-2-carboxylate and ethyl 4-methylpiperidine-4-carboxylate, the title compound was obtained in the similar manner as in Step D of Example 7.

MS (ESI+): $[M+H]^+$ 410.0.

F) Ethyl 1-(1,1-dimethyl-5-oxa-2,6-diazaspiro[3.4]oct-6-en-7-yl)-4-methylpiperidine-4-carboxylate A mixture of tert-butyl 7-(4-(ethoxycarbonyl)-4-methylpiperidin-1-yl)-1,1-dimethyl-5-oxa-2,6-diazaspiro[3.4]oct-6-ene-2-carboxylate (900 mg) and saturated hydrogen chloride-dioxane (60 mL) was stirred for 2 hours at room temperature. After the solvent was distilled off under reduced pressure, the obtained residue was neutralized with an aqueous saturated sodium hydrogen carbonate solution, and extraction thereof was performed using ethyl acetate. After the organic layer was dried over anhydrous sodium sulfate, the solvent was distilled off under reduced pressure, thereby obtaining the title compound (650 mg).

MS (ESI+): $[M+H]^+$ 310.4.

G) 4-(Bromomethyl)-2,6-diethoxy-4'-fluorobiphenyl

Phosphorus tribromide (0.980 mL) was added to a mixture of (2,6-diethoxy-4'-fluorobiphenyl-4-yl)methanol (2.00 g) and toluene (20 mL) in a nitrogen atmosphere, and the resultant was stirred for 3 hours at room temperature. The reaction mixture was added to ice water, and extraction thereof was performed using ethyl acetate. The obtained organic layer was washed with an aqueous saturated sodium hydrogen carbonate solution, dried over anhydrous sodium sulfate, and concentrated under reduced pressure. The obtained residue was purified by a silica gel column chromatography (hexane/ethyl acetate), thereby obtaining the title compound (2.00 g).

$^1$H NMR (300 MHz, $CDCl_3$) δ 1.18 (6H, m), 3.94-3.99 (4H, m), 4.48 (2H, s), 6.63 (2H, s), 7.04 (2H, t, J=8.8 Hz), 7.29-7.32 (2H, m).

H) Ethyl 1-(2-((2,6-diethoxy-4'-fluorobiphenyl-4-yl)methyl)-1,1-dimethyl-5-oxa-2,6-diazaspiro[3.4]oct-6-en-7-yl)-4-methylpiperidine-4-carboxylate Potassium carbonate (401 mg) and 4-(bromomethyl)-2,6-diethoxy-4'-fluorobiphenyl (617 mg) were added to a mixture of ethyl 1-(1,1-dimethyl-5-oxa-2,6-diazaspiro[3.4]oct-6-en-7-yl)-4-methylpiperidine-4-carboxylate (450 mg) and DMF (10 mL), and the resultant was stirred for 2 hours at 65° C. Water was added to the reaction mixture, and extraction thereof was performed using ethyl acetate. After the obtained organic layer was washed with a saturated saline solution, it was dried over anhydrous sodium sulfate, and concentrated under reduced pressure. The obtained residue was purified by a silica gel column chromatography (hexane/ethyl acetate), thereby obtaining the title compound (176 mg).

MS (ESI+): $[M+H]^+$ 582.2.

I) 1-(2-((2,6-Diethoxy-4'-fluorobiphenyl-4-yl)methyl)-1,1-dimethyl-5-oxa-2,6-diazaspiro[3.4]oct-6-en-7-yl)-4-methylpiperidine-4-carboxylic acid Using ethyl 1-(2-((2,6-diethoxy-4'-fluorobiphenyl-4-yl)methyl)-1,1-dimethyl-5-oxa-2,6-diazaspiro[3.4]oct-6-en-7-yl)-4-methylpiperidine-4-carboxylate, the title compound was obtained in the similar manner as in Example 2.

Example 217

1-(2-((2,6-Diethoxy-4'-fluorobiphenyl-4-yl)methyl)-1-methyl-5-oxa-2,6-diazaspiro[3.4]oct-6-en-7-yl)-4-methylpiperidine-4-carboxylic acid A) tert-Butyl 2-methyl-3-methyleneazetidine-1-carboxylate Potassium tert-butoxide (2.67 g) was added to a mixture of methyl(triphenyl)phosphonium bromide (8.49 g) and THE (80 mL), which was cooled to 0° C., and the resultant was stirred for 1 hour. tert-Butyl 2-methyl-3-oxoazetidine-1-carboxylate (4.00 g) was added thereto, and the resultant was stirred for 30 minutes at 50° C. After water was added to the reaction mixture, extraction thereof was performed using diethyl ether. After the obtained organic layer was washed with a saturated saline solution, it was dried over anhydrous sodium sulfate, and distilled off under reduced pressure. The obtained residue was purified by a silica gel column chromatography (hexane/ethyl acetate), thereby obtaining the title compound (2.20 g).

$^1$H NMR (400 MHz, $CDCl_3$) δ 1.39 (3H, d, J=6.4 Hz), 1.44 (9H, s), 4.33-4.44 (2H, m), 4.72 (1H, brs), 4.92 (2H, brs).

B) tert-Butyl 7-bromo-1-methyl-5-oxa-2,6-diazaspiro[3.4]oct-6-en-2-carboxylate

Sodium hydrogen carbonate (9.18 g) was added to a solution of tert-butyl 2-methyl-3-methyleneazetidine-1-carboxylate (2.00 g) and hydroxycarbonimidic dibromide (4.43 g) in ethyl acetate (50 mL), the resultant was stirred for 16 hours at room temperature, and was further stirred for 5 hours at 40° C. After water was added to the reaction mixture, the organic layer was separated. The obtained organic layer was washed with a saturated saline solution, was dried over anhydrous magnesium sulfate, and was concentrated under reduced pressure. The obtained residue was purified by a silica gel column chromatography (hexane/ethyl acetate), thereby obtaining the title compound (2.20 g).

$^1$H NMR (400 MHz, $CDCl_3$) δ 1.36 (3H, d, J=7.68 Hz), 1.45 (9H, s), 3.13 (1H, d, J=18.1 Hz), 3.45 (1H, d, J=18.1 Hz), 3.85 (1H, d, 9.8 Hz), 4.17 (1H, d, J=9.9 Hz), 4.42-4.50 (1H, m).

C) tert-Butyl 7-(4-(ethoxycarbonyl)-4-methylpiperidin-1-yl)-1-methyl-5-oxa-2,6-diazaspiro[3.4]oct-6-ene-2-carboxylate Sodium carbonate (1.25 g) was added to a mixture of tert-Butyl 7-bromo-1-methyl-5-oxa-2,6-diazaspiro[3.4]oct-6-ene-2-carboxylate (2.20 g), ethyl 4-methylpiperidine-4-carboxylate (1.49 g) and DMF (20 mL), and the resultant was stirred overnight at 130° C. After the reaction mixture was cooled to room temperature, water was added thereto, and extraction thereof was performed using ethyl acetate. After the obtained organic layer was dried over anhydrous sodium sulfate, the solvent was distilled off under reduced pressure. The obtained residue was purified by a silica gel column chromatography (hexane/ethyl acetate), thereby obtaining the title compound (1.80 g).

MS (ESI+): $[M+H]^+$ 396.0.

D) Ethyl 4-methyl-1-(1-methyl-5-oxa-2,6-diazaspiro[3.4]oct-6-en-7-yl)piperidine-4-carboxylate A mixture of tert-butyl 7-(4-(ethoxycarbonyl)-4-methylpiperidin-1-yl)-1-methyl-5-oxa-2,6-diazaspiro[3.4]oct-6-ene-2-carboxylate (1.60 g) and a solution (15 mL) of saturated hydrogen chloride in dioxane was stirred for 1 hour at room temperature, and then the solvent was distilled off under reduced pressure. The obtained residue was neutralized with an aqueous saturated sodium hydrogen carbonate solution, and extraction thereof was performed using ethyl acetate. After the organic layer was dried over anhydrous sodium sulfate, the solvent was distilled off under reduced pressure, thereby obtaining the title compound (1.00 g).

$^1$H NMR (400 MHz, $CDCl_3$) δ 1.17-1.19 (6H, s), 1.25 (3H, t, J=7.12 Hz), 1.40-1.49 (2H, m), 2.10 (2H, d, J=13.68 Hz), 2.90-2.99 (3H, m), 3.20 (1H, d, J=16.08 Hz), 3.35-3.41 (3H, m), 3.69 (1H, s), 3.81-3.83 (1H, m), 4.12-4.18 (2H, m).

E) Ethyl 1-(2-((2,6-diethoxy-4'-fluorobiphenyl-4-yl)methyl)-1-methyl-5-oxa-2,6-diazaspiro[3.4]oct-6-en-7-yl)-4-methylpiperidine-4-carboxylate Potassium carbonate (367 mg) and 4-(bromomethyl)-2,6-diethoxy-4'-fluorobiphenyl (689 mg) were added to a mixture of ethyl 4-methyl-1-(1-methyl-5-oxa-2,6-diazaspiro[3.4]oct-6-en-7-yl)piperidine-4-carboxylate (700 mg) and DMF (10 mL), and the resultant was stirred for 2 hours at 65° C. Water was added to the reaction mixture, and extraction thereof was performed using ethyl acetate. After the obtained organic layer was washed with a saturated saline solution, it was dried over anhydrous sodium sulfate, and concentrated under reduced pressure. The obtained residue was purified by a silica gel column chromatography (hexane/ethyl acetate), thereby obtaining the title compound (630 mg).

$^1$H NMR (400 MHz, $CDCl_3$) δ 1.06 (3H, d, J=6.3 Hz), 1.98-1.26 (12H, m), 1.44-1.47 (2H, m), 2.09-2.11 (2H, m), 2.92-2.98 (3H, m), 3.13 (1H, d, J=7.7 Hz), 3.21 (1H, d, J=16.2 Hz), 3.37-3.42 (3H, m), 3.48 (1H, d, J=7.8 Hz), 3.54-3.57 (1H, d, J=12.7 Hz), 3.68 (1H, d, J=12.6 Hz), 3.94 (4H, q, J=7.0 Hz), 4.15 (2H, q, J=7.1 Hz), 6.54 (2H, s), 7.03 (2H, t, J=8.8 Hz), 7.29-7.32 (2H, m).

F) 1-(2-((2,6-Diethoxy-4'-fluorobiphenyl-4-yl)methyl)-1-methyl-5-oxa-2,6-diazaspiro[3.4]oct-6-en-7-yl)-4-methylpiperidine-4-carboxylic acid Lithium hydroxide (294 mg) was added to a mixture of ethyl 1-(2-((2,6-diethoxy-4'-fluorobiphenyl-4-yl)methyl)-1-methyl-5-oxa-2,6-diazaspiro[3.4]oct-6-en-7-yl)-4-methylpiperidine-4-carboxylate (390 mg), THF (12.5 mL), methanol (5 mL) and water (2.5 mL) at 0° C., the resultant was stirred for 9 hours at mom temperature, and the solvent was distilled off under reduced pressure. After 1 M hydrochloric acid was added to the obtained residue to neutralize, extraction thereof was performed using dichloromethane. After the organic layer was washed with water, it was dried over anhydrous sodium sulfate, and the solvent was distilled off under reduced pressure. The obtained residue was purified by a silica gel column chromatography (dichloromethane/methanol), thereby obtaining the title compound (200 mg).

$^1$H NMR (400 MHz, $CDCl_3$) 1.14-1.19 (9H, m), 1.31 (3H, d, J=6.72 Hz), 1.35-1.45 (2H, m), 1.91-1.94 (2H, m), 2.90-2.93 (2H, m), 3.22-3.33 (2H, m), 3.34-3.41 (1H, m), 3.95-4.02 (5H, m), 4.19-4.21 (2H, m), 4.30-4.35 (1H, m), 4.39-4.44 (1H, m), 4.66-4.69 (1H, m), 6.98 (2H, s), 7.17 (2H, t, J=8.96 Hz), 7.25-7.29 (2H, m), 12.46 (1H, brs).

Example 218

1-(2-((6-Cyclopropyl-4-ethoxy-5-(4-fluorophenyl)pyridin-2-yl)methyl)-5-oxa-2,6-diazaspiro[3.4]oct-6-en-7-yl)-4-methylpiperidine-4-carboxylic acid A) 3-(Benzyloxy)-2-cyclopropyl-6-(((triisopropylsilyl)oxy)methyl)pyridine Using 3-(benzyloxy)-2-chloro-6-(((triisopropylsilyl)oxy)methyl)pyridine and cyclopropylboronic acid, the title compound was obtained in the similar manner as in Step D of Example 23.

$^1$H NMR (300 MHz, $CDCl_3$) δ 0.79-1.38 (25H, m), 2.39-2.63 (1H, m), 4.76 (2H, s), 5.09 (2H, s), 7.08-7.15 (1H, m), 7.18-7.24 (1H, m), 7.28-7.52 (5H, m).

B) 2-Cyclopropyl-6-(((triisopropylsilyl)oxy)methyl) pyridin-3-ol

Using 3-(Benzyloxy)-2-cyclopropyl-6-(((triisopropylsilyl)oxy)methyl)pyridine, the title compound was obtained in the similar manner as in Step F of Example 87.

$^1$H NMR (300 MHz, $CDCl_3$) δ 0.90-1.35 (25H, m), 2.13 (1H, quin, J=6.7 Hz), 4.78 (2H, s), 5.09-5.33 (1H, m), 7.10 (1H, d, J=8.2 Hz), 7.20-7.34 (1H, m).

C) 2-Cyclopropyl-3-(methoxymethoxy)-6-(((triisopropylsilyl)oxy)methyl)pyridine

Using 2-cyclopropyl-6-(((triisopropylsilyl)oxy)methyl) pyridin-3-ol, the title compound was obtained in the similar manner as in Step B of Example 88.

$^1$H NMR (300 MHz, $CDCl_3$) δ 0.83-1.33 (25H, m), 2.35-2.51 (1H, m), 3.51 (3H, s), 4.76 (2H, s), 5.21 (2H, s), 7.18-7.25 (1H, m), 7.30-7.35 (1H, m).

D) 2-Cyclopropyl-3-(methoxymethoxy)-6-(((triisopropylsilyl)oxy)methyl)pyridin-4-ol n-Butyllithium (1.6 M hexane solution, 18.3 mL) was added to a mixture of 2-cyclopropyl-3-(methoxymethoxy)-6-(((triisopropylsilyl)oxy)methyl)pyridine (8.23 g) and THF (50 mL) at −78° C., and the resultant was stirred for 30 minutes at the same temperature. Trimethoxyborane (3.32 mL) was added to the reaction mixture at −78° C., and the resultant was warmed to room temperature. Aqueous hydrogen peroxide solution (35%, 4.38 mL) and 8M aqueous sodium hydroxide solution (5.63 mL) were added to the reaction mixture at 0° C., and the resultant was stirred for 30 minutes at room temperature. After the reaction mixture was neutralized with hydrochloric acid, and extraction thereof was performed using ethyl acetate. The organic layer was dried over anhydrous magnesium sulfate, and was distilled off under reduced pressure. The obtained residue was purified by a silica gel column chromatography (hexane/ethyl acetate), thereby obtaining the title compound (7.52 g).

$^1$H NMR (300 MHz, $CDCl_3$) δ 0.72-0.85 (2H, m), 0.84-1.24 (23H, m), 2.35-2.54 (1H, m), 3.58 (3H, s), 4.67 (2H, s), 5.32 (2H, s), 6.17 (1H, s), 8.34 (1H, brs).

E) (6-Cyclopropyl-4-ethoxy-5-(methoxymethoxy) pyridin-2-yl)methanol

Using 2-cyclopropyl-3-(methoxymethoxy)-6-(((triisopropylsilyl)oxy)methyl)pyridin-4-ol, the title compound was obtained in the similar manner as in Step A of Example 1, and Step D of Example 176.

$^1$H NMR (300 MHz, $CDCl_3$) δ 0.90-1.00 (2H, m), 1.04-1.12 (2H, m), 1.46 (3H, t, J=7.0 Hz), 2.41-2.55 (1H, m), 3.62 (3H, s), 4.02 (1H, brs), 4.08 (2H, q, J=7.0 Hz), 4.56 (2H, s), 5.15 (2H, s), 6.47 (1H, s).

F) 6-Cyclopropyl-4-ethoxy-5-(methoxymethoxy) pyridine-2-carbaldehyde

Using (6-cyclopropyl-4-ethoxy-5-(methoxymethoxy) pyridin-2-yl)methanol, the title compound was obtained in the similar manner as in Step H of Example 210.

$^1$H NMR (300 MHz, $CDCl_3$) δ 0.93-1.06 (2H, m), 1.13-1.22 (2H, m), 1.48 (3H, t, J=7.0 Hz), 2.44-2.59 (1H, m), 3.62 (3H, s), 4.17 (2H, q, J=7.1 Hz), 5.27 (2H, s), 7.31 (1H, s), 9.82 (1H, s).

G) 6-Cyclopropyl-4-ethoxy-5-hydroxypyridine-2-carbaldehyde

Using 6-cyclopropyl-4-ethoxy-5-(methoxymethoxy)pyridine-2-carbaldehyde, the title compound was obtained in the similar manner as in Step I of Example 210.

$^1$H NMR (300 MHz, $CDCl_3$) δ 0.93-1.05 (2H, m), 1.12-1.20 (2H, m), 1.49 (3H, t, J=7.0 Hz), 2.36-2.50 (1H, m), 4.23 (2H, q, J=7.0 Hz), 7.33 (1H, s), 9.79 (1H, s).

H) 6-Cyclopropyl-4-ethoxy-5-(4-fluorophenyl)pyridine-2-carbaldehyde

Using 6-cyclopropyl-4-ethoxy-5-hydroxypyridine-2-carbaldehyde and (4-fluorophenyl)boronic acid, the title compound was obtained in the similar manner as in Step J of Example 210.

$^1$H NMR (300 MHz, $CDCl_3$) δ 0.79-0.91 (2H, m), 1.14-1.23 (2H, m), 1.25-1.33 (3H, m), 1.73-1.87 (1H, m), 4.10 (2H, q, J=7.0 Hz), 7.10-7.21 (2H, m), 7.28-7.37 (3H, m), 9.91 (1H, s).

I) Ethyl 1-(2-((6-cyclopropyl-4-ethoxy-5-(4-fluorophenyl)pyridin-2-yl)methyl)-5-oxa-2,6-diazaspiro [3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 6-cyclopropyl-4-ethoxy-5-(4-fluorophenyl)pyridine-2-carbaldehyde, the title compound was obtained in the similar manner as in Step G of Example 1.

MS (ESI+): $[M+H]^+$ 551.5.

J) 1-(2-((6-Cyclopropyl-4-ethoxy-5-(4-fluorophenyl) pyridin-2-yl)methyl)-5-oxa-2,6-diazaspiro[3.4]oct-6-en-7-yl)-4-methylpiperidine-4-carboxylic acid Using ethyl 1-(2-((6-cyclopropyl-4-ethoxy-5-(4-fluorophenyl)pyridin-2-yl)methyl)-5-oxa-2,6-diazaspiro[3.4]oct-6-en-7-yl)-4-methylpiperidine-4-carboxylate, the title compound was obtained in the similar manner as in Example 2.

Example 219

1-(2-((2-(Cyclohex-1-en-1-yl)-4'-fluoro-5-methoxybiphenyl-4-yl)methyl)-5-oxa-2,6-diazaspiro[3.4]oct-6-en-7-yl)-4-methylpiperidine-4-carboxylic acid A) 2-(Cyclohex-1-en-1-yl)-4'-fluoro-5-methoxybiphenyl-4-carbaldehyde Using 2-bromo-4'-fluoro-5-methoxybiphenyl-4-carbaldehyde and 2-(cyclohex-1-en-1-yl)-4,4,5,5-tetramethyl-1,3,2-dioxaborolane, the title compound was obtained in the similar manner as in Step D of Example 23.

MS (ESI+): $[M+H]^+$ 311.2.

B) Ethyl 1-(2-((2-(cyclohex-1-en-1-yl)-4'-fluoro-5-methoxybiphenyl-4-yl)methyl)-5-oxa-2,6-diazaspiro [3.4]oct-6-en-7-yl)-4-methylpiperidine-4-carboxylic acid Using tert-butyl 7-(4-(ethoxycarbonyl)-4-methylpiperidin-1-yl)-5-oxa-2,6-diazaspiro[3.4]oct-6-ene-2-carboxylate and 2-(cyclohex-1-en-1-yl)-4'-fluoro-5-methoxybiphenyl-4- carbaldehyde, the title compound was obtained in the similar manner as in Step G of Example 1.

MS (ESI+): $[M+H]^+$ 576.2.

C) 1-(2-((2-(Cyclohex-1-en-1-yl)-4'-fluoro-5-methoxybiphenyl-4-yl)methyl)-5-oxa-2,6-diazaspiro[3.4]oct-6-en-7-yl)-4-methylpiperidine-4-carboxylic acid Using ethyl 1-(2-((2-(cyclohex-1-en-1-yl)-4'-fluoro-5-methoxybiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 220

1-(2-((4'-Fluoro-2-(1-hydroxycyclobutyl)-5-methoxybiphenyl-4-yl)methyl)-5-oxa-2,6-diazaspiro[3.4]oct-6-en-7-yl)-4-methylpiperidine-4-carboxylic acid A) 2-(2-Bromo-4'-fluoro-5-methoxybiphenyl-4-yl)-1,3-dioxolane 2-Bromo-4'-fluoro-5-methoxybiphenyl-4-carbaldehyde (2.18 g), ethylene glycol (1.31 g) and para-toluenesulfonic acid monohydrate (0.27 g) were added to toluene (20 mL), the resultant was heated to reflux for 2 hours using Dean-Stark apparatus. The reaction mixture was cooled to room temperature, an aqueous saturated sodium hydrogen carbonate solution was added thereto, and then extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.10 g).

$^1H$ NMR (300 MHz, DMSO-$d_6$) δ 3.83 (3H, s), 3.90-4.11 (4H, m), 5.98 (1H, s), 7.03 (1H, s), 7.26-7.35 (2H, m), 7.44-7.53 (2H, m), 7.64 (1H, s).

B) 1-(4-(1,3-Dioxolan-2-yl)-4'-fluoro-5-methoxybiphenyl-2-yl)cyclobutanol n-Butyllithium (1.6 M hexane solution, 2.7 mL) was added dropwise to a solution of 2-(2-bromo-4'-fluoro-5-methoxybiphenyl-4-yl)-1,3-dioxolane in THF (15 mL) at −78° C. in an argon atmosphere, the resultant was stirred for 30 minutes at the same temperature, and cyclobutanone (0.298 g) was added dropwise thereto. The reaction mixture was warmed to room temperature, and the reaction mixture was stirred for 1 hour. After an aqueous saturated sodium hydrogen carbonate solution was added thereto, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (0.72 g).

$^1H$ NMR (300 MHz, $CDCl_3$) δ 1.26 (1H, t, J=7.1 Hz), 1.83-1.94 (2H, m), 1.95-2.14 (2H, m), 2.20-2.34 (2H, m), 3.86 (3H, s), 4.03-4.22 (4H, m), 6.16 (1H, s), 6.70 (1H, s), 7.07 (2H, t, J=8.8 Hz), 7.38-7.45 (2H, m), 7.52 (1H, s).

C) 4'-Fluoro-2-(1-hydroxycyclobutyl)-5-methoxybiphenyl-4-carbaldehyde

6 M hydrochloric acid (1.7 mL) was added to a solution of 1-(4-(1,3-dioxolan-2-yl)-4'-fluoro-5-methoxybiphenyl-2-yl)cyclobutanol (700 mg) in THF (5.0 mL) at room temperature, and the resultant was stirred for 30 minutes. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (420 mg).

$^1H$ NMR (300 MHz, DMSO-$d_6$) δ 1.35-1.47 (1H, m), 1.77-2.11 (5H, m), 3.94 (3H, s), 5.61 (1H, brs), 6.95 (1H, s), 7.19-7.29 (2H, m), 7.59-7.70 (3H, m), 10.38 (1H, s).

D) Ethyl 1-(2-((4'-fluoro-2-(1-hydroxycyclobutyl)-5-methoxybiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 4'-fluoro-2-(1-hydroxycyclobutyl)-5-methoxybiphenyl-4-carbaldehyde, the title compound was obtained in the similar manner as in Step G of Example 1.

MS (ESI+): $[M+H]^+$ 566.3.

E) 1-(2-((4'-Fluoro-2-(1-hydroxycyclobutyl)-5-methoxybiphenyl-4-yl)methyl)-5-oxa-2,6-diazaspiro[3.4]oct-6-en-7-yl)-4-methylpiperidine-4-carboxylic acid Using ethyl 1-(2-((4'-fluoro-2-(1-hydroxycyclobutyl)-5-methoxybiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 221

1-(2-((2'-Chloro-2,6-diethoxy-4'-fluorobiphenyl-4-yl)methyl)-5-oxa-2,6-diazaspiro[3.4]oct-6-en-7-yl)-4-ethylpiperidine-4-carboxylic acid A) 2'-Chloro-2,6-diethoxy-4'-fluorobiphenyl-4-carbaldehyde A mixture of 4-bromo-3,5-diethoxybenzaldehyde (3.75 g), (2-chloro-4-fluorophenyl)boronic acid (6.0 g), tripotassium phosphate (11.7 g), DMF (40 mL) and dioxane (40 mL) was degassed for 45 minutes, (1,1'-bis(diphenylphosphino)ferrocene)dichloropalladium(II) (1.20 g) and tetrabutylammonium bromide (886 mg) were added thereto, and the resultant was heated to reflux for 15 hours in an argon atmosphere. The reaction mixture was cooled to mom temperature, ethyl acetate was added thereto, and the organic layer was separated. The obtained organic layer was sequentially washed with water and a saturated saline solution, was dried over anhydrous sodium sulfate, and then the solvent was distilled off under reduced pressure. The obtained residue was purified by a silica gel column chromatography (hexane/ethyl acetate), thereby obtaining the title compound (300 mg).

$^1$H NMR (400 MHz, DMSO-$d_6$) δ 1.16 (6H, t, J=6.9 Hz), 4.03-4.12 (4H, m), 7.21-7.31 (4H, m), 7.50 (1H, dd, J=2.4, 9.1 Hz), 9.99 (1H, s).

B) Ethyl 1-(2-((2'-chloro-2,6-diethoxy-4'-fluorobiphenyl-4-yl)methyl)-5-oxa-2,6-diazaspiro[3.4]oct-6-en-7-yl)-4-ethylpiperidine-4-carboxylate After a mixture of tert-butyl 7-(4-(ethoxycarbonyl)-4-ethylpiperidin-1-yl)-5-oxa-2,6-diazaspiro[3.4]oct-6-ene-2-carboxylate (296 mg) and formic acid (6 mL) was stirred for 1 hour at 60° C., the solvent was distilled off under reduced pressure. The obtained residue was mixed with 2'-chloro-2,6-diethoxy-4'-fluorobiphenyl-4-carbaldehyde (290 mg) and THF (10 mL), sodium triacetoxyborohydride (317 mg) was added to the mixture, and the resultant was stirred for 15 hours at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (387 mg).

$^1$H NMR (300 MHz, $CDCl_3$) δ 0.82 (3H, t, J=7.5 Hz), 1.16-1.31 (9H, m), 1.36-1.48 (2H, m), 1.56 (2H, q, J=7.5 Hz), 2.14 (2H, d, J=13.4 Hz), 2.84-2.98 (2H, m), 3.26 (2H, s), 3.33-3.49 (4H, m), 3.56 (2H, d, J=9.0 Hz), 3.66 (2H, s), 3.88-4.06 (4H, m), 4.18 (2H, q, J=7.1 Hz), 6.53 (2H, s), 6.94-7.03 (1H, m), 7.14-7.22 (2H, m).

C) 1-(2-((2'-Chloro-2,6-diethoxy-4'-fluorobiphenyl-4-yl)methyl)-5-oxa-2,6-diazaspiro[3.4]oct-6-en-7-yl)-4-ethylpiperidine-4-carboxylic acid 2 M aqueous sodium hydroxide solution (2 mL) was added to a solution of ethyl 1-(2-((2'-chloro-2,6-diethoxy-4'-fluorobiphenyl-4-yl)methyl)-5-oxa-2,6-diazaspiro[3.4]oct-6-en-7-yl)-4-ethylpiperidine 4 carboxylate (381 mg) in ethanol (8 mL), the resultant was stirred for 15 hours at 80° C. 2 M aqueous sodium hydroxide solution (2 mL) was added thereto, and the resultant was stirred for 7 hours at 80° C. Further, 2 M aqueous sodium hydroxide solution (2 mL) was added thereto, the resultant was stirred for 15 hours at 80° C., and then the solvent was distilled off under reduced pressure. Water was added to the residue, the resultant was neutralized with 2 M hydrochloric acid, and then the obtained solid was collected by filtration. After the obtained solid was dissolved in ethyl acetate and THF, it was dried over anhydrous magnesium sulfate, and the solvent was distilled off under reduced pressure. The obtained residue was crystallized (hexane/ethanol), thereby obtaining the title compound (257 mg).

$^1$H NMR (300 MHz, DMSO-$d_6$) δ 0.78 (3H, t, J=7.5 Hz), 1.12 (6H, t, J=6.9 Hz), 1.27-1.41 (2H, m), 1.49 (2H, q, J=7.4 Hz), 1.93 (2H, d, J=13.9 Hz), 2.74-2.89 (2H, m), 3.19 (2H, d, J=6.8 Hz), 3.29-3.41 (4H, m), 3.49 (2H, d, J=7.4 Hz), 3.61 (2H, s), 3.88-4.04 (4H, m), 6.61 (2H, s), 7.14-7.26 (2H, m), 7.43 (1H, dd, J=9.0, 2.4 Hz).

Example 222

1-(2-(5-Cyclopropyl-4-(4,4-difluoropiperidin-1-yl)-2-ethoxybenzyl)-5-oxa-2,6-diazaspiro[3.4]oct-6-en-7-yl)-4-methylpiperidine-4-carboxylic acid A) Methyl 4-(1,4-dioxa-8-azaspiro[4,5]deca-8-yl)-2-ethoxybenzoate Using methyl 4-bromo-2-ethoxybenzoate and 1,4-dioxa-8-azaspiro[4.5]decane, the title compound was obtained in the similar manner as in Step A of Example 212.

$^1$H NMR (300 MHz, $CDCl_3$) δ 1.47 (3H, t, J=6.9 Hz), 1.75-1.84 (4H, m), 3.35-3.52 (4H, m), 3.83 (3H, s), 4.00 (4H, s), 4.09 (2H, q, J=7.0 Hz), 6.39 (1H, d, J=2.4 Hz), 6.47 (1H, dd, J=8.8, 2.3 Hz), 7.78 (1H, d, J=8.9 Hz).

B) Methyl 2-ethoxy-4-(4-oxopiperidin-1-yl)benzoate

Using methyl 4-(1,4-dioxa-8-azaspiro[4.5]deca-8-yl)-2-ethoxybenzoate, the title compound was obtained in the similar manner as in Step B of Example 212.

$^1$H NMR (300 MHz, $CDCl_3$) δ 1.49 (3H, t, J=7.0 Hz), 2.58 (4H, t, J=6.1 Hz), 3.72 (4H, t, J=6.1 Hz), 3.85 (3H, s), 4.11 (2H, q, J=7.0 Hz), 6.41 (1H, d, J=2.4 Hz), 6.49 (1H, dd, J=8.8, 2.4 Hz), 7.83 (1H, d, J=8.8 Hz).

C) Methyl 4-(4,4-difluoropiperidin-1-yl)-2-ethoxybenzoate

Using methyl 2-ethoxy-4-(4-oxopiperidin-1-yl)benzoate, the title compound was obtained in the similar manner as in Step B of Example 168.

$^1$H NMR (300 MHz, $CDCl_3$) δ 1.48 (3H, t, J=7.0 Hz), 1.97-2.17 (4H, m), 3.43-3.53 (4H, m), 3.84 (3H, s), 4.09 (2H, q, J=7.0 Hz), 6.40 (1H, d, J=2.4 Hz), 6.48 (1H, dd, J=8.8, 2.4 Hz), 7.80 (1H, d, J=8.8 Hz).

D) Methyl 5-bromo-4-(4,4-difluoropiperidin-1-yl)-2-ethoxybenzoate

Using methyl 4-(4,4-difluoropiperidin-1-yl)-2-ethoxybenzoate, the title compound was obtained in the similar manner as in Step B of Example 189.

$^1$H NMR (300 MHz, $CDCl_3$) δ 1.47 (3H, t, J=6.9 Hz), 2.04-2.30 (4H, m), 3.11-3.26 (4H, m), 3.86 (3H, s), 4.09 (2H, q, J=6.9 Hz), 6.58 (1H, s), 8.04 (1H, s).

E) Methyl 5-cyclopropyl-4-(4,4-difluoropiperidin-1-yl)-2-ethoxybenzoate

Using methyl 5-bromo-4-(4,4-difluoropiperidin-1-yl)-2-ethoxybenzoate and cyclopropylboronic acid, the title compound was obtained in the similar manner as in Step D of Example 23.

$^1$H NMR (300 MHz, $CDCl_3$) δ 0.69-0.77 (2H, m), 0.91-1.01 (2H, m), 1.45 (3H, t, J 7.0 Hz), 1.95-2.07 (1H, m), 2.08-2.25 (4H, m), 3.14-3.25 (4H, m), 3.85 (3H, s), 4.08 (2H, q, J=7.0 Hz), 6.56 (1H, s), 7.33 (1H, s).

F) 5-Cyclopropyl-4-(4,4-difluoropiperidin-1-yl)-2-ethoxybenzoic acid

Using methyl 5-cyclopropyl-4-(4,4-difluoropiperidin-1-yl)-2-ethoxybenzoate, the title compound was obtained in the similar manner as in Example 2.

$^1$H NMR (300 MHz, $CDCl_3$) δ 0.68-0.85 (2H, m), 0.90-1.10 (2H, m), 1.55 (3H, t, J=7.0 Hz), 1.94-2.06 (1H, m), 2.09-2.28 (4H, m), 3.12-3.30 (4H, m), 4.29 (2H, q, J=7.0 Hz), 6.57 (1H, s), 7.64 (1H, s), 10.88 (1H, s).

G) 5-Cyclopropyl-4-(4,4-difluoropiperidin-1-yl)-2-ethoxybenzaldehyde

Using 5-cyclopropyl-4-(4,4-difluoropiperidin-1-yl)-2-ethoxybenzoic acid, the title compound was obtained in the similar manner as in Step G of Example 212.

$^1$H NMR (300 MHz, $CDCl_3$) δ 0.71-0.80 (2H, m), 0.93-1.02 (2H, m), 1.46 (3H, t, J=7.0 Hz), 1.89-2.03 (1H, m), 2.10-2.26 (4H, m), 3.21-3.30 (4H, m), 4.12 (2H, q, J=7.0 Hz), 6.50 (1H, s), 7.34 (1H, s), 10.34 (1H, s).

H) Ethyl 1-(2-(5-cyclopropyl-4-(4,4-difluoropiperidin-1-yl)-2-ethoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 5-cyclopropyl-4-(4,4-difluoropiperidin-1-yl)-2-ethoxybenzaldehyde, the title compound was obtained in the similar manner as in Step G of Example 1.

MS (ESI+): $[M+H]^+$ 575.6.

I) 1-(2-(5-Cyclopropyl-4-(4,4-difluoropiperidin-1-yl)-2-ethoxybenzyl)-5-oxa-2,6-diazaspiro[3.4]oct-6-en-7-yl)-4-methylpiperidine-4-carboxylic acid Using ethyl 1-(2-(5-cyclopropyl-4-(4,4-difluoropiperidin-1-yl)-2-ethoxybenzyl)-5-oxa-2,6-diazaspiro[3.4]oct-6-en-7-yl)-4-methylpiperidine-4-carboxylate, the title compound was obtained in the similar manner as in Example 2.

Example 223

1-(2-(3-Chloro-5-cyclopropyl-4-(4,4-difluoropiperidin-1-yl)-2-ethoxybenzyl)-5-oxa-2,6-diazaspiro[3.4]oct-6-en-7-yl)-4-methylpiperidine-4-carboxylic acid A) 3-Chloro-5-cyclopropyl-4-(4,4-difluoropiperidin-1-yl)-2-ethoxybenzaldehyde N-Chlorosuccinimide (259 mg) was added to a mixture of 5-cyclopropyl-4-(4,4-difluoropiperidin-1-yl)-2-ethoxybenzaldehyde (600 mg) and acetonitrile (5 mL), the resultant was stirred for 30 minutes at 60° C., and the solvent of the reaction mixture was distilled off under reduced pressure. The obtained residue was purified by a silica gel column chromatography (hexane/ethyl acetate), thereby obtaining the title compound (320 mg).

$^1$H NMR (300 MHz, $CDCl_3$) δ 0.63-0.76 (2H, m), 0.94-1.05 (2H, m), 1.47 (3H, t, J=7.0 Hz), 1.99-2.28 (5H, m), 3.18-3.62 (4H, m, J=11.0 Hz), 4.04-4.16 (2H, m), 7.36 (1H, s), 10.25 (1H, s).

B) Ethyl 1-(2-(3-chloro-5-cyclopropyl-4-(4,4-difluoropiperidin-1-yl)-2-ethoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 3-chloro-5-cyclopropyl-4-(4,4-difluoropiperidin-1-yl)-2-ethoxybenzaldehyde, the title compound was obtained in the similar manner as in Step G of Example 1.

MS (ESI+): $[M+H]^+$ 609.5.

C) 1-(2-(3-Chloro-5-cyclopropyl-4-(4,4-difluoropiperidin-1-yl)-2-ethoxybenzyl)-5-oxa-2,6-diazaspiro[3.4]oct-6-en-7-yl)-4-methylpiperidine-4-carboxylic acid Using ethyl 1-(2-(3-chloro-5-cyclopropyl-4-(4,4-difluoropiperidin-1-yl)-2-ethoxybenzyl)-5-oxa-2,6-diaza spiro[3.4]oct-6-en-7-yl)-4-methylpiperidine-4-carboxylate, the title compound was obtained in the similar manner as in Example 2.

Example 224

1-(2-((2-Cyclopropyl-4-(4,4-difluoropiperidin-1-yl)-5-ethoxybenzyl)-5-oxa-2,6-diazaspiro[3.4]oct-6-en-7-yl)-4-methylpiperidine-4-carboxylic acid A) 2-Bromo-5-ethoxy-4-fluorobenzoic acid Bromine (2.52 mL) was added to a mixture of 3-ethoxy-4-fluorobenzoic acid (4.11 g), acetic acid (10 mL) and water (10 mL), and the resultant was stirred for 30 minutes at 60° C. The reaction mixture was set to 0° C., and the precipitated solid was washed with water, thereby obtaining the title compound (5.22 g).

$^1$H NMR (300 MHz, $CDCl_3$) δ 1.48 (3H, t, J=7.0 Hz), 4.15 (2H, q, J=7.0 Hz), 7.42 (1H, d, J=10.4 Hz), 7.66 (1H, d, J=8.7 Hz).

B) Ethyl 2-bromo-5-ethoxy-4-fluorobenzoate

Iodoethane (2.38 mL) was added to a mixture of 2-bromo-5-ethoxy-4-fluorobenzoic acid (5.22 g), potassium carbonate (4.11 g) and DMF (30 mL), and the resultant was stirred for 30 minutes at 60° C. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (5.58 g).

$^1$H NMR (300 MHz, $CDCl_3$) δ 1.41 (3H, t, J=7.1 Hz), 1.46 (3H, t, J=7.0 Hz), 4.13 (2H, q, J=7.0 Hz), 4.39 (2H, q, J=7.2 Hz), 7.37 (1H, d, J=10.4 Hz), 7.44 (1H, d, J=8.7 Hz).

C) Ethyl 2-cyclopropyl-5-ethoxy-4-fluorobenzoate

Using ethyl 2-bromo-5-ethoxy-4-fluorobenzoate and cyclopropylboronic acid, the title compound was obtained in the similar manner as in Step D of Example 23.

$^1$H NMR (300 MHz, $CDCl_3$) δ 0.50-0.67 (2H, m), 0.90-1.02 (2H, m), 1.35-1.48 (6H, m), 2.51-2.67 (1H, m), 4.12 (2H, q, J=7.1 Hz), 4.37 (2H, q, J=7.1 Hz), 6.73 (1H, d, J=12.7 Hz), 7.45 (1H, d, J=8.9 Hz).

D) Ethyl 2-cyclopropyl-4-(4,4-difluoropiperidin-1-yl)-5-ethoxybenzoate

Using ethyl 2-cyclopropyl-5-ethoxy-4-fluorobenzoate and 4,4-difluoropiperidine hydrochloride, the title compound was obtained in the similar manner as in Step A of Example 189.

$^1$H NMR (300 MHz, $CDCl_3$) δ 0.52-0.68 (2H, m), 0.85-0.98 (2H, m), 1.33-1.52 (6H, m), 2.07-2.24 (4H, m), 2.51-2.69 (1H, m), 3.14-3.31 (4H, m), 4.07-4.19 (2H, m), 4.29-4.42 (2H, m), 6.55 (1H, s), 7.36 (1H, s).

E) 2-Cyclopropyl-4-(4,4-difluoropiperidin-1-yl)-5-ethoxybenzaldehyde

Using ethyl 2-cyclopropyl-4-(4,4-difluoropiperidin-1-yl)-5-ethoxybenzoate, the title compound was obtained in the similar manner as in Example 2 and Step G of Example 212.

$^1$H NMR (300 MHz, $CDCl_3$) δ 0.68-0.77 (2H, m), 0.98-1.09 (2H, m), 1.46 (3H, t, J=6.9 Hz), 2.06-2.25 (4H, m), 2.31-2.47 (1H, m), 3.23-3.36 (4H, m), 4.11 (2H, q, J=6.9 Hz), 6.62 (1H, s), 7.33 (1H, s), 10.57 (1H, s).

F) Ethyl 1-(2-((2-cyclopropyl-4-(4,4-difluoropiperidin-1-yl)-5-ethoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4-(4,4-difluoropiperidin-1-yl)-5-ethoxybenzaldehyde, the title compound was obtained in the similar manner as in Step G of Example 1.

$^1$H NMR (300 MHz, $CDCl_3$) δ 0.52-0.62 (2H, m), 0.82-0.94 (2H, m), 1.21 (3H, s), 1.26 (3H, t, J=7.1 Hz), 1.38-1.52 (5H, m), 1.90 (1H, s), 2.00-2.23 (6H, m), 2.88-3.03 (2H, m), 3.14 (4H, t, J=5.5 Hz), 3.26 (2H, s), 3.32-3.45 (4H, m), 3.54-3.71 (2H, m), 3.84 (2H, s), 4.05 (2H, q, J=6.7 Hz), 4.16 (2H, q, J=7.1 Hz), 6.58 (1H, s), 6.82 (1H, s).

G) 1-(2-((2-Cyclopropyl-4-(4,4-difluoropiperidin-1-yl)-5-ethoxybenzyl)-5-oxa-2,6-diazaspiro[3.4]oct-6-en-7-yl)-4-methylpiperidine-4-carboxylic acid Using ethyl 1-(2-((2-cyclopropyl-4-(4,4-difluoropiperidin-1-yl)-5-ethoxybenzyl)-5-oxa-2,6-diazaspiro[3.4]oct-6-en-7-yl)-4-methylpiperidine-4-carboxylate, the title compound was obtained in the similar manner as in Example 2.

Example 225

Trans-4-(2-((2-Cyclopropyl-6-ethoxy-4'-fluorobiphenyl-4-yl)methyl)-5-oxa-2,6-diazaspiro[3.4]oct-6-en-7-yl)cyclohexanecarboxylic acid A) Methyl trans-4-(2-((2-cyclopropyl-6-ethoxy-4'-fluorobiphenyl-4-yl)methyl)-5-oxa-2,6-diazaspiro[3.4]oct-6-en-7-yl)cyclohexanecarboxylate Sodium triacetoxyborohydride (279 mg) was added to a mixture of methyl trans-4-(5-oxa-2,6-diazaspiro[3.4]oct-6-en-7-yl)cyclohexanecarboxylate hydrochloride (190 mg), 2-cyclopropyl-6-ethoxy-4'-fluorobiphenyl-4-carbaldehyde (206 mg), triethylamine (133 mg) and THF (10 mL), and the resultant was stirred for 16 hours at room temperature. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (307 mg).

$^1$H NMR (300 MHz, $CDCl_3$) δ 0.58-0.65 (2H, m), 0.70-0.79 (2H, m), 1.19 (3H, t, J=6.9 Hz), 1.30-1.65 (5H, m), 1.94-2.13 (4H, m), 2.23-2.44 (2H, m), 3.20 (2H, s), 3.36-3.42 (2H, m), 3.46-3.52 (2H, m), 3.63 (2H, s), 3.67 (3H, s), 3.94 (2H, q, J=7.0 Hz), 6.41 (1H, s), 6.70 (1H, s), 7.03-7.13 (2H, m), 7.21-7.30 (2H, m).

B) trans-4-(2-((2-Cyclopropyl-6-ethoxy-4'-fluorobiphenyl-4-yl)methyl)-5-oxa-2,6-diazaspiro[3.4]oct-6-en-7-yl)cyclohexanecarboxylic acid 2 M aqueous sodium hydroxide solution (2 mL) was added to a solution of methyl trans-4-(2-((2-cyclopropyl-6-ethoxy-4'-fluorobiphenyl-4-yl)methyl)-5-oxa-2,6-diazaspiro[3.4]oct-6-en-7-yl)cyclohexanecarboxylate (280 mg) in ethanol (8 mL), the resultant was stirred for 1 hour at 70° C., and then the solvent was distilled off under reduced pressure. Water was added to the obtained residue, the resultant was neutralized with 2 M hydrochloric acid, and then the precipitated solid was collected by filtration. After the obtained solid was dissolved in ethyl acetate and THF, it was dried over anhydrous magnesium sulfate, and the solvent was distilled off under reduced pressure. The obtained residue was crystallized (hexane/ethanol), thereby obtaining the title compound (210 mg).

$^1$H NMR (300 MHz, DMSO-$d_6$) δ 0.56-0.66 (2H, m), 0.68-0.78 (2H, m), 1.12 (3H, t, J=6.9 Hz), 1.22-1.53 (5H, m), 1.79-1.99 (4H, m), 2.11-2.24 (1H, m), 2.25-2.39 (1H, m), 3.22-3.51 (6H, m), 3.75 (2H, brs), 3.94 (2H, q, J=6.9 Hz), 6.52 (1H, brs), 6.89 (1H, brs), 7.16-7.32 (4H, m), 12.10 (1H, brs).

Example 226

1-(2-((2-Cyclopropyl-2',4'-difluoro-5-methoxybiphenyl-4-yl)methyl)-5-oxa-2,6-diazaspiro[3.4]oct-6-en-7-yl)-4-methylpiperidine-4-carboxylic acid A) 2',4'-Difluoro-3-methoxybiphenyl-4-carbaldehyde 4-Bromo-2-methoxybenzaldehyde (1.50 g), (2,4-difluorophenyl)boronic acid (1.65 g), dicyclohexyl(2',6'-dimethoxybiphenyl-2-yl)phosphine (430 mg), tris(dibenzylideneacetone)dipalladium(0) (447 mg) and 2 M aqueous sodium carbonate solution (10 mL) were added to toluene (30 mL), and the resultant was stirred for 2 hours at 100° C. The reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. The obtained residue was crystalized (ethanol/water), thereby obtaining the title compound (1.00 g).

$^1$H NMR (300 MHz, DMSO-$d_6$) δ 3.98 (3H, s), 7.21-7.30 (2H, m), 7.32-7.37 (1H, m), 7.39-7.49 (1H, m), 7.67-7.82 (2H, m), 10.39 (1H, s).

B) 2-Bromo-2',4'-difluoro-5-methoxybiphenyl carbaldehyde 1,3-Dibromo-1,3,5-triazine-2,4,6-trione (1.27 g) was added to a solution of 2',4'-difluoro-3-methoxybiphenyl-4-carbaldehyde (1.00 g) in DMF (9 mL) in the range of 15° C. to 30° C., the resultant was stirred for 3 hours at room temperature. Water (4.5 mL) was added thereto, and the resultant was stirred for 1 hour. After the precipitated crystals were collected by filtration, it was washed with water, thereby obtaining the title compound (1.06 g).

$^1$H NMR (300 MHz, DMSO-$d_6$) δ 3.94 (3H, s), 7.20-7.30 (1H, m), 7.32 (1H, s), 7.38-7.54 (2H, m), 7.91 (1H, s), 10.31 (1H, s).

C) 2-Cyclopropyl-2',4'-difluoro-5-methoxybiphenyl-4-carbaldehyde

2-Bromo-2',4'-difluoro-5-methoxybiphenyl-4-carbaldehyde (1.05 g), cyclopropylboronic acid (414 mg), dicyclohexyl(2',6'-dimethoxybiphenyl-2-yl)phosphine (198 mg), tris(dibenzylideneacetone)dipalladium(0) (206 mg) and 2 M aqueous sodium carbonate solution (4.8 mL) were added to toluene (15 mL), and the resultant was stirred for 2 hours at 100° C. The reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. After the obtained residue was passed through a short column of a silica gel (hexane/ethyl acetate), the filtrate was concentrated under reduced pressure. The obtained residue was crystallized (ethanol/water), thereby obtaining the title compound (924 mg).

$^1$H NMR (300 MHz, DMSO-$d_6$) δ 0.44-0.61 (2H, m), 0.66-0.84 (2H, m), 1.46-1.73 (1H, m), 3.90 (3H, s), 7.07 (1H, s), 7.17-7.29 (1H, m), 7.32 (1H, s), 7.36-7.55 (2H, m), 10.34 (1H, s).

D) 1-(2-((2-Cyclopropyl-2',4'-difluoro-5-methoxybiphenyl-4-yl)methyl)-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-5-oxa-2,6-diazaspiro[3.4]oct-6-ene-2-carboxylate (402 mg) was added to formic acid (3.0 mL), the resultant was stirred for 1 hour at 70° C., and then the solvent was distilled off under reduced pressure. The obtained residue was mixed with 2-cyclopropyl-2',4'-difluoro-5-methoxybiphenyl-4-carbaldehyde (302 mg) and THF (10 mL), sodium triacetoxyborohydride (333 mg) was added to the mixture, and the resultant was stirred for 3 hours at room temperature. After an aqueous saturated sodium hydrogen carbonate solution was added to the reaction mixture, extraction thereof was performed using ethyl acetate. The obtained organic layer was washed with a 5% saline solution, and the solvent was distilled off under reduced pressure. The obtained residue was purified by a silica gel chromatography (NH, hexane/ethyl acetate), thereby obtaining the title compound (550 mg).

$^1$H NMR (300 MHz, DMSO-$d_6$) δ 0.48 (2H, d, J=5.2 Hz), 0.65-0.78 (2H, m), 1.15 (3H, s), 1.19 (3H, t, J=7.1 Hz), 1.34-1.47 (2H, m), 1.51-1.62 (1H, m), 1.93 (2H, d, J=13.7 Hz), 2.86 (2H, t, J=10.2 Hz), 3.14 (2H, d, J=8.3 Hz), 3.24-3.36 (4H, m), 3.44 (2H, d, J=8.5 Hz), 3.54 (2H, s), 3.74 (3H, s), 4.11 (2H, q, J=7.1 Hz), 6.74 (1H, s), 6.85 (1H, s), 7.17 (1H, td, J=8.4, 2.5 Hz), 7.33 (1H, td, J=9.7, 2.5 Hz), 7.39-7.49 (1H, m).

E) 1-(2-((2-Cyclopropyl-2',4'-difluoro-5-methoxybiphenyl-4-yl)methyl)-5-oxa-2,6-diazaspiro[3.4]oct-6-en-7-yl)-4-methylpiperidine-4-carboxylic acid 2 M aqueous sodium hydroxide solution (3.2 mL) was added to a solution of 1-(2-((2-cyclopropyl-2',4'-difluoro-5-methoxybiphenyl-4-yl)methyl)-5-oxa-2,6-diazaspiro[3.4]oct-6-en-7-yl)-4-methylpiperidine-4-carboxylate (506 mg) in ethanol (5 mL), and the resultant was stirred for 2 hours at 70° C. The reaction mixture was cooled to room temperature, it was neutralized with 2 M hydrochloric acid, was stirred for 30 minutes at room temperature, and was further stirred for 30 minutes under ice-cooling. The precipitated solid was collected by filtration, and was washed with water. Recrystallization (DMSO/ethanol) of the obtained solid was performed, thereby obtaining the title compound (287 mg).

$^1$H NMR (300 MHz, DMSO-$d_6$) δ 0.43-0.53 (2H, m), 0.65-0.76 (2H, m), 1.14 (3H, s), 1.28-1.44 (2H, m), 1.50-1.61 (1H, m), 1.90 (2H, d, J=13.6 Hz), 2.88 (2H, t, J=10.3 Hz), 3.14 (2H, d, J=8.2 Hz), 3.20-3.38 (4H, m), 3.44 (2H, d, J=8.3 Hz), 3.54 (2H, s), 3.74 (3H, s), 6.74 (1H, s), 6.85 (1H, s), 7.17 (1H, td, J=8.4, 2.5 Hz), 7.33 (1H, td, J=9.7, 2.5 Hz), 7.38-7.49 (1H, m).

Example 227

1-(2-(4-Cyclobutyl-5-cyclopropyl-2-ethoxybenzyl)-5-oxa-2,6-diazaspiro[3.4]oct-6-en-7-yl)-4-methylpiperidine-4-carboxylic acid A) Methyl 4-cyclobutyl-2-ethoxybenzoate Iodine (20 mg) and 1,2-dibromoethane (0.2 mL) were added to a mixture of magnesium (7.09 g) and diethyl ether (100 mL). Furthermore, bromocyclobutane (26.46 g) was slowly added dropwise thereto. After the dropwise addition ended, the resultant was stirred for 2 hours at 40° C., and a solution of cyclobutylmagnesium bromide reagent was prepared. After zinc chloride (30 g) was heated at 160° C. in high vacuum, it was dissolved in THF (220 mL). The solution was added to the solution of cyclobutylmagnesium bromide reagent prepared in advance at 0° C., and the resultant was stirred for 1 hour at the same temperature. A mixture of methyl 2-ethoxy-4-iodobenzoate (10.0 g), tris(dibenzylideneacetone)dipalladium(0) (2.99 g), 4,5-bis(diphenylphosphino)-9,9-dimethylxanthene (1.89 g) and THF (200 mL) was added to the mixture, and the resultant was stirred overnight at 60° C. in an argon atmosphere. After the reaction mixture was filtered using celite, the obtained filtrate was concentrated under reduced pressure. Water and ethyl acetate were added to the obtained residue, and the organic layer was separated. After the obtained organic layer was washed with water, it was dried over sodium sulfate. The solvent was distilled off under reduced pressure, and the obtained residue was purified by a silica gel chromatography (hexane/ethyl acetate), thereby obtaining the title compound (4.3 g).

$^1$H NMR (400 MHz, $CDCl_3$) δ 1.45 (3H, t, J=6.96 Hz), 1.84-1.88 (1H, m), 1.96-2.18 (3H, m), 2.31-2.38 (2H, m), 3.49-3.57 (1H, m), 3.86 (3H, s), 4.11 (2H, q, J=6.9 Hz), 6.76 (1H, s), 6.80 (1H, d, J=8.24 Hz), 7.72 (1H, d, J=8.04 Hz).

B) Methyl 5-bromo-4-cyclobutyl-2-ethoxybenzoate

Bromine (7.65 g) was added to a mixture of methyl 4-cyclobutyl-2-ethoxybenzoate (8.6 g) and acetic acid (85 mL) under ice-cooling, and the resultant was stirred for 1 hour at the same temperature. After the reaction mixture was neutralized with an aqueous saturated sodium hydrogen carbonate solution, ethyl acetate was added thereto. The obtained organic layer was sequentially washed with an aqueous sodium hydrogen sulfite solution, and a saturated saline solution, was dried over sodium sulfate, and then the solvent was distilled off under reduced pressure. The obtained residue was purified by a silica gel chromatography (hexane/ethyl acetate), thereby obtaining the title compound (7.0 g).

$^1$H NMR (400 MHz, $CDCl_3$) δ 1.46 (3H, t, J=7 Hz), 1.79-1.84 (1H, m), 1.99-2.12 (3H, m), 2.40-2.47 (2H, m), 3.68-3.77 (1H, m), 3.86 (3H, s), 4.09-4.16 (2H, m), 6.89 (1H, s), 7.92 (1H, s).

C) Methyl 4-cyclobutyl-5-cyclopropyl-2-ethoxybenzoate

Cyclopropylboronic acid (3.29 g), dicyclohexyl (2',6'-dimethoxybiphenyl-2-yl)phosphine (1.57 g), sodium carbonate (8.14 g) and tris(dibenzylideneacetone)dipalladium (0) (1.75 g) were added to a mixture of methyl 5-bromo-4-cyclobutyl-2-ethoxybenzoate (6.0 g), toluene (48 mL) and water (12 mL), and the resultant was stirred for 16 hours at 100° C. in an argon atmosphere. After the reaction mixture was filtered using celite, the filtrate was extracted using ethyl acetate. The obtained organic layer was sequentially washed with water and a saturated saline solution, was dried over anhydrous magnesium sulfate, and then the solvent was distilled off under reduced pressure. The obtained residue was purified by a SFC (column: Chiralpak AD-H, mobile phase: carbon dioxide/2-propanol/methanol), thereby obtaining the title compound (2.3 g).

$^1$H NMR (400 MHz, $CDCl_3$) δ 0.55-0.60 (2H, m), 0.83-0.88 (2H, m), 1.44 (3H, t, J=7.0 Hz), 1.58-1.88 (2H, m), 1.99-2.20 (3H, m), 2.36-2.42 (2H, m), 3.85 (3H, s), 3.87-3.96 (1H, m), 4.12 (2H, q, J=7.0 Hz), 6.85 (1H, s), 7.42 (1H, s).

D) (4-Cyclobutyl-5-cyclopropyl-2-ethoxyphenyl) methanol

Lithium aluminum hydride (1 M THF solution, 9.23 mL) was added to a mixture of methyl 4-cyclobutyl-5-cyclopropyl-2-ethoxybenzoate (2.3 g) and THF (60 mL) at 0° C., and the resultant was stirred for 2 hours at room temperature. After an aqueous saturated sodium sulfate solution was added to the reaction mixture at 0° C., extraction thereof was performed using ethyl acetate. After the organic layer was sequentially washed with water and a saturated saline solution, it was dried over sodium sulfate. The solvent was distilled off under reduced pressure, thereby obtaining the title compound (2.0 g).

$^1$H NMR (400 MHz, $CDCl_3$) δ 0.54-0.58 (2H, m), 0.81-0.86 (2H, m), 1.43 (3H, t, J=6.96 Hz), 1.73-1.87 (2H, m), 1.98-2.19 (3H, m), 2.34-2.40 (3H, m), 3.88-3.97 (1H, m), 4.12 (2H, q, J=6.96 Hz), 4.61 (2H, d, J=6.36 Hz), 6.79 (1H, s), 6.86 (1H, s).

E) 4-Cyclobutyl-5-cyclopropyl-2-ethoxybenzaldehyde

Manganese dioxide (7.0 g) was added to a mixture of (4-cyclobutyl-5-cyclopropyl-2-ethoxyphenyl)methanol (2.0 g) and acetone (50 mL), and the resultant was stirred overnight at room temperature. After the reaction mixture was filtered using celite, the obtained filtrate was concentrated under reduced pressure. The obtained residue was purified by a silica gel chromatography (hexane/ethyl acetate), thereby obtaining the title compound (1.5 g).

$^1$H NMR (400 MHz, $CDCl_3$) δ 0.58-0.62 (2H, m), 0.84-0.88 (2H, m), 1.46 (3H, t, J=7.04 Hz), 1.71-1.77 (1H, m), 1.82-1.89 (1H, m), 2.03-2.22 (3H, m), 2.38-2.42 (2H, m), 3.89-3.98 (1H, m), 4.14-4.19 (2H, m), 6.85 (1H, s), 7.44 (1H, s), 10.40 (1H, s).

F) Ethyl 1-(2-(4-cyclobutyl-5-cyclopropyl-2-ethoxybenzyl)-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-5-oxa-2,6-diazaspiro[3.4]oct-6-ene-2-carboxylate (390 mg) was added to formic acid (3.0 mL), the resultant was stirred for 30 minutes at 70° C., and then the solvent was distilled off under reduced pressure. Sodium triacetoxyborohydride (325 mg) was added to a solution of the obtained residue and 4-cyclobutyl-5-cyclopropyl-2-ethoxybenzaldehyde (250 mg) in THF (10 mL), and the resultant was stirred for 3 hours at room temperature. After an aqueous saturated sodium hydrogen carbonate solution was added to the reaction mixture, extraction thereof was performed using ethyl acetate. The obtained organic layer was washed with a 5% saline solution, and the solvent was distilled off under reduced pressure. The obtained residue was purified by a silica gel column chromatography (NH, hexane/ethyl acetate), thereby obtaining the title compound (452 mg).

MS (ESI+): $[M+H]^+$ 510.2.

G) 1-(2-(4-Cyclobutyl-5-cyclopropyl-2-ethoxybenzyl)-5-oxa-2,6-diazaspiro[3.4]oct-6-en-7-yl)-4-methylpiperidine-4-carboxylic acid 2 M aqueous sodium hydroxide solution (3.1 mL) was added to a solution of ethyl 1-(2-(4-cyclobutyl-5-cyclopropyl-2-ethoxybenzyl)-5-oxa-2,6-diazaspiro[3.4]oct-6-en-7-yl)-4-methylpiperidine-4-carboxylate (450 mg) in ethanol (5 mL), and the resultant was stirred for 2 hours at 70° C. The reaction mixture was cooled to room temperature, it was neutralized with 2 M hydrochloric acid, and the solvent was distilled off under reduced pressure. Water was added to the obtained residue to crystallize, and the resultant was washed with ethyl acetate, thereby obtaining the title compound (140 mg).

$^1$H NMR (300 MHz, DMSO-$d_6$) δ 0.41-0.54 (2H, m), 0.78-0.88 (2H, m), 1.13 (3H, s), 1.26-1.44 (5H, m), 1.71-2.21 (7H, m), 2.25-2.40 (2H, m), 2.87 (2H, t, J=10.4 Hz), 3.09 (2H, d, J=7.2 Hz), 3.21-3.41 (6H, m), 3.48 (2H, s), 3.79-3.93 (1H, m), 4.03 (2H, q, J=6.9 Hz), 6.71-6.82 (2H, m), 12.42 (1H, brs).

Example 228

4-(2-((2,6-Diethoxy-4'-fluorobiphenyl-4-yl)methyl)-5-oxa-2,6-diazaspiro[3.4]oct-6-en-7-yl)bicyclo[2.2.1]heptane-1-carboxylic acid A) Cycloheptane-1,3-dicarboxylic acid Ruthenium(III) chloride (661 mg) was added to a mixed solution of bicyclo[2.2.1]hept-2-ene (15.0 g) in ethyl acetate (330 mL) and acetonitrile (330 mL) under ice-cooling, subsequently, aqueous solution (450 mL) of sodium periodate (140 g) was added thereto, and the resultant was stirred for 2 hours at room temperature. The reaction mixture was filtered using celite, the organic layer of the filtrate was separated, and then the obtained organic layer was extracted using 0.25 M aqueous sodium hydroxide solution. A pH of the solution of the obtained aqueous layer was set to pH 1 with concentrated hydrochloric acid, and extraction thereof was performed using ethyl acetate. After the obtained organic layer was dried over anhydrous sodium sulfate, the solvent was distilled off under reduced pressure, thereby obtaining the title compound (13.0 g).

$^1$H NMR (400 MHz, DMSO-$d_6$) δ 1.72-1.90 (5H, m), 2.06-2.13 (1H, m), 2.68-2.70 (2H, m), 12.06 (2H, s).

B) Dimethyl cycloheptane-1,3-dicarboxylate

Concentrated sulfuric acid (1.23 mL) was added to a solution of cyclopentane-1,3-dicarboxylic acid (20.0 g) in methanol (400 mL), the resultant was heated to reflux overnight, and then the solvent was distilled off under reduced pressure. The obtained residue was dissolved in ethyl acetate, it was washed with an aqueous saturated sodium carbonate solution, and subsequently, washed with a saturated saline solution. The obtained organic layer was dried over anhydrous sodium sulfate, and the solvent was distilled off under reduced pressure. The obtained residue was purified by a silica gel column chromatography (hexane/ethyl acetate), thereby obtaining the title compound (16.0 g).

$^1$H NMR (400 MHz, DMSO-$d_6$) δ 1.88-1.96 (4H, m), 2.02-2.11 (1H, m), 2.18-2.25 (1H, m), 2.76-2.81 (2H, m), 3.65 (6H, s).

C) Dimethyl bicyclo[2.2.1]heptane-1,4-dicarboxylate n-Butyl lithium (2.3 M hexane solution, 117 mL) was added to a solution of diisopropylamine (40.6 mL) in THF (120 mL) at −20° C. in an argon atmosphere, and the resultant was stirred for 30 minutes at the same temperature. The reaction mixture was further cooled to −75° C., a solution of dimethylcycloheptane-1,3-dicarboxylate (20.0 g) in THF (110 mL) was added thereto over 15 minutes while maintaining the temperature in the range of −75° C. to −70° C. The temperature of the reaction mixture was warmed to −10° C., and the reaction mixture was stirred for 30 minutes at the same temperature. The reaction mixture was cooled to −75° C. again, a solution of 1-bromo-2-chloroethane (15.2 mL) in THF (140 mL) was added thereto over 30 minutes while maintaining the temperature of equal to or less than −70° C. After the temperature of the reaction mixture was slowly warmed to room temperature over 1 hour, an aqueous saturated ammonium chloride solution was added thereto, and then extraction thereof was performed using ethyl acetate. The obtained organic layer was washed with water, dried over anhydrous sodium sulfate, and then the solvent was distilled off under reduced pressure. The obtained residue was purified by a silica gel column chromatography (hexane/ethyl acetate), thereby obtaining the title compound (10.5 g).

$^1$H NMR (400 MHz, DMSO-$d_6$) δ 1.64-1.67 (4H, m), 1.89 (2H, s), 2.01-2.02 (4H, m), 3.66 (6H, s).

D) 4-(Methoxycarbonyl)bicyclo[2.2.1]heptane-1-carboxylic acid

A solution of sodium hydroxide (940 mg) in methanol (10 mL) was added to a solution of dimethylbicyclo[2.2.1]heptane-1,4-dicarboxylate (5.00 g) in THF (150 mL), and the resultant was stirred overnight at room temperature. The reaction mixture was distilled off under reduced pressure, the obtained residue was dissolved in water, and extraction thereof was performed using dichloromethane. A pH of the obtained aqueous layer was set to pH 3 using 6 M hydrochloric acid, and extraction thereof was performed using ethyl acetate. The obtained organic layer was distilled off under reduced pressure, thereby obtaining the title compound (2.50 g).

$^1$H NMR (400 MHz, DMSO-$d_6$) δ 1.57-1.63 (4H, m), 1.72 (2H, s), 1.91-1.92 (4H, m), 3.60 (3H, s), 12.21 (1H, s).

E) Methyl 4-(hydroxymethyl)bicyclo[2.2.1]heptane-1-carboxylate

Borane-tetrahydrofuran complex (1 M THF solution, 22.7 mL) was added dropwise to a solution of 4-(methoxycarbonyl)bicyclo[2.2.1]heptane-1-carboxylic acid (3.00 g) in THF (60 mL) at −40° C., the resultant was stirred for 1 hour at the same temperature, and was further stirred for 2 hours at 0° C. An aqueous saturated sodium hydrogen carbonate solution was added to the reaction mixture at 0° C., and extraction thereof was performed using ethyl acetate. The obtained organic layer was sequentially washed with water and a saturated saline solution, dried over anhydrous sodium sulfate, and then the solvent was distilled off under reduced pressure, thereby obtaining the title compound (2.50 g).

$^1$H NMR (400 MHz, DMSO-$d_6$) δ 1.21-1.24 (2H, m), 1.42 (2H, s), 1.55-1.61 (4H, 1.82-1.89 (2H, m), 3.42 (2H, d, J=5.36 Hz), 3.58 (3H, s), 4.47 (1H, t, J=5.36 Hz).

F) Methyl 4-formylbicyclo[2.2.1]heptane-1-carboxylate

Pyridinium chlorochromate (10.1 g) was added to a solution of methyl 4-(hydroxymethyl)bicyclo[2.2.1]heptane-1-carboxylate (4.30 g) in dichloromethane (80 mL) at 0° C., and the resultant was stirred for 3 hours at room temperature. The reaction mixture was filtered using celite, and the filtrate was concentrated under reduced pressure. The obtained residue was purified by a silica gel column chromatography (hexane/ethyl acetate), thereby obtaining the title compound (2.60 g).

$^1$H NMR (400 MHz, DMSO-$d_6$) δ 1.44-1.49 (1H, m), 1.55-1.70 (3H, m), 1.81 (2H, s), 1.91-2.01 (4H, m), 3.60 (3H, s), 9.75 (1H, s).

G) Methyl 4-((E)-(hydroxyimino)methyl)bicyclo[2.2.1]heptane-1-carboxylate

Hydroxyamine hydrochloride (955 mg) was added to a mixture of methyl 4-formylbicyclo[2.2.1]heptane-1-carboxylate (2.50 g), sodium hydrogen carbonate (1.16 g) and methanol (50 mL) at room temperature, the resultant was stirred for 2 hours at the same temperature, and then the solvent was distilled off under reduced pressure. The obtained residue was diluted by water, and extraction thereof was performed using ethyl acetate. The obtained organic layer was sequentially washed with water and a saturated saline solution, dried over anhydrous sodium sulfate, and then the solvent was distilled off under reduced pressure, thereby obtaining the title compound (2.00 g).

$^1$H NMR (400 MHz, DMSO-$d_6$) δ 1.43-1.48 (2H, m), 1.59-1.84 (4H, m), 1.74-1.94 (4H, m), 3.61 (3H, s), 7.48 (1H, s), 10.52 (1H, s).

H) Methyl 4-((Z)-chloro(hydroxyimino)methyl)bicyclo[2.2.1]heptane-1-carboxylate

N-chlorosuccinimide (1.72 g) was added to a solution of methyl 4-((E)-(hydroxyimino)methyl)bicyclo[2.2.1]heptane-1-carboxylate (2.30 g) in DMF (45 mL) at room temperature, and the resultant was stirred for 2 hours at the same temperature. Water was added to the reaction mixture, and extraction thereof was performed using ethyl acetate. The obtained organic layer was sequentially washed with water and a saturated saline solution, dried over anhydrous sodium sulfate, and then the solvent was distilled off under reduced pressure, thereby obtaining the title compound (1.90 g).

$^1$H NMR (400 MHz, DMSO-$d_6$) δ 1.61-1.69 (4H, m), 1.82 (2H, s), 1.94-1.99 (4H, m), 3.61 (3H, s), 11.66 (1H, s).

I) tert-Butyl 7-(4-(methoxycarbonyl)bicyclo[2.2.1]hept-1-yl)-5-oxa-2,6-diazaspiro[3.4]oct-6-ene-2-carboxylate Triethylamine (1.81 mL) was added to a mixture of tert-butyl 3-methyleneazetidine-1-carboxylate (1.46 g), methyl 4-((Z)-chloro(hydroxyimino)methyl)bicyclo[2.2.1]heptane-1-carboxylate (2.0 g) and dichloromethane (140 mL) at room temperature, and the resultant was stirred for 24 hours at the same temperature. Water was added to the reaction mixture at room temperature, and extraction thereof was performed using dichloromethane. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.20 g).

$^1$H NMR (400 MHz, DMSO-$d_6$) δ 1.42 (9H, s), 1.62-1.75 (4H, m), 1.81 (2H, s), 1.91-1.94 (2H, m), 2.02-2.04 (2H, m), 3.18 (2H, s), 3.71 (3H, s), 3.96 (2H, d, J=9.72 Hz), 4.24 (2H, d, J=9.76 Hz).

J) (2,6-Diethoxy-4'-fluorobiphenyl-4-yl)methanol

Lithium aluminum hydride (1 M THF solution, 18.1 mL) was added dropwise to a solution of ethyl 2,6-diethoxy-4'-fluorobiphenyl-4-carboxylate (4.00 g) in THF (25 mL) at 0° C., and the resultant was stirred for 4 hours at room temperature in a nitrogen atmosphere. An aqueous saturated sodium sulfate solution was added to the reaction mixture, and extraction thereof was performed using ethyl acetate. The obtained organic layer was washed with a saturated saline solution, dried over anhydrous sodium sulfate, and then the solvent was distilled off under reduced pressure, thereby obtaining the title compound (2.80 g).

$^1$H NMR (400 MHz, DMSO-$d_6$) δ 1.24 (6H, t, J=7.04 Hz), 3.97 (4H, q, J=6.96 Hz), 4.68 (2H, s), 6.63 (2H, s), 7.02-7.06 (2H, m), 7.29-7.33 (2H, m).

K) 4-(Bromomethyl)-2,6-diethoxy-4'-fluorobiphenyl

Phosphorus tribromide (1.46 mL) was added to a solution of (2,6-diethoxy-4'-fluorobiphenyl-4-yl)methanol (3.00 g) in toluene (25 mL) at 0° C., and the resultant was stirred for 3 hours at room temperature. An aqueous saturated sodium sulfate solution was added to the reaction mixture, and extraction thereof was performed using ethyl acetate. After the obtained organic layer was washed with a saturated saline solution, it was dried over anhydrous sodium sulfate, and the solvent was distilled off under reduced pressure. The obtained residue was purified by a silica gel column chromatography (hexane/ethyl acetate), thereby obtaining the title compound (3.10 g).

$^1$H NMR (400 MHz, DMSO-$d_6$) δ 1.16 (6H, t, J=7.0 Hz), 3.94-4.02 (4H, m), 4.69 (2H, s), 6.82 (2H, s), 7.14-7.20 (2H, m), 7.27-7.31 (2H, m).

L) Methyl 4-(2-((2,6-diethoxy-4'-fluorobiphenyl-4-yl)methyl)-5-oxa-2,6-diazaspiro[3.4]oct-6-en-7-yl)bicyclo[2.2.1]heptane-1-carboxylate After a mixture of tert-butyl 7-(4-(methoxycarbonyl)bicyclo[2.2.1]hept-1-yl)-5-oxa-2,6-diazaspiro[3.4]oct-6-ene-2-carboxylate (750 mg) and hydrochloric acid-dioxane (10 mL) was stirred for 5 hours at room temperature, the solvent was distilled off under reduced pressure. Potassium carbonate (1.64 g) was added to a solution of the obtained residue in DMF (20 mL), the resultant was stirred for 10 minutes at room temperature, and 4-(bromomethyl)-2,6-diethoxy-4'-fluorobiphenyl (936 mg) was added thereto. The reaction mixture was stirred for 5 hours at room temperature, water was added thereto, and extraction thereof was performed using ethyl acetate. The obtained organic layer was sequentially washed with water and a saturated saline solution, was dried over anhydrous sodium sulfate, and then the solvent was distilled off under reduced pressure. The obtained residue was purified using HPLC (C18, mobile phase: water/acetonitrile (5 mM ammonium acetate-containing system)), thereby obtaining the title compound (350 mg).

$^1$H NMR (400 MHz, DMSO-$d_6$) δ 1.15 (6H, t, J=6.92 Hz), 1.52-1.56 (2H, m), 1.61-1.66 (2H, m), 1.73 (2H, s), 1.83-1.93 (4H, m), 3.24 (2H, d, J=8.32 Hz), 3.45 (2H, d, J=8.36 Hz), 3.58 (2H, s), 3.61 (2H, s), 3.61 (3H, s), 3.94 (4H, q, J=6.88 Hz), 6.61 (2H, s), 7.19-7.16 (2H, n), 7.25-7.27 (2H, m).

M) 4-(2-((2,6-Diethoxy-4'-fluorobiphenyl-4-yl)methyl)-5-oxa-2,6-diazaspiro[3.4]oct-6-en-7-yl)bicyclo[2.2.1]heptane-1-carboxylic acid An aqueous solution of lithium hydroxide monohydrate (47.0 mL) was added to a solution of methyl 4-(2-((2,6-diethoxy-4'-fluorobiphenyl-4-yl)methyl)-5-oxa-2,6-diazaspiro[3.4]oct-6-en-7-yl)bicyclo[2.2.1]heptane-1-carboxylate (200 mg) in THF (4 mL), the resultant was stirred for 6 hours at room temperature, and then the solvent was distilled off under reduced pressure. A pH of the obtained residue was set to pH 5 using 1 M hydrochloric acid, and extraction thereof was performed using dichloromethane. The obtained organic layer was sequentially washed with water and a saturated saline solution, dried over anhydrous sodium sulfate, and then the solvent was distilled off under reduced pressure, thereby obtaining the title compound (110 mg).

Example 229

4-(2-((2-Cyclopropyl-6-ethoxy-4'-fluorobiphenyl-4-yl)methyl)-5-oxa-2,6-diazaspiro[3.4]oct-6-en-7-yl)bicyclo[2.2.1]heptane-1-carboxylic acid A) (2-Cyclopropyl-6-ethoxy-4'-fluorobiphenyl-4-yl)methanol Using 2-cyclopropyl-6-ethoxy-4'-fluorobiphenyl-4-carbaldehyde, the title compound was obtained in the similar manner as in Step A of Example 97.

MS (ESI+): $[M+H]^+$ 287.2.

B) 4-(Bromomethyl)-2-cyclopropyl-6-ethoxy-4'-fluorobiphenyl

Using (2-cyclopropyl-6-ethoxy-4'-fluorobiphenyl-4-yl) methanol, the title compound was obtained in the similar manner as in Step K of Example 228.

$^1$H NMR (400 MHz, DMSO-$d_6$) δ 0.70-0.74 (2H, m), 0.75-0.78 (2H, m), 1.20 (3H, t, J=7.00 Hz), 1.55-1.60 (1H, m), 3.95 (2H, q, J=6.93 Hz), 4.47 (2H, s), 6.54 (1H, s), 6.79 (1H, s), 7.18-7.25 (2H, t, J=8.72 Hz), 7.23-7.26 (2H, m).

C) Methyl 4-(2-((2-cyclopropyl-6-ethoxy-4'-fluoro-biphenyl-4-yl)methyl)-5-oxa-2,6-diazaspiro[3.4]oct-6-en-7-yl)bicyclo[2.2.1]heptane-1-carboxylate Using tert-butyl 7-(4-(methoxycarbonyl)bicyclo[2.2.1]hept-1-yl)-5-oxa-2,6-diazaspiro[3.4]oct-6-ene-2-carboxylate and 4-(bromomethyl)-2-cyclopropyl-6-ethoxy-4'-fluorobiphenyl, the title compound was obtained in the similar manner as in Step L of Example 228.

MS (ESI+): $[M+H]^+$ 533.2.

D) 4-(2-((2-Cyclopropyl-6-ethoxy-4'-fluorobiphenyl-4-yl)methyl)-5-oxa-2,6-diazaspiro[3.4]oct-6-en-7-yl)bicyclo[2.2.1]heptane-1-carboxylic acid Using methyl 4-(2-((2-cyclopropyl-6-ethoxy-4'-fluorobiphenyl-4-yl)methyl)-5-oxa-2,6-diazaspiro[3.4]oct-6-en-7-yl)bicyclo[2.2.1]heptane-1-carboxylate, the title compound was obtained in the similar manner as in Step M of Example 228.

Example 230

4-(2-((2,6-Diethoxy-4'-fluorobiphenyl-4-yl)methyl)-5-oxa-2,6-diazaspiro[3.4]oct-6-en-7-yl)bicyclo[2.2.2]octane-1-carboxylic acid A) Dimethyl 2,5-dioxobicyclo[2.2.2]octane-1,4-dicarboxylate Sodium hydride (60% dispersion in oil, 2.10 g) was added to a solution of dimethyl 2,5-dioxocyclohexane-1,4-dicarboxylate (5.00 g) in dimethoxyethane (8 mL) under ice-cooling, the resultant was stirred for 4 hours at 130° C., and then the solvent was distilled off under reduced pressure. Dibromoethane (188 mL) was added to the obtained residue, while heating to reflux the resultant, dibromoethane (188 mL) was further added thereto, and the resultant was heated to reflux for 72 hours. The reaction mixture was distilled off under reduced pressure, dichloromethane was added to the obtained residue, the resultant was filtered, and then the filtrate was concentrated under reduced pressure. The obtained residue was sequentially washed with hexane and ethanol, thereby obtaining the title compound (2.20 g).

$^1$H NMR (400 MHz, DMSO-$d_6$) δ 2.08-2.15 (2H, m), 2.46-2.55 (2H, m), 2.69-2.75 (2H, m), 3.04-3.09 (2H, m), 3.79 (6H, s).

B) Dimethyl 1'H,4'H-dispiro[1,3-dithiolane-2,2'-bicyclo[2.2.2]octane-5',2''-[1,3]dithiolane]-1',4'-dicarboxylate A solution of dimethyl 2,5-dioxobicyclo[2.2.2]octane-1,4-dicarboxylate (500 mg) and ethanedithiol (0.82 mL) in chloroform (20 mL) was added dropwise to a solution of boron trifluoride diethylether complex (1.17 mL) in chloroform (50 mL) at 0° C., and the reaction mixture was stirred for 2 hours at the same temperature. 2M aqueous sodium hydroxide solution was added to the reaction mixture, and extraction thereof was performed using dichloromethane. The obtained organic layer was further washed with 2 M aqueous sodium hydroxide solution, dried over anhydrous sodium sulfate, and then the solvent was distilled off under reduced pressure, thereby obtaining the title compound (1.64 g).

$^1$H NMR (400 MHz, $CDCl_3$) δ 1.93-1.97 (2H, m), 2.48-2.51 (2H, m), 2.84-2.88 (2H, m), 2.97-3.03 (4H, m), 3.27-3.36 (6H, m), 3.67 (6H, s).

C) Dimethyl bicyclo[2,2,2]octane-1,4-dicarboxylate

A solution of dimethyl 1'H,4'H-dispiro[1,3-dithiolane-2,2'-bicyclo[2.2.2]octane-5',2''-[1,3]dithiolane]-1',4'-dicarboxylate (9.00 g) in ethanol (50 mL) was added to a suspension of Raney nickel (65.0 g) in ethanol (125 mL), and the resultant was heated to reflux for 24 hours in an argon atmosphere. After the reaction mixture was filtered using celite, Raney nickel (65.0 mL) was added to the filtrate, and the resultant was heated to reflux for 24 hours. After the reaction mixture was filtered using celite, the filtrate was concentrated under reduced pressure, thereby obtaining the title compound (3.80 g).

$^1$H NMR (400 MHz, DMSO-$d_6$) δ 1.79 (12H, s), 3.63 (6H, s).

D) 4-(Methoxycarbonyl)bicyclo[2.2.2]octane-1-carboxylic acid

Using dimethyl bicyclo[2.2.2]octane-1,4-dicarboxylate, the title compound was obtained in the similar manner as in Step D of Example 228.

$^1$H NMR (400 MHz, DMSO-$d_6$) δ 1.69 (12H, s), 3.56 (3H, s), 12.07 (1H, s).

E) Methyl 4-(hydroxymethyl)bicyclo[2.2.2]octane-1-carboxylate

Using 4-(methoxycarbonyl)bicyclo[2.2.2]octane-1-carboxylic acid, the title compound was obtained in the similar manner as in Step E of Example 228.

$^1$H NMR (400 MHz, DMSO-$d_6$) δ 1.31-1.35 (6H, m), 1.64-1.68 (6H, m), 3.02 (2H, d, J=5.4 Hz), 3.55 (3H, s), 4.35 (1H, t, J=5.4 Hz).

F) Methyl 4-formylbicyclo[2.2.2]octane-1-carboxylate

Using methyl 4-(hydroxymethyl)bicyclo[2.2.2]octane-1-carboxylate, the title compound was obtained in the similar manner as in Step F of Example 228.

$^1$H NMR (400 MHz, DMSO-$d_6$) δ 1.56-1.60 (6H, m), 1.71-1.75 (6H, m), 3.58 (3H, s), 9.41 (1H, s).

G) Methyl 4-((E)-(hydroxyimino)methyl)bicyclo[2.2.2]octane-1-carboxylate

Using methyl 4-formylbicyclo[2.2.2]octane-1-carboxylate, the title compound was obtained in the similar manner as in Step G of Example 228.

$^1$H NMR (400 MHz, DMSO-$d_6$) δ 1.54-1.58 (6H, m), 1.69-1.73 (6H, m), 3.56 (3H, s), 7.14 (1H, s), 10.43 (1H, s).

H) Methyl 4-((Z)-chloro(hydroxyimino)methyl) bicyclo[2.2.2]octane-1-carboxylate

Using methyl 4-((E)-(hydroxyimino)methyl)bicyclo [2.2.2]octane-1-carboxylate, the title compound was obtained in the similar manner as in Step H of Example 228.

$^1$H NMR (400 MHz, DMSO-$d_6$) δ 1.69-1.1.75 (12H, m), 3.56 (3H, s), 11.05 (1H, s).

I) tert-Butyl 7-(4-(methoxycarbonyl)bicyclo[2.2.2] oct-1-yl)-5-oxa-2,6-diazaspiro[3.4]oct-6-ene-2-carboxylate Using tert-butyl 3-methyleneazetidine-1-carboxylate and methyl 4-((Z)-chloro(hydroxyimino)methyl)bicyclo[2.2.2] octane-1-carboxylate, the title compound was obtained in the similar manner as in Step I of Example 228.

$^1$H NMR (400 MHz, $CDCl_3$) δ 1.42 (9H, s), 1.64-1.73 (6H, m), 1.81-1.85 (6H, m), 3.1 (2H, s), 3.62 (3H, s), 3.92 (2H, d, J=9.72 Hz), 4.19 (2H, d, J=9.72).

J) Methyl 4-(2-((2,6-diethoxy-4'-fluorobiphenyl-4-yl)methyl)-5-oxa-2,6-diazaspiro[3.4]oct-6-en-7-yl) bicyclo[2.2.2]octane-1-carboxylate Using tert-butyl 7-(4-(methoxycarbonyl)bicyclo[2.2.2] oct-1-yl)-5-oxa-2,6-diazaspiro[3.4]oct-6-ene-2-carboxylate and 4-(bromomethyl)-2,6-diethoxy-4'-fluorobiphenyl, the title compound was obtained in the similar manner as in Step L of Example 228.

$^1$H NMR (400 MHz, $CDCl_3$) δ 1.22 (6H, t, J=6.96 Hz), 1.70-1.74 (6H, m), 1.82-1.85 (6H, m), 3.16 (2H, s), 3.37 (2H, d, J=8.56 Hz), 3.48 (2H, d, J=8.56 Hz), 3.64 (5H, s), 3.94 (4H, q, J=6.92 Hz), 6.52 (2H, s), 7.03 (2H, t, J=8.72 Hz), 7.29-7.32 (2H, m).

K) 4-(2-((2,6-Diethoxy-4'-fluorobiphenyl-4-yl) methyl)-5-oxa-2,6-diazaspiro[3.4]oct-6-en-7-yl)bicyclo[2.2.2]octane-1-carboxylic acid Using methyl 4-(2-((2,6-diethoxy-4'-fluorobiphenyl-4-yl) methyl)-5-oxa-2,6-diazaspiro[3.4]oct-6-en-7-yl)bicyclo [2.2.2]octane-1-carboxylate, the title compound was obtained in the similar manner as in Step M of Example 228.

Example 231

4-(2-((2-Cyclopropyl-6-ethoxy-4'-fluorobiphenyl-4-yl)methyl)-5-oxa-2,6-diazaspiro[3.4]oct-6-en-7-yl) bicyclo[2.2.2]octane-1-carboxylic acid A) Methyl 4-(2-((2-cyclopropyl-6-ethoxy-4'-fluoro-biphenyl-4-yl)methyl)-5-oxa-2,6-diazaspiro[3.4]oct-6-en-7-yl)bicyclo[2.2.2]octane-1-carboxylate Using tert-butyl 7-(4-(methoxycarbonyl)bicyclo[2.2.2] oct-1-yl)-5-oxa-2,6-diazaspiro[3.4]oct-6-ene-2-carboxylate and 4-(bromomethyl)-2-cyclopropyl-6-ethoxy-4'-fluorobiphenyl, the title compound was obtained in the similar manner as hi Step L of Example 228.

$^1$H NMR (400 MHz, $CDCl_3$) δ 0.58-0.62 (2H, m), 0.70-0.73 (2H, m), 1.17 (3H, t, J=6.92 Hz), 1.55-1.57 (1H, m), 1.70-1.73 (6H, m), 1.81-1.85 (6H, m), 3.15 (2H, s), 3.35 (2H, d, J=8.76 Hz), 3.45 (2H, d, J=8.76 Hz), 3.61 (2H, s), 3.64 (3H, s), 3.90 (2H, q, J=6.96 Hz), 6.39 (1H, s), 6.68 (1H, s), 7.06 (2H, t, J=8.72 Hz), 7.22-7.25 (2H, m).

B) 4-(2-((2-Cyclopropyl-6-ethoxy-4'-fluorobiphenyl-4-yl)methyl)-5-oxa-2,6-diazaspiro[3.4]oct-6-en-7-yl)bicyclo[2.2.2]octane-1-carboxylic acid Using methyl 4-(2-((2-cyclopropyl-6-ethoxy-4'-fluorobiphenyl-4-yl)methyl)-5-oxa-2,6-diazaspiro[3.4]oct-6-en-7-yl)bicyclo[2.2.2]octane-1-carboxylate, the title compound was obtained in the similar manner as in Step M of Example 228.

Example 232

Same as 1G 1-(2-((2-cyclopropyl-5-ethyl-4'-fluorobiphenyl-4-yl) methyl)-5-oxa-2,6-diazaspiro[3.4]oct-6-en-7-yl)-4-methylpiperidine-4-carboxylic acid A) Methyl 2-cyclopropyl-4'-fluoro-5-vinylbiphenyl-4-carboxylate Using methyl 2-cyclopropyl-4'-fluoro-5-(((trifluoromethyl)sulfonyl)oxy)biphenyl-4-carboxylate and 4,4,5,5-tetramethyl-2-vinyl-1,3,2-dioxaborolane, the title compound was obtained in the similar manner as in Step D of Example 23.

$^1$H NMR (300 MHz, DMSO-$d_6$) δ 0.62-0.74 (2H, m), 0.80-0.93 (2H, m), 1.74-1.87 (1H, m), 3.84 (3H, s), 5.19-5.42 (1H, m), 5.79 (1H, dd, J=17.6, 1.0 Hz), 7.22-7.40 (4H, m), 7.47-7.58 (3H, m).

B) 2-Cyclopropyl-5-ethyl-4'-fluorobiphenyl-4-carbaldehyde

Using methyl 2-cyclopropyl-4'-fluoro-5-vinylbiphenyl-4-carboxylate, the title compound was obtained in the similar manner as in Step C of Example 7, Step E of Example 16 and Step H of Example 210.

MS (ESI+): $[M+H]^+$ 269.2.

C) Ethyl 1-(2-((2-cyclopropyl-5-ethyl-4'-fluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-5-ethyl-4'-fluorobiphenyl-4-carbaldehyde, the title compound was obtained in the similar manner as in Step G of Example 1.

MS (ESI+): $[M+H]^+$ 534.2.

D) 1-(2-((2-Cyclopropyl-5-ethyl-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-5-ethyl-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 233

1-(2-(4-Cyclobutyl-3-cyclopropyl-5-ethoxybenzyl)-5-oxa-2,6-diazaspiro[3.4]oct-6-en-7-yl)-4-methylpiperidine-4-carboxylic acid A) Ethyl 3-ethoxy-5-hydroxy-4-iodobenzoate Sodium hydride (60% dispersion in oil, 3.99 g) was added to a solution of ethyl 3,5-dihydroxy-4-iodobenzoate (15.0 g)

in DMF (100 mL), and the resultant was stirred for 30 minutes at 0° C. in a nitrogen atmosphere. Iodoethane (4.09 mL) was added to the reaction mixture, and the resultant was stirred for 2 hours at room temperature. Water was added to the reaction mixture, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (7.59 g).

$^1$H NMR (300 MHz, $CDCl_3$) δ 1.39 (3H, t, J=7.1 Hz), 1.50 (3H, t, J=7.0 Hz), 4.16 (2H, q, J=6.9 Hz), 4.37 (2H, q, J=7.2 Hz), 5.59 (1H, s), 7.02 (1H, d, J=1.6 Hz), 7.31 (1H, d, J=1.7 Hz).

B) Ethyl 3-(benzyloxy)-5-ethoxy-4-iodobenzoate

Benzylbromide (2.95 mL) was added to a suspension of ethyl 3-ethoxy-5-hydroxy-4-iodobenzoate (7.59 g), potassium carbonate (4.68 g) in DMF (200 mL), and the resultant was stirred for 2 hours at 60° C. After the reaction mixture was cooled to room temperature, water was added thereto, and extraction thereof was performed using ethyl acetate. The obtained organic layer was washed with a saturated saline solution, it was passed through a short column of a silica gel (NH), and the solvent was distilled off under reduced pressure. The obtained residue was purified by a silica gel column chromatography (hexane/ethyl acetate), thereby obtaining the title compound (7.09 g).

$^1$H NMR (300 MHz, $CDCl_3$) δ 1.40 (3H, t, J=7.1 Hz), 1.51 (3H, t, J=7.0 Hz), 4.17 (2H, q, J=7.1 Hz), 4.38 (2H, q, J=7.1 Hz), 5.22 (2H, s), 7.14 (1H, d, J=1.4 Hz), 7.20 (1H, d, J=1.4 Hz), 7.31-7.46 (3H, m), 7.54 (2H, d, J=7.2 Hz).

C) Ethyl 3-(benzyloxy)-4-cyclobutyl-5-ethoxybenzoate

After a catalytic amount of iodine was added to a mixture of magnesium (10.8 g) and THF (180 mL), a solution of cyclobutylbromide (30.0 g) in THF (90 mL) was slowly added thereto at room temperature, and the resultant was stirred for 2 hours at the same temperature. A solution of zinc bromide (50.0 g) in THF (120 mL) was added to the reaction mixture at 0° C., and the resultant was stirred for 2 hours at the same temperature. A zinc reagent (140 mL) prepared in advance was added to a mixture of ethyl 3-(benzyloxy)-5-ethoxy-4-iodobenzoate (10.0 g), tris(dibenzylideneacetone) dipalladium(0) (644 mg), dicyclohexyl(2',6'-dimethoxybiphenyl-2-yl)phosphine (482 mg) and DMF (100 mL), and the resultant was stirred for 16 hours at 100° C. in an argon atmosphere. After the reaction mixture was cooled to room temperature, ethyl acetate was added thereto, and the resultant was filtered using celite. The filtrate was washed with water and a saturated saline solution, dried over anhydrous sodium sulfate, and then the solvent was distilled off under reduced pressure. The obtained residue was purified by a silica gel column chromatography (hexane/ethyl acetate), thereby obtaining the title compound (3.50 g).

MS (ESI+): $[M+H]^+$ 355.

D) Ethyl 4-cyclobutyl-3-ethoxy-5-(((trifluoromethyl)sulfonyl)oxy)benzoate

10% palladium on carbon (2.55 g) was added to a mixture of ethyl 3-(benzyloxy)-4-cyclobutyl-5-ethoxybenzoate (8.50 g) and methanol (100 mL), and the resultant was stirred for 5 hours at room temperature in a hydrogen atmosphere. After the reaction mixture was filtered using celite, the filtrate was concentrated. Triethylamine (6.1 mL) was added to a mixture of the obtained residue and dichloromethane (60 mL), the resultant was stirred for 20 minutes at 0° C. Trifluoromethanesulfonic anhydride (5.56 mL) was added to the reaction mixture, and the resultant was stirred for 12 hours at mom temperature. Water was added to the reaction mixture, and extraction thereof was performed three times using dichloromethane. The collected organic layer was washed with water and saturated saline, dried over anhydrous sodium sulfate, and then the solvent was distilled off under reduced pressure. The obtained residue was purified by a silica gel column chromatography (hexane/ethyl acetate), thereby obtaining the title compound (6.00 g).

MS (ESI+): $[M+H]^+$ 397.

E) 4-Cyclobutyl-3-cyclopropyl-5-ethoxybenzaldehyde

Using ethyl 4-cyclobutyl-3-ethoxy-5-(((trifluoromethyl)sulfonyl)oxy)benzoate, the title compound was obtained in the similar manner as in Step D of Example 23, Step E of Example 16, and Step H of Example 210.

MS (ESI+): $[M+H]^+$ 245.

F) Ethyl 1-(2-(4-cyclobutyl-3-cyclopropyl-5-ethoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 4-cyclobutyl-3-cyclopropyl-5-ethoxybenzaldehyde, the title compound was obtained in the similar manner as in Step G of Example 1.

MS (ESI+): $[M+H]^+$ 510.5.

G) 1-(2-(4-Cyclobutyl-3-cyclopropyl-5-ethoxybenzyl)-5-oxa-2,6-diazaspiro[3.4]oct-6-en-7-yl)-4-methylpiperidine-4-carboxylic acid Using ethyl 1-(2-(4-cyclobutyl-3-cyclopropyl-5-ethoxybenzyl)-5-oxa-2,6-diazaspiro[3.4]oct-6-en-7-yl)-4-methylpiperidine-4-carboxylate, the title compound was obtained in the similar manner as in Example 2.

Example 234

1-(2-((2-Cyclopropyl-3',4'-difluoro-5-methoxybiphenyl-4-yl)methyl)-5-oxa-2,6-diazaspiro[3.4]oct-6-en-7-yl)-4-methylpiperidine-4-carboxylic acid A) 3',4'-Difluoro-3-methoxybiphenyl-4-carbaldehyde Using 4-bromo-2-methoxybenzaldehyde and (3,4-difluorophenyl)boronic acid, the title compound was obtained in the similar manner as in Step D of Example 23.

$^1$H NMR (300 MHz, DMSO-$d_6$) δ 4.04 (3H, s), 7.41 (1H, d, J=8.0 Hz), 7.49 (1H, d, J=1.3 Hz), 7.52-7.64 (1H, m), 7.66-7.73 (1H, m), 7.77 (1H, d, J=8.1 Hz), 7.92-8.03 (1H, m), 10.37 (1H, s).

B) 2-Bromo-3',4'-difluoro-5-methoxybiphenyl-4-carbaldehyde

Using 3',4'-difluoro-3-methoxybiphenyl-4-carbaldehyde, the title compound was obtained in the similar manner as in Step B of Example 114.

$^1$H NMR (300 MHz, DMSO-$d_6$) δ 3.97 (3H, s), 7.25-7.41 (2H, m), 7.52-7.71 (2H, m), 7.91 (1H, s), 10.30 (1H, s).

C) 2-Cyclopropyl-3',4'-difluoro-5-methoxybiphenyl-4-carbaldehyde

Using 2-bromo-3',4'-difluoro-5-methoxybiphenyl-4-carbaldehyde and cyclopropyl boronic acid, the title compound was obtained in the similar manner as in Step D of Example 23.

$^1$H NMR (300 MHz, DMSO-$d_6$) δ 0.52-0.60 (2H, m), 0.75-0.85 (2H, m), 1.72-1.84 (1H, m), 3.93 (3H, s), 7.08 (1H, s), 7.32-7.69 (3H, m), 7.76-7.85 (1H, m), 10.33 (1H, s).

D) Ethyl 1-(2-((2-cyclopropyl-3',4'-difluoro-5-methoxybiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-3',4'-difluoro-5-methoxybiphenyl-4-carbaldehyde, the title compound was obtained in the similar manner as in Step G of Example 1.

MS (ESI+): $[M+H]^+$ 554.1.

E) 1-(2-((2-Cyclopropyl-3',4'-difluoro-5-methoxybiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-3',4'-difluoro-5-methoxybiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 235

1-(2-((2-Cyclopropyl-5-ethoxy-2',4'-difluorobiphenyl-4-yl)methyl)-5-oxa-2,6-diazaspiro[3.4]oct-6-en-7-yl)-4-methylpiperidine-4-carboxylic acid A) Methyl 2-ethoxy-4-iodobenzoate Using methyl 2-hydroxy-4-iodobenzoate and iodoethane, the title compound was obtained in the similar manner as in Step A of Example 1.

$^1$H NMR (300 MHz, DMSO-$d_6$) δ 1.31 (3H, t, J=6.9 Hz), 3.77 (3H, s), 4.10 (2H, q, J=7.0 Hz), 7.39 (2H, d, J=0.5 Hz), 7.47 (1H, s).

B) Methyl 3-ethoxy-2',4'-difluorobiphenyl-4-carboxylate

Using methyl 2-ethoxy-4-iodobenzoate and (2,4-difluorophenyl)boronic acid, the title compound was obtained in the similar manner as in Step D of Example 23.

MS (ESI+): $[M+H]^+$ 293.2

C) Methyl 2-bromo-5-ethoxy-2',4'-difluorobiphenyl-4-carboxylate

Using methyl 3-ethoxy-2',4'-difluorobiphenyl-4-carboxylate, the title compound was obtained in the similar manner as in Step B of Example 114.

$^1$H NMR (300 MHz, DMSO-$d_6$) δ 1.31 (3H, t, J=6.9 Hz), 3.82 (3H, s), 4.12 (2H, q, J=7.0 Hz), 7.15-7.28 (2H, m), 7.35-7.52 (2H, m), 7.92 (1H, s).

D) Methyl 2-cyclopropyl-5-ethoxy-2',4'-difluorobiphenyl-4-carboxylate

Using methyl 2-bromo-5-ethoxy-2',4'-difluorobiphenyl-4-carboxylate, the title compound was obtained in the similar manner as in Step D of Example 23.

$^1$H NMR (300 MHz, DMSO-$d_6$) δ 0.47-0.56 (2H, m), 0.68-0.77 (2H, m), 1.29 (3H, t, J=6.9 Hz), 1.52-1.63 (1H, m), 3.79 (3H, s), 4.07 (2H, q, J=7.0 Hz), 6.94 (1H, s), 7.17-7.26 (2H, m), 7.32-7.53 (2H, m).

E) 2-Cyclopropyl-5-ethoxy-2',4'-difluorobiphenyl-4-carbaldehyde

Using methyl 2-cyclopropyl-5-ethoxy-2',4'-difluorobiphenyl-4-carboxylate, the title compound was obtained in the similar manner as in Step E of Example 16 and Step H of Example 210.

$^1$H NMR (300 MHz, DMSO-$d_6$) δ 0.47-0.57 (2H, m), 0.69-0.79 (2H, m), 1.37 (3H, t, J=6.9 Hz), 1.52-1.64 (1H, m), 4.18 (2H, q, J=7.0 Hz), 7.06 (1H, s), 7.19-7.33 (2H, m), 7.36-7.55 (2H, m), 10.37 (1H, s).

F) Ethyl 1-(2-((2-cyclopropyl-5-ethoxy-2',4'-difluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-5-ethoxy-2',4'-difluorobiphenyl-4-carbaldehyde, the title compound was obtained in the similar manner as in Step G of Example 1.

MS (ESI+): $[M+H]^+$ 568.3.

G) 1-(2-((2-Cyclopropyl-5-ethoxy-2',4'-difluorobiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-5-ethoxy-2',4'-difluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 236

1-(2-((2-Cyclopropyl-5-ethoxy-2'-fluorobiphenyl-4-yl)methyl)-5-oxa-2,6-diazaspiro[3.4]oct-6-en-7-yl)-4-methylpiperidine-4-carboxylic acid A) Methyl 2-ethoxy-4-iodobenzoate Using methyl 2-hydroxy-4-iodobenzoate and iodoethane, the title compound was obtained in the similar manner as in Step A of Example 1.

$^1$H NMR (300 MHz, $CDCl_3$) δ 1.46 (3H, t, J=7.0 Hz), 3.87 (3H, s), 4.09 (2H, q, J=7.0 Hz), 7.28-7.34 (2H, m), 7.48 (1H, d, J=8.0 Hz).

B) Methyl 3-ethoxy-2'-fluorobiphenyl-4-carboxylate

Using methyl 2-ethoxy-4-iodobenzoate and (2-fluorophenyl)boronic acid, the title compound was obtained in the similar manner as in Step E of Example 43.

MS (ESI+): $[M+H]^+$ 275.2.

C) Methyl 2-bromo-5-ethoxy-2'-fluorobiphenyl-4-carboxylate

Using methyl 3-ethoxy-2'-fluorobiphenyl-4-carboxylate, the title compound was obtained in the similar manner as in Step B of Example 114.

$^1$H NMR (300 MHz, $CDCl_3$) δ 1.45 (3H, t, J=7.0 Hz), 3.91 (3H, s), 4.10 (2H, q, J=7.0 Hz), 6.92 (1H, s), 7.13-7.33 (3H, m), 7.36-7.47 (1H, m), 8.07 (1H, s).

D) (2-Cyclopropyl-5-ethoxy-2'-fluorobiphenyl-4-yl) methanol

Using methyl 2-bromo-5-ethoxy-2'-fluorobiphenyl 1 carboxylate and cyclopropyl boronic acid, the title compound was obtained in the similar manner as in Step D of Example 23 and Step E of Example 16.

$^1$H NMR (300 MHz, $CDCl_3$) δ 0.52-0.60 (2H, m), 0.67-0.76 (2H, m), 1.42 (3H, t, J=6.9 Hz), 1.62-1.75 (1H, m), 2.41 (1H, t, J=6.6 Hz), 4.07 (2H, q, J=7.0 Hz), 4.70 (2H, d, J=6.5 Hz), 6.73 (1H, s), 6.90 (1H, s), 7.10-7.23 (2H, m), 7.28-7.40 (2H, m).

E) 2-Cyclopropyl-5-ethoxy-2'-fluorobiphenyl-4-carbaldehyde

Using (2-cyclopropyl-5-ethoxy-2'-fluorobiphenyl-4-yl) methanol, the title compound was obtained in the similar manner as in Step H of Example 210.

MS (ESI+): $[M+H]^+$ 285.2.

F) Ethyl 1-(2-((2-cyclopropyl-5-ethoxy-2'-fluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-5-ethoxy-2'-fluorobiphenyl-4-carbaldehyde, the title compound was obtained in the similar manner as in Step G of Example 1.

MS (ESI+): $[M+H]^+$ 550.5.

G) 1-(2-((2-Cyclopropyl-5-ethoxy-2'-fluorobiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-5-ethoxy-2'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 237

1-(2-((2-Cyclopropyl-5-ethoxy-2',6'-difluorobiphenyl-4-yl)methyl)-5-oxa-2,6-diazaspiro[3.4]oct-6-en-7-yl)-4-methylpiperidine-4-carboxylic acid A) Methyl 2-ethoxy-4-iodobenzoate Using methyl 2-hydroxy-4-iodobenzoate and iodoethane, the title compound was obtained in the similar manner as in Step A of Example 1.

$^1$H NMR (300 MHz, $CDCl_3$) δ 1.46 (3H, t, J=7.0 Hz), 3.87 (3H, s), 4.09 (2H, q, J=7.0 Hz), 7.28-7.34 (2H, m), 7.48 (1H, d, J=8.0 Hz).

B) Methyl 2-ethoxy-4-(4,4,5,5-tetramethyl-1,3,2-dioxaborolan-2-yl)benzoate

Using methyl 2-ethoxy-4-iodobenzoate, bis(pinacolato) diboron, and potassium acetate instead of cesium fluoride, the title compound was obtained in the similar manner as in Step E of Example 43.

MS (ESI+): $[M+H]^+$ 307.3.

C) Methyl 3-ethoxy-2',6'-difluorobiphenyl-4-carboxylate

Using methyl 2-ethoxy-4-(4,4,5,5-tetramethyl-1,3,2-dioxaborolan-2-yl)benzoate and 1,3-difluoro-2-iodobenzene, the title compound was obtained in the similar manner as in Step E of Example 43.

MS (ESI+): $[M+H]^+$ 293.2.

D) Methyl 2-bromo-5-ethoxy-2',6'-difluorobiphenyl-4-carboxylate

Using methyl 3-ethoxy-2',6'-difluorobiphenyl-4-carboxylate, the title compound was obtained in the similar manner as in Step B of Example 114.

$^1$H NMR (300 MHz, $CDCl_3$) δ 1.45 (3H, t, J=6.9 Hz), 3.92 (3H, s), 4.10 (2H, q, J=6.9 Hz), 6.91 (1H, s), 6.96-7.05 (2H, m), 7.33-7.45 (1H, m), 8.08 (1H, s).

E) (2-Cyclopropyl-5-ethoxy-2',6'-difluorobiphenyl-4-yl)methanol

Using methyl 2-bromo-5-ethoxy-2',6'-difluorobiphenyl-4-carboxylate and cyclopropyl boronic acid, the title compound was obtained in the similar manner as in Step D of Example 23 and Step E of Example 16.

$^1$H NMR (300 MHz, $CDCl_3$) δ 0.50-0.59 (2H, m), 0.64-0.72 (2H, m), 1.42 (3H, t, J=7.0 Hz), 1.59-1.67 (1H, m), 2.40 (1 t, J=6.5 Hz), 4.06 (2H, q, J=7.0 Hz), 4.70 (2H, d, J=6.0 Hz), 6.72 (1H, s), 6.94-7.02 (3H, m), 7.27-7.39 (1H, m).

F) 2-Cyclopropyl-5-ethoxy-2',6'-difluorobiphenyl-4-carbaldehyde

Using (2-cyclopropyl-5-ethoxy-2',6'-difluorobiphenyl-4-yl)methanol, the title compound was obtained in the similar manner as in Step H of Example 210.

MS(ESI+): $[M+H]^+$ 303.2.

G) Ethyl 1-(2-((2-cyclopropyl-5-ethoxy-2',6'-difluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-5-ethoxy-2',6'-difluorobiphenyl-4-carbaldehyde, the title compound was obtained in the similar manner as in Step G of Example 1.

MS(ESI+):$[M+H]^+$ 568.5.

H) 1-(2-((2-Cyclopropyl-5-ethoxy-2',6'-difluorobiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-5-ethoxy-2',6'-difluorobiphenyl-4-yl)methyl)-5-oxa-2,6-diazaspiro[3.4]oct-6-en-7- yl)-4-methylpiperidine-4-carboxylate, the title compound was obtained in the similar manner as in Example 2.

Example 238

1-(2-((2-Chloro-6-cyclopropyl-4'-fluoro-3-methoxybiphenyl-4-yl)methyl)-5-oxa-2,6-diazaspiro[3.4]oct-6-en-7-yl)-4-methylpiperidine-4-carboxylic acid A) Methyl 4'-fluoro-3-hydroxybiphenyl-4-carboxylate Palladium(II) acetate (2.02 g) was added to a mixture of methyl 2-hydroxy-4-iodobenzoate (25.0 g), (4-fluorophenyl)boronic acid (18.9 g), tricyclohexylphosphine (20% toluene solution, 31.9 mL) and tripotassium phosphate (57.3 g) in toluene (250 mL) and water (125 mL), and the resultant was heated and stirred overnight at 90° C. After the reaction mixture was cooled to room temperature, it was diluted by ethyl acetate and water, and the organic layer was separated. The obtained organic layer was washed with a saturated saline solution, dried over anhydrous magnesium sulfate, and then the solvent was distilled off under reduced pressure. The obtained residue was dissolved in toluene, activated carbon was added thereto, the resultant was stirred for 30 minutes at room temperature, and it was filtered. After the filtrate was concentrated under reduced pressure, the obtained residue was dissolved in methanol. It was heated to reflux for 30 minutes, and stirred for 1 hour at room temperature. The obtained crystals were collected by filtration, thereby obtaining the title compound (23.0 g).

$^1$H NMR (300 MHz, DMSO-$d_6$) δ 3.92 (3H, s), 7.11-7.50 (4H, m), 7.64-8.03 (3H, m), 10.60 (1H, s).

B) Methyl 2-bromo-4'-fluoro-5-hydroxybiphenyl-4-carboxylate

Bromine (14.8 g) was added to a solution of methyl 4'-fluoro-3-hydroxybiphenyl-4-carboxylate (21.7 g) in ethyl acetate (420 mL) in the range of 40° C. to 55° C., and the resultant was stirred for 1 hour at 50° C. Bromine (2.11 g) was further added thereto, the reaction mixture was stirred for 1 hour at the same temperature. After the reaction mixture was filtered, an aqueous sodium thiosulfate solution was added to the filtrate, and the organic layer was separated. The obtained organic layer was sequentially washed with an aqueous sodium thiosulfate solution and a saturated saline solution, dried over anhydrous magnesium sulfate, and then the solvent was distilled off under reduced pressure. The obtained residue was crystallized (methanol), thereby obtaining the title compound (16.7 g).

$^1$H NMR (300 MHz, DMSO-$d_6$) δ 3.90 (3H, s), 7.01 (1H, s), 7.25-7.37 (2H, m), 7.42-7.53 (2H, m), 8.00 (1H, s), 10.53 (1H, brs).

C) Methyl 2-cyclopropyl-4'-fluoro-5-hydroxybiphenyl-4-carboxylate

Tris(dibenzylideneacetone)dipalladium(0) (1.86 g) was added to a mixture of methyl 2-bromo-4'-fluoro-5-hydroxybiphenyl-4-carboxylate (16.5 g), cyclopropyl boronic acid (6.54 g), dicyclohexyl(2',6'-dimethoxybiphenyl-2-yl)phosphine (2.08 g), 2 M aqueous sodium carbonate solution (76 mL) and toluene (150 mL), and the resultant was stirred for 1 hour at 100° C. in a nitrogen atmosphere. After the reaction mixture was cooled to room temperature, it was diluted by ethyl acetate and water, and the organic layer was separated. The solvent of the obtained organic layer was distilled off under reduced pressure. The obtained residue was passed through a short column of a silica gel, and it was crystallized (methanol), thereby obtaining the title compound (12.7 g).

$^1$H NMR (300 MHz, DMSO-$d_6$) δ 0.47-0.58 (2H, m), 0.72-0.82 (2H, m), 1.65-1.79 (1H, m), 3.90 (3H, s), 6.82 (1H, s), 7.24-735 (2H, m), 7.41 (1H, s), 7.46-7.55 (2H, m), 10.35 (1H, brs).

D) Methyl 2-chloro-6-cyclopropyl-4'-fluoro-3-hydroxybiphenyl-4-carboxylate

N-chlorosuccinimide (2.08 g) was added to a solution of methyl 2-cyclopropyl-4'-fluoro-5-hydroxybiphenyl-4-carboxylate (3.71 g) in DMF (40 mL) at room temperature, and the resultant was stirred for 4 hours at the same temperature in a nitrogen atmosphere. Water was added to the reaction mixture, the resultant was stirred for 1 hour at room temperature, and then the precipitated crystals were collected by filtration, thereby obtaining the title compound (3.82 g).

$^1$H NMR (300 MHz, $CDCl_3$) δ 0.52-0.60 (2H, m), 0.66-0.74 (2H, m), 1.40-1.52 (1H, m), 3.99 (3H, s), 7.12-7.25 (4H, m), 7.40 (1H, s), 11.27 (1H, s).

E) Methyl 2-chloro-6-cyclopropyl-4'-fluoro-3-methoxybiphenyl-4-carboxylate

Iodomethane (2.54 g) was added to a mixture of methyl 2-chloro-6-cyclopropyl-4'-fluoro-3-hydroxybiphenyl-4-carboxylate (3.82 g), potassium carbonate (3.29 g) and DMF (60 mL) at room temperature. The reaction mixture was stirred for 2 hours at 60° C. in a nitrogen atmosphere. Water was added to the reaction mixture at room temperature, and extraction thereof was performed using ethyl acetate. The obtained organic layer was sequentially washed with water and a saturated saline solution, was dried over anhydrous magnesium sulfate, and then the solvent was distilled off under reduced pressure. The obtained residue was purified by a silica gel column chromatography (NH, hexane/ethyl acetate), thereby obtaining the title compound (3.79 g).

$^1$H NMR (300 MHz, $CDCl_3$) δ 0.60-0.67 (2H, m), 0.72-0.79 (2H, m), 1.44-1.54 (1H, m), 3.93 (3H, s), 3.94 (3H, s), 7.12-7.26 (4H, m), 7.27 (1H, s).

F) (2-Chloro-6-cyclopropyl-4'-fluoro-3-methoxybiphenyl-4-yl)methanol

Diisobutylaluminium hydride (1.5 M toluene solution, 17 mL) was added to a solution of methyl 2-chloro-6-cyclopropyl-4'-fluoro-3-methoxybiphenyl-4-carboxylate (3.77 g) in THF (60 mL) at 0° C. After the reaction mixture was stirred for 2 hours at room temperature in a nitrogen atmosphere, diisobutylaluminium hydride (1.5 M toluene solution, 12 mL) was further added thereto at 0° C. The reaction mixture was stirred for 30 minutes at room temperature in a nitrogen atmosphere. Sodium sulfate decahydrate was added to the reaction mixture at 0° C., and the resultant was stirred for 30 minutes at room temperature. The reaction mixture was filtered using celite, and the filtrate was concentrated under reduced pressure. The obtained residue was purified by a silica gel column chromatography (hexane/ethyl acetate), thereby obtaining the title compound (3.45 g).

$^1$H NMR (300 MHz, $CDCl_3$) δ 0.58-0.65 (2H, m), 0.69-0.78 (2H, m), 1.43-1.55 (1H, m), 2.09 (1H, t, J=6.2 Hz), 3.90 (3H, s), 4.74 (2H, d, J=6.1 Hz), 6.86 (1H, s), 7.10-7.25 (4H, m).

G) 2-Chloro-6-cyclopropyl-4'-fluoro-3-methoxybiphenyl-4-carbaldehyde

Manganese dioxide (7.82 g) was added to a solution of (2-chloro-6-cyclopropyl-4'-fluoro-3-methoxybiphenyl-4-yl) methanol (3.45 g) in toluene (60 mL) at room temperature. The reaction mixture was stirred for 2 hours at 80° C. in a nitrogen atmosphere. After the reaction mixture was filtered using celite, the filtrate was concentrated under reduced pressure. The obtained residue was purified by a silica gel column chromatography (hexane/ethyl acetate), thereby obtaining the title compound (3.19 g).

$^1$H NMR (300 MHz, $CDCl_3$) δ 0.64-0.71 (2H, m), 0.74-0.82 (2H, m), 1.44-1.54 (1H, m), 3.99 (3H, s), 7.14-7.26 (4H, m), 7.34 (1H, s), 10.37 (1H, s).

H) 1-Benzyl 4-ethyl piperidine-1,4-dicarboxylate

Benzyl chloroformate (29.5 mL) was added to a solution of ethyl piperidine-4-carboxylate (25.0 g) and diisopropylethylamine (55.5 mL) in THF (150 mL) at 0° C., and the resultant was stirred for 2 hours at 0° C. After an aqueous saturated sodium hydrogen carbonate solution was added to the reaction mixture, extraction thereof was performed using ethyl acetate. The obtained organic layer was sequentially washed with an aqueous saturated sodium hydrogen carbonate solution, 1M hydrochloric acid and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (30.1 g).

$^1$H NMR (400 MHz, $CDCl_3$) δ 1.25 (3H, t, J=7.0 Hz), 1.58-1.73 (2H, m), 1.88 (2H, brs), 2.38-2.52 (1H, m), 2.93 (2H, t, J=11.6 Hz), 4.01-4.19 (4H, m), 5.13 (2H, s), 7.27-7.40 (5H, m).

I) 1-Benzyl 4-ethyl 4-methylpiperidine-1,4-dicarboxylate

Lithium bis(trimethylsilyl)amide (1.0 M THF solution, 233 mL) was added to a solution of 1-benzyl 4-ethyl piperidine-1,4-dicarboxylate (40.0 g) in THF (160 mL) at −40° C. After the reaction mixture was stirred for 1 hour at −40° C., iodoethane (39.0 g) was added thereto, and the resultant was stirred for 2 hours at room temperature. After an aqueous saturated sodium hydrogen carbonate solution was added to the reaction mixture, the resultant was filtered using celite, and the organic layer of the filtrate was separated. The obtained organic layer was washed with water and a saturated saline solution, dried over anhydrous sodium sulfate, and then the solvent was distilled off under reduced pressure. The obtained residue was purified by a silica gel column chromatography (NH, hexane/ethyl acetate), thereby obtaining the title compound (34.0 g).

$^1$H NMR (400 MHz, $CDCl_3$) δ 1.20 (3H, s), 1.26 (3H, t, J=7.0 Hz), 1.31-1.44 (2H, m), 2.08 (2H, d, J=13.2 Hz), 2.99-3.13 (2H, m), 3.86 (2H, d, J=8.4 Hz), 4.16 (2H, q, J=7.0 Hz), 5.12 (2H, s), 7.28-7.39 (5H, m).

J) Ethyl 4-methylpiperidine-4-carboxylate

20% palladium hydroxide (50% water content, 4.00 g) was added to a solution of 1-benzyl 4-ethyl 4-methylpiperidine-1,4-dicarboxylate (34.0 g) in methanol (340 mL), and the resultant was stirred for 4 hours at room temperature in a hydrogen atmosphere. After the catalyst was filtered of the filtrate was concentrated under reduced pressure, thereby obtaining the title compound (19.0 g).

$^1$H NMR (400 MHz, $CDCl_3$) δ 1.19 (3H, s), 1.26 (3H, t, J=7.1 Hz), 1.31-1.42 (2H, m), 2.08 (2H, d, J=13.6 Hz), 2.62-2.74 (2H, m), 2.87-2.96 (2H, m), 4.16 (2H, q, J=7.1 Hz).

K) tert-Butyl 3-methyleneazetidine-1-carboxylate

Potassium tert-butoxide (13.3 g) was added to a mixture of methyl(triphenyl)phosphonium bromide (38.7 g) and THF (150 mL) at 0° C., the resultant was stirred for 1 hour at room temperature. A solution of tert-butyl 3-oxoazetidin-1-carboxylate (16.9 g) in THF (50 mL) was added to the reaction mixture, and the resultant was stirred for 2 hours at 50° C. After water was added to the reaction mixture, extraction thereof was performed using ethyl acetate. The obtained organic layer was washed with water and a saturated saline solution, dried over anhydrous sodium sulfate, and then the solvent was distilled off under reduced pressure. The obtained residue was dissolved in a solution in which ethyl acetate and hexane are mixed at a ratio of 1:3, the resultant was filtered using celite, and then the filtrate was concentrated under reduced pressure. The obtained residue was purified by a silica gel column chromatography (hexane/ethyl acetate), thereby obtaining the title compound (10.9 g).

$^1$H NMR (300 MHz, DMSO-$d_6$) δ 1.45 (9H, s), 4.46-4.51 (4H, m), 4.96-5.02 (2H, m).

L) tert-Butyl 7-bromo-5-oxa-2,6-diazaspiro[3.4]oct-6-ene-2-carboxylate

Sodium hydrogen carbonate (101 g) was added to a mixture of tert-butyl 3-methyleneazetidine-1-carboxylate (20.4 g), hydroxycarbonimidic dibromide (48.8 g) and ethyl acetate (400 mL), the resultant was stirred for 15 hours at mom temperature, and it was further stilled for 4 hours at 50° C. After water was added to the reaction mixture at room temperature, the filtrate was extracted using ethyl acetate. The obtained organic layer was washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (27.8 g).

$^1$H NMR (400 MHz, $CDCl_3$) δ 1.44 (9H, s), 3.44 (2H, s), 4.02-4.07 (2H, m), 4.26-4.32 (2H, m).

M) tert-Butyl 7-(4-(ethoxycarbonyl)-4-methylpiperidin-1-yl)-5-oxa-2,6-diazaspiro[3.4]oct-6-ene-2-carboxylate tert-Butyl 7-bromo-5-oxa-2,6-diazaspiro[3.4]oct-6-ene-2-carboxylate (18.0 g), ethyl 4-methylpiperidine-4-carboxylate (14.8 g) and sodium carbonate (19.7 g) were added to DMF (90 mL), and the resultant was stirred overnight at 130° C. After the reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. The obtained residue was crystallized (hexane/ethyl acetate), thereby obtaining the title compound (18.1 g).

$^1$H NMR (400 MHz, DMSO-$d_6$) δ 1.15 (3H, s), 1.19 (3H, t, J=7.0 Hz), 1.31-1.46 (11H, m), 1.93 (2H, d, J=13.6 Hz), 2.87 (2H, t, J=10.4 Hz), 3.23-3.36 (4H, m), 3.88 (2H, d, J=9.3 Hz), 4.02 (2H, d, J=9.0 Hz), 4.11 (2H, q, J=6.9 Hz).

N) Ethyl 1-(2-((2-chloro-6-cyclopropyl-4'-fluoro-3-methoxybiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (3.23 g) and formic acid (50 mL) was stirred for 1 hour at 60° C., the solvent was distilled off under reduced pressure. Sodium triacetoxyborohydride (3.59 g) was added to a mixture of the obtained residue, 2-chloro-6-cyclopropyl-4'-fluoro-3-methoxybiphenyl-4-carbaldehyde (2.84 g) and THF (50 mL), and the resultant was stirred for 16 hours at room temperature in a nitrogen atmosphere. After an aqueous saturated sodium hydrogen carbonate solution was added to the reaction mixture, extraction thereof was performed using ethyl acetate. The obtained organic layer was sequentially washed with water and a saturated saline solution, was dried over anhydrous magnesium sulfate, and then the solvent was distilled off under reduced pressure. The obtained residue was purified by a silica gel column chromatography (hexane/ethyl acetate), thereby obtaining the title compound (4.39 g).

$^1$H NMR (300 MHz, $CDCl_3$) δ 0.55-0.61 (2H, m), 0.67-0.76 (2H, m), 1.21 (3H, s), 1.26 (3H, t, J=7.1 Hz), 1.40-1.53 (3H, m), 2.11 (2H, d, J=13.5 Hz), 2.91-3.03 (2H, m), 3.25 (2H, s), 3.34-3.43 (4H, m), 3.52-3.57 (2H, m), 3.71 (2H, s), 3.84 (3H, s), 4.17 (2H, q, J=7.1 Hz), 6.78 (1H, s), 7.09-7.25 (4H, m).

O) 1-(2-((2-Chloro-6-cyclopropyl-4'-fluoro-3-methoxybiphenyl-4-yl)methyl)-5-oxa-2,6-diazaspiro[3.4]oct-6-en-7-yl)-4-methylpiperidine-4-carboxylic acid 2 M aqueous sodium hydroxide solution (20 mL) was added to a solution of ethyl 1-(2-((2-chloro-6-cyclopropyl-4'-fluoro-3-methoxybiphenyl-4-yl)methyl)-5-oxa-2,6-diazaspiro[3.4]oct-6-en-7-yl)-4-methylpiperidine-4-carboxylate (4.38 g) in ethanol (50 mL) at room temperature. After the reaction mixture was stirred for 16 hours at 80° C. in a nitrogen atmosphere, the solvent was distilled off under reduced pressure. Water was added to the residue, the resultant was neutralized with 2 M hydrochloric acid. The obtained solid was collected by filtration, and it was dissolved in ethanol. After the obtained solution was filtered, the filtrate was concentrated under reduced pressure. The obtained residue was crystallized (hexane/ethyl acetate), and further recrystallized (hexane/ethanol), thereby obtaining the title compound (3.03 g).

$^1$H NMR (300 MHz, DMSO-$d_6$) δ 0.54-0.62 (2H, m), 0.66-0.74 (2H, m), 1.14 (3H, s), 1.31-1.48 (3H, m), 1.91 (2H, d, J=13.5 Hz), 2.82-2.95 (2H, m), 3.19 (2H, d, J=8.2 Hz), 3.25-3.35 (4H, m), 3.47 (2H, d, J=8.2 Hz), 3.63 (2H, s), 3.76 (3H, s), 6.87 (1H, s), 7.25-7.32 (4H, m).

Example 239

1-(2-((2-Chloro-6-cyclopropyl-3-ethoxy-4'-fluorobiphenyl-4-yl)methyl)-5-oxa-2,6-diazaspiro[3.4]oct-6-en-7-yl)-4-methylpiperidine 1 carboxylic acid A) Methyl 2-chloro-6-cyclopropyl-3-ethoxy-4'-fluorobiphenyl-4-carboxylate A mixture of methyl 2-chloro-6-cyclopropyl-4'-fluoro-3-hydroxybiphenyl-4-carboxylate (1.33 g), iodoethane (1.29 g), potassium carbonate (1.15 g) and DMF (10 mL) was stirred for 1 hour at room temperature. Water was added to the reaction mixture, and extraction thereof was performed using ethyl acetate. The obtained organic layer was sequentially washed with a saturated saline solution and water, and the solvent was distilled off. The obtained residue was crystallized using methanol/water (12 mL to 1.0 mL), thereby obtaining the title compound (1.20 g).

$^1$H NMR (300 MHz, DMSO-$d_6$) δ 0.58-0.77 (4H, m), 1.32 (3H, t, J=6.9 Hz), 1.38-1.49 (1H, m), 3.86 (3H, s), 4.02 (2H, q, J=7.0 Hz), 7.23 (1H, s), 7.28-7.38 (4H, m).

B) 2-Chloro-6-cyclopropyl-3-ethoxy-4'-fluorobiphenyl-4-carbaldehyde

Diisobutylaluminium hydride (1.5 M toluene solution, 6.88 mL) was added dropwise to a solution of methyl 2-chloro-6-cyclopropyl-3-ethoxy-4'-fluorobiphenyl-4-carboxylate (1.20 g) in THF (20 mL) at 0° C., and the resultant was stirred for 1 hour at the same temperature. Sodium sulfate decahydrate was added thereto, and the resultant was stirred for 1 hour at room temperature. After the reaction mixture was filtered using celite, the filtrate was concentrated under reduced pressure. After the obtained residue was passed through a short column of a silica gel, the filtrate was concentrated under reduced pressure. Manganese dioxide (2.99 g) was added to a solution of the obtained residue in THF (30 mL), and the resultant was stirred for 2 hours at room temperature. After the reaction mixture was filtered using celite, the filtrate was concentrated under reduced pressure, and the obtained residue was purified by a silica gel column chromatography (hexane/ethyl acetate), thereby obtaining the title compound (760 mg).

$^1$H NMR (ma MHz, DMSO-$d_6$) δ 0.60-0.80 (4H, m), 1.35-1.51 (4H, m), 4.13 (2H, q, J=7.0 Hz), 7.26-7.39 (5H, m), 10.26 (1H, s).

C) Ethyl 1-(2-((2-chloro-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylate tert-Butyl 7-(4-(ethoxycarbonyl)-4-methylpiperidin-1-yl)-5-oxa-2,6-diazaspiro[3.4]oct-6-ene-2-carboxylate (407 mg) was added to formic acid (2.0 mL), the resultant was stirred for 1 hour at 70° C., and then the solvent was distilled off under reduced pressure. Sodium triacetoxyborohydride (339 mg) was added to a solution of the obtained residue and 2-chloro-6-cyclopropyl-3-ethoxy-4'-fluorobiphenyl-4-carbaldehyde (340 mg) in THF (10 mL), and the resultant was stirred for 3 hours at room temperature. After an aqueous saturated sodium hydrogen carbonate solution was added to the reaction mixture, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (610 mg).

MS (ESI+): $[M+H]^+$ 584.5.

D) 1-(2-((2-Chloro-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylic acid 2 M aqueous sodium hydroxide solution (3.6 mL) was added to a solution of ethyl 1-(2-((2-chloro-6-cyclopropyl- 3-ethoxy-4'-fluorobiphenyl-4-yl)methyl)-5-oxa-2,6-diazaspiro[3.4]oct-6-en-7-yl)-4-methylpiperidine-4-carboxylate (600 mg) in ethanol (7.0 mL), and the resultant was stirred for 2 hours at 70° C. The reaction mixture was cooled to room temperature, it was neutralized with 2 M hydrochloric acid, was stirred for 30 minutes, and then the precipitated crystals were collected by filtration. The obtained residue was recrystallized (ethanol), thereby obtaining the title compound (441 mg).

$^1$H NMR (300 MHz, DMSO-$d_6$) δ 0.53-0.62 (2H, m), 0.65-0.75 (2H, m), 1.14 (3H, s), 1.30-1.47 (6H, m), 1.90 (2H, d, J=13.8 Hz), 2.88 (2H, t, J=10.2 Hz), 3.19 (2H, d, J=8.1 Hz), 3.23-3.40 (4H, m), 3.46 (2H, d, J=8.2 Hz), 3.62 (2H, s), 3.95 (2H, q, J=6.8 Hz), 6.86 (1H, s), 7.24-7.33 (4H, m).

Example 240

1-(2-((2-Bromo-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylic acid

A) Methyl 2-bromo-6-cyclopropyl-4'-fluoro-3-hydroxybiphenyl-4-carboxylate

Using methyl 2-cyclopropyl-4'-fluoro-5-hydroxybiphenyl-4-carboxylate, the title compound was obtained in the similar manner as in Step B of Example 114.

MS (ESI+): [M+H]$^+$ 365.1, 367.1.

B) Methyl 2-bromo-6-cyclopropyl-3-ethoxy-4'-fluorobiphenyl-4-carboxylate

Using methyl 2-bromo-6-cyclopropyl-4'-fluoro-3-hydroxybiphenyl-4-carboxylate and iodoethane, the title compound was obtained in the similar manner as in Step A of Example 1.

$^1$H NMR (300 MHz, DMSO-$d_6$) δ 0.58-0.74 (4H, m), 1.33 (3H, t, J=7.0 Hz), 1.38-1.47 (1H, m), 3.86 (3H, s), 4.00 (2H, q, J=7.1 Hz), 7.19-7.40 (5H, m).

C) 2-Bromo-6-cyclopropyl-3-ethoxy-4'-fluorobiphenyl-4-carbaldehyde

Using methyl 2-bromo-6-cyclopropyl-3-ethoxy-4'-fluorobiphenyl-4-carboxylate, the title compound was obtained in the similar manner as in Step E of Example 16 and Step H of Example 210.

MS (ESI+): [M+H]$^+$ 363.1, 365.1.

D) Ethyl 1-(2-((2-bromo-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-bromo-6-cyclopropyl-3-ethoxy-4'-fluorobiphenyl-4-carbaldehyde, the title compound was obtained in the similar manner as in Step G of Example 1.

MS (ESI+): [M+H]$^+$ 628.1, 630.1.

E) 1-(2-((2-Bromo-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((2-bromo-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 241

1-(2-((6-Cyclopropyl-3-ethoxy-4'-fluoro-2-methylbiphenyl-4-yl)methyl)-5-oxa-2,6-diazaspiro[3.4]oct-6-en-7-yl)-4-methylpiperidine-4-carboxylic acid

A) Methyl 6-cyclopropyl-3-ethoxy-4'-fluoro-2-methylbiphenyl-4-carboxylate

A mixture of methyl 2-bromo-6-cyclopropyl-3-ethoxy-4'-fluorobiphenyl-4-carboxylate (1.12 g), 1,2,3,4,5-pentaphenyl-1'-(di-tert-butylphosphino)ferrocene (101 mg), tris(dibenzylideneacetone)dipalladium(0) (130 mg), chloromethyl zinc (2 M TIE solution, 2.14 mL) and THF (20 mL) was stirred for 1 hour in a nitrogen atmosphere. The reaction mixture was diluted by ethyl acetate and water, it was filtered using celite, and the organic layer was separated. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (890 mg).

$^1$H NMR (300 MHz, DMSO-$d_6$) δ 0.51-0.59 (2H, m), 0.61-0.70 (2H, m), 1.30 (3H, t, J=7.0 Hz), 1.35-1.43 (1H, m), 1.90 (3H, s), 3.80-3.93 (5H, m), 7.11 (1H, s), 7.22-7.36 (4H, m).

B) 6-Cyclopropyl-3-ethoxy-4'-fluoro-2-methylbiphenyl-4-carbaldehyde

Using methyl 6-cyclopropyl-3-ethoxy-4'-fluoro-2-methylbiphenyl-4-carboxylate, the title compound was obtained in the similar manner as in Step E of Example 16 and Step H of Example 210.

$^1$H NMR (300 MHz, DMSO-$d_6$) δ 0.54-0.62 (2H, m), 0.64-0.73 (2H, m), 1.33-1.45 (4H, m), 1.93 (3H, s), 3.98 (2H, q, J=7.0 Hz), 7.19 (1H, s), 7.23-7.39 (4H, m), 10.27 (1H, s).

C) Ethyl 1-(2-((6-cyclopropyl-3-ethoxy-4'-fluoro-2-methylbiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 6-cyclopropyl-3-ethoxy-4'-fluoro-2-methylbiphenyl-4-carbaldehyde, the title compound was obtained in the similar manner as in Step G of Example 1.

MS (ESI+): [M+H]$^+$ 564.2.

D) 1-(2-((6-Cyclopropyl-3-ethoxy-4'-fluoro-2-methylbiphenyl-4-yl)methyl)-5-oxa-2,6-diazaspiro[3.4]oct-6-en-7-yl)-4-methylpiperidine-4-carboxylic acid Using ethyl 1-(2-((6-cyclopropyl-3-ethoxy-4'-fluoro-2-methylbiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 242

1-(2-((2-Cyano-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylic acid A) Methyl 6-cyclopropyl-4'-fluoro-3-hydroxy-2-iodobiphenyl-4-carboxylate N-iodosuccinimide (22.0 g) was added to a solution of methyl 2-cyclopropyl-4'-fluoro-5-hydroxybiphenyl-4-carboxylate (7.00 g) in DMF (56 mL) at 30° C., and the resultant was stirred for 2 hours at 40° C. The reaction mixture was cooled to room temperature, it was poured into water, and extraction thereof was performed using ethyl acetate. The obtained organic layer was washed with a saturated saline solution and an aqueous saturated sodium thiosulfate solution, dried over anhydrous magnesium sulfate, and then the solvent was distilled off under reduced pressure. Methanol was added to the obtained residue, and the precipitated crystals were collected by filtration, thereby obtaining the title compound (4.40 g).

MS (ESI+): $[M+H]^+$ 413.1.

B) Methyl 6-cyclopropyl-3-ethoxy-4'-fluoro-2-iodobiphenyl-4-carboxylate

Using methyl 6-cyclopropyl-4'-fluoro-3-hydroxy-2-iodobiphenyl-4-carboxylate and iodoethane, the title compound was obtained hi the similar manner as in Step A of Example 1.

$^1$H NMR (300 MHz, DMSO-$d_6$) δ 0.52-0.75 (4H, m), 1.29-1.49 (4H, m), 3.86 (3H, s), 3.96 (2H, q, J=7.0 Hz), 7.15-7.41 (5H, m).

C) 6-Cyclopropyl-3-ethoxy-4'-fluoro-2-iodobiphenyl-4-carbaldehyde

Using methyl 6-cyclopropyl-3-ethoxy-4'-fluoro-2-iodobiphenyl-4-carboxylate, the title compound was obtained in the similar manner as in Step F and Step G of Example 238.

$^1$H NMR (300 MHz, DMSO-$d_6$) δ 0.58-0.76 (4H, m), 1.40-1.49 (4H, m), 3.98-4.10 (2H, m), 7.19-7.28 (2H, m), 7.29-7.39 (3H, m), 10.21 (1H, s).

D) 2-(6-Cyclopropyl-3-ethoxy-4'-fluoro-2-iodobiphenyl-4-yl)-1,3-dioxolane

A mixture of 4-methylbenzenesulfonic acid monohydrate (362 mg), ethylene glycol (2.95 g), 6-cyclopropyl-3-ethoxy-4'-fluoro-2-iodobiphenyl-4-carbaldehyde (3.90 g) and toluene (80 mL) was heated to reflux for 3 hours. The reaction mixture was cooled to 0° C., an aqueous saturated sodium hydrogen carbonate solution was added thereto, and extraction thereof was performed using ethyl acetate: After the obtained organic layer was washed with water, the solvent was distilled off under reduced pressure. After the obtained residue was passed through a short column of a silica gel (NH), the filtrate was concentrated under reduced pressure. Ethanol/Water (5:1, 25 mL) was added to the obtained residue, the resultant was stirred for 30 minutes, and then the precipitated crystals were collected by filtration, thereby obtaining the title compound (3.86 g).

MS (ESI+): $[M+H]^+$ 455.2.

E) 6-Cyclopropyl-3-ethoxy-4'-fluoro-4-formylbiphenyl-2-carbonitrile

A mixture of zinc cyanide (775 mg), tetrakistriphenylphosphine palladium (382 mg), 2-(6-cyclopropyl-3-ethoxy-4'-fluoro-2-iodobiphenyl-4-yl)-1,3-dioxolane (1.50 g), and DMF (10 mL) was stirred for 24 hours at 90° C. The reaction mixture was cooled to room temperature, and it was poured into water. It was filtered using celite, and the organic layer was separated. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate). After a mixture of the obtained purified product, 6 M hydrochloric acid (2.5 mL) and THF (5.0 mL) was stirred for 30 minutes at room temperature, it was neutralized with an aqueous saturated sodium hydrogen carbonate solution. Extraction was performed on the reaction mixture using ethyl acetate, the obtained organic layer was washed with a saturated saline solution, dried over anhydrous magnesium sulfate, and the solvent was distilled off under reduced pressure. The obtained residue was purified by a silica gel column chromatography (hexane/ethyl acetate), thereby obtaining the title compound (891 mg).

MS (ESI+): $[M+H]^+$ 310.2.

F) Ethyl 1-(2-((2-cyano-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 6-cyclopropyl-3-ethoxy-4'-fluoro-4-formylbiphenyl-2-carbonitrile, the title compound was obtained in the similar manner as in Step G of Example 1.

MS(ESI+):$[M+H]^+$ 575.5.

G) 1-(2-((2-Cyano-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((2-cyano-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 243

1-(2-((6-Cyclopropyl-3-ethoxy-2,4'-difluorobiphenyl-4-yl)methyl)-5-oxa-2,6-diazaspiro[3.4]oct-6-en-7-yl)-4-methylpiperidine-4-carboxylic acid A) 6-Cyclopropyl-3-ethoxy-2,4'-difluorobiphenyl-4-carbaldehyde n-Butyllithium (1.6 M hexane solution, 3.7 mL) was added dropwise to a solution of 2-(6-cyclopropyl-3-ethoxy-4'-fluoro-2-iodobiphenyl-4-yl)-1,3-dioxolane (1.80 g) in THF (20 mL) at −78° C. in an argon atmosphere, the resultant was stirred for 1 hour at the same temperature, and a solution of N-fluoro-N-(phenylsulfonyl)benzenesulfonamide (2.50 g) in THF (15 mL) was added dropwise thereto. The temperature of the reaction mixture was warmed to room temperature, it was stirred overnight, poured into water, and extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (NH, hexane/ethyl acetate). Ethanol/Water (4:1, 10 mL) was added to the obtained purified product, and the precipitated crystals were collected by filtration. After the filtrate was concentrated under reduced pressure, THF (10 ml) and 6 M hydrochloric acid (2.0 mL) were added thereto, and the resultant was stirred for 10 minutes at room temperature. After the reaction mixture was neutralized with an aqueous saturated sodium hydrogen carbonate solution, extraction thereof was performed using ethyl acetate. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (400 mg).

MS (ESI+): $[M+H]^+$ 303.2.

B) Ethyl 1-(2-((6-cyclopropyl-3-ethoxy-2,4'-difluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 6-cyclopropyl-3-ethoxy-2,4'-difluorobiphenyl-4-carbaldehyde, the title compound was obtained in the similar manner as in Step G of Example 1.

MS (ESI+): $[M+H]^+$ 568.5.

C) 1-(2-((6-Cyclopropyl-3-ethoxy-2,4'-difluorobiphenyl-4-yl)methyl)-5-oxa-2,6-diazaspiro[3.4]oct-6-en-7-yl)-4-methylpiperidine-4-carboxylic acid Using ethyl 1-(2-((6-cyclopropyl-3-ethoxy-2,4'-difluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 244

1-(2-((2-Cyclopropyl-3,4'-difluoro-5-methoxybiphenyl-4-yl)methyl)-5-oxa-2,6-diazaspiro[3.4]oct-6-en-7-yl)-4-methylpiperidine-4-carboxylic acid A) 4-Bromo-2-fluoro-6-methoxybenzaldehyde A solution of sodium methoxide (870 mg) in methanol (50 mL) was added dropwise to a solution of 4-bromo-2,6-difluorobenzaldehyde (3.56 g) in methanol (20 mL) at −18° C. The temperature of the reaction mixture was slowly warmed to room temperature, and it was stirred overnight at room temperature in a nitrogen atmosphere. Water was added to the reaction mixture, the solvent was distilled off under reduced pressure, the resultant was diluted by ethyl acetate and water, and the organic layer was separated. The obtained organic layer was washed with a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.00 g).

MS (ESI+): $[M+H]^+$ 233.1, 235.1.

B) 3,4'-Difluoro-5-methoxybiphenyl-4-carbaldehyde

Using 4-bromo-2-fluoro-6-methoxybenzaldehyde and (4-fluorophenyl)boronic acid, the title compound was obtained in the similar manner as in Step D of Example 16.

$^1H$ NMR (300 MHz, $CDCl_3$) δ 4.01 (3H, s), 6.84-6.97 (2H, m), 7.12-7.21 (2H, m), 7.53-7.61 (2H, m), 10.44 (1H, d, J=0.8 Hz).

C) 2-Bromo-3,4'-difluoro-5-methoxybiphenyl-4-carbaldehyde

Using 3,4'-difluoro-5-methoxybiphenyl-4-carbaldehyde, the title compound was obtained in the similar manner as in Step B of Example 114.

$^1H$ NMR (300 MHz, $CDCl_3$) δ 3.95 (3H, s), 6.76 (1H, d, J=1.4 Hz), 7.12-7.22 (2H, m), 7.34-7.46 (2H, m), 10.42 (1H, d, J=1.2 Hz).

D) 2-Cyclopropyl-3,4'-difluoro-5-methoxybiphenyl-4-carbaldehyde

Using 2-bromo-3,4'-difluoro-5-methoxybiphenyl-4-carbaldehyde and cyclopropyl boronic acid, the title compound was obtained in the similar manner as in Step D of Example 23.

MS (ESI+): $[M+H]^+$ 289.2.

E) Ethyl 1-(2-((2-cyclopropyl-3,4'-difluoro-5-methoxybiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-3,4'-difluoro-5-methoxybiphenyl-4-carbaldehyde, the title compound was obtained in the similar manner as in Step G of Example 1.

MS (ESI+): $[M+H]^+$ 554.5.

F) 1-(2-((2-Cyclopropyl-3,4'-difluoro-5-methoxybiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-3,4'-difluoro-5-methoxybiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 245

1-(2-(4-Cyclobutyl-5-cyclopropyl-2-methoxybenzyl)-5-oxa-2,6-diazaspiro[3.4]oct-6-en-7-yl)-4-methylpiperidine-4-carboxylic acid A) Methyl 2-(benzyloxy)-4-cyclobutylbenzoate Iodine (40 mg) and 1,2-dibromoethane (0.5 mL) were added to a mixture of magnesium (11.8 g) and, diethyl ether anhydride (250 mL), bromocyclobuthane (44.0 g) was slowly added thereto, and the resultant was stirred for 2 hours at 40° C. A solution of zinc chloride (54 g) prepared at 160° C. in high vacuum in THF (450 mL) was added to the reaction mixture at 0° C., and the resultant was stirred for 1 hour at the same temperature. A mixture of methyl 2-(benzyloxy)-4-iodobenzoate (20 g), tris(dibenzylideneacetone)dipalladium(0) (4.97 g), 4,5-bis(diphenylphosphino)-9,9-dimethylxanthene (3.14 g) and THF (500 mL) was degassed under an argon flow, the zinc reagent (350 mL) prepared in advance was added thereto, and the resultant was stirred overnight at 60° C. The reaction mixture was filtered using celite. The solvent was concentrated under reduced pressure. Water was added to the obtained residue, and extraction thereof was performed three times using ethyl acetate. The combined organic layer was washed with water, dried over anhydrous sodium sulfate, and then the solvent was distilled off under reduced pressure. The obtained residue was purified by a silica gel column chromatography (hexane/ethyl acetate), thereby obtaining the title compound (9.5 g).

MS (ESI+): $[M+H]^+$ 297.3.

B) Methyl 2-(benzyloxy)-5-bromo-4-cyclobutylbenzoate

After sodium carbonate (7.51 g) was added to a solution of methyl 2-(benzyloxy)-4-cyclobutylbenzoate (14 g) in dichloromethane (150 mL), a solution of bromine (3.17 mL) in dichloromethane (25 mL) was slowly added thereto at 10° C., and the resultant was stirred for 1 hour at the same temperature. After an aqueous saturated sodium hydrogen carbonate solution was added to the reaction mixture, extraction thereof was performed twice using ethyl acetate. The obtained organic layer was sequentially washed with an aqueous saturated sodium hydrogen sulfite solution and a saturated saline solution, dried over sodium sulfate, and then the solvent was distilled off under reduced pressure. The obtained residue was purified by a silica gel column chromatography (hexane/ethyl acetate), thereby obtaining the title compound (12.2 g).

MS (ESI+): $[M+H]^+$ 375.1, 377.2.

C) Methyl 2-(benzyloxy)-4-cyclobutyl-5-cyclopropylbenzoate

Cyclopropyl boronic acid (6.18 g) and sodium carbonate (15.3 g) were added to a mixture of methyl 2-(benzyloxy)-5-bromo-4-cyclobutylbenzoate (13.5 g) in toluene (240 mL) and water (60 mL), and the resultant was degassed for 20 minutes under an argon flow. Tris(dibenzylideneacetone) dipalladium(0) (6.25 and dicyclohexyl(2',6'-dimethoxybiphenyl-2-yl)phosphine (2.80 g) were added thereto, and the resultant was degassed for 5 minutes. The reaction mixture was stirred for 16 hours at 100° C. The reaction mixture was filtered using celite, and the celite was washed with ethyl acetate. The combined organic layer was sequentially washed with water and a saturated saline solution, and the solvent was distilled off under reduced pressure. The obtained residue was purified by a silica gel column chromatography (hexane/ethyl acetate), thereby obtaining the title compound (8.5 g).

MS (ESI+): $[M+H]^+$ 337.3.

D) Methyl 4-cyclobutyl-5-cyclopropyl-2-hydroxybenzoate

After a solution of methyl 2-(benzyloxy)-4-cyclobutyl-5-cyclopropylbenzoate (8.5 g) in methanol (100 mL) was degassed for 20 minutes under a nitrogen flow, 10% palladium on carbon (55% water content 1.1 g) was added thereto, and the resultant was stirred for 3 hours at room temperature in a hydrogen atmosphere. The reaction mixture was filtered using celite, and the solvent was distilled off under reduced pressure, thereby obtaining the title compound (6.0 g).

MS (ESI+): $[M+H]^+$ 247.2.

E) Methyl 4-cyclobutyl-5-cyclopropyl-2-methoxybenzoate

Cesium carbonate (7.93 g) and iodomethane (1.1 mL) were added to a solution of methyl 4-cyclobutyl-5-cyclopropyl-2-hydroxybenzoate (3.0 g) in DMF (50 mL) under ice-cooling, and the resultant was stirred overnight at room temperature. The reaction mixture was diluted by water, and extraction thereof was performed twice by using ethyl acetate. The combined organic layer was sequentially washed with water and a saturated saline solution, dried over anhydrous sodium sulfate, and then the solvent was distilled off under reduced pressure, thereby obtaining the title compound (3.0 g).

MS (ESI+): $[M+H]^+$ 261.3.

F) 4-Cyclobutyl-5-cyclopropyl-2-methoxybenzaldehyde

Lithium aluminum hydride (1 M THF solution, 13.8 mL) was added to a solution of methyl 4-cyclobutyl-5-cyclopropyl-2-methoxybenzoate (3.0 g) in THF (30 mL) at 0° C. The reaction mixture was stirred for 2 hours at room temperature. An aqueous saturated sodium sulfate solution was added to the reaction mixture at 0° C., and extraction thereof was performed using ethyl acetate. The obtained organic layer was sequentially washed with water and a saturated saline solution, dried over anhydrous sodium sulfate, and then the solvent was distilled off under reduced pressure. Manganese dioxide (8.99 g) was added little by little to a solution of the obtained residue in acetone (50 mL) at room temperature, and the resultant was stirred overnight at room temperature. The reaction mixture was filtered using celite, and the solvent was distilled off under reduced pressure. The obtained residue was purified by a silica gel column chromatography (hexane/ethyl acetate), thereby obtaining the title compound (2.1 g).

MS (ESI+): $[M+H]^+$ 231.2.

G) Ethyl 1-(2-(4-cyclobutyl-5-cyclopropyl-2-methoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 4-cyclobutyl-5-cyclopropyl-2-methoxybenzaldehyde, the title compound was obtained in the similar manner as in Step G of Example 1.

MS (ESI+): $[M+H]^+$ 496.5.

H) 1-(2-(4-Cyclobutyl-5-cyclopropyl-2-methoxybenzyl)-5-oxa-2,6-diazaspiro[3.4]oct-6-en-7-yl)-4-methylpiperidine-4-carboxylic acid Using ethyl 1-(2-(4-cyclobutyl-5-cyclopropyl-2-methoxybenzyl)-5-oxa-2,6-diazaspiro[3.4]oct-6-en-7-yl)-4-methylpiperidine-4-carboxylate, the title compound was obtained in the similar manner as in Example 2.

Example 246

1-(2-(4-Cyclobutyl-5-cyclopropyl-2-isopropoxybenzyl)-5-oxa-2,6-diazaspiro[3.4]oct-6-en-7-yl)piperidine-4-carboxylic acid A) Methyl 4-cyclobutyl-5-cyclopropyl-2-isopropoxybenzoate Cesium carbonate (7.93 g) and 2-iodopropane (2.62 mL) were added to a solution of methyl 4-cyclobutyl-5-cyclopropyl-2-hydroxybenzoate (3.0 g) in DMF (50 mL) under ice-cooling, and the resultant was stirred overnight at room temperature. The reaction mixture was diluted by water, and extraction thereof was performed by using ethyl acetate. The obtained organic layer was sequentially washed with water and a saturated saline solution, dried over anhydrous sodium sulfate, and then the solvent was distilled off under reduced pressure, thereby obtaining the title compound (3.2 g).

MS (ESI+): $[M+H]^+$ 289.3.

B) 4-Cyclobutyl-5-cyclopropyl-2-isopropoxybenzaldehyde

Lithium aluminum hydride (1 M THF solution, 12.5 mL) was added to a solution of methyl 4-cyclobutyl-5-cyclopropyl-2-isopropoxybenzoate (3.0 g) in THF (30 mL) at 0° C. The reaction mixture was stirred for 2 hours at room temperature. An aqueous saturated sodium sulfate solution was added to the reaction mixture at 0° C., and extraction thereof was performed using ethyl acetate. The obtained organic layer was sequentially washed with water and a saturated saline solution, dried over anhydrous sodium sulfate, and then the solvent was distilled off under reduced pressure. Manganese dioxide (8.36 g) was added little by little to a solution of the obtained residue in acetone (50 mL) at room temperature, and the resultant was stirred overnight at room temperature. The reaction mixture was filtered using celite, and the solvent was distilled off under reduced pressure. The obtained residue was purified by a silica gel column chromatography (hexane/ethyl acetate), thereby obtaining the title compound (2.2 g).

$^1$H NMR (400 MHz, $CDCl_3$) δ 0.58-0.63 (2H, m), 0.84-0.88 (2H, m), 1.39 (6H, d, J=6.1 Hz), 1.71-1.77 (1H, m), 1.83-1.89 (1H, m), 2.02-2.18 (3H, m), 2.38-2.44 (2H, m), 3.91-3.96 (1H, m), 4.65-4.71 (1H, m), 6.86 (1H, s), 7.43 (1H, s), 10.38 (1H, s).

C) Ethyl 1-(2-(4-cyclobutyl-5-cyclopropyl-2-isopropoxybenzyl)-5-oxa-2,6-diazaspiro[3.4]oct-6-en-7-yl)piperidine-4-carboxylate Using tert-butyl 7-(4-(ethoxycarbonyl)piperidin-1-yl)-5-oxa-2,6-diazaspiro[3.4]oct-6-ene-2-carboxylate and 4-cyclobutyl-5-cyclopropyl-2-isopropoxybenzaldehyde, the title compound was obtained in the similar manner as in Step G of Example 1.

MS(ESI+):$[M+H]^+$ 510.4.

D) 1-(2-(4-Cyclobutyl-5-cyclopropyl-2-isopropoxybenzyl)-5-oxa-2,6-diazaspiro[3.4]oct-6-en-7-yl)piperidine-4-carboxylic acid Using ethyl 1-(2-(4-cyclobutyl-5-cyclopropyl-2-isopropoxybenzyl)-5-oxa-2,6-diazaspiro[3.4]oct-6-en-7-yl)piperidine-4-carboxylate, the title compound was obtained in the similar manner as in Example 2.

Example 247

1-(2-(4-Cyclobutyl-5-cyclopropyl-2-ethoxybenzyl)-5-oxa-2,6-diazaspiro[3.4]oct-6-en-7-yl)piperidine 4 carboxylic acid A) Ethyl 1-(2-(4-cyclobutyl-5-cyclopropyl-2-ethoxybenzyl)-5-oxa-2,6-diazaspiro[3.4]oct-6-en-7-yl)piperidine-4-carboxylate Using tert-butyl 7-(4-(ethoxycarbonyl)piperidin-1-yl)-5-oxa-2,6-diazaspiro[3.4]oct-6-ene-2-carboxylate and 4-cyclobutyl-5-cyclopropyl-2-ethoxybenzaldehyde, the title compound was obtained in the similar manner as in Step G of Example 1.

MS (ESI+): $[M+H]^+$ 496.5.

B) 1-(2-(4-Cyclobutyl-5-cyclopropyl-2-ethoxybenzyl)-5-oxa-2,6-diazaspiro[3.4]oct-6-en-7-yl)piperidine carboxylic acid Using ethyl 1-(2-((4-cyclobutyl-5-cyclopropyl-2-ethoxybenzyl)-5-oxa-2,6-diazaspiro[3.4]oct-6-en-7-yl)piperidine-4-carboxylate, the title compound was obtained in the similar manner as in Example 2.

Example 248

1-(2-(4,5-Dicyclopropyl-2-isopropoxybenzyl)-5-oxa-2,6-diazaspiro[3.4]oct-6-en-7-yl)-4-methylpiperidine-4-carboxylic acid A) Methyl 4-iodo-2-isopropoxybenzoate 2-Iodopropane (6.42 g) was added to a mixture of methyl 2-hydroxy-4-iodobenzoate (7.00 g), potassium carbonate (6.96 g) and DMF (100 mL) at room temperature, and the resultant was stirred for 2 days at 70° C. in a nitrogen atmosphere. Water was added to the reaction mixture at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (7.92 g).

$^1$H NMR (300 MHz, $CDCl_3$) δ 1.37 (6H, d, J=6.0 Hz), 3.86 (3H, s), 4.49-4.63 (1H, m), 7.28-7.33 (2H, m), 7.46 (1H, d, J=8.5 Hz).

B) Methyl 4-cyclopropyl-2-isopropoxybenzoate

Cyclopropyl boronic acid (3.19 g), 2 M aqueous sodium carbonate solution (37 mL), tris(dibenzylideneacetone)dipalladium(0) (1.59 g) and dicyclohexyl(2',6'-dimethoxybiphenyl-2-yl)phosphine (1.52 g) were added to a solution of methyl 4-iodo-2-isopropoxybenzoate (7.92 g) in toluene (100 mL) at room temperature, and the resultant was stirred 15 hours at 100° C. in an argon atmosphere. Water was added to the reaction mixture at room temperature, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (5.43 g).

$^1$H NMR (300 MHz, $CDCl_3$) δ 0.70-0.76 (2H, m), 0.98-1.05 (2H, m), 1.36 (6H, d, J=6.1 Hz), 1.82-1.93 (1H, m), 3.85 (3H, s), 4.49-4.63 (1H, m), 6.62 (1H, dd, J=8.1, 1.6 Hz), 6.69 (1H, d, J=1.5 Hz), 7.69 (1H, d, J=8.1 Hz).

C) Methyl 5-bromo-4-cyclopropyl-2-isopropoxybenzoate 1,3-Dibromo-1,3,5-triazine-2,4,6-trione (3.99 g) was added to a solution of methyl 4-cyclopropyl-2-isopropoxybenzoate (5.43 g) in DMF (80 mL) at room temperature, and the resultant was stirred for 1 hour at 90° C. in a nitrogen atmosphere. An aqueous sodium thiosulfate solution was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (6.89 g).

$^1$H NMR (300 MHz, $CDCl_3$) δ 0.65-0.72 (2H, m), 1.04-1.11 (2H, m), 1.34 (6H, d, J=6.1 Hz), 2.12-2.23 (1H, m), 3.86 (3H, s), 4.42-4.56 (1H, m), 6.50 (1H, s), 7.96 (1H, s).

D) Methyl 4,5-dicyclopropyl-2-isopropoxybenzoate

Cyclopropyl boronic acid (2.83 g), 2 M aqueous sodium carbonate solution (33 mL), tris(dibenzylideneacetone)dipalladium(0) (1.41 and dicyclohexyl(2',6'-dimethoxybiphenyl-2-yl)phosphine (1.36 g) were added to a solution of methyl 5-bromo-4-cyclopropyl-2-isopropoxybenzoate (6.89 g) in toluene (100 mL) at room temperature, and the resultant was stirred 15 hours at 100° C. in an argon atmosphere. Water was added to the reaction mixture at room temperature, the resultant was filtered using celite, and then the filtrate was extracted using ethyl acetate. The obtained organic layer was sequentially washed with water and a saturated saline solution, dried over anhydrous magnesium sulfate, and then the solvent was distilled of under reduced pressure. The obtained residue was purified by a silica gel column chromatography (hexane/ethyl acetate), thereby obtaining the title compound (5.90 g).

$^1$H NMR (300 MHz, $CDCl_3$) δ 0.62-0.72 (4H, m), 0.88-0.96 (2H, m), 0.98-1.06 (2H, m), 1.33 (6H, d, J=6.1 Hz), 1.99-2.11 (1H, m), 2.21-2.32 (1H, m), 3.85 (3H, s), 4.40-4.53 (1H, m), 6.51 (1H, s), 7.43 (1H, d, J=0.4 Hz).

E) (4,5-Dicyclopropyl-2-isopropoxyphenyl)methanol

A solution of methyl 4,5-dicyclopropyl-2-isopropoxybenzoate (5.90 g) in THF (15 mL) was added to a mixture of lithium aluminum hydride (1.71 g) and THF (85 mL) at 0° C., and the resultant was stirred for 30 minutes at room temperature in a nitrogen atmosphere. Water (1.8 mL), 1 M aqueous sodium hydroxide solution (1.8 mL) and water (5.4 mL) were sequentially added to the reaction mixture at 0° C., the resultant was filtered using celite, and then the filtrate was concentrated under reduced pressure. The obtained residue was purified by a silica gel column chromatography (hexane/ethyl acetate), thereby obtaining the title compound (5.22 g).

$^1$H NMR (300 MHz, $CDCl_3$) δ 0.59-0.68 (4H, m), 0.86-1.00 (4H, m), 1.33 (6H, d, J=6.0 Hz), 2.02-2.13 (1H, m), 2.15-2.27 (1H, m), 2.41 (1H, t, J=6.5 Hz), 4.48-4.64 (3H, m), 6.49 (1H, s), 6.86 (1H, s).

F) 4,5-Dicyclopropyl-2-isopropoxybenzaldehyde

Manganese dioxide (14.7 g) was added to a solution of (4,5-dicyclopropyl-2-isopropoxyphenyl)methanol (5.22 g) in toluene (80 mL), and the resultant was stirred for 1 hour at 80° C. in a nitrogen atmosphere. The reaction mixture was filtered using celite, and the filtrate was concentrated. The obtained residue was purified by a silica gel column chromatography (hexane/ethyl acetate), thereby obtaining the title compound (4.88 g).

$^1$H NMR (300 MHz, $CDCl_3$) δ 0.64-0.76 (4H, m), 0.88-0.96 (2H, m), 1.03-1.11 (2H, m), 1.36 (6H, d, J=6.0 Hz), 1.98-2.09 (1H, m), 2.25-2.37 (1H, m), 4.53-4.66 (1H, m), 6.49 (1H, s), 7.47 (1H, d, J=0.6 Hz), 10.37 (1H, s).

G) Ethyl 1-(2-(4,5-dicyclopropyl-2-isopropoxybenzyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (419 mg) and formic acid (6 mL) was stirred for 30 minutes at 60° C., the solvent was distilled off under reduced pressure. Sodium triacetoxyborohydride (466 mg) was added to a mixture of the obtained residue and 4,5-dicyclopropyl-2-isopropoxybenzaldehyde (322 mg) and THF (8 mL), and the resultant was stirred for 15 hours at the same temperature. An aqueous saturated sodium hydrogen carbonate solution was added to the reaction mixture at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (496 mg).

$^1$H NMR (300 MHz, $CDCl_3$) δ 0.58-0.67 (4H, m), 0.85-0.98 (4H, m), 1.20 (3H, s), 1.23-1.31 (9H, m), 1.39-1.52 (2H, m), 2.00-2.26 (4H, m), 2.89-3.01 (2H, m), 3.25 (2H, s), 3.33-3.43 (4H, m), 3.52 (2H, d, J=8.7 Hz), 3.61 (2H, s), 4.16 (2H, q, J=7.1 Hz), 4.38-4.53 (1H, m), 6.44 (1H, s), 6.85 (1H, s).

H) 1-(2-(4,5-Dicyclopropyl-2-isopropoxybenzyl)-5-oxa-2,6-diazaspiro[3.4]oct-6-en-7-yl)-4-methylpiperidine-4-carboxylic acid 2 M aqueous sodium hydroxide solution (3.1 mL) was added to a solution of ethyl 1-(2-(4,5-dicyclopropyl-2-isopropoxybenzyl)-5-oxa-2,6-diazaspiro[3.4]oct-6-en-7-yl)-4-methylpiperidine-4-carboxylate (472 mg) in ethanol (8 mL) at room temperature. After the reaction mixture was stirred for 15 hours at 80° C., the solvent was distilled off under reduced pressure. Water was added to the residue, the resultant was neutralized with 2 M hydrochloric acid. The obtained solid was collected by filtration, and it was dissolved in a mixture of ethyl acetate and THF. After the obtained solution was dried over anhydrous magnesium sulfate, the solvent was distilled off under reduced pressure. The obtained residue was crystallized (hexane/ethyl acetate), and further recrystallized (hexane/ethanol), thereby obtaining the title compound (220 mg).

$^1$H NMR (300 MHz, DMSO-$d_6$) δ 0.49-0.58 (2H, m), 0.59-0.67 (2H, m), 0.83-0.97 (4H, m), 1.13 (3H, s), 1.21 (6H, d, J=6.0 Hz), 1.30-1.43 (2H, m), 1.90 (2H, d, J=13.8 Hz), 1.99-2.11 (1H, m), 2.12-2.23 (1H, m), 2.79-2.94 (2H, m), 3.10 (2H, d, J=7.5 Hz), 3.22-3.34 (4H, m), 3.40 (2H, d, J=7.6 Hz), 3.46 (2H, s), 4.46-4.58 (1H, m), 6.44 (1H, s), 6.78 (1H, s).

Example 249

1-(2-(4-Cyclobutyl-5-cyclopropyl-2-isopropoxybenzyl)-5-oxa-2,6-diazaspiro[3.4]oct-6-en-7-yl)-4-methylpiperidine-4-carboxylic acid A) Ethyl 1-(2-(4-cyclobutyl-5-cyclopropyl-2-isopropoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 4-cyclobutyl-5-cyclopropyl-2-isopropoxybenzaldehyde, the title compound was obtained in the similar manner as in Step G of Example 1.

MS (ESI+): $[M+H]^+$ 524.5.

B) 1-(2-(4-Cyclobutyl-5-cyclopropyl-2-isopropoxybenzyl)-5-oxa-2,6-diazaspiro[3.4]oct-6-en-7-yl)-4-methylpiperidine-4-carboxylic acid Using ethyl 1-(2-(4-cyclobutyl-5-cyclopropyl-2-isopropoxybenzyl)-5-oxa-2,6-diazaspiro[3.4]oct-6-en-7-yl)-4-methylpiperidine-4-carboxylate, the title compound was obtained in the similar manner as in Example 2.

Example 250

1-(2-(4,5-Dicyclopropyl-2-ethoxybenzyl)-5-oxa-2,6-diazaspiro[3.4]oct-6-en-7-yl)-4-methylpiperidine-4-carboxylic acid A) Methyl 2-ethoxy-4-iodobenzoate Iodoethane (3.53 g) was added to a mixture of methyl 2-hydroxy-4-iodobenzoate (4.19 g), potassium carbonate (4.17 g) and DMF (50 mL) at room temperature, and the resultant was stirred for 1 hour at 70° C. in a nitrogen atmosphere. Water was added to the reaction mixture at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (4.52 g).

$^1H$ NMR (300 MHz, $CDCl_3$) δ 1.46 (3H, t, J=7.0 Hz), 3.87 (3H, s), 4.09 (2H, q, J=7.0 Hz), 7.29-7.34 (2H, m), 7.48 (1H, d, J=8.1 Hz).

B) Methyl 4-cyclopropyl-2-ethoxybenzoate

Cyclopropyl boronic acid (1.90 g), 2 M aqueous sodium carbonate solution (22 mL), tris(dibenzylideneacetone)dipalladium(0) (944 mg) and dicyclohexyl(2',6'-dimethoxybiphenyl-2-yl)phosphine (907 mg) were added to a solution of methyl 2-ethoxy-4-iodobenzoate (4.51 g) in toluene (80 mL) at room temperature, and the resultant was stirred 18 hours at 100° C. in an argon atmosphere. Water was added to the reaction mixture at room temperature, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (3.25 g).

$^1H$ NMR (300 MHz, $CDCl_3$) δ 0.71-0.78 (2H, m), 0.98-1.06 (2H, m), 1.46 (3H, t, J=7.0 Hz), 1.83-1.94 (1H, m), 3.86 (3H, s), 4.11 (2H, q, J=6.9 Hz), 6.61 (1H, dd, J=8.1, 1.6 Hz), 6.67 (1H, d, J=1.5 Hz), 7.71 (1H, d, J=8.1 Hz).

C) Methyl 5-bromo-4-cyclopropyl-2-ethoxybenzoate 1,3-Dibromo-1,3,5-triazine-2,4,6-trione (2.54 g) was added to a solution of methyl 4-cyclopropyl-2-ethoxybenzoate (3.25 g) in DMF (60 mL) at room temperature, and the resultant was stirred for 1 hour at 90° C. in a nitrogen atmosphere. 1,3-Dibromo-1,3,5-triazine-2,4,6-trione (423 mg) was added to the reaction mixture, the resultant was stirred for 30 minutes at 90° C. in a nitrogen atmosphere. An aqueous sodium thiosulfate solution was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (4.08 g).

$^1H$ NMR (300 MHz, $CDCl_3$) δ 0.66-0.74 (2H, m), 1.04-1.12 (2H, m), 1.44 (3H, t, J=7.0 Hz), 2.12-2.24 (1H, m), 3.86 (3H, s), 4.06 (2H, q, J=7.0 Hz), 6.48 (1H, s), 7.97 (1H, s).

D) Methyl 4,5-dicyclopropyl-2-ethoxybenzoate

Cyclopropyl boronic acid (1.76 g), 2 M aqueous sodium carbonate solution (20 mL), tris(dibenzylideneacetone)dipalladium(0) (874 mg) and dicyclohexyl(2',6'-dimethoxybiphenyl-2-yl)phosphine (840 mg) were added to a solution of methyl 5-bromo-4-cyclopropyl-2-epoxybenzoate (4.08 g) in toluene (70 mL) at room temperature, and the resultant was stirred 18 hours at 100° C. in an argon atmosphere. Water was added to the reaction mixture at room temperature, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (3.27 g).

$^1H$ NMR (300 MHz, $CDCl_3$) δ 0.62-0.73 (4H, m), 0.88-0.96 (2H, m), 0.98-1.06 (2H, m), 1.42 (3H, t, J=7.0 Hz), 1.99-2.10 (1H, m), 2.22-2.33 (1H, m), 3.85 (3H, s), 4.06 (2H, q, J=7.0 Hz), 6.49 (1H, s), 7.45 (1H, s).

E) (4,5-Dicyclopropyl-2-ethoxyphenyl)methanol

A solution of methyl 4,5-dicyclopropyl-2-ethoxybenzoate (3.26 g) in THF (15 mL) was added to a mixture of lithium aluminum hydride (998 mg) and THF (65 mL) at 0° C., and the resultant was stirred for 1 hour at room temperature in a nitrogen atmosphere. Water (1 mL), 1 M aqueous sodium hydroxide solution (1 mL) and water (3 mL) were sequentially added to the reaction mixture at 0° C., the resultant was filtered using celite, and then the filtrate was concentrated under reduced pressure. The obtained residue was purified by a silica gel column chromatography (hexane/ethyl acetate), thereby obtaining the title compound (2.84 g).

$^1$H NMR (300 MHz, $CDCl_3$) δ 0.59-0.69 (4H, m), 0.86-1.00 (4H, m), 1.41 (3H, t, J=7.0 Hz), 2.02-2.14 (1H, m), 2.17-2.27 (1H, m), 2.35 (1H, t, J=6.5 Hz), 4.05 (2H, q, J=7.0 Hz), 4.61 (2H, d, J=6.3 Hz), 6.47 (1H, s), 6.87 (1H, s).

F) 4,5-Dicyclopropyl-2-ethoxybenzaldehyde

Manganese dioxide (8.50 g) was added to a solution of (4,5-dicyclopropyl-2-ethoxyphenyl)methanol (2.84 g) in toluene (50 mL) at room temperature, and the resultant was stirred for 1 hour at 80° C. in a nitrogen atmosphere. After the reaction mixture was filtered using celite, the filtrate was concentrated. The obtained residue was purified by a silica gel column chromatography (hexane/ethyl acetate), thereby obtaining the title compound (2.68 g).

$^1$H NMR (300 MHz, $CDCl_3$) δ 0.63-0.70 (2H, m), 0.71-0.78 (2H, m), 0.89-0.96 (2H, m), 1.03-1.11 (2H, m), 1.44 (3H, t, J=6.9 Hz), 1.98-2.10 (1H, m), 2.27-2.37 (1H, m), 4.10 (2H, q, J=7.0 Hz), 6.47 (1H, s), 7.47 (1H, s), 10.39 (1H, s).

G) Ethyl 1-(2-(4,5-dicyclopropyl-2-ethoxybenzyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (403 mg) and formic acid (6 mL) was stirred for 1 hour at 60° C. in a nitrogen atmosphere, the solvent was distilled off under reduced pressure. Sodium triacetoxyborohydride (448 mg) was added to a mixture of the obtained residue and 4,5-dicyclopropyl-2-ethoxybenzaldehyde (292 mg) and THF (10 mL) at room temperature, and the resultant was stirred for 16 hours at the same temperature in a nitrogen atmosphere. An aqueous saturated sodium hydrogen carbonate solution was added to the reaction mixture at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (441 mg).

$^1$H NMR (300 MHz, $CDCl_3$) δ 0.57-0.68 (4H, m), 0.84-0.98 (4H, m), 1.20 (3H, s), 1.23-1.29 (3H, m), 1.34-1.51 (5H, m), 2.01-2.26 (4H, m), 2.89-3.01 (2H, m), 3.25 (2H, s), 3.32-3.42 (4H, m), 3.48-3.54 (2H, m), 3.62 (2H, s), 3.97 (2H, q, J=7.0 Hz), 4.16 (2H, q, J=7.1 Hz), 6.43 (1H, s), 6.84 (1H, s).

H) 1-(2-(4,5-Dicyclopropyl-2-ethoxybenzyl)-5-oxa-2,6-diazaspiro[3.4]oct-6-en-7-yl)-4-methylpiperidine-4-carboxylic acid 2 M aqueous sodium hydroxide solution (3.1 mL) was added to a solution of ethyl 1-(2-(4,5-dicyclopropyl-2-ethoxybenzyl)-5-oxa-2,6-diazaspiro[3.4]oct-6-en-7-yl)-4-methylpiperidine-4-carboxylate (420 mg) in ethanol (8 mL) at room temperature. After the reaction mixture was stirred for 15 hours at 80° C. in a nitrogen atmosphere, the solvent was distilled off under reduced pressure. Water was added to the residue, the resultant was neutralized with 2 M hydrochloric acid. The obtained solid was collected by filtration, and it was dissolved in a mixture of ethyl acetate and THF. After the obtained solution was dried over anhydrous magnesium sulfate, the solvent was distilled off under reduced pressure. The obtained residue was crystallized (hexane/ethyl acetate), and further recrystallized (hexane/ethanol), thereby obtaining the title compound (236 mg).

$^1$H NMR (300 MHz, DMSO-$d_6$) δ 0.50-0.57 (2H, m), 0.61-0.68 (2H, m), 0.85-0.96 (4H, m), 1.13 (3H, s), 1.25-1.42 (5H, m), 1.84-1.96 (2H, m), 2.01-2.11 (1H, m), 2.12-2.23 (1H, m), 2.80-2.95 (2H, m), 3.13 (2H, brs), 3.25-3.34 (4H, m), 3.38-3.52 (4H, m), 3.96 (2H, q, J=6.9 Hz), 6.43 (1H, s), 6.78 (1H, s).

Example 251

1-(2-((2-Cyclopropyl-4'-fluoro-6-methoxybiphenyl-4-yl)methyl)-5-oxa-2,6-diazaspiro[3.4]oct-6-en-7-yl)-4-methylpiperidine-4-carboxylic acid A) 3-Cyclopropyl-4-iodo-5-methoxybenzaldehyde Using 3-cyclopropyl-5-hydroxy-4-iodobenzaldehyde and iodomethane, the title compound was obtained in the similar manner as in Step A of Example 93.

MS (ESI+): $[M+H]^+$ 303.1.

B) 2-Cyclopropyl-4'-fluoro-6-methoxybiphenyl-4-carbaldehyde

Using 3-cyclopropyl-4-iodo-5-methoxybenzaldehyde and (4-fluorophenyl)boronic acid, the title compound was obtained in the similar manner as in Step B of Example 93.

MS (ESI+): $[M+H]^+$ 271.3.

C) Ethyl 1-(2-((2-cyclopropyl-4'-fluoro-6-methoxybiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-cyclopropyl-4'-fluoro-6-methoxybiphenyl-4-carbaldehyde, the title compound was obtained in the similar manner as in Step C of Example 93.

MS (ESI+): $[M+H]^+$ 536.5.

D) 1-(2-((2-Cyclopropyl-4'-fluoro-6-methoxybiphenyl-4-yl)methyl)-5-oxa-2,6-diazaspiro[3.4]oct-6-en-7-yl)-4-methylpiperidine-4-carboxylic acid Using ethyl 1-(2-((2-cyclopropyl-4'-fluoro-6-methoxybiphenyl-4-yl)methyl)-5-oxa-2,6-diazaspiro[3.4]oct-6-en-7-yl)-4-methylpiperidine-4-carboxylate, the title compound was obtained in the similar manner as in Step D of Example 93.

Example 252

1-(2-((2-Chloro-6-cyclopropyl-4'-fluoro-3-methoxybiphenyl-4-yl)methyl)-5-oxa-2,6-diazaspiro[3.4]oct-6-en-7-yl)-4-ethylpiperidine-4-carboxylic acid A) Ethyl 1-(2-((2-chloro-6-cyclopropyl-4'-fluoro-3-methoxybiphenyl-4-yl)methyl)-5-oxa-2,6-diazaspiro[3.4]oct-6-en-7-yl)-4-ethylpiperidine-4-carboxylate Using tert-butyl 7-(4-(ethoxycarbonyl)-4-ethylpiperidin-1-yl)-5-oxa-2,6-diazaspiro[3.4]oct-6-ene-2-carboxylate and 2-chloro-6-cyclopropyl-4'-fluoro-3-methoxybiphenyl-4-carbaldehyde, the title compound was obtained in the similar manner as in Step G of Example 1.

MS (ESI+): $[M+H]^+$ 584.5.

B) 1-(2-((2-Chloro-6-cyclopropyl-4'-fluoro-3-methoxybiphenyl-4-yl)methyl)-5-oxa-2,6-diazaspiro[3.4]oct-6-en-7-yl)-4-ethylpiperidine-4-carboxylic acid Using ethyl 1-(2-((2-chloro-6-cyclopropyl-4'-fluoro-3-methoxybiphenyl-4-yl)methyl)-5-oxa-2,6-diazaspiro[3.4]oct-6-en-7-yl)-4-ethylpiperidine-4-carboxylate, the title compound was obtained in the similar manner as in Example 2.

Example 253

1-(2-(3-Chloro-4,5-dicyclopropyl-2-isopropoxybenzyl)-5-oxa-2,6-diazaspiro[3.4]oct-6-en-7-yl)-4-methylpiperidine-4-carboxylic acid A) Methyl 4-cyclopropyl-2-hydroxybenzoate Using methyl 2-hydroxy-4-iodobenzoate and cyclopropyl boronic acid, the title compound was obtained in the similar manner as in Step C of Example 238.

MS (ESI+): $[M+H]^+$ 193.2.

B) Methyl 5-bromo-4-cyclopropyl-2-hydroxybenzoate

Using methyl 4-cyclopropyl-2-hydroxybenzoate and bromine, the title compound was obtained in the similar manner as in Step B of Example 113.

$^1$H NMR (300 MHz, $CDCl_3$) δ 0.70-0.77 (2H, m), 1.04-1.12 (2H, m), 2.12-2.24 (1H, m), 3.94 (3H, s), 6.49 (1H, s), 7.98 (1H, s), 10.57 (1H, s).

C) Methyl 5-bromo-4-cyclopropyl-2-(methoxymethoxy)benzoate

Using methyl 5-bromo-4-cyclopropyl-2-hydroxybenzoate and chloro(methoxy)methane, the title compound was obtained in the similar manner as in Step D of Example 113.

$^1$H NMR (300 MHz, $CDCl_3$) δ 0.68-0.75 (2H, m), 1.03-1.12 (2H, m), 2.12-2.23 (1H, m), 3.50 (3H, s), 3.87 (3H, s), 5.19 (2H, s), 6.73 (1H, s), 7.98 (1H, s).

D) Methyl 4,5-dicyclopropyl-2-(methoxymethoxy)benzoate

Using methyl 5-bromo-4-cyclopropyl-2-(methoxymethoxy)benzoate and cyclopropyl boronic acid, the title compound was obtained in the similar manner as in Step C of Example 238.

$^1$H NMR (300 MHz, $CDCl_3$) δ 0.63-0.75 (4H, m), 0.89-0.97 (2H, m), 0.98-1.06 (2H, m), 2.01-2.12 (1H, m), 2.20-2.32 (1H, m), 3.51 (3H, s), 3.86 (3H, s), 5.18 (2H, s), 6.71 (1H, s), 7.44 (1H, s).

E) Methyl 4,5-dicyclopropyl-2-hydroxybenzoate

Using methyl 4,5-dicyclopropyl-2-(methoxymethoxy)benzoate, the title compound was obtained in the similar manner as in Step G of Example 113.

MS (ESI+): $[M+H]^+$ 233.3.

F) Methyl 3-chloro-4,5-dicyclopropyl-2-hydroxybenzoate

Using methyl 4,5-dicyclopropyl-2-hydroxybenzoate and N-chlorosuccinimide, the title compound was obtained in the similar manner as in Step D of Example 238.

$^1$H NMR (300 MHz, $CDCl_3$) δ 0.59-0.66 (2H, m), 0.77-0.85 (2H, m), 0.92-1.01 (2H, m), 1.13-1.22 (2H, m), 1.81-1.94 (1H, m), 2.17-2.29 (1H, m), 3.94 (3H, s), 7.33 (1H, s), 11.15 (1H, s).

G) Methyl 3-chloro-4,5-dicyclopropyl-2-isopropoxybenzoate

Using methyl 3-chloro-4,5-dicyclopropyl-2-hydroxybenzoate and 2-iodopropane, the title compound was obtained in the similar manner as in Step E of Example 238.

$^1$H NMR (300 MHz, $CDCl_3$) δ 0.66-0.72 (2H, m), 0.73-0.79 (2H, m), 0.96-1.04 (2H, m), 1.11-1.20 (2H, m), 1.29 (6H, d, J=6.2 Hz), 1.80-1.91 (1H, m), 2.26-2.37 (1H, m), 3.88 (3H, s), 4.24-4.38 (1H, m), 7.16 (1H, s).

H) (3-Chloro-4,5-dicyclopropyl-2-isopropoxyphenyl)methanol

Using methyl 3-chloro-4,5-dicyclopropyl-2-isopropoxybenzoate, the title compound was obtained in the similar manner as in Step F of Example 238.

$^1$H NMR (300 MHz, $CDCl_3$) δ 0.63-0.69 (2H, m), 0.70-0.77 (2H, m), 0.93-1.01 (2H, m), 1.08-1.16 (2H, m), 1.32 (6H, d, J=6.1 Hz), 1.82 (1H, tt, J=8.4, 5.8 Hz), 2.22 (1H, t, J=6.1 Hz), 2.26-2.37 (1H, m), 4.46-4.60 (1H, m), 4.65 (2H, d, J=5.9 Hz), 6.75 (1H, s).

I) 3-Chloro-4,5-dicyclopropyl-2-isopropoxybenzaldehyde

Using (3-chloro-4,5-dicyclopropyl-2-isopropoxyphenyl)methanol, the title compound was obtained in the similar manner as in Step G of Example 238.

$^1$H NMR (300 MHz, DMSO-$d_6$) δ 0.65-0.76 (4H, m), 0.98-1.06 (2H, m), 1.14-1.22 (2H, m), 1.29 (6H, d, J=6.1 Hz), 1.88-2.00 (1H, m), 2.29-2.40 (1H, m), 4.34-4.49 (1H, m), 7.18 (1H, s), 10.19 (1H, s).

J) Ethyl 1-(2-(3-chloro-4,5-dicyclopropyl-2-isopropoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 3-chloro-4,5-dicyclopropyl-2-isopropoxybenzaldehyde, the title compound was obtained in the similar manner as in Step G of Example 1.

$^1$H NMR (300 MHz, $CDCl_3$) δ 0.60-0.68 (2H, m), 0.69-0.76 (2H, m), 0.92-1.00 (2H, m), 1.05-1.14 (2H, m), 1.20 (3H, s), 1.23-1.31 (9H, m), 1.38-1.52 (2H, m), 1.74-1.85 (1H, m), 2.10 (2H, d, J=13.5 Hz), 2.24-2.36 (1H, m), 2.90-3.02 (2H, m), 3.22 (2H, s), 3.29-3.42 (4H, m), 3.44-3.50 (2H, m), 3.64 (2H, s), 4.16 (2H, q, J=7.1 Hz), 4.36-4.50 (1H, m), 6.72 (1H, s).

K) 1-(2-(3-Chloro-4,5-dicyclopropyl-2-isopropoxybenzyl)-5-oxa-2,6-diazaspiro[3.4]oct-6-en-7-yl)-4-methylpiperidine-4-carboxylic acid Using ethyl 1-(2-(3-chloro-4,5-dicyclopropyl-2-isopropoxybenzyl)-5-oxa-2,6-diazaspiro[3.4]oct-6-en-7-yl)-4- methylpiperidine-4-carboxylate, the title compound was obtained in the similar manner as in Example 2.

Example 254

1-(2-(3-Chloro-4,5-dicyclopropyl-2-methoxybenzyl)-5-oxa-2,6-diazaspiro[3.4]oct-6-en-7-yl)-4-methylpiperidine-4-carboxylic acid A) Methyl 3-chloro-4,5-dicyclopropyl-2-methoxybenzoate Using methyl 3-chloro-4,5-dicyclopropyl-2-hydroxybenzoate and iodomethane, the title compound was obtained in the similar manner as in Step E of Example 238.

$^1$H NMR (300 MHz, $CDCl_3$) δ 0.65-0.72 (2H, m), 0.74-0.82 (2H, m), 0.96-1.04 (2H, m), 1.12-1.21 (2H, m), 1.80-1.92 (1H, m), 2.26-2.37 (1H, m), 3.88 (3H, s), 3.90 (3H, s), 7.22 (1H, s).

B) (3-Chloro-4,5-dicyclopropyl-2-methoxyphenyl)methanol

Using methyl 3-chloro-4,5-dicyclopropyl-2-methoxybenzoate, the title compound was obtained in the similar manner as in Step F of Example 238.

$^1$H NMR (300 MHz, $CDCl_3$) δ 0.62-0.69 (2H, m), 0.71-0.78 (2H, m), 0.94-1.02 (2H, m), 1.08-1.17 (2H, m), 1.76-1.88 (1H, m), 2.06 (1H, t, J=6.1 Hz), 2.27-2.38 (1H, m), 3.85 (3H, s), 4.65 (2H, d, J=5.9 Hz), 6.76 (1H, s).

C) 3-Chloro-4,5-dicyclopropyl-2-methoxybenzaldehyde

Using (3-chloro-4,5-dicyclopropyl-2-methoxyphenyl)methanol, the title compound was obtained in the similar manner as in Step G of Example 238.

$^1$H NMR (300 MHz, DMSO-$d_6$) δ 0.65-0.77 (4H, m), 0.98-1.06 (2H, m), 1.14-1.23 (2H, m), 1.88-2.00 (1H, m), 2.29-2.41 (1H, m), 3.88 (3H, s), 7.19 (1H, s), 10.17 (1H, s).

D) Ethyl 1-(2-(3-chloro-4,5-dicyclopropyl-2-methoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 3-chloro-4,5-dicyclopropyl-2-methoxybenzaldehyde, the title compound was obtained in the similar manner as in Step G of Example 1.

$^1$H NMR (400 MHz, $CDCl_3$) δ 0.60-0.66 (2H, m), 0.71-0.77 (2H, m), 0.93-0.99 (2H, m), 1.07-1.14 (2H, m), 1.20 (3H, s), 1.23-1.28 (3H, m), 1.40-1.50 (2H, m), 1.75-1.84 (1H, m), 2.10 (2H, d, J=13.6 Hz), 2.25-2.36 (1H, m), 2.91-3.00 (2H, m), 3.22 (2H, s), 3.30-3.41 (4H, m), 3.46-3.51 (2H, m), 3.63 (2H, s), 3.79 (3H, s), 4.16 (2H, q, J=7.1 Hz), 6.70 (1H, s).

E) 1-(2-(3-Chloro-4,5-dicyclopropyl-2-methoxybenzyl)-5-oxa-2,6-diazaspiro[3.4]oct-6-en-7-yl)-4-methylpiperidine-4-carboxylic acid Using ethyl 1-(2-(3-chloro-4,5-dicyclopropyl-2-methoxybenzyl)-5-oxa-2,6-diazaspiro[3.4]oct-6-en-7-yl)-4-methylpiperidine-4-carboxylate, the title compound was obtained in the similar manner as in Example 2.

Example 255

1-(2-(3-Chloro-4,5-dicyclopropyl-2-ethoxybenzyl)-5-oxa-2,6-diazaspiro[3.4]oct-6-en-7-yl)-4-methylpiperidine-4-carboxylic acid A) Methyl 3-chloro-4,5-dicyclopropyl-2-ethoxybenzoate Using methyl 3-chloro-4,5-dicyclopropyl-2-hydroxybenzoate and iodoethane, the title compound was obtained in the similar manner as in Step E of Example 238.

$^1$H NMR (400 MHz, $CDCl_3$) δ 0.65-0.71 (2H, m), 0.74-0.80 (2H, m), 0.96-1.03 (2H, m), 1.12-1.19 (2H, m), 1.43 (3H, t, J=7.0 Hz), 1.81-1.90 (1H, m), 2.26-2.35 (1H, m), 3.89 (3H, s), 4.04 (2H, q, J=6.9 Hz), 7.21 (1H, s).

B) (3-Chloro-4,5-dicyclopropyl-2-ethoxyphenyl)methanol

Using methyl 3-chloro-4,5-dicyclopropyl-2-ethoxybenzoate, the title compound was obtained in the similar manner as in Step F of Example 238.

$^1$H NMR (300 MHz, $CDCl_3$) δ 0.62-0.69 (2H, m), 0.71-0.77 (2H, m), 0.93-1.01 (2H, m), 1.08-1.16 (2H, m), 1.44 (3H, t, J=7.0 Hz), 1.76-1.88 (1H, m), 2.10 (1H, t, J=6.2 Hz), 2.26-2.39 (1H, m), 4.03 (2H, q, J=7.0 Hz), 4.64 (2H, d, J=5.9 Hz), 6.75 (1H, s).

C) 3-Chloro-4,5-dicyclopropyl-2-ethoxybenzaldehyde

Using (3-chloro-4,5-dicyclopropyl-2-ethoxyphenyl)methanol, the title compound was obtained in the similar manner as in Step G of Example 238.

$^1$H NMR (400 MHz, $CDCl_3$) δ 0.68-0.75 (2H, m), 0.77-0.83 (2H, m), 0.98-1.05 (2H, m), 1.16-1.23 (2H, m), 1.46 (3H, t, J=7.0 Hz), 1.83-1.93 (1H, m), 2.28-2.37 (1H, m), 4.11 (2H, q, J=7.0 Hz), 7.26 (1H, s), 10.29 (1H, s).

D) Ethyl 1-(2-(3-chloro-4,5-dicyclopropyl-2-ethoxybenzyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 3-chloro-4,5-dicyclopropyl-2-ethoxybenzaldehyde, the title compound was obtained in the similar manner as in Step G of Example 1.

$^1$H NMR (300 MHz, $CDCl_3$) δ 0.60-0.67 (2H, m), 0.70-0.77 (2H, m), 0.92-0.99 (2H, m), 1.05-1.14 (2H, m), 1.20 (3H, s), 1.26 (3H, t, J=7.1 Hz), 1.38-1.51 (5H, m), 1.74-1.86 (1H, m), 2.06-2.15 (2H, m), 2.24-2.36 (1H, m), 2.90-3.02 (2H, m), 3.22 (2H, s), 3.29-3.43 (4H, m), 3.45-3.52 (2H, m), 3.62 (2H, s), 3.94 (2H, q, J=7.0 Hz), 4.16 (2H, q, J=7.1 Hz), 6.70 (1H, s).

E) 1-(2-(3-Chloro-4,5-dicyclopropyl-2-ethoxybenzyl)-5-oxa-2,6-diazaspiro[3.4]oct-6-en-7-yl)-4-methylpiperidine-4-carboxylic acid Using ethyl 1-(2-(3-chloro-4,5-dicyclopropyl-2-ethoxybenzyl)-5-oxa-2,6-diazaspiro[3.4]oct-6-en-7-yl)-4-methylpiperidine-4-carboxylate, the title compound was obtained in the similar manner as in Example 2.

Example 256

1-(2-(4,5-Dicyclopropyl-3-fluoro-2-isopropoxybenzyl)-5-oxa-2,6-diazaspiro[3.4]oct-6-en-7-yl)-4-methylpiperidine-4-carboxylic acid A) 4-Cyclopropyl-2,3-difluorobenzaldehyde Cyclopropyl boronic acid (1.77 g), 2 M aqueous sodium carbonate solution (21 mL), tris(dibenzylideneacetone)dipalladium(0) (882 mg) and dicyclohexyl(2',6'-dimethoxybiphenyl-2-yl)phosphine (847 mg) were added to a solution of 4-bromo-2,3-difluorobenzaldehyde (3.04 g) in toluene (70 mL) at room temperature, and the resultant was stirred 15 hours at 100° C. in an argon atmosphere. Water was added to the reaction mixture at room temperature, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.18 g).

$^1$H NMR (300 MHz, $CDCl_3$) δ 0.82-0.90 (2H, m), 1.11-1.20 (2H, m), 2.14-2.25 (1H, m), 6.70 (1H, ddd, J=8.2, 6.3, 1.7 Hz), 7.51 (1H, ddd, J=8.3, 6.3, 1.8 Hz), 10.27 (1H, d, J=0.6 Hz).

B) 4-Cyclopropyl-3-fluoro-2-methoxybenzaldehyde

Sodium methoxide (28% methanol solution, 3.43 g) was added to a solution of 4-cyclopropyl-2,3-difluorobenzaldehyde (2.16 g) in methanol (100 mL) at room temperature, and the resultant was stirred for 15 hours at 70° C. in a nitrogen atmosphere. Water was added to the reaction mixture, and methanol was distilled off under reduced pressure. Extraction was performed on the residue using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (2.11 g).

$^1$H NMR (400 MHz, $CDCl_3$) δ 0.79-0.84 (2H, m), 1.07-1.14 (2H, m), 2.13-2.22 (1H, m), 4.08 (3H, d, J=2.4 Hz), 6.59 (1H, dd, J=8.2, 6.4 Hz), 7.50 (1H, dd, J=8.3, 1.4 Hz), 10.31 (1H, d, J=0.6 Hz).

C) 4-Cyclopropyl-3-fluoro-2-hydroxybenzaldehyde

Boron tribromide (1M dichloromethane solution, 18.5 mL) was added to a solution of 4-cyclopropyl-3-fluoro-2-methoxybenzaldehyde (1.79 g) in dichloromethane (70 mL) at −78° C., the resultant was stirred for 2 hours at the same temperature in a nitrogen atmosphere, and stirred for 1 hour at 0° C. An aqueous saturated sodium hydrogen carbonate solution was added to the reaction mixture at 0° C., and dichloromethane was distilled off under reduced pressure. Extraction was performed on the obtained residue using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.50 g).

$^1$H NMR (300 MHz, $CDCl_3$) δ 0.81-0.89 (2H, m), 1.09-1.18 (2H, m), 2.17-2.28 (1H, m), 6.44 (1H, dd, J=8.2, 5.9 Hz), 7.23 (1H, dd, J=82, 1.3 Hz), 9.82 (1H, d, J=1.9 Hz), 11.02 (1H, s).

D) 5-Bromo-4-cyclopropyl-3-fluoro-2-hydroxybenzaldehyde 1,3-Dibromo-1,3,5-triazine-2,4,6-trione (1.43 g) was added to a solution of 4-cyclopropyl-3-fluoro-2-hydroxybenzaldehyde (1.50 g) in DMF (50 mL) at room temperature, the resultant was stirred for 3 hours at the same temperature in a nitrogen atmosphere. An aqueous sodium thiosulfate solution was added to the reaction mixture at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.73 g).

$^1$H NMR (400 MHz, $CDCl_3$) δ 1.04-1.18 (4H, m), 1.89-1.98 (1H, m), 7.55 (1H, d, J=1.9 Hz), 9.80 (1H, d, J=1.9 Hz), 10.81 (1H, s).

E) 4,5-Dicyclopropyl-3-fluoro-2-hydroxybenzaldehyde

Cyclopropyl boronic acid (1.72 g), 2 M aqueous sodium carbonate solution (13 mL), tris(dibenzylideneacetone)dipalladium(0) (611 mg) and dicyclohexyl(2',6'-dimethoxybiphenyl-2-yl)phosphine (548 mg) were added to a solution of 5-bromo-4-cyclopropyl-3-fluoro-2-hydroxybenzaldehyde (1.73 g) in toluene (50 mL) at room temperature, and the resultant was stirred 15 hours at 100° C. in an argon atmosphere. Water was added to the reaction mixture at room temperature, the resultant was filtered using celite, and then the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.31 g).

$^1$H NMR (300 MHz, $CDCl_3$) δ 0.62-0.69 (2H, m), 0.94-1.02 (2H, m), 1.04-1.12 (4H, m), 1.97-2.17 (2H, m), 6.97 (1H, dd, J=1.4, 0.8 Hz), 9.79 (1H, d, J=1.9 Hz), 10.78 (1H, s).

F) 4,5-Dicyclopropyl-3-fluoro-2-isopropoxybenzaldehyde

2-Iodopropane (862 mg) was added to a mixture of 4,5-dicyclopropyl-3-fluoro-2-hydroxybenzaldehyde (744 mg), potassium carbonate (934 mg) and DMF (20 mL) at room temperature, and the resultant was stirred for 2 hours at 60° C. in a nitrogen atmosphere. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (865 mg).

$^1$H NMR (300 MHz, $CDCl_3$) δ 0.67-0.75 (2H, m), 0.90-1.02 (4H, m), 1.03-1.12 (2H, m), 1.34 (6H, dd, J=6.1, 0.8 Hz), 1.88-2.00 (1H, m), 2.11-2.23 (1H, m), 4.41-4.56 (1H, m), 7.19 (1H, d, J=1.0 Hz), 10.30 (1H, s).

G) Ethyl 1-(2-(4,5-dicyclopropyl-3-fluoro-2-isopropoxybenzyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (384 mg) and formic acid (8 mL) was stirred for 30 minutes at 70° C. in a nitrogen atmosphere, the solvent was distilled off under reduced pressure. Sodium triacetoxyborohydride (426 mg) was added to a mixture of the obtained residue, 4,5-dicyclopropyl-3-fluoro-2-isopropoxybenzaldehyde (290 mg) and THF (10 mL), the resultant was stirred for 15 hours at room temperature in a nitrogen atmosphere. After an aqueous saturated sodium hydrogen carbonate solution was added to the reaction mixture, extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (453 mg).

$^1$H NMR (300 MHz, $CDCl_3$) δ 0.60-0.67 (2H, m), 0.76-0.83 (2H, m), 0.90-1.01 (4H, m), 1.20 (3H, s), 1.23-1.31 (9H, m), 1.38-1.51 (2H, m), 1.75-1.87 (1H, m), 2.04-2.24 (3H, m), 2.89-3.02 (2H, m), 3.22 (2H, s), 3.30-3.42 (4H, m), 3.45-3.52 (2H, m), 3.61 (2H, s), 4.16 (2H, q, J=7.2 Hz), 4.29-4.39 (1H, m), 6.58 (1H, d, J=1.0 Hz).

H) 1-(2-(4,5-Dicyclopropyl-3-fluoro-2-isopropoxybenzyl)-5-oxa-2,6-diazaspiro[3.4]oct-6-en-7-yl)-4-methylpiperidine-4-carboxylic acid 2 M aqueous sodium hydroxide solution (2.5 mL) was added to a solution of ethyl 1-(2-(4,5-dicyclopropyl-3-fluoro-2-isopropoxybenzyl)-5-oxa-2,6-diazaspiro[3.4]oct-6-en-7-yl)-4-methylpiperidine-4-carboxylate (435 mg) in ethanol (10 mL) at room temperature. After the reaction mixture was stirred for 3 hours at 80° C. in a nitrogen atmosphere, the solvent was distilled off under reduced pressure. Water was added to the residue, the resultant was neutralized with 2 M hydrochloric acid. The obtained solid was collected by filtration, and it was dissolved in ethanol. After the obtained solution was filtered, the filtrate was concentrated under reduced pressure. The obtained residue was crystallized (hexane/ethyl acetate), and further recrystallized (hexane/ethanol), thereby obtaining the title compound (330 mg).

$^1$H NMR (300 MHz, DMSO-$d_6$) δ 0.56-0.64 (2H, m), 0.66-0.73 (2H, m), 0.90-1.01 (4H, m), 1.13 (3H, s), 1.21 (6H, d, J=5.6 Hz), 1.36 (2H, ddd, J=13.6, 10.0, 3.9 Hz), 1.75-1.96 (3H, m), 2.13-2.25 (1H, m), 2.81-2.94 (2H, m), 3.10 (2H, d, J=8.5 Hz), 3.24-3.33 (4, m), 3.38 (2H, d, J=8.5 Hz), 3.50 (2H, s), 4.16-4.31 (1H, m), 6.60 (1H, s).

Example 257

1-(2-(4,5-Dicyclopropyl-2-ethoxy-3-fluorobenzyl)-5-oxa-2,6-diaza spiro[3.4]oct-6-en-7-yl)-4-methylpiperidine-4-carboxylic acid A) 4,5-Dicyclopropyl-2-ethoxy-3-fluorobenzaldehyde 2-Iodoethane (760 mg) was added to a mixture of 4,5-dicyclopropyl-3-fluoro-2-hydroxybenzaldehyde (715 mg), potassium carbonate (898 mg) and DMF (20 mL), and the resultant was stirred for 3 hours at 60° C. in a nitrogen atmosphere. Water was added to the reaction mixture, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (782 mg).

$^1$H NMR (300 MHz, $CDCl_3$) δ 0.67-0.74 (2H, m), 0.91-1.02 (4H, m), 1.04-1.12 (2H, m), 1.40 (3H, td, J=7.0, 0.7 Hz), 1.88-2.00 (1H, m), 2.11-2.22 (1H, m), 4.20 (2H, qd, J=7.1, 1.2 Hz), 7.18 (1H, d, J=1.0 Hz), 10.31 (1H, s).

B) Ethyl 1-(2-(4,5-dicyclopropyl-2-ethoxy-3-fluorobenzyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (355 mg) and formic acid (8 mL) was stirred for 30 minutes at 70° C. in a nitrogen atmosphere, the solvent was distilled off under reduced pressure. Sodium triacetoxyborohydride (395 mg) was added to a mixture of the obtained residue, 4,5-dicyclopropyl-2-ethoxy-3-fluorobenzaldehyde (254 mg) and THF (10 mL), the resultant was stirred for 15 hours at room temperature in a nitrogen atmosphere. After an aqueous saturated sodium hydrogen carbonate solution was added to the reaction mixture, extraction thereof was performed using ethyl acetate. The obtained organic layer was sequentially washed with water and a saturated saline solution, was dried over anhydrous magnesium sulfate, and then the solvent was distilled off under reduced pressure. The obtained residue was purified by a silica gel column chromatography (hexane/ethyl acetate), thereby obtaining the title compound (402 mg).

$^1$H NMR (300 MHz, $CDCl_3$) δ 0.60-0.67 (2H, m), 0.77-0.84 (2H, m), 0.88-1.01 (4H, m), 1.20 (3H, s), 1.26 (3H, t, J=7.1 Hz), 1.32-1.39 (3H, m), 1.39-1.51 (2H, m), 1.75-1.88 (1H, m), 2.04-2.24 (3H, m), 2.89-3.03 (2H, m), 3.22 (2H, s), 3.29-3.42 (4H, m), 3.45-3.52 (2H, m), 3.60 (2H, s), 4.02 (2H, qd, J=7.1, 0.8 Hz), 4.16 (2H, q, J=7.1 Hz), 6.57 (1H, d, J=1.1 Hz).

C) 1-(2-(4,5-Dicyclopropyl-2-ethoxy-3-fluorobenzyl)-5-oxa-2,6-diazaspiro[3.4]oct-6-en-7-yl)-4-methylpiperidine-4-carboxylic acid 2 M aqueous sodium hydroxide solution (2.5 mL) was added to a solution of ethyl 1-(2-(4,5-dicyclopropyl-2-ethoxy-3-fluorobenzyl)-5-oxa-2,6-diazaspiro[3.4]oct-6-en-7-yl)-4-methylpiperidine-4-carboxylate (376 mg) in ethanol (8 mL) at room temperature. After the reaction mixture was stirred for 4 hours at 80° C. in a nitrogen atmosphere, the solvent was distilled off under reduced pressure. Water was added to the residue, the resultant was neutralized with 2 M hydrochloric acid. The obtained solid was collected by filtration, and it was dissolved in ethanol. After the resultant solution was filtered, the filtrate was concentrated under reduced pressure. The obtained residue was crystallized (hexane/ethyl acetate), and further recrystallized (hexane/ethanol), thereby obtaining the title compound (262 mg).

$^1$H NMR (300 MHz, DMSO-$d_6$) δ 0.59-0.66 (2H, m), 0.67-0.75 (2H, m), 0.91-1.03 (4H, m), 1.14 (3H, s), 1.25-

1.43 (5H, m), 1.77-1.96 (3H, m), 2.14-2.25 (1H, m), 2.82-2.97 (2H, m), 3.22-3.40 (8H, m), 3.64 (2H, brs), 3.97 (2H, q, J=7.0 Hz), 6.66 (1H, brs).

Example 258

1-(2-((2-Chloro-6-cyclopropyl-2',4'-difluoro-3-methoxybiphenyl-4-yl)methyl)-5-oxa-2,6-diazaspiro[3.4]oct-6-en-7-yl)-4-methylpiperidine-4-carboxylic acid

A) Methyl 3-(benzyloxy)-2',4'-difluorobiphenyl-4-carboxylate

A mixture of methyl 2-hydroxy-4-iodobenzoate (22.0 g), (2,4-difluorophenyl)boronic acid (25.0 g), dicyclohexyl (2',6'-dimethoxybiphenyl-2-yl)phosphine (4.87 g), 2 M aqueous sodium carbonate solution (119 mL), tris(dibenzylideneacetone)dipalladium(0) (5.07 g) and toluene (150 mL) was stirred 2 hours at 100° C. The reaction mixture was poured into water at room temperature, it was filtered using celite, and then the filtrate was extracted using ethyl acetate. The obtained organic layer was washed with a saturated saline solution, it was passed through a short column of a silica gel (NH), and the solvent was distilled off under reduced pressure. benzylbromide (10.4 mL) was added to a mixture of the obtained residue, potassium carbonate (21.9 g) and DMF (100 mL), the resultant was stirred for 1 hour at 70° C. in a nitrogen atmosphere. Water was added to the reaction mixture at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (30.5 g).

$^1$H NMR (300 MHz, $CDCl_3$) δ 3.92 (3H, s), 5.22 (2H, s), 6.85-7.02 (2H, m), 7.09-7.19 (2H, m), 7.28-7.45 (3H, m), 7.47-7.56 (2H, m), 7.62 (1H, dd, J=6.8, 2.9 Hz), 7.90 (1H, d, J=8.0 Hz).

B) Methyl 5-(benzyloxy)-2-bromo-2',4'-difluorobiphenyl-4-carboxylate 1,3-Dibromo-1,3,5-triazine-2,4,6-trione (15.9 g) was added to a solution of methyl 3-(benzyloxy)-2',4'-difluorobiphenyl-4-carboxylate (28.0 g) in DMF (150 mL) at room temperature, the resultant was stirred overnight at the same temperature. Water was added to the reaction mixture at room temperature, and extraction thereof was performed using ethyl acetate. The obtained organic layer was sequentially washed with water and a saturated saline solution, dried over anhydrous magnesium sulfate, and then the solvent was distilled of under reduced pressure. The obtained residue was purified by a silica gel column chromatography (hexane/ethyl acetate), thereby obtaining the title compound (34.0 g).

$^1$H NMR (300 MHz, $CDCl_3$) δ 3.92 (3H, s), 5.15 (2H, s), 6.87-7.01 (3H, m), 7.10-7.55 (6H, m), 8.11 (1H, s).

C) Methyl 5-(benzyloxy)-2-cyclopropyl-2',4'-difluorobiphenyl-4-carboxylate

A mixture of methyl 5-(benzyloxy)-2-bromo-2',4'-difluorobiphenyl-4-carboxylate (34.3 g), cyclopropylboronic acid (17.0 g), dicyclohexyl (2',6'-dimethoxybiphenyl-2-yl)phosphine (4.87 g), 2 M aqueous sodium carbonate solution (119 mL), tris(dibenzylideneacetone)dipalladium(0) (5.07 g) and toluene (150 mL) was stirred overnight at 100° C. The reaction mixture was poured into water at room temperature, and extraction thereof was performed using ethyl acetate. The obtained organic layer was washed with a saturated saline solution, it was passed through a short column of a silica gel (NH), and the solvent was distilled off under reduced pressure. The obtained residue was purified by a silica gel column chromatography (hexane/ethyl acetate), thereby obtaining the title compound (20.3 g).

$^1$H NMR (300 MHz, $CDCl_3$) δ 0.54-0.63 (2H, m), 0.70-0.80 (2H, m), 1.59-1.72 (1H, m), 3.87-3.93 (3H, m), 5.14 (2H, s), 6.83-7.01 (3H, m), 7.18-7.41 (4H, m), 7.44-7.51 (3H, m).

D) Methyl 2-cyclopropyl-2',4'-difluoro-5-hydroxybiphenyl-4-carboxylate

A mixture of methyl 5-(benzyloxy)-2-cyclopropyl-2',4'-difluorobiphenyl-4-carboxylate (20.3 g), 10% palladium on carbon (55% water content, 10 g) and THF (100 mL) was stirred for 1 hour at room temperature in a hydrogen atmosphere. After the catalyst was removed by filtration, the filtrate was concentrated under reduced pressure. The obtained residue was purified by a silica gel column chromatography (hexane/ethyl acetate), thereby obtaining the title compound (15.0 g).

$^1$H NMR (300 MHz, $CDCl_3$) δ 0.48-0.58 (2H, m), 0.65-0.78 (2H, m), 1.57-1.70 (1H, m), 3.96 (3H, s), 6.85 (1H, s), 6.86-7.00 (2H, m), 7.19-7.34 (1H, m), 7.50 (1H, s), 10.58 (1H, s).

E) Methyl 2-chloro-6-cyclopropyl-2',4'-difluoro-3-hydroxybiphenyl-4-carboxylate N-chlorosuccinimide (1.65 g) was added to a solution of methyl 2-cyclopropyl-2',4'-difluoro-5-hydroxybiphenyl-4-carboxylate (3.13 g) in DMF (40 mL) at room temperature, the resultant was stirred for 3 hours at the same temperature in a nitrogen atmosphere. N-chlorosuccinimide (549 mg) was further added thereto, and the resultant was stirred for 16 hours at the same temperature in a nitrogen atmosphere. Water was added to the reaction mixture at room temperature, and the resultant was stirred for 1 hour at 0° C. The precipitated crystals were collected by filtration, and the obtained crystals were dissolved in ethyl acetate. It was dried over anhydrous magnesium sulfate, and the solvent was distilled off under reduced pressure, thereby obtaining the title compound (3.17 g).

$^1$H NMR (300 MHz, $CDCl_3$) δ 0.48-0.72 (4H, m), 1.43-1.53 (1H, m), 3.99 (3H, s), 6.90-7.04 (2H, m), 7.14-7.25 (1H, m), 7.46 (1H, d, J=0.7 Hz), 11.26 (1H, s).

F) Methyl 2-chloro-6-cyclopropyl-2',4'-difluoro-3-methoxybiphenyl-4-carboxylate Iodomethane (1.04 g) was added to a mixture of methyl 2-chloro-6-cyclopropyl-2',4'-difluoro-3-hydroxybiphenyl-4-carboxylate (1.66 g), potassium carbonate (1.36 g) and DMF (30 mL) at room temperature, and the resultant was stirred for 3 hours at 60° C. in a nitrogen atmosphere. Water was added to the reaction mixture at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.20 g).

$^1$H NMR (300 MHz, $CDCl_3$) δ 0.56-0.78 (4H, m), 1.45-1.55 (1H, m), 3.93 (3H, s), 3.94 (3H, s), 6.90-7.04 (2H, m), 7.14-7.25 (1H, m), 7.33 (1H, s).

G) (2-Chloro-6-cyclopropyl-2',4'-difluoro-3-methoxybiphenyl-4-yl)methanol

Diisobutylaluminium hydride (1.5 M toluene solution, 6 mL) was added to a solution of methyl 2-chloro-6-cyclopropyl-2',4'-difluoro-3-methoxybiphenyl-4-carboxylate (1.17 g) in THF (40 mL) at 0° C., and the resultant was stirred for 1 hour at room temperature in a nitrogen atmosphere. Diisobutylaluminium hydride (1.5 M toluene solution, 2 mL) was added to the reaction mixture, and the resultant was stirred for 30 minutes at room temperature in a nitrogen atmosphere. Diisobutylaluminium hydride (1.5 M toluene solution, 2 mL) was further added thereto, and the resultant was stirred for 30 minutes at room temperature in a nitrogen atmosphere. Sodium sulfate decahydrate was added to the reaction mixture at 0° C., the resultant was filtered using celite, and then the filtrate was concentrated under reduced pressure. The obtained residue was purified by a silica gel column chromatography (hexane/ethyl acetate), thereby obtaining the title compound (1.07 g).

$^1$H NMR (300 MHz, $CDCl_3$) δ 0.54-0.76 (4H, m), 1.44-1.56 (1H, m), 2.07-2.16 (1H, m), 3.90 (3H, s), 4.67-4.82 (2H, m), 6.89-7.02 (3H, m), 7.15-7.24 (1H, m).

H) 2-Chloro-6-cyclopropyl-2',4'-difluoro-3-methoxybiphenyl-4-carbaldehyde

Manganese dioxide (2.29 g) was added to a solution of (2-chloro-6-cyclopropyl-2',4'-difluoro-3-methoxybiphenyl-4-yl)methanol (1.07 g) in toluene (30 mL), and the resultant was stirred for 1 hour at 80° C. in a nitrogen atmosphere. After the reaction mixture was filtered using celite, the filtrate was concentrated under reduced pressure. The obtained residue was purified by a silica gel column chromatography (hexane/ethyl acetate), thereby obtaining the title compound (978 mg).

$^1$H NMR (300 MHz, $CDCl_3$) δ 0.60-0.81 (4H, m), 1.45-1.56 (1H, m), 4.00 (3H, s), 6.93-7.06 (2H, m), 7.16-7.26 (1H, m), 7.40 (1H, s), 10.38 (1H, s).

I) Ethyl 1-(2-((2-chloro-6-cyclopropyl-2',4'-difluoro-3-methoxybiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (329 mg) and formic acid (8 mL) was stirred for 30 minutes at 70° C. in a nitrogen atmosphere, the solvent was distilled off under reduced pressure. Sodium triacetoxyborohydride (365 mg) was added to a mixture of the obtained residue, 2-chloro-6-cyclopropyl-2',4'-difluoro-3-methoxybiphenyl-4-carbaldehyde (306 mg) and THF (8 mL), and the resultant was stirred for 16 hours at room temperature in a nitrogen atmosphere. After an aqueous saturated sodium hydrogen carbonate solution was added to the reaction mixture, extraction thereof was performed using ethyl acetate. The obtained organic layer was sequentially washed with water and a saturated saline solution, was dried over anhydrous magnesium sulfate, and then the solvent was distilled off under reduced pressure. The obtained residue was purified by a silica gel column chromatography (hexane/ethyl acetate), thereby obtaining the title compound (383 mg).

$^1$H NMR (300 MHz, $CDCl_3$) δ 0.50-0.66 (2H, m), 0.67-0.74 (2H, m), 1.21 (3H, s), 1.26 (3H, t, J=7.1 Hz), 1.40-1.55 (3H, m), 2.11 (2H, d, J=13.6 Hz), 2.90-3.04 (2H, m), 3.25 (2H, s), 3.34-3.43 (4H, m), 3.52-3.59 (2H, m), 3.71 (2H, d, J=1.0 Hz), 3.84 (3H, s), 4.17 (2H, q, J=7.1 Hz), 6.85 (1H, s), 6.88-7.01 (2H, m), 7.14-7.24 (1H, m).

J) 1-(2-((2-Chloro-6-cyclopropyl-2',4'-difluoro-3-methoxybiphenyl-4-yl)methyl)-5-oxa-2,6-diazaspiro[3.4]oct-6-en-7-yl)-4-methylpiperidine-4-carboxylic acid 2 M aqueous sodium hydroxide solution (2 mL) was added to a solution of ethyl 1-(2-((2-chloro-6-cyclopropyl-2',4'-fluoro-3-methoxybiphenyl-4-yl)methyl)-5-oxa-2,6-diazaspiro[3.4]oct-6-en-7-yl)-4-methylpiperidine-4-carboxylate (358 mg) in ethanol (8 mL) at room temperature. After the reaction mixture was stirred for 3 hours at 80° C. in a nitrogen atmosphere, the solvent was distilled off under reduced pressure. Water was added to the residue, the resultant was neutralized with 2 M hydrochloric acid. The obtained solid was collected by filtration, and it was dissolved in ethanol. After the reaction solution was filtered, the filtrate was concentrated under reduced pressure. The obtained residue was crystallized (hexane/ethyl acetate), and further recrystallized (hexane/ethanol), thereby obtaining the title compound (232 mg).

$^1$H NMR (300 MHz, DMSO-$d_6$) δ 0.52-0.62 (2H, m), 0.66-0.77 (2H, m), 1.14 (3H, s), 1.30-1.49 (3H, m), 1.91 (2H, d, J=13.6 Hz), 2.83-2.95 (2H, m), 3.16-3.36 (6H, m), 3.48 (2H, d, J=7.1 Hz), 3.65 (2H, brs), 3.77 (3H, s), 6.93 (1H, s), 7.16-7.25 (1H, m), 7.32-7.43 (2H, m).

Example 259

1-(2-((6-Cyclopropyl-2,2',4'-trifluoro-3-methoxybiphenyl-4-yl)methyl)-5-oxa-2,6-diazaspiro[3.4]oct-6-en-7-yl)-4-methylpiperidine-4-carboxylic acid A) 2,2',4'-Tetrafluorobiphenyl-4-carbaldehyde (2,4-Difluorophenyl)boronic acid (5.39 g), dicyclohexyl (2',6'-dimethoxybiphenyl-2-yl)phosphine (1.40 g), 2 M aqueous sodium carbonate solution (34.1 mL) and tris (dibenzylideneacetone)dipalladium(0) (1.46 g) were added to a solution of 4-bromo-2,3-difluorobenzaldehyde (5.03 g) in toluene (150 mL) at room temperature, and the resultant was stirred 16 hours at 100° C. in a nitrogen atmosphere. Water was added to the reaction mixture at room temperature, and the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (5.49 g).

$^1$H NMR (300 MHz, $CDCl_3$) δ 6.93-7.06 (2H, m), 7.23-7.30 (1H, m), 7.35-7.44 (1H, m), 7.70 (1H, ddd, J=8.1, 6.2, 1.8 Hz), 10.39 (1H, d, J=0.6 Hz).

B) 2,2',4'-Trifluoro-3-methoxybiphenyl-4-carbaldehyde

Sodium methoxide (28% methanol solution, 5.64 g) was added to a solution of 2,2',3,4'-tetrafluorobiphenyl-4-carbaldehyde (4.95 g) in methanol (120 mL) at room temperature, and the resultant was heated to reflux for 16 hours in a nitrogen atmosphere. After the reaction mixture was cooled to room temperature, the solvent was distilled off under reduced pressure. The obtained residue was diluted by ethyl acetate and water, and extraction thereof was performed using ethyl acetate. The obtained organic layer was sequentially washed with water and a saturated saline solution, dried over anhydrous magnesium sulfate, and then the solvent was distilled off under reduced pressure, thereby obtaining the title compound (5.14 g).

$^1$H NMR (300 MHz, $CDCl_3$) δ 4.13 (3H, d, J=2.6 Hz), 6.91-7.05 (2H, m), 7.09-7.16 (1H, m), 7.32-7.43 (1H, m), 7.67 (1H, dd, J=8.1, 1.4 Hz), 10.43 (1H, d, J=0.8 Hz).

C) 2,2",4"-Trifluoro-3-hydroxybiphenyl-4-carbaldehyde

48% Hydrobromic acid (22.0 mL) was added to a solution of 2,2",4"-trifluoro-3-methoxybiphenyl-4-carbaldehyde (5.14 g) in acetic acid (120 mL) at room temperature, and the resultant was stirred for 16 hour at 120° C. in a nitrogen atmosphere. After the reaction mixture was cooled to room temperature, the solvent was distilled off under reduced pressure. The obtained residue was neutralized with 1 M aqueous sodium hydroxide solution, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was passed through a short column of a silica gel (hexane/ethyl acetate), thereby obtaining the title compound (4.60 g).

$^1$H NMR (300 MHz, $CDCl_3$) δ 6.91-7.05 (3H, m), 7.34-7.46 (2H, m), 9.96 (1H, d, J=1.8 Hz), 11.07 (1H, s).

D) 6-Bromo-2,2',4'-trifluoro-3-hydroxybiphenyl-4-carbaldehyde 1,3-Dibromo-1,3,5-triazine-2,4,6-trione (2.25 g) was added to a solution of 2,2',4'-trifluoro-3-hydroxybiphenyl-4-carbaldehyde (3.29 g) in DMF (90 mL) at mom temperature, and the resultant was stirred for 3 hours at the same temperature in a nitrogen atmosphere. An aqueous saturated sodium thiosulfate solution was added to the reaction mixture at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was sequentially purified by a silica gel column chromatography (hexane/ethyl acetate) and a diol-supported silica gel column chromatography (hexane/ethyl acetate), thereby obtaining the title compound (3.15 g).

$^1$H NMR (300 MHz, $CDCl_3$) δ 6.93-7.06 (2H, m), 7.22-7.32 (1H, m), 7.71 (1H, d, J=1.9 Hz), 9.92 (1H, d, J=1.9 Hz), 10.90 (1H, brs).

E) 6-Bromo-2,2',4'-trifluoro-3-methoxybiphenyl-4-carbaldehyde

Iodomethane (907 mg) was added to a mixture of 6-bromo-2,2',4'-trifluoro-3-hydroxybiphenyl-4-carbaldehyde (1.41 g), potassium carbonate (1.18 g) and DMF (20 mL) at room temperature, and the resultant was stirred for 3 hours at 60° C. in a nitrogen atmosphere. Water was added to the reaction mixture at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.37 g).

$^1$H NMR (300 MHz, $CDCl_3$) δ 4.11 (3H, d, J=2.9 Hz), 6.92-7.07 (2H, m), 7.23-7.33 (1H, m), 7.93 (1H, d, J=1.9 Hz), 10.37 (1H, s).

F) 6-Cyclopropyl-2,2',4'-trifluoro-3-methoxybiphenyl-4-carbaldehyde

Cyclopropylboronic acid (1.01 g), dicyclohexyl (2',6'-dimethoxybiphenyl-2-yl)phosphine (323 mg), 2 M aqueous sodium carbonate solution (7.87 mL) and tris(dibenzylideneacetone)dipalladium(0) (360 mg) were added to a solution of 6-bromo-2,2',4'-trifluoro-3-methoxybiphenyl 1 carbaldehyde (1.36 g) in toluene (30 mL) at room temperature, and the resultant was stirred for 16 hours at 100° C. in an argon atmosphere. Water was added to the reaction mixture at room temperature, and the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (1.11 g).

$^1$H NMR (400 MHz, $CDCl_3$) δ 0.59-0.66 (1H, m), 0.69-0.75 (1H, m), 0.77-0.83 (2H, m), 1.53-1.61 (1H, m), 4.07 (3H, d, J=2.3 Hz), 6.93-7.05 (2H, m), 7.25 (1H, d, J=0.9 Hz), 7.27-7.35 (1H, m), 10.39 (1H, s).

G) Ethyl 1-(2-((6-cyclopropyl-2,2',4'-trifluoro-3-methoxybiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (322 mg) and formic acid (8 mL) was stirred for 30 minutes at 70° C. in a nitrogen atmosphere, the solvent was distilled off under reduced pressure. Sodium triacetoxyborohydride (358 mg) was added to a mixture of the obtained residue, 6-cyclopropyl-2,2',4'-trifluoro-3-methoxybiphenyl-4-carbaldehyde (285 mg) and THF (8 mL), and the resultant was stirred for 15 hours at mom temperature in a nitrogen atmosphere. After an aqueous saturated sodium hydrogen carbonate solution was added to the reaction mixture, extraction thereof was performed using ethyl acetate. The obtained organic layer was sequentially washed with water and a saturated saline solution, was dried over anhydrous magnesium sulfate, and then the solvent was distilled off under reduced pressure. The obtained residue was purified by a silica gel column chromatography (hexane/ethyl acetate), thereby obtaining the title compound (413 mg).

$^1$H NMR (300 MHz, $CDCl_3$) δ 0.50-0.68 (2H, m), 0.70-0.77 (2H, m), 1.21 (3H, s), 1.23-1.29 (3H, m), 1.40-1.60 (3H, m), 2.11 (2H, d, J=13.6 Hz), 2.90-3.03 (2H, m), 3.25 (2H, s), 3.33-3.43 (4H, m), 3.51-3.58 (2H, m), 3.62-3.74

(2H, m), 3.89 (3H, d, J=1.7 Hz), 4.16 (2H, q, J=7.1 Hz), 6.68 (1H, d, J=1.1 Hz), 6.89-7.01 (2H, m), 7.24-7.33 (1H, m).

H) 1-(2-((6-Cyclopropyl-2,2',4'-trifluoro-3-methoxy-biphenyl-4-yl)methyl)-5-oxa-2,6-diazaspiro[3.4]oct-6-en-7-yl)-4-methylpiperidine-4-carboxylic acid 2 M aqueous sodium hydroxide solution (2.5 mL) was added to a solution of ethyl 1-(2-((6-cyclopropyl-2,2',4'-trifluoro-3-methoxybiphenyl-4-yl)methyl)-5-oxa-2,6-diazaspiro[3.4]oct-6-en-7-yl)-4-methylpiperidine-4-carboxylate (389 mg) in ethanol (8 mL) at room temperature. After the reaction mixture was stirred for 4 hours at 80° C. in a nitrogen atmosphere, the solvent was distilled off under reduced pressure. Water was added to the residue, the resultant was neutralized with 2 M hydrochloric acid. The obtained solid was collected by filtration, and it was dissolved in ethanol. The obtained residue was crystallized (hexane/ethyl acetate), and further recrystallized (hexane/ethanol), thereby obtaining the title compound (283 mg).

$^1$H NMR (300 MHz, DMSO-$d_6$) δ 0.54-0.62 (2H, m), 0.71-0.79 (2H, m), 1.14 (3H, s), 1.31-1.43 (2H, m), 1.45-1.56 (1H, m), 1.91 (2H, d, J=13.7 Hz), 2.83-2.95 (2H, m), 3.15-3.22 (2H, m), 3.25-3.35 (4H, m), 3.46 (2H, d, J=8.5 Hz), 3.61 (2H, s), 3.80 (3H, d, J=1.1 Hz), 6.75 (1H, d, J=0.9 Hz), 7.16-7.26 (1H, m), 7.35-7.53 (2H, m).

Example 260

1-(2-((6-Cyclopropyl-3-ethoxy-2,2',4'-trifluorobiphenyl-4-yl)methyl)-5-oxa-2,6-diazaspiro[3.4]oct-6-en-7-yl)-4-methylpiperidine-4-carboxylic acid A) 6-Bromo-3-ethoxy-2,2',4'-trifluorobiphenyl-4-carbaldehyde Using 6-bromo-2,2',4'-trifluoro-3-hydroxybiphenyl-4-carbaldehyde and iodoethane, the title compound was obtained in the similar manner as in Step E of Example 259.

$^1$H NMR (300 MHz, $CDCl_3$) δ 1.45 (3H, td, J=7.0, 0.8 Hz), 4.29-4.39 (2H, m), 6.92-7.06 (2H, m), 7.23-7.32 (1H, m), 7.93 (1H, d, J=1.8 Hz), 10.39 (1H, s).

B) 6-Cyclopropyl-3-ethoxy-2,2',4'-trifluorobiphenyl-4-carbaldehyde

Using 6-bromo-3-ethoxy-2,2',4'-trifluorobiphenyl-4-carbaldehyde and cyclopropylboronic acid, the title compound was obtained in the similar manner as in Step F of Example 259.

$^1$H NMR (300 MHz, $CDCl_3$) δ 0.59-0.67 (1H, m), 0.67-0.76 (1H, m), 0.77-0.83 (2H, m), 1.43 (3H, td, J=7.1, 0.7 Hz), 1.50-1.63 (1H, m), 4.28 (2H, qt, J=7.0, 1.3 Hz), 6.92-7.05 (2H, m), 7.24-7.36 (2H, m), 10.41 (1H, s).

C) Ethyl 1-(2-((6-cyclopropyl-3-ethoxy-2,2',4'-trifluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 6-cyclopropyl-3-ethoxy-2,2',4'-trifluorobiphenyl-4-carbaldehyde, the title compound was obtained in the similar manner as in Step G of Example 259.

MS (ESI+): $[M+H]^+$ 586.3.

D) 1-(2-((6-Cyclopropyl-3-ethoxy-2,2',4'-trifluorobiphenyl-4-yl)methyl)-5-oxa-2,6-diazaspiro[3.4]oct-6-en-7-yl)-4-methylpiperidine-4-carboxylic acid Using ethyl 1-(2-((6-cyclopropyl-3-ethoxy-2,2',4'-trifluorobiphenyl-4-yl)methyl)-5-oxa-2,6-diazaspiro[3.4]oct-6-en-7-yl)-4-methylpiperidine-4-carboxylate, the title compound was obtained in the similar manner as in Step H of Example 259.

Example 261

1-(2-((6-Cyclopropyl-3-ethoxy-2,4'-difluorobiphenyl-4-yl)methyl)-5-oxa-2,6-diazaspiro[3.4]oct-6-en-7-yl)piperidine-4-carboxylic acid A) 1-Bromo-2-fluoro-3-(methoxymethoxy)benzene Chloro(methoxy)methane (11.8 mL) was added to a mixture of 3-bromo-2-fluorophenol (15.0 g), diisopropylethylamine (41.1 mL) and THF (150 mL), and the resultant was stirred overnight at room temperature in a nitrogen atmosphere. After the reaction mixture was filtered using celite, the filtrate was sequentially washed with 1 M hydrochloric acid and an aqueous saturated sodium hydrogen carbonate solution, and the obtained organic layer was distilled off under reduced pressure. The residue was passed through a short column of a silica gel (NH), thereby obtaining the title compound (17.9 g).

$^1$H NMR (300 MHz, DMSO-$d_6$) δ 3.41 (3H, s), 5.27 (2H, s), 7.06-7.14 (1H, m), 7.24-7.34 (2H, m).

B) 2,4'-Difluoro-3-(methoxymethoxy)biphenyl

A mixture of 1-bromo-2-fluoro-3-(methoxymethoxy)benzene (17.9 g), (4-fluorophenyl)boronic acid (16.0 g), tris(dibenzylideneacetone)dipalladium(0) (3.49 mg), 2 M aqueous sodium carbonate solution (114 mL), dicyclohexyl (2',6'-dimethoxybiphenyl-2-yl)phosphine (3.13 g) and toluene (180 mL) was stirred for 2 hours at 100° C. in a nitrogen atmosphere. The reaction mixture was cooled to room temperature, and it was filtered using celite. The organic layer was separated, and the solvent of the obtained organic layer was distilled off under reduced pressure. The residue was passed through a short column of a silica gel (NH), thereby obtaining the title compound (19.0 g).

$^1$H NMR (300 MHz, DMSO-$d_6$) δ 3.44 (3H, s), 5.28 (2H, s), 7.08-7.36 (5H, m), 7.54-7.63 (2H, m).

C) 2,4'-Difluoro-3-(methoxymethoxy)biphenyl-4-carbaldehyde n-Butyl lithium (1.6 M hexane solution, 52.2 mL) was added dropwise to a solution of 2,4'-difluoro-3-(methoxymethoxy)biphenyl (19.0 g) in THF (200 mL) at −78° C. in an argon atmosphere, and the resultant was stirred for 1 hour at the same temperature. DMF (12.9 mL) was added dropwise thereto, and the resultant was stirred for 3 hours in the range of −78° C. to 0° C. An aqueous saturated ammonium chloride solution was added to the reaction mixture, and extraction thereof was performed using ethyl acetate. The organic layer was washed with a saturated saline solution, dried over anhydrous magnesium sulfate, and then the solvent was distilled off under reduced pressure.

The obtained residue was washed with hexane (100 mL), thereby obtaining the title compound (16.4 g).

$^1H$ NMR (300 MHz, DMSO-$d_6$) δ 3.54 (3H, s), 5.31 (2H, d, J=0.8 Hz), 7.32-7.49 (3H, m), 7.62-7.73 (3H, m), 10.31 (1H, d, J=0.8 Hz).

D) 2,4'-Difluoro-3-hydroxybiphenyl-4-carbaldehyde

6 M hydrochloric acid (49 mL) was added to a solution of 2,4'-difluoro-3-(methoxymethoxy)biphenyl-4-carbaldehyde (16.4 g) in ethanol (160 mL), the resultant was stirred for 30 minutes at 50° C., and it was further stirred for 2 hours at room temperature. The precipitated solid was collected by filtration, it was sequentially washed with a mixed solution of ethanol-water (volume ratio 1:1, 50 mL) and water (50 mL), thereby obtaining the title compound (12.7 g).

$^1H$ NMR (300 MHz, DMSO-$d_6$) δ 7.10 (1H, dd, J=7.8, 6.8 Hz), 7.31-7.40 (2H, m), 7.56 (1H, dd, J=8.2, 1.4 Hz), 7.62-7.70 (2H, m), 10.29 (1H, s), 11.02 (1H, s).

E) 6-Bromo-2,4'-difluoro-3-hydroxybiphenyl-4-carbaldehyde 1,3-Dibromo-1,3,5-triazine-2,4,6-trione (8.87 g) was added to a solution of 2,4'-difluoro-3-hydroxybiphenyl-4-carbaldehyde (12.7 g) in DMF (75 mL) at room temperature, and the resultant was stirred for 30 minutes at the same temperature. Water (50 mL) was added dropwise to the reaction mixture, and the resultant was stirred for 1 hour at 0° C. The precipitated crystals were collected by filtration, washed with a mixed solution of DMF-water (volume ratio 1:1, 40 mL), and dried, thereby obtaining the title compound (17.6 g).

$^1H$ NMR (300 MHz, DMSO-$d_6$) δ 7.27-7.50 (4H, m), 7.77 (1H, d, J=1.8 Hz), 10.27 (1H, s), 11.15 (1H, s).

F) 6-Bromo-3-ethoxy-2,4'-difluorobiphenyl-4-carbaldehyde

A mixture of 6-bromo-2,4'-difluoro-3-hydroxybiphenyl 4 carbaldehyde (7.00 g), iodoethane (6.97 g), potassium carbonate (6.18 g) and acetone (50 mL) was stirred for 3 hours at 50° C. The reaction mixture was filtered using celite, and the filtrate was concentrated under reduced pressure. The obtained residue was purified by a silica gel column chromatography (hexane/ethyl acetate), thereby obtaining the title compound (3.35 g).

$^1H$ NMR (300 MHz, DMSO-$d_6$) δ 1.37 (3H, td, J=7.0, 0.6 Hz), 4.29 (2H, qd, J=7.0, 1.4 Hz), 7.33-7.42 (2H, m), 7.42-7.50 (2H, m), 7.83 (1H, d, J=1.9 Hz), 10.27 (1H, s).

G) 6-Cyclopropyl-3-ethoxy-2,4'-difluorobiphenyl-4-carbaldehyde

A mixture of 6-bromo-3-ethoxy-2,4'-difluorobiphenyl-4-carbaldehyde (3.30 g), cyclopropylboronic acid (1.66 g), tris(dibenzylideneacetone)dipalladium(0) (620 mg), 2 M aqueous sodium carbonate solution (14.5 mL), dicyclohexyl (2',6'-dimethoxybiphenyl-2-yl)phosphine (596 mg) and toluene (40 mL) was stirred overnight at 100° C. in a nitrogen atmosphere. The reaction mixture was cooled to room temperature, it was diluted by ethyl acetate and water and filtered using celite. The organic layer was separated, and the solvent of the obtained organic layer was distilled off under reduced pressure. The residue was purified by a silica gel chromatography (hexane/ethyl acetate), thereby obtaining the title compound (2.63 g).

$^1H$ NMR (300 MHz, DMSO-$d_6$) δ 0.61-0.69 (2H, m), 0.76-0.84 (2H, m), 1.35 (3H, td, J=7.0, 0.5 Hz), 1.53-1.64 (1H, m), 4.22 (2H, qd, J=7.0, 1.2 Hz), 7.15 (1H, d, J=1.2 Hz), 7.31-7.40 (2H, m), 7.43-7.51 (2H, m), 10.28 (1H, s).

H) Ethyl 1-(2-((6-cyclopropyl-3-ethoxy-2,4'-difluorobiphenyl-4-yl)methyl)-5-oxa-2,6-diazaspiro[3.4]oct-6-en-7-yl)piperidine-4-carboxylate After a mixture of tert-butyl 7-(4-(ethoxycarbonyl)piperidin-1-yl)-5-oxa-2,6-diazaspiro[3.4]oct-6-ene-2-carboxylate (375 mg) and formic acid (6 mL) was stirred for 30 minutes at 70° C. in a nitrogen atmosphere, the solvent was distilled off under reduced pressure. Sodium triacetoxyborohydride (432 mg) was added to a mixture of the obtained residue, 6-cyclopropyl-3-ethoxy-2,4'-difluorobiphenyl-4-carbaldehyde (339 mg) and THF (8 mL), and the resultant was stirred for 48 hours at room temperature in a nitrogen atmosphere. After an aqueous saturated sodium hydrogen carbonate solution was added to the reaction mixture, extraction thereof was performed using ethyl acetate. The obtained organic layer was sequentially washed with water and a saturated saline solution, was dried over anhydrous magnesium sulfate, and then the solvent was distilled off under reduced pressure. The obtained residue was purified by a silica gel column chromatography (hexane/ethyl acetate), thereby obtaining the title compound (444 mg).

$^1H$ NMR (300 MHz, $CDCl_3$) δ 0.57-0.65 (2H, m), 0.71-0.80 (2H, m), 1.23-1.29 (3H, m), 1.34-1.41 (3H, m), 1.54-1.65 (1H, m), 1.66-1.81 (2H, m), 1.88-1.99 (2H, m), 2.39-2.51 (1H, m), 2.82-2.95 (2H, m), 3.26 (2H, s), 3.35-3.42 (2H, m), 3.51-3.63 (4H, m), 3.69 (2H, s), 4.04-4.19 (4H, m), 6.63 (1H, d, J=1.1 Hz), 7.09-7.18 (2H, m), 7.29-7.37 (2H, m).

I) 1-(2-((6-Cyclopropyl-3-ethoxy-2,4'-difluorobiphenyl-4-yl)methyl)-5-oxa-2,6-diazaspiro[3.4]oct-6-en-7-yl)piperidine-4-carboxylic acid 2 M aqueous sodium hydroxide solution (2 mL) was added to a solution of ethyl 1-(2-((6-cyclopropyl-3-ethoxy-2,4'-difluorobiphenyl-4-yl)methyl)-5-oxa-2,6-diazaspiro[3.4]oct-6-en-7-yl)piperidine-4-carboxylate (427 mg) in ethanol (8 mL) at room temperature. After the reaction mixture was stirred for 4 hours at 80° C. in a nitrogen atmosphere, the solvent was distilled off under reduced pressure. Water was added to the residue, the resultant was neutralized with 2 M hydrochloric acid. The obtained solid was collected by filtration, and it was dissolved in ethanol. After the obtained solution was filtered, the filtrate was concentrated under reduced pressure. The obtained residue was crystallized (hexane/ethyl acetate), and further recrystallized (hexane/ethanol), thereby obtaining the title compound (326 mg).

$^1H$ NMR (300 MHz, DMSO-$d_6$) δ 0.54-0.64 (2H, m), 0.70-0.81 (2H, m), 1.30 (3H, t, J=7.0 Hz), 1.43-1.62 (3H, m), 1.72-1.87 (2H, m), 2.34-2.46 (1H, m), 2.75-2.89 (2H, m), 3.18 (2H, d, J=8.1 Hz), 3.30 (2H, brs), 3.40-3.51 (4H, m), 3.60 (2H, s), 4.01 (2H, q, J=6.9 Hz), 6.70 (1H, s), 7.24-7.35 (2H, m), 7.36-7.45 m), 12.23 (1H, brs).

Example 262

1-(2-((2-Chloro-6-cyclopropyl-2',4'-difluoro-3-methoxybiphenyl-4-yl)methyl)-5-oxa-2,6-diazaspiro[3.4]oct-6-en-7-yl)-4-ethylpiperidine carboxylic acid A) Ethyl 1-(2-((2-chloro-6-cyclopropyl-2',4'-difluoro-3-methoxybiphenyl-4-yl)methyl)-5-oxa-2,6-diazaspiro[3.4]oct-6-en-7-yl)-4-ethylpiperidine-4-carboxylate After a mixture of tert-butyl 7-(4-(ethoxycarbonyl)-4-ethylpiperidin-1-yl)-5-oxa-2,6-diazaspiro[3.4]oct-6-ene-2-carboxylate (351 mg) and formic acid (8 mL) was stirred for 30 minutes at 70° C. in a nitrogen atmosphere, the solvent was distilled off under reduced pressure. Sodium triacetoxyborohydride (376 mg) was added to a mixture of the obtained residue, 2-chloro-6-cyclopropyl-2',4'-difluoro-3-methoxybiphenyl-4-carbaldehyde (315 mg) and THF (8 mL), and the resultant was stirred for 16 hours at room temperature in a nitrogen atmosphere. After an aqueous saturated sodium hydrogen carbonate solution was added to the reaction mixture, extraction thereof was performed using ethyl acetate. The obtained organic layer was sequentially washed with water and a saturated saline solution, was dried over anhydrous magnesium sulfate, and then the solvent was distilled off under reduced pressure. The obtained residue was purified by a silica gel column chromatography (hexane/ethyl acetate), thereby obtaining the title compound (408 mg).

$^1$H NMR (300 MHz, $CDCl_3$) δ 0.50-0.66 (2H, m), 0.67-0.74 (2H, m), 0.82 (3H, t, J=7.6 Hz), 1.27 (3H, t, J=7.1 Hz), 1.36-1.62 (5H, m), 2.14 (2H, d, J=13.1 Hz), 2.85-2.98 (2H, m), 3.25 (2H, s), 3.36-3.49 (4H, m), 3.51-3.58 (2H, m), 3.65-3.76 (2H, m), 3.84 (3H, s), 4.18 (2H, q, J=7.1 Hz), 6.85 (1H, s), 6.88-7.01 (2H, m), 7.14-7.24 (1H, m).

B) 1-(2-((2-Chloro-6-cyclopropyl-2',4'-difluoro-3-methoxybiphenyl-4-yl)methyl)-5-oxa-2,6-diazaspiro[3.4]oct-6-en-7-yl)-4-ethylpiperidine-4-carboxylic acid 2 M aqueous sodium hydroxide solution (4 mL) was added to a solution of ethyl 1-(2-((2-chloro-6-cyclopropyl-2',4'-difluoro-3-methoxybiphenyl-4-yl)methyl)-5-oxa-2,6-diazaspiro[3.4]oct-6-en-7-yl)-4-ethylpiperidine-4-carboxylate (388 mg) in ethanol (6 mL) at room temperature. After the reaction mixture was heated to reflux for 5 hours in a nitrogen atmosphere, 2 M sodium hydroxide aqueous solution (4 mL) was added thereto, and the resultant was heated to reflux for 16 hours. The solvent of the reaction mixture was distilled off under reduced pressure. Water was added to the residue, the resultant was neutralized with 2 M hydrochloric acid. The obtained solid was collected by filtration, and it was dissolved in ethanol. After the obtained solution was filtered, the filtrate was concentrated under reduced pressure. The obtained residue was crystallized (hexane/ethyl acetate), and further recrystallized (hexane/ethanol), thereby obtaining the title compound (267 mg).

$^1$H NMR (300 MHz, DMSO-$d_6$) δ 0.51-0.64 (2H, m), 0.67-0.83 (5H, m), 1.27-1.56 (5H, m), 1.93 (2H, d, J=13.8 Hz), 2.75-2.89 (2H, m), 3.14-3.40 (6H, m), 3.48 (2H, brs), 3.66 (2H, brs), 3.77 (3H, s), 6.94 (1H, brs), 7.20 (1H, td, J=8.3, 2.4 Hz), 7.32-7.44 (2H, m), 12.42 (1H, brs).

Example 263

1-(2-((2-Chloro-6-cyclopropyl-3-ethoxy-2',4'-difluorobiphenyl-4-yl)methyl)-5-oxa-2,6-diazaspiro[3.4]oct-6-en-7-yl)-4-methylpiperidine-4-carboxylic acid A) Methyl 2-chloro-6-cyclopropyl-3-ethoxy-2',4'-difluorobiphenyl-4-carboxylate Using methyl 2-chloro-6-cyclopropyl-2',4'-difluoro-3-hydroxybiphenyl-4-carboxylate and iodoethane, the title compound was obtained in the similar manner as in Step F of Example 258.

$^1$H NMR (300 MHz, $CDCl_3$) δ 0.56-0.77 (4H, m), 1.40-1.54 (4H, m), 3.93 (3H, s), 4.11 (2H, q, J=7.0 Hz), 6.90-7.03 (2H, m), 7.14-7.24 (1H, m), 7.32 (1H, s).

B) (2-Chloro-6-cyclopropyl-3-ethoxy-2',4'-difluorobiphenyl-4-yl)methanol

Using methyl 2-chloro-6-cyclopropyl-3-ethoxy-2',4'-difluorobiphenyl-4-carboxylate, the title compound was obtained in the similar manner as in Step G of Example 258.

$^1$H NMR (300 MHz, $CDCl_3$) δ 0.49-0.77 (4H, m), 1.37-1.55 (4H, m), 3.97-4.19 (2H, m), 4.63-4.84 (2H, m), 6.87-7.04 (3H, m), 7.19 (1H, td, J=8.3, 6.6 Hz).

C) 2-Chloro-6-cyclopropyl-3-ethoxy-2',4'-difluorobiphenyl-4-carbaldehyde

Using (2-chloro-6-cyclopropyl-3-ethoxy-2',4'-difluorobiphenyl-4-yl)methanol, the title compound was obtained in the similar manner as in Step H of Example 258.

$^1$H NMR (300 MHz, $CDCl_3$) δ 0.54-0.85 (4H, m), 1.40-1.55 (4H, m), 4.13-4.24 (2H, m), 6.84-7.08 (2H, m), 7.20 (1H, td, J=8.2, 6.4 Hz), 7.39 (1H, s), 10.38 (1H, s).

D) Ethyl 1-(2-((2-chloro-6-cyclopropyl-3-ethoxy-2',4'-difluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-chloro-6-cyclopropyl-3-ethoxy-2',4'-difluorobiphenyl-4-carbaldehyde, the title compound was obtained in the similar manner as in Step I of Example 258.

$^1$H NMR (300 MHz, $CDCl_3$) δ 0.50-0.64 (2H, m), 0.65-0.75 (2H, m), 1.21 (3H, s), 1.26 (3H, t, J=7.1 Hz), 1.39-1.54 (6H, m), 2.11 (2H, d, J=13.5 Hz), 2.97 (2H, ddd, J=13.4, 10.7, 3.0 Hz), 3.25 (2H, s), 3.33-3.45 (4H, m), 3.51-3.59 (2H, m), 3.64-3.77 (2H, m), 3.94-4.06 (2H, m), 4.17 (2H, q, J=7.1 Hz), 6.86 (1H, s), 6.88-7.01 (2H, m), 7.14-7.24 (1H, m).

E) 1-(2-((2-Chloro-6-cyclopropyl-3-ethoxy-2',4'-difluorobiphenyl-4-yl)methyl)-5-oxa-2,6-diazaspiro[3.4]oct-6-en-7-yl)-4-methylpiperidine-4-carboxylic acid Using ethyl 1-(2-((2-chloro-6-cyclopropyl-3-ethoxy-2',4'-difluorobiphenyl-4-yl)methyl)-5-oxa-2,6-diazaspiro[3.4]oct-6-en-7-yl)-4-methylpiperidine-4-carboxylate, the title compound was obtained in the similar manner as in Step J of Example 258.

Example 264

1-(2-((6-Cyclopropyl-2,2',4'-trifluoro-3-isopropoxybiphenyl-4-yl)methyl)-5-oxa-2,6-diazaspiro[3.4]oct-6-en-7-yl)piperidine-4-carboxylic acid

A) 6-Bromo-2,2',4'-trifluoro-3-isopropoxybiphenyl-4-carbaldehyde

Using 6-bromo-2,2',4'-trifluoro-3-hydroxybiphenyl-4-carbaldehyde and 2-iodopropane, the title compound was obtained in the similar manner as in Step E of Example 259.

$^1$H NMR (300 MHz, $CDCl_3$) δ 1.39 (6H, dd, J=6.0, 3.1 Hz), 4.57-4.71 (1H, m), 6.91-7.07 (2H, m), 7.23-7.33 (1H, m), 7.94 (1H, d, J=1.8 Hz), 10.38 (1H, s).

B) 6-Cyclopropyl-2,2',4'-trifluoro-3-isopropoxybiphenyl-4-carbaldehyde

Using 6-bromo-2,2',4'-trifluoro-3-isopropoxybiphenyl-4-carbaldehyde and cyclopropylboronic acid, the title compound was obtained in the similar manner as in Step F of Example 259.

$^1$H NMR (300 MHz, DMSO-$d_6$) δ 0.59-0.72 (2H, m), 0.74-0.87 (2H, m), 1.31 (6H, dd, J=6.0, 2.6 Hz), 1.50-1.62 (1H, m), 4.42-4.54 (1H, m), 7.19 (1H, d, J=1.1 Hz), 7.27 (1H, tdd, J=8.5, 2.5, 0.9 Hz), 7.41-7.50 (1H, m), 7.56 (1H, td, J=8.5, 6.5 Hz), 10.29 (1H, s).

C) Ethyl 1-(2-((6-cyclopropyl-2,2',4'-trifluoro-3-isopropoxybiphenyl-4-yl)methyl)-5-oxa-2,6-diazaspiro[3.4]oct-6-en-7-yl)piperidine-4-carboxylate Using tert-butyl 7-(4-(ethoxycarbonyl)piperidin-1-yl)-5-oxa-2,6-diazaspiro[3.4]oct-6-ene-2-carboxylate and 6-cyclopropyl-2,2',4'-trifluoro-3-isopropoxybiphenyl-4-carbaldehyde, the title compound was obtained in the similar manner as in Step G of Example 259.

MS (ESI+): $[M+H]^+$ 586.3.

D) 1-(2-((6-Cyclopropyl-2,2',4'-trifluoro-3-isopropoxybiphenyl-4-yl)methyl)-5-oxa-2,6-diazaspiro[3.4]oct-6-en-7-yl)piperidine-4-carboxylic acid Using ethyl 1-(2-((6-cyclopropyl-2,2',4'-trifluoro-3-isopropoxybiphenyl-4-yl)methyl)-5-oxa-2,6-diazaspiro[3.4]oct-6-en-7-yl)piperidine-4-carboxylate, the title compound was obtained in the similar manner as in Step H of Example 259.

Example 265

1-(2-((6-Cyclopropyl-2,4'-difluoro-3-methoxybiphenyl-4-yl)methyl)-5-oxa-2,6-diazaspiro[3.4]oct-6-en-7-yl)-4-methylpiperidine-4-carboxylic acid

A) 2,3,4'-Trifluorobiphenyl-4-carbaldehyde (4-Fluorophenyl)boronic acid (17.3 g), dicyclohexyl (2',6'-dimethoxybiphenyl-2-yl)phosphine (5.09 g), 2 M aqueous sodium carbonate solution (124 mL) and tris(dibenzylideneacetone)dipalladium(0) (5.29 g) were added to a solution of 4-bromo-2,3-difluorobenzaldehyde (18.3 g) in toluene (300 mL) at room temperature, and the resultant was stirred 16 hours at 100° C. in an argon atmosphere. Water was added to the reaction mixture at room temperature, the resultant was filtered using celite, and the filtrate was extracted using ethyl acetate. The obtained organic layer was sequentially washed with water and a saturated saline solution, dried over anhydrous magnesium sulfate, and then the solvent was distilled off under reduced pressure. After the obtained residue was passed through a short column of a silica gel (hexane/ethyl acetate), the solvent was distilled off under reduced pressure. The obtained residue was crystallized (hexane/ethyl acetate), and further recrystallized (hexane/ethyl acetate), thereby obtaining the title compound (15.1 g).

$^1$H NMR (300 MHz, $CDCl_3$) δ 7.15-7.24 (2H, m), 7.27-7.35 (1H, m), 7.53-7.61 (2H, m), 7.69 (1H, ddd, J=8.2, 6.3, 1.7 Hz), 10.37 (1H, d, J=0.6 Hz).

B) 2,4'-Difluoro-3-methoxybiphenyl-4-carbaldehyde

Sodium methoxide (28% methanol solution, 18.5 g) was added to a solution of 2,3,4'-trifluorobiphenyl-4-carbaldehyde (15.1 g) in methanol (300 mL) at room temperature, and the resultant was heated to reflux for 16 hours in a nitrogen atmosphere. After the reaction mixture was cooled to room temperature, the solvent was distilled off under reduced pressure. The obtained residue was diluted by ethyl acetate and water, and extraction thereof was performed using ethyl acetate. The obtained organic layer was sequentially washed with water and a saturated saline solution, dried over anhydrous magnesium sulfate, and then the solvent was distilled off under reduced pressure, thereby obtaining the title compound (15.6 g).

$^1$H NMR (300 MHz, $CDCl_3$) δ 4.13 (3H, d, J=2.5 Hz), 7.14-7.22 (3H, m), 7.50-7.58 (2H, m), 7.66 (1H, dd, J=8.2, 1.4 Hz), 10.41 (1H, d, J=0.8 Hz).

C) 2,4'-Difluoro-3-hydroxybiphenyl-4-carbaldehyde

48% hydrobromic acid (71.4 mL) was added to a solution of 2,4'-difluoro-3-methoxybiphenyl carbaldehyde (15.6 g) in acetic acid (300 mL) at room temperature, and the resultant was stirred for 16 hour at 120° C. in a nitrogen atmosphere. After the reaction mixture was cooled to room temperature, the solvent was distilled off under reduced pressure, and the obtained residue was diluted by ethyl acetate and water. After the organic layer was separated, the obtained aqueous layer was neutralized with 1 M aqueous sodium hydroxide solution, and extraction thereof was performed using ethyl acetate. The combined organic layer was sequentially washed with water and a saturated saline solution, dried over anhydrous magnesium sulfate, and then the solvent was distilled off under reduced pressure. The obtained residue was passed through a short column of a silica gel (hexane/ethyl acetate), thereby obtaining the title compound (13.6 g).

$^1$H NMR (400 MHz, DMSO-$d_6$) δ 7.09 (1H, t, J=7.4 Hz), 7.36 (2H, t, J=8.8 Hz), 7.56 (1H, d, J=8.3 Hz), 7.66 (2H, dd, J=7.2, 6.0 Hz), 10.30 (1H, s), 11.03 (1H, brs).

D) 6-Bromo-2,4'-difluoro-3-hydroxybiphenyl-4-carbaldehyde 1,3-Dibromo-1,3,5-triazine-2,4,6-trione (10.0 g) was added to a solution of 2,4'-difluoro-3-hydroxybiphenyl-4-carbaldehyde (13.6 g) in DMF (250 mL) at room temperature, and the resultant was stirred for 3 hours at the same temperature in a nitrogen atmosphere. An aqueous saturated sodium thiosulfate solution was added to the reaction mixture at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (12.7 g).

$^1$H NMR (300 MHz, $CDCl_3$) δ 7.14-7.23 (2H, m), 7.28-7.37 (2H, m), 7.69-7.73 (1H, m), 9.90 (1H, d, J=1.8 Hz), 10.90 (1H, brs).

E) 6-Bromo-2,4'-difluoro-3-methoxybiphenyl-4-carbaldehyde

Iodomethane (3.77 mg) was added to a mixture of 6-bromo-2,4'-difluoro-3-hydroxybiphenyl-4-carbaldehyde (5.55 g), potassium carbonate (4.90 g) and DMF (80 mL) at room temperature, and the resultant was stirred for 48 hours at 60° C. in a nitrogen atmosphere. Water was added to the reaction mixture at room temperature, and extraction thereof was performed using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (5.22 g).

$^1$H NMR (300 MHz, $CDCl_3$) δ 4.10 (3H, d, J=2.7 Hz), 7.15-7.23 (2H, m), 7.28-7.35 (2H, m), 7.92 (1H, d, J=1.9 Hz), 10.36 (1H, s).

F) 6-Cyclopropyl-2,4'-difluoro-3-methoxybiphenyl-4-carbaldehyde

Cyclopropylboronic acid (2.74 g), dicyclohexyl (2',6'-dimethoxybiphenyl-2-yl)phosphine (1.31 g), 2 M aqueous sodium carbonate solution (23.9 mL) and tris(dibenzylideneacetone)dipalladium(0) (1.46 g) were added to a solution of 6-bromo-2,4'-difluoro-3-methoxybiphenyl-4-carbaldehyde (5.22 g) in toluene (80 mL) at room temperature, and the resultant was stirred for 16 hours at 100° C. in an argon atmosphere. Water was added to the reaction mixture at room temperature, the resultant was filtered using celite, and the filtrate was extracted using ethyl acetate. The obtained organic layer was sequentially washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (4.33 g).

$^1$H NMR (300 MHz, $CDCl_3$) δ 0.65-0.72 (2H, m), 0.78-0.86 (2H, m), 1.56-1.64 (1H, m), 4.06 (3H, d, J=2.2 Hz), 7.13-7.23 (3H, m), 7.31-7.39 (2H, m), 10.38 (1H, s).

G) 1-Benzyl 4-ethyl piperidine-1,4-dicarboxylate

Benzyl chloroformate (29.5 mL) was added to a solution of ethyl piperidine-4-carboxylate (25.0 g) and diisopropylethylamine (55.5 mL) in THF (150 mL) at 0° C., and the resultant was stirred for 2 hours at 0° C. After an aqueous saturated sodium hydrogen carbonate solution was added to the reaction mixture, extraction thereof was performed using ethyl acetate. The obtained organic layer was sequentially washed with an aqueous saturated sodium hydrogen carbonate solution, 1 M hydrochloric acid and a saturated saline solution, dried over anhydrous magnesium sulfate, and then the solvent was distilled off under reduced pressure. The obtained residue was purified by a silica gel chromatography (hexane/ethyl acetate), thereby obtaining the title compound (30.1 g).

$^1$H NMR (400 MHz, $CDCl_3$) δ 1.25 (3H, t, J=7.0 Hz), 1.58-1.73 (2H, m), 1.88 (2H, brs), 2.38-2.52 (1H, m), 2.93 (2H, t, J=11.6 Hz), 4.01-4.19 (4H, m), 5.13 (2H, s), 7.27-7.40 (5H, m).

H) 1-Benzyl 4-ethyl 4-methylpiperidine-1,4-dicarboxylate

Lithium bis(trimethylsilyl)amide (1.0 M THF solution, 233 mL) was added to a solution of 1-benzyl 4-ethyl piperidine-1,4-dicarboxylate (40.0 g) in THF (160 mL) at −40° C. After the reaction mixture was stirred for 1 hour at −40° C., iodomethane (39.0 g) was added thereto, and the resultant was stirred for 2 hours at room temperature. After an aqueous saturated sodium hydrogen carbonate solution was added to the reaction mixture, the resultant was filtered using celite, and the organic layer of the filtrate was separated. The obtained organic layer was sequentially washed with water and a saturated saline solution, dried over anhydrous magnesium sulfate, and then the solvent was distilled off under reduced pressure. The obtained residue was purified by a silica gel column chromatography (NH, hexane/ethyl acetate), thereby obtaining the title compound (34.0 g).

$^1$H NMR (400 MHz, $CDCl_3$) δ 1.20 (3H, s), 1.26 (3H, t, J=7.0 Hz), 1.31-1.44 (2H, m), 2.08 (2H, d, J=13.2 Hz), 2.99-3.13 (2H, m), 3.86 (2H, d, J=8.4 Hz), 4.16 (2H, q, J=7.0 Hz), 5.12 (2H, s), 7.28-7.39 (5H, m).

I) Ethyl 4-methylpiperidine-4-carboxylate

20% palladium hydroxide (50% water content, 4.00 g) was added to a solution of 1-benzyl 4-ethyl 4-methylpiperidine-1,4-dicarboxylate (34.0 g) in methanol (340 mL), and the resultant was stirred for 4 hours at room temperature in a hydrogen atmosphere. After the catalyst was filtered off, the filtrate was concentrated under reduced pressure, thereby obtaining the title compound (19.0 g).

$^1$H NMR (400 MHz, $CDCl_3$) δ 1.19 (3H, s), 1.26 (3H, t, J=7.1 Hz), 1.31-1.42 (2H, m), 2.08 (2H, d, J=13.6 Hz), 2.62-2.74 (2H, m), 2.87-2.96 (2H, m), 4.16 (2H, q, J=7.1 Hz).

J) tert-Butyl 3-methyleneazetidine-1-carboxylate

Potassium tert-butoxide (13.3 g) was added to a mixture of methyl(triphenyl)phosphonium bromide (38.7 g) and THF (150 mL) at 0° C., the resultant was stirred for 1 hour at room temperature. A solution of tert-butyl 3-oxoazetidine-1-carboxylate (16.9 g) in THF (50 mL) was added to the reaction mixture, and the resultant was stirred for 2 hours at 50° C. After water was added to the reaction mixture, extraction thereof was performed using ethyl acetate. The obtained organic layer was washed with water and a saturated saline solution, dried over anhydrous magnesium sulfate, and then the solvent was distilled off under reduced pressure. The obtained residue was dissolved in a solution in which ethyl acetate and hexane are mixed at a volume ratio of 1:3, the resultant was filtered using celite, and then the filtrate was concentrated under reduced pressure. The obtained residue was purified by a silica gel column chromatography (hexane/ethyl acetate), thereby obtaining the title compound (10.9 g).

$^1$H NMR (300 MHz, DMSO-$d_6$) δ 1.45 (9H, s), 4.46-4.51 (4H, m), 4.96-5.02 (2H, m).

K) tert-Butyl 7-bromo-5-oxa-2,6-diazaspiro[3.4]oct-6-ene-2-carboxylate

Sodium hydrogen carbonate (101 g) was added to a mixture of tert-butyl 3-methyleneazetidine-1-carboxylate (20.4 g), hydroxycarbonimidic dibromide (48.8 g) and ethyl acetate (400 mL), the resultant was stirred for 15 hours at room temperature, and it was further stirred for 4 hours at 50° C. After water was added to the reaction mixture at room temperature, the filtrate was extracted using ethyl acetate. The obtained organic layer was washed with water and a saturated saline solution, dried over anhydrous magnesium sulfate, and then the solvent was distilled off under reduced pressure. The obtained residue was purified by a silica gel column chromatography (hexane/ethyl acetate), thereby obtaining the title compound (27.8 g).

$^1$H NMR (400 MHz, $CDCl_3$) δ 1.44 (9H, s), 3.44 (2H, s), 4.02-4.07 (2H, m), 4.26-4.32 (2H, m).

L) tert-Butyl 7-(4-(ethoxycarbonyl)-4-methylpiperidin-1-yl)-5-oxa-2,6-diazaspiro[3.4]oct-6-ene-2-carboxylate tert-Butyl 7-bromo-5-oxa-2,6-diazaspiro[3.4]oct-6-ene-2-carboxylate (18.0 g), ethyl 4-methylpiperidine-4-carboxylate (14.8 g) and sodium carbonate (19.7 g) were added to DMF (90 mL), and the resultant was stirred overnight at 130° C. After the reaction mixture was cooled to room temperature, it was poured into water, and extraction thereof was performed using ethyl acetate. The obtained organic layer was washed with a saturated saline solution, dried over anhydrous magnesium sulfate, and then the solvent was distilled off under reduced pressure. The obtained residue was crystallized (hexane/ethyl acetate), thereby obtaining the title compound (18.1 g).

$^1$H NMR (400 MHz, DMSO-$d_6$) δ 1.15 (3H, s), 1.19 (3H, t, J=7.0 Hz), 1.31-1.46 (11H, m), 1.93 (2H, d, J=13.6 Hz), 2.87 (2H, t, J=10.4 Hz), 3.23-3.36 (4H, m), 3.88 (2H, d, J=9.3 Hz), 4.02 (2H, d, J=9.0 Hz), 4.11 (2H, q, J=6.9 Hz).

M) Ethyl 1-(2-((6-cyclopropyl-2,4'-difluoro-3-methoxybiphenyl-4-yl)methyl)-5-oxa-2,6-diazaspiro[3.4]oct-6-en-7-yl)-4-methylpiperidine-4-carboxylate After a mixture of tert-butyl 7-(4-(ethoxycarbonyl)-4-methylpiperidin-1-yl)-5-oxa-2,6-diazaspiro[3.4]oct-6-ene-2-carboxylate (5.21 g) and formic acid (30 mL) was stirred for 30 minutes at 70° C. in a nitrogen atmosphere, the solvent was distilled off under reduced pressure. Sodium triacetoxyborohydride (5.79 g) was added to a mixture of the obtained residue, 6-cyclopropyl-2,4'-difluoro-3-methoxybiphenyl-4-carbaldehyde (4.33 g) and THF (60 mL), and the resultant was stirred for 16 hours at room temperature in a nitrogen atmosphere. After an aqueous saturated sodium hydrogen carbonate solution was added to the reaction mixture, extraction thereof was performed using ethyl acetate. The obtained organic layer was sequentially washed with water and a saturated saline solution, was dried over anhydrous magnesium sulfate, and then the solvent was distilled off under reduced pressure.

The obtained residue was purified by a silica gel column chromatography (hexane/ethyl acetate), thereby obtaining the title compound (6.57 g).

$^1$H NMR (300 MHz, $CDCl_3$) δ 0.56-0.63 (2H, m), 0.72-0.80 (2H, m), 1.21 (3H, s), 1.26 (3H, t, J=7.1 Hz), 1.38-1.51 (1H, m), 1.55-1.64 (2H, m), 2.11 (2H, d, J=13.8 Hz), 2.91-3.03 (2H, m), 3.25 (2H, s), 3.33-3.43 (4H, m), 3.54 (2H, d, J=8.7 Hz), 3.67 (2H, s), 3.88 (3H, d, J=0.6 Hz), 4.16 (2H, q, J=6.9 Hz), 6.62 (1H, s), 7.09-7.17 (2H, m), 7.29-7.36 (2H, m).

N) 1-(2-((6-Cyclopropyl-2,4'-difluoro-3-methoxybiphenyl-4-yl)methyl)-5-oxa-2,6-diazaspiro[3.4]oct-6-en-7-yl)-4-methylpiperidine-4-carboxylic acid 2 M aqueous sodium hydroxide solution (35 mL) was added to a solution of ethyl 1-(2-((6-cyclopropyl-2,4'-difluoro-3-methoxybiphenyl-4-yl)methyl)-5-oxa-2,6-diazaspiro[3.4]oct-6-en-7-yl)-4-methylpiperidine-4-carboxylate (6.57 g) in ethanol (60 mL) at room temperature. After the reaction mixture was stirred for 3 hours at 80° C. in a nitrogen atmosphere, the solvent was distilled off under reduced pressure. Water was added to the residue, the resultant was neutralized with 2 M hydrochloric acid, and extraction thereof was performed using a mixed solution of ethyl acetate and THF. The obtained organic layer was sequentially washed with water and a saturated saline solution, was dried over anhydrous magnesium sulfate, and then the solvent was distilled off under reduced pressure. The obtained residue was crystallized (hexane/ethyl acetate), and further recrystallized (hexane/ethanol), thereby obtaining the title compound (5.48 g).

$^1$H NMR (300 MHz, DMSO-$d_6$) δ 0.56-0.64 (2H, m), 0.71-0.81 (2H, m), 1.14 (3H, s), 1.31-1.43 (2H, m), 1.49-1.61 (1H, m), 1.85-1.97 (2H, m), 2.83-2.95 (2H, m), 3.24-3.37 (6H, m), 3.44-3.74 (4H, m), 3.81 (3H, s), 6.73 (1H, brs), 7.26-7.35 (2H, m), 7.37-7.46 (2H, m), 12.41 (1H, brs).

Example 266

1-(2-((6-Cyclopropyl-2,4'-difluoro-3-methoxybiphenyl-4-yl)methyl)-5-oxa-2,6-diazaspiro[3.4]oct-6-en-7-yl)piperidine-4-carboxylic acid A) Ethyl 1-(2-((6-cyclopropyl-2,4'-difluoro-3-methoxybiphenyl-4-yl)methyl)-5-oxa-2,6-diazaspiro[3.4]oct-6-en-7-yl)piperidine 1 carboxylate After a mixture of tert-butyl 7-(4-(ethoxycarbonyl)piperidin-1-yl)-5-oxa-2,6-diazaspiro[3.4]oct-6-ene-2-carboxylate (351 mg) and formic acid (8 mL) was stirred for 30 minutes at 70° C. in a nitrogen atmosphere, the solvent was distilled off under reduced pressure. Sodium triacetoxyborohydride (405 mg) was added to a mixture of the obtained residue, 6-cyclopropyl-2,4'-difluoro-3-methoxybiphenyl-4-carbaldehyde (303 mg) and THF (8 mL), and the resultant was stirred for 48 hours at room temperature in a nitrogen atmosphere. After an aqueous saturated sodium hydrogen carbonate solution was added to the reaction mixture, extraction thereof was performed using ethyl acetate. The obtained organic layer was sequentially washed with water and a saturated saline solution, was dried over anhydrous magnesium sulfate, and then the solvent was distilled off under reduced pressure. The obtained residue was purified by a silica gel column chromatography (hexane/ethyl acetate), thereby obtaining the title compound (397 mg).

$^1$H NMR (300 MHz, $CDCl_3$) δ 0.57-0.64 (2H, m), 0.72-0.80 (2H, m), 1.26 (3H, t, J=7.1 Hz), 1.54-1.65 (1H, m), 1.72-1.81 (2H, m), 1.88-1.98 (2H, m), 2.39-2.51 (1H, m), 2.82-2.94 (2H, m), 3.26 (2H, s), 3.36-3.42 (2H, m), 3.52-

3.62 (4H, m), 3.68 (2H, s), 3.88 (3H, d, J=1.6 Hz), 4.15 (2H, q, J=7.2 Hz), 6.62 (1H, d, J=1.2 Hz), 7.09-7.18 (2H, m), 7.29-7.37 (2H, m).

B) 1-(2-((6-Cyclopropyl-2,4'-difluoro-3-methoxybiphenyl-4-yl)methyl)-5-oxa-2,6-diazaspiro[3.4]oct-6-en-7-yl)piperidine-4-carboxylic acid 2 M aqueous sodium hydroxide solution (2 mL) was added to a solution of ethyl 1-(2-((6-cyclopropyl-2,4'-difluoro-3-methoxybiphenyl-4-yl)methyl)-5-oxa-2,6-diazaspiro[3.4]oct-6-en-7-yl)piperidine-4-carboxylate (379 mg) in ethanol (8 mL) at room temperature. After the reaction mixture was stirred for 3 hours at 80° C. in a nitrogen atmosphere, the solvent was distilled off under reduced pressure. Water was added to the residue, the resultant was neutralized with 2 M hydrochloric acid. The obtained solid was collected by filtration, and it was dissolved in ethanol. After the obtained solution was filtered, the filtrate was concentrated under reduced pressure. The obtained residue was crystallized (hexane/ethyl acetate), and further recrystallized (hexane/ethyl acetate), thereby obtaining the title compound (252 mg).

$^1$H NMR (300 MHz, DMSO-$d_6$) δ 0.65 (2H, brs), 0.77 (2H, d, J=8.2 Hz), 1.42-1.64 (3H, m), 1.73-1.88 (2H, m), 2.34-2.48 (1H, m), 2.84 (2H, t, J=11.0 Hz), 3.17-3.55 (8H, m), 3.72-4.04 (5H, m), 6.82 (1H, brs), 7.26-7.37 (2H, m), 7.37-7.46 (2H, m).

Example 267

1-(2-((2-Ethoxy-4'-fluoro-6-propoxybiphenyl-4-yl)methyl)-5-oxa-2,6-diazaspiro[3.4]oct-6-en-7-yl)-4-methylpiperidine-4-carboxylic acid A) Ethyl 4-bromo-3-ethoxy-5-propoxybenzoate Using ethyl 4-bromo-3-hydroxy-5-propoxybenzoate and iodoethane, the title compound was obtained in the similar manner as in Step A of Example 1.

$^1$H NMR (300 MHz, $CDCl_3$) δ 1.09 (3H, t, J=7.4 Hz), 1.40 (3H, t, J=7.1 Hz), 1.49 (3H, t, J=7.0 Hz), 1.82-1.94 (2H, m), 4.05 (2H, t, J=6.5 Hz), 4.17 (2H, q, J=6.9 Hz), 4.38 (2H, q, J=7.1 Hz), 7.21 (2H, s).

B) 2-Ethoxy-4'-fluoro-6-propoxybiphenyl-4-carbaldehyde

Using ethyl 4-bromo-3-ethoxy-5-propoxybenzoate and (4-fluorophenyl)boronic acid, the title compound was obtained in the similar manner as in Step B of Example 1, Step E of Example 16 and Step H of Example 210.

$^1$H NMR (300 MHz, $CDCl_3$) δ 0.89 (3H, t, J=7.4 Hz), 1.29 (3H, t, J=6.9 Hz), 1.59-1.78 (2H, m), 3.94 (2H, t, J=6.4 Hz), 4.06 (2H, q, J=6.9 Hz), 7.04-7.11 (2H, m), 7.12 (2H, s), 7.30-7.38 (2H, m), 9.94 (1H, s).

C) Ethyl 1-(2-((2-ethoxy-4'-fluoro-6-propoxybiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2-ethoxy-4'-fluoro-6-propoxybiphenyl-4-carbaldehyde, the title compound was obtained in the similar manner as in Step G of Example 1.

MS (ESI+): $[M+H]^+$ 568.5.

D) 1-(2-((2-Ethoxy-4'-fluoro-6-propoxybiphenyl-4-yl)methyl)-5-oxa-2,6-diazaspiro[3.4]oct-6-en-7-yl)-4-methylpiperidine-4-carboxylic acid Using ethyl 1-(2-((2-ethoxy-4'-fluoro-6-propoxybiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Example 268

1-(2-((2,6-Dicyclopropyl-4'-fluorobiphenyl-4-yl)methyl)-5-oxa-2,6-diazaspiro[3.4]oct-6-en-7-yl)-4-methylpiperidine-4-carboxylic acid A) 6-Cyclopropyl-4'-fluoro-4-formylbiphenyl-2-yl trifluoromethanesulfonate Using 2-cyclopropyl-4'-fluoro-6-hydroxybiphenyl-4-carbaldehyde and trifluoromethanesulfonic anhydride, the title compound was obtained in the similar manner as in Step G of Example 87.

$^1$H NMR (300 MHz, $CDCl_3$) δ 0.75-0.83 (2H, m), 0.91-0.98 (2H, m), 1.64-1.75 (1H, m), 7.16-7.24 (2H, m), 7.28-7.35 (2H, m), 7.46 (1H, d, J=1.3 Hz), 7.66 (1H, d, J=1.4 Hz), 9.99 (1H, s).

B) 2,6-Dicyclopropyl-4'-fluorobiphenyl-4-carbaldehyde

Using 6-cyclopropyl-4'-fluoro-4-formylbiphenyl-2-yl trifluoromethanesulfonate and cyclopropylboronic acid, the title compound was obtained in the similar manner as in Step D of Example 23.

$^1$H NMR (300 MHz, $CDCl_3$) δ 0.64-0.72 (4H, m), 0.73-0.83 (4H, m), 1.47-1.60 (2H, m), 7.12-7.21 (2H, m), 7.23-7.30 (4H, m), 9.94 (1H, d, J=0.8 Hz).

C) Ethyl 1-(2-((2,6-dicyclopropyl-4'-fluorobiphenyl-4-yl)methyl)-5-oxa-2,6-diazaspiro[3.4]oct-6-en-7-yl)-4-methylpiperidine-4-carboxylate Using tert-butyl 7-(4-(ethoxycarbonyl)-4-methylpiperidin-1-yl)-5-oxa-2,6-diazaspiro[3.4]oct-6-ene-2-carboxylate and 2,6-dicyclopropyl-4'-fluorobiphenyl-4-carbaldehyde, the title compound was obtained in the similar manner as in Step G of Example 1.

MS (ESI+): $[M+H]^+$ 546.3.

D) 1-(2-((2,6-Dicyclopropyl-4'-fluorobiphenyl-4-yl)methyl)-5-oxa-2,6-diazaspiro[3.4]oct-6-en-7-yl)-4-methylpiperidine-4-carboxylic acid Using ethyl 1-(2-((2,6-dicyclopropyl-4'-fluorobiphenyl-4-yl)methyl)-5-oxa-2,6-diazaspiro[3.4]oct-6-en-7-yl)-4-methylpiperidine-4-carboxylate, the title compound was obtained in the similar manner as in Example 2.

Table 1 shows compound names, structural formulas, measured values of MS and NMR spectral data of the compounds of the examples. The measured values of MS show values measured in a positive mode (ESI+) or a negative mode (ESI−).

TABLE 1

| Example No. | IUPAC Name | Structure | MS, NMR |
|---|---|---|---|
| 1 | Ethyl 1-(2-((2,6-diethoxy-4'-fluorobiphenyl-4-yl)methyl)-5-oxa-2,6-diazaspiro[3.4]oct-6-en-7-yl)piperidine-4-carboxylate | 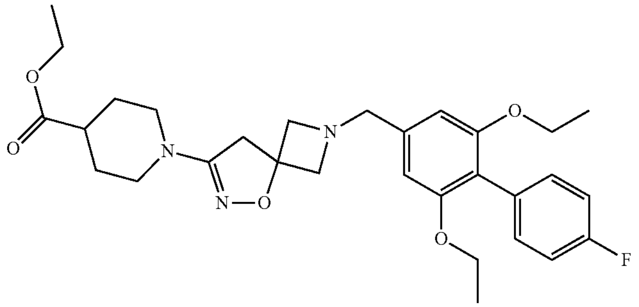 [SMILES: CCOC(=O)C1CCN(C2=NOC3(C2)CN(Cc2cc(OCC)c(-c4ccc(F)cc4)c(OCC)c2)C3)CC1] | 540.5 |
| 2 | 1-(2-((2,6-Diethoxy-4'-fluoro-biphenyl-4-yl)methyl)-5-oxa-2,6-diazaspiro[3.4]oct-6-en-7-yl)piperidine-4-carboxylic acid | 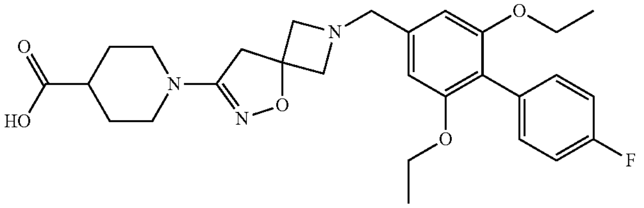 [SMILES: CCOc1cc(CN2CC3(CC(N4CCC(C(=O)O)CC4)=NO3)C2)cc(OCC)c1-c1ccc(F)cc1] | 512.5 |
| 3 | Methyl trans-4-(2-((2,6-diethoxy-4'-fluorobiphenyl-4-yl)methyl)-5-oxa-2,6-diazaspiro[3.4]oct-6-en-7-yl)cyclohexane-carboxylate | 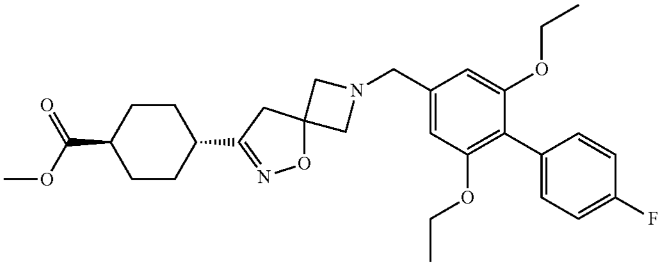 [SMILES: CCOc1cc(CN2CC3(CC([C@H]4CC[C@H](C(=O)OC)CC4)=NO3)C2)cc(OCC)c1-c1ccc(F)cc1] | 525.3 |
| 4 | trans-4-(2-((2,6-Diethoxy-4'-fluorobiphenyl-4-yl)methyl)-5-oxa-2,6-diazaspiro[3.4]oct-6-en-7-yl)cyclohexane-carboxylic acid | 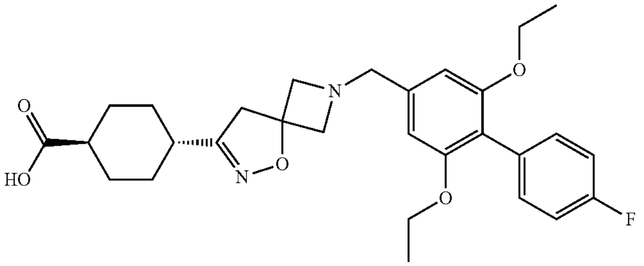 [SMILES: CCOc1cc(CN2CC3(CC([C@H]4CC[C@H](C(=O)O)CC4)=NO3)C2)cc(OCC)c1-c1ccc(F)cc1] | 511.3 |
| 5 | 1-(2-((2,6-Diethoxy-4'-fluoro-biphenyl-4-yl)methyl)-5-oxa-2,6-diazaspiro[3.4]oct-6-en-7-yl)piperidin-4-yl)acetic acid | 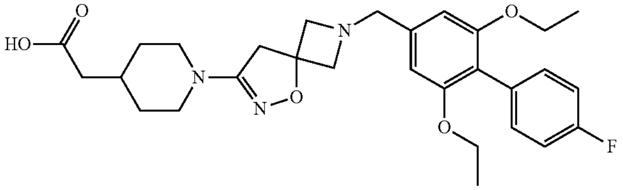 [SMILES: CCOc1cc(CN2CC3(CC(N4CCC(CC(=O)O)CC4)=NO3)C2)cc(OCC)c1-c1ccc(F)cc1] | 526.5 |
| 6 | 1-(2-((2,6-Diethoxy-4'-fluoro-biphenyl-4-yl)methyl)-5-oxa-2,6-diazaspiro[3.4]oct-6-en-7-yl)azetidine-3-carboxylic acid | 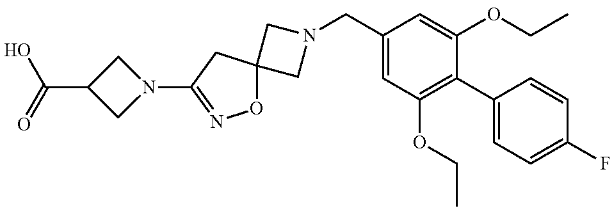 [SMILES: CCOc1cc(CN2CC3(CC(N4CC(C(=O)O)C4)=NO3)C2)cc(OCC)c1-c1ccc(F)cc1] | 484.5 |

TABLE 1-continued

| Example No. | IUPAC Name | Structure | MS, NMR |
|---|---|---|---|
| 7 | Ethyl 1-(2-((2,6-diethoxy-4'-fluorobiphenyl-4-yl)methyl)-5-oxa-2,6-diazaspiro[3.4]oct-6-en-7-yl)-4-methyl-piperidine-4-carboxylate | 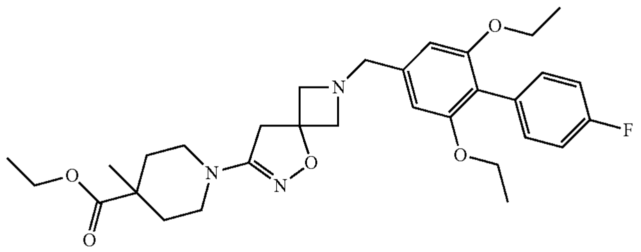 [SMILES: CCOC(=O)C1(C)CCN(C2=NOC3(C2)CN(Cc2cc(OCC)c(-c4ccc(F)cc4)c(OCC)c2)C3)CC1] | 554.6 |
| 8 | 1-(2-((2,6-Diethoxy-4'-fluoro-biphenyl-4-yl)methyl)-5-oxa-2,6-diazaspiro[3.4]oct-6-en-7-yl)-4-methyl-piperidine-4-carboxylic acid | 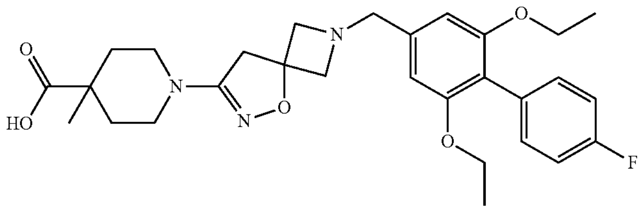 [SMILES: CCOc1cc(CN2CC3(CC(N4CCC(C)(C(=O)O)CC4)=NO3)C2)cc(OCC)c1-c1ccc(F)cc1] | 526.6 |
| 9 | 1-(2-((1-Ethyl-1H-indol-6-yl)methyl)-5-oxo-2,6-diazaspiro[3.4]oct-6-en-7-yl)piperidine-4-carboxylic acid | 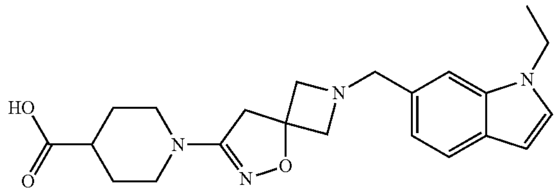 [SMILES: CCn1ccc2ccc(CN3CC4(CC(N5CCC(C(=O)O)CC5)=NO4)C3)cc21] | 397.5 |
| 10 | 1-(2-((3-Chloro-1-ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylic acid | 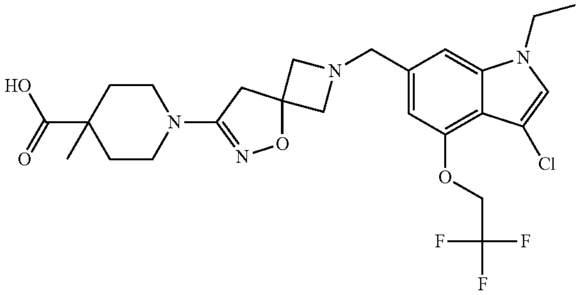 [SMILES: CCn1cc(Cl)c2c(OCC(F)(F)F)cc(CN3CC4(CC(N5CCC(C)(C(=O)O)CC5)=NO4)C3)cc21] | 543.5 |
| 11 | 1-(2-((2,6-Diethoxy-4'-fluoro-biphenyl-4-yl)methyl)-5-oxa-2,6-diazaspiro[3.4]oct-6-en-7-yl)pyrrolidine-3-carboxylic acid | 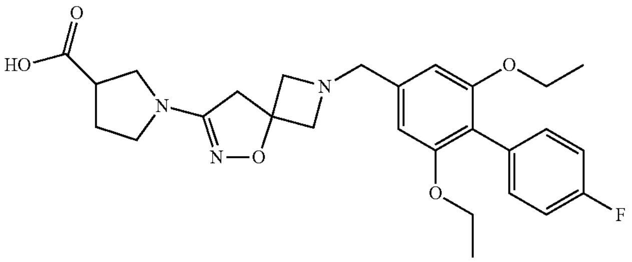 [SMILES: CCOc1cc(CN2CC3(CC(N4CCC(C(=O)O)C4)=NO3)C2)cc(OCC)c1-c1ccc(F)cc1] | 1H NMR (400 MHz, DMSO-$d_6$) δ 1.15 (6H, t, J = 6.9 Hz), 1.95-2.16 (2H, m), 3.01-3.12 (1H, m), 3.12-3.52 (10H, m), 3.58 (2H, s), 3.95 (4H, q, J = 6.9 Hz), 6.61 (2H, s), 7.10-7.18 (2H, m), 7.23-7.31 (2H, m). |
| 12 | 1-(2-((2,6-Diethoxy-4'-fluoro-biphenyl-4-yl)methyl)-8-methyl-5-oxa-2,6-diazaspiro[3.4]oct-6-en-7-yl)-4-methylpiperidine-4-carboxylic acid | 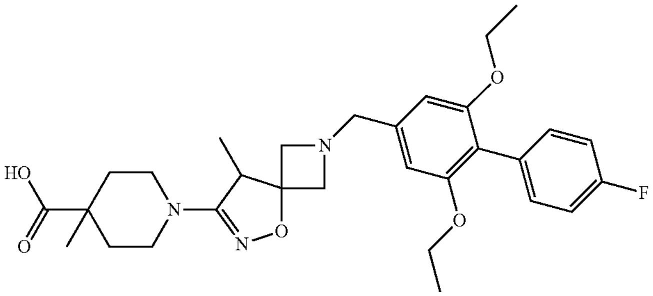 [SMILES: CCOc1cc(CN2CC3(C2)ON=C(N2CCC(C)(C(=O)O)CC2)C3C)cc(OCC)c1-c1ccc(F)cc1] | 1H NMR (400 MHz, DMSO-$d_6$) δ 1.05 (3H, d, J = 7.0 Hz), 1.09-1.19 (9H, m), 1.27-1.45 (2H, m), 1.92 (2H, t, J = 13.6 Hz), 2.89 (2H, t, J = 10.5 Hz), 3.06 (1H, d, J = 7.2 Hz), 3.13 (1H, d, J = 8.3 Hz), 3.19-3.43 (4H, m), 3.53 (1H, d, J = 8.2 Hz), 3.59 (2H, s), 3.95 (4H, q, J = 6.9 Hz), 6.61 (2H, s), 7.10-7.19 (2H, m), 7.22-7.31 (2H, m), 12.44 (1H, brs). |

TABLE 1-continued

| Example No. | IUPAC Name | Structure | MS, NMR |
|---|---|---|---|
| 13 | 1-(2-((2,6-Diethoxy-4'-fluoro-biphenyl-4-yl)methyl)-5-oxa-2,6-diazaspiro[3.4]oct-6-en-7-yl)piperidine-4-carboxylic acid | 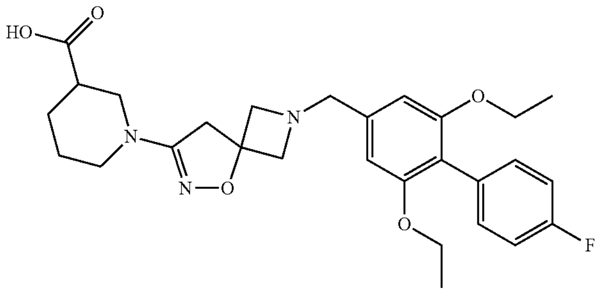 [SMILES: CCOc1cc(CN2CC3(CC(N4CCCC(C(=O)O)C4)=NO3)C2)cc(OCC)c1-c1ccc(F)cc1] | 512.5 |
| 14 | 1-(2-((2,6-Diethoxy-4'-fluoro-biphenyl-4-yl)methyl)-5-oxa-2,6-diazaspiro[3.4]oct-6-en-7-yl)-4-fluoropiperidine-4-carboxylic acid | 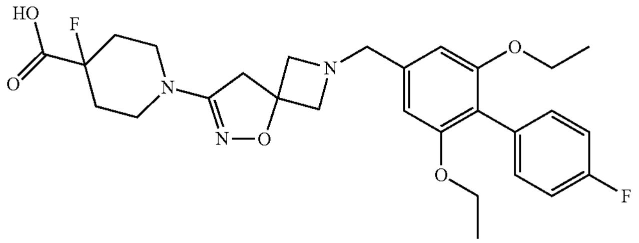 [SMILES: CCOc1cc(CN2CC3(CC(N4CCC(F)(C(=O)O)CC4)=NO3)C2)cc(OCC)c1-c1ccc(F)cc1] | 530.5 |
| 15 | 3-(1-(2-((2,6-Diethoxy-4'-fluoro-biphenyl-4-yl)methyl)-5-oxa-2,6-diazaspiro[3.4]oct-6-en-7-yl)piperidin-4-yl)propionic acid | 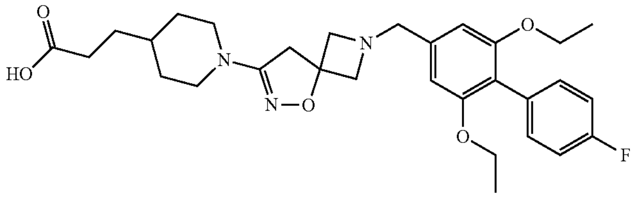 [SMILES: CCOc1cc(CN2CC3(CC(N4CCC(CCC(=O)O)CC4)=NO3)C2)cc(OCC)c1-c1ccc(F)cc1] | 540.6 |
| 16 | 1-(2-((2-Ethoxy-4'-fluoro-6-methyl-biphenyl-4-yl)methyl)-5-oxa-2,6-diazaspiro[3.4]oct-6-en-7-yl)-4-methylpiperidine-4-carboxylic acid | 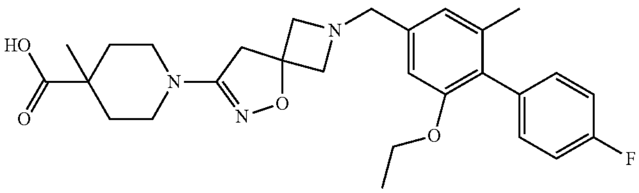 [SMILES: CCOc1cc(CN2CC3(CC(N4CCC(C)(C(=O)O)CC4)=NO3)C2)cc(C)c1-c1ccc(F)cc1] | 496.3 |
| 17 | 1-(2-((2-Ethoxy-4'-fluoro-6-(2,2,2-trifluoroethoxy)biphenyl-4-yl)methyl)-5-oxa-2,6-diazaspiro[3.4]oct-6-en-7-yl)-4-methylpiperidine-4-carboxylic acid | 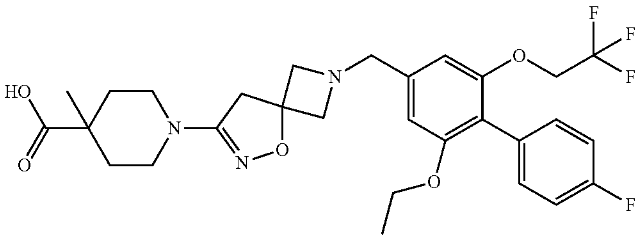 [SMILES: CCOc1cc(CN2CC3(CC(N4CCC(C)(C(=O)O)CC4)=NO3)C2)cc(OCC(F)(F)F)c1-c1ccc(F)cc1] | 580.5 |
| 18 | 4-Benzyl-1-(2-((2,6-diethoxy-4'-fluorobiphenyl-4-yl)methyl)-5-oxa-2,6-diazaspiro[3.4]oct-6-en-7-yl)piperidine-4-carboxylic acid | 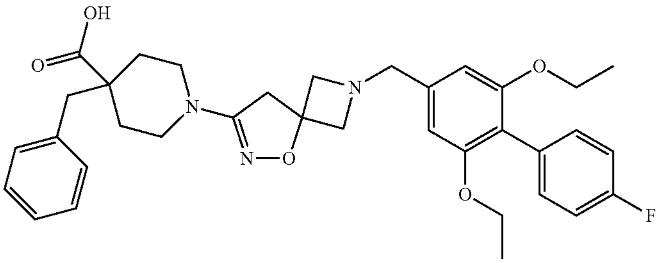 [SMILES: CCOc1cc(CN2CC3(CC(N4CCC(Cc5ccccc5)(C(=O)O)CC4)=NO3)C2)cc(OCC)c1-c1ccc(F)cc1] | 602.6 |

TABLE 1-continued

| Example No. | IUPAC Name | Structure | MS, NMR |
|---|---|---|---|
| 19 | 1-(2-((2,6-Diethoxy-4'-fluoro-biphenyl-4-yl)methyl)-5-oxa-2,6-diazaspiro[3.4]oct-6-en-7-yl)-4-ethylpiperidine-4-carboxylic acid | 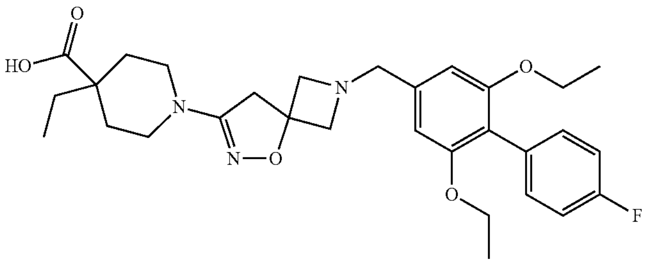 [SMILES: CCOc1cc(CN2CC3(CC(N4CCC(CC)(C(=O)O)CC4)=NO3)C2)cc(OCC)c1-c1ccc(F)cc1] | 540.6 |
| 20 | 1-(2-((2-Ethoxy-4'-fluorobiphenyl-4-yl)methyl)-5-oxa-2,6-diazaspiro[3.4]oct-6-en-7-yl)-4-methylpiperidine-4-carboxylic acid | 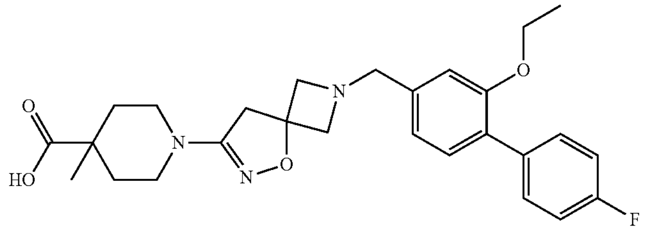 [SMILES: CCOc1cc(CN2CC3(CC(N4CCC(C)(C(=O)O)CC4)=NO3)C2)ccc1-c1ccc(F)cc1] | 482.3 |
| 21 | 1-(2-((1-(4-Fluoro-phenyl)-5-isopropyl-1H-pyrazolo[3,4-d][1,3]thiazol-3-yl)methyl)-5-oxa-2,6-diazaspiro[3.4]oct-6-en-7-yl)-4-methylpiperidine-4-carboxylic acid | 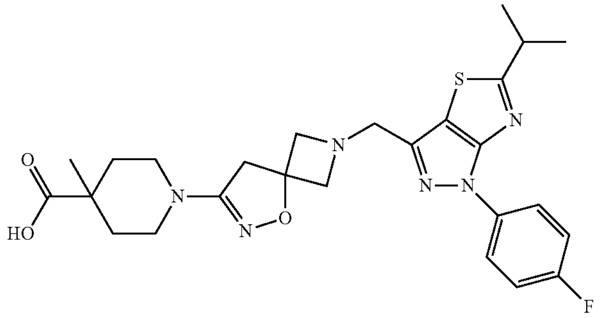 [SMILES: CC(C)c1nc2c(s1)c(CN1CC3(CC(N4CCC(C)(C(=O)O)CC4)=NO3)C1)nn2-c1ccc(F)cc1] | 527.3 |
| 22 | 4-Methyl-1-(2-(3-methyl-5-(1-phenyl-ethoxy)benzyl)-5-oxa-2,6-diazaspiro[3.4]oct-6-en-7-yl)piperidine-4-carboxylic acid | 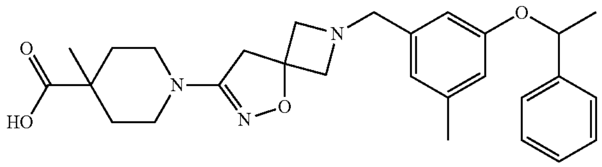 [SMILES: Cc1cc(CN2CC3(CC(N4CCC(C)(C(=O)O)CC4)=NO3)C2)cc(OC(C)c2ccccc2)c1] | 478.2 |
| 23 | Ethyl 1-(2-((2-cyclopropyl-6-ethoxy-4'-fluoro-biphenyl-4-yl)methyl)-5-oxa-2,6-diazaspiro[3.4]oct-6-en-7-yl)-4-methylpiperidine-4-carboxylate | 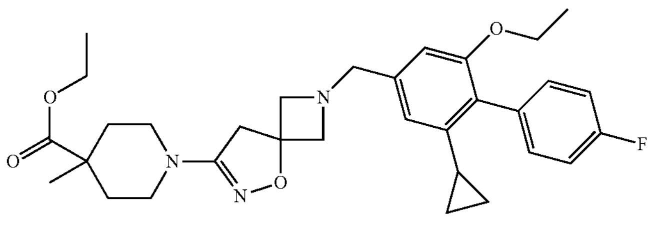 [SMILES: CCOC(=O)C1(C)CCN(C2=NOC3(C2)CN(Cc2cc(OCC)c(-c4ccc(F)cc4)c(C4CC4)c2)C3)CC1] | 550.5 |
| 24 | 1-(2-((2-Cyclo-propyl-6-ethoxy-4'-fluorobiphenyl-4-yl)methyl)-5-oxa-2,6-diazaspiro[3.4]oct-6-en-7-yl)-4-methylpiperidine-4-carboxylic acid | 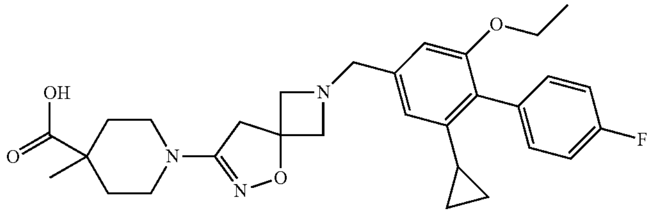 [SMILES: CCOc1cc(CN2CC3(CC(N4CCC(C)(C(=O)O)CC4)=NO3)C2)cc(C2CC2)c1-c1ccc(F)cc1] | 522.5 |

TABLE 1-continued

| Example No. | IUPAC Name | Structure | MS, NMR |
|---|---|---|---|
| 25 | 1-(2-((2-Ethoxy-4'-fluoro-6-methoxylbiphenyl-4-yl)methyl)-5-oxa-2,6-diazaspiro[3.4]oct-6-en-7-yl)-4-methylpiperidine-4-carboxylic acid | 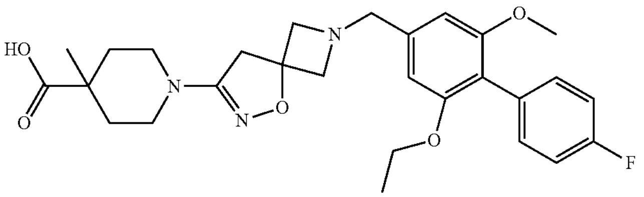 [SMILES: CCOc1cc(CN2CC3(CC(N4CCC(C)(C(=O)O)CC4)=NO3)C2)cc(OC)c1-c1ccc(F)cc1] | 512.5 |
| 26 | 1-(2-((4'-Fluoro-2-propylbiphenyl-4-yl)methyl)-5-oxa-2,6-diazaspiro[3.4]oct-6-en-7-yl)-4-methylpiperidine-4-carboxylic acid | 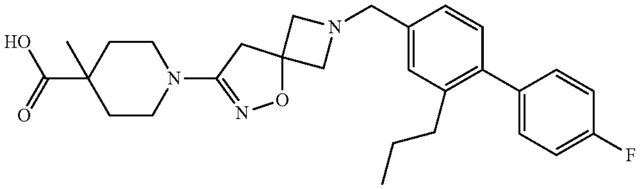 [SMILES: CCCc1cc(CN2CC3(CC(N4CCC(C)(C(=O)O)CC4)=NO3)C2)ccc1-c1ccc(F)cc1] | 480.5 |
| 27 | 1-(2-(3,5-Dichlorobenzyl)-5-oxa-2,6-diazaspiro[3.4]oct-6-en-7-yl)-4-methylpiperidine-4-carboxylic acid | 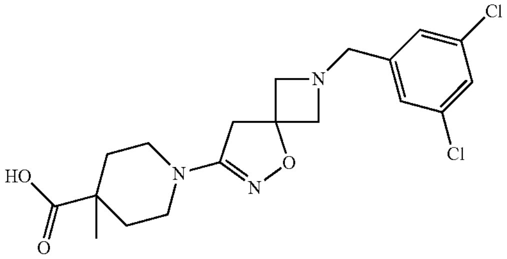 [SMILES: CC1(C(=O)O)CCN(C2=NOC3(C2)CN(Cc2cc(Cl)cc(Cl)c2)C3)CC1] | 412 |
| 28 | 1-(2-(3,5-Bis(trifluoromethyl)benzyl)-5-oxa-2,6-diazaspiro[3.4]oct-6-en-7-yl)-4-methylpiperidine-4-carboxylic acid | 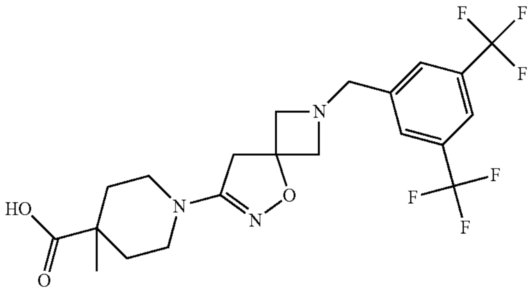 [SMILES: CC1(C(=O)O)CCN(C2=NOC3(C2)CN(Cc2cc(C(F)(F)F)cc(C(F)(F)F)c2)C3)CC1] | 480.1 |
| 29 | 1-(2-((4,5-Dibromo-2-thienyl)methyl)-5-oxa-2,6-diazaspiro[3.4]oct-6-en-7-yl)-4-methylpiperidine-4-carboxylic acid | 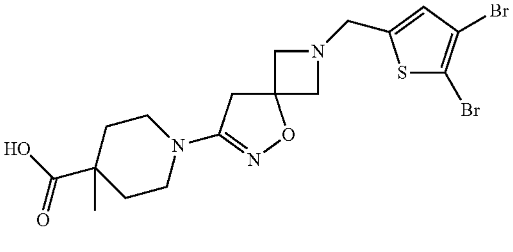 [SMILES: CC1(C(=O)O)CCN(C2=NOC3(C2)CN(Cc2cc(Br)c(Br)s2)C3)CC1] | 507.9 |
| 30 | 4-Methyl-1-(2-((1-phenyl-3-(pyridin-3-yl)-1H-pyrazol-4-yl)methyl)-5-oxa-2,6-diazaspiro[3.4]oct-6-en-7-yl)piperidine-4-carboxylic acid | 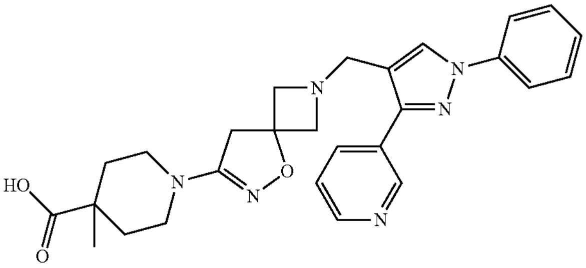 [SMILES: CC1(C(=O)O)CCN(C2=NOC3(C2)CN(Cc2cn(-c4ccccc4)nc2-c2cccnc2)C3)CC1] | 487.3 |

TABLE 1-continued

| Example No. | IUPAC Name | Structure | MS, NMR |
|---|---|---|---|
| 31 | 1-(2-(2-Bromo-5-ethoxybenzyl)-5-oxa-2,6-diazaspiro[3.4]oct-6-en-7-yl)-4-methylpiperidine-4-carboxylic acid | 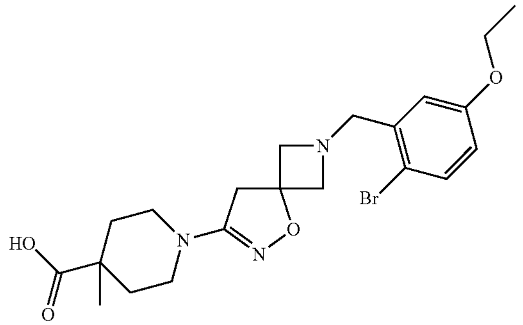 [SMILES: CCOc1ccc(Br)c(CN2CC3(CC(N4CCC(C)(C(=O)O)CC4)=NO3)C2)c1] | 466.1 |
| 32 | 1-(2-(4-(4-Fluorophenoxy)benzyl)-5-oxa-2,6-diazaspiro[3.4]oct-6-en-7-yl)-4-methylpiperidine-4-carboxylic acid | 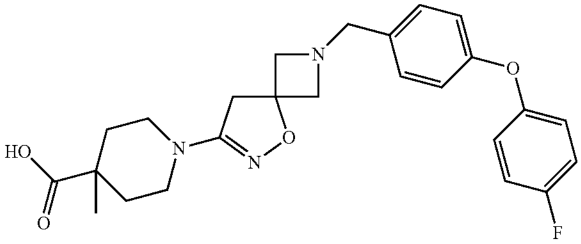 [SMILES: CC1(C(=O)O)CCN(C2=NOC3(C2)CN(Cc2ccc(Oc4ccc(F)cc4)cc2)C3)CC1] | 454.1 |
| 33 | 1-(2-(4-(Benzyloxy)-3-ethoxybenzyl)-5-oxa-2,6-diazaspiro[3.4]oct-6-en-7-yl)-4-methylpiperidine-4-carboxylic acid | 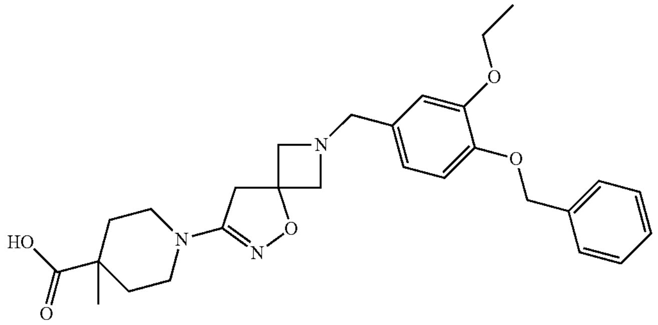 [SMILES: CCOc1cc(CN2CC3(CC(N4CCC(C)(C(=O)O)CC4)=NO3)C2)ccc1OCc1ccccc1] | 494.2 |
| 34 | 1-(2-((7-Ethoxy-2,2-methyl-2,3-dihydro-1-benzofuran-5-yl)methyl)-5-oxa-2,6-diazaspiro[3.4]oct-6-en-7-yl)-4-methylpiperidine-4-carboxylic acid | 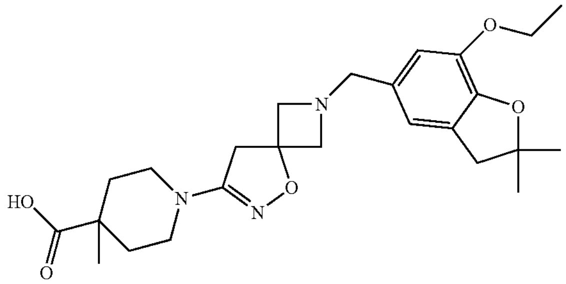 [SMILES: CCOc1cc(CN2CC3(CC(N4CCC(C)(C(=O)O)CC4)=NO3)C2)cc2c1OC(C)(C)C2] | 458.2 |
| 35 | 1-(2-(3,5-Dibromobenzyl)-5-oxa-2,6-diazaspiro[3.4]oct-6-en-7-yl)-4-methylpiperidine-4-carboxylic acid | 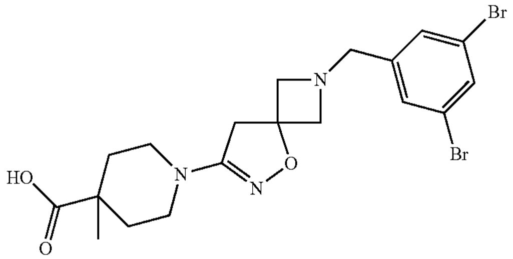 [SMILES: CC1(C(=O)O)CCN(C2=NOC3(C2)CN(Cc2cc(Br)cc(Br)c2)C3)CC1] | 502 |

TABLE 1-continued

| Example No. | IUPAC Name | Structure | MS, NMR |
|---|---|---|---|
| 36 | 1-(2-(4-Chloro-5-methoxybenzyl)-5-oxa-2,6-diazaspiro[3.4]oct-6-en-7-yl)-4-methylpiperidine-4-carboxylic acid | 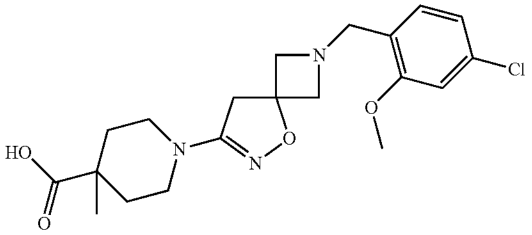 [SMILES: COc1cc(Cl)ccc1CN1CC2(CC(N3CCC(C)(C(=O)O)CC3)=NO2)C1] | 408 |
| 37 | 1-(2-(3-Bromobenzyl)-5-oxa-2,6-diazaspiro[3.4]oct-6-en-7-yl)-4-methylpiperidine-4-carboxylic acid | 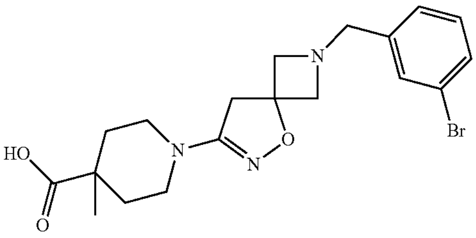 [SMILES: CC1(C(=O)O)CCN(C2=NOC3(C2)CN(Cc2cccc(Br)c2)C3)CC1] | 421.9 |
| 38 | 1-(2-((2-Anilino-4-chloro-1,3-thiazol-5-yl)methyl)-5-oxa-2,6-diazaspiro[3.4]oct-6-en-7-yl)-4-methylpiperidine-4-carboxylic acid | 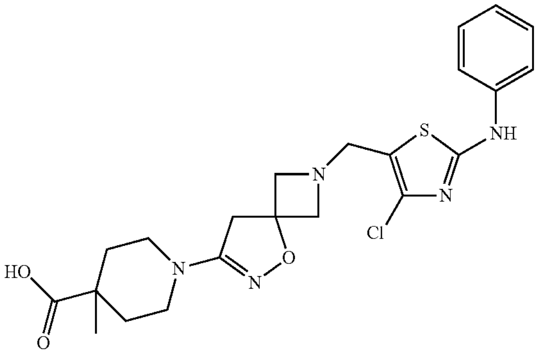 [SMILES: CC1(C(=O)O)CCN(C2=NOC3(C2)CN(Cc2sc(Nc4ccccc4)nc2Cl)C3)CC1] | 474.2 |
| 39 | 1-(2-(3-Ethoxy-4-((5-methyl-2-phenyl-1,3-oxazol-4-yl)methoxy)benzyl)-5-oxa-2,6-diazaspiro[3.4]oct-6-en-7-yl)-4-methylpiperidine-4-carboxylic acid | 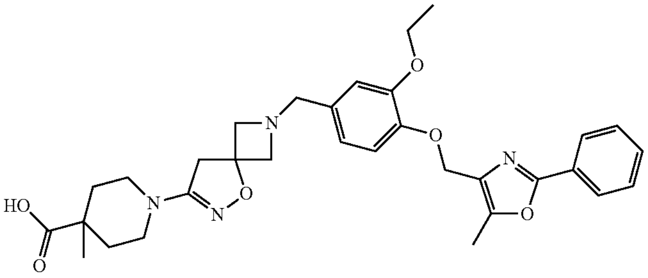 [SMILES: CCOc1cc(CN2CC3(CC(N4CCC(C)(C(=O)O)CC4)=NO3)C2)ccc1OCc1nc(-c2ccccc2)oc1C] | 573.4 |
| 40 | 1-(2-((2-Cyclopropyl-7-ethoxy-1-benzofuran-5-yl)methyl-5-oxa-2,6-diazaspiro[3.4]oct-6-en-7-yl)-4-methylpiperidine-4-carboxylic acid | 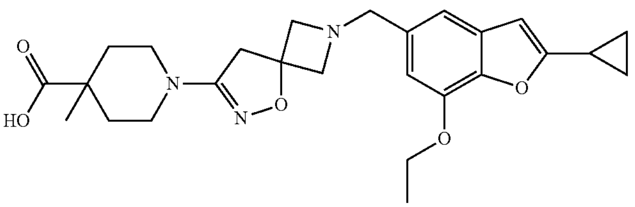 [SMILES: CCOc1cc(CN2CC3(CC(N4CCC(C)(C(=O)O)CC4)=NO3)C2)cc2cc(C3CC3)oc12] | 468.2 |
| 41 | 1-(2-(3-Chloro-5-ethoxy-4-(2,2,2-trifluoroethoxy)benzyl)-5-oxa-2,6-diazaspiro[3.4]oct-6-en-7-yl)-4-methylpiperidine-4-carboxylic acid | 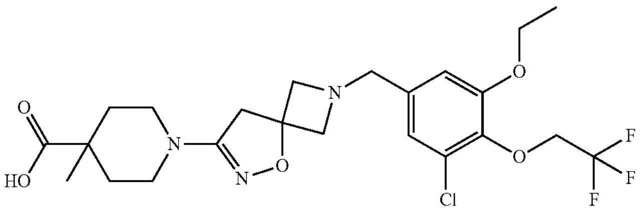 [SMILES: CCOc1cc(CN2CC3(CC(N4CCC(C)(C(=O)O)CC4)=NO3)C2)cc(Cl)c1OCC(F)(F)F] | 520.2 |

TABLE 1-continued

| Example No. | IUPAC Name | Structure | MS, NMR |
|---|---|---|---|
| 42 | 1-(2-((2-Ethoxy-6-ethyl-4'-fluoro-biphenyl-4-yl)methyl)-5-oxa-2,6-diazaspiro[3.4]oct-6-en-7-yl)-4-methylpiperidine-4-carboxylic acid | 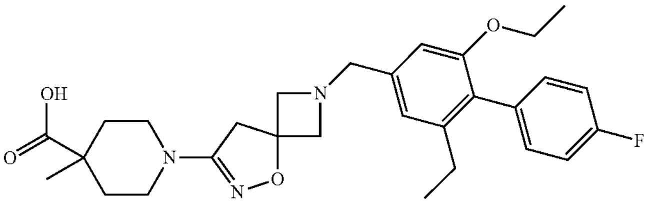 [SMILES: CCOc1cc(CN2CC3(CC(N4CCC(C)(C(=O)O)CC4)=NO3)C2)cc(CC)c1-c1ccc(F)cc1] | 510.5 |
| 43 | 1-(2-((2-Chloro-6-ethyl-4'-fluoro-biphenyl-4-yl)methyl)-5-oxa-2,6-diazaspiro[3.4]oct-6-en-7-yl)-4-methylpiperidine-4-carboxylic acid | 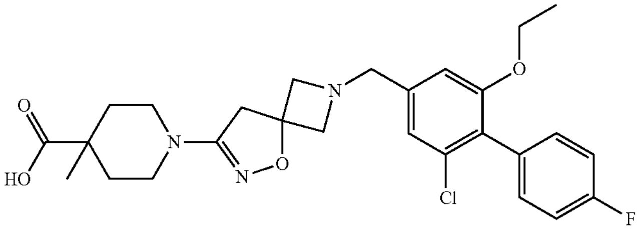 [SMILES: CCOc1cc(CN2CC3(CC(N4CCC(C)(C(=O)O)CC4)=NO3)C2)cc(Cl)c1-c1ccc(F)cc1] | 516.2 |
| 44 | 1-(2-(4-(Benzyloxy)-3-chloro-5-ethoxy-benzyl)-5-oxa-2,6-diazaspiro[3.4]oct-6-en-7-yl)-4-methylpiperidine-4-carboxylic acid | 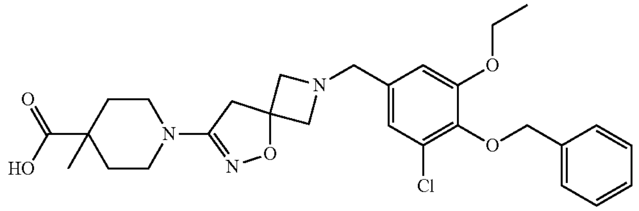 [SMILES: CCOc1cc(CN2CC3(CC(N4CCC(C)(C(=O)O)CC4)=NO3)C2)cc(Cl)c1OCc1ccccc1] | 528.3 |
| 45 | 1-(2-(3,5-Diethoxy-4-(morpholin-4-yl)benzyl)-5-oxa-2,6-diazaspiro[3.4]oct-6-en-7-yl)-4-methylpiperidine-4-carboxylic acid | 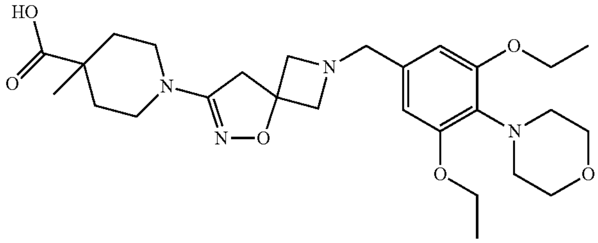 [SMILES: CCOc1cc(CN2CC3(CC(N4CCC(C)(C(=O)O)CC4)=NO3)C2)cc(OCC)c1N1CCOCC1] | 517.5 |
| 46 | 1-(2-((7-(4-Fluoro-phenyl)-2,2-dimethyl-2,3-dihydro-1-benzo-furan-4-yl)methyl)-5-oxa-2,6-diazaspiro[3.4]oct-6-en-7-yl)-4-methylpiperidine-4-carboxylic acid | 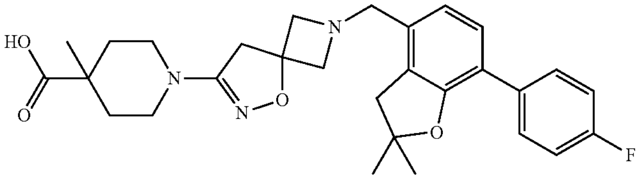 [SMILES: CC1(C)Cc2c(CN3CC4(CC(N5CCC(C)(C(=O)O)CC5)=NO4)C3)ccc(-c3ccc(F)cc3)c2O1] | 508.6 |
| 47 | cis-4-(2-((2,6-Diethoxy-4'-fluoro-biphenyl-4-yl)methyl)-5-oxo-2,6-diazaspiro[3.4]oct-6-en-7-yl)cyclo-hexanecarboxylic acid | 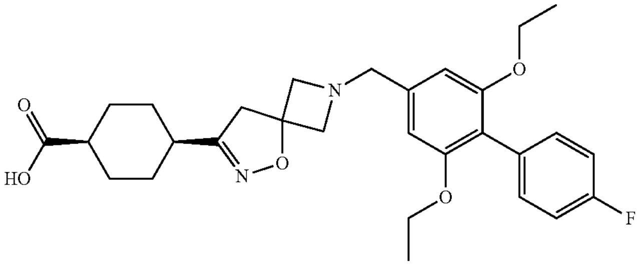 [SMILES: CCOc1cc(CN2CC3(CC([C@H]4CC[C@@H](C(=O)O)CC4)=NO3)C2)cc(OCC)c1-c1ccc(F)cc1] | 511.3 |

TABLE 1-continued

| Example No. | IUPAC Name | Structure | MS, NMR |
|---|---|---|---|
| 48 | trans-4-(2-((2-Chloro-6-ethoxy-4'-fluorobiphenyl-4-yl)methyl)-5-oxo-2,6-diazaspiro[3.4]oct-6-en-7-yl)cyclohexanecarboxylic acid | 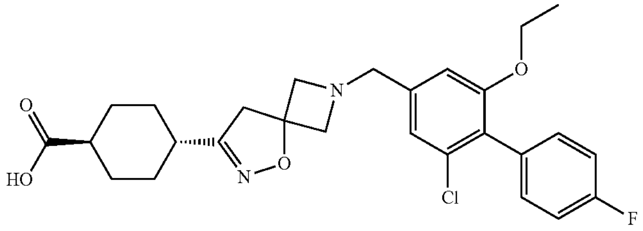 [SMILES: CCOc1cc(CN2CC3(CC([C@H]4CC[C@H](C(=O)O)CC4)=NO3)C2)cc(Cl)c1-c1ccc(F)cc1] | 501.4 |
| 49 | 1-(2-(3,5-Diethoxy-4-(1-methyl-1H-pyrazol-4-yl)benzyl)-5-oxa-2,6-diazaspiro[3.4]oct-6-en-7-yl)-4-methylpiperidine-4-carboxylic acid | 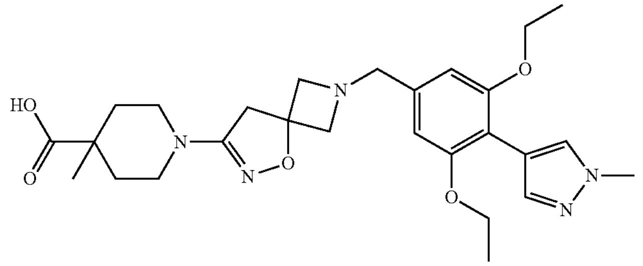 [SMILES: CCOc1cc(CN2CC3(CC(N4CCC(C)(C(=O)O)CC4)=NO3)C2)cc(OCC)c1-c1cnn(C)c1] | 512.3 |
| 50 | 1-(2-(4-(1,3-Dimethyl-1H-pyrazol-4-yl)-3,5-diethoxybenzyl)-5-oxa-2,6-diazaspiro[3.4]oct-6-en-7-yl)-4-methylpiperidine-4-carboxylic acid | 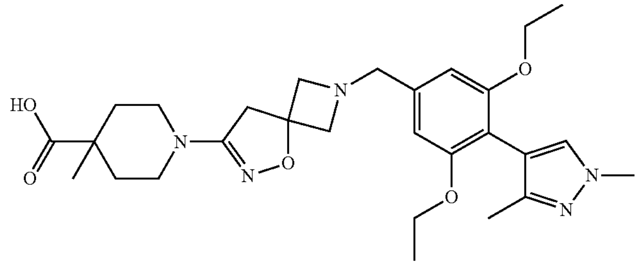 [SMILES: CCOc1cc(CN2CC3(CC(N4CCC(C)(C(=O)O)CC4)=NO3)C2)cc(OCC)c1-c1cn(C)nc1C] | 526.3 |
| 51 | 1-(2-(4-(1,5-Dimethyl-1H-pyrazol-4-yl)-3,5-diethoxybenzyl)-5-oxa-2,6-diazaspiro[3.4]oct-6-en-7-yl)-4-methylpiperidine-4-carboxylic acid | 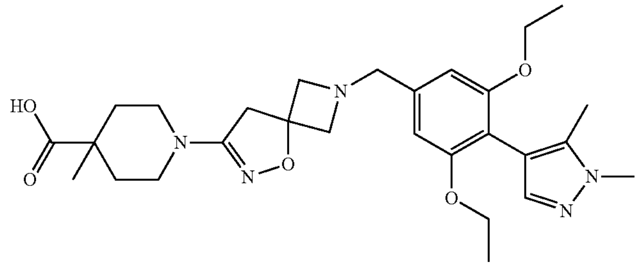 [SMILES: CCOc1cc(CN2CC3(CC(N4CCC(C)(C(=O)O)CC4)=NO3)C2)cc(OCC)c1-c1cnn(C)c1C] | 526.3 |
| 52 | 1-(2-(3,5-Diethoxy-4-(1-methyl-1H-pyrazol-3-yl)benzyl)-5-oxa-2,6-diazaspiro[3.4]oct-6-en-7-yl)-4-methylpiperidine-4-carboxylic acid | 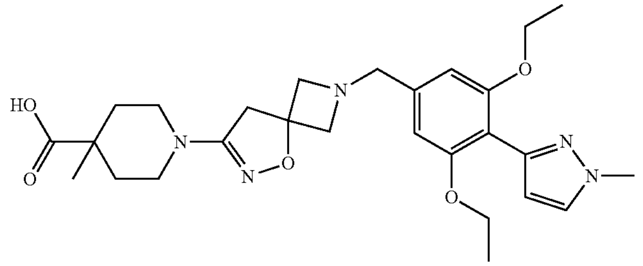 [SMILES: CCOc1cc(CN2CC3(CC(N4CCC(C)(C(=O)O)CC4)=NO3)C2)cc(OCC)c1-c1ccn(C)n1] | 512.2 |

TABLE 1-continued

| Example No. | IUPAC Name | Structure | MS, NMR |
|---|---|---|---|
| 53 | 1-(2-(4-(3,5-Dimethyl-1,2-oxazol-4-yl)-3,5-diethoxy-benzyl)-5-oxa-2,6-diazaspiro[3.4]oct-6-en-7-yl)-4-methylpiperidine-4-carboxylic acid | 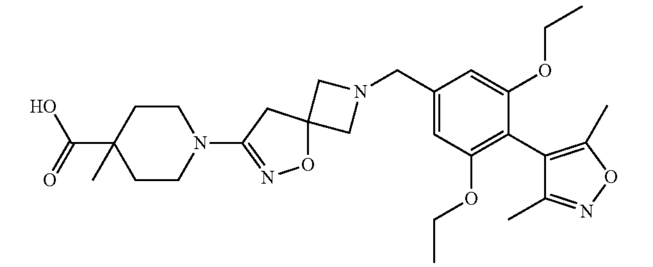 [SMILES: CCOc1cc(CN2CC3(CC(N4CCC(C)(C(=O)O)CC4)=NO3)C2)cc(OCC)c1-c1c(C)noc1C] | 527.3 |
| 54 | 1-(2-(4-(2,4-Dimethyl-1,3-thiazol-5-yl)-3,5-diethoxy-benzyl)-5-oxa-2,6-diazaspiro[3.4]oct-6-en-7-yl)-4-methylpiperidine-4-carboxylic acid | 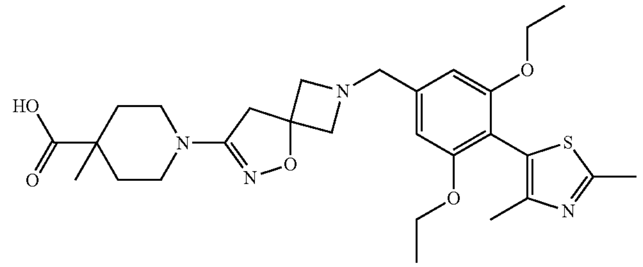 [SMILES: CCOc1cc(CN2CC3(CC(N4CCC(C)(C(=O)O)CC4)=NO3)C2)cc(OCC)c1-c1sc(C)nc1C] | 543.3 |
| 55 | 1-(2-((4'-Chloro-2,6-diethoxybiphenyl-4-yl)methyl)-5-oxa-2,6-diazaspiro[3.4]oct-6-en-7-yl)-4-methylpiperidine-4-carboxylic acid | 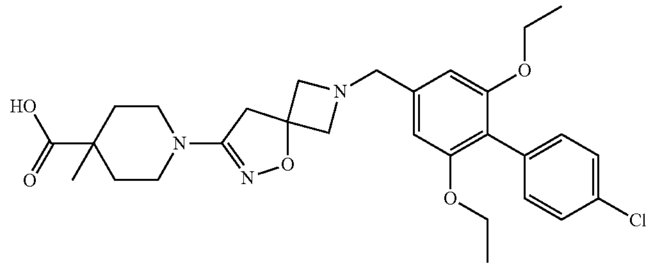 [SMILES: CCOc1cc(CN2CC3(CC(N4CCC(C)(C(=O)O)CC4)=NO3)C2)cc(OCC)c1-c1ccc(Cl)cc1] | 542.2 |
| 56 | 1-(2-((4'-Cyclo-propyl-2,6-diethoxy-biphenyl-4-yl)methyl)-5-oxa-2,6-diazaspiro[3.4]oct-6-en-7-yl)-4-methylpiperidine-4-carboxylic acid | 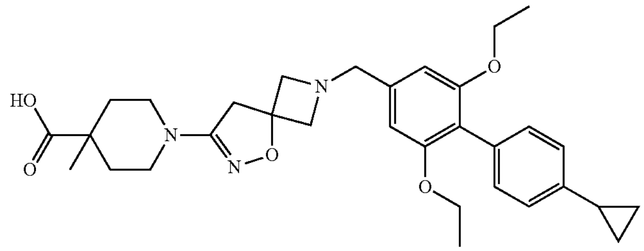 [SMILES: CCOc1cc(CN2CC3(CC(N4CCC(C)(C(=O)O)CC4)=NO3)C2)cc(OCC)c1-c1ccc(C2CC2)cc1] | 548.3 |
| 57 | 1-(2-((2,6-Diethoxy-4'-(trifluoromethyl)biphenyl-4-yl)methyl)-5-oxa-2,6-diazaspiro[3.4]oct-6-en-7-yl)-4-methylpiperidine-4-carboxylic acid | 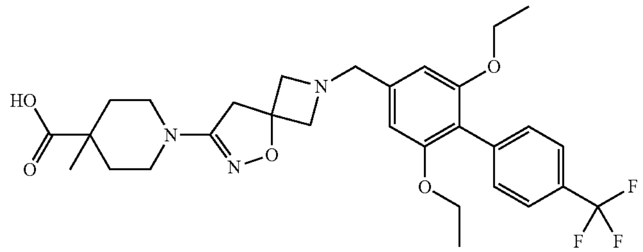 [SMILES: CCOc1cc(CN2CC3(CC(N4CCC(C)(C(=O)O)CC4)=NO3)C2)cc(OCC)c1-c1ccc(C(F)(F)F)cc1] | 576.2 |

TABLE 1-continued

| Example No. | IUPAC Name | Structure | MS, NMR |
|---|---|---|---|
| 58 | 1-(2-((2,6-Diethoxy-4'-methoxybiphenyl-4-yl)methyl)-5-oxa-2,6-diazaspiro[3.4]oct-6-en-7-yl)-4-methylpiperidine-4-carboxylic acid | 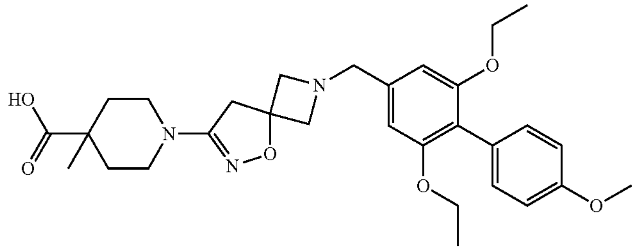 [SMILES: CCOc1cc(CN2CC3(CC(N4CCC(C)(C(=O)O)CC4)=NO3)C2)cc(OCC)c1-c1ccc(OC)cc1] | 538.3 |
| 59 | 1-(2-((4'-(Dimethylamino)-2,6-diethoxybiphenyl-4-yl)methyl)-5-oxa-2,6-diazaspiro[3.4]oct-6-en-7-yl)-4-methylpiperidine-4-carboxylic acid | 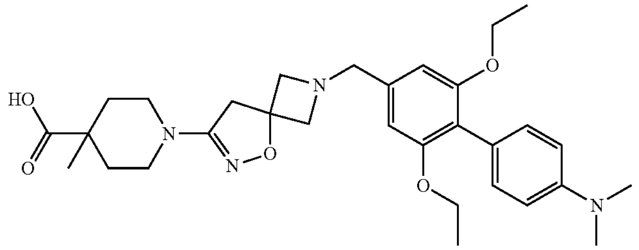 [SMILES: CCOc1cc(CN2CC3(CC(N4CCC(C)(C(=O)O)CC4)=NO3)C2)cc(OCC)c1-c1ccc(N(C)C)cc1] | 551.3 |
| 60 | 1-(2-((4'-(Cyano-2,6-diethoxybiphenyl-4-yl)methyl)-5-oxa-2,6-diazaspiro[3.4]oct-6-en-7-yl)-4-methylpiperidine-4-carboxylic acid | 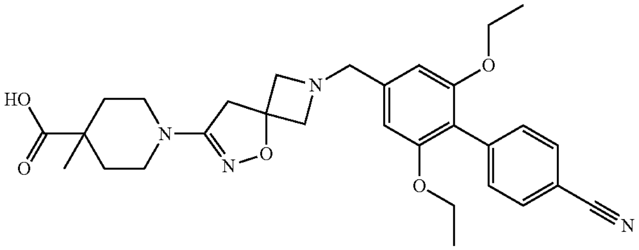 [SMILES: CCOc1cc(CN2CC3(CC(N4CCC(C)(C(=O)O)CC4)=NO3)C2)cc(OCC)c1-c1ccc(C#N)cc1] | 533.3 |
| 61 | 1-(2-((2,6-Diethoxy-4'-(methylsulfonyl)biphenyl-4-yl)methyl)-5-oxa-2,6-diazaspiro[3.4]oct-6-en-7-yl)-4-methylpiperidine-4-carboxylic acid | 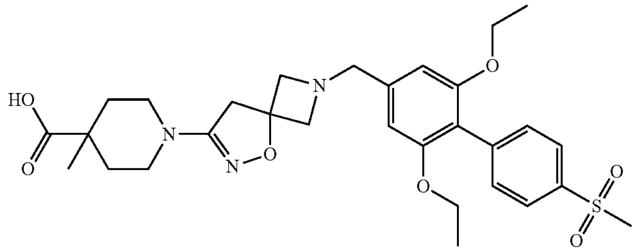 [SMILES: CCOc1cc(CN2CC3(CC(N4CCC(C)(C(=O)O)CC4)=NO3)C2)cc(OCC)c1-c1ccc(S(C)(=O)=O)cc1] | 586.3 |
| 62 | 1-(2-((2,6-Diethoxy-3'-fluorobiphenyl-4-yl)methyl)-5-oxa-2,6-diazaspiro[3.4]oct-6-en-7-yl)-4-piperidine-4-carboxylic acid | 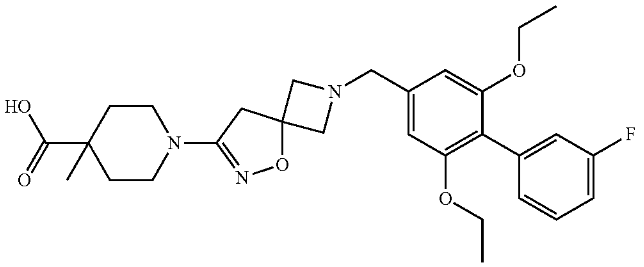 [SMILES: CCOc1cc(CN2CC3(CC(N4CCC(C)(C(=O)O)CC4)=NO3)C2)cc(OCC)c1-c1cccc(F)c1] | 526.3 |
| 63 | 1-(2-((2,6-Diethoxy-3'-(trifluoromethyl)biphenyl-4-yl)methyl)-5-oxa-2,6-diazaspiro[3.4]oct-6-en-7-yl)-4-methylpiperidine-4-carboxylic acid | 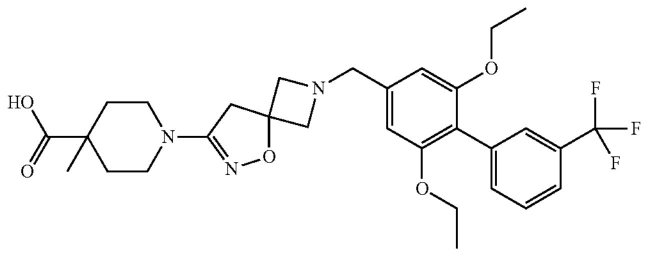 [SMILES: CCOc1cc(CN2CC3(CC(N4CCC(C)(C(=O)O)CC4)=NO3)C2)cc(OCC)c1-c1cccc(C(F)(F)F)c1] | 576.3 |

TABLE 1-continued

| Example No. | IUPAC Name | Structure | MS, NMR |
|---|---|---|---|
| 64 | 1-(2-((2,6-Diethoxy-3'-methoxybiphenyl-4-yl)methyl)-5-oxa-2,6-diazaspiro[3.4]oct-6-en-7-yl)-4-methylpiperidine-4-carboxylic acid | 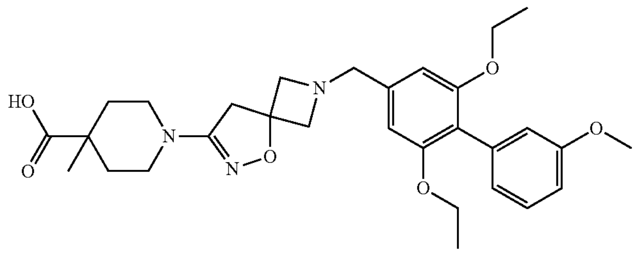 [SMILES: CCOc1cc(CN2CC3(CC(N4CCC(C)(C(=O)O)CC4)=NO3)C2)cc(OCC)c1-c1cccc(OC)c1] | 538.3 |
| 65 | 1-(2-((2,6-Diethoxy-2'-(trifluoromethyl)biphenyl-4-yl)methyl)-5-oxa-2,6-diazaspiro[3.4]oct-6-en-7-yl)-4-methylpiperidine-4-carboxylic acid | 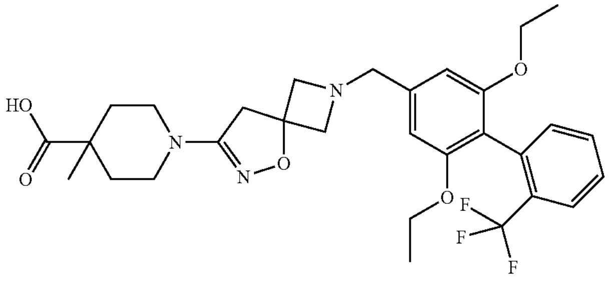 [SMILES: CCOc1cc(CN2CC3(CC(N4CCC(C)(C(=O)O)CC4)=NO3)C2)cc(OCC)c1-c1ccccc1C(F)(F)F] | 576.3 |
| 66 | 1-(2-((3',5'-Dichloro-2,6-diethoxy-biphenyl-4-yl)methyl)-5-oxa-2,6-diazaspiro[3.4]oct-6-en-7-yl)-4-methylpiperidine-4-carboxylic acid | 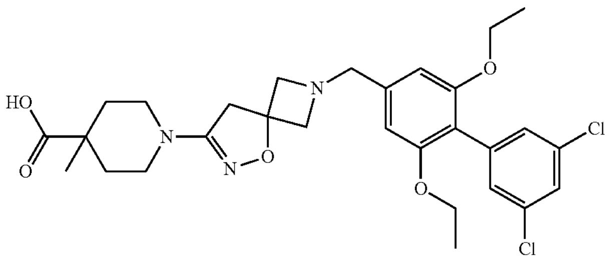 [SMILES: CCOc1cc(CN2CC3(CC(N4CCC(C)(C(=O)O)CC4)=NO3)C2)cc(OCC)c1-c1cc(Cl)cc(Cl)c1] | 576.2 |
| 67 | 1-(2-((2,6-Diethoxy-3',5'-dimethoxy-biphenyl-4-yl)methyl)-5-oxa-2,6-diazaspiro[3.4]oct-6-en-7-yl)-4-methylpiperidine-4-carboxylic acid | 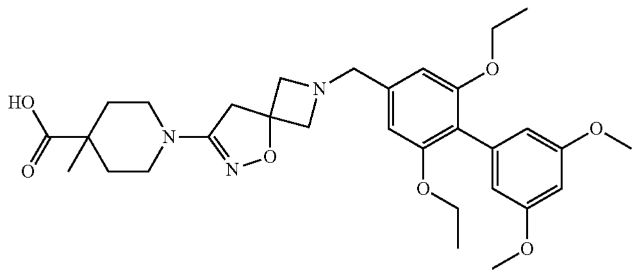 [SMILES: CCOc1cc(CN2CC3(CC(N4CCC(C)(C(=O)O)CC4)=NO3)C2)cc(OCC)c1-c1cc(OC)cc(OC)c1] | 568.3 |
| 68 | 1-(2-(3,5-Diethoxy-4-(pyrimidin-5-yl)benzyl)-5-oxa-2,6-diazaspiro[3.4]oct-6-en-7-yl)-4-methylpiperidine-4-carboxylic acid | 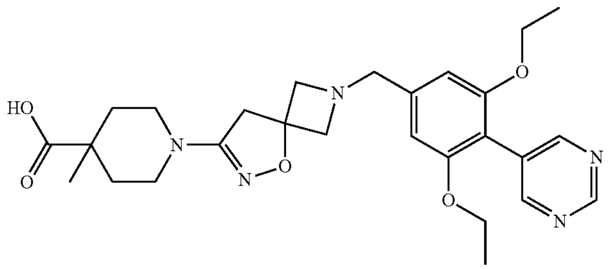 [SMILES: CCOc1cc(CN2CC3(CC(N4CCC(C)(C(=O)O)CC4)=NO3)C2)cc(OCC)c1-c1cncnc1] | 510.2 |

TABLE 1-continued

| Example No. | IUPAC Name | Structure | MS, NMR |
|---|---|---|---|
| 69 | 1-(2-(3,5-Diethoxy-4-(pyridin-3-yl)benzyl)-5-oxa-2,6-diazaspiro[3.4]oct-6-en-7-yl)-4-methylpiperidine-4-carboxylic acid | 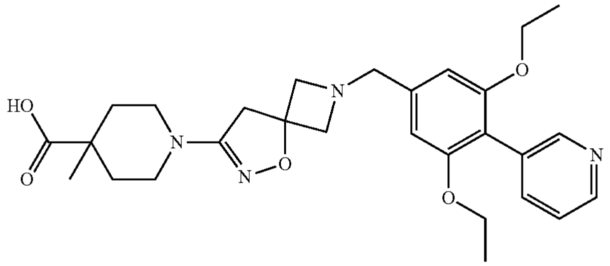 [SMILES: CCOc1cc(CN2CC3(CC(N4CCC(C)(C(=O)O)CC4)=NO3)C2)cc(OCC)c1-c1cccnc1] | 509.2 |
| 70 | 1-(2-((2,6-Diethoxy-2'-methoxybiphenyl-4-yl)methyl-5-oxa-2,6-diazaspiro[3.4]oct-6-en-7-yl)-4-methylpiperidine-4-carboxylic acid | 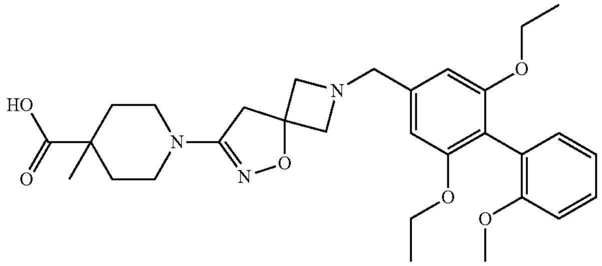 [SMILES: CCOc1cc(CN2CC3(CC(N4CCC(C)(C(=O)O)CC4)=NO3)C2)cc(OCC)c1-c1ccccc1OC] | 538.3 |
| 71 | 1-(2-(3,5-Diethoxy-4-(1H-pyrazol-4-yl)benzyl)-5-oxa-2,6-diazaspiro[3.4]oct-6-en-7-yl)-4-methylpiperidine-4-carboxylic acid | 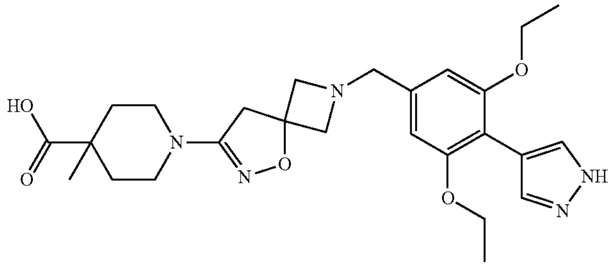 [SMILES: CCOc1cc(CN2CC3(CC(N4CCC(C)(C(=O)O)CC4)=NO3)C2)cc(OCC)c1-c1cn[nH]c1] | 498.2 |
| 72 | 1-(2-((2,6-Diethoxy-2'-fluorobiphenyl-4-yl)methyl-5-oxa-2,6-diazaspiro[3.4]oct-6-en-7-yl)-4-methylpiperidine-4-carboxylic acid | 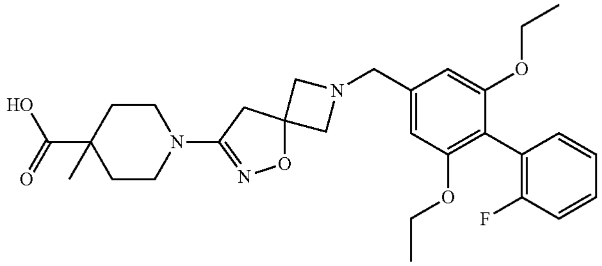 [SMILES: CCOc1cc(CN2CC3(CC(N4CCC(C)(C(=O)O)CC4)=NO3)C2)cc(OCC)c1-c1ccccc1F] | 526.3 |
| 73 | 1-(2-(4-Cyclopropyl-3,5-diethoxybenzyl)-5-oxa-2,6-diazaspiro[3.4]oct-6-en-7-yl)-4-methylpiperidine-4-carboxylic acid | 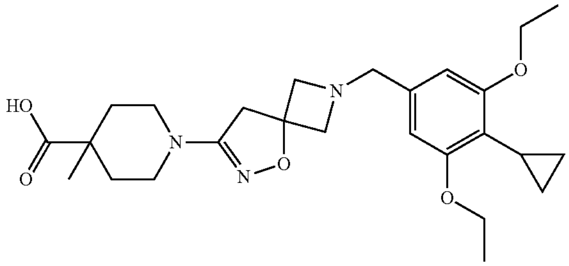 [SMILES: CCOc1cc(CN2CC3(CC(N4CCC(C)(C(=O)O)CC4)=NO3)C2)cc(OCC)c1C1CC1] | 472.1 |

TABLE 1-continued

| Example No. | IUPAC Name | Structure | MS, NMR |
|---|---|---|---|
| 74 | 1-(2-(3,5-Diethoxy-4-(5-methyl-2-thienyl)benzyl)-5-oxa-2,6-diazaspiro[3.4]oct-6-en-7-yl)-4-methylpiperidine-4-carboxylic acid | 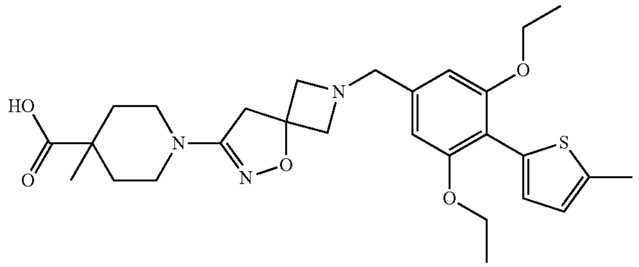 [SMILES: CCOc1cc(CN2CC3(CC(N4CCC(C)(C(=O)O)CC4)=NO3)C2)cc(OCC)c1-c1ccc(C)s1] | 528.2 |
| 75 | 1-(2-((2,6-Diethoxy-2',4'-difluoro-biphenyl-4-yl)methyl)-5-oxa-2,6-diazaspiro[3.4]oct-6-en-7-yl)-4-methylpiperidine-4-carboxylic acid | 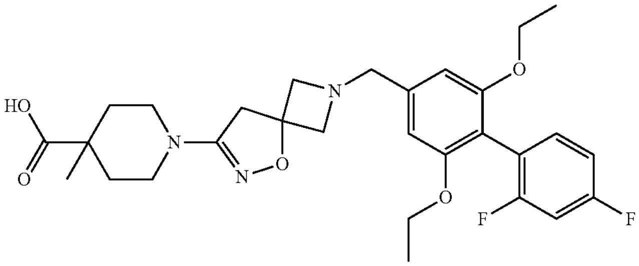 [SMILES: CCOc1cc(CN2CC3(CC(N4CCC(C)(C(=O)O)CC4)=NO3)C2)cc(OCC)c1-c1ccc(F)cc1F] | 544.3 |
| 76 | 1-(2-((2,6-Diethoxy-2',3',4'-trifluoro-biphenyl-4-yl)methyl)-5-oxa-2,6-diazaspiro[3.4]oct-6-en-7-yl)-4-methylpiperidine-4-carboxylic acid | 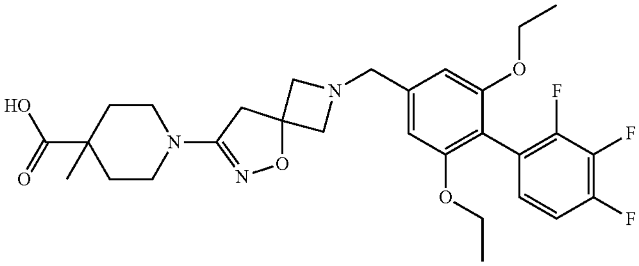 [SMILES: CCOc1cc(CN2CC3(CC(N4CCC(C)(C(=O)O)CC4)=NO3)C2)cc(OCC)c1-c1ccc(F)c(F)c1F] | 562.2 |
| 77 | 1-(2-((2,6-Diethoxy-3',4'-difluoro-biphenyl-4-yl)methyl)-5-oxa-2,6-diazaspiro[3.4]oct-6-en-7-yl)-4-methylpiperidine-4-carboxylic acid | 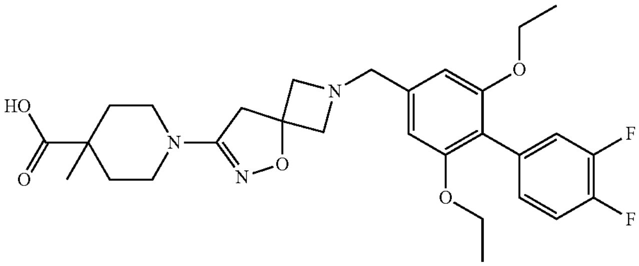 [SMILES: CCOc1cc(CN2CC3(CC(N4CCC(C)(C(=O)O)CC4)=NO3)C2)cc(OCC)c1-c1ccc(F)c(F)c1] | 544.4 |
| 78 | 1-(2-((2,6-Diethoxy-4'-fluorobiphenyl-4-yl)methyl-5-oxa-2,6-diazaspiro[3.4]oct-6-en-7-yl)-4-hydroxypiperidine-4-carboxylic acid | 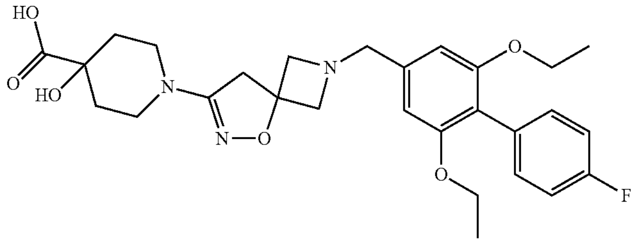 [SMILES: CCOc1cc(CN2CC3(CC(N4CCC(O)(C(=O)O)CC4)=NO3)C2)cc(OCC)c1-c1ccc(F)cc1] | 528.5 |
| 79 | 1-(2-((4'-Fluoro-2,6-dimethyl-biphenyl-4-yl)methyl-5-oxa-2,6-diazaspiro[3.4]oct-6-en-7-yl)-4-methylpiperidine-4-carboxylic acid | 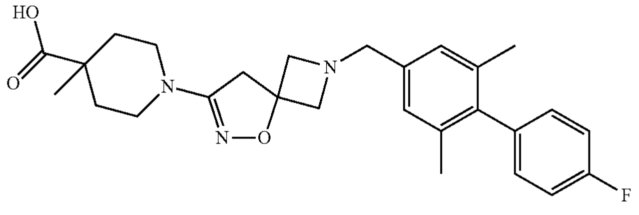 [SMILES: Cc1cc(CN2CC3(CC(N4CCC(C)(C(=O)O)CC4)=NO3)C2)cc(C)c1-c1ccc(F)cc1] | 466.4 |

TABLE 1-continued

| Example No. | IUPAC Name | Structure | MS, NMR |
|---|---|---|---|
| 80 | 4-Methyl-1-(2-((2,2,4-trimethyl-2,3-dihydro-1-benzofuran-6-yl)methyl)-5-oxa-2,6-diazaspiro[3.4]oct-6-en-7-yl)piperidine-4-carboxylic acid | 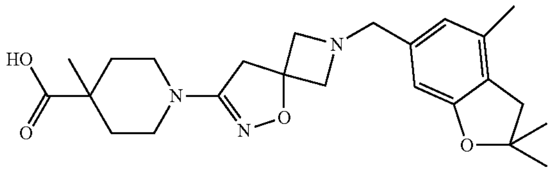 [SMILES: Cc1cc(CN2CC3(CC(N4CCC(C)(C(=O)O)CC4)=NO3)C2)cc2c1CC(C)(C)O2] | 428.4 |
| 81 | 1-(2-((2,6-Diethoxy-4'-fluorobiphenyl-4-yl)methyl-5-oxa-2,6-diazaspiro[3.4]oct-6-en-7-yl)-4-methoxypiperidine-4-carboxylic acid | 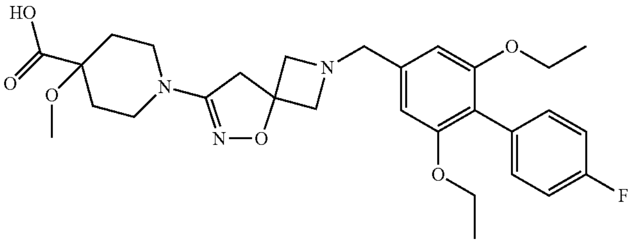 [SMILES: CCOc1cc(CN2CC3(CC(N4CCC(OC)(C(=O)O)CC4)=NO3)C2)cc(OCC)c1-c1ccc(F)cc1] | 542.5 |
| 82 | 1-(2-((4-(4-Fluorophenyl)-1-isopropyl-1H-Indol-3-yl)methyl)-5-oxa-2,6-diazaspiro[3.4]oct-6-en-7-yl)-4-methylpiperidine-4-carboxylic acid | 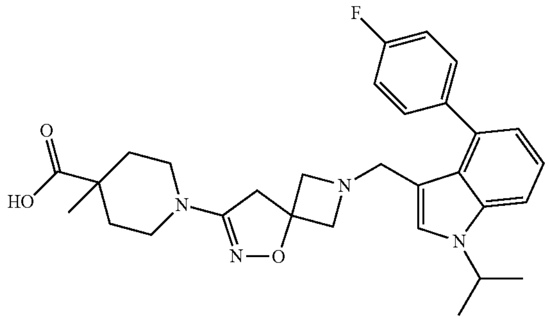 [SMILES: CC(C)n1cc(CN2CC3(CC(N4CCC(C)(C(=O)O)CC4)=NO3)C2)c2c(-c3ccc(F)cc3)cccc21] | 519.5 |
| 83 | 1-(2-(3-Chloro-4-(cyclopentyloxy)-5-ethoxybenzyl)-5-oxa-2,6-diazaspiro[3.4]oct-6-en-7-yl)-4-methylpiperidine-4-carboxylic acid | 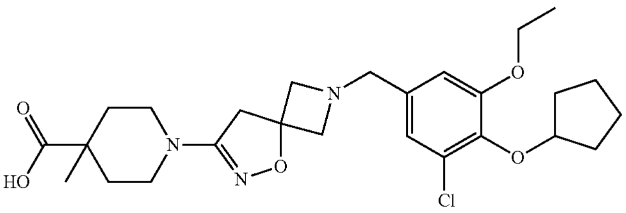 [SMILES: CCOc1cc(CN2CC3(CC(N4CCC(C)(C(=O)O)CC4)=NO3)C2)cc(Cl)c1OC1CCCC1] | 506.2 |
| 84 | 1-(2-((5-Cyclopropyl-2-ethoxy-4'-fluorobiphenyl-4-yl)methyl-5-oxa-2,6-diazaspiro[3.4]oct-6-en-7-yl)-4-methylpiperidine-4-carboxylic acid | 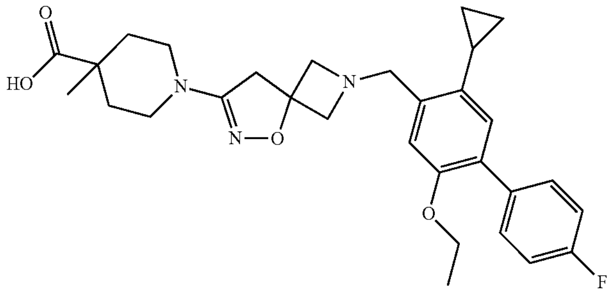 [SMILES: CCOc1cc(CN2CC3(CC(N4CCC(C)(C(=O)O)CC4)=NO3)C2)c(C2CC2)cc1-c1ccc(F)cc1] | 522.5 |
| 85 | 1-(2-((3-Cyclopropyl-1-ethyl-4-(2,2,2-trifluoroethoxy)-1H-indol-6-yl)methyl)-5-oxa-2,6-diazaspiro[3.4]oct-6-en-7-yl)-4-methylpiperidine-4-carboxylic acid | 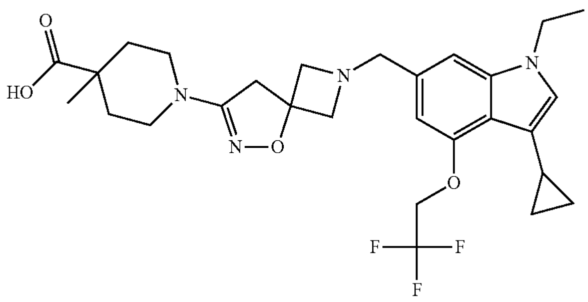 [SMILES: CCn1cc(C2CC2)c2c(OCC(F)(F)F)cc(CN3CC4(CC(N5CCC(C)(C(=O)O)CC5)=NO4)C3)cc21] | 549.5 |

TABLE 1-continued

| Example No. | IUPAC Name | Structure | MS, NMR |
|---|---|---|---|
| 86 | 1-(2-((5-Bromo-2-ethoxy-4'-fluorobiphenyl-4-yl)methyl-5-oxa-2,6-diazaspiro[3.4]oct-6-en-7-yl)-4-methylpiperidine-4-carboxylic acid | 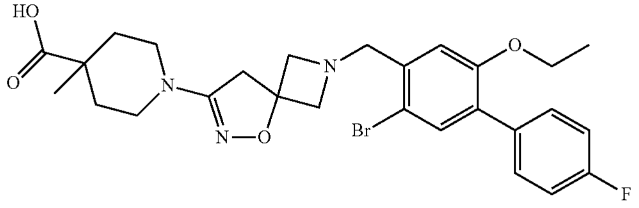 [SMILES: CCOc1cc(CN2CC3(CC(N4CCC(C)(C(=O)O)CC4)=NO3)C2)c(Br)cc1-c1ccc(F)cc1] | 561.4 |
| 87 | 1-(2-((2-Ethoxy-4'-fluoro-6-(trifluoromethyl)biphenyl-4-yl)methyl-5-oxa-2,6-diazaspiro[3.4]oct-6-en-7-yl)-4-methylpiperidine-4-carboxylic acid | 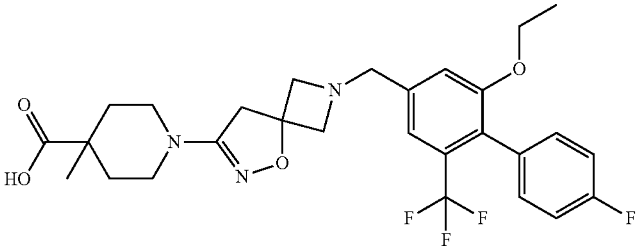 [SMILES: CCOc1cc(CN2CC3(CC(N4CCC(C)(C(=O)O)CC4)=NO3)C2)cc(C(F)(F)F)c1-c1ccc(F)cc1] | 550.2 |
| 88 | 1-(2-((2-Cyclopropyl-4'-fluoro-6-(2,2,2-(trifluoroethoxy)biphenyl-4-yl)methyl-5-oxa-2,6-diazaspiro[3.4]oct-6-en-7-yl)-4-methylpiperidine-4-carboxylic acid | 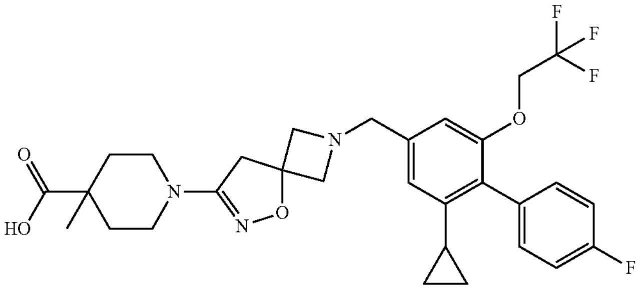 [SMILES: CC1(C(=O)O)CCN(C2=NOC3(C2)CN(Cc2cc(OCC(F)(F)F)c(-c4ccc(F)cc4)c(C4CC4)c2)C3)CC1] | 576.2 |
| 89 | 1-(2-((1-Ethyl-4-(2,2,2-(trifluoroethoxy)-1H-indol-6-yl)methyl)-5-oxa-2,6-diazaspiro[3.4]oct-6-en-7-yl)-4-methylpiperidine-4-carboxylic acid | 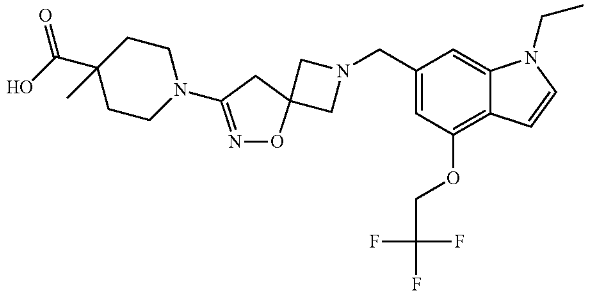 [SMILES: CCn1ccc2c(OCC(F)(F)F)cc(CN3CC4(CC(N5CCC(C)(C(=O)O)CC5)=NO4)C3)cc21] | 509.4 |
| 90 | 1-(2-((2,2'-Diethoxy-4'-fluorobiphenyl-4-yl)methyl)-5-oxa-2,6-diazaspiro[3.4]oct-6-en-7-yl)-4-piperidine-4-carboxylic acid | 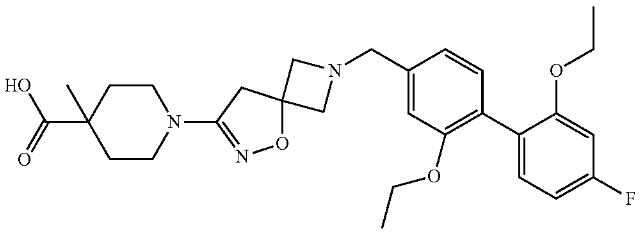 [SMILES: CCOc1cc(F)ccc1-c1ccc(CN2CC3(CC(N4CCC(C)(C(=O)O)CC4)=NO3)C2)cc1OCC] | 526.5 |
| 91 | 1-(2-((2,6-Diethoxy-4'-fluoro-3-iodobiphenyl-4-yl)methyl)-5-oxa-2,6-diazaspiro[3.4]oct-6-en-7-yl)-4-methylpiperidine-4-carboxylic acid | 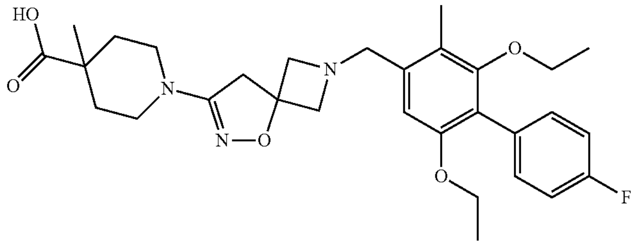 [SMILES: CCOc1cc(CN2CC3(CC(N4CCC(C)(C(=O)O)CC4)=NO3)C2)c(C)c(OCC)c1-c1ccc(F)cc1] | 652.4 |

TABLE 1-continued

| Example No. | IUPAC Name | Structure | MS, NMR |
|---|---|---|---|
| 92 | 1-(2-((3-Cyclopropyl-2,6-diethoxy-4'-fluorobiphenyl-4-yl)methyl)-5-oxa-2,6-diazaspiro[3.4]oct-6-en-7-yl)-4-methylpiperidine-4-carboxylic acid | 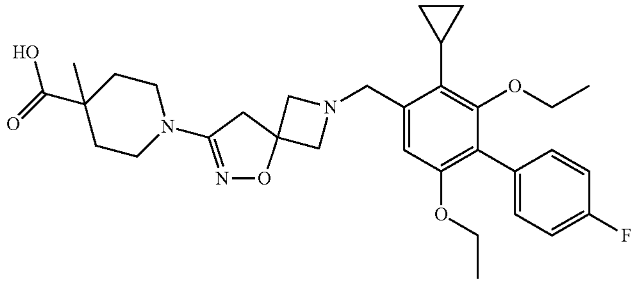 [SMILES: CCOc1cc(CN2CC3(CC(N4CCC(C)(C(=O)O)CC4)=NO3)C2)c(C2CC2)c(OCC)c1-c1ccc(F)cc1] | 566.5 |
| 93 | 1-(2-((2-Cyclopropyl-6-(cyclopropyl-methoxy)-4'-fluorobiphenyl-4-yl)methyl)-5-oxa-2,6-diazaspiro[3.4]oct-6-en-7-yl)-4-methylpiperidine-4-carboxylic acid | 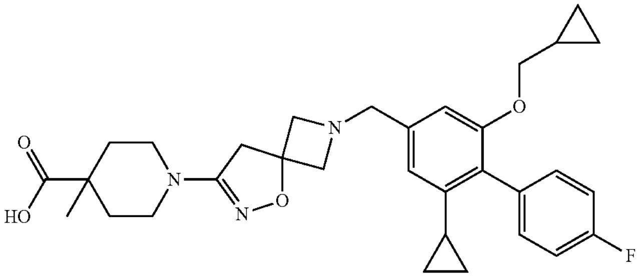 [SMILES: CC1(C(=O)O)CCN(C2=NOC3(C2)CN(Cc2cc(OCC4CC4)c(-c4ccc(F)cc4)c(C4CC4)c2)C3)CC1] | 548.3 |
| 94 | 1-(2-((2-Cyclopropyl-4'-fluoro-6-propoxy-biphenyl-4-yl)methyl)-5-oxa-2,6-diazaspiro[3.4]oct-6-en-7-yl)-4-methylpiperidine-4-carboxylic acid | 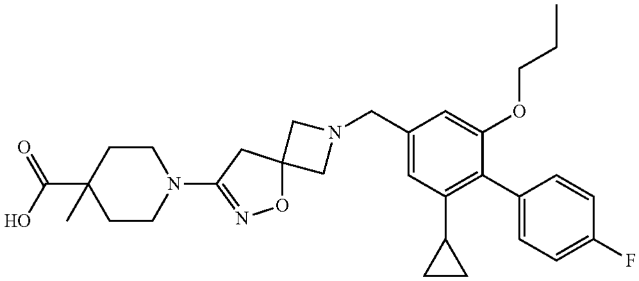 [SMILES: CCCOc1cc(CN2CC3(CC(N4CCC(C)(C(=O)O)CC4)=NO3)C2)cc(C2CC2)c1-c1ccc(F)cc1] | 536.5 |
| 95 | 1-(2-((2-Cyclopropyl-6-(2,2-difluoro-ethoxy)-4'-fluorobiphenyl-4-yl)methyl)-5-oxa-2,6-diazaspiro[3.4]oct-6-en-7-yl)-4-methylpiperidine-4-carboxylic acid | 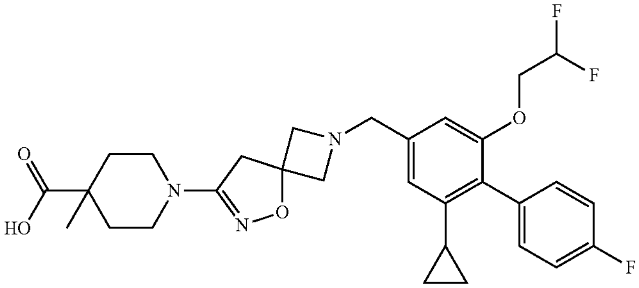 [SMILES: CC1(C(=O)O)CCN(C2=NOC3(C2)CN(Cc2cc(OCC(F)F)c(-c4ccc(F)cc4)c(C4CC4)c2)C3)CC1] | 558.3 |
| 96 | 1-(2-((2'-(Benzyloxy)-2-ethoxy-4'-fluorobiphenyl-4-yl)methyl)-5-oxa-2,6-diazaspiro[3.4]oct-6-en-7-yl)-4-methylpiperidine-4-carboxylic acid | 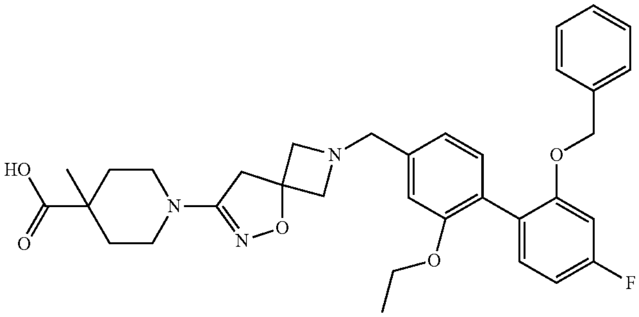 [SMILES: CCOc1cc(CN2CC3(CC(N4CCC(C)(C(=O)O)CC4)=NO3)C2)ccc1-c1ccc(F)cc1OCc1ccccc1] | 588.5 |

TABLE 1-continued

| Example No. | IUPAC Name | Structure | MS, NMR |
|---|---|---|---|
| 97 | 1-(2-((2-Cyano-6-ethoxy-4'-fluorobiphenyl-4-yl)methyl)-5-oxa-2,6-diazaspiro[3.4]oct-6-en-7-yl)-4-methylpiperidine-4-carboxylic acid | 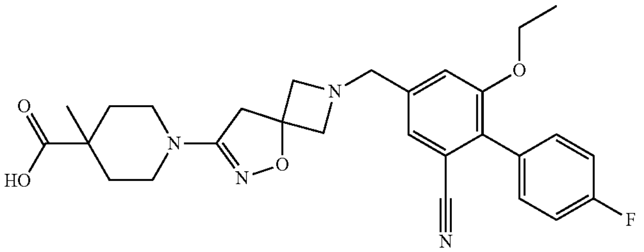 [SMILES: CCOc1cc(CN2CC3(CC(N4CCC(C)(C(=O)O)CC4)=NO3)C2)cc(C#N)c1-c1ccc(F)cc1] | 507.4 |
| 98 | 1-(2-(4-(3,5-Difluoro-pyridin-2-yl)-3,5-diethoxybenzyl)-5-oxa-2,6-diazaspiro[3.4]oct-6-en-7-yl)-4-methylpiperidine-4-carboxylic acid | 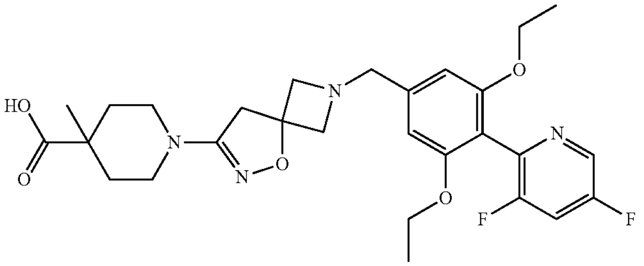 [SMILES: CCOc1cc(CN2CC3(CC(N4CCC(C)(C(=O)O)CC4)=NO3)C2)cc(OCC)c1-c1ncc(F)cc1F] | 545.3 |
| 99 | 1-(2-(3,5-Diethoxy-4-(pentafluoroethyl)benzyl)-5-oxa-2,6-diazaspiro[3.4]oct-6-en-7-yl)-4-methylpiperidine-4-carboxylic acid | 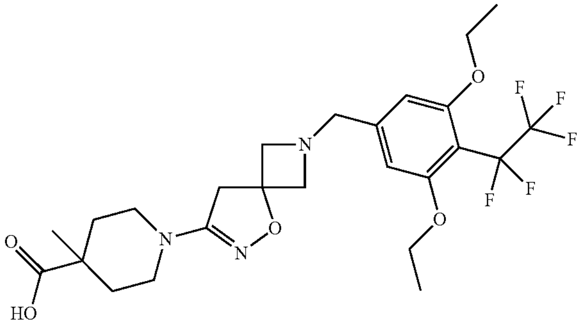 [SMILES: CCOc1cc(CN2CC3(CC(N4CCC(C)(C(=O)O)CC4)=NO3)C2)cc(OCC)c1C(F)(F)C(F)(F)F] | 550.2 |
| 100 | 1-(2-(4-Cyclobutyl-3,5-diethoxy-benzyl)-5-oxa-2,6-diazaspiro[3.4]oct-6-en-7-yl)-4-methylpiperidine-4-carboxylic acid | 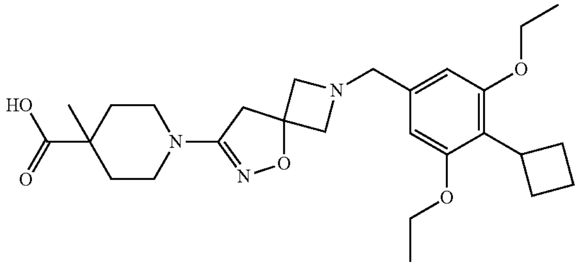 [SMILES: CCOc1cc(CN2CC3(CC(N4CCC(C)(C(=O)O)CC4)=NO3)C2)cc(OCC)c1C1CCC1] | 486.3 |
| 101 | 1-(2-((1-Benzyl-5-isopropyl-1H-pyrazolo[3,4-d][1,3]thiazol-3-yl)methyl)-5-oxa-2,6-diazaspiro[3.4]oct-6-en-7-yl)-4-methylpiperidine-4-carboxylic acid | 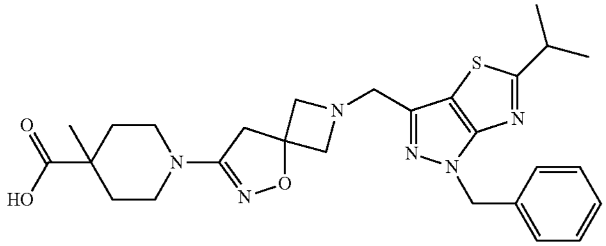 [SMILES: CC(C)c1nc2c(s1)c(CN1CC3(CC(N4CCC(C)(C(=O)O)CC4)=NO3)C1)nn2Cc1ccccc1] | 523.3 |

TABLE 1-continued

| Example No. | IUPAC Name | Structure | MS, NMR |
|---|---|---|---|
| 102 | 1-(2-((2'-(Cyclopropylmethoxy)-2-ethoxy-4'-fluorobiphenyl-4-yl)methyl)-5-oxa-2,6-diazaspiro[3.4]oct-6-en-7-yl)-4-methylpiperidine-4-carboxylic acid | 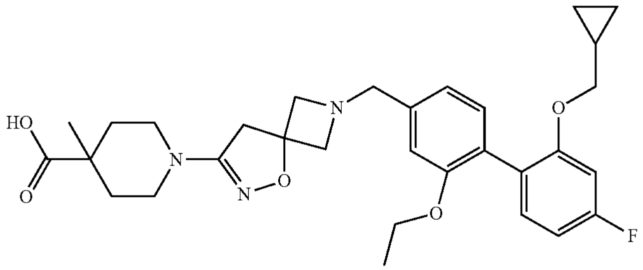 [SMILES: CCOc1cc(CN2CC3(CC(N4CCC(C)(C(=O)O)CC4)=NO3)C2)ccc1-c1ccc(F)cc1OCC1CC1] | 552.5 |
| 103 | 1-(2-((2-Ethoxy-4'-fluoro-2'-(2-methoxyethoxy)biphenyl-4-yl)methyl)-5-oxa-2,6-diazaspiro[3.4]oct-6-en-7-yl)-4-methylpiperidine-4-carboxylic acid | 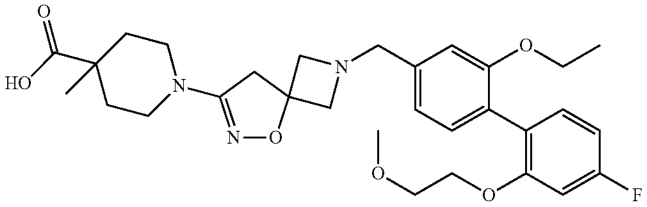 [SMILES: CCOc1cc(CN2CC3(CC(N4CCC(C)(C(=O)O)CC4)=NO3)C2)ccc1-c1ccc(F)cc1OCCOC] | 556.5 |
| 104 | 1-(2-((2-Cyclopropyl-6-((2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylic acid | 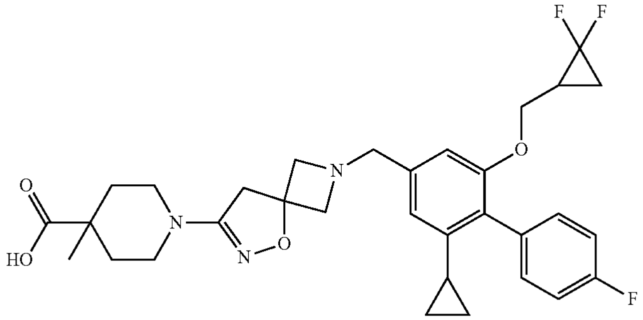 [SMILES: CC1(C(=O)O)CCN(C2=NOC3(C2)CN(Cc2cc(OCC4CC4(F)F)c(-c4ccc(F)cc4)c(C4CC4)c2)C3)CC1] | 584.3 |
| 105 | 1-(2-((3,5-Diethoxy-4-(5-fluoropyridin-2-yl)benzyl)-5-oxa-2,6-diazaspiro[3.4]oct-6-en-7-yl)-4-methylpiperidine-4-carboxylic acid | 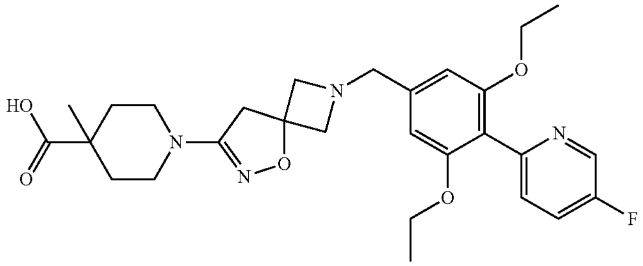 [SMILES: CCOc1cc(CN2CC3(CC(N4CCC(C)(C(=O)O)CC4)=NO3)C2)cc(OCC)c1-c1ccc(F)cn1] | 527.3 |
| 106 | 1-(2-((2-Cyclopropyl-4'-fluoro-6-(3,3,3-trifluoropropoxy)biphenyl-4-yl)methyl)-5-oxa-2,6-diazaspiro[3.4]oct-6-en-7-yl)-4-methylpiperidine-4-carboxylic acid | 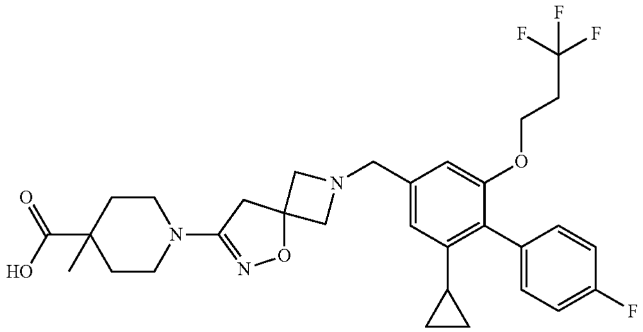 [SMILES: CC1(C(=O)O)CCN(C2=NOC3(C2)CN(Cc2cc(OCCC(F)(F)F)c(-c4ccc(F)cc4)c(C4CC4)c2)C3)CC1] | 590.2 |

TABLE 1-continued

| Example No. | IUPAC Name | Structure | MS, NMR |
| --- | --- | --- | --- |
| 107 | 1-(2-((2-Cyclobutyl-6-ethoxy-4'-fluoro-biphenyl-4-yl)methyl)-5-oxa-2,6-diazaspiro[3.4]oct-6-en-7-yl)-4-methylpiperidine-4-carboxylic acid | 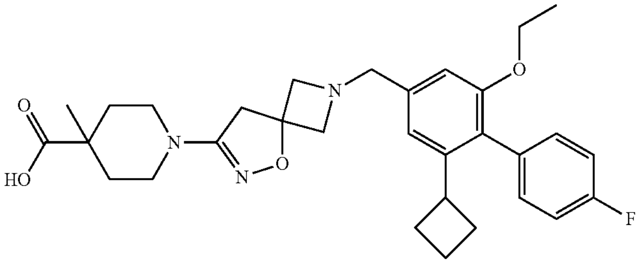 [SMILES: CCOc1cc(CN2CC3(CC(N4CCC(C)(C(=O)O)CC4)=NO3)C2)cc(C2CCC2)c1-c1ccc(F)cc1] | 536.5 |
| 108 | 1-(2-(3,5-Diethoxy-4-(1-(2,2,3,3,3-pentafluoropropyl)piperidin-4-yl)benzyl)-5-oxa-2,6-diazaspiro[3.4]oct-6-en-7-yl)-4-methyl-piperidine-4-carboxylic acid | 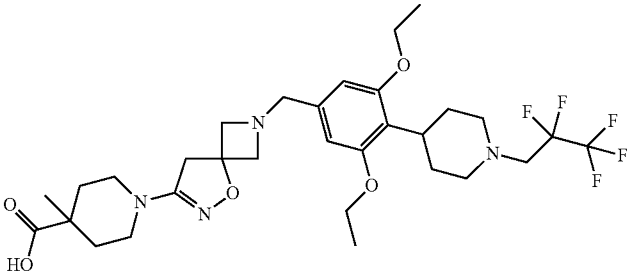 [SMILES: CCOc1cc(CN2CC3(CC(N4CCC(C)(C(=O)O)CC4)=NO3)C2)cc(OCC)c1C1CCN(CC(F)(F)C(F)(F)F)CC1] | 647.3 |
| 109 | 1-(2-((2,6-diethoxy-4'-fluorobiphenyl-4-yl)methyl)-8-methyl-5-oxa-2,6-diazaspiro[3.4]oct-6-en-7-yl)-4-methylpiperidine-4-carboxylic acid | 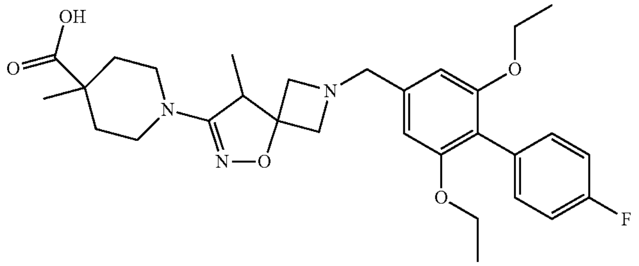 [SMILES: CCOc1cc(CN2CC3(C2)ON=C(N2CCC(C)(C(=O)O)CC2)C3C)cc(OCC)c1-c1ccc(F)cc1] | 540.5 |
| 110 | 1-(2-((2,6-diethoxy-4'-fluorobiphenyl-4-yl)methyl)-8-methyl-5-oxa-2,6-diazaspiro[3.4]oct-6-en-7-yl)-4-methylpiperidine-4-carboxylic acid | 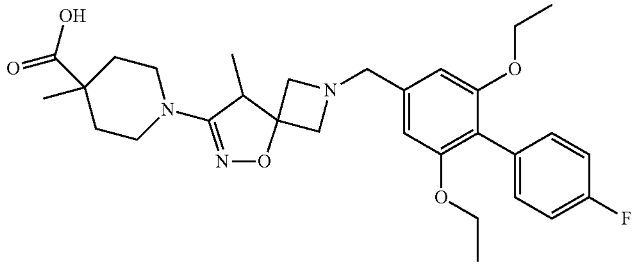 [SMILES: CCOc1cc(CN2CC3(C2)ON=C(N2CCC(C)(C(=O)O)CC2)C3C)cc(OCC)c1-c1ccc(F)cc1] | 540.5 |
| 111 | 1-(2-((2-Cyclopropyl-4'-fluoro-6-(2-methoxyethoxy)biphenyl-4-yl)methyl)-5-oxa-2,6-diazaspiro[3.4]oct-6-en-7-yl)-4-methylpiperidine-4-carboxylic acid | 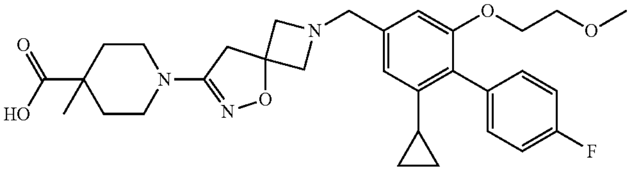 [SMILES: COCCOc1cc(CN2CC3(CC(N4CCC(C)(C(=O)O)CC4)=NO3)C2)cc(C2CC2)c1-c1ccc(F)cc1] | 552.3 |
| 112 | 1-(2-((2-(2,2-Difluorocyclopropyl)-6-ethoxy-4'-fluorobiphenyl-4-yl)methyl)-5-oxa-2,6-diazaspiro[3.4]oct-6-en-7-yl)-4-methylpiperidine-4-carboxylic acid | 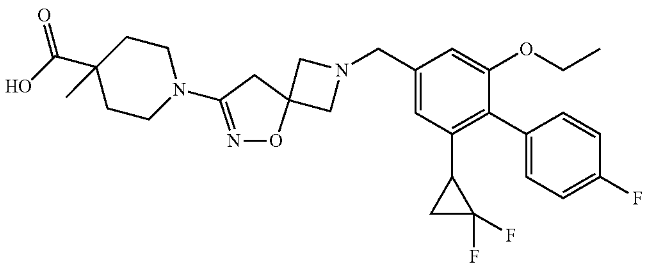 [SMILES: CCOc1cc(CN2CC3(CC(N4CCC(C)(C(=O)O)CC4)=NO3)C2)cc(C2CC2(F)F)c1-c1ccc(F)cc1] | 558.5 |

TABLE 1-continued

| Example No. | IUPAC Name | Structure | MS, NMR |
|---|---|---|---|
| 113 | trans-4-(2-((2-Cyclopropyl-4'-fluoro-5-methoxybiphenyl-4-yl)methyl)-5-oxa-2,6-diazaspiro[3.4]oct-6-en-7-yl)cyclohexanecarboxylic acid | 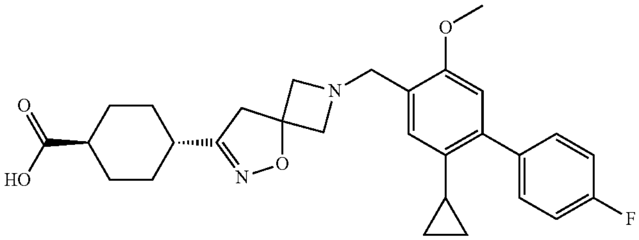 [SMILES: COc1cc(-c2ccc(F)cc2)c(C2CC2)cc1CN1CC2(CC([C@H]3CC[C@H](C(=O)O)CC3)=NO2)C1] | 493.4 |
| 114 | 1-(2-((2-Cyclopropyl-4'-fluoro-5-methoxybiphenyl-4-yl)methyl)-5-oxa-2,6-diazaspiro[3.4]oct-6-en-7-yl)-4-methylpiperidine-4-carboxylic acid | 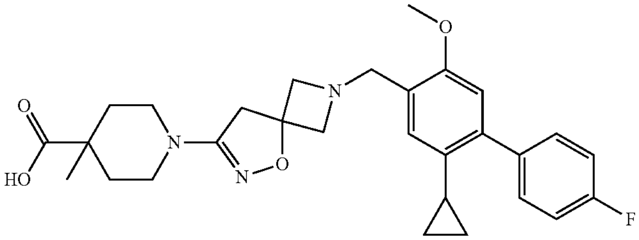 [SMILES: COc1cc(-c2ccc(F)cc2)c(C2CC2)cc1CN1CC2(CC(N3CCC(C)(C(=O)O)CC3)=NO2)C1] | 508.1 |
| 115 | 1-(2-((2-Ethoxy-4'-fluoro-2'-(3,3,3-trifluoropropoxy)biphenyl-4-yl)methyl)-5-oxa-2,6-diazaspiro[3.4]oct-6-en-7-yl)-4-methylpiperidine-4-carboxylic acid | 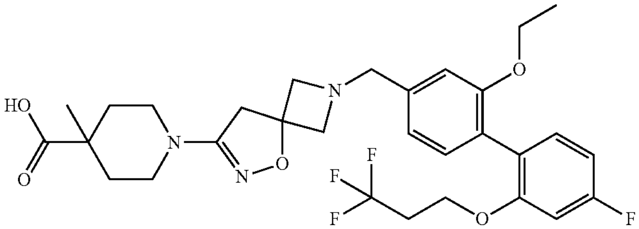 [SMILES: CCOc1cc(CN2CC3(CC(N4CCC(C)(C(=O)O)CC4)=NO3)C2)ccc1-c1ccc(F)cc1OCCC(F)(F)F] | 594.2 |
| 116 | 1-(2-((2-Ethoxy-4'-fluoro-6-(pyrrolidin-1-yl)biphenyl-4-yl)methyl)-5-oxa-2,6-diazaspiro[3.4]oct-6-en-7-yl)-4-methylpiperidine-4-carboxylic acid | 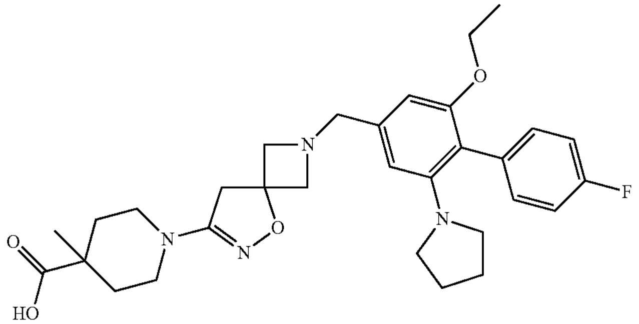 [SMILES: CCOc1cc(CN2CC3(CC(N4CCC(C)(C(=O)O)CC4)=NO3)C2)cc(N2CCCC2)c1-c1ccc(F)cc1] | 551.3 |
| 117 | 1-(2-((2-Cyclopropyl-4'-fluoro-6-(3-methoxypropoxy)biphenyl-4-yl)methyl)-5-oxa-2,6-diazaspiro[3.4]oct-6-en-7-yl)-4-methylpiperidine-4-carboxylic acid | 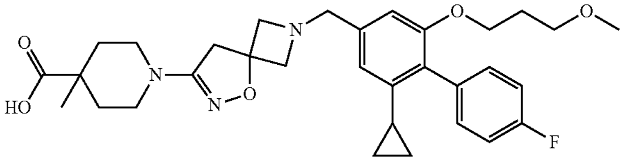 [SMILES: COCCCOc1cc(CN2CC3(CC(N4CCC(C)(C(=O)O)CC4)=NO3)C2)cc(C2CC2)c1-c1ccc(F)cc1] | 566.3 |
| 118 | 1-(2-((2-Cyclopropyl-6-ethoxy-2',4'-difluorobiphenyl-4-yl)methyl)-5-oxa-2,6-diazaspiro[3.4]oct-6-en-7-yl)-4-methylpiperidine-4-carboxylic acid | 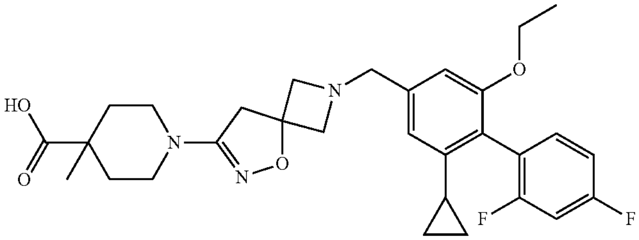 [SMILES: CCOc1cc(CN2CC3(CC(N4CCC(C)(C(=O)O)CC4)=NO3)C2)cc(C2CC2)c1-c1ccc(F)cc1F] | 540.4 |

TABLE 1-continued

| Example No. | IUPAC Name | Structure | MS, NMR |
|---|---|---|---|
| 119 | 1-(2-((2-Cyclopropyl-6-ethoxy-3',4',5'-trifluorobiphenyl-4-yl)methyl)-5-oxa-2,6-diazaspiro[3.4]oct-6-en-7-yl)-4-methylpiperidine-4-carboxylic acid | 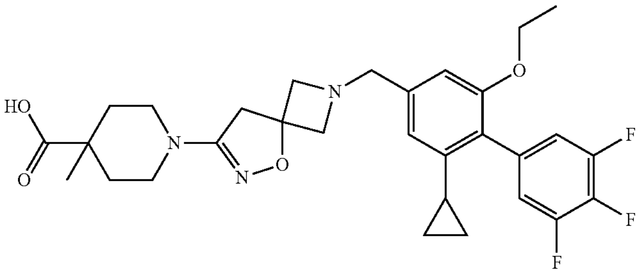 [SMILES: CCOc1cc(CN2CC3(CC(N4CCC(C)(C(=O)O)CC4)=NO3)C2)cc(C2CC2)c1-c1cc(F)c(F)c(F)c1] | 558.3 |
| 120 | 1-(2-((2-Cyclopropyl-6-ethoxy-2',3',4',5'-tetrafluorobiphenyl-4-yl)methyl)-5-oxa-2,6-diazaspiro[3.4]oct-6-en-7-yl)-4-methylpiperidine-4-carboxylic acid | 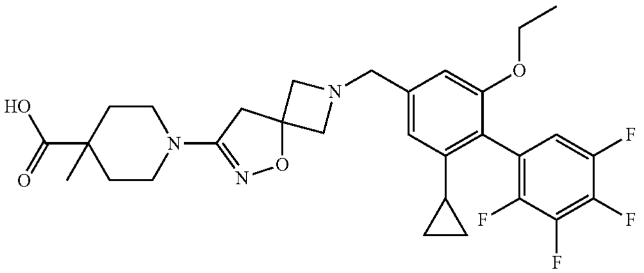 [SMILES: CCOc1cc(CN2CC3(CC(N4CCC(C)(C(=O)O)CC4)=NO3)C2)cc(C2CC2)c1-c1cc(F)c(F)c(F)c1F] | 576.2 |
| 121 | 1-(2-((2-Cyclopropyl-6-ethoxy-2',6'-difluorobiphenyl-4-yl)methyl)-5-oxa-2,6-diazaspiro[3.4]oct-6-en-7-yl)-4-methylpiperidine-4-carboxylic acid | 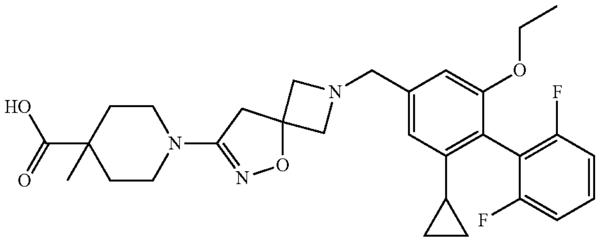 [SMILES: CCOc1cc(CN2CC3(CC(N4CCC(C)(C(=O)O)CC4)=NO3)C2)cc(C2CC2)c1-c1c(F)cccc1F] | 540.3 |
| 122 | 1-(2-((2-Cyclopropyl-6-ethoxy-2',4',5'-trifluorobiphenyl-4-yl)methyl)-5-oxa-2,6-diazaspiro[3.4]oct-6-en-7-yl)-4-methylpiperidine-4-carboxylic acid | 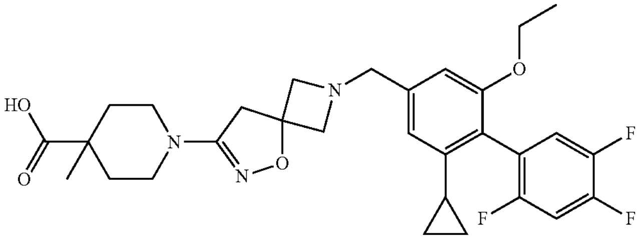 [SMILES: CCOc1cc(CN2CC3(CC(N4CCC(C)(C(=O)O)CC4)=NO3)C2)cc(C2CC2)c1-c1cc(F)c(F)cc1F] | 558.2 |
| 123 | 1-(2-((2-Cyclopropyl-6-ethoxybiphenyl-4-yl)methyl)-5-oxa-2,6-diazaspiro[3.4]oct-6-en-7-yl)-4-methylpiperidine-4-carboxylic acid | 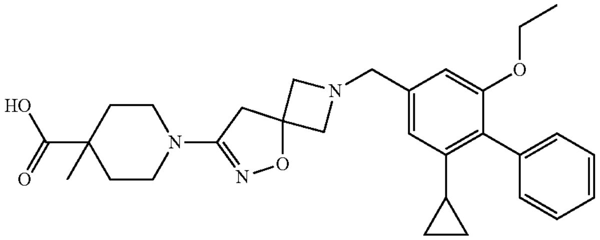 [SMILES: CCOc1cc(CN2CC3(CC(N4CCC(C)(C(=O)O)CC4)=NO3)C2)cc(C2CC2)c1-c1ccccc1] | 504.2 |
| 124 | 1-(2-((2-Cyclopropyl-6-ethoxy-4'-methylbiphenyl-4-yl)methyl)-5-oxa-2,6-diazaspiro[3.4]oct-6-en-7-yl)-4-methylpiperidine-4-carboxylic acid | 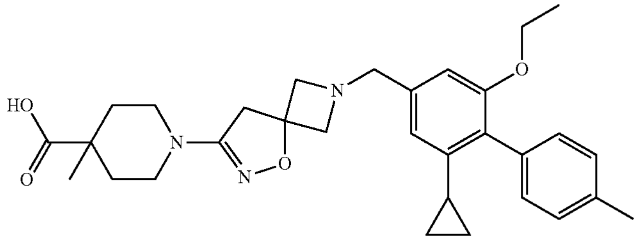 [SMILES: CCOc1cc(CN2CC3(CC(N4CCC(C)(C(=O)O)CC4)=NO3)C2)cc(C2CC2)c1-c1ccc(C)cc1] | 518.3 |

TABLE 1-continued

| Example No. | IUPAC Name | Structure | MS, NMR |
|---|---|---|---|
| 125 | 1-(2-((3'-Chloro-2-cyclopropyl-6-ethoxy-4'-fluoro-biphenyl-4-yl)methyl)-5-oxa-2,6-diazaspiro[3.4]oct-6-en-7-yl)-4-methylpiperidine-4-carboxylic acid | 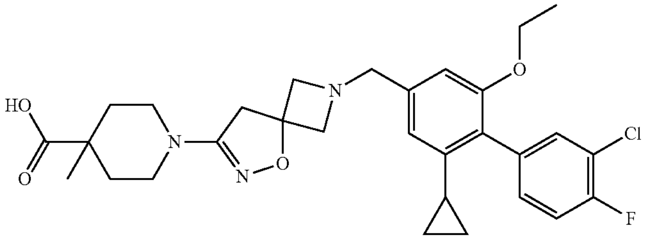 [SMILES: CCOc1cc(CN2CC3(CC(N4CCC(C)(C(=O)O)CC4)=NO3)C2)cc(C2CC2)c1-c1ccc(F)c(Cl)c1] | 556.2 |
| 126 | 1-(2-((2-Cyclopropyl-6-ethoxy-4'-fluoro-3'-methyl-biphenyl-4-yl)methyl)-5-oxa-2,6-diazaspiro[3.4]oct-6-en-7-yl)-4-methylpiperidine-4-carboxylic acid | 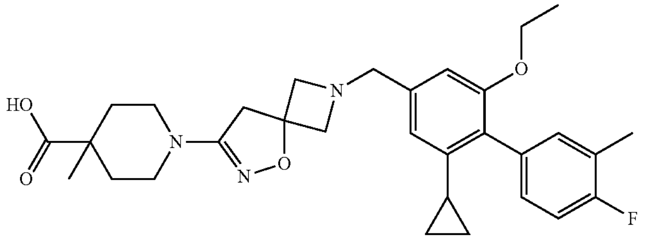 [SMILES: CCOc1cc(CN2CC3(CC(N4CCC(C)(C(=O)O)CC4)=NO3)C2)cc(C2CC2)c1-c1ccc(F)c(C)c1] | 536.3 |
| 127 | 1-(2-((2'-Chloro-2-cyclopropyl-6-ethoxy-4'-fluoro-biphenyl-4-yl)methyl)-5-oxa-2,6-diazaspiro[3.4]oct-6-en-7-yl)-4-methylpiperidine-4-carboxylic acid | 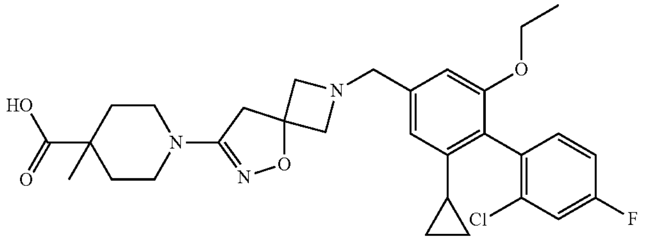 [SMILES: CCOc1cc(CN2CC3(CC(N4CCC(C)(C(=O)O)CC4)=NO3)C2)cc(C2CC2)c1-c1ccc(F)cc1Cl] | 556.2 |
| 128 | 1-(2-((2-Cyclopropyl-6-ethoxy-4'-fluoro-2'-methyl-biphenyl-4-yl)methyl)-5-oxa-2,6-diazaspiro[3.4]oct-6-en-7-yl)-4-methylpiperidine-4-carboxylic acid | 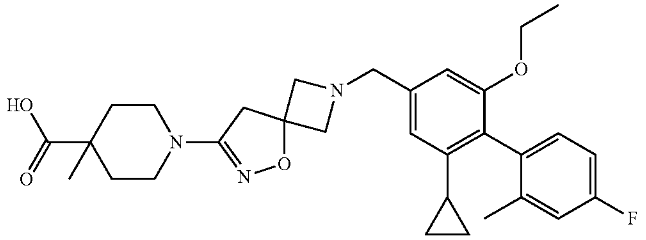 [SMILES: CCOc1cc(CN2CC3(CC(N4CCC(C)(C(=O)O)CC4)=NO3)C2)cc(C2CC2)c1-c1ccc(F)cc1C] | 536.3 |
| 129 | 1-(2-((2-Cyclopropyl-6-ethoxy-4'-fluoro-2'-(trifluoro-methyl)biphenyl-4-yl)methyl)-5-oxa-2,6-diazaspiro[3.4]oct-6-en-7-yl)-4-methylpiperidine-4-carboxylic acid | 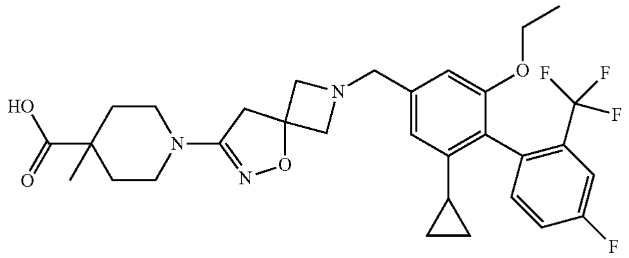 [SMILES: CCOc1cc(CN2CC3(CC(N4CCC(C)(C(=O)O)CC4)=NO3)C2)cc(C2CC2)c1-c1ccc(F)cc1C(F)(F)F] | 590.2 |
| 130 | 1-(2-((2-Cyclopropyl-6-ethoxy-2',4'-difluoro-5'-methyl-biphenyl-4-yl)methyl)-5-oxa-2,6-diazaspiro[3.4]oct-6-en-7-yl)-4-methylpiperidine-4-carboxylic acid | 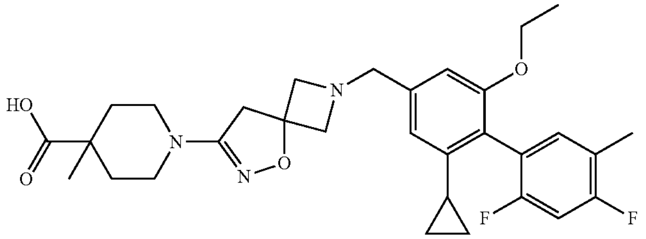 [SMILES: CCOc1cc(CN2CC3(CC(N4CCC(C)(C(=O)O)CC4)=NO3)C2)cc(C2CC2)c1-c1cc(C)c(F)cc1F] | 554.3 |

TABLE 1-continued

| Example No. | IUPAC Name | Structure | MS, NMR |
|---|---|---|---|
| 131 | 1-(2-((2-Cyclopropyl-6-ethoxy-2'-fluorobiphenyl-4-yl)methyl)-5-oxa-2,6-diazaspiro[3.4]oct-6-en-7-yl)-2-methylpiperidine-4-carboxylic acid | 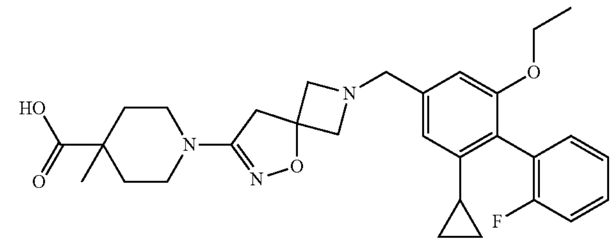 [SMILES: CCOc1cc(CN2CC3(CC(N4CCC(C)(C(=O)O)CC4)=NO3)C2)cc(C2CC2)c1-c1ccccc1F] | 522.2 |
| 132 | 1-(2-((2-Cyclopropyl-6-ethoxy-2',3',4'-trifluorobiphenyl-4-yl)methyl)-5-oxa-2,6-diazaspiro[3.4]oct-6-en-7-yl)-4-methylpiperidine-4-carboxylic acid | 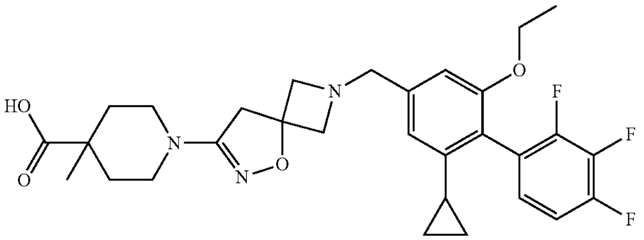 [SMILES: CCOc1cc(CN2CC3(CC(N4CCC(C)(C(=O)O)CC4)=NO3)C2)cc(C2CC2)c1-c1ccc(F)c(F)c1F] | 558.3 |
| 133 | 1-(2-((4'-Cyano-2-cyclopropyl-6-ethoxy-2'-methylbiphenyl-4-yl)methyl)-5-oxa-2,6-diazaspiro[3.4]oct-6-en-7-yl)-4-methylpiperidine-4-carboxylic acid | 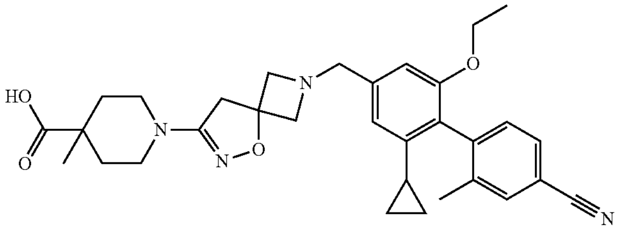 [SMILES: CCOc1cc(CN2CC3(CC(N4CCC(C)(C(=O)O)CC4)=NO3)C2)cc(C2CC2)c1-c1ccc(C#N)cc1C] | 543.3 |
| 134 | 1-(2-((2'-Cyano-2-cyclopropyl-6-ethoxybiphenyl-4-yl)methyl)-5-oxa-2,6-diazaspiro[3.4]oct-6-en-7-yl)-4-methylpiperidine-4-carboxylic acid | 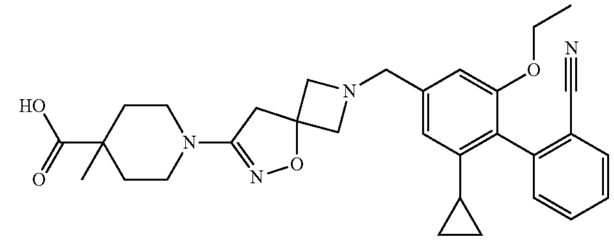 [SMILES: CCOc1cc(CN2CC3(CC(N4CCC(C)(C(=O)O)CC4)=NO3)C2)cc(C2CC2)c1-c1ccccc1C#N] | 529.3 |
| 135 | 1-(2-((2-Cyclopropyl-2',6-diethoxy-4'-fluorobiphenyl-4-yl)methyl)-5-oxa-2,6-diazaspiro[3.4]oct-6-en-7-yl)-4-methylpiperidine-4-carboxylic acid | 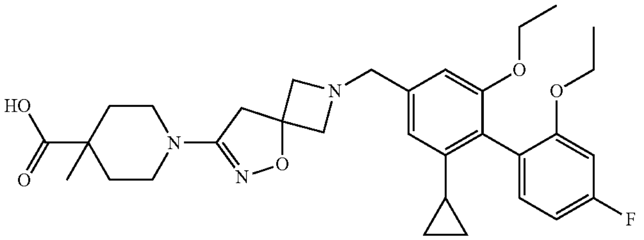 [SMILES: CCOc1cc(F)ccc1-c1c(OCC)cc(CN2CC3(CC(N4CCC(C)(C(=O)O)CC4)=NO3)C2)cc1C1CC1] | 566.3 |
| 136 | 1-(2-((2-Cyclopropyl-6-ethoxy-4'-(methoxymethyl)biphenyl-4-yl)methyl)-5-oxa-2,6-diazaspiro[3.4]oct-6-en-7-yl)-4-methylpiperidine-4-carboxylic acid | 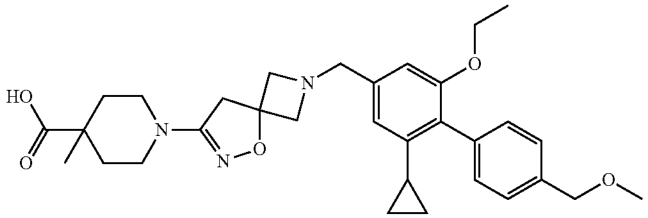 [SMILES: CCOc1cc(CN2CC3(CC(N4CCC(C)(C(=O)O)CC4)=NO3)C2)cc(C2CC2)c1-c1ccc(COC)cc1] | 548.3 |

TABLE 1-continued

| Example No. | IUPAC Name | Structure | MS, NMR |
|---|---|---|---|
| 137 | 1-(2-((2-Cyclopropyl-6-ethoxy-2'-fluoro-4'-methylbiphenyl-4-yl)methyl)-5-oxa-2,6-diazaspiro[3.4]oct-6-en-7-yl)-4-methylpiperidine-4-carboxylic acid | 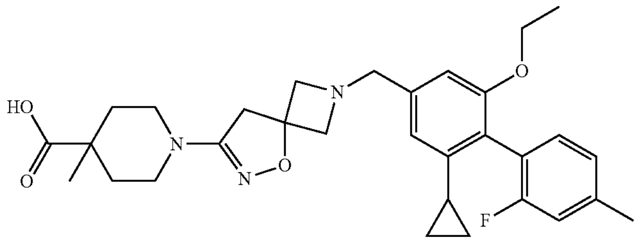 [SMILES: CCOc1cc(CN2CC3(CC(N4CCC(C)(C(=O)O)CC4)=NO3)C2)cc(C2CC2)c1-c1ccc(C)cc1F] | 536.3 |
| 138 | 1-(2-((2-Cyclopropyl-6-ethoxy-3'-fluorobiphenyl-4-yl)methyl)-5-oxa-2,6-diazaspiro[3.4]oct-6-en-7-yl)-4-methylpiperidine-4-carboxylic acid | 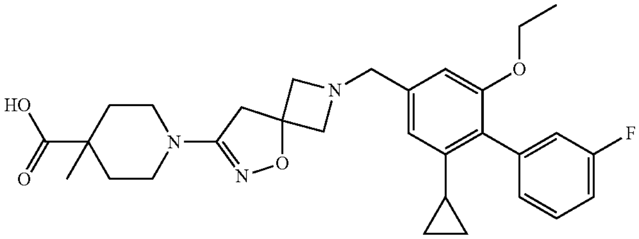 [SMILES: CCOc1cc(CN2CC3(CC(N4CCC(C)(C(=O)O)CC4)=NO3)C2)cc(C2CC2)c1-c1cccc(F)c1] | 522.3 |
| 139 | 1-(2-((2-Cyclopropyl-6-ethoxy-2'-methylbiphenyl-4-yl)methyl)-5-oxa-2,6-diazaspiro[3.4]oct-6-en-7-yl)-4-methylpiperidine-4-carboxylic acid | 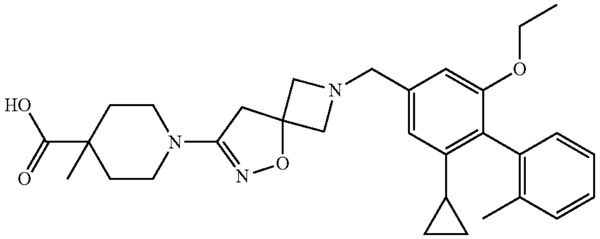 [SMILES: CCOc1cc(CN2CC3(CC(N4CCC(C)(C(=O)O)CC4)=NO3)C2)cc(C2CC2)c1-c1ccccc1C] | 518.3 |
| 140 | 1-(2-((2'-Chloro-2-cyclopropyl-6-ethoxybiphenyl-4-yl)methyl)-5-oxa-2,6-diazaspiro[3.4]oct-6-en-7-yl)-4-methylpiperidine-4-carboxylic acid | 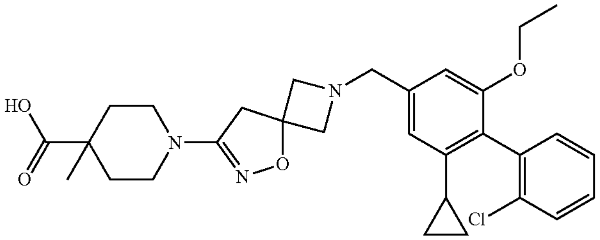 [SMILES: CCOc1cc(CN2CC3(CC(N4CCC(C)(C(=O)O)CC4)=NO3)C2)cc(C2CC2)c1-c1ccccc1Cl] | 538.2 |
| 141 | 1-(2-((2-Cyclopropyl-6-ethoxy-2'-(trifluoromethyl)biphenyl-4-yl)methyl)-5-oxa-2,6-diazaspiro[3.4]oct-6-en-7-yl)-4-methylpiperidine-4-carboxylic acid | 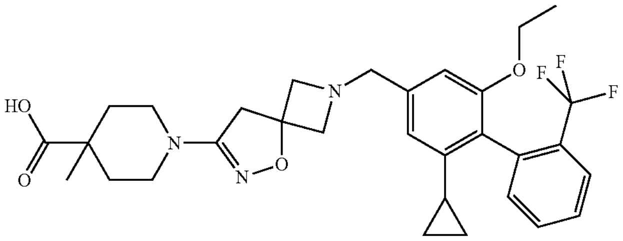 [SMILES: CCOc1cc(CN2CC3(CC(N4CCC(C)(C(=O)O)CC4)=NO3)C2)cc(C2CC2)c1-c1ccccc1C(F)(F)F] | 572.3 |
| 142 | 1-(2-((3-Cyclopropyl-5-ethoxy-4-(6-fluoropyridin-3-yl)benzyl)-5-oxa-2,6-diazaspiro[3.4]oct-6-en-7-yl)-4-methylpiperidine-4-carboxylic acid | 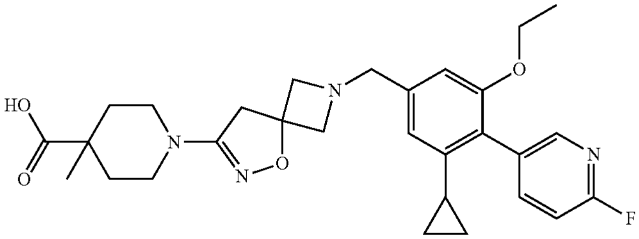 [SMILES: CCOc1cc(CN2CC3(CC(N4CCC(C)(C(=O)O)CC4)=NO3)C2)cc(C2CC2)c1-c1ccc(F)nc1] | 523.3 |

TABLE 1-continued

| Example No. | IUPAC Name | Structure | MS, NMR |
|---|---|---|---|
| 143 | 1-(2-((3-Cyclopropyl-5-ethoxy-4-(6-methoxypyridin-3-yl)benzyl)-5-oxa-2,6-diazaspiro[3.4]oct-6-en-7-yl)-4-methylpiperidine-4-carboxylic acid | 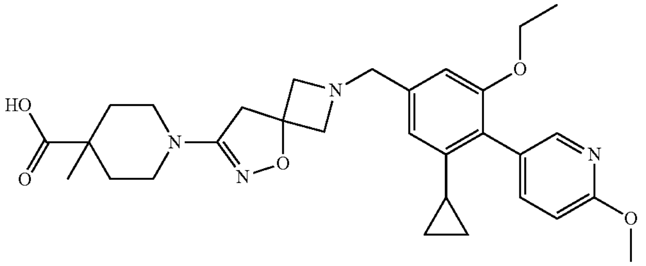 [SMILES: CCOc1cc(CN2CC3(CC(N4CCC(C)(C(=O)O)CC4)=NO3)C2)cc(C2CC2)c1-c1ccc(OC)nc1] | 535.3 |
| 144 | 1-(2-((3-Cyclopropyl-5-ethoxy-4-(6-(trifluoromethyl)pyridin-3-yl)benzyl)-5-oxa-2,6-diazaspiro[3.4]oct-6-en-7-yl)-4-methylpiperidine-4-carboxylic acid | 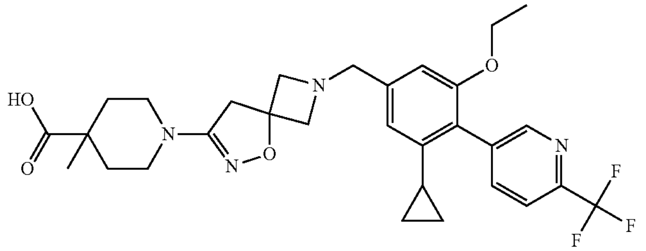 [SMILES: CCOc1cc(CN2CC3(CC(N4CCC(C)(C(=O)O)CC4)=NO3)C2)cc(C2CC2)c1-c1ccc(C(F)(F)F)nc1] | 573.3 |
| 145 | 1-(2-(3-Cyclopropyl-5-ethoxy-4-(6-methylpyridin-3-yl)benzyl)-5-oxa-2,6-diazaspiro[3.4]oct-6-en-7-yl)-4-methylpiperidine-4-carboxylic acid | 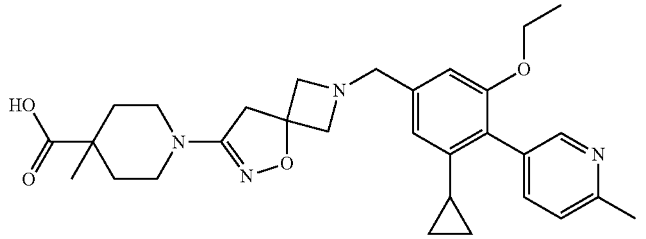 [SMILES: CCOc1cc(CN2CC3(CC(N4CCC(C)(C(=O)O)CC4)=NO3)C2)cc(C2CC2)c1-c1ccc(C)nc1] | 519.3 |
| 146 | 1-(2-(3-Cyclopropyl-5-ethoxy-4-(pyridin-3-yl)benzyl)-5-oxa-2,6-diazaspiro[3.4]oct-6-en-7-yl)-4-methylpiperidine-4-carboxylic acid | 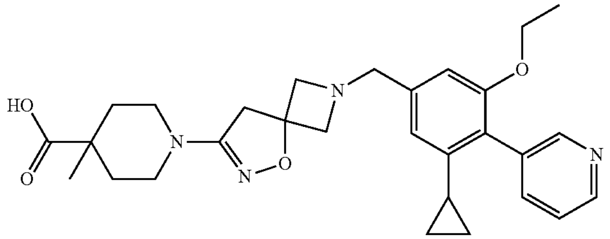 [SMILES: CCOc1cc(CN2CC3(CC(N4CCC(C)(C(=O)O)CC4)=NO3)C2)cc(C2CC2)c1-c1cccnc1] | 505.3 |
| 147 | 1-(2-(3-Cyclopropyl-5-ethoxy-4-(5-fluoropyridin-3-yl)benzyl)-5-oxa-2,6-diazaspiro[3.4]oct-6-en-7-yl)-4-methylpiperidine-4-carboxylic acid | 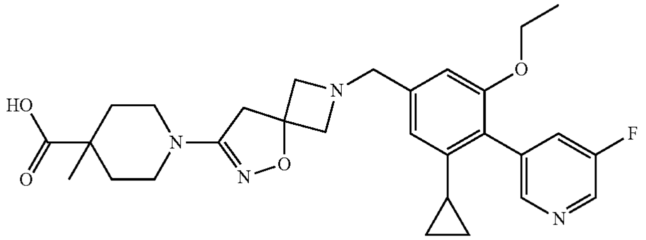 [SMILES: CCOc1cc(CN2CC3(CC(N4CCC(C)(C(=O)O)CC4)=NO3)C2)cc(C2CC2)c1-c1cncc(F)c1] | 523.2 |
| 148 | 1-(2-(3-Cyclopropyl-5-ethoxy-4-(2-fluoropyridin-3-yl)benzyl)-5-oxa-2,6-diazaspiro[3.4]oct-6-en-7-yl)-4-methylpiperidine-4-carboxylic acid | 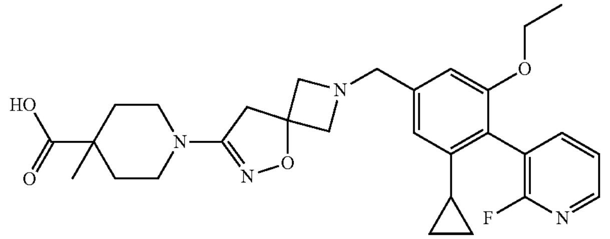 [SMILES: CCOc1cc(CN2CC3(CC(N4CCC(C)(C(=O)O)CC4)=NO3)C2)cc(C2CC2)c1-c1cccnc1F] | 523.2 |

TABLE 1-continued

| Example No. | IUPAC Name | Structure | MS, NMR |
|---|---|---|---|
| 149 | 1-(2-(3-Cyclopropyl-5-ethoxy-4-(5-methylpyridin-3-yl)benzyl)-5-oxa-2,6-diazaspiro[3.4]oct-6-en-7-yl)-4-methylpiperidine-4-carboxylic acid | 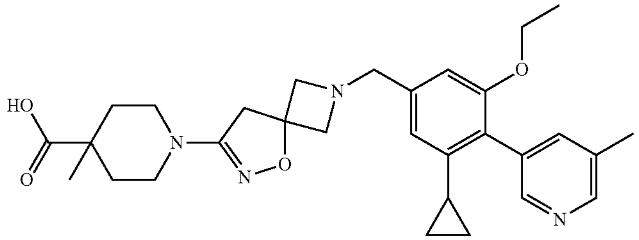 [SMILES: CCOc1cc(CN2CC3(CC(N4CCC(C)(C(=O)O)CC4)=NO3)C2)cc(C2CC2)c1-c1cncc(C)c1] | 519.3 |
| 150 | 1-(2-(4-(5-Chloro-2-thienyl)-3-cyclopropyl-5-ethoxybenzyl)-5-oxa-2,6-diazaspiro[3.4]oct-6-en-7-yl)-4-methylpiperidine-4-carboxylic acid | 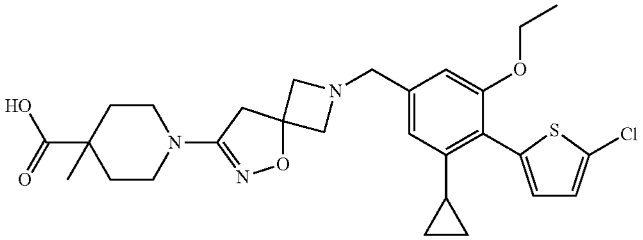 [SMILES: CCOc1cc(CN2CC3(CC(N4CCC(C)(C(=O)O)CC4)=NO3)C2)cc(C2CC2)c1-c1ccc(Cl)s1] | 544.2 |
| 151 | 1-(2-(3-Cyclopropyl-5-ethoxy-4-(5-methyl-2-thienyl)benzyl)-5-oxa-2,6-diazaspiro[3.4]oct-6-en-7-yl)-4-methylpiperidine-4-carboxylic acid | 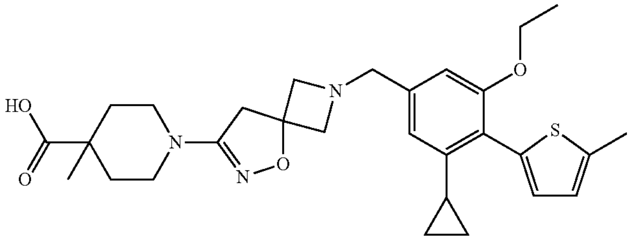 [SMILES: CCOc1cc(CN2CC3(CC(N4CCC(C)(C(=O)O)CC4)=NO3)C2)cc(C2CC2)c1-c1ccc(C)s1] | 524.2 |
| 152 | 1-(2-(3,4-Dicyclopropyl-5-ethoxybenzyl)-5-oxa-2,6-diazaspiro[3.4]oct-6-en-7-yl)-4-methylpiperidine-4-carboxylic acid | 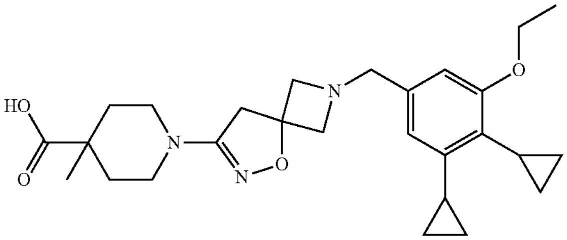 [SMILES: CCOc1cc(CN2CC3(CC(N4CCC(C)(C(=O)O)CC4)=NO3)C2)cc(C2CC2)c1C1CC1] | 468.2 |
| 153 | 1-(2-((4'-Cyano-2-cyclopropyl-6-ethoxy-2'-fluorobiphenyl-4-yl)methyl)-5-oxa-2,6-diazaspiro[3.4]oct-6-en-7-yl)-4-methylpiperidine-4-carboxylic acid | 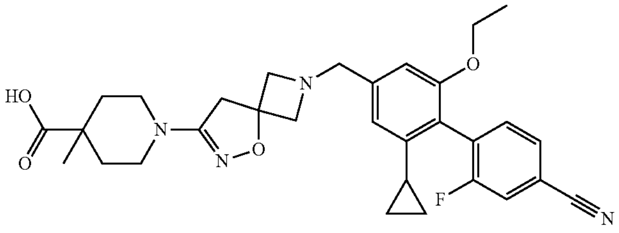 [SMILES: CCOc1cc(CN2CC3(CC(N4CCC(C)(C(=O)O)CC4)=NO3)C2)cc(C2CC2)c1-c1ccc(C#N)cc1F] | 547.3 |
| 154 | 1-(2-((4'-Cyano-2-cyclopropyl-6-ethoxy-3'-fluorobiphenyl-4-yl)methyl)-5-oxa-2,6-diazaspiro[3.4]oct-6-en-7-yl)-4-methylpiperidine-4-carboxylic acid | 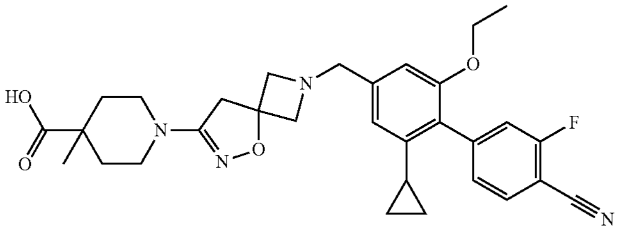 [SMILES: CCOc1cc(CN2CC3(CC(N4CCC(C)(C(=O)O)CC4)=NO3)C2)cc(C2CC2)c1-c1ccc(C#N)c(F)c1] | 547.3 |

TABLE 1-continued

| Example No. | IUPAC Name | Structure | MS, NMR |
|---|---|---|---|
| 155 | 1-(2-((3'-Chloro-4'-cyano-2-cyclopropyl-6-ethoxybiphenyl-4-yl)methyl)-5-oxa-2,6-diazaspiro[3.4]oct-6-en-7-yl)-4-methylpiperidine-4-carboxylic acid | 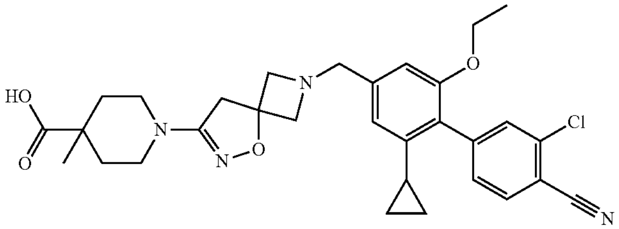 [SMILES: CCOc1cc(CN2CC3(CC(N4CCC(C)(C(=O)O)CC4)=NO3)C2)cc(C2CC2)c1-c1ccc(C#N)c(Cl)c1] | 563.3 |
| 156 | 1-(2-((3'-Cyano-2-cyclopropyl-6-ethoxybiphenyl-4-yl)methyl)-5-oxa-2,6-diazaspiro[3.4]oct-6-en-7-yl)-4-methylpiperidine-4-carboxylic acid | 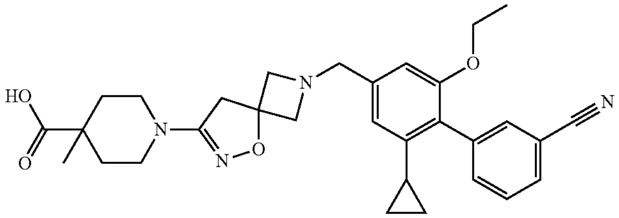 [SMILES: CCOc1cc(CN2CC3(CC(N4CCC(C)(C(=O)O)CC4)=NO3)C2)cc(C2CC2)c1-c1cccc(C#N)c1] | 529.3 |
| 157 | 1-(2-((3'-Cyano-2-cyclopropyl-6-ethoxy-4'-fluoro-biphenyl-4-yl)methyl)-5-oxa-2,6-diazaspiro[3.4]oct-6-en-7-yl)-4-methylpiperidine-4-carboxylic acid | 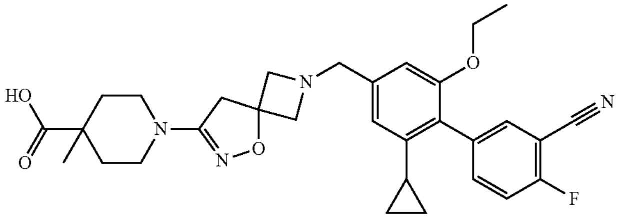 [SMILES: CCOc1cc(CN2CC3(CC(N4CCC(C)(C(=O)O)CC4)=NO3)C2)cc(C2CC2)c1-c1ccc(F)c(C#N)c1] | 547.3 |
| 158 | 1-(2-((5'-Cyano-2-cyclopropyl-6-ethoxy-2'-fluoro-biphenyl-4-yl)methyl)-5-oxa-2,6-diazaspiro[3.4]oct-6-en-7-yl)-4-methylpiperidine-4-carboxylic acid | 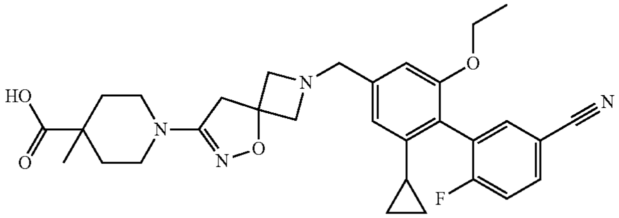 [SMILES: CCOc1cc(CN2CC3(CC(N4CCC(C)(C(=O)O)CC4)=NO3)C2)cc(C2CC2)c1-c1cc(C#N)ccc1F] | 547.2 |
| 159 | 1-(2-((4'-Cyano-2-cyclopropyl-6-ethoxybiphenyl-4-yl)methyl)-5-oxa-2,6-diazaspiro[3.4]oct-6-en-7-yl)-4-methylpiperidine-4-carboxylic acid | 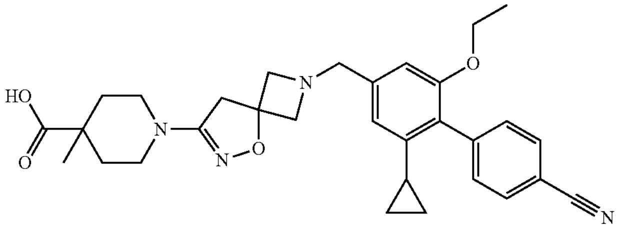 [SMILES: CCOc1cc(CN2CC3(CC(N4CCC(C)(C(=O)O)CC4)=NO3)C2)cc(C2CC2)c1-c1ccc(C#N)cc1] | 529.3 |
| 160 | 1-(2-(3-Cyclopropyl-4-(5,6-difluoropyridin-3-yl)-5-ethoxybenzyl)-5-oxa-2,6-diazaspiro[3.4]oct-6-en-7-yl)-4-methylpiperidine-4-carboxylic acid | 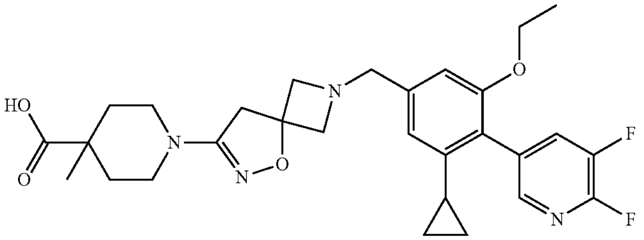 [SMILES: CCOc1cc(CN2CC3(CC(N4CCC(C)(C(=O)O)CC4)=NO3)C2)cc(C2CC2)c1-c1cnc(F)c(F)c1] | 541.3 |

TABLE 1-continued

| Example No. | IUPAC Name | Structure | MS, NMR |
|---|---|---|---|
| 161 | 1-(2-(3-Cyclopropyl-4-(2,6-difluoropyridin-3-yl)-5-ethoxybenzyl)-5-oxa-2,6-diazaspiro[3.4]oct-6-en-7-yl)-4-methylpiperidine-4-carboxylic acid | 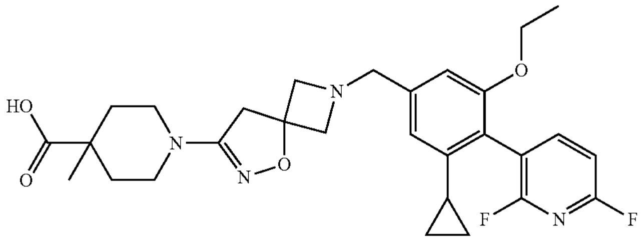 [SMILES: CCOc1cc(CN2CC3(CC(N4CCC(C)(C(=O)O)CC4)=NO3)C2)cc(C2CC2)c1-c1ccc(F)nc1F] | 541.3 |
| 162 | 1-(2-((2-Cyclopropyl-6-ethoxy-3',4'-difluorobiphenyl-4-yl)methyl)-5-oxa-2,6-diazaspiro[3.4]oct-6-en-7-yl)-4-methylpiperidine-4-carboxylic acid | 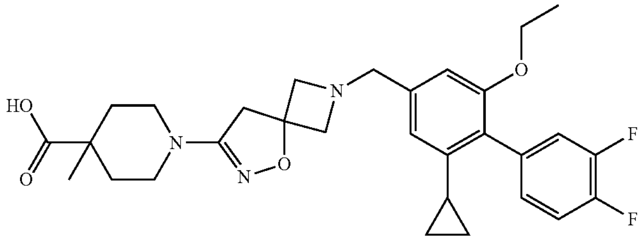 [SMILES: CCOc1cc(CN2CC3(CC(N4CCC(C)(C(=O)O)CC4)=NO3)C2)cc(C2CC2)c1-c1ccc(F)c(F)c1] | 540.4 |
| 163 | 1-(2-((2-(2,2-Difluoro-1-methylcyclopropyl)-6-ethoxy-4'-fluorobiphenyl-4-yl)methyl)-5-oxa-2,6-diazaspiro[3.4]oct-6-en-7-yl)-4-methylpiperidine-4-carboxylic acid | 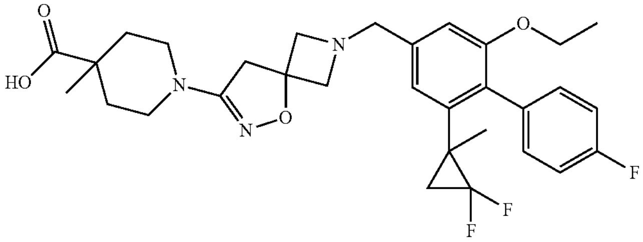 [SMILES: CCOc1cc(CN2CC3(CC(N4CCC(C)(C(=O)O)CC4)=NO3)C2)cc(C2(C)CC2(F)F)c1-c1ccc(F)cc1] | 572.4 |
| 164 | 1-(2-(3-Cyclopropyl-5-ethoxy-4-(piperidin-1-yl)benzyl)-5-oxa-2,6-diazaspiro[3.4]oct-6-en-7-yl)-4-methylpiperidine-4-carboxylic acid | 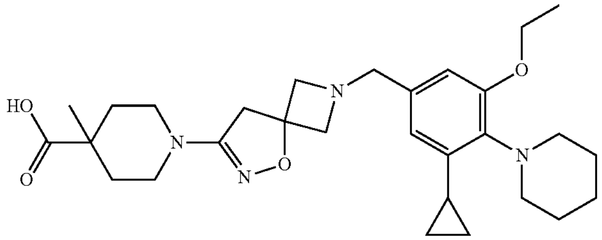 [SMILES: CCOc1cc(CN2CC3(CC(N4CCC(C)(C(=O)O)CC4)=NO3)C2)cc(C2CC2)c1N1CCCCC1] | 511.3 |
| 165 | 1-(2-((2-Cyclopropyl-2'-ethoxy-4'-fluorobiphenyl-4-yl)methyl)-5-oxa-2,6-diazaspiro[3.4]oct-6-en-7-yl)-4-methylpiperidine-4-carboxylic acid | 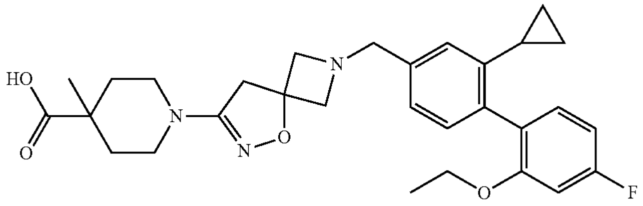 [SMILES: CCOc1cc(F)ccc1-c1ccc(CN2CC3(CC(N4CCC(C)(C(=O)O)CC4)=NO3)C2)cc1C1CC1] | 522.4 |
| 166 | 1-(2-((2-Cyclopropyl-4'-fluoro-6-((1-fluorocyclopropyl)methoxy)biphenyl-4-yl)methyl)-5-oxa-2,6-diazaspiro[3.4]oct-6-en-7-yl)-4-methylpiperidine-4-carboxylic acid | 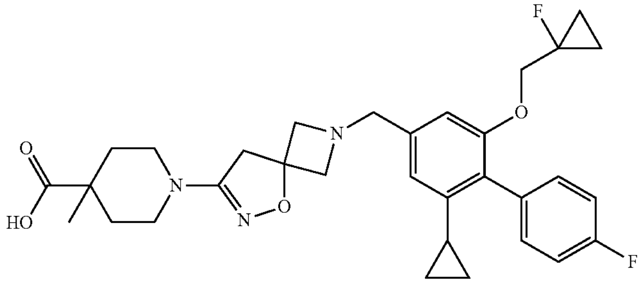 [SMILES: CC1(C(=O)O)CCN(C2=NOC3(C2)CN(Cc2cc(OCC4(F)CC4)c(-c4ccc(F)cc4)c(C4CC4)c2)C3)CC1] | 566.4 |

TABLE 1-continued

| Example No. | IUPAC Name | Structure | MS, NMR |
|---|---|---|---|
| 167 | 1-(2-((2-Ethoxy-4'-fluoro-6-(pentafluoroethyl)biphenyl-4-yl)methyl)-5-oxa-2,6-diazaspiro[3.4]oct-6-en-7-yl)-4-methylpiperidine-4-carboxylic acid | 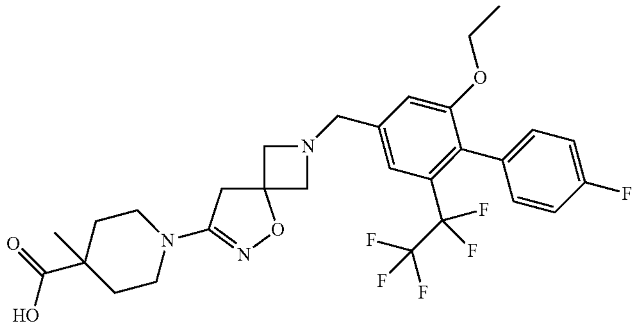 [SMILES: CCOc1cc(CN2CC3(CC(N4CCC(C)(C(=O)O)CC4)=NO3)C2)cc(C(F)(F)C(F)(F)F)c1-c1ccc(F)cc1] | 600.4 |
| 168 | 1-(2-((2-Cyclopropyl-6-(2,2-difluoropropoxy)-4'-fluorobiphenyl-4-yl)methyl)-5-oxa-2,6-diazaspiro[3.4]oct-6-en-7-yl)-4-methylpiperidine-4-carboxylic acid | 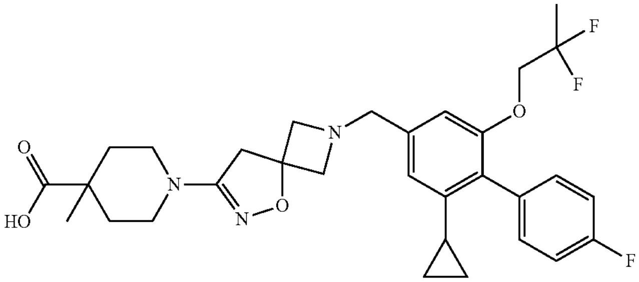 [SMILES: CC(F)(F)COc1cc(CN2CC3(CC(N4CCC(C)(C(=O)O)CC4)=NO3)C2)cc(C2CC2)c1-c1ccc(F)cc1] | 572.4 |
| 169 | 1-(2-((2-Cyclopropyl-2',4'-difluoro-6-propoxybiphenyl-4-yl)methyl)-5-oxa-2,6-diazaspiro[3.4]oct-6-en-7-yl)-4-methylpiperidine-4-carboxylic acid | 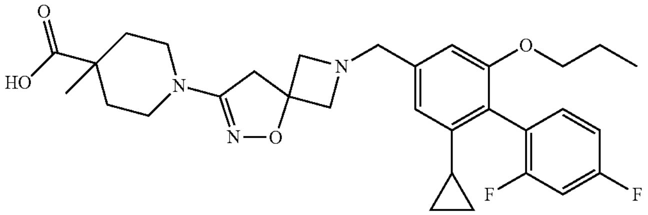 [SMILES: CCCOc1cc(CN2CC3(CC(N4CCC(C)(C(=O)O)CC4)=NO3)C2)cc(C2CC2)c1-c1ccc(F)cc1F] | 554.3 |
| 170 | 1-(2-((2-Cyclopropyl-6-(2-(2,2-difluorocyclopropyl)ethoxy)-4'-fluorobiphenyl-4-yl)methyl)-5-oxa-2,6-diazaspiro[3.4]oct-6-en-7-yl)-4-methylpiperidine-4-carboxylic acid | 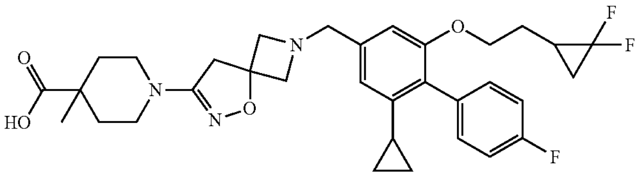 [SMILES: CC1(C(=O)O)CCN(C2=NOC3(C2)CN(Cc2cc(OCCC4CC4(F)F)c(-c4ccc(F)cc4)c(C4CC4)c2)C3)CC1] | 598.4 |
| 171 | 1-(2-((2-(2,2-difluorocyclopropyl)-6-ethoxy-4'-fluorobiphenyl-4-yl)methyl)-5-oxa-2,6-diazaspiro[3.4]oct-6-en-7-yl)-4-methylpiperidine-4-carboxylic acid | 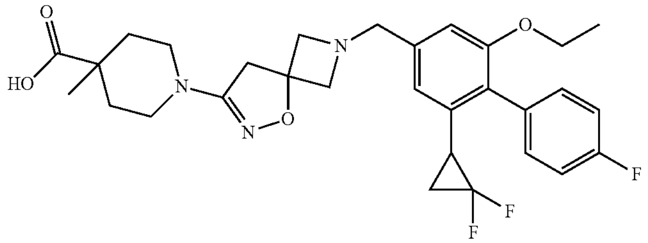 [SMILES: CCOc1cc(CN2CC3(CC(N4CCC(C)(C(=O)O)CC4)=NO3)C2)cc(C2CC2(F)F)c1-c1ccc(F)cc1] | 558.3 |
| 172 | 1-(2-((2-(2,2-difluorocyclopropyl)-6-ethoxy-4'-fluorobiphenyl-4-yl)methyl)-5-oxa-2,6-diazaspiro[3.4]oct-6-en-7-yl)-4-methylpiperidine-4-carboxylic acid | 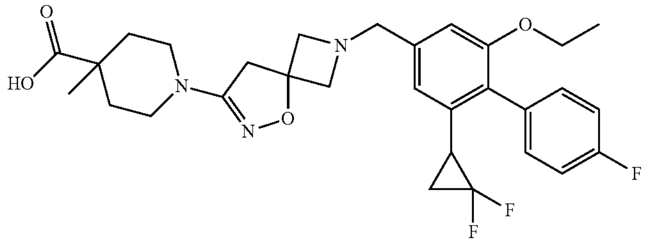 [SMILES: CCOc1cc(CN2CC3(CC(N4CCC(C)(C(=O)O)CC4)=NO3)C2)cc(C2CC2(F)F)c1-c1ccc(F)cc1] | 558.3 |

TABLE 1-continued

| Example No. | IUPAC Name | Structure | MS, NMR |
|---|---|---|---|
| 173 | 1-(2-((2-Cyclopropyl-4'-fluoro-6-(3-(methylsulfonyl)propoxy)biphenyl-4-yl)methyl)-5-oxa-2,6-diazaspiro[3.4]oct-6-en-7-yl)-4-methylpiperidine-4-carboxylic acid | 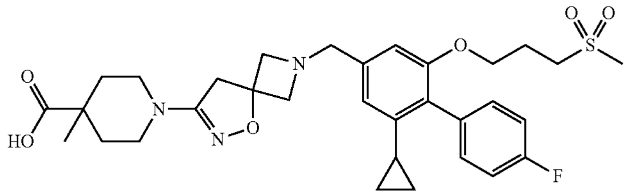 [SMILES: CC1(C(=O)O)CCN(C2=NOC3(C2)CN(Cc2cc(OCCCS(C)(=O)=O)c(-c4ccc(F)cc4)c(C4CC4)c2)C3)CC1] | 614.5 |
| 174 | 1-(2-((2-Cyclopropyl-6-ethoxy-4'-fluorobiphenyl-4-yl)methyl)-5-oxa-2,6-diazaspiro[3.4]oct-6-en-7-yl)-4-ethylpiperidine-4-carboxylic acid | 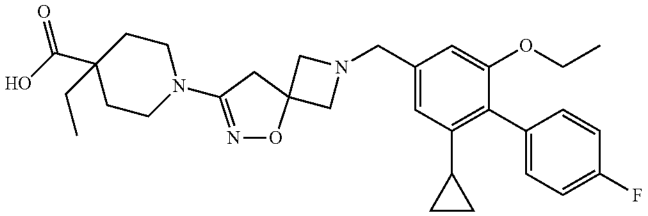 [SMILES: CCOc1cc(CN2CC3(CC(N4CCC(CC)(C(=O)O)CC4)=NO3)C2)cc(C2CC2)c1-c1ccc(F)cc1] | 536.3 |
| 175 | 1-(2-((2-Cyclopropyl-6-(2-ethoxyethoxy)-4'-fluorobiphenyl-4-yl)methyl)-5-oxa-2,6-diazaspiro[3.4]oct-6-en-7-yl)-4-methylpiperidine-4-carboxylic acid | 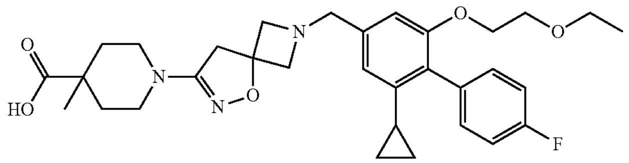 [SMILES: CCOCCOc1cc(CN2CC3(CC(N4CCC(C)(C(=O)O)CC4)=NO3)C2)cc(C2CC2)c1-c1ccc(F)cc1] | 566.5 |
| 176 | 1-(2-(3,5-Diethoxy-4-(1-methoxycyclobutyl)benzyl)-5-oxa-2,6-diazaspiro[3.4]oct-6-en-7-yl)-4-methylpiperidine-4-carboxylic acid | 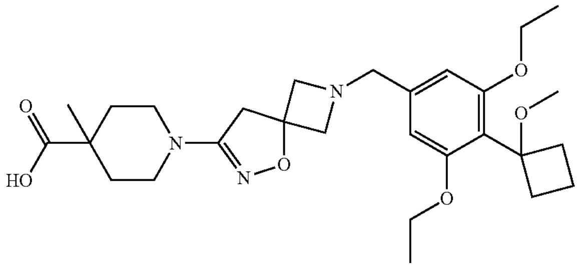 [SMILES: CCOc1cc(CN2CC3(CC(N4CCC(C)(C(=O)O)CC4)=NO3)C2)cc(OCC)c1C1(OC)CCC1] | 516.5 |
| 177 | 1-(2-((2-Cyclopropyl-4'-fluoro-5-propoxybiphenyl-4-yl)methyl)-5-oxa-2,6-diazaspiro[3.4]oct-6-en-7-yl)-4-methylpiperidine-4-carboxylic acid | 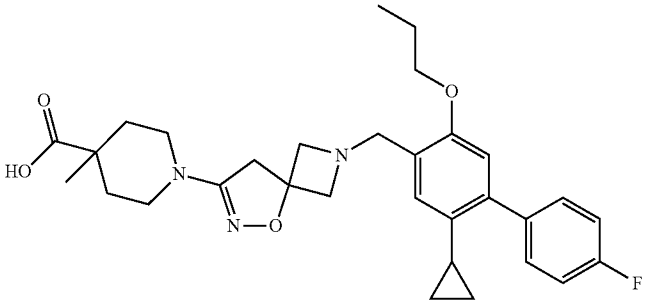 [SMILES: CCCOc1cc(-c2ccc(F)cc2)c(C2CC2)cc1CN1CC2(CC(N3CCC(C)(C(=O)O)CC3)=NO2)C1] | 536.3 |
| 178 | 1-(2-((2,6-Diethoxy-3',4'-difluorobiphenyl-4-yl)methyl-5-oxa-2,6-diazaspiro[3.4]oct-6-en-7-yl)-4-ethylpiperidine-4-carboxylic acid | 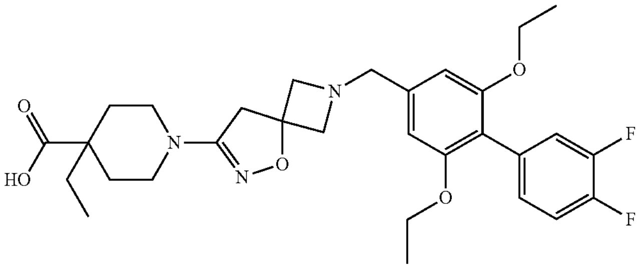 [SMILES: CCOc1cc(CN2CC3(CC(N4CCC(CC)(C(=O)O)CC4)=NO3)C2)cc(OCC)c1-c1ccc(F)c(F)c1] | 558.4 |

TABLE 1-continued

| Example No. | IUPAC Name | Structure | MS, NMR |
|---|---|---|---|
| 179 | 1-(2-((2-Cyclopropyl-4'-fluoro-5-(2-methoxyethoxy)biphenyl-4-yl)methyl)-5-oxa-2,6-diazaspiro[3.4]oct-6-en-7-yl)-4-methylpiperidine-4-carboxylic acid | 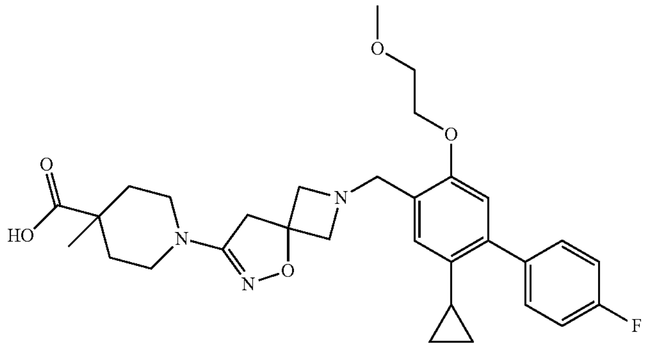 [SMILES: COCCOc1cc(-c2ccc(F)cc2)c(C2CC2)cc1CN1CC2(CC(N3CCC(C)(C(=O)O)CC3)=NO2)C1] | 552.2 |
| 180 | 1-(2-((2,5-Dicyclopropyl-4'-fluorobiphenyl-4-yl)methyl)-5-oxa-2,6-diazaspiro[3.4]oct-6-en-7-yl)-4-methylpiperidine-4-carboxylic acid | 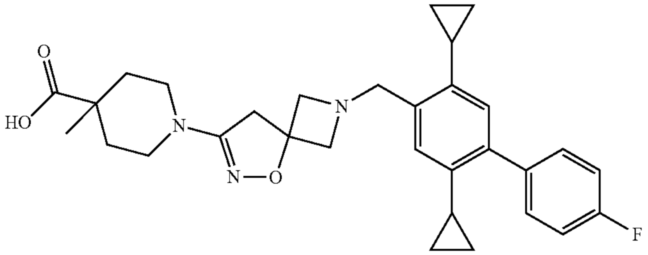 [SMILES: CC1(C(=O)O)CCN(C2=NOC3(C2)CN(Cc2cc(C4CC4)c(-c4ccc(F)cc4)cc2C2CC2)C3)CC1] | 518.1 |
| 181 | 1-(2-((2-Cyclopropyl-4'-fluoro-5-isopropoxybiphenyl-4-yl)methyl)-5-oxa-2,6-diazaspiro[3.4]oct-6-en-7-yl)-4-methylpiperidine-4-carboxylic acid | 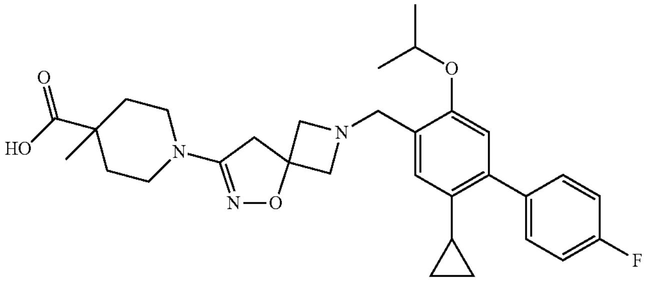 [SMILES: CC(C)Oc1cc(-c2ccc(F)cc2)c(C2CC2)cc1CN1CC2(CC(N3CCC(C)(C(=O)O)CC3)=NO2)C1] | 536.1 |
| 182 | 1-(2-((2,6-Diethoxy-2',4'-difluorobiphenyl-4-yl)methyl)-5-oxa-2,6-diazaspiro[3.4]oct-6-en-7-yl)-4-ethylpiperidine-4-carboxylic acid | 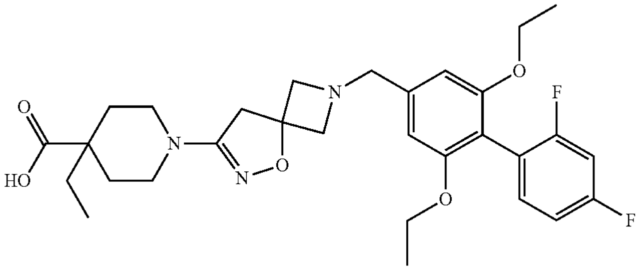 [SMILES: CCOc1cc(CN2CC3(CC(N4CCC(CC)(C(=O)O)CC4)=NO3)C2)cc(OCC)c1-c1ccc(F)cc1F] | 558.4 |
| 183 | 1-(2-((2-Cyclopropyl-6-(((1R)-2,2-difluorocyclopropyl)methoxy)-4'-fluorobiphenyl-4-yl)methyl)-5-oxa-2,6-diazaspiro[3.4]oct-6-en-7-yl)-4-methylpiperidine-4-carboxylic acid | 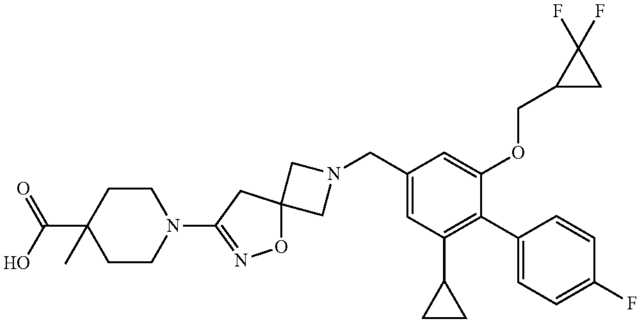 [SMILES: CC1(C(=O)O)CCN(C2=NOC3(C2)CN(Cc2cc(OCC4CC4(F)F)c(-c4ccc(F)cc4)c(C4CC4)c2)C3)CC1] | 584.4 |

TABLE 1-continued

| Example No. | IUPAC Name | Structure | MS, NMR |
|---|---|---|---|
| 184 | 1-(2-((2-Cyclopropyl-4'-fluoro-6-(2,2,2-trifluoroethoxy)biphenyl-4-yl)methyl)-5-oxa-2,6-diazaspiro[3.4]oct-6-en-7-yl)-4-methylpiperidine-4-carboxylic acid | 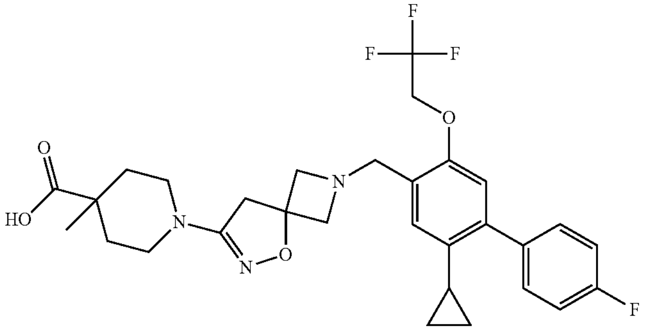 [SMILES: CC1(C(=O)O)CCN(C2=NOC3(C2)CN(Cc2cc(C4CC4)c(-c4ccc(F)cc4)cc2OCC(F)(F)F)C3)CC1] | 576.2 |
| 185 | 1-(2-(5-Cyclopropyl-4-(3,3-difluoro-cyclobutyl)-2-methoxybenzyl)-5-oxa-2,6-diazaspiro[3.4]oct-6-en-7-yl)-4-methylpiperidine-4-carboxylic acid | 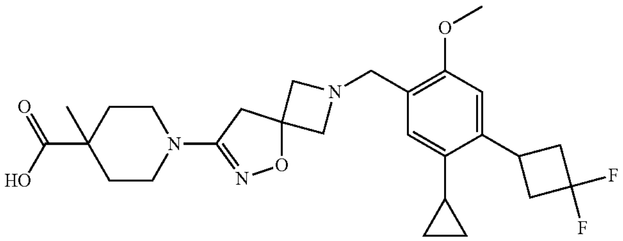 [SMILES: COc1cc(C2CC(F)(F)C2)c(C2CC2)cc1CN1CC2(CC(N3CCC(C)(C(=O)O)CC3)=NO2)C1] | 504.4 |
| 186 | 1-(2-((2-(3,3-Difluorocyclobutyl)-6-ethoxy-4'-fluoro-biphenyl-4-yl)methyl)-5-oxa-2,6-diazaspiro[3.4]oct-6-en-7-yl)-4-methylpiperidine-4-carboxylic acid | 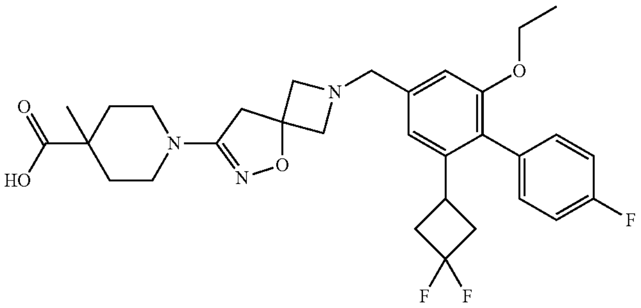 [SMILES: CCOc1cc(CN2CC3(CC(N4CCC(C)(C(=O)O)CC4)=NO3)C2)cc(C2CC(F)(F)C2)c1-c1ccc(F)cc1] | 572.4 |
| 187 | 1-(2-((2-Cyclopropyl-6-(((1S)-2,2-difluorocyclopropyl)methoxy)-4'-fluoro-biphenyl-4-yl)methyl)-5-oxa-2,6-diazaspiro[3.4]oct-6-en-7-yl)-4-methylpiperidine-4-carboxylic acid | 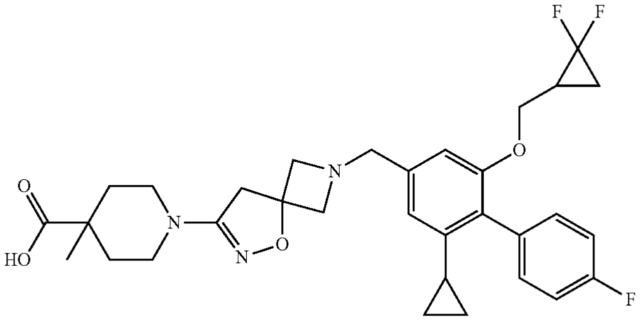 [SMILES: CC1(C(=O)O)CCN(C2=NOC3(C2)CN(Cc2cc(OCC4CC4(F)F)c(-c4ccc(F)cc4)c(C4CC4)c2)C3)CC1] | 584.4 |
| 188 | 1-(2-((2-Cyclopropyl-2'-fluoro-6-propoxy-biphenyl-4-yl)methyl)-5-oxa-2,6-diazaspiro[3.4]oct-6-en-7-yl)-4-methylpiperidine-4-carboxylic acid | 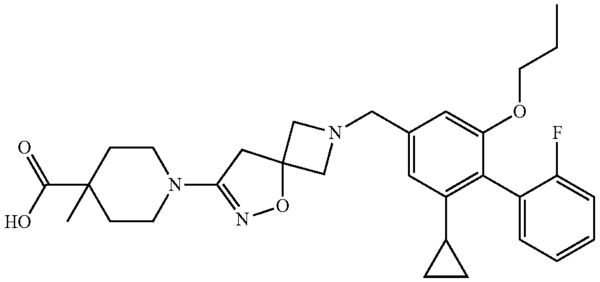 [SMILES: CCCOc1cc(CN2CC3(CC(N4CCC(C)(C(=O)O)CC4)=NO3)C2)cc(C2CC2)c1-c1ccccc1F] | 536.4 |

TABLE 1-continued

| Example No. | IUPAC Name | Structure | MS, NMR |
|---|---|---|---|
| 189 | 1-(2-(5-Cyclopropyl-4-(4,4-difluoro-pyridin-1-yl)-2-methoxybenzyl)-5-oxa-2,6-diazaspiro[3.4]oct-6-en-7-yl)-4-methylpiperidine-4-carboxylic acid | 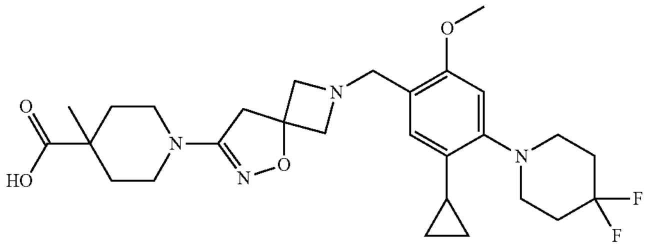 [SMILES: COc1cc(N2CCC(F)(F)CC2)c(C2CC2)cc1CN1CC2(CC(N3CCC(C)(C(=O)O)CC3)=NO2)C1] | 533.4 |
| 190 | 1-(2-((5-Cyano-2-cyclopropyl-4'-fluorobiphenyl-4-yl)methyl)-5-oxa-2,6-diazaspiro[3.4]oct-6-en-7-yl)-4-methylpiperidine-4-carboxylic acid | 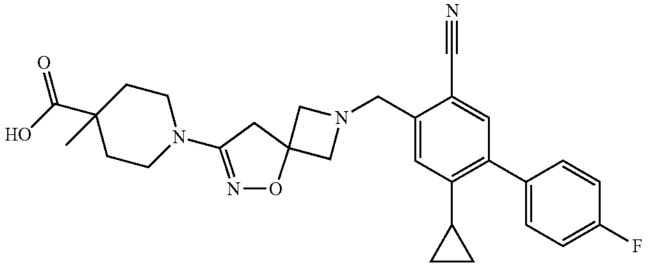 [SMILES: CC1(C(=O)O)CCN(C2=NOC3(C2)CN(Cc2cc(C4CC4)c(-c4ccc(F)cc4)cc2C#N)C3)CC1] | 521.1 |
| 191 | 1-(2-((2-Cyclopropyl-6-(cyclopropyl-methoxy)-2',4'-difluorobiphenyl-4-yl)methyl)-5-oxa-2,6-diazaspiro[3.4]oct-6-en-7-yl)-4-methylpiperidine-4-carboxylic acid | 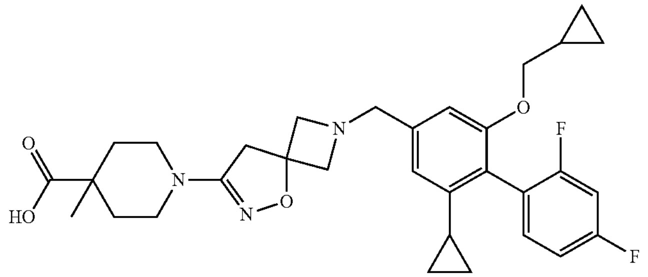 [SMILES: CC1(C(=O)O)CCN(C2=NOC3(C2)CN(Cc2cc(OCC4CC4)c(-c4ccc(F)cc4F)c(C4CC4)c2)C3)CC1] | 566.5 |
| 192 | 1-(2-((2-Cyclopropyl-4'-fluoro-5-methoxy-biphenyl-4-yl)methyl)-5-oxa-2,6-diazaspiro[3.4]oct-6-en-7-yl)-4-ethylpiperidine-4-carboxylic acid | 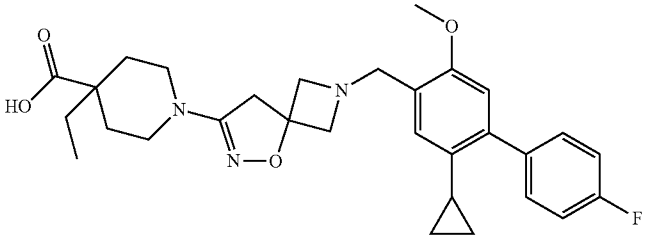 [SMILES: CCC1(C(=O)O)CCN(C2=NOC3(C2)CN(Cc2cc(C4CC4)c(-c4ccc(F)cc4)cc2OC)C3)CC1] | 522.2 |
| 193 | 1-(2-((2-Cyclopropyl-2'-fluoro-6-propoxy-biphenyl-4-yl)methyl)-5-oxa-2,6-diazaspiro[3.4]oct-6-en-7-yl)-4-ethylpiperidine-4-carboxylic acid | 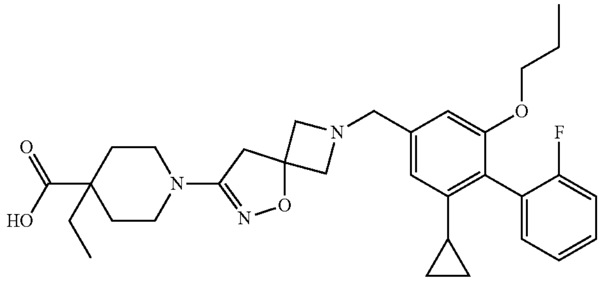 [SMILES: CCCOc1cc(CN2CC3(CC(N4CCC(CC)(C(=O)O)CC4)=NO3)C2)cc(C2CC2)c1-c1ccccc1F] | 550.4 |

TABLE 1-continued

| Example No. | IUPAC Name | Structure | MS, NMR |
|---|---|---|---|
| 194 | trans-4-(2-((2-Cyclopropyl-5-ethoxy-4'-fluorobiphenyl-4-yl)methyl)-5-oxa-2,6-diazaspiro[3.4]oct-6-en-7-yl)cyclohexanecarboxylic acid | 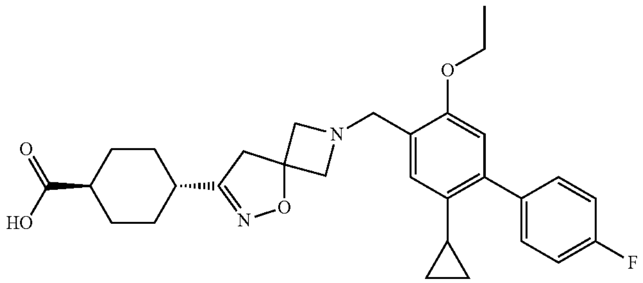 [SMILES: CCOc1cc(-c2ccc(F)cc2)c(C2CC2)cc1CN1CC2(CC([C@H]3CC[C@H](C(=O)O)CC3)=NO2)C1] | 507.4 |
| 195 | 1-(2-((6-Cyclopropyl-4'-fluoro-4-methoxybiphenyl-3-yl)methyl)-5-oxa-2,6-diazaspiro[3.4]oct-6-en-7-yl)-4-methylpiperidine-4-carboxylic acid | 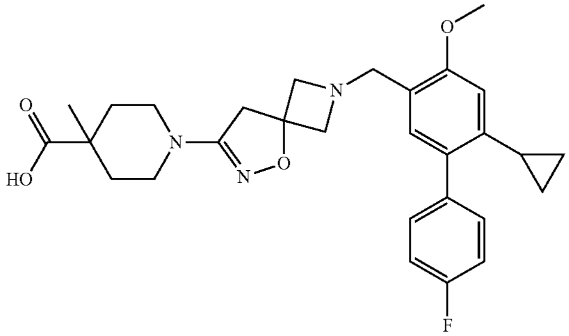 [SMILES: COc1cc(C2CC2)c(-c2ccc(F)cc2)cc1CN1CC2(CC(N3CCC(C)(C(=O)O)CC3)=NO2)C1] | 508.4 |
| 196 | 1-(2-((2-Cyclopropyl-4'-fluoro-5-(oxetane-3-yloxy)biphenyl-4-yl)methyl)-5-oxa-2,6-diazaspiro[3.4]oct-6-en-7-yl)-4-methylpiperidine-4-carboxylic acid | 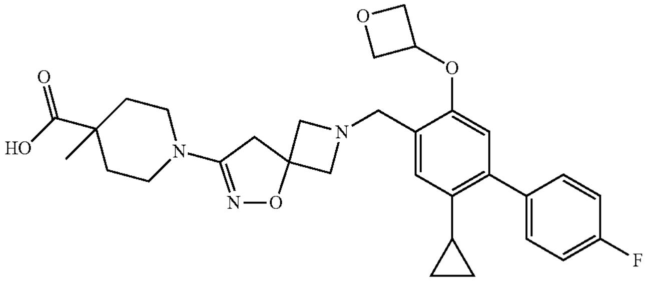 [SMILES: CC1(C(=O)O)CCN(C2=NOC3(C2)CN(Cc2cc(C4CC4)c(-c4ccc(F)cc4)cc2OC2COC2)C3)CC1] | 550.3 |
| 197 | 1-(2-((2-Cyclopropyl-4'-fluoro-5-hydroxybiphenyl-4-yl)methyl)-5-oxa-2,6-diazaspiro[3.4]oct-6-en-7-yl)-4-methylpiperidine-4-carboxylic acid | 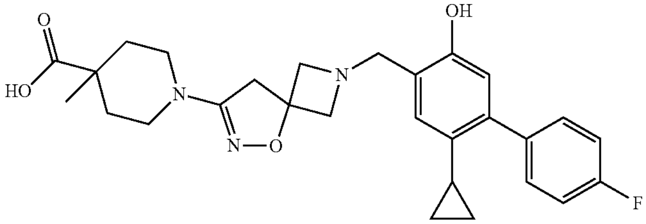 [SMILES: CC1(C(=O)O)CCN(C2=NOC3(C2)CN(Cc2cc(C4CC4)c(-c4ccc(F)cc4)cc2O)C3)CC1] | 494.2 |
| 198 | 1-(2-(5-Cyclopropyl-4-(3,3-difluoropyrrolidin-1-yl)-2-methoxybenzyl)-5-oxa-2,6-diazaspiro[3.4]oct-6-en-7-yl)-4-methylpiperidine-4-carboxylic acid | 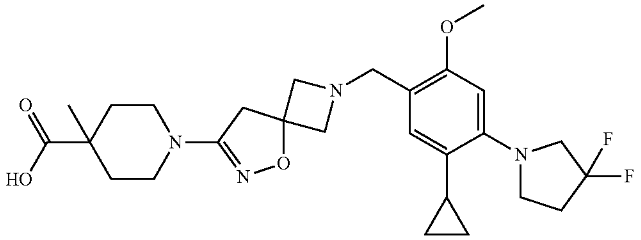 [SMILES: COc1cc(N2CCC(F)(F)C2)c(C2CC2)cc1CN1CC2(CC(N3CCC(C)(C(=O)O)CC3)=NO2)C1] | 519.4 |

TABLE 1-continued

| Example No. | IUPAC Name | Structure | MS, NMR |
| --- | --- | --- | --- |
| 199 | 1-(2-(5-Cyclopropyl-2-ethoxybenzyl)-5-oxa-2,6-diazaspiro[3.4]oct-6-en-7-yl)-4-methylpiperidine-4-carboxylic acid | 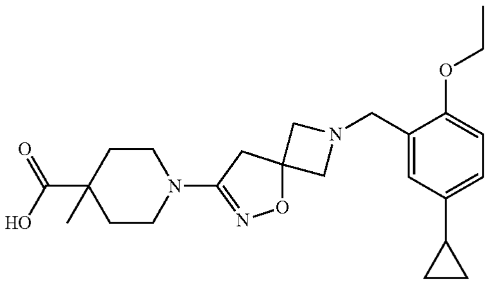 [SMILES: CCOc1ccc(C2CC2)cc1CN1CC2(CC(N3CCC(C)(C(=O)O)CC3)=NO2)C1] | 428.4 |
| 200 | 1-(2-(5-Cyclopropyl-4-(4-fluoropiperidin-1-yl)-2-methoxy-benzyl)-5-oxa-2,6-diazaspiro[3.4]oct-6-en-7-yl)-4-methylpiperidine-4-carboxylic acid | 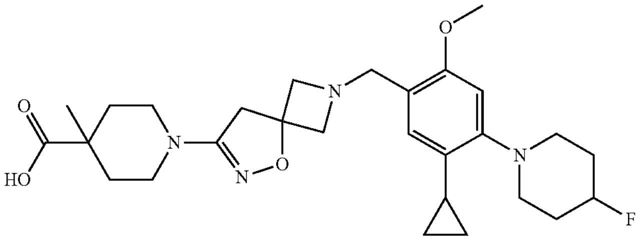 [SMILES: COc1cc(N2CCC(F)CC2)c(C2CC2)cc1CN1CC2(CC(N3CCC(C)(C(=O)O)CC3)=NO2)C1] | 515.4 |
| 201 | 1-(2-((2-Cyclopropyl-4'-fluoro-5-(morpholin-4-yl)biphenyl-4-yl)methyl)-5-oxa-2,6-diazaspiro[3.4]oct-6-en-7-yl)-4-methylpiperidine-4-carboxylic acid | 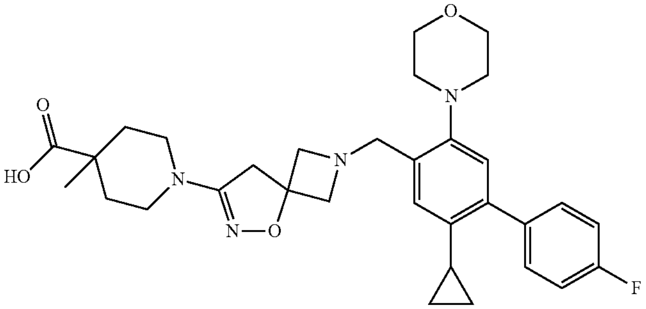 [SMILES: CC1(C(=O)O)CCN(C2=NOC3(C2)CN(Cc2cc(C4CC4)c(-c4ccc(F)cc4)cc2N2CCOCC2)C3)CC1] | 563.3 |
| 202 | 1-(2-((5-Cyclopropyl-2-ethoxy-6-(4-fluoro-phenyl)pyridin-3-yl)methyl)-5-oxa-2,6-diazaspiro[3.4]oct-6-en-7-yl)-4-methylpiperidine-4-carboxylic acid | 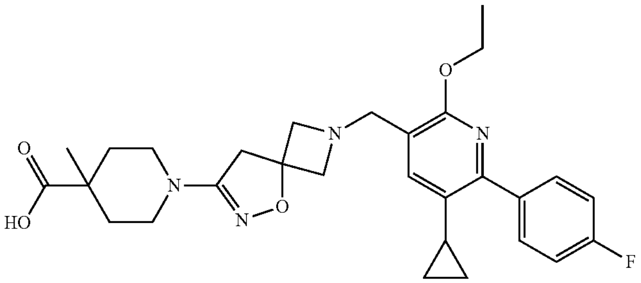 [SMILES: CCOc1nc(-c2ccc(F)cc2)c(C2CC2)cc1CN1CC2(CC(N3CCC(C)(C(=O)O)CC3)=NO2)C1] | 523.4 |
| 203 | 1-(2-(5-Cyclopropyl-2-methoxy-4-(piperidin-1-yl)benzyl)-5-oxa-2,6-diazaspiro[3.4]oct-6-en-7-yl)-4-methylpiperidine-4-carboxylic acid | 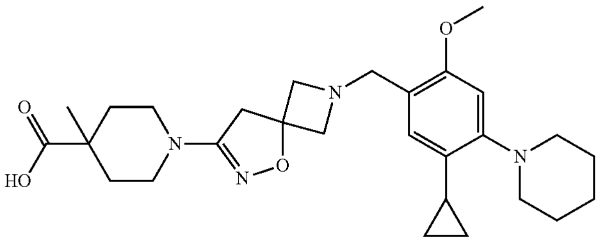 [SMILES: COc1cc(N2CCCCC2)c(C2CC2)cc1CN1CC2(CC(N3CCC(C)(C(=O)O)CC3)=NO2)C1] | 497.4 |

TABLE 1-continued

| Example No. | IUPAC Name | Structure | MS, NMR |
|---|---|---|---|
| 204 | 1-(2-((5-Cyclopropyl-2-ethoxybiphenyl-3-yl)methyl)-5-oxa-2,6-diazaspiro[3.4]oct-6-en-7-yl)-4-methylpiperidine-4-carboxylic acid | 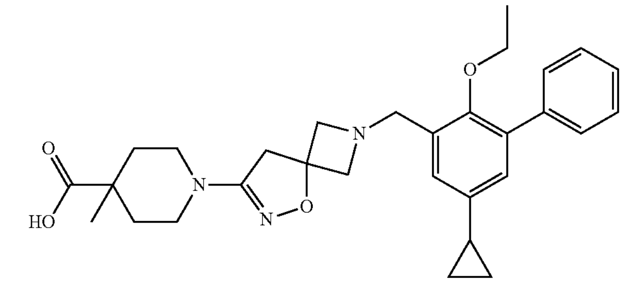 [SMILES: CCOc1c(CN2CC3(CC(N4CCC(C)(C(=O)O)CC4)=NO3)C2)cc(C2CC2)cc1-c1ccccc1] | 504.4 |
| 205 | 1-(2-((2-Cyclopropyl-5-ethoxy-4'-fluorobiphenyl-4-yl)methyl)-5-oxa-2,6-diazaspiro[3.4]oct-6-en-7-yl)-4-methylpiperidine-4-carboxylic acid | 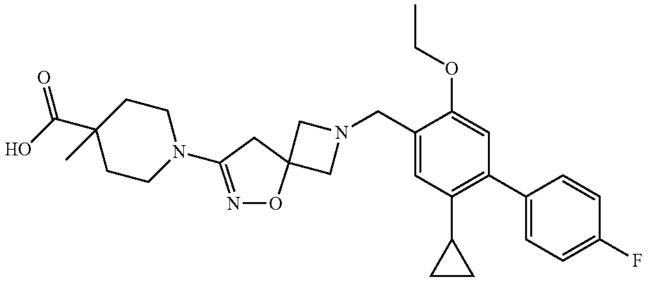 [SMILES: CCOc1cc(-c2ccc(F)cc2)c(C2CC2)cc1CN1CC2(CC(N3CCC(C)(C(=O)O)CC3)=NO2)C1] | 522.4 |
| 206 | 1-(2-((2-Cyclopropyl-4'-fluoro-6-isopropoxybiphenyl-4-yl)methyl)-5-oxa-2,6-diazaspiro[3.4]oct-6-en-7-yl)-4-methylpiperidine-4-carboxylic acid | 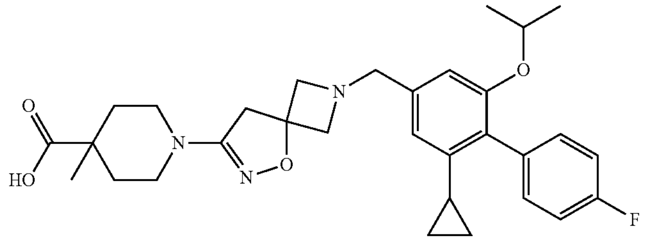 [SMILES: CC(C)Oc1cc(CN2CC3(CC(N4CCC(C)(C(=O)O)CC4)=NO3)C2)cc(C2CC2)c1-c1ccc(F)cc1] | 536.5 |
| 207 | 1-(2-((2-Cyclopropyl-4'-fluoro-5-(tetrahydro-2H-pyran-4-yl)biphenyl-4-yl)methyl)-5-oxa-2,6-diazaspiro[3.4]oct-6-en-7-yl)-4-methylpiperidine-4-carboxylic acid | 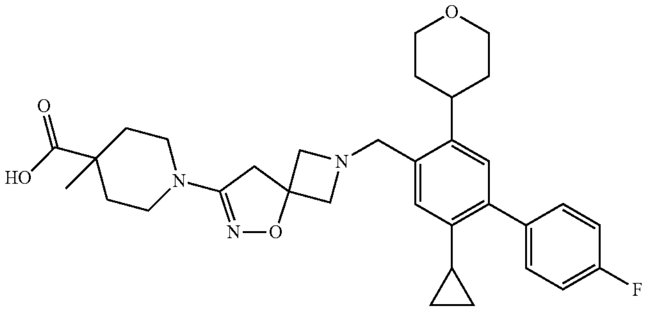 [SMILES: CC1(C(=O)O)CCN(C2=NOC3(C2)CN(Cc2cc(C4CC4)c(-c4ccc(F)cc4)cc2C2CCOCC2)C3)CC1] | 562.3 |
| 208 | trans-4-(2-((2-Cyclopropyl-4'-fluoro-6-propoxybiphenyl-4-yl)methyl)-5-oxa-2,6-diazaspiro[3.4]oct-6-en-7-yl)cyclohexanecarboxylic acid | 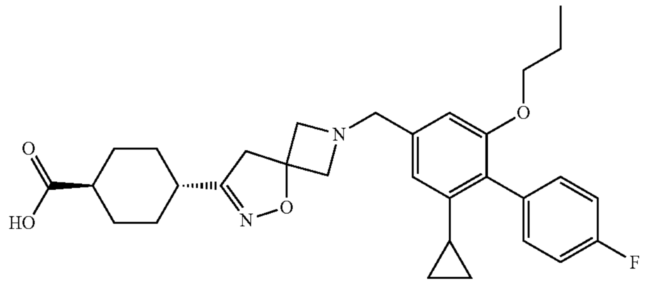 [SMILES: CCCOc1cc(CN2CC3(CC([C@H]4CC[C@H](C(=O)O)CC4)=NO3)C2)cc(C2CC2)c1-c1ccc(F)cc1] | 521.5 |

TABLE 1-continued

| Example No. | IUPAC Name | Structure | MS, NMR |
|---|---|---|---|
| 209 | 1-(2-((2-Cyclopropyl-4'-fluoro-6-propoxybiphenyl-4-yl)methyl)-5-oxa-2,6-diazaspiro[3.4]oct-6-en-7-yl)piperidine-4-carboxylic acid | 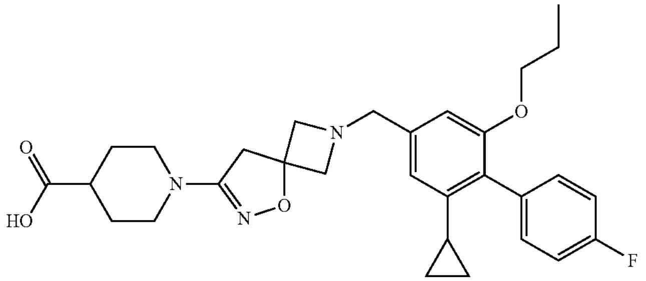 [SMILES: CCCOc1cc(CN2CC3(CC(N4CCC(C(=O)O)CC4)=NO3)C2)cc(C2CC2)c1-c1ccc(F)cc1] | 522.5 |
| 210 | 1-(2-((4-Cyclopropyl-6-ethoxy-5-(4-fluorophenyl)pyridin-2-yl)methyl)-5-oxa-2,6-diazaspiro[3.4]oct-6-en-7-yl)-4-methylpiperidine-4-carboxylic acid | 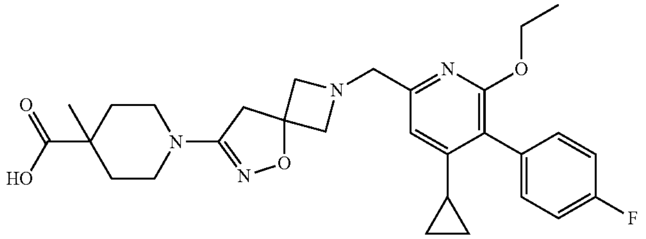 [SMILES: CCOc1nc(CN2CC3(CC(N4CCC(C)(C(=O)O)CC4)=NO3)C2)cc(C2CC2)c1-c1ccc(F)cc1] | 523.4 |
| 211 | 1-(2-((2-Cyclopropyl-4'-fluoro-5-(thiomorpholin-4-yl)biphenyl-4-yl)methyl)-5-oxa-2,6-diazaspiro[3.4]oct-6-en-7-yl)-4-methylpiperidine-4-carboxylic acid | 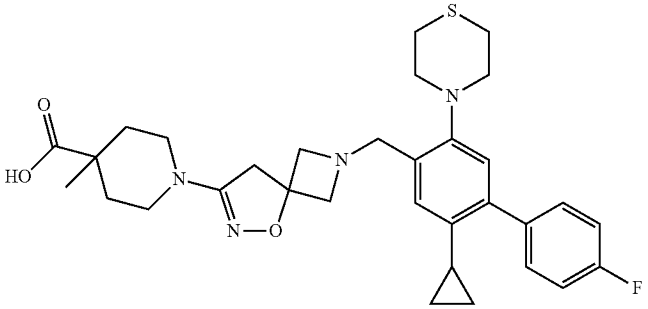 [SMILES: CC1(C(=O)O)CCN(C2=NOC3(C2)CN(Cc2cc(C4CC4)c(-c4ccc(F)cc4)cc2N2CCSCC2)C3)CC1] | 578.1 |
| 212 | 1-(2-(5-Cyclopropyl-4-(4,4-difluoropiperidin-1-yl)-2-isopropoxybenzyl)-5-oxa-2,6-diazaspiro[3.4]oct-6-en-7-yl)-4-methylpiperidine-4-carboxylic acid | 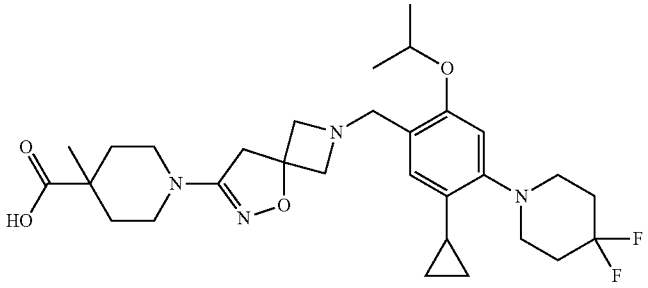 [SMILES: CC(C)Oc1cc(N2CCC(F)(F)CC2)c(C2CC2)cc1CN1CC2(CC(N3CCC(C)(C(=O)O)CC3)=NO2)C1] | 561.5 |
| 213 | 1-(2-(5-Cyclopropyl-4-(4,4-difluoropiperidin-1-yl)-2-isopropoxybenzyl)-5-oxa-2,6-diazaspiro[3.4]oct-6-en-7-yl)-4-ethylpiperidine-4-carboxylic acid | 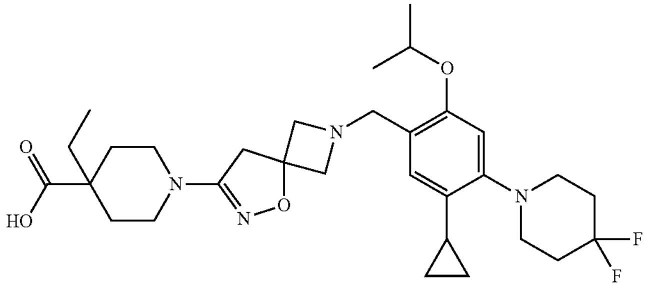 [SMILES: CCC1(C(=O)O)CCN(C2=NOC3(C2)CN(Cc2cc(C4CC4)c(N4CCC(F)(F)CC4)cc2OC(C)C)C3)CC1] | 575.5 |

TABLE 1-continued

| Example No. | IUPAC Name | Structure | MS, NMR |
|---|---|---|---|
| 214 | 1-(2-((2-Cyclopropyl-4'-fluoro-5-methoxybiphenyl-4-yl)methyl)-5-oxa-2,6-diazaspiro[3.4]oct-6-en-7-yl)piperidine-4-carboxylic acid | 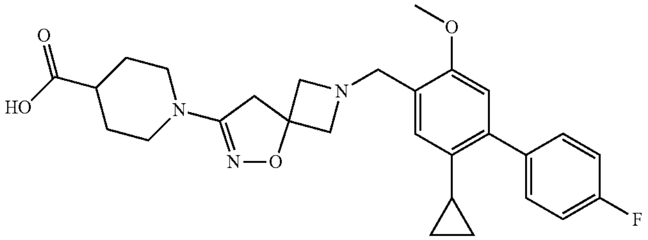 [SMILES: COc1cc(-c2ccc(F)cc2)c(C2CC2)cc1CN1CC2(CC(N3CCC(C(=O)O)CC3)=NO2)C1] | 494.2 |
| 215 | 1-(2-((2-Cyclopropyl-5-ethoxy-4'-fluorobiphenyl-4-yl)methyl)-5-oxa-2,6-diazaspiro[3.4]oct-6-en-7-yl)piperidine-4-carboxylic acid | 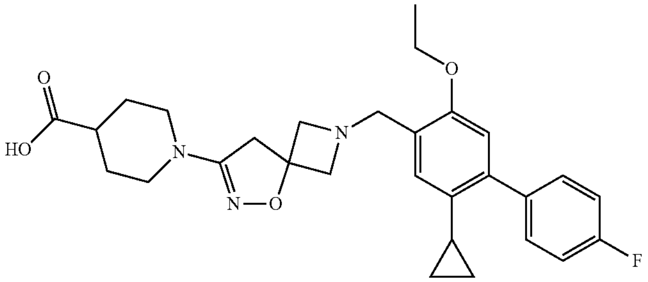 [SMILES: CCOc1cc(-c2ccc(F)cc2)c(C2CC2)cc1CN1CC2(CC(N3CCC(C(=O)O)CC3)=NO2)C1] | 508.3 |
| 216 | 1-(2-((2,6-Diethoxy-4'-fluorobiphenyl-4-yl)methyl)-1,1-dimethyl-5-oxa-2,6-diazaspiro[3.4]oct-6-en-7-yl)-4-methylpiperidine-4-carboxylic acid | 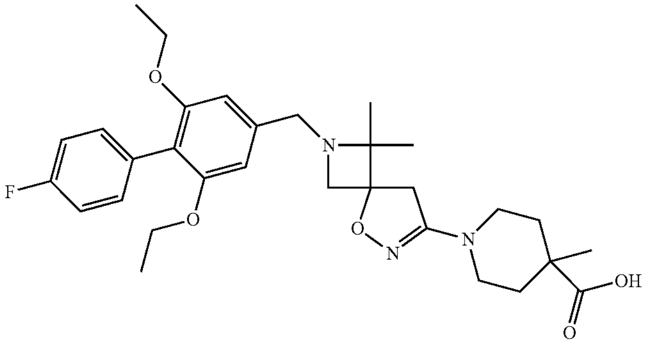 [SMILES: CCOc1cc(CN2CC3(CC(N4CCC(C)(C(=O)O)CC4)=NO3)C2(C)C)cc(OCC)c1-c1ccc(F)cc1] | 554.2 |
| 217 | 1-(2-((2,6-Diethoxy-4'-fluorobiphenyl-4-yl)methyl)-1-methyl-5-oxa-2,6-diazaspiro[3.4]oct-6-en-7-yl)-4-methylpiperidine-4-carboxylic acid | 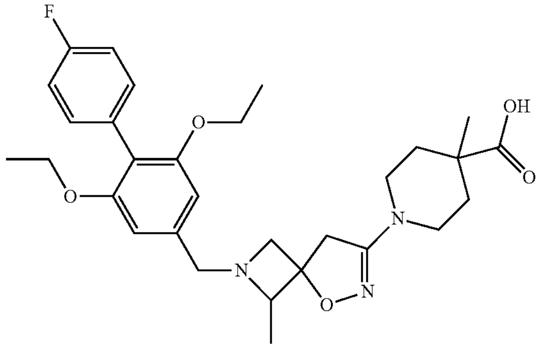 [SMILES: CCOc1cc(CN2CC3(CC(N4CCC(C)(C(=O)O)CC4)=NO3)C2C)cc(OCC)c1-c1ccc(F)cc1] | 540.2 |
| 218 | 1-(2-((6-Cyclopropyl-4-ethoxy-5-(4-fluorophenyl)pyridin-2-yl)methyl)-5-oxa-2,6-diazaspiro[3.4]oct-6-en-7-yl)-4-methylpiperidine-4-carboxylic acid | 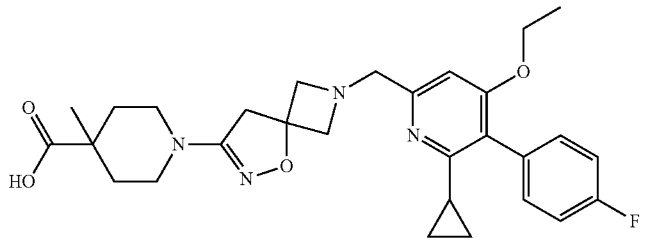 [SMILES: CCOc1cc(CN2CC3(CC(N4CCC(C)(C(=O)O)CC4)=NO3)C2)nc(C2CC2)c1-c1ccc(F)cc1] | 523.5 |

TABLE 1-continued

| Example No. | IUPAC Name | Structure | MS, NMR |
|---|---|---|---|
| 219 | 1-(2-((2-Cyclohex-1-en-1-yl)-4'-fluoro-5-methoxybiphenyl-4-yl)methyl)-5-oxa-2,6-diazaspiro[3.4]oct-6-en-7-yl)-4-methylpiperidine-4-carboxylic acid | 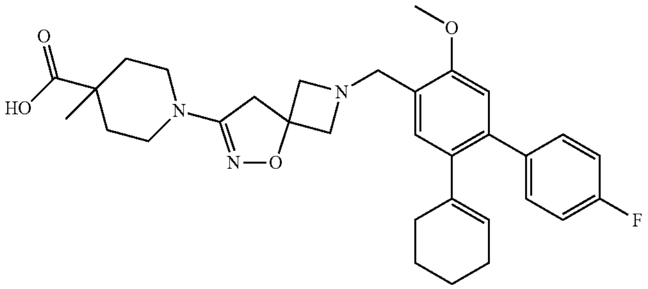 [SMILES: COc1cc(-c2ccc(F)cc2)c(C2=CCCCC2)cc1CN1CC2(CC(N3CCC(C)(C(=O)O)CC3)=NO2)C1] | 548.1 |
| 220 | 1-(2-((4'-Fluoro-2-(1-hydroxycyclobutyl)-5-methoxybiphenyl-4-yl)methyl)-5-oxa-2,6-diazaspiro[3.4]oct-6-en-7-yl)-4-methylpiperidine-4-carboxylic acid | 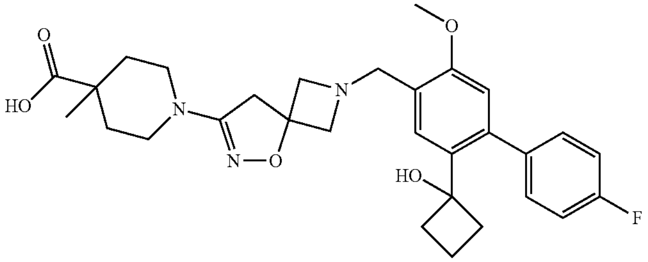 [SMILES: COc1cc(-c2ccc(F)cc2)c(C2(O)CCC2)cc1CN1CC2(CC(N3CCC(C)(C(=O)O)CC3)=NO2)C1] | 538.1 |
| 221 | 1-(2-((2'-Chloro-2,6-diethoxy-4'-fluoro-biphenyl-4-yl)methyl)-5-oxa-2,6-diazaspiro[3.4]oct-6-en-7-yl)-4-ethylpiperidine-4-carboxylic acid | 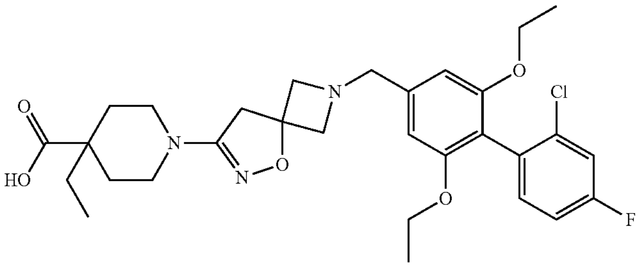 [SMILES: CCOc1cc(CN2CC3(CC(N4CCC(CC)(C(=O)O)CC4)=NO3)C2)cc(OCC)c1-c1ccc(F)cc1Cl] | 574.4 |
| 222 | 1-(2-(5-Cyclopropyl-4-(4,4-difluoro-piperidin-1-yl)-2-ethoxybenzyl)-5-oxa-2,6-diazaspiro[3.4]oct-6-en-7-yl)-4-methylpiperidine-4-carboxylic acid | 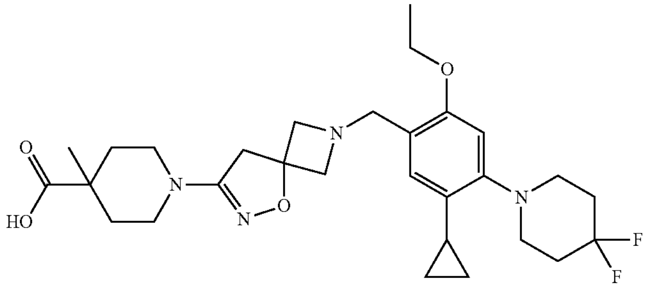 [SMILES: CCOc1cc(N2CCC(F)(F)CC2)c(C2CC2)cc1CN1CC2(CC(N3CCC(C)(C(=O)O)CC3)=NO2)C1] | 547.5 |
| 223 | 1-(2-(3-Chloro-5-cyclopropyl-4-(4,4-difluoropiperidin-1-yl)-2-ethoxybenzyl)-5-oxa-2,6-diazaspiro[3.4]oct-6-en-7-yl)-4-methylpiperidine-4-carboxylic acid | 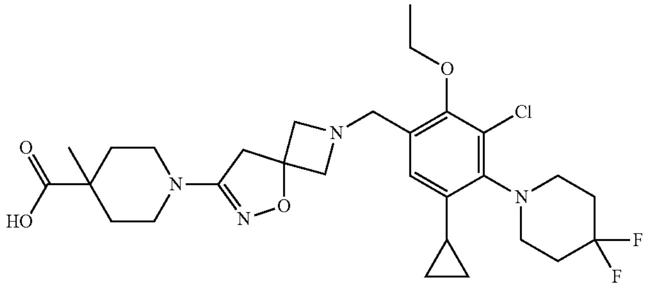 [SMILES: CCOc1c(CN2CC3(CC(N4CCC(C)(C(=O)O)CC4)=NO3)C2)cc(C2CC2)c(N2CCC(F)(F)CC2)c1Cl] | 581.4 |

TABLE 1-continued

| Example No. | IUPAC Name | Structure | MS, NMR |
|---|---|---|---|
| 224 | 1-(2-(2-Cyclopropyl-4-(4,4-difluoro-piperidin-1-yl)-5-ethoxybenzyl)-5-oxa-2,6-diazaspiro[3.4]oct-6-en-7-yl)-4-methylpiperidine-4-carboxylic acid | 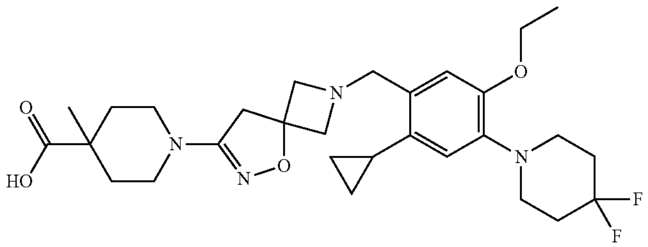 [SMILES: CCOc1cc(CN2CC3(CC(N4CCC(C)(C(=O)O)CC4)=NO3)C2)c(C2CC2)cc1N1CCC(F)(F)CC1] | 547.5 |
| 225 | trans-4-(2-((2-Cyclo-propyl-6-ethoxy-4'-fluorobiphenyl-4-yl)methyl)-5-oxa-2,6-diazaspiro[3.4]oct-6-en-7-yl)cyclo-hexanecarboxylic acid | 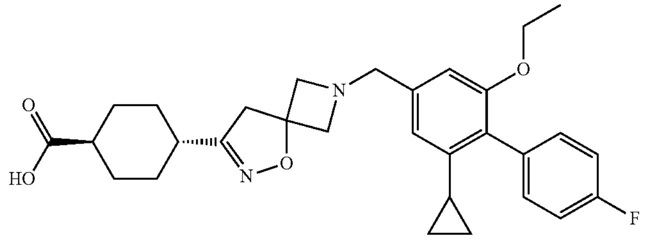 [SMILES: CCOc1cc(CN2CC3(CC([C@H]4CC[C@H](C(=O)O)CC4)=NO3)C2)cc(C2CC2)c1-c1ccc(F)cc1] | 507.4 |
| 226 | 1-(2-((2-Cyclopropyl-2',4'-difluoro-5-methoxybiphenyl-4-yl)methyl)-5-oxa-2,6-diazaspiro[3.4]oct-6-en-7-yl)-4-methylpiperidine-4-carboxylic acid | 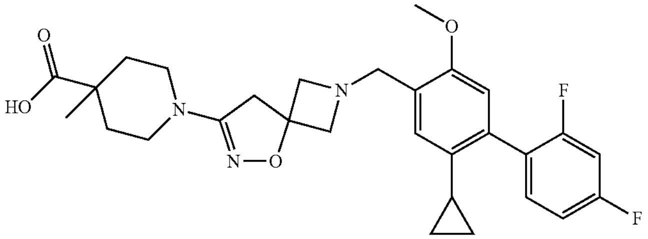 [SMILES: COc1cc(-c2ccc(F)cc2F)c(C2CC2)cc1CN1CC2(CC(N3CCC(C)(C(=O)O)CC3)=NO2)C1] | 526.1 |
| 227 | 1-(2-(4-Cyclobutyl-5-cyclopropyl-2-ethoxybenzyl)-5-oxa-2,6-diazaspiro[3.4]oct-6-en-7-yl)-4-methylpiperidine-4-carboxylic acid | 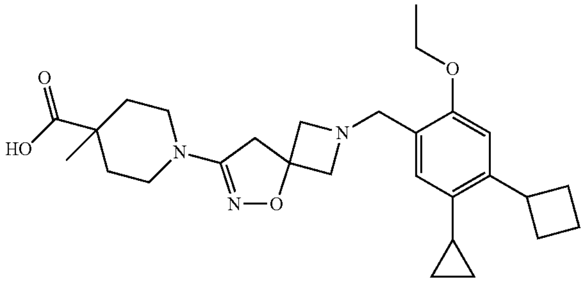 [SMILES: CCOc1cc(C2CCC2)c(C2CC2)cc1CN1CC2(CC(N3CCC(C)(C(=O)O)CC3)=NO2)C1] | 482.3 |
| 228 | 4-(2-((2,6-Diethoxy-4'-fluorobiphenyl-4-yl)methyl)-5-oxa-2,6-diazaspiro[3.4]oct-6-en-7-yl)bicyclo[2.2.1]heptane-1-carboxylic acid | 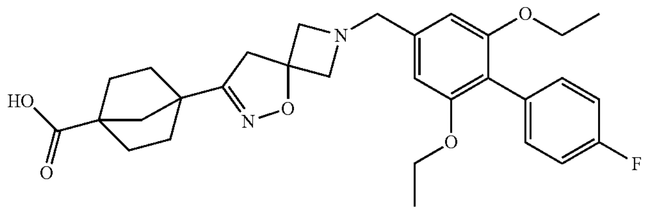 [SMILES: CCOc1cc(CN2CC3(CC(C45CCC(C(=O)O)(CC4)C5)=NO3)C2)cc(OCC)c1-c1ccc(F)cc1] | 523.2 |
| 229 | 4-(2-((2-Cyclo-propyl-6-ethoxy-4'-fluorobiphenyl-4-yl)methyl)-5-oxa-2,6-diazaspiro[3.4]oct-6-en-7-yl)bicyclo[2.2.1]heptane-1-carboxylic acid | 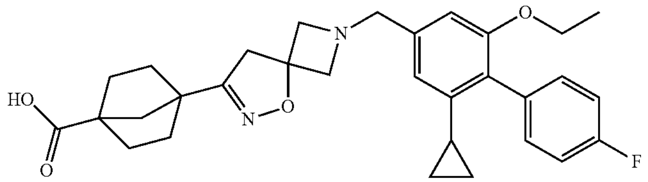 [SMILES: CCOc1cc(CN2CC3(CC(C45CCC(C(=O)O)(CC4)C5)=NO3)C2)cc(C2CC2)c1-c1ccc(F)cc1] | 519.2 |

TABLE 1-continued

| Example No. | IUPAC Name | Structure | MS, NMR |
|---|---|---|---|
| 230 | 4-(2-((2,6-Diethoxy-4'-fluorobiphenyl-4-yl)methyl)-5-oxa-2,6-diazaspiro[3.4]oct-6-en-7-yl)bicyclo[2.2.2]octane-1-carboxylic acid | 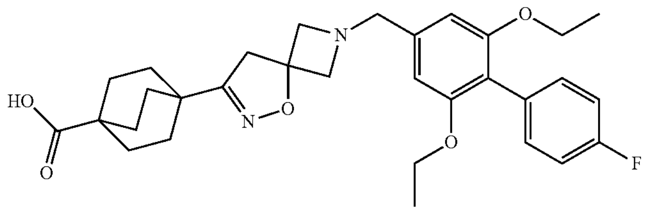 [SMILES: CCOc1cc(CN2CC3(CC(C45CCC(C(=O)O)(CC4)CC5)=NO3)C2)cc(OCC)c1-c1ccc(F)cc1] | 537.2 |
| 231 | 4-(2-((2-Cyclopropyl-6-ethoxy-4'-fluoro-biphenyl-4-yl)methyl)-5-oxa-2,6-diazaspiro[3.4]oct-6-en-7-yl)bicyclo[2.2.2]octane-1-carboxylic acid | 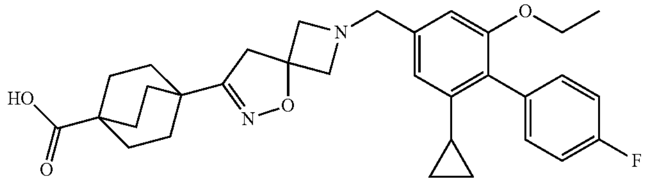 [SMILES: CCOc1cc(CN2CC3(CC(C45CCC(C(=O)O)(CC4)CC5)=NO3)C2)cc(C2CC2)c1-c1ccc(F)cc1] | 533.3 |
| 232 | 1-(2-((2-cyclopropyl-5-ethyl-4'-fluoro-biphenyl-4-yl)methyl)-5-oxa-2,6-diazaspiro[3.4]oct-6-en-7-yl)-4-methyl-piperidine-4-carboxylic acid | 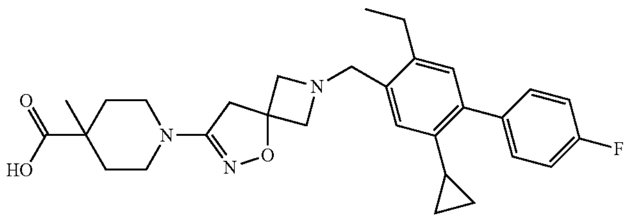 [SMILES: CCc1cc(-c2ccc(F)cc2)c(C2CC2)cc1CN1CC2(CC(N3CCC(C)(C(=O)O)CC3)=NO2)C1] | 506.3 |
| 233 | 1-(2-(4-Cyclobutyl-3-cyclopropyl-5-ethoxybenzyl)-5-oxa-2,6-diazaspiro[3.4]oct-6-en-7-yl)-4-methylpiperidine-4-carboxylic acid | 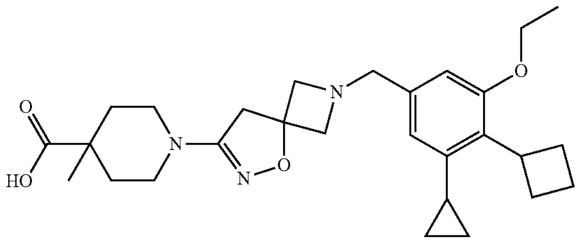 [SMILES: CCOc1cc(CN2CC3(CC(N4CCC(C)(C(=O)O)CC4)=NO3)C2)cc(C2CC2)c1C1CCC1] | 482.2 |
| 234 | 1-(2-((2-Cyclopropyl-3',4'-difluoro-5-methoxybiphenyl-4-yl)methyl)-5-oxa-2,6-diazaspiro[3.4]oct-6-en-7-yl)-4-methylpiperidine-4-carboxylic acid | 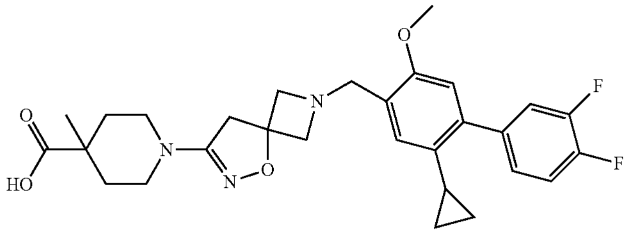 [SMILES: COc1cc(-c2ccc(F)c(F)c2)c(C2CC2)cc1CN1CC2(CC(N3CCC(C)(C(=O)O)CC3)=NO2)C1] | 526.2 |
| 235 | 1-(2-((2-Cyclopropyl-5-ethoxy-2',4'-difluorobiphenyl-4-yl)methyl)-5-oxa-2,6-diazaspiro[3.4]oct-6-en-7-yl)-4-methylpiperidine-4-carboxylic acid | 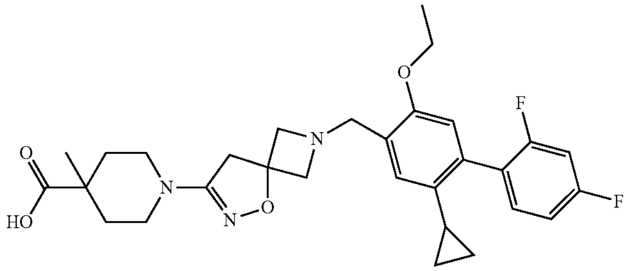 [SMILES: CCOc1cc(-c2ccc(F)cc2F)c(C2CC2)cc1CN1CC2(CC(N3CCC(C)(C(=O)O)CC3)=NO2)C1] | 540.3 |

TABLE 1-continued

| Example No. | IUPAC Name | Structure | MS, NMR |
|---|---|---|---|
| 236 | 1-(2-((2-Cyclopropyl-5-ethoxy-2'-fluoro-biphenyl-4-yl)methyl)-5-oxa-2,6-diazaspiro[3.4]oct-6-en-7-yl)-4-methylpiperidine-4-carboxylic acid | 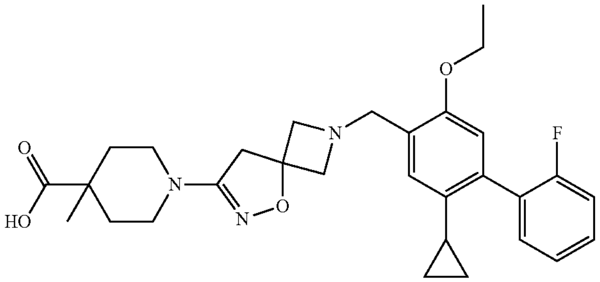 [SMILES: CCOc1cc(-c2ccccc2F)c(C2CC2)cc1CN1CC2(CC(N3CCC(C)(C(=O)O)CC3)=NO2)C1] | 522.2 |
| 237 | 1-(2-((2-Cyclopropyl-5-ethoxy-2',6'-difluorobiphenyl-4-yl)methyl)-5-oxa-2,6-diazaspiro[3.4]oct-6-en-7-yl)-4-methylpiperidine-4-carboxylic acid | 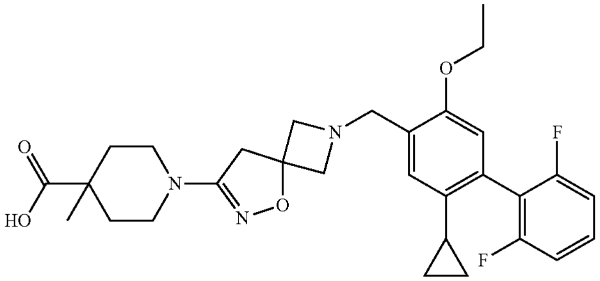 [SMILES: CCOc1cc(-c2c(F)cccc2F)c(C2CC2)cc1CN1CC2(CC(N3CCC(C)(C(=O)O)CC3)=NO2)C1] | 540.3 |
| 238 | 1-(2-((2-Chloro-6-cyclopropyl-4'-fluoro-3-methoxybiphenyl-4-yl)methyl)-5-oxa-2,6-diazaspiro[3.4]oct-6-en-7-yl)-4-methylpiperidine-4-carboxylic acid | 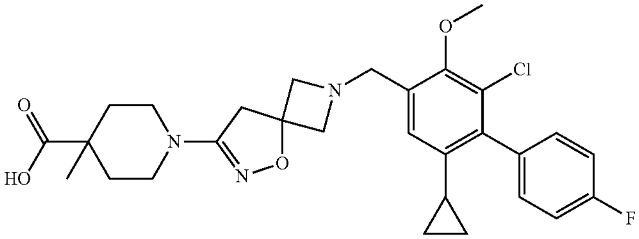 [SMILES: COc1c(CN2CC3(CC(N4CCC(C)(C(=O)O)CC4)=NO3)C2)cc(C2CC2)c(-c2ccc(F)cc2)c1Cl] | 542.1 |
| 239 | 1-(2-((2-Chloro-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylic acid | 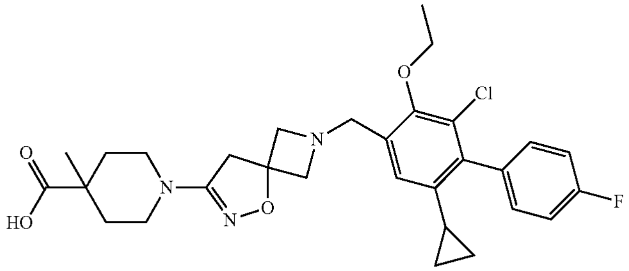 | 556.2 |
| 240 | 1-(2-((2-Bromo-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylic acid | 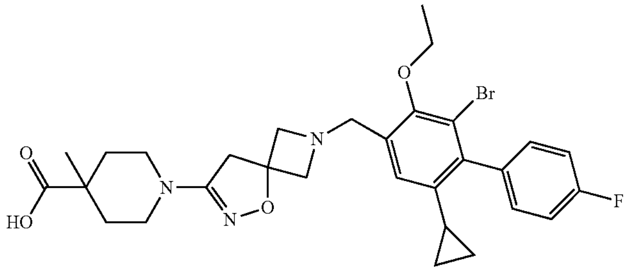 [SMILES: CCOc1c(CN2CC3(CC(N4CCC(C)(C(=O)O)CC4)=NO3)C2)cc(C2CC2)c(-c2ccc(F)cc2)c1Br] | 600.1 |

TABLE 1-continued

| Example No. | IUPAC Name | Structure | MS, NMR |
| --- | --- | --- | --- |
| 241 | 1-(2-((6-Cyclopropyl-3-ethoxy-4'-fluoro-2-methylbiphenyl-4-yl)methyl)-5-oxa-2,6-diazaspiro[3.4]oct-6-en-7-yl)-4-methylpiperidine-4-carboxylic acid | 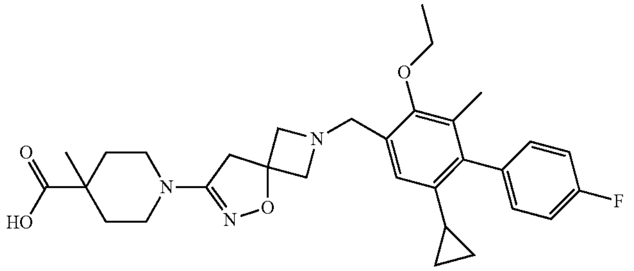 [SMILES: CCOc1c(CN2CC3(CC(N4CCC(C)(C(=O)O)CC4)=NO3)C2)cc(C2CC2)c(-c2ccc(F)cc2)c1C] | 536.2 |
| 242 | 1-(2-((2-Cyano-6-cyclopropyl-3-ethoxy-4'-fluorobiphenyl-4-yl)methyl)-5-oxa-2,6-diazaspiro[3.4]oct-6-en-7-yl)-4-methylpiperidine-4-carboxylic acid | 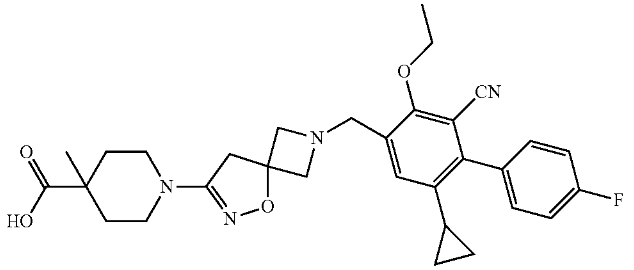 [SMILES: CCOc1c(CN2CC3(CC(N4CCC(C)(C(=O)O)CC4)=NO3)C2)cc(C2CC2)c(-c2ccc(F)cc2)c1C#N] | 547.2 |
| 243 | 1-(2-((6-Cyclopropyl-3-ethoxy-2,4'-difluorobiphenyl-4-yl)methyl)-5-oxa-2,6-diazaspiro[3.4]oct-6-en-7-yl)-4-methylpiperidine-4-carboxylic acid | 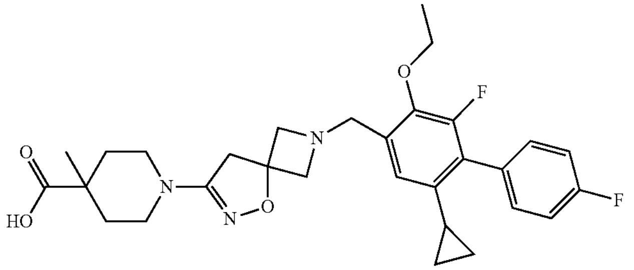 [SMILES: CCOc1c(CN2CC3(CC(N4CCC(C)(C(=O)O)CC4)=NO3)C2)cc(C2CC2)c(-c2ccc(F)cc2)c1F] | 540.3 |
| 244 | 1-(2-((2-Cyclopropyl-3,4'-difluoro-5-methoxybiphenyl-4-yl)methyl)-5-oxa-2,6-diazaspiro[3.4]oct-6-en-7-yl)-4-methylpiperidine-4-carboxylic acid | 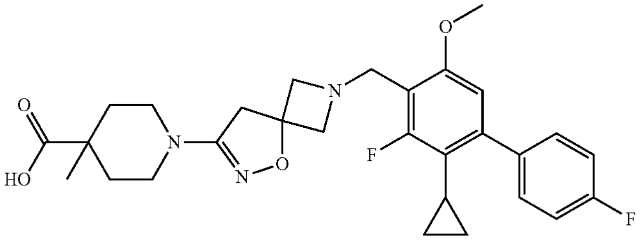 [SMILES: COc1cc(-c2ccc(F)cc2)c(C2CC2)c(F)c1CN1CC2(CC(N3CCC(C)(C(=O)O)CC3)=NO2)C1] | 526.2 |
| 245 | 1-(2-(4-Cyclobutyl-5-cyclopropyl-2-methoxybenzyl)-5-oxa-2,6-diazaspiro[3.4]oct-6-en-7-yl)-4-methylpiperidine-4-carboxylic acid | 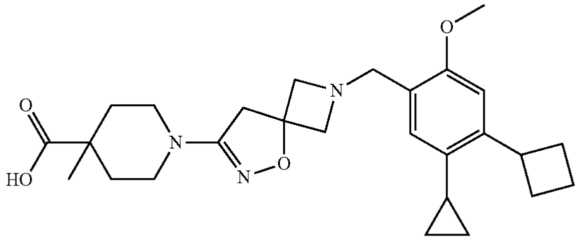 [SMILES: COc1cc(C2CCC2)c(C2CC2)cc1CN1CC2(CC(N3CCC(C)(C(=O)O)CC3)=NO2)C1] | 468.2 |

TABLE 1-continued

| Example No. | IUPAC Name | Structure | MS, NMR |
| --- | --- | --- | --- |
| 246 | 1-(2-(4-Cyclobutyl-5-cyclopropyl-2-iso-propoxybenzyl)-5-oxa-2,6-diazaspiro[3.4]oct-6-en-7-yl)piperidine-4-carboxylic acid | 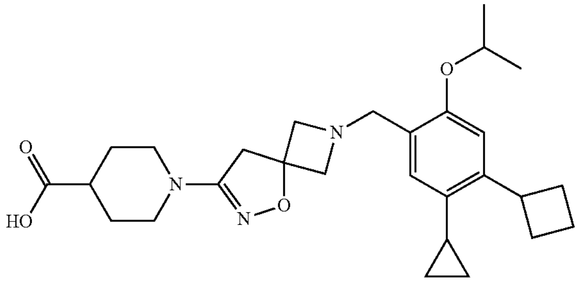 [SMILES: CC(C)Oc1cc(C2CCC2)c(C2CC2)cc1CN1CC2(CC(N3CCC(C(=O)O)CC3)=NO2)C1] | 482.2 |
| 247 | 1-(2-(4-Cyclobutyl-5-cyclopropyl-2-ethoxybenzyl)-5-oxa-2,6-diazaspiro[3.4]oct-6-en-7-yl)piperidine-4-carboxylic acid | 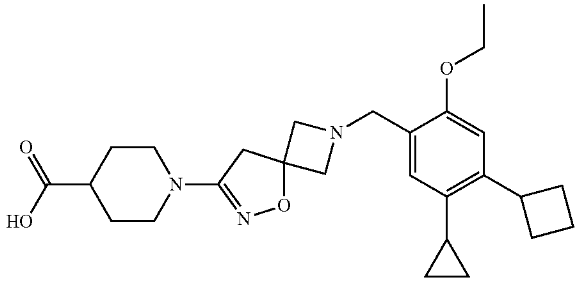 [SMILES: CCOc1cc(C2CCC2)c(C2CC2)cc1CN1CC2(CC(N3CCC(C(=O)O)CC3)=NO2)C1] | 468.2 |
| 248 | 1-(2-(4,5-Dicyclo-propyl-2-isopropoxy-benzyl)-5-oxa-2,6-diazaspiro[3.4]oct-6-en-7-yl)-4-methyl-piperidine-4-carboxylic acid | 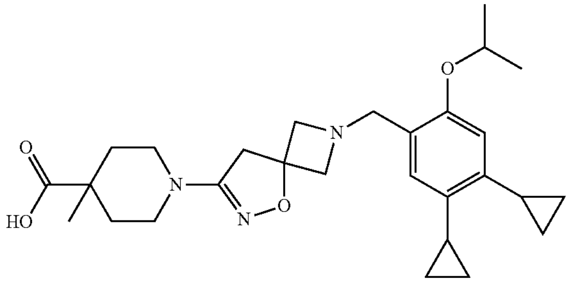 [SMILES: CC(C)Oc1cc(C2CC2)c(C2CC2)cc1CN1CC2(CC(N3CCC(C)(C(=O)O)CC3)=NO2)C1] | 482.2 |
| 249 | 1-(2-(4-Cyclobutyl-5-cyclopropyl-2-isopropoxybenzyl)-5-oxa-2,6-diazaspiro[3.4]oct-6-en-7-yl)-4-methyl-piperidine-4-carboxylic acid | 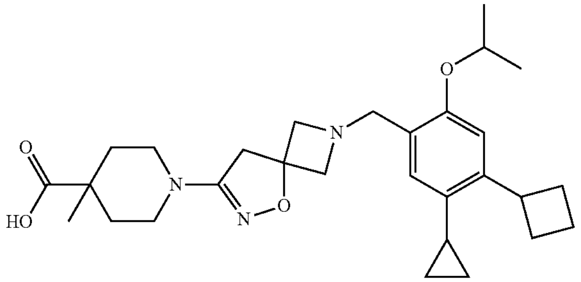 [SMILES: CC(C)Oc1cc(C2CCC2)c(C2CC2)cc1CN1CC2(CC(N3CCC(C)(C(=O)O)CC3)=NO2)C1] | 496.3 |
| 250 | 1-(2-(4,5-Dicyclo-propyl-2-ethoxy-benzyl)-5-oxa-2,6-diazaspiro[3.4]oct-6-en-7-yl)-4-methyl-piperidine-4-carboxylic acid | 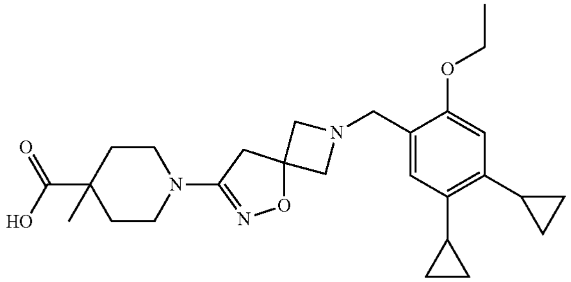 [SMILES: CCOc1cc(C2CC2)c(C2CC2)cc1CN1CC2(CC(N3CCC(C)(C(=O)O)CC3)=NO2)C1] | 468.2 |

TABLE 1-continued

| Example No. | IUPAC Name | Structure | MS, NMR |
|---|---|---|---|
| 251 | 1-(2-((2-Cyclopropyl-4'-fluoro-6-methoxy-biphenyl-4-yl)methyl)-5-oxa-2,6-diazaspiro[3.4]oct-6-en-7-yl)-4-methyl-piperidine-4-carboxylic acid | 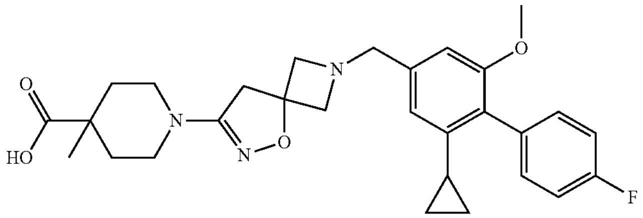 [SMILES: COc1cc(CN2CC3(CC(N4CCC(C)(C(=O)O)CC4)=NO3)C2)cc(C2CC2)c1-c1ccc(F)cc1] | 508.2 |
| 252 | 1-(2-((2-Chloro-6-cyclopropyl-4'-fluoro-3-methoxy-biphenyl-4-yl)methyl)-5-oxa-2,6-diazaspiro[3.4]oct-6-en-7-yl)-4-ethyl-piperidine-4-carboxylic acid | 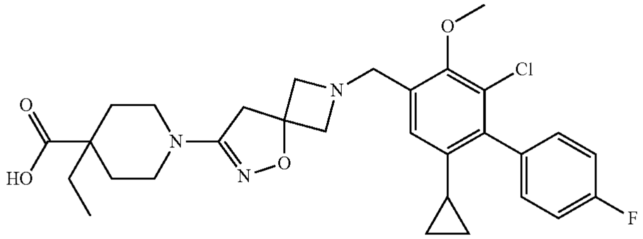 [SMILES: CCC1(C(=O)O)CCN(C2=NOC3(C2)CN(Cc2cc(C4CC4)c(-c4ccc(F)cc4)c(Cl)c2OC)C3)CC1] | 556.2 |
| 253 | 1-(2-(3-Chloro-4,5-dicyclopropyl-2-isopropoxybenzyl)-5-oxa-2,6-diazaspiro[3.4]oct-6-en-7-yl)-4-methyl-piperidine-4-carboxylic acid | 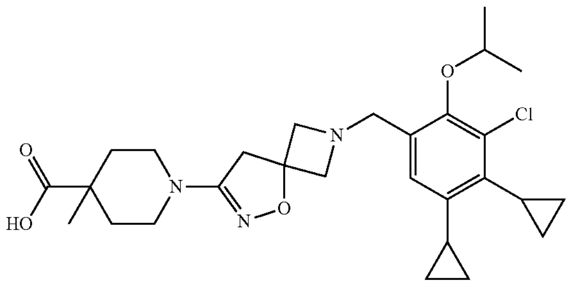 [SMILES: CC(C)Oc1c(CN2CC3(CC(N4CCC(C)(C(=O)O)CC4)=NO3)C2)cc(C2CC2)c(C2CC2)c1Cl] | 516.2 |
| 254 | 1-(2-(3-Chloro-4,5-dicyclopropyl-2-methoxybenzyl)-5-oxa-2,6-diazaspiro[3.4]oct-6-en-7-yl)-4-methylpiperidine-4-carboxylic acid | 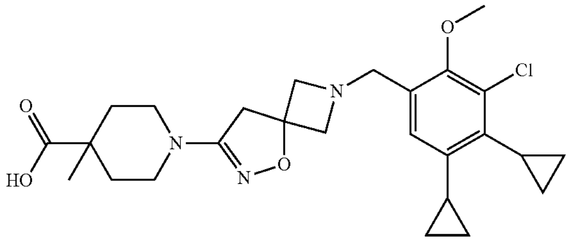 [SMILES: COc1c(CN2CC3(CC(N4CCC(C)(C(=O)O)CC4)=NO3)C2)cc(C2CC2)c(C2CC2)c1Cl] | 488.2 |
| 255 | 1-(2-(3-Chloro-4,5-dicyclopropyl-2-ethoxybenzyl)-5-oxa-2,6-diazaspiro[3.4]oct-6-en-7-yl)-4-methylpiperidine-4-carboxylic acid | 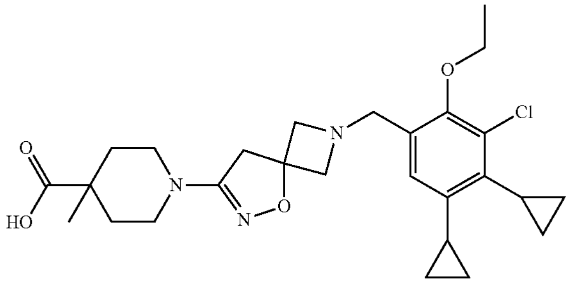 [SMILES: CCOc1c(CN2CC3(CC(N4CCC(C)(C(=O)O)CC4)=NO3)C2)cc(C2CC2)c(C2CC2)c1Cl] | 502.2 |
| 256 | 1-(2-(4,5-Dicyclopropyl-3-fluoro-2-isopropoxybenzyl)-5-oxa-2,6-diazaspiro[3.4]oct-6-en-7-yl)-4-methyl-piperidine-4-carboxylic acid | 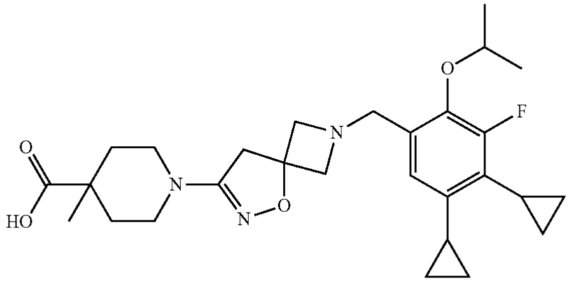 [SMILES: CC(C)Oc1c(CN2CC3(CC(N4CCC(C)(C(=O)O)CC4)=NO3)C2)cc(C2CC2)c(C2CC2)c1F] | 500.3 |

TABLE 1-continued

| Example No. | IUPAC Name | Structure | MS, NMR |
|---|---|---|---|
| 257 | 1-(2-(4,5-Dicyclopropyl-2-ethoxy-3-fluorobenzyl)-5-oxa-2,6-diazaspiro[3.4]oct-6-en-7-yl)-4-methylpiperidine-4-carboxylic acid | 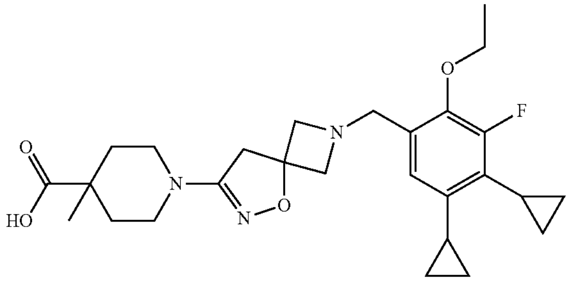 [SMILES: CCOc1c(CN2CC3(CC(N4CCC(C)(C(=O)O)CC4)=NO3)C2)cc(C2CC2)c(C2CC2)c1F] | 486.2 |
| 258 | 1-(2-((2-Chloro-6-cyclopropyl-2',4'-difluoro-3-methoxybiphenyl-4-yl)methyl)-5-oxa-2,6-diazaspiro[3.4]oct-6-en-7-yl)-4-methylpiperidine-4-carboxylic acid | 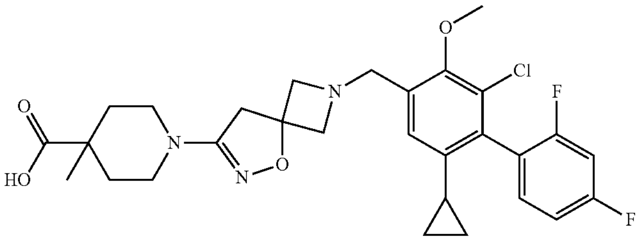 [SMILES: COc1c(CN2CC3(CC(N4CCC(C)(C(=O)O)CC4)=NO3)C2)cc(C2CC2)c(-c2ccc(F)cc2F)c1Cl] | 560.1 |
| 259 | 1-(2-((6-Cyclopropyl-2,2',4'-trifluoro-3-methoxybiphenyl-4-yl)methyl)-5-oxa-2,6-diazaspiro[3.4]oct-6-en-7-yl)-4-methylpiperidine-4-carboxylic acid | 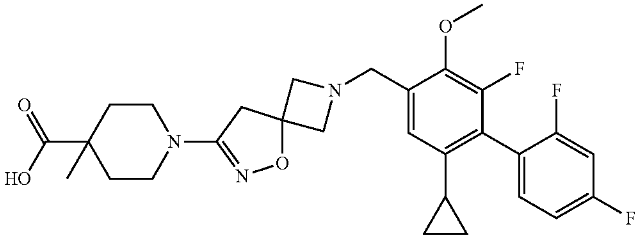 [SMILES: COc1c(CN2CC3(CC(N4CCC(C)(C(=O)O)CC4)=NO3)C2)cc(C2CC2)c(-c2ccc(F)cc2F)c1F] | 544.1 |
| 260 | 1-(2-((6-Cyclopropyl-3-ethoxy-2,2',4'-trifluorobiphenyl-4-yl)methyl)-5-oxa-2,6-diazaspiro[3.4]oct-6-en-7-yl)-4-methylpiperidine-4-carboxylic acid | 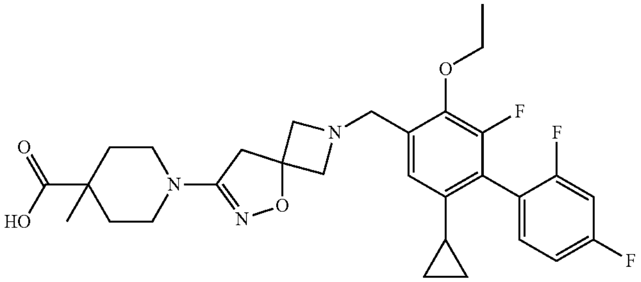 [SMILES: CCOc1c(CN2CC3(CC(N4CCC(C)(C(=O)O)CC4)=NO3)C2)cc(C2CC2)c(-c2ccc(F)cc2F)c1F] | 558.2 |
| 261 | 1-(2-((6-Cyclopropyl-3-ethoxy-2,4'-difluorobiphenyl-4-yl)methyl)-5-oxa-2,6-diazaspiro[3.4]oct-6-en-7-yl)piperidine-4-carboxylic acid | 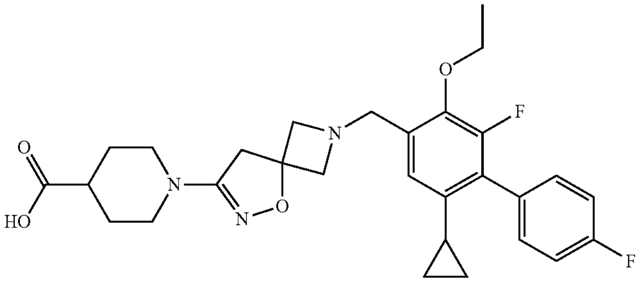 [SMILES: CCOc1c(CN2CC3(CC(N4CCC(C(=O)O)CC4)=NO3)C2)cc(C2CC2)c(-c2ccc(F)cc2)c1F] | 526.1 |

TABLE 1-continued

| Example No. | IUPAC Name | Structure | MS, NMR |
| --- | --- | --- | --- |
| 262 | 1-(2-((2-Chloro-6-cyclopropyl-2',4'-difluoro-3-methoxy-biphenyl-4-yl)methyl)-5-oxa-2,6-diazaspiro[3.4]oct-6-en-7-yl)-4-ethyl-piperidine-4-carboxylic acid | 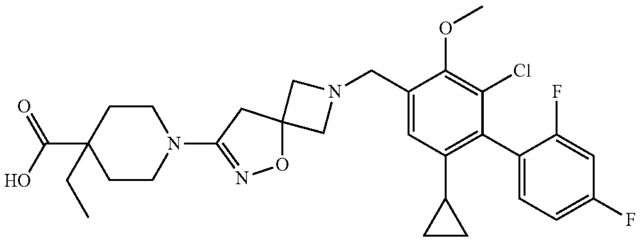 [SMILES: CCC1(C(=O)O)CCN(C2=NOC3(C2)CN(Cc2cc(C4CC4)c(-c4ccc(F)cc4F)c(Cl)c2OC)C3)CC1] | 574.1 |
| 263 | 1-(2-((2-Chloro-6-cyclopropyl-3-ethoxy-2',4'-difluorobiphenyl-4-yl)methyl)-5-oxa-2,6-diazaspiro[3.4]oct-6-en-7-yl)-4-methyl-piperidine-4-carboxylic acid | 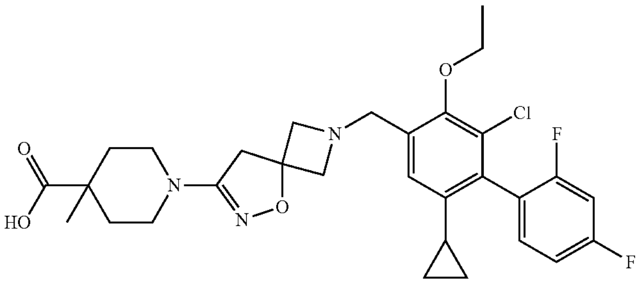 [SMILES: CCOc1c(CN2CC3(CC(N4CCC(C)(C(=O)O)CC4)=NO3)C2)cc(C2CC2)c(-c2ccc(F)cc2F)c1Cl] | 574.1 |
| 264 | 1-(2-((6-Cyclopropyl-2,2',4'-trifluoro-3-isopropoxybiphenyl-4-yl)methyl)-5-oxa-2,6-diazaspiro[3.4]oct-6-en-7-yl)piperidine-4-carboxylic acid | 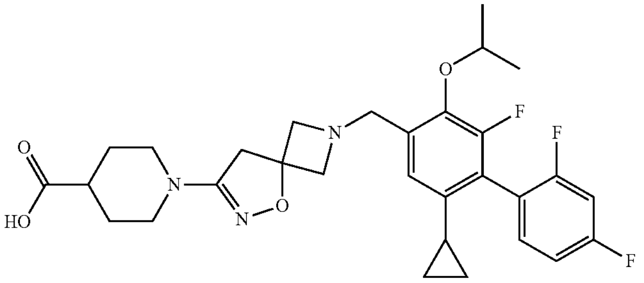 [SMILES: CC(C)Oc1c(CN2CC3(CC(N4CCC(C(=O)O)CC4)=NO3)C2)cc(C2CC2)c(-c2ccc(F)cc2F)c1F] | 558.2 |
| 265 | 1-(2-((6-Cyclopropyl-2,4'-difluoro-3-methoxybiphenyl-4-yl)methyl)-5-oxa-2,6-diazaspiro[3.4]oct-6-en-7-yl)-4-methyl-piperidine-4-carboxylic acid | 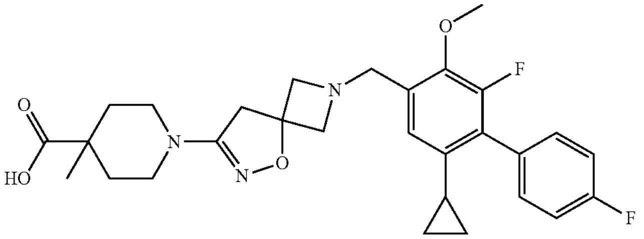 [SMILES: COc1c(CN2CC3(CC(N4CCC(C)(C(=O)O)CC4)=NO3)C2)cc(C2CC2)c(-c2ccc(F)cc2)c1F] | 526.1 |
| 266 | 1-(2-((6-Cyclopropyl-2,4'-difluoro-3-methoxybiphenyl-4-yl)methyl)-5-oxa-2,6-diazaspiro[3.4]oct-6-en-7-yl)piperidine-4-carboxylic acid | 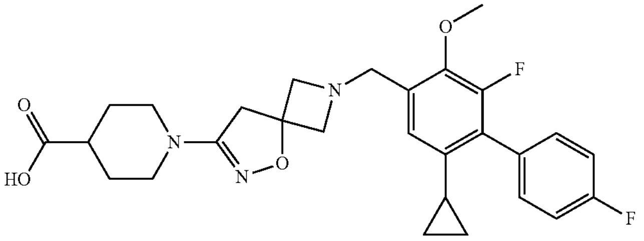 [SMILES: COc1c(CN2CC3(CC(N4CCC(C(=O)O)CC4)=NO3)C2)cc(C2CC2)c(-c2ccc(F)cc2)c1F] | 512.1 |

TABLE 1-continued

| Example No. | IUPAC Name | Structure | MS, NMR |
|---|---|---|---|
| 267 | 1-(2-((2-Ethoxy-4'-fluoro-6-propoxy-biphenyl-4-yl)methyl)-5-oxa-2,6-diazaspiro[3.4]oct-6-en-7-yl)-4-methyl-piperidine-4-carboxylic acid | 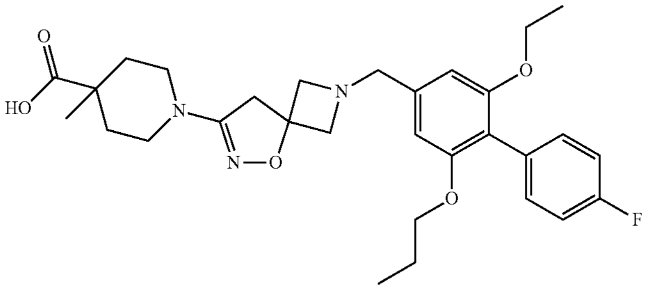 [SMILES: CCCOc1cc(CN2CC3(CC(N4CCC(C)(C(=O)O)CC4)=NO3)C2)cc(OCC)c1-c1ccc(F)cc1] | 540.1 |
| 268 | 1-(2-((2,6-Dicyclo-propyl-4'-fluoro-biphenyl-4-yl)methyl)-5-oxa-2,6-diazaspiro[3.4]oct-6-en-7-yl)-4-methyl-piperidine-4-carboxylic acid | 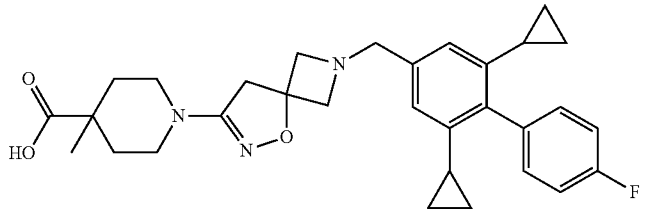 [SMILES: CC1(C(=O)O)CCN(C2=NOC3(C2)CN(Cc2cc(C4CC4)c(-c4ccc(F)cc4)c(C4CC4)c2)C3)CC1] | 518.1 |

Test Example 1

Evaluation of Human SSTR5 Antagonist Activity Using an Intracellular cAMP Concentration as an Indicator Measurement of the intracellular cAMP concentration was performed using a HTRF cAMP dynamic 2 kit (manufactured by Cisbio). A test compound which was diluted with an assay buffer (5 mM HEPES (pH 7.5) (manufactured by Invitrogen Corp.), 0.1% Fatty-acid free BSA (manufactured by Sigma-Aldrich, Inc.), HESS (manufactured by Invitrogen Corp.) containing 500 μM IBMX (manufactured by Wako Pure Chemical Industries, Ltd) was added by 2 μL/well to a 384 well white plate (manufactured by Greiner) such that a final concentration become 1 μM. A frozen stock, which was stably expressed dihydrofolate reductase-deficient (dhfr-) CHO cells in which human SSTR5 gene (Accession No. NM001053), was melted in a thermostatic chamber at 37° C., and it was suspended on a medium of subculture (medium prepared from MEM alpha (Nikken Biomedical Institute Ltd.), 10% dialyzed serum (manufactured by Gemini Co., Ltd.) and 50 μg/mL gentamicin (manufactured by Invitrogen Corp.). After centrifuging the cell suspension, the cell suspension was resuspended using the assay buffer, and the resultant was added to each well by 2 μL/well to be 3760 cells/well. After a test compound and cells were mixed, the resultant was incubated for 15 minutes. An assay buffer which contains 1 nM of somatostatin 14 (manufactured by PEPTIDE INSTITUTE, INC.) and 0.3 μM of forskolin (manufactured by Wako Pure Chemical Industries, Ltd) as a final concentration was added by 2 μM/well, and incubation was performed for 30 minutes at room temperature. Each of cAMP-d2 and anti-cAMP-cryptate was added by 3 μL/well, it was allowed to stand for 60 minutes at room temperature, and FRET (Fluorescence resonance energy transfer) intensity was measured using Multi-label reader Envision (manufactured by Perkin Elmer Inc.). Using the calibration curve prepared from the FRET intensity of well groups in which cAMP as arbitrary concentration was added to any assay buffer, FRET intensity of wells in which a test compound group was added was converted into cAMP concentration. Inhibitory activity of compounds was calculated using the following equation.

$$\text{Inhibitory activity } (\%) = (C-B)/(A-B) \times 100$$

A: cAMP concentration calculated from wells in which 0.3 μM of forskolin is added B: cAMP concentration calculated from wells in which 0.3 μM of forskolin and 1 nM of somatostatin 14 are added C: cAMP concentration wells in which 0.3 μM of forskolin, 1 nM of somatostatin 14 and 1 μM of test compound are added Inhibition rates (%) are described in Table 2 with respect to SSTR5 in concentration of 1 μM of a test compound.

TABLE 2

| Example No. | Inhibition rate (%) with respect to SSTR5 in concentration of 1 μM |
|---|---|
| 1 | 72 |
| 2 | 120 |
| 3 | 89 |
| 4 | 102 |
| 7 | 62 |
| 8 | 104 |
| 12 | 103 |
| 16 | 103 |
| 17 | 83 |
| 19 | 91 |
| 23 | 90 |
| 24 | 105 |
| 42 | 114 |
| 43 | 83 |
| 77 | 80 |
| 84 | 85 |
| 87 | 108 |
| 88 | 114 |
| 93 | 96 |
| 94 | 88 |
| 95 | 90 |
| 97 | 94 |
| 100 | 108 |
| 104 | 100 |
| 106 | 91 |

TABLE 2-continued

| Example No. | Inhibition rate (%) with respect to SSTR5 in concentration of 1 μM |
|---|---|
| 107 | 111 |
| 109 | 103 |
| 112 | 102 |
| 113 | 95 |
| 114 | 111 |
| 118 | 90 |
| 162 | 102 |
| 163 | 83 |
| 164 | 94 |
| 166 | 109 |
| 167 | 102 |
| 168 | 90 |
| 169 | 91 |
| 171 | 97 |
| 172 | 91 |
| 174 | 111 |
| 178 | 88 |
| 182 | 100 |
| 183 | 101 |
| 185 | 85 |
| 186 | 102 |
| 187 | 96 |
| 188 | 112 |
| 189 | 99 |
| 191 | 83 |
| 192 | 117 |
| 193 | 105 |
| 194 | 117 |
| 202 | 101 |
| 205 | 89 |
| 206 | 101 |
| 208 | 85 |
| 209 | 105 |
| 210 | 116 |
| 214 | 96 |
| 215 | 111 |
| 217 | 95 |
| 225 | 97 |

As clearly shown in Table 2, the compounds of the present invention exhibited excellent SSTR5 antagonistic action.

Test Example 2

Evaluation of Human SSTR5 Antagonist Activity Using an Intracellular cAMP Concentration as an Indicator Measurement of the intracellular cAMP concentration was performed using a HTRF cAMP dynamic 2 kit (manufactured by Cisbio). A test compound which was diluted with an assay buffer (5 mM HEPES (pH 7.5) (manufactured by Invitrogen Corp.), 0.1% fatty-acid free BSA (manufactured by Sigma-Aldrich, Inc.), HBSS (manufactured by Invitrogen Corp.) containing 500 μM IBMX (manufactured by Wako Pure Chemical Industries, Ltd) was added by 2 μL/well to a 384 well white plate (manufactured by Greiner) such that a final concentration become 1 μM. A frozen stock, which was stably expressed dihydrofolate reductase-deficient CHO (dhfr-) cells in which human SSTR5 gene (Accession No. NM001053) was melted in a thermostatic chamber at 37° C., and it was suspended on a medium of subculture (medium prepared from MEM alpha (manufactured by Wako Pure Chemical Industries, Ltd.), 10% dialyzed serum (manufacture by Gemini Co., Ltd.) and 50 μg/mL gentamicin (manufactured by Invitrogen Corp.). After centrifuging the cell suspension, the cell suspension was resuspended using the assay buffer, and the resultant was added to each well by 2 μL/well to be 4000 cells/well. After a test compound and cells were incubated for 15 minutes. An assay buffer which contains 0.1 nM of somatostatin 28 (manufactured by Toray Research Center) and 0.3 μM of forskolin (manufactured by Wako Pure Chemical Industries, Ltd) as a final concentration was added by 2 μM/well, and incubation was performed for 30 minutes at room temperature. Each of cAMP-d2 and anti-cAMP-cryptate was added by 3 μL/well, it was allowed to stand for 60 minutes at room temperature, and FRET (Fluorescence resonance energy transfer) intensity was measured using Multi-label reader Envision (manufactured by Perkin Elmer Inc.). Using the calibration curve prepared from the FRET intensity of well groups in which cAMP as arbitrary concentration was added to an assay buffer, FRET intensity of wells in which a test compound group was added was converted into cAMP concentration. Inhibitory activity of compounds was calculated using the following equation.

$$\text{Inhibitory activity (\%)} = (C-B)/(A-B) \times 100$$

A: cAMP concentration calculated from wells in which 0.3 μM of forskolin is added B: cAMP concentration calculated from wells in which 0.3 μM of forskolin and 1 nM of somatostatin 28 are added C: cAMP concentration wells in which 0.3 μM of forskolin, 1 nM of somatostatin 28 and 1 μM of test compound are added Inhibition rates (%) are described in Table 3 with respect to SSTR5 in concentration of 1 μM of a test compound.

TABLE 3

| Example No. | Inhibition rate (%) with respect to SSTR5 in concentration of 1 μM |
|---|---|
| 238 | 99 |
| 239 | 94 |
| 248 | 102 |
| 250 | 98 |
| 256 | 121 |
| 257 | 117 |
| 258 | 124 |
| 259 | 90 |
| 261 | 92 |
| 262 | 100 |
| 265 | 92 |
| 266 | 88 |

As clearly shown in Table 3, the compounds of the present invention exhibited excellent SSTR5 antagonistic action.

Test Example 3

Evaluation of Glucose Lowering Effect 8-week-old male C57BL/6J mice were purchased from CLEA Japan, Inc. After feeding high fat diet (HFD; D12492, Research Diets, Inc.) for a week, weight of mice is measured a day before the experiment, and the mice were separated in groups based on the weight. On the day of experiment, vehicle (0.5% methyl cellulose solution) or test drug (0.5% methyl cellulose suspension) were orally administered 1 hour after fasting was started and glucose load was given orally 9 hours after fasting was started. Just before the glucose load, Blood Glucose (BG) was measured by drawing blood from the tail (pre), and BG was measured again from the tail 10 minutes, 30 minutes, 60 minutes and 120 minutes after the glucose load. All values were indicated with Mean±Standard Deviation (SD), and in the statistical analysis, Williams test was used for the case of equal variance and Shirley-Williams test was used for non-equal variance in the comparison of the vehicle group and test drug group. The result is shown in the table below:

TABLE 4

| compounds | dose | pre | 10 min | 30 min | 60 min | 120 min | AUCpre-120 min |
|---|---|---|---|---|---|---|---|
| vehicle | 0 | 169 ± 14 | 330 ± 42 | 462 ± 61 | 440 ± 40 | 217 ± 26 | 728 ± 66 |
| Example 238 | 3 mg/kg | 148 ± 19 | 261 ± 42 ## | 350 ± 49 ### | 345 ± 38 ## | 188 ± 22 | 576 ± 52 ### |

Mean ± SD,
n = 6,
$p < 0.01$,
$p < 0.001$ (Williams' test)

As clearly shown in Table 4, the compounds of the present invention exhibited glucose lowering effect.

Test Example 4 hERG Activity Measurement by IonWorks Quattro

A cell strain CYL3038 having hERG stably expressed in CHO cells was purchased from Millipore LIMITED. A subculture of CYL3038 was prepared using Ham's F-12 medium containing 10% FBS and 500 μg/mL Geneticin, under the presence of 5% $CO_2$ at 32° C. hERG current inhibition was measured by PPC mode of IonWorks Quattro (Molecular Devices, Inc.). As an extracellular fluid, PBS (+) was used. As an intracellular fluid, 20 mM HEPES buffer (pH 7.3) containing 140 mM KCl, 2 mM $MgCl_2$ and 1 mM EGTA was used, and the cell was perforated by amphotericin. As the voltage protocol, holding potential was set to −80 mV, prepulsevoltage was set to 40 mV (2 seconds) and test pulsevoltage was set to −50 mV (2 seconds). Current values before and after addition of compound are respectively recorded as pre-compound hERG current and post-compound hERG current. Exposure time for the compound was set to 5 minutes. hERG current inhibition rate (%) was calculated based on the equation as shown below:

% hERG inhibition=100−(post-compound hERG current/pre-compound hERG current)×100

TABLE 5

| Example No. | % hERG inhibition (10 μM) |
|---|---|
| 8 | 13 |
| 238 | 10 |
| 265 | 18 |

As shown in Table 5, the compounds of the present invention exhibited low hERG inhibition rate.

| Formulation Example 1 (Preparation of capsules) | |
|---|---|
| 1) Compound of Example 1 | 30 mg |
| 2) Fine powder cellulose | 10 mg |
| 3) Lactose | 19 mg |
| 4) Magnesium stearate | 1 mg |
| Total | 60 mg |

1), 2), 3) and 4) are mixed, and the mixed material is filled in a gelatin capsule.

| Formulation Example 2 (Preparation of tablets) | |
|---|---|
| 1) Compound of Example 1 | 30 g |
| 2) Lactose | 50 g |
| 3) Corn starch | 15 g |

-continued

| Formulation Example 2 (Preparation of tablets) | |
|---|---|
| 4) Carboxymethylcellulose calcium | 44 g |
| 5) Magnesium stearate | 1 g |
| 1000 tablets Total | 140 g |

The total amount of 1), 2) and 3), and 30 g of 4) are kneaded with water, vacuum-dried, and granulation is performed. 14 g of 4) and 1 g of 5) are mixed with the granules, and the resultant is tableted using a tableting machine. Thus, 1000 tablets containing 30 mg of the compound of Example 1 per each tablet are obtained.

INDUSTRIAL APPLICABILITY

The compounds of the invention have a somatostatin receptor subtype 5 antagonistic action, and are useful in prevention and treatment of diabetes and obesity.

The invention claimed is:

1. A compound represented by the following formula:

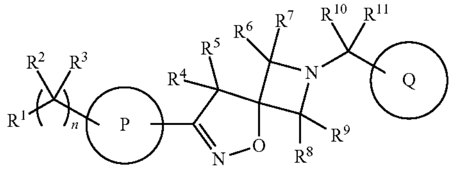

wherein ring P is pyrrolidine, piperidine, cyclohexane or bicyclo [2.2.2]octane, each of which is optionally substituted with a $C_{1-6}$ alkyl group optionally substituted with an $C_{6-14}$ aryl group, an $C_{1-6}$ alkoxy group, or a hydroxyl group, ring Q is benzene optionally substituted with 1 to 4 substituents selected from the following (a) to (j):

(a) a halogen atom;

(b) a $C_{3-10}$ cycloalkyl group optionally substituted with 1 to 3 substituents selected from a halogen atom, an $C_{1-6}$ alkoxy group, a hydroxyl group, and an $C_{1-6}$ alkyl group;

(c) a $C_{1-6}$ alkoxy group optionally substituted with 1 to 3 substituents selected from a halogen atom, an optionally halogenated $C_{3-10}$ cycloalkyl group, an $C_{1-6}$ alkoxy group, a $C_{6-14}$ aryl group, a 5- to 14-membered aromatic heterocyclic group optionally substituted with 1 to 3 substituents selected from a $C_{1-6}$ alkyl group and a $C_{6-14}$ aryl group, and an $C_{1-6}$ alkylsulfonyl group;

(d) a 3- to 8-membered monocyclic non-aromatic heterocyclic group optionally substituted with 1 to 3 substituents selected from a halogen atom, and a halogenated $C_{1-6}$ alkyl group;

(e) a $C_{6-14}$ aryl group optionally substituted with 1 to 3 substituents selected from a halogen atom, an $C_{1-6}$ alkyl group, a halogenated $C_{1-6}$ alkyl group, an amino group optionally substituted with 1 or 2 $C_{1-6}$ alkyl group, a cyano group, an $C_{1-6}$ alkylsulfonyl group; an $C_{1-6}$ alkoxy group optionally substituted with a $C_{6-14}$ aryl group or a halogen atom, and a $C_{3-6}$ cycloalkyl group;

(f) a $C_{1-6}$ alkyl group optionally substituted with 1 to 3 substituents selected from a halogen atom, an optionally halogenated $C_{3-10}$ cycloalkyl group, and an $C_{1-6}$ alkoxy group;

(g) a $C_{6-14}$ aryloxy group optionally substituted with 1 to 3 substituents selected from a halogen atom;

(h) a 5- to 6-membered monocyclic aromatic heterocyclic group optionally substituted with 1 to 3 substituents selected from an optionally halogenated $C_{1-6}$ alkyl group, a halogen atom; and (i) a $C_{3-10}$ cycloalkyloxy group, (j) a $C_{3-10}$ cycloalkenyl group, or 5- to 14-membered heterocycle optionally substituted with 1 to 4 substituents selected from the following (k) to (s):

(k) a halogen atom, (l) a $C_{1-6}$ alkyl group, (m) a $C_{3-10}$ cycloalkyl group, (n) a $C_{1-6}$ alkoxy group optionally substituted with 1 to 3 substituents selected from a halogen atom, a $C_{6-14}$ aryl group, (o) a 5- to 6-membered monocyclic aromatic heterocyclic group, (p) a $C_{6-14}$ aryl group optionally substituted with 1 to 3 substituents selected from a halogen atom, (q) a $C_{7-16}$ aralkyl group, (r) an amino group optionally substituted with 1 to 2 substituents selected from an $C_{6-14}$ aryl group, (s) a hydroxyl group optionally substituted with a halogenated $C_{6-14}$ aryl group, $R^1$ is $CO_2H$, $CO_2CH_3$, or $CO_2CH_2CH_3$, $R^2$ and $R^3$ are each independently a hydrogen atom, a halogen atom or a $C_{1-6}$ alkyl group, $R^4$, $R^5$, $R^6$, $R^7$, $R^8$, $R^9$, $R^{10}$ and $R^{11}$ are each independently a hydrogen atom or a methyl group, and n is 0 to 2 or a salt thereof.

2. The compound or a salt thereof according to claim 1, wherein ring P is piperidine or cyclohexane, each optionally substituted with a $C_{1-6}$ alkyl group.

3. The compound or a salt thereof according to claim 1, wherein ring Q is benzene optionally substituted with 1 to 4 substituents selected from (a) a halogen atom, (b) a $C_{3-10}$ cycloalkyl group optionally substituted with 1 to 3 halogen atoms, (c) a $C_{1-6}$ alkoxy group optionally substituted with an optionally halogenated $C_{3-10}$ cycloalkyl group, (d) a 3- to 8-membered monocyclic non-aromatic heterocyclic group optionally substituted with 1 to 3 halogen atoms, and (e) a $C_{6-14}$ aryl group optionally substituted with 1 to 3 halogen atoms.

4. The compound or a salt thereof according to claim 1, wherein $R^1$ is $CO_2H$.

5. The compound or a salt thereof according to claim 1, wherein $R^4$, $R^5$, $R^6$, $R^7$, $R^8$, $R^9$, $R^{10}$ and $R^{11}$ are hydrogen atoms.

6. The compound or a salt thereof according to claim 1, wherein n is 0.

7. The compound or a salt thereof according to claim 1, wherein ring P is piperidine or cyclohexane, each optionally substituted with a $C_{1-6}$ alkyl group;

ring Q is benzene optionally substituted with 1 to 4 substituents selected from (a) a halogen atom, (b) a $C_{3-10}$ cycloalkyl group optionally substituted with 1 to 3 halogen atoms, (c) a $C_{1-6}$ alkoxy group optionally substituted with an optionally halogenated $C_{3-10}$ cycloalkyl group, (d) a 3- to 8-membered monocyclic non-aromatic heterocyclic group optionally substituted with 1 to 3 halogen atoms, and (e) a $C_{6-14}$ aryl group optionally substituted with 1 to 3 halogen atoms;

$R^1$ is $CO_2H$;

$R^4$, $R^5$, $R^6$, $R^7$, $R^8$, $R^9$, $R^{10}$ and $R^{11}$ are hydrogen atoms; and n is 0.

8. The compound or a salt thereof according to claim 1, wherein ring P is piperidine optionally substituted with a $C_{1-6}$ alkyl group;

ring Q is benzene optionally substituted with 3 to 4 substituents selected from (a) a halogen atom, (b) a $C_{3-10}$ cycloalkyl group, (c) a $C_{1-6}$ alkoxy group, and (d) a $C_{6-14}$ aryl group optionally substituted with 1 to 3 halogen atoms;

$R^1$ is $CO_2H$;

$R^4$, $R^5$, $R^6$, $R^7$, $R^8$, $R^9$, $R^{10}$ and $R^{11}$ are hydrogen atoms; and n is 0.

9. 1-(2-((2-Chloro-6-cyclopropyl-4'-fluoro-3-methoxybiphenyl-4-yl)methyl)-5-oxa-2,6-diazaspiro[3.4]octa-6-en-7-yl)-4-methylpiperidine-4-carboxylic acid or a salt thereof.

10. 1-(2-((6-Cyclopropyl-2,4'-difluoro-3-methoxybiphenyl-4-yl)methyl)-5-oxa-2,6-diazaspiro[3.4]octa-6-en-7-yl)-4-methylpiperidine-4-carboxylic acid or a salt thereof.

11. 1-(2-((2,6-Diethoxy-4'-fluorobiphenyl-4-yl)methyl)-5-oxa-2,6-diazaspiro[3.4]octa-6-en-7-yl)-4-methylpiperidine-4-carboxylic acid or a salt thereof.

12. A pharmaceutical agent comprising the compound or a salt thereof according to claim 1 and a pharmacologically acceptable carrier.

* * * * *